US012653809B2

(12) United States Patent
Sands et al.

(10) Patent No.: US 12,653,809 B2

(45) Date of Patent: Jun. 16, 2026

(54) UREA, AMIDE, AND SUBSTITUTED HETEROARYL COMPOUNDS FOR CBL-B INHIBITION

(71) Applicant: Nurix Therapeutics, Inc., San Francisco, CA (US)

(72) Inventors: Arthur T. Sands, San Francisco, CA (US); Neil F. Bence, San Francisco, CA (US); Christoph W. Zapf, San Francisco, CA (US); Frederick Cohen, San Francisco, CA (US); Chenbo Wang, San Francisco, CA (US); Thomas Cummins, San Francisco, CA (US); Hiroko Tanaka, San Francisco, CA (US); Morgan Lawrenz, San Francisco, CA (US); Mario Cardozo, San Francisco, CA (US); Dahlia Weiss, San Mateo, CA (US); Jennifa Gosling, San Francisco, CA (US)

(73) Assignee: Nurix Therapeutics, Inc., San Francisco, CA (US)

( * ) Notice: Subject to any disclaimer, the term of this patent is extended or adjusted under 35 U.S.C. 154(b) by 1056 days.

(21) Appl. No.: 17/631,886

(22) PCT Filed: Jul. 27, 2020

(86) PCT No.: PCT/US2020/043788

§ 371 (c)(1),
(2) Date: Jan. 31, 2022

(87) PCT Pub. No.: WO2021/021761

PCT Pub. Date: Feb. 4, 2021

(65) Prior Publication Data

US 2022/0387395 A1 Dec. 8, 2022

Related U.S. Application Data

(60) Provisional application No. 62/880,310, filed on Jul. 30, 2019.

(51) Int. Cl.

*A61K 31/4196* (2006.01)
*A61K 31/047* (2006.01)
(Continued)

(52) U.S. Cl.

CPC ........ *A61K 31/4196* (2013.01); *A61K 31/047* (2013.01); *A61K 31/10* (2013.01);
(Continued)

(58) Field of Classification Search

CPC .... A61K 31/4196; A61K 47/54; A61K 47/05; A61K 33/243; A61K 40/42; A61K 40/11; A61K 31/047; A61K 31/10; A61K 31/131; A61K 31/136; A61K 31/137; A61K 31/155; A61K 31/282; A61K 31/336; A61K 31/337; A61K 31/351; A61K 31/396; A61K 31/407; A61K 31/4184; A61K 31/422; A61K 31/427; A61K 31/437;
(Continued)

(56) References Cited

U.S. PATENT DOCUMENTS 5,273,986 A 12/1993 Holland et al.
6,143,780 A 11/2000 Brouwer et al.
(Continued)

FOREIGN PATENT DOCUMENTS

CN 101918544 A 12/2010
CN 103898051 A 7/2014
(Continued)

OTHER PUBLICATIONS

C. Riling et al., "Small-Molecule Cbl-B Inhibitors As Novel Intracellular Checkpoint Inhibitors For Cancer Immunotherapy [Abstract]", Proceedings of the AACR-NCI-EORTC International Conference: Molecular Targets and Cancer Therapeutics; Oct. 26-30, 2017; Philadelphia, PA. : AACR; Mol Can (Year: 2017).*
(Continued)

*Primary Examiner* — Kortney L. Klinkel
*Assistant Examiner* — Grace Ching Hsu
(74) *Attorney, Agent, or Firm* — Squire Patton Boggs (US) LLP

(57) ABSTRACT

Compounds of formulae (I) and (II), compositions, and methods for use in inhibiting the E3 enzyme Cbl-b in the ubiquitin proteasome pathway are disclosed. The compounds, compositions, and methods can be used to modulate the immune system, to treat diseases amenable to immune system modulation, and for treatment of cells invivo, in vitro, or ex vivo.

(I)

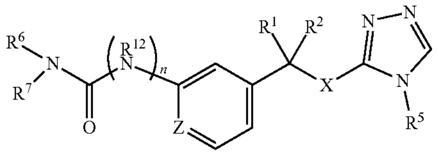

(II)

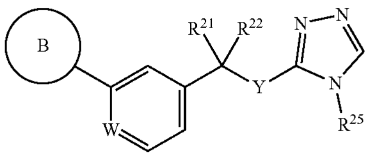

25 Claims, No Drawings

Specification includes a Sequence Listing.

(51) Int. Cl.

| | |
|---|---|
| ***A61K 31/10*** | (2006.01) |
| ***A61K 31/131*** | (2006.01) |
| ***A61K 31/136*** | (2006.01) |
| ***A61K 31/137*** | (2006.01) |
| ***A61K 31/155*** | (2006.01) |
| ***A61K 31/282*** | (2006.01) |
| ***A61K 31/336*** | (2006.01) |
| ***A61K 31/337*** | (2006.01) |
| ***A61K 31/351*** | (2006.01) |
| ***A61K 31/396*** | (2006.01) |
| ***A61K 31/407*** | (2006.01) |
| ***A61K 31/4184*** | (2006.01) |
| ***A61K 31/422*** | (2006.01) |
| ***A61K 31/427*** | (2006.01) |
| ***A61K 31/437*** | (2006.01) |
| ***A61K 31/4375*** | (2006.01) |
| ***A61K 31/438*** | (2006.01) |
| ***A61K 31/439*** | (2006.01) |
| ***A61K 31/4439*** | (2006.01) |
| ***A61K 31/444*** | (2006.01) |
| ***A61K 31/4709*** | (2006.01) |
| ***A61K 31/473*** | (2006.01) |
| ***A61K 31/495*** | (2006.01) |
| ***A61K 31/496*** | (2006.01) |
| ***A61K 31/4985*** | (2006.01) |
| ***A61K 31/4995*** | (2006.01) |
| ***A61K 31/501*** | (2006.01) |
| ***A61K 31/506*** | (2006.01) |
| ***A61K 31/513*** | (2006.01) |
| ***A61K 31/517*** | (2006.01) |
| ***A61K 31/519*** | (2006.01) |
| ***A61K 31/52*** | (2006.01) |
| ***A61K 31/537*** | (2006.01) |
| ***A61K 31/5377*** | (2006.01) |
| ***A61K 31/5383*** | (2006.01) |
| ***A61K 31/5386*** | (2006.01) |
| ***A61K 31/541*** | (2006.01) |
| ***A61K 31/573*** | (2006.01) |
| ***A61K 31/635*** | (2006.01) |
| ***A61K 31/655*** | (2006.01) |
| ***A61K 31/66*** | (2006.01) |
| ***A61K 31/7028*** | (2006.01) |
| ***A61K 31/704*** | (2006.01) |
| ***A61K 31/7048*** | (2006.01) |
| ***A61K 31/706*** | (2006.01) |
| ***A61K 31/7068*** | (2006.01) |
| ***A61K 31/7072*** | (2006.01) |
| ***A61K 31/7076*** | (2006.01) |
| ***A61K 33/243*** | (2019.01) |
| ***A61K 38/08*** | (2019.01) |
| ***A61K 38/12*** | (2006.01) |
| ***A61K 38/14*** | (2006.01) |
| ***A61K 38/17*** | (2006.01) |
| ***A61K 39/395*** | (2006.01) |
| ***A61K 40/11*** | (2025.01) |
| ***A61K 40/42*** | (2025.01) |
| ***A61K 47/54*** | (2017.01) |
| ***A61P 35/00*** | (2006.01) |
| ***C07D 249/08*** | (2006.01) |
| ***C07D 249/10*** | (2006.01) |
| ***C07D 401/12*** | (2006.01) |
| ***C07D 401/14*** | (2006.01) |
| ***C07D 403/12*** | (2006.01) |
| ***C07D 405/06*** | (2006.01) |
| ***C07D 405/14*** | (2006.01) |
| ***C07D 413/12*** | (2006.01) |
| ***C07D 413/14*** | (2006.01) |
| ***C07D 417/12*** | (2006.01) |
| ***C07D 471/04*** | (2006.01) |
| ***C07D 471/10*** | (2006.01) |
| ***C07D 471/20*** | (2006.01) |
| ***C07D 487/04*** | (2006.01) |
| ***C07D 487/10*** | (2006.01) |
| ***C07D 491/107*** | (2006.01) |
| ***C07D 498/04*** | (2006.01) |
| ***C07D 498/10*** | (2006.01) |
| ***C07D 498/20*** | (2006.01) |
| ***C07F 5/02*** | (2006.01) |
| ***C12N 5/0783*** | (2010.01) |
| ***C12N 15/62*** | (2006.01) |
| ***C12N 15/86*** | (2006.01) |

(52) U.S. Cl.

CPC .......... *A61K 31/131* (2013.01); *A61K 31/136* (2013.01); *A61K 31/137* (2013.01); *A61K 31/155* (2013.01); *A61K 31/282* (2013.01); *A61K 31/336* (2013.01); *A61K 31/337* (2013.01); *A61K 31/351* (2013.01); *A61K 31/396* (2013.01); *A61K 31/407* (2013.01); *A61K 31/4184* (2013.01); *A61K 31/422* (2013.01); *A61K 31/427* (2013.01); *A61K 31/437* (2013.01); *A61K 31/4375* (2013.01); *A61K 31/438* (2013.01); *A61K 31/439* (2013.01); *A61K 31/4439* (2013.01); *A61K 31/444* (2013.01); *A61K 31/4709* (2013.01); *A61K 31/473* (2013.01); *A61K 31/495* (2013.01); *A61K 31/496* (2013.01); *A61K 31/4985* (2013.01); *A61K 31/4995* (2013.01); *A61K 31/501* (2013.01); *A61K 31/506* (2013.01); *A61K 31/513* (2013.01); *A61K 31/517* (2013.01); *A61K 31/519* (2013.01); *A61K 31/52* (2013.01); *A61K 31/537* (2013.01); *A61K 31/5377* (2013.01); *A61K 31/5383* (2013.01); *A61K 31/5386* (2013.01); *A61K 31/541* (2013.01); *A61K 31/573* (2013.01); *A61K 31/635* (2013.01); *A61K 31/655* (2013.01); *A61K 31/66* (2013.01); *A61K 31/7028* (2013.01); *A61K 31/704* (2013.01); *A61K 31/7048* (2013.01); *A61K 31/706* (2013.01); *A61K 31/7068* (2013.01); *A61K 31/7072* (2013.01); *A61K 31/7076* (2013.01); *A61K 33/243* (2019.01); *A61K 38/08* (2013.01); *A61K 38/12* (2013.01); *A61K 38/14* (2013.01); *A61K 38/1774* (2013.01); *A61K 39/3955* (2013.01); *A61K 40/11* (2025.01); *A61K 40/42* (2025.01); *A61K 47/545* (2017.08); *A61P 35/00* (2018.01); *C07D 249/08* (2013.01); *C07D 249/10* (2013.01); *C07D 401/12* (2013.01); *C07D 401/14* (2013.01); *C07D 403/12* (2013.01); *C07D 405/06* (2013.01); *C07D 405/14* (2013.01); *C07D 413/12* (2013.01); *C07D 413/14* (2013.01); *C07D 417/12* (2013.01); *C07D 471/04* (2013.01); *C07D 471/10* (2013.01); *C07D 471/20* (2013.01); *C07D 487/04* (2013.01); *C07D 487/10* (2013.01); *C07D 491/107* (2013.01); *C07D 498/04* (2013.01); *C07D 498/10* (2013.01); *C07D 498/20* (2013.01); *C07F 5/022* (2013.01); *C12N 5/0636* (2013.01); *C12N 15/625*

(2013.01); *C12N 15/86* (2013.01); *C12N 2501/2302* (2013.01); *C12N 2501/999* (2013.01); *C12N 2740/10043* (2013.01)

(58) Field of Classification Search
CPC .............. A61K 31/4375; A61K 31/438; A61K 31/439; A61K 31/4439; A61K 31/444; A61K 31/4709; A61K 31/473; A61K 31/495; A61K 31/496; A61K 31/4985; A61K 31/4995; A61K 31/501; A61K 31/506; A61K 31/513; A61K 31/517; A61K 31/519; A61K 31/52; A61K 31/537; A61K 31/5377; A61K 31/5383; A61K 31/5386; A61K 31/541; A61K 31/573; A61K 31/635; A61K 31/655; A61K 31/66; A61K 31/7028; A61K 31/704; A61K 31/7048; A61K 31/706; A61K 31/7068; A61K 31/7072; A61K 31/7076; A61K 38/08; A61K 38/12; A61K 38/14; A61K 38/1774; A61K 39/3955; A61P 35/00; C07D 249/08; C07D 249/10; C07D 401/12; C07D 401/14; C07D 403/12; C07D 405/06; C07D 405/14; C07D 413/12; C07D 413/14; C07D 417/12; C07D 471/04; C07D 471/10; C07D 471/20; C07D 487/04; C07D 487/10; C07D 491/107; C07D 498/04; C07D 498/10; C07D 498/20; C07F 5/022; C12N 5/0636; C12N 15/625; C12N 15/86
USPC ........................................................... 514/64
See application file for complete search history.

(56) References Cited

U.S. PATENT DOCUMENTS

| | | | |
|---|---|---|---|
| 8,809,288 | B2 | 8/2014 | Baier et al. |
| 11,401,267 | B2 | 8/2022 | Sands et al. |
| 11,464,802 | B2 | 10/2022 | Sands et al. |
| 11,530,229 | B2 | 12/2022 | Sands et al. |
| 11,951,133 | B2 | 4/2024 | Sands et al. |
| 2006/0063782 | A1 | 3/2006 | Murray et al. |
| 2007/0054355 | A1 | 3/2007 | Reiss et al. |
| 2014/0010781 | A1 | 1/2014 | Lametschwandtner et al. |
| 2017/0015655 | A1 | 1/2017 | Kaieda et al. |
| 2018/0207201 | A1 | 7/2018 | Wardell et al. |
| 2020/0323904 | A1 | 10/2020 | Sands et al. |
| 2021/0053961 | A1 | 2/2021 | Sands et al. |
| 2021/0053986 | A1 | 2/2021 | Sands et al. |
| 2021/0085717 | A1 | 3/2021 | Gosling et al. |
| 2021/0087259 | A1 | 3/2021 | Gosling et al. |
| 2021/0198280 | A1 | 7/2021 | Kelly et al. |
| 2022/0324835 | A1 | 10/2022 | Barsanti et al. |
| 2022/0339152 | A1 | 10/2022 | Guiducci et al. |
| 2022/0378839 | A1 | 12/2022 | Sands et al. |
| 2022/0387395 | A1 | 12/2022 | Sands et al. |
| 2023/0086137 | A1 | 3/2023 | Somanath et al. |
| 2023/0355599 | A1 | 11/2023 | Powers et al. |
| 2023/0414598 | A1 | 12/2023 | Brown et al. |
| 2024/0293458 | A1 | 9/2024 | Sands et al. |
| 2024/0409555 | A1 | 12/2024 | Sands et al. |
| 2025/0009731 | A1 | 1/2025 | Gallota et al. |
| 2025/0161303 | A1 | 5/2025 | Guiducci et al. |

FOREIGN PATENT DOCUMENTS

| | | | |
|---|---|---|---|
| EP | 1 364 949 | A1 | 11/2003 |
| EP | 3 254 701 | A1 | 12/2017 |
| WO | WO 1986/05779 | A1 | 10/1986 |
| WO | WO 2001/027107 | A2 | 4/2001 |
| WO | WO 2001/053274 | A1 * | 7/2001 |
| WO | WO 2005/021532 | A1 | 3/2005 |
| WO | WO 2005/080367 | A1 | 9/2005 |
| WO | WO 2007/072225 | A2 | 6/2007 |
| WO | WO 2008/033403 | A2 | 3/2008 |
| WO | WO 2009/073905 | A2 | 6/2009 |
| WO | WO 2009/098144 | A1 | 8/2009 |
| WO | WO 2011/076725 | A1 | 6/2011 |
| WO | WO 2011/140488 | A1 | 11/2011 |
| WO | WO 2012/020008 | A1 | 2/2012 |
| WO | WO 2012/089736 | A1 | 7/2012 |
| WO | WO 2012/175513 | A1 | 12/2012 |
| WO | WO 2013/067264 | A1 | 5/2013 |
| WO | WO 2013/067274 | A1 | 5/2013 |
| WO | WO 2013/106643 | A2 | 7/2013 |
| WO | WO 2014/040965 | A1 | 3/2014 |
| WO | WO 2015/031295 | A1 | 3/2015 |
| WO | WO 2015/084998 | A1 | 6/2015 |
| WO | WO 2016/196776 | A2 | 12/2016 |
| WO | WO 2018/098275 | A1 | 5/2018 |
| WO | WO 2018/215801 | A1 | 11/2018 |
| WO | WO 2019/063748 | A1 | 4/2019 |
| WO | WO 2019/148005 | A1 | 8/2019 |
| WO | WO 2019/158942 | A1 | 8/2019 |
| WO | WO 2020/081450 | A1 | 4/2020 |
| WO | WO 2020/167518 | A1 | 8/2020 |
| WO | WO 2020/210508 | A1 | 10/2020 |
| WO | WO 2020/236654 | A1 | 11/2020 |
| WO | WO 2020/264398 | A1 | 12/2020 |
| WO | WO 2021/021761 | A1 | 2/2021 |
| WO | WO 2021/061853 | A1 | 4/2021 |
| WO | WO 2021/091575 | A1 | 5/2021 |
| WO | WO 2021/113557 | A1 | 6/2021 |
| WO | WO 2022/217123 | A1 | 10/2022 |
| WO | WO 2023/250097 | A1 | 12/2023 |

OTHER PUBLICATIONS

J. Gosling et al., "Genetic And Pharmacologic Evaluation Of The Ubiquitin Ligase CBL-B As A Small-Molecule, Tumor Immunotherapy Target [Abstract]", . In: Proceedings of the American Association for Cancer Research Annual Meeting 2019; Mar. 29-Apr. 3, 2019; Atlanta, GA: AACR; Cancer Res (Year: 2019).*

International Search Report and Written Opinion for International Patent Application PCT/US2019/015250, 10 pages, Jun. 11, 2019.

International Search Report and Written Opinion for International Patent Application PCT/US2019/056112, 8 pages, Dec. 6, 2019.

International Search Report and Written Opinion for International Patent Application PCT/US2020/016489, 8 pages, May 27, 2020.

International Search Report and Written Opinion for International Patent Application PCT/US2020/027492, 21 pages, Aug. 11, 2020.

International Search Report and Written Opinion for International Patent Application PCT/US2020/039957, 16 pages, Oct. 5, 2020.

International Search Report and Written Opinion for International Patent Application PCT/US2020/033274, 19 pages, Oct. 23, 2020.

International Search Report and Written Opinion for International Patent Application PCT/US2019/043788, 13 pages, Oct. 23, 2020.

International Search Report and Written Opinion for International Patent Application PCT/US2020/052335, 12 pages, Apr. 1, 2021.

International Search Report and Written Opinion for International Patent Application PCT/US2019/060584, pages, May 14, 2021.

Extended European Search Report for European Patent Application No. 19744118.1, 12 pages dated Sep. 22, 2021.

Riling et al.: "Abstract A206: Small-molecule Cbl-b inhibitors as novel intracellular checkpoint inhibitors for cancer immunotherapy | Molecular Cancer Therapeutics", Jan. 1, 2018 (Jan. 1, 2018), XP055700949, Retrieved from the Internet: URL:https:// mct.aacrjournals.org/content/17/1_Supplement/A206 [retrieved on Jun. 4, 2020].

Gosling et al.: "Abstract 2696: Genetic and pharmacologic evaluation of the ubiquitin ligase CBL-B as a small-molecule, tumor immunotherapy target | Cancer Research", Apr. 3, 2019 (Apr. 3, 2019), XP055701108, Retrieved from the Internet: URL:https:// cancerres.aacrjournals.org/content/79/13_Supplement/2696 [retrieved on Jun. 4, 2020].

(56) References Cited

OTHER PUBLICATIONS

Marelli et al., Tumor targeting via integrin ligands, Frontiers in Oncology, vol. 3, Article 222, pp. 1-12, 2013.
Wang et al., Mathematical modeling in cancer drug discovery, Drug Discovery Today, vol. 19, No. 2, pp. 145-150, 2014.
Pearce et al., “Failure modes in anticancer drug discovery and development”, Cancer Drug Design and Discovery Edited by Stephen Neidle, Chapter 18, pp. 424-435 (2008).
Johnson et al., “Relationships between drug activity in NCI preclinical in vitro and in vivo models and early clinical trials”, British Journal of Cancer (2001) 64(10): 1424-1431.
Tigno-Aranjuez et al., “Inhibition of RIP2's tyrosine kinase activity limits NOD2-driven cytokine responses”, Genes & Development, 2010, 24:2666-2677; http://www.genesdev.org/cgi/doi/10.1101/gad.964410.
International Search Report and Written Opinion for International Patent Application PCT/US2020/024119, 19 19 pages, Jan. 5, 2023.
International Search Report and Written Opinion for International Patent Application PCT/US2022/049171, 14 pages, Mar. 16, 2023.
Acute Leukemia, Merck Manual (Online Edition) 6 pages, pp. 1-6 (2013).
Gura, T. “Systems for Identifying New Drugs Are Often Faulty,” Cancer Models, Science, vol. 278, No. 5340, pp. 1041-1042, Nov. 1997.
Jack, J. et al., “Gene Expression and Linkage Analysis implicate CBLB as a mediator of rituximab reistsance,” The Pharmacogenomics Journal (2018) 18: 467-473.
Ray, A. et al., “A novel TLR-9 agonist C792 inhibits plasmacytoid dendritic cell-induced myeloma cell growth and enhance cytotoxicity of bortexomib,” Leukemia, Nature Publishing Group UK, London, vol. 28, No. 8 Jan. 30, 2014, pp. 1716-1724. DOI:10.1038/LEU.2014.46.
Simone, Oncology: Introduction, Cecil Textbook of Medicine, 20th Edition, vol. 1, pp. 1004-1010, 1996.
Sitaram, P. et al., “Beyond the Cell Surface: Targeting Intracellular Negative Regulators to Enhance T cell Anti-Tumor Activity,” International Journal of Molecular Sciences, 20, 5821, 28 pages (2019).
Extended European Search Report for European Patent Application No. 22721939.1, 15 pages dated May 7, 2025.
International Search Report and Written Opinion for International Patent Application PCT/US2023/026004+, 14 pages, Nov. 13, 2023.
Augustin et al., “Targeting cbl-b in cancer immunotherapy”, Journal for Immunotherapy of Cancer (2023) 11(2): pp. 1-17.
Bartlett “Exploiting Chemical Divrsity for Drug Discovery” Edited by Paul A. Bartlee and Michael Entzeroth, the Royal Society of Chemistry, 2006 pp. 113-118.
Bachmaier K et al: “Negative regulation of lymphocyte activation and autoimmunity by the molecular adaptor Cbl-b”, Nature, Nature Publishing Group UK, London, vol. 403, No. 6766, Jan. 13, 2000 (Jan. 13, 2000), pp. 211-216, XP002575145, ISSN: 0028-0836, DOI: 10.1038/35003228 the whole document abstract.
Bajgain et al., “Optimizing the production of suspension cells using the G-Rex ”M“ series ” Mol Ther Methods Clin Dev., May 14, 2014:1:14015. Doi: 10.1038/mtm.2014.15. eCollection 2014.
Chimera L. et al: “c-Cbl: An Important Regulator and a Target in Angiogenesis and Tumorigenesis”, CELLS, vol. 8, No. 5, May 23, 2019 (May 23, 2019), p. 498, XP93071522, DOI: 10.3390/ce11s8050498 the whole document figure 3.
Crawford et al., “Discovery of GDC-0853: A Potent, Selective and Noncovalent Bruton's Tyrosine Kinase Inhibitor in Early Child Development”Journal of Medicinal Chemistry 2018, 61:2227-2245.
Find ETDs Home—Thesis Resources—Find ETDs“ online: ”https: ndltd.org/theses=resources/find-etds/Jan. 31, 2023.
Irwin “Zinc—A Free Database of Commercially Available Compounds fro Virtual Screening”, J. Chem. Inf. Model. 2005, 45 177-182.
Kim “Pubchem in 2021: new data content and improved web interfaces” Nucleic Acids Research, 2021, vol. 49, Database issue Published online on Nov. 5, 2020.
Loeser et al., “Spontaneous tumor rejection by cbl-b-deficient CD8+ T cells”, The Journal of Experimental Medicine, vol. 204, No. 4, pp. 879-891, 2007.
Lupher et al: “Cbl-mediated negative regulation of the Syk tyrosine kinase. A critical role for Cbl phosphotyrosine-binding domain binding to Syk phosphotyrosine 323”, The Journal of biological chemistry, Dec. 25, 1998 (Dec. 25, 1998), pp. 35273-35281, XP93071643, United States DOI:10.1074/jbc.273.52.35273.
Lyle et al., “c-CBL: An Important Regulator and a Taregt in Angiogenesis and Tumorigenesis” Cells Review 2019, 8, 498; doi:10.3390/cells8050498.
Ota Y et al: “The Product of the Proto-Oncogene c-cbl: A Negative Regulator of the Syk Tyrosine Kinase”, Science Apr. 18, 1997;276(5311): 418-20, Jan. 1, 1997(Jan. 1, 1997), XP93071617, Retrieved from the Internet: URL:https://www.science.org/doi/pdf/10.112 6/science.276.5311.418 [retrieved on Aug. 8, 2023] the whole document, p. 419,col. 2.
Ota Y et al: “Characterization of Cbl tyrosine phosphorylation and a Cbl-Syk complex in RBL-2H3 cells.”, Journal of Experimental Medicine, vol. 184, No. 5, Nov. 1, 1996 (Nov. 1, 1996), pp. 1713-1723, XP93071596 ISSN: 0022-1007, DOI 10.1084/Jem.184.5.1713.
Ozcan et al., “Oxadiazole-isopropylamides as Poetnt and Noncovalent Proteasome Inhibitors”, Journal of Mecdinal Chemistry, 2013, 56:3783-3805 doi.org/10/1021/jm4022id.
STN International Search—Stereochemistry searched—Performed by Examiner in USSN 16_964_979 (Final OA dated Oct. 23, 2023).
STN Registry/Z/Registry (CAS Registrysm Sep. 2016, 2 pages.
RN: 2013242-80-1, Supplier: Ukrorgsyntez Ltd., Entered STN: Oct. 16, 2016, Supplier: Ukrorgsyntez Ltd. CN: 3-[(2-bromophenyl)methyl]-4-cyclopropyl-4H-1,2,4-Triazole, MF: C12 H12 Br N3 (2016).
Stewart et al., “Efforts toward elucidating Thalidomide's molecular target: an expedient synthesis of the first Thalidomide biotin analogue”, Org. Biomol. Chem., 2010, 8:4059-4062.
Synergies LLC: Antiemetics Review, Feb. 17, 2009, pp. 1-15 Retrieved from Internet: URL:https://medicaid.nv.gov/downloads/provided/NVRx_DCR_20090625_Antiemetics.pdf [Retrieved from Internet Aug. 31, 2023].
Wermuth et al., Comprehensive Medicinal Chemistryll, vol. 2, p. 649-711 online Apr. 2, 2007. (The Practice of Medicinal Chemistry, 2015, Academic Press (Year 2015).

* cited by examiner

UREA, AMIDE, AND SUBSTITUTED HETEROARYL COMPOUNDS FOR CBL-B INHIBITION

CROSS-REFERENCE TO RELATED APPLICATIONS

This application claims the benefit of U.S. Provisional Application No. 62/880,310, filed Jul. 30, 2019, the content of which is hereby incorporated by reference in its entirety.

REFERENCE TO SEQUENCE LISTING

This patent application includes an electronically submitted sequence listing in .txt format. The .txt file contains a sequence listing entitled “121843.00133_ST25.txt” created on Jun. 13, 2025, and is 3,805 bytes in size. The sequence listing contained in this .txt file is part of the specification and is hereby incorporated by reference herein in its entirety.

FIELD

Provided herein are compounds and compositions for inhibition of the Cbl-b enzyme and methods of use thereof in modulating the immune system, treatment of diseases, and treatment of cells in vivo, in vitro, or ex vivo.

BACKGROUND

The ubiquitin proteasome pathway is a complex system involved in the regulation of protein function and catabolism. Proteins in eukaryotic cells are conjugated with ubiquitin, a 76 amino acid, 8.5 kilodalton protein. This conjugation, known as ubiquitination, results in altered function or degradation of the target protein. Ubiquitination of the target protein occurs via a coupled series of reactions involving ubiquitin and a set of enzymes known as E1, E2, and E3 enzymes. Ubiquitin is activated by the ubiquitin-activating enzyme, or E1 enzyme. Ubiquitin is then transferred to a ubiquitin-conjugating enzyme, or E2 enzyme. Finally, a ubiquitin ligase, or E3 enzyme, promotes the transfer of ubiquitin from the E2 enzyme to the target protein. Polyubiquitination of the target protein predominantly serves as a signal leading to degradation of the ubiquitin-conjugated protein by the proteasome, where it undergoes proteolysis. Ubiquitination by E3 ligases can also result in altered protein activity, interactions, or localization. Ubiquitination regulates diverse biology including cell division, DNA repair, and cellular signaling.

The synthesis and degradation of proteins in the cell is critical for cell cycle regulation, cell proliferation, apoptosis, and many other cellular processes. Thus, the ability to modulate the ubiquitin proteasome pathway offers a wealth of opportunities to intervene in disease processes. Mechanisms for intervention can include enhanced degradation of oncogene products, reduced degradation of tumor-suppressor proteins, and modulation of immune cell response.

Approximately 35 E2 enzymes and over 500 E3 enzymes are encoded in the human genome. Casitas B-lineage lymphoma proto-oncogene-b (Cbl-b) is an E3 ubiquitin ligase that negatively regulates T-cell activation (Wallner et al., Clin Dev Immunol, 2012: 692639). Discovery of agents that modulate E2 or E3 enzymes accordingly provides the potential for therapies directed against disease processes involving a particular E2 or E3 enzyme. This disclosure is directed to agents that inhibit one such E3 enzyme, Casitas B-lineage lymphoma proto-oncogene-b (Cbl-b).

SUMMARY

Disclosed herein are compounds and compositions for inhibition of the Cbl-b enzyme and methods of use thereof in modulating the immune system, treatment of diseases, and treatment of cells in vivo, in vitro, or ex vivo. Also disclosed herein are methods for use of a Cbl-b inhibitor in treating cancer. In brief, the Cbl-b inhibitor may be administered to an individual with cancer, either alone or as part of a combination therapy with one or more of an immune checkpoint inhibitor, an anti-neoplastic agent, and radiation therapy. Additionally, cells treated in vivo and/or in vitro with a compound or composition as disclosed herein may be used in adoptive cell therapy for treating cancer.

Disclosed herein are compounds of Formula (I):

(I)

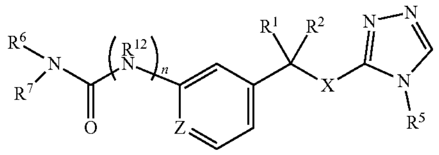

or a tautomer thereof, or a pharmaceutically acceptable salt thereof, wherein:

$R^1$ and $R^2$ are independently H, $C_1$-$C_6$ alkyl, halo, or $C_1$-$C_6$ haloalkyl, provided that when X is S, $R^1$ and $R^2$ are not both H, and provided that $R^1$ and $R^2$ are not halo when X is S or a bond;

or $R^1$ and $R^2$ are taken together with the carbon atom to which they are attached to form

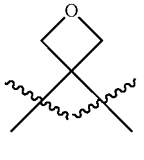 , 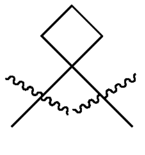 , or 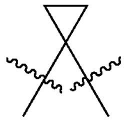 ;

X is $CR^3R^4$ or S;

$R^3$ and $R^4$ are independently H, $C_1$-$C_6$ alkyl, halo, or $C_1$-$C_6$ haloalkyl;

or $R^1$ and $R^3$ are taken together with the carbon atoms to which they are attached to form the moiety;

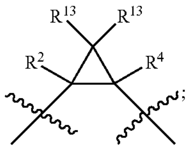

$R^5$ is $C_1$-$C_6$ alkyl, $C_1$-$C_6$ haloalkyl, or $C_3$-$C_6$ cycloalkyl;

Z is CH or N;

n is 0 or 1;

$R^6$ is H, $C_1$-$C_6$ alkyl, or $C_1$-$C_6$ haloalkyl;

$R^7$ is $C_1$-$C_6$ alkyl-OH, —$(CR^8R^9)_m$-(5- to 10-membered monocyclic or fused bicyclic heteroaryl), —$(CR^8R^9)_m$-(4- to 10-membered monocyclic or fused bicyclic heterocyclyl), —$(CR^8R^9)_m$—($C_6$-$C_{10}$ aryl), or —$(CR^8R^9)_m$—($C_3$-$C_6$ cycloalkyl), wherein each heteroaryl, heterocyclyl, aryl, or cycloalkyl group is optionally substituted by 1-5 $R^{10}$ groups;

or $R^6$ and $R^7$ are taken together with the nitrogen atom to which they are attached to form a 5- to 10-membered monocyclic or fused bicyclic heteroaryl, or a 4- to 10-membered monocyclic or fused bicyclic heterocyclyl, each of which heteroaryl or heterocyclyl optionally contains 1-2 additional heteroatoms selected from the group consisting of N, S, and O, and each of which heteroaryl or heterocyclyl is optionally substituted by 1-5 $R^{10}$ groups;

m is zero or one; $R^8$ and $R^9$ are independently H, $C_1$-$C_6$ alkyl, or $C_1$-$C_6$ haloalkyl;

each $R^{10}$ is independently $C_1$-$C_6$ alkyl, $C_1$-$C_6$ haloalkyl, $C_1$-$C_6$ alkyl-OH, —CN, $C_1$-$C_6$ alkyl-CN, —O($C_1$-$C_6$ alkyl), —O($C_1$-$C_6$ haloalkyl), halo, hydroxy, oxo, —$CO_2$H, —C(O)NH($C_1$-$C_6$ alkyl), —C(O)N($C_1$-$C_6$ alkyl)$_2$, —C(O)NH($C_1$-$C_6$ haloalkyl), —C(O)O($C_1$-$C_6$ alkyl), —$SO_2$—($C_1$-$C_6$ alkyl), —$SO_2$—NH($C_1$-$C_6$ alkyl), —$SO_2$—N($C_1$-$C_6$ alkyl)$_2$, —C(O)($C_1$-$C_6$ alkyl), —($C_1$-$C_6$ alkylene)-C(O)N($C_1$-$C_6$ alkyl)$_2$, —($C_1$-$C_6$ alkylene)-C(O)NH($C_1$-$C_6$ alkyl), $C_3$-$C_6$ cycloalkyl, 5- to 6-membered heterocyclyl, 5- to 6-membered heteroaryl, —($C_1$-$C_6$ alkylene)-(5- to 6-membered heterocyclyl), —($C_1$-$C_6$ alkylene)-(5- to 6-membered heteroaryl), —C(O)-(5- to 6-membered heterocyclyl), —C(O)-(5- to 6-membered heteroaryl), or $C_6$-$C_{10}$ aryl, wherein each cycloalkyl, heterocyclyl, heteroaryl, or aryl group is optionally substituted by 1-5 $R^{11}$ groups;

or two $R^{10}$ groups attached to the same carbon atom are taken together with the carbon atom to which they are attached to form a spiro $C_3$-$C_6$ cycloalkyl or a spiro 4- to 6-membered heterocyclyl, each of which is optionally substituted by 1-5 $R^{11}$ groups;

each $R^{11}$ is independently $C_1$-$C_6$ alkyl, hydroxy, oxo, or —C(O)($C_1$-$C_6$ alkyl);

$R^{12}$ is H, $C_1$-$C_6$ alkyl, or $C_1$-$C_6$ haloalkyl, or when $R^6$ and $R^7$ are taken together with the nitrogen atom to which they are attached to form a 4- to 10-membered monocyclic or fused bicyclic heterocyclyl optionally containing 1-2 additional heteroatoms selected from the group consisting of N, S, and O, $R^{12}$ is $C_1$-$C_6$ alkylene which connects to the 4- to 10-membered monocyclic or fused bicyclic heterocyclyl to form a 7- to 14-membered fused bicyclic or tricyclic heterocyclyl, each of which heterocyclyl is optionally substituted by 1-5 $R^{10}$ groups; and each $R^{13}$ is independently H, $C_1$-$C_3$ alkyl, $C_1$-$C_3$ alkyl-OH, or $C_1$-$C_3$ haloalkyl.

In some embodiments, $R^1$ and $R^2$ are independently H, $C_1$-$C_3$ alkyl, halo, or $C_1$-$C_3$ haloalkyl. In some embodiments, $R^1$ and $R^2$ are independently H, —$CH_3$, F, or —$CF_3$. In some embodiments, $R^1$ and $R^2$ are taken together with the carbon atom to which they are attached to form the group

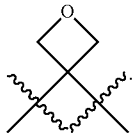

In some embodiments, X is S. In some embodiments, X is $CR^3R^4$.

In some embodiments, $R^3$ and $R^4$ are independently H, halo, $C_1$-$C_3$ alkyl, or $C_1$-$C_3$ haloalkyl. In some embodiments, $R^3$ and $R^4$ are independently H, F, —$CH_3$, or —$CF_3$.

In some embodiments, $R^1$ and $R^3$ are taken together with the carbon atoms to which they are attached to form the moiety

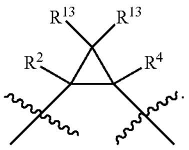

In some embodiments, $R^2$ is H, $C_1$-$C_3$ alkyl, halo, or $C_1$-$C_3$ haloalkyl; $R^4$ is H, $C_1$-$C_3$ alkyl, halo, or $C_1$-$C_3$ haloalkyl; and each $R^{13}$ is independently H, $C_1$-$C_2$ alkyl, $C_1$-$C_2$ alkyl-OH, or $C_1$-$C_2$ haloalkyl. In some embodiments, $R^2$ is H, —$CH_3$, F, or —$CF_3$; $R^4$ is H, —$CH_3$, F, or —$CF_3$; and each $R^{13}$ is independently H, —$CH_3$, —$CH_2$OH, or —$CF_3$. In some embodiments, $R^2$ and $R^4$ are each H; and each $R^{13}$ is H.

In some embodiments, $R^5$ is $C_1$-$C_3$ alkyl, $C_1$-$C_3$ haloalkyl, or $C_3$-$C_4$ cycloalkyl. In some embodiments, $R^5$ is —$CH_3$, —$CHF_2$, or cyclopropyl.

In some embodiments, Z is CH. In some embodiments, Z is N.

In some embodiments, n is zero. In some embodiments, n is one.

In some embodiments, $R^6$ is H, $C_1$-$C_3$ alkyl, or $C_1$-$C_3$ haloalkyl. In some embodiments, $R^6$ is H or —$CH_3$.

In some embodiments, $R^7$ is $C_1$-$C_3$ alkyl-OH, —$(CR^8R^9)_m$-(5- to 6-membered monocyclic heteroaryl), —$(CR^8R^9)_m$-(8- to 10-membered fused bicyclic heteroaryl), —$(CR^8R^9)_m$-(4- to 6-membered monocyclic heterocyclyl), —$(CR^8R^9)_m$-(8- to 10-membered fused bicyclic heterocyclyl), —$(CR^8R^9)_m$—($C_6$-$C_{10}$ aryl), or —$(CR^8R^9)_m$—($C_3$-$C_6$ cycloalkyl), wherein each heteroaryl, heterocyclyl, aryl, or cycloalkyl group is optionally substituted by 1-5 $R^{10}$ groups. In some embodiments, m is zero. In some embodiments, m is one. In some embodiments, $R^8$ and $R^9$ are independently H, $C_1$-$C_3$ alkyl, or $C_1$-$C_3$ haloalkyl. In some embodiments, $R^8$ and $R^9$ are independently H, —$CH_3$, or —$CF_3$. In some embodiments, $R^7$ is selected from the group consisting of

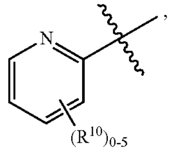 ,

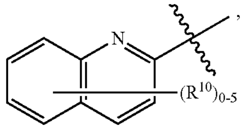 ,

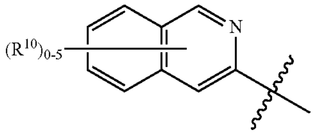 ,

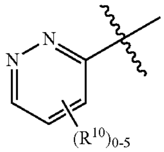 ,

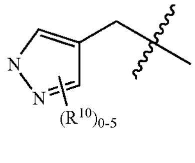 ,

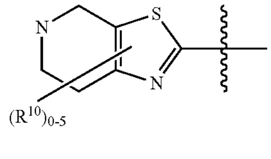 ,

-continued

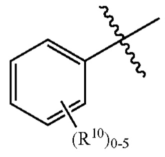,
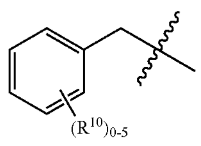,
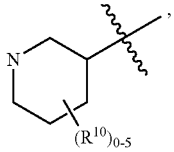,
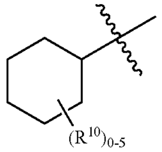,
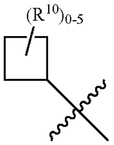, and
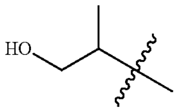.

In some embodiments, $R^6$ and $R^7$ are taken together with the nitrogen atom to which they are attached to form a 5- to 10-membered monocyclic or fused bicyclic heteroaryl, or a 4- to 10-membered monocyclic or fused bicyclic heterocyclyl, each of which heteroaryl or heterocyclyl optionally contains 1-2 additional heteroatoms selected from the group consisting of N, S, and O, and each of which heteroaryl or heterocyclyl is optionally substituted by 1-5 $R^{10}$ groups. In some embodiments, $R^6$ and $R^7$ are taken together with the nitrogen atom to which they are attached to form a 5- to 6-membered monocyclic heteroaryl, 8- to 10-membered fused bicyclic heteroaryl, a 4- to 6-membered monocyclic heterocyclyl, or 8- to 10-membered fused bicyclic heterocyclyl, each of which heteroaryl or heterocyclyl optionally contains 1-2 additional heteroatoms selected from the group consisting of N, S, and O, and each of which heteroaryl or heterocyclyl is optionally substituted by 1-5 $R^{10}$ groups. In some embodiments, $R^6$ and $R^7$ are taken together with the nitrogen atom to which they are attached to form

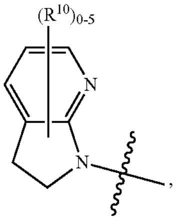,
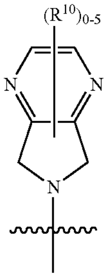,
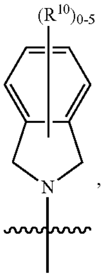,
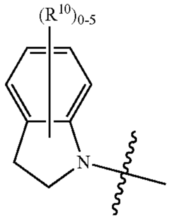,
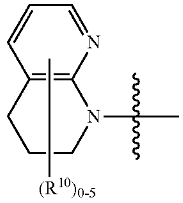,

-continued

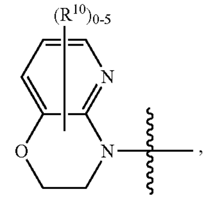,
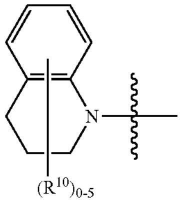,
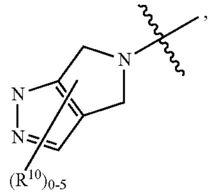,
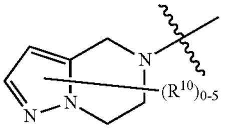,
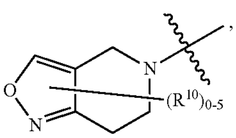,
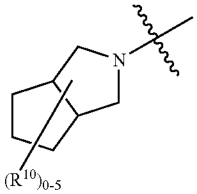,
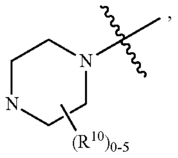,
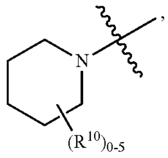,
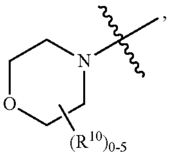,
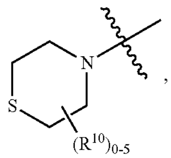,
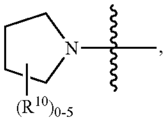, or
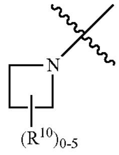.

In some embodiments, each $R^{10}$, where present, is independently $C_1$-$C_3$ alkyl, $C_1$-$C_3$ haloalkyl, $C_1$-$C_3$ alkyl-OH, —CN, $C_1$-$C_3$ alkyl-CN, —O($C_1$-$C_3$ alkyl), —O($C_1$-$C_3$ haloalkyl), halo, hydroxy, oxo, —$CO_2$H, —C(O)NH($C_1$-$C_3$ alkyl), —C(O)NH($C_1$-$C_3$ haloalkyl), —C(O)O($C_1$-$C_3$ alkyl), —$SO_2$—($C_1$-$C_3$ alkyl), —$SO_2$—NH($C_1$-$C_3$ alkyl), —$SO_2$—N($C_1$-$C_3$ alkyl)$_2$, —C(O)($C_1$-$C_3$ alkyl), —($C_1$-$C_3$ alkylene)-C(O)N($C_1$-$C_3$ alkyl)$_2$, —($C_1$-$C_3$ alkylene)-C(O)NH($C_1$-$C_3$ alkyl), $C_3$-$C_6$ cycloalkyl, 5- to 6-membered heterocyclyl, 5- to 6-membered heteroaryl, —($C_1$-$C_3$ alkylene)-(5- to 6-membered heterocyclyl), —($C_1$-$C_3$ alkylene)-(5- to 6-membered heteroaryl), —C(O)-(5- to 6-membered heterocyclyl), —C(O)-(5- to 6-membered heteroaryl), or $C_6$-$C_{10}$ aryl, wherein each cycloalkyl, heterocyclyl, heteroaryl, or aryl group is optionally substituted by 1-5 $R^{11}$ groups; or two $R^{10}$ groups attached to the same carbon atom are taken together with the carbon atom to which they are attached to form a spiro $C_3$-$C_6$ cycloalkyl or a spiro 4- to 6-membered heterocyclyl, each of which is optionally substituted by 1-5 $R^{11}$ groups. In some embodiments, each $R^{10}$ is independently —$CH_3$, —$CH_2CH_3$, —$CH(CH_3)_2$, —$CF_3$, —$CHF_2$, —$CH_2CF_3$, —$CH_2OH$, —CN, —$CH_2CN$, —$OCH_3$, —$OCF_3$, Br, F, hydroxy, oxo, —$CO_2$H, —C(O)NH($CH_3$), —C(O)N($CH_3$)$_2$, —C(O)NH($CF_3$), —C(O)O$CH_3$, —$SO_2CH_3$, —$SO_2$NH($CH_3$), —$SO_2$N($CH_3$)$_2$, —C(O)$CH_3$, —($CH_2$)—C(O)N($CH_3$)$_2$, —($CH_2$)—C(O)NH($CH_3$),

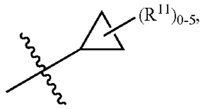

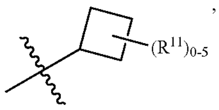

,

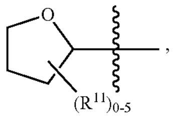

,

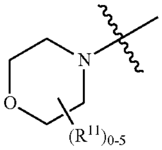

,

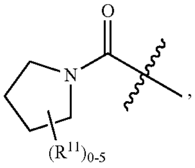

,

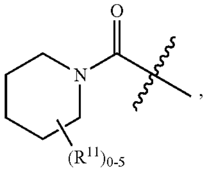

,

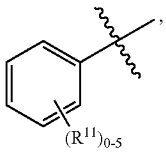

,

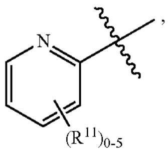

,

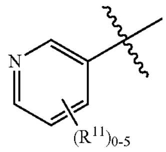

,

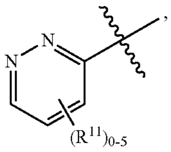

,

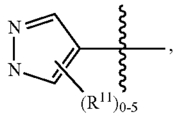

, or

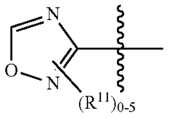

.

In some embodiments, two $R^{10}$ groups attached to the same carbon atom are taken together with the carbon atom to which they are attached to form

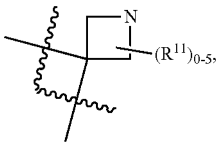

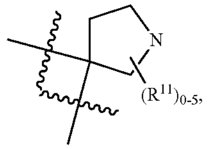

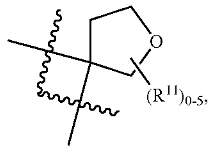

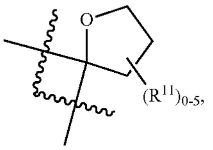

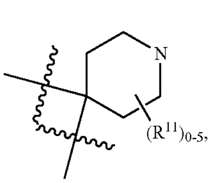

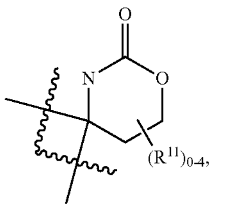

-continued

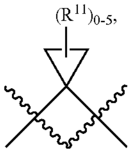

or

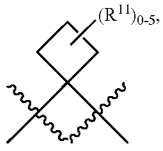

wherein the nitrogen atoms of the heterocyclyl groups are bound to H when not substituted by $R^{11}$.

In some embodiments, each $R^{11}$, where present, is independently $C_1$-$C_3$ alkyl, hydroxy, oxo, or —C(O)($C_1$-$C_3$ alkyl). In some embodiments, each $R^{11}$ is independently —$CH_3$, hydroxy, oxo, or —C(O)$CH_3$.

In some embodiments, $R^{12}$ is H, $C_1$-$C_3$ alkyl, or $C_1$-$C_3$ haloalkyl. In some embodiments, $R^{12}$ is H, —$CH_3$, or —$CF_3$. In some embodiments, $R^{12}$ is H.

In some embodiments, $R^6$ and $R^7$ are taken together with the nitrogen atom to which they are attached to form a 4- to 10-membered monocyclic or fused bicyclic heterocyclyl optionally containing 1-2 additional heteroatoms selected from the group consisting of N, S, and O, and $R^{12}$ is $C_1$-$C_6$ alkylene which connects to the 4- to 10-membered monocyclic or fused bicyclic heterocyclyl to form a 7- to 18-membered fused bicyclic or tricyclic heterocyclyl, each of which heterocyclyl is optionally substituted by 1-5 $R^{10}$ groups. In some embodiments, $R^6$ and $R^7$ are taken together with the nitrogen atom to which they are attached to form a 4- to 6-membered monocyclic heterocyclyl optionally containing 1-2 additional heteroatoms selected from the group consisting of N, S, and O, and $R^{12}$ is $C_1$-$C_3$ alkylene which connects to the 4- to 6-membered monocyclic heterocyclyl to form a 7- to 11-membered fused bicyclic heterocyclyl, each of which heterocyclyl is optionally substituted by 1-5 $R^{10}$ groups; or $R^6$ and $R^7$ are taken together with the nitrogen atom to which they are attached to form a 8- to 10-membered fused bicyclic heterocyclyl optionally containing 1-2 additional heteroatoms selected from the group consisting of N, S, and O, and $R^{12}$ is $C_1$-$C_3$ alkylene which connects to the 8- to 10-membered fused bicyclic heterocyclyl to form a 11- to 15-membered fused tricyclic heterocyclyl, each of which heterocyclyl is optionally substituted by 1-5 $R^{10}$ groups. In some embodiments, $R^6$ and $R^7$ are taken together with the nitrogen atom to which they are attached to form a 5- to 6-membered monocyclic heterocyclyl, and $R^{12}$ is —$CH_2$— which connects to the 5- to 6-membered monocyclic heterocyclyl to form

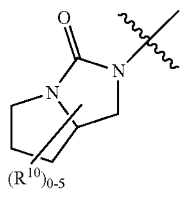

or

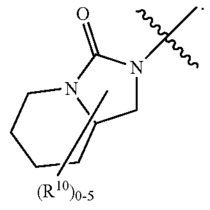

Also disclosed herein are compounds of Formula (II)

(II)

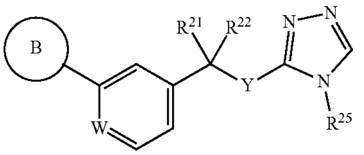

or a tautomer thereof, or a pharmaceutically acceptable salt thereof, wherein $R^{21}$ and $R^{22}$ are independently H, $C_1$-$C_6$ alkyl, halo, $C_1$-$C_6$ haloalkyl, or $C_3$-$C_6$ cycloalkyl, provided that $R^{21}$ and $R^{22}$ are not halo when Y is S or a bond;

or $R^{21}$ and $R^{22}$ are taken together with the carbon atom to which they are attached to form

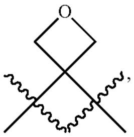, 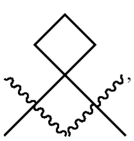, or

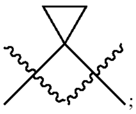;

Y is $CR^{23}R^{24}$, S, or a bond;

$R^{23}$ and $R^{24}$ are independently H, halo, $C_1$-$C_6$ alkyl, or $C_1$-$C_6$ haloalkyl;

or $R^{21}$ and $R^{23}$ are taken together with the carbon atoms to which they are attached to form the moiety;

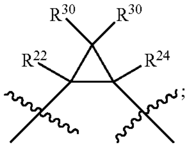;

$R^{25}$ is $C_1$-$C_6$ alkyl, $C_1$-$C_6$ haloalkyl, or $C_3$-$C_6$ cycloalkyl;

W is CH or N;

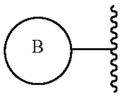

is selected from the group consisting of

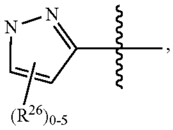, 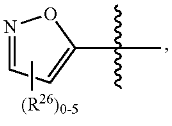,

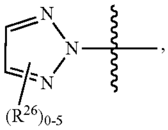, 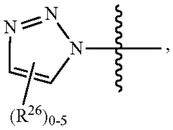,

-continued

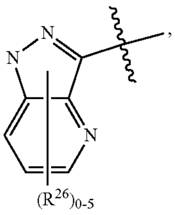, and 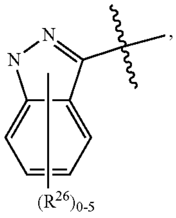, wherein the nitrogen atoms, where necessary to complete the valency, are bound to H when not substituted by $R^{26}$;

each $R^{26}$ is independently ($C_1$-$C_6$ alkyl, $C_1$-$C_6$ haloalkyl, $C_1$-$C_6$ alkyl-OH, $C_1$-$C_6$ alkyl-CN, —$(CR^{28}R^{29})_p$-(4- to 6-membered heterocyclyl), —$(CR^{28}R^{29})_p$-(5- to 6-membered heteroaryl), —$(CR^{28}R^{29})_p$—($C_6$-$C_{10}$ aryl), or —$(CR^{28}R^{29})_p$—($C_3$-$C_6$ cycloalkyl), wherein each cycloalkyl, heterocyclyl, heteroaryl, or aryl group is optionally substituted by 1-5 $R^{27}$ groups;

each $R^{27}$ is independently $C_1$-$C_6$ alkyl, $C_1$-$C_6$ alkyl-OH, $C_1$-$C_6$ haloalkyl, $C_1$-$C_6$ alkyl-CN, —CN, halo, hydroxy, —O—($C_1$-$C_6$ alkyl), —O($C_1$-$C_6$ haloalkyl), oxo, —C(O)$NH_2$, —C(O)NH($C_1$-$C_6$ alkyl), —C(O)N($C_1$-$C_6$ alkyl)$_2$, —C(O)NH($C_1$-$C_6$ haloalkyl), —$CO_2$H, —C(O)O($C_1$-$C_6$ alkyl), —$SO_2$—($C_1$-$C_6$ alkyl), —$SO_2$—NH($C_1$-$C_6$ alkyl), —$SO_2$—N($C_1$-$C_6$ alkyl)$_2$, —C(O)($C_1$-$C_6$ alkyl), —($C_1$-$C_6$ alkylene)-C(O)N($C_1$-$C_6$ alkyl)$_2$, or —($C_1$-$C_6$ alkylene)-C(O)NH($C_1$-$C_6$ alkyl);

p is 0 or 1;

$R^{28}$ and $R^{29}$ are independently H, $C_1$-$C_6$ alkyl, or $C_1$-$C_6$ haloalkyl; and each $R^{30}$ is independently H, $C_1$-$C_3$ alkyl, $C_1$-$C_3$ haloalkyl, or $C_1$-$C_3$ alkyl-OH.

In some embodiments, $R^{21}$ and $R^{22}$ are independently H, $C_1$-$C_3$ alkyl, halo, $C_1$-$C_3$ haloalkyl, or $C_3$-$C_5$ cycloalkyl. In some embodiments, $R^{21}$ and $R^{22}$ are independently H, —$CH_3$, F, —$CF_3$, or cyclobutyl. In some embodiments, $R^{21}$ and $R^{22}$ are taken together with the carbon atom to which they are attached to form

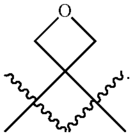.

In some embodiments, Y is S. In some embodiments, Y is $CR^{23}R^{24}$. In some embodiments, Y is a bond.

In some embodiments, $R^{23}$ and $R^{24}$ are independently H, halo, $C_1$-$C_3$ alkyl, or $C_1$-$C_3$ haloalkyl. In some embodiments, $R^{23}$ and $R^{24}$ are independently H, F, —$CH_3$, or —$CF_3$.

In some embodiments, $R^{21}$ and $R^{23}$ are taken together with the carbon atoms to which they are attached to form the moiety

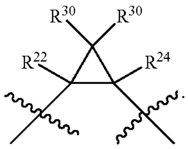.

In some embodiments, $R^{22}$ is H, $C_1$-$C_3$ alkyl, halo, or $C_1$-$C_3$ haloalkyl; $R^{24}$ is H, $C_1$-$C_3$ alkyl, halo, or $C_1$-$C_3$ haloalkyl; and each $R^{30}$ is independently H, $C_1$-$C_2$ alkyl, $C_1$-$C_2$ haloalkyl, or $C_1$-$C_2$ alkyl-OH. In some embodiments, $R^{22}$ is H, —$CH_3$, F, or —$CF_3$; $R^{24}$ is H, —$CH_3$, F, or —$CF_3$; and each $R^{30}$ is independently H, —$CH_3$, —$CF_3$, or —$CH_2OH$. In some embodiments, $R^{22}$ and $R^{24}$ are each H; and each $R^{30}$ is H.

In some embodiments, $R^{25}$ is $C_1$-$C_3$ alkyl, $C_1$-$C_3$ haloalkyl, or $C_3$-$C_4$ cycloalkyl. In some embodiments, $R^{25}$ is —$CH_3$, —$CF_3$, or cyclopropyl.

In some embodiments, W is CH. In some embodiments, W is N.

In some embodiments, each $R^{26}$, where present, is independently $C_1$-$C_3$ alkyl, $C_1$-$C_3$ haloalkyl, $C_1$-$C_3$ alkyl-OH, $C_1$-$C_3$ alkyl-CN, —$(CR^{28}R^{29})_p$-(4- to 6-membered heterocyclyl), —$(CR^{28}R^{29})_p$-(5- to 6-membered heteroaryl), —$(CR^{28}R^{29})_p$—($C_6$-$C_{10}$ aryl), or —$(CR^{28}R^{29})_p$—($C_3$-$C_6$ cycloalkyl), wherein each heterocyclyl, heteroaryl, aryl, or cycloalkyl group is optionally substituted by 1-5 $R^{27}$ groups. In some embodiments, p is 0. In some embodiments, p is 1. In some embodiments, $R^{28}$ and $R^{29}$ are independently H, $C_1$-$C_3$ alkyl, or $C_1$-$C_3$ haloalkyl. In some embodiments, $R^{28}$ and $R^{29}$ are independently H, —$CH_3$, or —$CF_3$. In some embodiments, each $R^{26}$ is independently —$CH_3$, —$CF_3$, —$CH_2OH$, —$CH_2CN$,

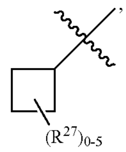,
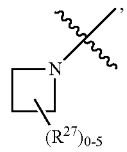,
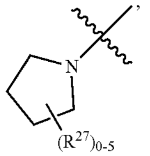,
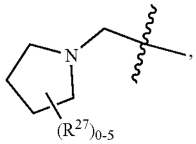,
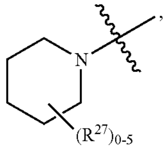,
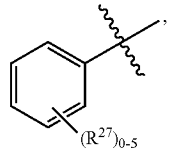,
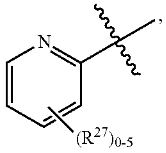, or
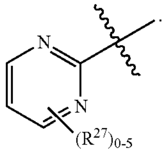.

In some embodiments, each $R^{27}$, where present, is independently $C_1$-$C_3$ alkyl, $C_1$-$C_3$ alkyl-OH, $C_1$-$C_3$ haloalkyl, $C_1$-$C_3$ alkyl-CN, —CN, halo, hydroxy, —O—($C_1$-$C_3$ alkyl), —O($C_1$-$C_3$ haloalkyl), oxo, —C(O)$NH_2$, —C(O)NH($C_1$-$C_3$ alkyl), —C(O)NH($C_1$-$C_3$ haloalkyl), —C(O)N($C_1$-$C_3$ alkyl)$_2$, —$CO_2H$, —C(O)O($C_1$-$C_3$ alkyl), —$SO_2$—($C_1$-$C_3$ alkyl), —$SO_2$—NH($C_1$-$C_3$ alkyl), —$SO_2$—N($C_1$-$C_3$ alkyl)$_2$, —C(O)($C_1$-$C_3$ alkyl), —($C_1$-$C_3$ alkylene)-C(O)N($C_1$-$C_3$ alkyl)$_2$, or —($C_1$-$C_3$ alkylene)-C(O)NH($C_1$-$C_3$ alkyl). In some embodiments, each $R^{27}$ is independently —$CH_3$, —$CH_2OH$, —$CF_3$, —$CH_2CN$, —CN, F, Cl, hydroxy, —$OCH_3$, —$OCF_3$, oxo, —C(O)$NH_2$, —C(O)NH($CH_3$), —C(O)NH($CF_3$), —C(O)N($CH_3$)$_2$, —$CO_2H$, —C(O)$OCH_3$, —$SO_2$—($CH_3$), —$SO_2$—NH($CH_3$), —$SO_2$—N($CH_3$)$_2$, —C(O)($CH_3$), —($CH_2$)—C(O)N($CH_3$)$_2$, or —($CH_2$)—C(O)NH($CH_3$).

Also disclosed herein is a compound selected from the compounds in Table 1, or a tautomer thereof, or a pharmaceutically acceptable salt thereof. Also disclosed herein is a compound selected from the compounds in Table 2, or a tautomer thereof, or a pharmaceutically acceptable salt thereof. Also disclosed herein is a compound selected from any compound disclosed above or herein, or a tautomer thereof, or a pharmaceutically acceptable salt thereof, and a pharmaceutically acceptable excipient.

Also disclosed herein is a method of modulating activity of an immune cell, the method comprising contacting the immune cell with an effective amount of any compound disclosed above or herein, or a tautomer thereof, or a pharmaceutically acceptable salt thereof.

Also disclosed herein is a method of treating a cancer responsive to inhibition of Cbl-b activity in an individual in need thereof, the method comprising administering an effective amount of any compound disclosed above or herein, or a tautomer thereof, or a pharmaceutically acceptable salt thereof, to the individual.

Also disclosed herein is a method of inhibiting Cbl-b activity in an individual in need thereof, the method comprising administering an effective amount of any compound disclosed above or herein, or a tautomer thereof, or a pharmaceutically acceptable salt thereof, to the individual.

Also disclosed herein is a method for treating or preventing a disease or condition associated with Cbl-b activity in an individual in need thereof, the method comprising administering any compound disclosed above or herein, or a tautomer thereof, or a pharmaceutically acceptable salt thereof, to the individual.

Also disclosed herein is a method of producing a modified immune cell, the method comprising culturing a cell population containing an immune cell in the presence of an effective amount of any compound disclosed above or herein, or a tautomer thereof, or a pharmaceutically acceptable salt thereof.

Also disclosed herein is a modified immune cell comprising a Cbl-b inhibitor, wherein the Cbl-b inhibitor is any compound disclosed above or herein, or a tautomer thereof, or a pharmaceutically acceptable salt thereof.

Also disclosed herein is an isolated modified immune cell, wherein the immune cell has been contacted or is in contact with any compound disclosed above or herein, or a tautomer thereof, or a pharmaceutically acceptable salt thereof.

Also disclosed herein is a composition comprising a cell population containing an isolated modified immune cell, wherein the immune cell has been contacted or is in contact with any compound disclosed above or herein, or a tautomer thereof, or a pharmaceutically acceptable salt thereof.

Also disclosed herein is a method of inhibiting abnormal cell proliferation, the method comprising administering an effective amount of an isolated modified immune cell, wherein the immune cell has been contacted or is in contact with any compound disclosed above or herein, or a tautomer thereof, or a pharmaceutically acceptable salt thereof, to an individual in need thereof.

Also disclosed herein is a method of inhibiting abnormal cell proliferation, the method comprising administering a composition comprising a cell population containing an isolated modified immune cell, wherein the immune cell has been contacted or is in contact with any compound disclosed above or herein, or a tautomer thereof, or a pharmaceutically acceptable salt thereof, to an individual in need thereof.

Also disclosed herein is a method of inhibiting abnormal cell proliferation, the method comprising administering an effective amount of any compound disclosed above or herein, or a tautomer thereof, or a pharmaceutically acceptable salt thereof.

Also disclosed herein is a cell culture composition comprising a cell population containing an immune cell and a Cbl-b inhibitor, wherein the Cbl-b inhibitor is any compound disclosed above or herein, or a tautomer thereof, or a pharmaceutically acceptable salt thereof.

Also disclosed herein is a pharmaceutical composition comprising a Cbl-b inhibitor and one or both of an adjuvant and an antigen, wherein the Cbl-b inhibitor is any compound disclosed above or herein, or a tautomer thereof, or a pharmaceutically acceptable salt thereof.

Also disclosed herein is an article of manufacture comprising any modified immune cell as disclosed herein, any composition comprising a cell population as disclosed herein, any cell culture composition as disclosed herein, or any pharmaceutical composition as disclosed herein.

Also disclosed herein is a kit comprising any modified immune cell as disclosed herein or any composition comprising a cell population as disclosed herein.

Also disclosed herein is the use of a Cbl-b inhibitor in the manufacture of a medicament for treating or preventing a disease or condition associated with Cbl-b activity, wherein the Cbl-b inhibitor is any compound disclosed above or herein, or a tautomer thereof, or a pharmaceutically acceptable salt thereof.

In any of the embodiments disclosed herein, the Cbl-b protein can be a mammalian Cbl-b, or a human Cbl-b.

DETAILED DESCRIPTION

Provided herein are compounds and pharmaceutical compositions that inhibit the Cbl-b enzyme, as well as methods of treatment using such compounds and pharmaceutical compositions. The compounds and compositions can be used in methods of modulating the immune system, for treatment of diseases, and for treatment of cells in vivo, in vitro, or ex vivo.

T-cell activation and T-cell tolerance are tightly controlled processes regulating the immune response to tumors while preventing autoimmunity. Tolerance prevents the immune system from attacking cells expressing "self" antigens. During peripheral tolerance, T-cells that recognize "self" antigens (i.e., self-reactive T-cells) become functionally unresponsive or are deleted after encountering "self" antigens outside of the thymus. Peripheral tolerance processes therefore are important for preventing autoimmune diseases. Normally, cancer cells are removed by activated T-cells that recognize tumor antigens expressed on the surface of the cancer cells. However, in cancer, the tumor microenvironment can support T-cell tolerance to cancer cells, which allows cancer cells to avoid recognition and removal by the immune system. The ability of cancer cells to avoid tumor immunosurveillance can contribute to uncontrolled tumor growth. Therefore, T-cell tolerance can be a form of T-cell dysfunction. General principles of T-cell dysfunction are well known in the art (see Schietinger et al., Trends Immunol., 35: 51-60, 2014). Additional types of T-cell dysfunction that can contribute to uncontrolled tumor growth include T-cell exhaustion, T-cell senescence, and/or T-cell anergy. Therefore, treating T-cell dysfunction, for example, by increasing T-cell activation, increasing T-cell proliferation, decreasing T-cell tolerance, and/or decreasing T-cell exhaustion, is beneficial for preventing or treating cancer. Additional cells of the immune system are important for recognition and removal of cancer cells during immune surveillance. For example, Natural Killer (NK)-cells are lymphocytes of the innate immune system that are able to identify and kill cancer cells (see Martinez-Losato et al., Clin Cancer Res., 21: 5048-5056, 2015). Recent studies have also shown that B-cell subsets with distinct phenotypes and functions exhibit diverse roles in the anti-tumor response (see Saravaria et al., Cell Mol Immunol., 14: 662-674, 2017). Due to their role in tumor surveillance, NK-cells and B-cells may also be amenable as therapeutic targets for the prevention or treatment of cancer.

Cbl-b is a RING-type E3 ligase that plays an important role in the immune system due to its function as a negative regulator of immune activation. Cbl-b has an essential role in decreasing the activation of T-cells, thereby enhancing T-cell tolerance. Studies have found that Cbl-b-deficient T-cells display lower thresholds for activation by antigen recognition receptors and co-stimulatory molecules (e.g., CD28). For example, loss of Cbl-b in T-cells uncouples the requirement for CD28 costimulation during T-cell activation and proliferation (see Bachmaier et al., Nature, 403: 211-216, 2000). Such cbl-b−/− T-cells are largely resistant to T-cell anergy, a tolerance mechanism in which T-cells are functionally inactivated and T-cell proliferation is greatly impaired (see Jeon et al., Immunity, 21: 167-177, 2004; and Schwartz et al., Annu Rev Immunol., 21: 305-34, 2003). In support of this, loss of Cbl-b in cbl-b knockout mice resulted in impaired induction of T-cell tolerance and exacerbated autoimmunity (see Jeon et al., Immunity, 21: 167-177, 2004). Importantly, loss of Cbl-b in mice also resulted in a robust anti-tumor response that depends primarily on cytotoxic T-cells. One study showed that cbl-b−/− CD8+ T-cells are resistant to T regulatory cell-mediated suppression and exhibit enhanced activation and tumor infiltration. Therapeutic transfer of naive cbl-b−/− CD8+ T-cells was sufficient to mediate rejection of established tumors (see Loeser et al., J Exp Med., 204: 879-891, 2007). Recent studies have shown that Cbl-b also plays a role in NK-cell activation. Genetic deletion of Cbl-b or targeted inactivation of its E3 ligase activity allowed NK-cells to spontaneously reject metastatic tumors in a mouse model (see Paolino et al., Nature, 507: 508-512, 2014).

Provided herein are compounds and compositions that are potent inhibitors of Cbl-b and can be used in novel approaches to treat diseases such as cancer. In some embodiments, the compounds and compositions provided herein can be used in methods of modulating the immune system, such as increasing activation of T-cells, NK-cells and B-cells, as well as in the treatment of such cells in vivo, in vitro, or ex vivo.

I. Definitions

An "effective amount" of an agent disclosed herein is an amount sufficient to carry out a specifically stated purpose. An "effective amount" may be determined empirically and in a routine manner, in relation to the stated purpose. An "effective amount" or an "amount sufficient" of an agent is that amount adequate to produce a desired biological effect, such as a beneficial result, including a beneficial clinical result. In some embodiments, the term "effective amount" refers to an amount of an agent effective to "treat" a disease or disorder in an individual (e.g., a mammal such as a human).

The term "Cbl-b" as used herein refers to a Cbl-b protein. The term also includes naturally occurring variants of Cbl-b, including splice variants or allelic variants. The term also includes non-naturally occurring variants of Cbl-b, such as a recombinant Cbl-b protein or truncated variants thereof, which generally preserve the binding ability of naturally occurring Cbl-b or naturally occurring variants of Cbl-b (e.g., the ability to bind to an E2 enzyme).

The terms "pharmaceutical formulation" and "pharmaceutical composition" refer to preparations that are in such form as to permit the biological activity of the active ingredient to be effective, and that contain no additional components that are unacceptably toxic to an individual to which the formulation or composition would be administered. Such formulations or compositions may be sterile.

"Excipients" as used herein include pharmaceutically acceptable excipients, carriers, vehicles, or stabilizers that are nontoxic to the cell or mammal being exposed thereto at the dosages and concentrations employed. Often the physiologically acceptable excipient is an aqueous pH buffered solution.

Reference to a compound as described in a pharmaceutical composition, or to a compound as described in a claim to a pharmaceutical composition, refers to the compound described by the formula recited in the pharmaceutical composition, without the other elements of the pharmaceutical composition, that is, without carriers, excipients, etc.

The terms "treating" or "treatment" of a disease refer to executing a protocol, which may include administering one or more therapeutic agent to an individual (human or otherwise), in an effort to obtain beneficial or desired results in the individual, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total). "Treatment" also can mean prolonging survival as compared to expected survival of an individual not receiving treatment. Further, "treating" and "treatment" may occur by administration of one dose of a therapeutic agent or therapeutic agents, or may occur upon administration of a series of doses of a therapeutic agent or therapeutic agents. "Treating" or "treatment" does not require complete alleviation of signs or symptoms, and does not require a cure. "Treatment" also can refer to clinical intervention, such as administering one or more therapeutic agents to an individual, designed to alter the natural course of the individual or cell being treated (i.e., to alter the course of the individual or cell that would occur in the absence of the clinical intervention). The term "therapeutic agent" can refer to a Cbl-b inhibitor, a modified immune cell, or compositions thereof.

As used herein, an "individual" or a "subject" is a mammal. A "mammal" for purposes of treatment includes humans; non-human primates; domestic and farm animals; and zoo, sports, or pet animals, such as dogs, horses, rabbits, cattle, pigs, hamsters, gerbils, mice, ferrets, rats, cats, etc. In some embodiments, the individual or subject is human.

As used herein, the term "T-cell dysfunction" refers to a state of reduced immune responsiveness to antigenic stimulation. The term "T-cell dysfunction" includes common elements of both T-cell exhaustion and/or T-cell anergy in which antigen recognition may occur, but the ensuing immune response is ineffective to control tumor growth. The term "T-cell dysfunction" also includes being refractory or unresponsive to antigen recognition, such as, impaired capacity to translate antigen recognition to downstream T-cell effector functions, such as proliferation, cytokine production, and/or target cell killing.

The term "T-cell anergy" refers to the state of unresponsiveness to antigen stimulation resulting from incomplete or insufficient signals delivered through the T-cell receptor. "T-cell anergy" can also result upon stimulation with antigen in the absence of co-stimulation, resulting in the cell becoming refractory to subsequent activation by the antigen even in the context of co-stimulation.

The term "T-cell exhaustion" refers to a state of T-cell dysfunction that arises from sustained TCR signaling that can occur during cancer. It is distinguished from anergy in that it arises not through incomplete or deficient signaling, but from sustained signaling. It is defined by poor effector function, sustained expression of inhibitory receptors, and a transcriptional state distinct from that of functional effector or memory T-cell.

A "T-cell dysfunction disorder" is a disorder or condition characterized by decreased responsiveness of T-cells to antigenic stimulation. Decreased responsiveness may result in ineffective control of a tumor. In some embodiments, the term "T-cell dysfunction disorder" encompasses cancer such as a hematologic cancer or a non-hematologic cancer. In some embodiments, a "T-cell dysfunctional disorder" is one in which T-cells are anergic or have decreased ability to secrete cytokines, proliferate, or execute cytolytic activity.

"Enhancing T-cell function" means to induce, cause, or stimulate a T-cell to have a sustained or amplified biological function, or renew or reactivate exhausted or inactive T-cells. Examples of enhanced T-cell function include increased T-cell activation (e.g., increased cytokine production, increased expression of T-cell activation markers, etc.), increased T-cell proliferation, decreased T-cell exhaustion, and/or decreased T-cell tolerance relative to the state of the T-cells before treatment with a Cbl-b inhibitor. Methods of measuring enhancement of T-cell function are known in the art.

"Proliferation" is used herein to refer to the proliferation of a cell. Increased proliferation encompasses the production of a greater number of cells relative to a baseline value. Decreased proliferation encompasses the production of a reduced number of cells relative to a baseline value. In some embodiments, the cell is an immune cell such as a T-cell and increased proliferation is desired. In some embodiments, the cell is a cancer cell and reduced proliferation is desired.

"Alkyl" as used herein refers to a saturated linear (i.e., unbranched) or branched univalent hydrocarbon chain or combination thereof. Particular alkyl groups are those having a designated number of carbon atoms, for example, an alkyl group having 1 to 20 carbon atoms (a "$C_1$-$C_{20}$ alkyl"), having 1 to 10 carbon atoms (a "$C_1$-$C_{10}$" alkyl), having 1 to 8 carbon atoms (a "$C_1$-$C_8$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e., unbranched) or branched univalent hydrocarbon chain or combination thereof, having at least one site of olefinic unsaturation (i.e., having at least one moiety of the formula C═C). Particular alkenyl groups are those having a designated number of carbon atoms, for example, an alkenyl group having 2 to 20 carbon atoms (a "$C_2$-$C_{20}$ alkenyl"), having 2 to 10 carbon atoms (a "$C_2$-$C_{10}$" alkenyl), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "C2-C4 alkenyl"). The alkenyl group may be in "cis" or "trans" configurations or, alternatively, in "E" or "Z" configurations. Examples of alkenyl groups include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear (i.e., unbranched) or branched univalent hydrocarbon chain or combination thereof, having at least one site of acetylenic unsaturation (i.e., having at least one moiety of the formula C≡C). Particular alkynyl groups are those having a designated number of carbon atoms, for example, an alkynyl group having 2 to 20 carbon atoms (a "$C_2$-$C_{20}$ alkynyl"), having 2 to 10 carbon atoms (a "$C_2$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl groups include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene"), or 1 to 3 carbon atoms (a "$C_1$-$C_3$ alkylene"). Examples of alkylene groups include, but are not limited to, groups such as methylene ($—CH_2—$), ethylene ($—CH_2CH_2—$), propylene ($—CH_2CH_2CH_2—$), butylene ($—CH_2CH_2CH_2CH_2—$), and the like.

"Cycloalkyl" as used herein refers to non-aromatic, saturated or unsaturated, cyclic univalent hydrocarbon structures. Particular cycloalkyl groups are those having a designated number of annular (i.e., ring) carbon atoms, for example, a cycloalkyl group having from 3 to 12 annular carbon atoms (a "$C_3$-$C_{12}$ cycloalkyl"). A particular cycloalkyl is a cyclic hydrocarbon having from 3 to 8 annular carbon atoms (a "$C_3$-$C_8$ cycloalkyl"), or having 3 to 6 annular carbon atoms (a "$C_3$-$C_6$ cycloalkyl"). Cycloalkyl can consist of one ring, such as cyclohexyl, or multiple rings, such as adamantyl, but excludes aryl (i.e., aromatic) groups. A cycloalkyl comprising more than one ring may be fused, spiro, or bridged, or combinations thereof. Examples of cycloalkyl groups include, but are not limited to, cyclopropyl

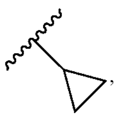 [SMILES: *C1CC1], cyclobutyl,

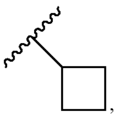, cyclopentyl

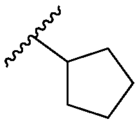, cyclohexyl,

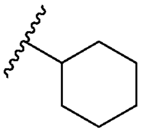, 1-cyclohexenyl, 3-cyclohexenyl, cycloheptyl

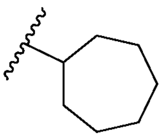, norbornyl, and the like.

"Cycloalkylene" as used herein refers to the same residues as cycloalkyl, but having bivalency. Particular cycloalkylene groups are those having 3 to 12 annular carbon atoms (a "$C_3$-$C_{12}$ cycloalkylene"), having from 3 to 8 annular carbon atoms (a "$C_3$-$C_8$ cycloalkylene"), or having 3 to 6 annular carbon atoms (a "$C_3$-$C_6$ cycloalkylene"). Examples of cycloalkylene groups include, but are not limited to, cyclopropylene

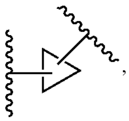, cyclobutylene

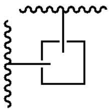, cyclopentylene

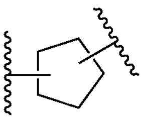, cyclohexylene,

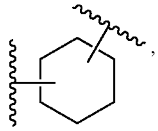

1,2-cyclohexenylene, 1,3-cyclohexenylene, 1,4-cyclohexenylene, cycloheptylene

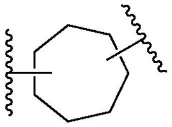

norbornylene, and the like.

"Aryl" as used herein refers to an aromatic carbocyclic group having a single ring (e.g., phenyl), or multiple condensed rings (e.g., naphthyl or anthryl) where one or more of the condensed rings may not be aromatic. Particular aryl groups are those having from 6 to 14 annular (i.e., ring) carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position. Examples of aryls include, but are not limited to, groups such as phenyl, naphthyl, 1-naphthyl, 2-naphthyl, 1,2,3,4-tetrahydronaphthalen-6-yl

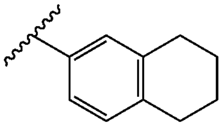

and the like.

"Carbocyclyl" or "carbocyclic" refers to an aromatic or non-aromatic univalent cyclic group in which all of the ring members are carbon atoms, such as cyclohexyl, phenyl, 1,2-dihydronaphthyl, etc.

"Arylene" as used herein refers to the same residues as aryl, but having bivalency. Particular arylene groups are those having from 6 to 14 annular carbon atoms (a "$C_6$-$C_{14}$ arylene"). Examples of arylene include, but are not limited to, groups such as phenylene, o-phenylene (i.e., 1,2-phenylene), m-phenylene (i.e., 1,3-phenylene), p-phenylene (i.e., 1,4-phenylene), naphthylene, 1,2-naphthylene, 1,3-naphthylene, 1,4-naphthylene, 2,7-naphthylene, 2,6-naphthylene, and the like.

"Heteroaryl" as used herein refers to an unsaturated aromatic cyclic group having from 1 to 14 annular carbon atoms and at least one annular heteroatom, including, but not limited to, heteroatoms such as nitrogen (N), oxygen (O), and sulfur (S). A heteroaryl group may have a single ring (e.g., pyridyl or imidazolyl) or multiple condensed rings (e.g., indolizinyl, indolyl, or quinolinyl) where at least one of the condensed rings is aromatic. Particular heteroaryl groups are 5- to 14-membered rings having 1 to 12 annular carbon atoms and 1 to 6 annular heteroatoms independently selected from the group consisting of nitrogen, oxygen, and sulfur (a "5- to 14-membered heteroaryl"); 5- to 10-membered rings having 1 to 8 annular carbon atoms and 1 to 4 annular heteroatoms independently selected from the group consisting of nitrogen, oxygen, and sulfur (a "5- to 10-membered heteroaryl"); or 5-, 6-, or 7-membered rings having 1 to 5 annular carbon atoms and 1 to 4 annular heteroatoms independently selected from the group consisting of nitrogen, oxygen, and sulfur (a "5- to 7-membered heteroaryl"). In one variation, heteroaryl includes monocyclic aromatic 5-, 6-, or 7-membered rings having from 1 to 6 annular carbon atoms and 1 to 4 annular heteroatoms independently selected from the group consisting of nitrogen (N), oxygen (O), and sulfur (S). In another variation, heteroaryl includes polycyclic aromatic rings having from 1 to 12 annular carbon atoms and 1 to 6 annular heteroatoms independently selected from the group consisting of nitrogen, oxygen, and sulfur. A heteroaryl group having more than one ring where at least one ring is non-aromatic may be connected to the parent structure at either an aromatic ring position or at a non-aromatic ring position. Examples of heteroaryl include, but are not limited to, groups such as pyridyl, benzimidazolyl, benzotriazolyl, benzo[b]thienyl, quinolinyl, indolyl, benzothiazolyl, and the like. "Heteroaryl" also includes moieties such as

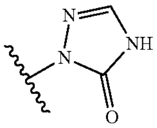 [SMILES: *n1nc[nH]c1=O]

(2,4-dihydro-3H-1,2,4-triazol-3-one-2-yl), which has the aromatic tautomeric structure

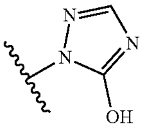 [SMILES: *n1ncnc1O]

(1H-1,2,4-triazol-5-ol-1-yl).

"Heterocyclyl" and "heterocyclic groups" as used herein refer to non-aromatic saturated or partially unsaturated cyclic groups having the number of atoms and heteroatoms as specified, or if no number of atoms or heteroatoms is specified, having at least three annular atoms, from 1 to 14 annular carbon atoms, and at least one annular heteroatom, including, but not limited to, heteroatoms such as nitrogen, oxygen, and sulfur. A heterocyclic group may have a single ring (e.g., tetrahydrothiophenyl, oxazolidinyl) or multiple condensed rings (e.g., decahydroquinolinyl, octahydrobenzo[d]oxazolyl). Multiple condensed rings include, but are not limited to, bicyclic, tricyclic, and quadracylic rings, as well as bridged or spirocyclic ring systems. Examples of heterocyclic groups include, but are not limited to, aziridinyl, azetidinyl, pyrrolidinyl, piperidinyl, oxiranyl, oxetanyl, tetrahydrofuranyl, tetrahydropyranyl, oxazolidinyl, piperazinyl, morpholinyl, dioxanyl, 3,6-dihydro-2H-pyranyl, 2,3-dihydro-1H-imidazolyl, and the like.

"Heteroarylene" as used herein refers to the same residues as heteroaryl, but having bivalency. Particular heteroarylene groups are 5- to 14-membered rings having 1 to 12 annular carbon atoms and 1 to 6 annular heteroatoms independently selected from the group consisting of nitrogen, oxygen, and sulfur (a "5- to 14-membered heteroarylene"); 5- to 10-membered rings having 1 to 8 annular carbon atoms and 1 to 4 annular heteroatoms independently selected from the group consisting of nitrogen, oxygen, and sulfur (a "5- to 10-membered heteroarylene"); or 5-, 6-, or 7-membered rings having 1 to 5 annular carbon atoms and 1 to 4 annular heteroatoms independently selected from the group consisting of nitrogen, oxygen, and sulfur (a "5- to 7-membered heteroarylene"). Examples of heteroarylene include, but are not limited to, groups such as pyridylene, benzimidazolylene, benzotriazolylene, benzo[b]thienylene, quinolinylene, indolylene, benzothiazolylene, and the like.

"Halo" or "halogen" refers to elements of the Group 17 series having atomic number 9 to 85. Halo groups include fluoro (F), chloro (Cl), bromo (Br), and iodo (I).

"Haloalkyl," "haloalkylene," "haloaryl," "haloarylene," "haloheteroaryl," and similar terms refer to a moiety substituted with at least one halo group. Where a haloalkyl moiety or other halo-substituted moiety is substituted with more than one halogen, it may be referred to by using a prefix corresponding to the number of halogen moieties attached. For example, dihaloaryl, dihaloalkyl, trihaloaryl, trihaloalkyl, etc., refer to aryl and alkyl substituted with two ("di") or three ("tri") halo groups, which may be, but are not necessarily, the same halo; thus, for example, the haloaryl group 4-chloro-3-fluorophenyl is within the scope of dihaloaryl. The subset of haloalkyl groups in which each hydrogen (H) of an alkyl group is replaced with a halo group is referred to as a "perhaloalkyl." A particular perhaloalkyl group is trifluoroalkyl ($—CF_3$). Similarly, "perhaloalkoxy" refers to an alkoxy group in which a halogen takes the place of each hydrogen (H) in the hydrocarbon making up the alkyl moiety of the alkoxy group. An example of a perhaloalkoxy group is trifluoromethoxy ($—OCF_3$). "Haloalkyl" includes monohaloalkyl, dihaloalkyl, trihaloalkyl, perhaloalkyl, and any other number of halo substituents possible on an alkyl group; and similarly for other groups such as haloalkylene, haloaryl, haloarylene, haloheteroaryl, etc.

"Amino" refers to the group $—NH_2$.

"Oxo" refers to the group =O, that is, an oxygen atom doubly bonded to carbon or another chemical element.

"Optionally substituted," unless otherwise specified, means that a group is unsubstituted or substituted by one or more (e.g., 1, 2, 3, 4, or 5) of the substituents listed for that group, in which the substituents may be the same or different. In one embodiment, an optionally substituted group is unsubstituted. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, or 1 to 5 substituents. When multiple substituents are present, each substituent is independently chosen unless indicated otherwise. For example, each ($C_1$-$C_4$ alkyl) substituent on the group $—N(C_1$-$C_4$ alkyl)($C_1$-$C_4$ alkyl) can be selected independently from the other, so as to generate groups such as $—N(CH_3)(CH_2CH_3)$, etc.

In addition to the disclosure herein, the term "substituted," when used to modify a specified group or radical, can also mean that one or more hydrogen atoms (H) of the specified group or radical are each, independently of one another, replaced with the same or different substituent groups as defined herein. In some embodiments, a group that is substituted has 1, 2, 3, or 4 substituents, 1, 2, or 3 substituents, 1 or 2 substituents, or one substituent.

Substituents can be attached to any chemically possible location on the specified group or radical, unless indicated otherwise. Thus, in one embodiment, $—C_1$-$C_8$ alkyl-OH includes, for example, $—CH_2CH_2OH$, $—CH(OH)—CH_3$, $—CH_2C(OH)(CH_3)_2$, and the like. By way of further example, in one embodiment, $C_1$-$C_6$ alkyl-OH includes, for example, $—CH_2CH_2OH$, $—CH(OH)CH_3$, $—CH_2C(OH)(CH_3)_2$, and the like. By way of further example, in one embodiment, $C_1$-$C_6$ alkyl-CN includes, for example, $—CH_2CH_2CN$, $—CH(CN)CH_3$, $—CH_2C(CN)(CH_3)_2$, and the like.

Unless a specific isotope of an element is indicated in a formula, this disclosure includes all isotopologues of the compounds disclosed herein, such as, for example, deuterated derivatives of the compounds (where H can be $^2H$, i.e., deuterium (D)). Deuterated compounds may provide favorable changes in pharmacokinetic (ADME) properties. Isotopologues can have isotopic replacements at any or at all locations in a structure, or can have atoms present in natural abundance at any or all locations in a structure.

A "small molecule" as used herein refers to a compound of 1,000 daltons or less in molecular weight.

Hydrogen atoms can also be replaced with close bioisosteres, such as fluorine, provided that such replacements result in stable compounds.

This disclosure also includes any or all of the stereochemical forms, including any enantiomeric or diastereomeric forms of the compounds described herein, and cis/trans or E/Z isomers. Unless stereochemistry is explicitly indicated in a chemical structure or name, the structure or name is intended to embrace all possible stereoisomers of a compound depicted. In addition, where a specific stereochemical form is depicted, it is understood that all other stereochemical forms are also described and embraced by this disclosure, as well as the general non-stereospecific form and mixtures of the disclosed compounds in any ratio, including mixtures of two or more stereochemical forms of a disclosed compound in any ratio, such that racemic, non-racemic, enantioenriched and scalemic mixtures of a compound are embraced. Compositions comprising a disclosed compound also are intended, such as a composition of a substantially pure compound, including a specific stereochemical form thereof. Compositions comprising a mixture of disclosed compounds in any ratio also are embraced by this disclosure, including compositions comprising mixtures of two or more stereochemical forms of a disclosed compound in any ratio, such that racemic, non-racemic, enantioenriched, and scalemic mixtures of a compound are embraced by this disclosure. If stereochemistry is explicitly indicated for one portion or portions of a molecule, but not for another portion or portions of a molecule, the structure is intended to embrace all possible stereoisomers for the portion or portions where stereochemistry is not explicitly indicated.

This disclosure also embraces any and all tautomeric forms of the compounds described herein.

This disclosure is intended to embrace all salts of the compounds described herein, as well as methods of using such salts of the compounds. In one embodiment, the salts of the compounds comprise pharmaceutically acceptable salts. Pharmaceutically acceptable salts are those salts that can be administered as drugs or pharmaceuticals to humans and/or animals and that, upon administration, retain at least some of the biological activity of the free compound (i.e., neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, also can be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, also can be prepared. For lists of pharmaceutically acceptable salts, see, for example, P. H. Stahl and C. G. Wermuth (eds.) "Handbook of Pharmaceutical Salts, Properties, Selection and Use" Wiley-VCH, 2011 (ISBN: 978-3-90639-051-2). Several pharmaceutically acceptable salts are also disclosed in Berge, J. Pharm. Sci. 66:1 (1977).

As described in Biological Example 1A, a Cbl-b activity assay (Cbl-b inhibition assay) used to measure the $IC_{50}$ values for Cbl-b inhibition uses a mixture comprising candidate compound, Cbl-b (truncated, with an Avitag, and biotinylated), a fluorescently-labeled E2 enzyme UbcH5B labelled with ubiquitin conjugated to BODIPY-fluorescein (UbcH5B-Ub), streptavidin-terbium, and assay buffer. In one embodiment, the Cbl-b activity assay (Cbl-b inhibition assay) used to measure $IC_{50}$ for inhibition of Cbl-b uses the conditions described in Biological Example 1A with 12 nM Cbl-b. Inhibition of fluorescence energy transfer indicates Cbl-b activity. In another embodiment, the Cbl-b activity assay (Cbl-b inhibition assay) used to measure $IC_{50}$ for inhibition of Cbl-b uses the conditions described in Biological Example 1B, with candidate compound, 0.125 nM Cbl-b (truncated, with an avitag, and biotinylated), fluorescently labelled inhibitor probe, and assay buffer. Displacement of the inhibitor probe indicates Cbl-b activity.

It is appreciated that certain features disclosed herein, which are, for clarity, described in the context of separate embodiments, also may be provided in combination in a single embodiment. Conversely, various features disclosed herein, which are, for brevity, described in the context of a single embodiment, also may be provided separately or in any suitable subcombination. All combinations of the embodiments pertaining to the chemical groups represented by the variables are specifically embraced by this disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables also are specifically embraced by this disclosure and are disclosed herein just as if each and every such subcombination of chemical groups was individually and explicitly disclosed herein.

It is understood that aspects and embodiments described herein as "comprising" include "consisting of" and "consisting essentially of" embodiments.

As used herein and in the appended claims, the singular forms "a," "an," and "the" include plural referents unless otherwise indicated or clear from context. For example, "an" excipient includes one or more excipients.

Reference to "about" a value, encompasses from 90% to 110% of that value. For instance, about 50 billion cells refers to 45 to 55 billion cells, and includes 50 billion cells. For instance, a temperature of "about 100 degrees" refers to a temperature of about 90 degrees to about 110 degrees.

When numerical ranges of compounds are given, all compounds within those numerical limits designated "a" and "b" are included, unless expressly excluded. For example, reference to compounds 20-25 refers to compounds 20, 21, 22, 23, 24, and 25.

II. Compounds

In one aspect, provided is a compound of Formula (I):

(I)

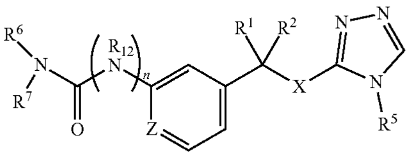

or a tautomer thereof, or a pharmaceutically acceptable salt thereof, wherein:

$R^1$ and $R^2$ are independently H, $C_1$-$C_6$ alkyl, halo, or $C_1$-$C_6$ haloalkyl, provided that when X is S, $R^1$ and $R^2$ are not both H, and provided that $R^1$ and $R^2$ are not halo when X is S or a bond;

or $R^1$ and $R^2$ are taken together with the carbon atom to which they are attached to form

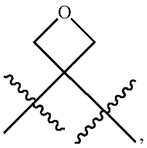, 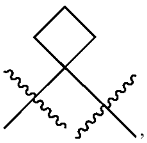, or 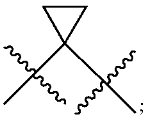;

X is $CR^3R^4$ or S;

$R^3$ and $R^4$ are independently H, $C_1$-$C_6$ alkyl, halo, or $C_1$-$C_6$ haloalkyl;

or $R^1$ and $R^3$ are taken together with the carbon atoms to which they are attached to form the moiety

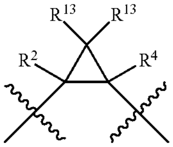;

$R^8$ is $C_1$-$C_6$ alkyl, $C_1$-$C_6$ haloalkyl, or $C_3$-$C_6$ cycloalkyl;

Z is CH or N;

n is 0 or 1;

$R^6$ is H, $C_1$-$C_6$ alkyl, or $C_1$-$C_6$ haloalkyl;

$R^7$ is $C_1$-$C_6$ alkyl-OH, —$(CR^8R^9)_m$-(5- to 10-membered monocyclic or fused bicyclic heteroaryl), —$(CR^8R^9)_m$-(4- to 10-membered monocyclic or fused bicyclic heterocyclyl), —$(CR^8R^9)_m$—($C_6$-$C_{10}$ aryl), or —$(CR^8R^9)_m$—($C_3$-$C_6$ cycloalkyl), wherein each heteroaryl, heterocyclyl, aryl, or cycloalkyl group is optionally substituted by 1-5 $R^{10}$ groups;

or $R^6$ and $R^7$ are taken together with the nitrogen atom to which they are attached to form a 5- to 10-membered monocyclic or fused bicyclic heteroaryl, or a 4- to 10-membered monocyclic or fused bicyclic heterocyclyl, each of which heteroaryl or heterocyclyl optionally contains 1-2 additional heteroatoms selected from the group consisting of N, S, and O, and each of which heteroaryl or heterocyclyl is optionally substituted by 1-5 $R^{10}$ groups;

m is zero or one;

$R^8$ and $R^9$ are independently H, $C_1$-$C_6$ alkyl, or $C_1$-$C_6$ haloalkyl;

each $R^{10}$ is independently $C_1$-$C_6$ alkyl, $C_1$-$C_6$ haloalkyl, $C_1$-$C_6$ alkyl-OH, —CN, $C_1$-$C_6$ alkyl-CN, —O($C_1$-$C_6$ alkyl), —O($C_1$-$C_6$ haloalkyl), halo, hydroxy, oxo, —$CO_2$H, —C(O)NH($C_1$-$C_6$ alkyl), —C(O)N($C_1$-$C_6$ alkyl)$_2$, —C(O)NH($C_1$-$C_6$ haloalkyl), —C(O)O($C_1$-$C_6$ alkyl), —$SO_2$—($C_1$-$C_6$ alkyl), —$SO_2$—NH($C_1$-$C_6$ alkyl), —$SO_2$—N($C_1$-$C_6$ alkyl)$_2$, —C(O)($C_1$-$C_6$ alkyl), —($C_1$-$C_6$ alkylene)-C(O)N($C_1$-$C_6$ alkyl)$_2$, —($C_1$-$C_6$ alkylene)-C(O)NH($C_1$-$C_6$ alkyl), $C_3$-$C_6$ cycloalkyl, 5- to 6-membered heterocyclyl, 5- to 6-membered heteroaryl, —($C_1$-$C_6$ alkylene)-(5- to 6-membered heterocyclyl), —($C_1$-$C_6$ alkylene)-(5- to 6-membered heteroaryl), —C(O)-(5- to 6-membered heterocyclyl), —C(O)-(5- to 6-membered heteroaryl), or $C_6$-$C_{10}$ aryl, wherein each cycloalkyl, heterocyclyl, heteroaryl, or aryl group is optionally substituted by 1-5 $R^{11}$ groups;

or two $R^{10}$ groups attached to the same carbon atom are taken together with the carbon atom to which they are attached to form a spiro $C_3$-$C_6$ cycloalkyl or a spiro 4- to 6-membered heterocyclyl, each of which is optionally substituted by 1-5 $R^{11}$ groups;

each $R^{11}$ is independently $C_1$-$C_6$ alkyl, hydroxy, oxo, or —C(O)($C_1$-$C_6$ alkyl);

$R^{12}$ is H, $C_1$-$C_6$ alkyl, or $C_1$-$C_6$ haloalkyl, or when $R^6$ and $R^7$ are taken together with the nitrogen atom to which they are attached to form a 4- to 10-membered monocyclic or fused bicyclic heterocyclyl optionally containing 1-2 additional heteroatoms selected from the group consisting of N, S, and O, $R^{12}$ is $C_1$-$C_6$ alkylene which connects to the 4- to 10-membered monocyclic or fused bicyclic heterocyclyl to form a 7- to 14-membered fused bicyclic or tricyclic heterocyclyl, each of which heterocyclyl is optionally substituted by 1-5 $R^{10}$ groups; and each $R^{13}$ is independently H, $C_1$-$C_3$ alkyl, $C_1$-$C_3$ alkyl-OH, or $C_1$-$C_3$ haloalkyl.

In some embodiments, Z is CH or N. In some embodiments, Z is CH. In other embodiments, Z is N.

In some embodiments, $R^1$ and $R^2$ are independently H, $C_1$-$C_6$ alkyl, halo, or $C_1$-$C_6$ haloalkyl, provided that when X is S, $R^1$ and $R^2$ are not both H, and provided that $R^1$ and $R^2$ are not halo when X is S or a bond (that is, when X is S or a bond, neither $R^1$ nor $R^2$ is halo). In some embodiments, $R^1$ and $R^2$ are independently H, $C_1$-$C_3$ alkyl, halo, or $C_1$-$C_3$ haloalkyl, provided that when X is S, $R^1$ and $R^2$ are not both H, and provided that $R^1$ and $R^2$ are not halo when X is S or a bond. In some embodiments, $R^1$ and $R^2$ are independently H, —$CH_3$, F, or —$CF_3$, provided that when X is S, $R^1$ and $R^2$ are not both H, and provided that $R^1$ and $R^2$ are not halo when X is S or a bond.

In some embodiments, $R^1$ is H.

In some embodiments, $R^1$ is $C_1$-$C_6$ alkyl. In some embodiments, $R^1$ is $C_1$-$C_3$ alkyl. In some embodiments, $R^1$ is methyl, ethyl, n-propyl, or isopropyl. In some embodiments, $R^1$ is —$CH_3$.

In some embodiments, $R^1$ is halo. In some embodiments, $R^1$ is chloro, fluoro, or bromo. In some embodiments, $R^1$ is chloro or fluoro. In some embodiments, $R^1$ is fluoro.

In some embodiments, $R^1$ is $C_1$-$C_6$ haloalkyl. In some embodiments, $R^1$ is $C_1$-$C_6$ haloalkyl containing 1-7 halogen atoms. In some embodiments, $R^1$ is $C_1$-$C_3$ haloalkyl. In some embodiments, $R^1$ is $C_1$-$C_3$ haloalkyl containing 1-7 halogen atoms. In some embodiments, $R^1$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^1$ is —$CF_3$, —$CCl_3$, —$CF_2Cl$, —$CFCl_2$, —$CHF_2$, —$CH_2F$, —$CHCl_2$, or —CHFCl. In some embodiments, $R^1$ is —$CF_3$.

In some embodiments, $R^2$ is H.

In some embodiments, $R^2$ is $C_1$-$C_6$ alkyl. In some embodiments, $R^2$ is $C_1$-$C_3$ alkyl. In some embodiments, $R^2$ is methyl, ethyl, n-propyl, or isopropyl. In some embodiments, $R^2$ is —$CH_3$.

In some embodiments, $R^2$ is halo. In some embodiments, $R^2$ is chloro, fluoro, or bromo. In some embodiments, $R^2$ is chloro or fluoro. In some embodiments, $R^2$ is fluoro.

In some embodiments, $R^2$ is $C_1$-$C_6$ haloalkyl. In some embodiments, $R^2$ is $C_1$-$C_6$ haloalkyl containing 1-7 halogen atoms. In some embodiments, $R^2$ is $C_1$-$C_3$ haloalkyl. In some embodiments, $R^2$ is $C_1$-$C_3$ haloalkyl containing 1-7 halogen atoms. In some embodiments, $R^2$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^2$ is —$CF_3$, —$CCl_3$, —$CF_2Cl$, —$CFCl_2$, —$CHF_2$, —$CH_2F$, —$CHCl_2$, or —CHFCl. In some embodiments, $R^2$ is —$CF_3$.

In some embodiments, $R^1$ is H and $R^2$ is $C_1$-$C_6$ alkyl. In some embodiments, $R^1$ is H and $R^2$ is $C_1$-$C_3$ alkyl. In some embodiments, $R^1$ is H and $R^2$ is methyl, ethyl, n-propyl, or isopropyl. In some embodiments, $R^1$ is H and $R^2$ is methyl. In some embodiments, $R^1$ and $R^2$ are each H when X is $CR^3R^4$. In some embodiments, $R^2$ is H and $R^1$ is $C_1$-$C_6$ alkyl. In some embodiments, $R^2$ is H and $R^1$ is $C_1$-$C_3$ alkyl. In some embodiments, $R^2$ is H and $R^1$ is methyl, ethyl, n-propyl, or isopropyl. In some embodiments, $R^2$ is H and $R^1$ is methyl.

In some embodiments, $R^1$ is halo, and $R^2$ is $C_1$-$C_6$ alkyl. In some embodiments, $R^1$ is halo (such as chloro, fluoro, or bromo), and $R^2$ is $C_1$-$C_3$ alkyl (such as methyl, ethyl, n-propyl, or isopropyl). In some embodiments, $R^1$ is fluoro and $R^2$ is methyl.

In some embodiments, $R^2$ is halo, and $R^1$ is $C_1$-$C_6$ alkyl. In some embodiments, $R^2$ is halo (such as chloro, fluoro, or bromo), and $R^1$ is $C_1$-$C_3$ alkyl (such as methyl, ethyl, n-propyl, or isopropyl). In some embodiments, $R^2$ is fluoro and $R^1$ is methyl.

In some embodiments, $R^1$ and $R^2$ are taken together with the carbon atom to which they are attached to form

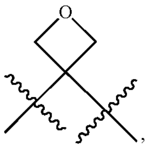, 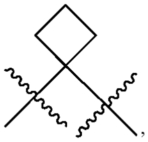, or 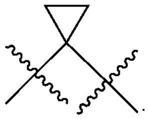.

In some embodiments, $R^1$ and $R^2$ are taken together with the carbon atom to which they are attached to form

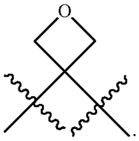 [SMILES: *C1(*)COC1].

In some embodiments, $R^1$ and $R^2$ are taken together with the carbon atom to which they are attached to form

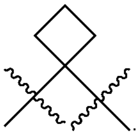 [SMILES: *C1(*)CCC1].

In some embodiments, $R^1$ and $R^2$ are taken together with the carbon atom to which they are attached to form

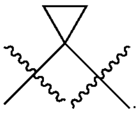 [SMILES: *C1(*)CC1].

In some embodiments, X is $CR^3R^4$ or S. In some embodiments, X is S. In other embodiments, X is $CR^3R^4$.

In some embodiments, $R^3$ and $R^4$ are independently H, $C_1$-$C_6$ alkyl, halo, or $C_1$-$C_6$ haloalkyl. In some embodiments, $R^3$ and $R^4$ are independently H, halo, $C_1$-$C_3$ alkyl, or $C_1$-$C_3$ haloalkyl. In some embodiments, $R^3$ and $R^4$ are independently H, F, $—CH_3$, or $—CF_3$.

In some embodiments, $R^3$ is H.

In some embodiments, $R^3$ is $C_1$-$C_6$ alkyl. In some embodiments, $R^3$ is $C_1$-$C_3$ alkyl. In some embodiments, $R^3$ is methyl, ethyl, n-propyl, or isopropyl. In some embodiments, $R^3$ is $—CH_3$.

In some embodiments, $R^3$ is halo. In some embodiments, $R^3$ is chloro, fluoro, or bromo. In some embodiments, $R^3$ is chloro or fluoro. In some embodiments, $R^3$ is fluoro.

In some embodiments, $R^3$ is $C_1$-$C_6$ haloalkyl. In some embodiments, $R^3$ is $C_1$-$C_6$ haloalkyl containing 1-7 halogen atoms. In some embodiments, $R^3$ is $C_1$-$C_3$ haloalkyl. In some embodiments, $R^3$ is $C_1$-$C_3$ haloalkyl containing 1-7 halogen atoms. In some embodiments, $R^3$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^3$ is $—CF_3$, $—CCl_3$, $—CF_2Cl$, $—CFCl_2$, $—CHF_2$, $—CH_2F$, $—CHCl_2$, or $—CHFCl$. In some embodiments, $R^3$ is $—CF_3$.

In some embodiments, $R^4$ is H.

In some embodiments, $R^4$ is $C_1$-$C_6$ alkyl. In some embodiments, $R^4$ is $C_1$-$C_3$ alkyl. In some embodiments, $R^4$ is methyl, ethyl, n-propyl, or isopropyl. In some embodiments, $R^4$ is $—CH_3$.

In some embodiments, $R^4$ is halo. In some embodiments, $R^4$ is chloro, fluoro, or bromo. In some embodiments, $R^4$ is chloro or fluoro. In some embodiments, $R^4$ is fluoro.

In some embodiments, $R^4$ is $C_1$-$C_6$ haloalkyl. In some embodiments, $R^4$ is $C_1$-$C_6$ haloalkyl containing 1-7 halogen atoms. In some embodiments, $R^4$ is $C_1$-$C_3$ haloalkyl. In some embodiments, $R^4$ is $C_1$-$C_3$ haloalkyl containing 1-7 halogen atoms. In some embodiments, $R^4$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^4$ is $—CF_3$, $—CCl_3$, $—CF_2Cl$, $—CFCl_2$, $—CHF_2$, $—CH_2F$, $—CHCl_2$, or $—CHFCl$. In some embodiments, $R^4$ is $—CF_3$.

In some embodiments, $R^3$ and $R^4$ are each H. In some embodiments, $R^3$ is H and $R^4$ is $C_1$-$C_6$ alkyl. In some embodiments, $R^3$ is H and $R^4$ is $C_1$-$C_3$ alkyl. In some embodiments, $R^3$ is H and $R^4$ is methyl. In some embodiments, $R^4$ is H and $R^3$ is $C_1$-$C_6$ alkyl. In some embodiments, $R^4$ is H and $R^3$ is $C_1$-$C_3$ alkyl. In some embodiments, $R^4$ is H and $R^3$ is methyl.

In some embodiments, $R^3$ and $R^4$ are each independently halo. In some embodiments, $R^3$ is fluoro, and $R^4$ is fluoro, chloro, or bromo. In some embodiments, $R^4$ is fluoro, and $R^3$ is fluoro, chloro, or bromo. In some embodiments, $R^3$ and $R^4$ are each fluoro.

In some embodiments, $R^1$ and $R^3$ are taken together with the carbon atoms to which they are attached to form the moiety

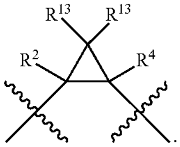.

In some embodiments, $R^2$ is H, $C_1$-$C_6$ alkyl, halo, or $C_1$-$C_6$ haloalkyl; $R^4$ is H, $C_1$-$C_6$ alkyl, halo, or $C_1$-$C_6$ haloalkyl; and each $R^3$ is independently H, $C_1$-$C_3$ alkyl, $C_1$-$C_3$ alkyl-OH, or $C_1$-$C_3$ haloalkyl. In some embodiments, $R^2$ is H, $C_1$-$C_3$ alkyl, halo, or $C_1$-$C_3$ haloalkyl; $R^4$ is H, $C_1$-$C_3$ alkyl, halo, or $C_1$-$C_3$ haloalkyl; and each $R^{13}$ is independently H, $C_1$-$C_2$ alkyl, $C_1$-$C_2$ alkyl-OH, or $C_1$-$C_2$ haloalkyl. In some embodiments, $R^2$ is H, $—CH_3$, F, or $—CF_3$; $R^4$ is H, $—CH_3$, F, or $—CF_3$; and each $R^{13}$ is independently H, $—CH_3$, $—CH_2OH$, or $—CF_3$. In some embodiments, $R^2$ and $R^4$ are each H; and each $R^{13}$ is H.

In some embodiments, $R^5$ is $C_1$-$C_6$ alkyl, $C_1$-$C_6$ haloalkyl, or $C_3$-$C_6$ cycloalkyl. In some embodiments, $R^5$ is $C_1$-$C_3$ alkyl, $C_1$-$C_3$ haloalkyl, or $C_3$-$C_4$ cycloalkyl. In some embodiments, $R^5$ is —$CH_3$, —$CHF_2$, or cyclopropyl.

In some embodiments, $R^5$ is $C_1$-$C_6$ alkyl. In some embodiments, $R^5$ is $C_1$-$C_3$ alkyl. In some embodiments, $R^5$ is methyl, ethyl, n-propyl, or isopropyl. In some embodiments, $R^5$ is —$CH_3$.

In some embodiments, $R^5$ is $C_1$-$C_6$ haloalkyl. In some embodiments, $R^5$ is $C_1$-$C_6$ haloalkyl containing 1-7 halogen atoms. In some embodiments, $R^5$ is $C_1$-$C_3$ haloalkyl. In some embodiments, $R^5$ is $C_1$-$C_3$ haloalkyl containing 1-7 halogen atoms. In some embodiments, $R^5$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^5$ is —$CF_3$, —$CCl_3$, —$CF_2Cl$, —$CFCl_2$, —$CHF_2$, —$CH_2F$, —$CHCl_2$, or —CHFCl. In some embodiments, $R^5$ is —$CHF_2$.

In some embodiments, $R^5$ is $C_3$-$C_6$ cycloalkyl. In some embodiments, $R^5$ is $C_3$-$C_5$ cycloalkyl. In some embodiments, $R^5$ is $C_3$-$C_4$ cycloalkyl. In some embodiments, $R^5$ is cyclopropyl, cyclobutyl, or cyclopentyl. In some embodiments, $R^5$ is cyclopropyl.

In some embodiments, n is zero. In other embodiments, n is one.

In some embodiments, $R^6$ is H, $C_1$-$C_6$ alkyl, or $C_1$-$C_6$ haloalkyl. In some embodiments, $R^6$ is H, $C_1$-$C_3$ alkyl, or $C_1$-$C_3$ haloalkyl. In some embodiments, $R^6$ is H or —$CH_3$.

In some embodiments, $R^6$ is H.

In some embodiments, $R^6$ is $C_1$-$C_6$ alkyl. In some embodiments, $R^6$ is $C_1$-$C_3$ alkyl. In some embodiments, $R^6$ is methyl, ethyl, n-propyl, or isopropyl. In some embodiments, $R^6$ is —$CH_3$.

In some embodiments, $R^6$ is $C_1$-$C_6$ haloalkyl. In some embodiments, $R^6$ is $C_1$-$C_6$ haloalkyl containing 1-7 halogen atoms. In some embodiments, $R^6$ is $C_1$-$C_3$ haloalkyl. In some embodiments, $R^6$ is $C_1$-$C_3$ haloalkyl containing 1-7 halogen atoms. In some embodiments, $R^6$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^6$ is —$CF_3$, —$CCl_3$, —$CF_2Cl$, —$CFCl_2$, —$CHF_2$, —$CH_2F$, —$CHCl_2$, —CHFCl, —$CH_2CF_3$, —$CH_2CCl_3$, —$CH_2CH_2F$, or —$CH_2CH_2Cl$.

In some embodiments, $R^7$ is $C_1$-$C_6$ alkyl-OH, —$(CR^8R^9)_m$-(5- to 10-membered monocyclic or fused bicyclic heteroaryl), —$(CR^8R^9)_m$-(4- to 10-membered monocyclic or fused bicyclic heterocyclyl), —$(CR^8R^9)_m$—($C_6$-$C_{10}$ aryl), or —$(CR^8R^9)_m$—($C_3$-$C_6$ cycloalkyl), wherein each heteroaryl, heterocyclyl, aryl, or cycloalkyl group is optionally substituted by 1-5 $R^{10}$ groups. In some embodiments, $R^7$ is $C_1$-$C_3$ alkyl-OH, —$(CR^8R^9)_m$-(5- to 6-membered monocyclic heteroaryl), —$(CR^8R^9)_m$-(8- to 10-membered fused bicyclic heteroaryl), —$(CR^8R^9)_m$-(4- to 6-membered monocyclic heterocyclyl), —$(CR^8R^9)_m$-(8- to 10-membered fused bicyclic heterocyclyl), —$(CR^8R^9)_m$—($C_6$-$C_{10}$ aryl), or —$(CR^8R^9)_m$—($C_3$-$C_6$ cycloalkyl), wherein each heteroaryl, heterocyclyl, aryl, or cycloalkyl group is optionally substituted by 1-5 $R^{10}$ groups.

In some embodiments, $R^7$ is $C_1$-$C_6$ alkyl-OH. In some embodiments, $R^7$ is linear $C_1$-$C_6$ alkyl-OH. In some embodiments, $R^7$ is branched $C_1$-$C_6$ alkyl-OH. In some embodiments, $R^7$ is $C_1$-$C_4$ alkyl-OH. In some embodiments, $R^7$ is $C_1$-$C_3$ alkyl-OH. In some embodiments, $R^7$ is —$CH_2OH$, —$CH_2CH_2OH$, —$CH_2CH_2CH_2OH$, or —$C(CH_3)_2OH$. In some embodiments, $R^7$ is —$CH(CH_3)CH_2OH$, —$C(CH_3)_2CH_2OH$, —$CH_2CH(CH_3)OH$, or —$CH_2C(CH_3)_2OH$. In some embodiments, $R^7$ is —$CH(CH_3)CH_2OH$.

In some embodiments, $R^7$ is —$(CR^8R^9)_m$-(5- to 10-membered monocyclic or fused bicyclic heteroaryl), wherein the heteroaryl is optionally substituted by 1-5 $R^{10}$ groups. In some embodiments, m is zero and $R^7$ is 5- to 10-membered monocyclic or fused bicyclic heteroaryl, wherein the heteroaryl is optionally substituted by 1-5 $R^{10}$ groups. In some embodiments, m is one and $R^7$ is —$CR^8R^9$-(5- to 10-membered monocyclic or fused bicyclic heteroaryl), wherein the heteroaryl is optionally substituted by 1-5 $R^{10}$ groups. In some embodiments, $R^7$ is —$(CR^8R^9)_m$-(5- to 6-membered monocyclic heteroaryl), wherein the heteroaryl is optionally substituted by 1-5 $R^{10}$ groups. In some embodiments, m is zero and $R^7$ is 5- to 6-membered monocyclic heteroaryl, wherein the heteroaryl is optionally substituted by 1-5 $R^{10}$ groups. In some embodiments, m is one and $R^7$ is —$CR^8R^9$-(5- to 6-membered monocyclic heteroaryl), wherein the heteroaryl is optionally substituted by 1-5 $R^{10}$ groups. In some embodiments, $R^7$ is —$(CR^8R^9)_m$-(8- to 10-membered fused bicyclic heteroaryl), wherein the heteroaryl is optionally substituted by 1-5 $R^{10}$ groups. In some embodiments, m is zero and $R^7$ is 8- to 10-membered fused bicyclic heteroaryl, wherein the heteroaryl is optionally substituted by 1-5 $R^{10}$ groups. In some embodiments, m is one and $R^7$ is —$CR^8R^9$-(8- to 10-membered fused bicyclic heteroaryl), wherein the heteroaryl is optionally substituted by 1-5 $R^{10}$ groups. In some embodiments, the fused bicyclic heteroaryl contains an unsaturated or partially saturated ring fused to an aromatic ring. In some embodiments, the fused bicyclic heteroaryl contains an aromatic ring fused to a second aromatic ring. In some embodiments, the heteroaryl contains 1-3 nitrogen atoms. In some embodiments, the heteroaryl contains one nitrogen atom. In some embodiments, the heteroaryl contains two nitrogen atoms. In some embodiments, the heteroaryl contains 1-2 nitrogen atoms and 1-2 sulfur atoms. In some embodiments, the heteroaryl contains two nitrogen atoms and one sulfur atom. In some embodiments, the heteroaryl contains 1-2 nitrogen atoms and 1-2 oxygen atoms. In some embodiments, the heteroaryl contains one nitrogen atom and one oxygen atom. In some embodiments, the heteroaryl is substituted by 1-5 $R^{10}$ groups. In some embodiments, the heteroaryl is substituted by one $R^{10}$ group. In some embodiments, the heteroaryl is substituted by two $R^{10}$ groups. In some embodiments, the heteroaryl is substituted by three $R^{10}$ groups. In some embodiments, the heteroaryl is substituted by four $R^{10}$ groups. In some embodiments, the heteroaryl is substituted by five $R^{10}$ groups. In some embodiments, the heteroaryl is unsubstituted. In some embodiments, the heteroaryl is pyridyl, imidazolyl, triazolyl, pyrrolyl, quinolinyl, isoquinolinyl, pyridazinyl, pyrazolyl, pyrimidinyl, pyrazinyl, or thiazolyl. In some embodiments, $R^7$ is

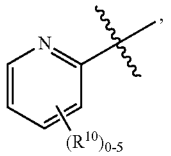,
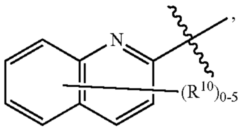,
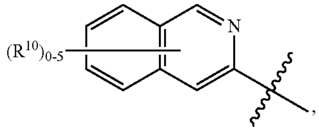,
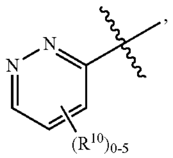,
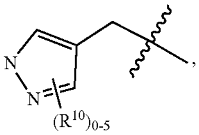, or
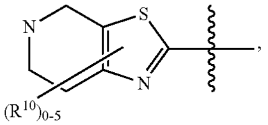, wherein —$(R^{10})_{0-5}$ represents optional substitution of either of the two rings which make up the fused bicyclic ring system, or any atom of the monocyclic ring system, and wherein the nitrogen atom is bound to H when not substituted by $R^{10}$ if needed to complete the valency of the nitrogen atom. In some embodiments, both rings of the fused bicyclic ring system are substituted. In some embodiments, one of the two rings of the fused bicyclic ring system is substituted and the other ring is unsubstituted. In some embodiments, both rings of the fused bicyclic ring system are unsubstituted.

In some embodiments, $R^7$ is —$(CR^8R^9)_m$-(4- to 10-membered monocyclic or fused bicyclic heterocyclyl), wherein the heterocyclyl is optionally substituted by 1-5 $R^{10}$ groups. In some embodiments, m is zero and $R^7$ is 4- to 10-membered monocyclic or fused bicyclic heterocyclyl, wherein the heterocyclyl is optionally substituted by 1-5 $R^{10}$ groups. In some embodiments, m is one and $R^7$ is —$CR^8R^9$-(4- to 10-membered monocyclic or fused bicyclic heterocyclyl), wherein the heterocyclyl is optionally substituted by 1-5 $R^{10}$ groups. In some embodiments, $R^7$ is —$(CR^8R^9)_m$-(4- to 6-membered monocyclic heterocyclyl), wherein the heterocyclyl is optionally substituted by 1-5 $R^{10}$ groups. In some embodiments, m is zero and $R^7$ is 4- to 6-membered monocyclic heterocyclyl, wherein the heterocyclyl is optionally substituted by 1-5 $R^{10}$ groups. In some embodiments, m is one and $R^7$ is —$CR^8R^9$-(4- to 6-membered monocyclic heterocyclyl), wherein the heterocyclyl is optionally substituted by 1-5 $R^{10}$ groups. In some embodiments, $R^7$ is —$(CR^8R^9)_m$-(8- to 10-membered fused bicyclic heterocyclyl), wherein the heterocyclyl is optionally substituted by 1-5 $R^{10}$ groups. In some embodiments, m is zero and $R^7$ is 8- to 10-membered fused bicyclic heterocyclyl, wherein the heterocyclyl is optionally substituted by 1-5 $R^{10}$ groups. In some embodiments, m is one and $R^7$ is —$CR^8R^9$-(8- to 10-membered fused bicyclic heterocyclyl), wherein the heterocyclyl is optionally substituted by 1-5 $R^{10}$ groups. In some embodiments, the heterocyclyl contains 1-3 nitrogen atoms. In some embodiments, the heterocyclyl contains one nitrogen atom. In some embodiments, the heterocyclyl contains two nitrogen atoms. In some embodiments, the heterocyclyl contains 1-2 nitrogen atoms and 1-2 sulfur atoms. In some embodiments, the heterocyclyl contains two nitrogen atoms and one sulfur atom. In some embodiments, the heterocyclyl contains 1-2 nitrogen atoms and 1-2 oxygen atoms. In some embodiments, the heterocyclyl contains one nitrogen atom and one oxygen atom. In some embodiments, the heterocyclyl contains one oxygen atom. In some embodiments, the heterocyclyl contains one sulfur atom. In some embodiments, the heterocyclyl is substituted by 1-5 $R^{10}$ groups. In some embodiments, the heterocyclyl is substituted by one $R^{10}$ group. In some embodiments, the heterocyclyl is substituted by two $R^{10}$ groups. In some embodiments, the heterocyclyl is substituted by three $R^{10}$ groups. In some embodiments, the heterocyclyl is substituted by four $R^{10}$ groups. In some embodiments, the heterocyclyl is substituted by five $R^{10}$ groups. In some embodiments, the heterocyclyl is unsubstituted. In some embodiments, the heterocyclyl is pyrrolidinyl, piperidinyl, or tetrahydrofuranyl. In some embodiments, $R^7$ is

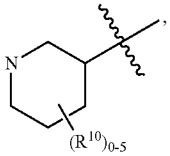, wherein the nitrogen atom is bound to H when not substituted by $R^{10}$.

In some embodiments, $R^7$ is —$(CR^8R^9)_m$—($C_6$-$C_{10}$ aryl), wherein the aryl is optionally substituted by 1-5 $R^{10}$ groups. In some embodiments, m is zero and $R^7$ is $C_6$-$C_{10}$ aryl, wherein the aryl is optionally substituted by 1-5 $R^{10}$ groups. In some embodiments, m is one and $R^7$ is —$CR^8R^9$—($C_6$-$C_{10}$ aryl), wherein the aryl is optionally substituted by 1-5 $R^{10}$ groups. In some embodiments, $R^7$ is —$(CR^8R^9)_m$—($C_6$ aryl), wherein the aryl is optionally substituted by 1-5 $R^{10}$ groups. In some embodiments, m is zero and $R^7$ is $C_6$-$C_{10}$ aryl, wherein the aryl is optionally substituted by 1-5 $R^{10}$ groups. In some embodiments, the aryl is a monocyclic aromatic ring. In some embodiments, the aryl is a fused bicyclic ring. In some embodiments, the aryl contains an aromatic ring fused to a second aromatic ring. In some embodiments, the aryl contains an aromatic ring fused to a saturated or partially unsaturated ring. In some embodiments, the aryl is substituted by 1-5 $R^{10}$ groups. In some embodiments, the aryl is substituted by one $R^{10}$ group. In some embodiments, the aryl is substituted by two $R^{10}$ groups. In some embodiments, the aryl is substituted by three $R^{10}$ groups. In some embodiments, the aryl is substituted by four $R^{10}$ groups. In some embodiments, the aryl is substituted by five $R^{10}$ groups. In some embodiments, the aryl is unsubstituted. In some embodiments, the aryl is phenyl. In some embodiments, $R^7$ is

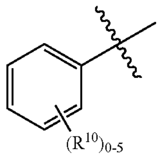 or 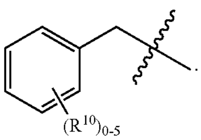.

In some embodiments, $R^7$ is —$(CR^8R^9)_m$—($C_3$-$C_6$ cycloalkyl), wherein the cycloalkyl is optionally substituted by 1-5 $R^{10}$ groups. In some embodiments, m is zero and $R^7$ is $C_3$-$C_6$ cycloalkyl, wherein the cycloalkyl is optionally substituted by 1-5 $R^{10}$ groups. In some embodiments, m is one and $R^7$ is —$CR^8R^9$—($C_3$-$C_6$ cycloalkyl), wherein the cycloalkyl is optionally substituted by 1-5 $R^{10}$ groups. In some embodiments, the cycloalkyl is substituted by 1-5 $R^{10}$ groups. In some embodiments, the cycloalkyl is substituted by one $R^{10}$ group. In some embodiments, the cycloalkyl is substituted by two $R^{10}$ groups. In some embodiments, the cycloalkyl is substituted by three $R^{10}$ groups. In some embodiments, the cycloalkyl is substituted by four $R^{10}$ groups. In some embodiments, the cycloalkyl is substituted by five $R^{10}$ groups. In some embodiments, the cycloalkyl is unsubstituted. In some embodiments, the cycloalkyl is cyclopropyl, cyclobutyl, cyclopentyl, or cyclohexyl. In some embodiments, the cycloalkyl is cyclobutyl or cyclohexyl. In some embodiments, $R^7$ is

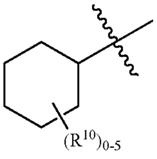

or

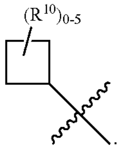

.

In some embodiments, $R^7$ is selected from the group consisting of

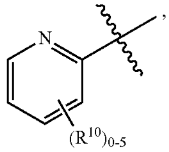

,

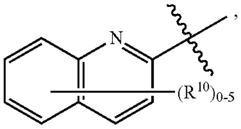

,

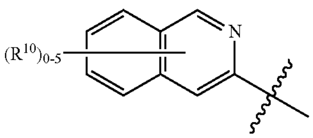

,

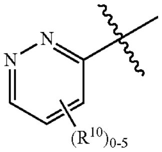

,

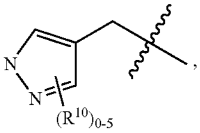

,

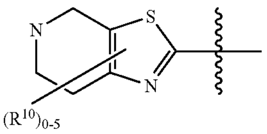

,

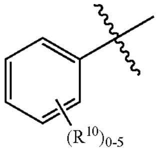

,

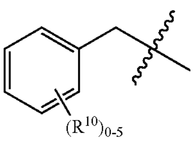

,

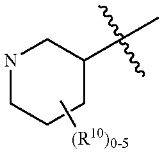

,

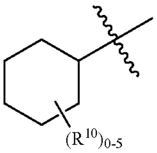

,

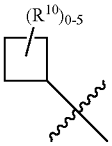

, and

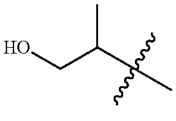

, wherein $—(R^{10})_{0-5}$ represents optional substitution of either of the two rings which make up the fused bicyclic ring system, or any atom of the monocyclic ring system, and wherein the nitrogen atom is bound to H when not substituted by $R^{10}$ if needed to complete the valency of the nitrogen atom. In some embodiments, both rings of the fused bicyclic ring system are substituted. In some embodiments, one of the two rings of the fused bicyclic ring system is substituted and the other ring is unsubstituted. In some embodiments, both rings of the fused bicyclic ring system are unsubstituted.

In some embodiments, $R^6$ and $R^7$ are taken together with the nitrogen atom to which they are attached to form a 5- to 10-membered monocyclic or fused bicyclic heteroaryl, or a 4- to 10-membered monocyclic or fused bicyclic heterocyclyl, each of which heteroaryl or heterocyclyl optionally contains 1-2 additional heteroatoms selected from the group consisting of N, S, and O, and each of which heteroaryl or heterocyclyl is optionally substituted by 1-5 $R^{10}$ groups. In some embodiments, $R^6$ and $R^7$ are taken together with the nitrogen atom to which they are attached to form a 5- to 6-membered monocyclic heteroaryl, 8- to 10-membered fused bicyclic heteroaryl, a 4- to 6-membered monocyclic heterocyclyl, or 8- to 10-membered fused bicyclic heterocyclyl, each of which heteroaryl or heterocyclyl optionally contains 1-2 additional heteroatoms selected from the group consisting of N, S, and O, and each of which heteroaryl or heterocyclyl is optionally substituted by 1-5 $R^{10}$ groups.

In some embodiments, $R^6$ and $R^7$ are taken together with the nitrogen atom to which they are attached to form a 5- to 10-membered monocyclic or fused bicyclic heteroaryl, wherein the heteroaryl optionally contains 1-2 additional heteroatoms selected from the group consisting of N, S, and O, and wherein the heteroaryl is optionally substituted by 1-5 $R^{10}$ groups. In some embodiments, $R^6$ and $R^7$ are taken together with the nitrogen atom to which they are attached to form a 5- to 6-membered monocyclic heteroaryl, wherein the heteroaryl optionally contains 1-2 additional heteroatoms selected from the group consisting of N, S, and O, and wherein the heteroaryl is optionally substituted by 1-5 $R^{10}$ groups. In some embodiments, $R^6$ and $R^7$ are taken together with the nitrogen atom to which they are attached to form a 8- to 10-membered fused bicyclic heteroaryl, wherein the heteroaryl optionally contains 1-2 additional heteroatoms selected from the group consisting of N, S, and O, and wherein the heteroaryl is optionally substituted by 1-5 $R^{10}$ groups. In some embodiments, the fused bicyclic heteroaryl contains a saturated or partially unsaturated ring fused to an aromatic ring. In some embodiments, the fused bicyclic heteroaryl contains an aromatic ring fused to a second aromatic ring. In some embodiments, the heteroaryl contains 1-2 additional heteroatoms selected from the group consisting of N, S, and O. In some embodiments, the heteroaryl contains one additional nitrogen atom. In some embodiments, the heteroaryl contains two additional nitrogen atoms. In some embodiments, the heteroaryl contains one additional nitrogen atom and one oxygen atom. In some embodiments, the heteroaryl contains one additional nitrogen atom and one sulfur atom. In some embodiments, the heteroaryl is substituted by 1-5 $R^{10}$ groups. In some embodiments, the heteroaryl is substituted by one $R^{10}$ group. In some embodiments, the heteroaryl is substituted by two $R^{10}$ groups. In some embodiments, the heteroaryl is substituted by three $R^{10}$ groups. In some embodiments, the heteroaryl is substituted by four $R^{10}$ groups. In some embodiments, the heteroaryl is substituted by five $R^{10}$ groups. In some embodiments, the heteroaryl is unsubstituted. In some embodiments, both rings of the fused bicyclic heteroaryl are substituted. In some embodiments, one of the rings of the fused bicyclic heteroaryl is substituted and the second ring is unsubstituted. In some embodiments, $R^6$ and $R^7$ are taken together with the nitrogen atom to which they are attached to form

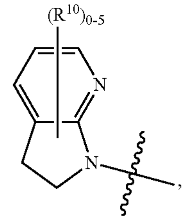,
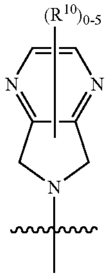,
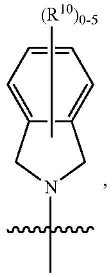,
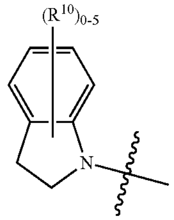,
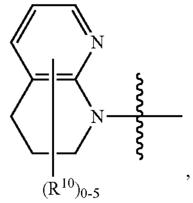,
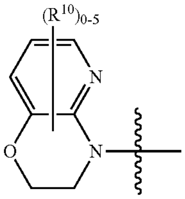,
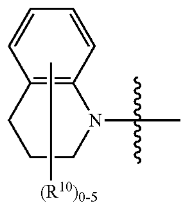,
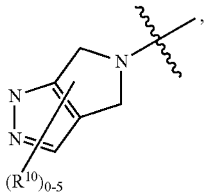,
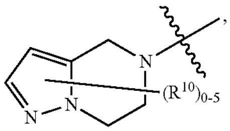, or
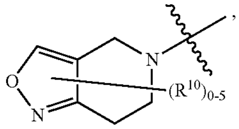, wherein —$(R^{10})_{0-5}$ represents optional substitution of either of the two rings which make up the fused bicyclic ring system, and wherein the nitrogen atom is bound to H when not substituted by $R^{10}$ if needed to complete the valency of the nitrogen atom. In some embodiments, both rings of the fused bicyclic ring system are substituted. In some embodiments, one of the two rings of the fused bicyclic ring system is substituted and the other ring is unsubstituted. In some embodiments, both rings of the fused bicyclic ring system are unsubstituted.

In some embodiments, $R^6$ and $R^7$ are taken together with the nitrogen atom to which they are attached to form a 4- to 10-membered monocyclic or fused bicyclic heterocyclyl, wherein the heterocyclyl optionally contains 1-2 additional heteroatoms selected from the group consisting of N, S, and O, and wherein the heterocyclyl is optionally substituted by 1-5 $R^{10}$ groups. In some embodiments, $R^6$ and $R^7$ are taken together with the nitrogen atom to which they are attached to form a 4- to 6-membered monocyclic heterocyclyl, wherein the heterocyclyl optionally contains 1-2 additional heteroatoms selected from the group consisting of N, S, and O, and wherein the heterocyclyl is optionally substituted by 1-5 $R^{10}$ groups. In some embodiments, $R^6$ and $R^7$ are taken together with the nitrogen atom to which they are attached to form a 8- to 10-membered fused bicyclic heterocyclyl, wherein the heterocyclyl optionally contains 1-2 additional heteroatoms selected from the group consisting of N, S, and O, and wherein the heterocyclyl is optionally substituted by 1-5 $R^{10}$ groups. In some embodiments, the heterocyclyl contains 1-2 additional heteroatoms selected from the group consisting of N, S, and O. In some embodiments, the heterocyclyl contains one additional nitrogen atom. In some embodiments, the heterocyclyl contains two additional nitrogen atoms. In some embodiments, the heterocyclyl contains one additional nitrogen atom and one oxygen atom. In some embodiments, the heterocyclyl contains one additional nitrogen atom and one sulfur atom. In some embodiments, the heterocyclyl is substituted by 1-5 $R^{10}$ groups. In some embodiments, the heterocyclyl is substituted by one $R^{10}$ group. In some embodiments, the heterocyclyl is substituted by two $R^{10}$ groups. In some embodiments, the heterocyclyl is substituted by three $R^{10}$ groups. In some embodiments, the heterocyclyl is substituted by four $R^{10}$ groups. In some embodiments, the heterocyclyl is substituted by five $R^{10}$ groups. In some embodiments, the heterocyclyl is unsubstituted. In some embodiments, both rings of the fused bicyclic heterocyclyl are substituted. In some embodiments, one of the rings of the fused bicyclic heterocyclyl is substituted and the second ring is unsubstituted. In some embodiments, $R^6$ and $R^7$ are taken together with the nitrogen atom to which they are attached to form

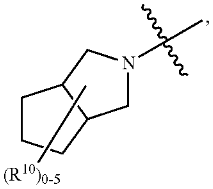,
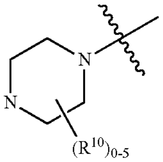,
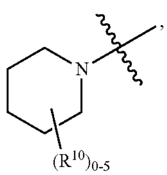,
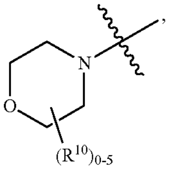,
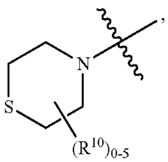,
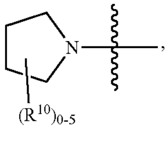, or
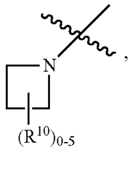, wherein —$(R^{10})_{0-5}$ represents optional substitution of either of the two rings which make up the fused bicyclic ring system, or any atom of the monocyclic ring system, and wherein the nitrogen atom is bound to H when not substituted by $R^{10}$ if needed to complete the valency of the nitrogen atom. In some embodiments, both rings of the fused bicyclic ring system are substituted. In some embodiments, one of the two rings of the fused bicyclic ring system is substituted and the other ring is unsubstituted. In some embodiments, both rings of the fused bicyclic ring system are unsubstituted.

In some embodiments, $R^6$ and $R^7$ are taken together with the nitrogen atom to which they are attached to

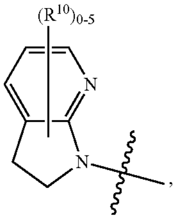,
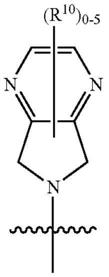,
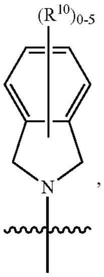,
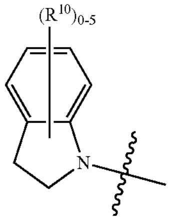,
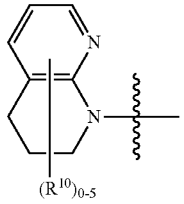,
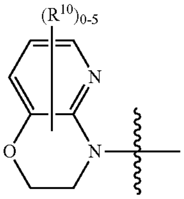,
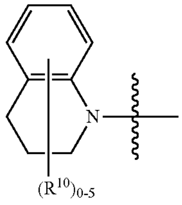,
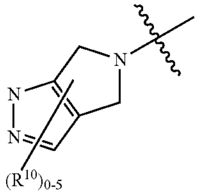,
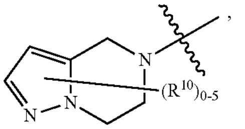,
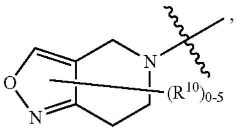,
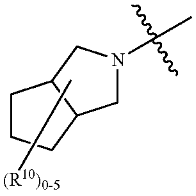,
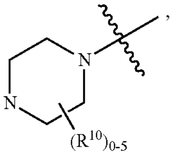,
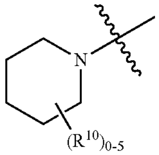,
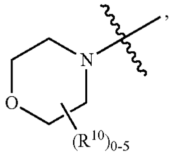,
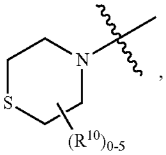,
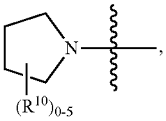, or
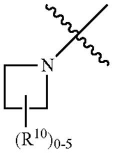, wherein —$(R^{10})_{0-5}$ represents optional substitution of either of the two rings which make up the fused bicyclic ring system, or any atom of the monocyclic ring system, and wherein the nitrogen atom is bound to H when not substituted by $R^{10}$ if needed to complete the valency of the nitrogen atom. In some embodiments, both rings of the fused bicyclic ring system are substituted. In some embodiments, one of the two rings of the fused bicyclic ring system is substituted and the other ring is unsubstituted. In some embodiments, both rings of the fused bicyclic ring system are unsubstituted.

In some embodiments, m is zero. In other embodiments, m is one.

In some embodiments, $R^8$ and $R^9$ are independently H, $C_1$-$C_6$ alkyl, or $C_1$-$C_6$ haloalkyl. In some embodiments, $R^8$ and $R^9$ are independently H, $C_1$-$C_3$ alkyl, or $C_1$-$C_3$ haloalkyl. In some embodiments, $R^8$ and $R^9$ are independently H, —$CH_3$, or —$CF_3$.

In some embodiments, $R^8$ is H. In some embodiments, $R^9$ is H. In some embodiments, $R^8$ and $R^9$ are both H. In some embodiments, one of $R^8$ and $R^9$ is H, and the other is $C_1$-$C_6$ alkyl or $C_1$-$C_6$ haloalkyl. In some embodiments, one of $R^8$ and $R^9$ is H, and the other is $C_1$-$C_3$ alkyl or $C_1$-$C_3$ haloalkyl. In some embodiments, one of $R^8$ and $R^9$ is H, and the other is —$CH_3$ or —$CF_3$.

In some embodiments, $R^8$ and $R^9$ are independently $C_1$-$C_6$ alkyl. In some embodiments, $R^8$ and $R^9$ are independently $C_1$-$C_3$ alkyl. In some embodiments, $R^8$ and $R^9$ are independently methyl, ethyl, n-propyl, or isopropyl. In some embodiments, $R^8$ and $R^9$ are independently —$CH_3$. In some embodiments, $R^8$ and $R^9$ are both —$CH_3$.

In some embodiments, $R^8$ and $R^9$ are independently $C_1$-$C_6$ haloalkyl. In some embodiments, $R^8$ and $R^9$ are independently $C_1$-$C_6$ haloalkyl containing 1-7 halogen atoms. In some embodiments, $R^8$ and $R^9$ are independently $C_1$-$C_3$ haloalkyl. In some embodiments, $R^8$ and $R^9$ are independently $C_1$-$C_3$ haloalkyl containing 1-7 halogen atoms. In some embodiments, $R^8$ and $R^9$ are independently $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^8$ and $R^9$ are independently —$CF_3$, —$CCl_3$, —$CF_2Cl$, —$CFCl_2$, —$CHF_2$, —$CH_2F$, —$CHCl_2$, or —CHFCl. In some embodiments, $R^8$ and $R^9$ are independently —$CF_3$. In some embodiments, $R^8$ and $R^9$ are both —$CF_3$.

In some embodiments, each $R^{10}$ is independently $C_1$-$C_6$ alkyl, $C_1$-$C_6$ haloalkyl, $C_1$-$C_6$ alkyl-OH, —CN, $C_1$-$C_6$ alkyl-CN, —O($C_1$-$C_6$ alkyl), —O($C_1$-$C_6$ haloalkyl), halo, hydroxy, oxo, —$CO_2$H, —C(O)NH($C_1$-$C_6$ alkyl), —C(O)N($C_1$-$C_6$ alkyl)$_2$, —C(O)NH($C_1$-$C_6$ haloalkyl), —C(O)O($C_1$-$C_6$ alkyl), —$SO_2$—($C_1$-$C_6$ alkyl), —$SO_2$—NH($C_1$-$C_6$ alkyl), —$SO_2$—N($C_1$-$C_6$ alkyl)$_2$, —C(O)($C_1$-$C_6$ alkyl), —($C_1$-$C_6$ alkylene)-C(O)N($C_1$-$C_6$ alkyl)$_2$, —($C_1$-$C_6$ alkylene)-C(O)NH($C_1$-$C_6$ alkyl), $C_3$-$C_6$ cycloalkyl, 5- to 6-membered heterocyclyl, 5- to 6-membered heteroaryl, —($C_1$-$C_6$ alkylene)-(5- to 6-membered heterocyclyl), —($C_1$-$C_6$ alkylene)-(5- to 6-membered heteroaryl), —C(O)-(5- to 6-membered heterocyclyl), —C(O)-(5- to 6-membered heteroaryl), or $C_6$-$C_{10}$ aryl, wherein each cycloalkyl, heterocyclyl, heteroaryl, or aryl group is optionally substituted by 1-5 $R^{11}$ groups. In some embodiments, each $R^{10}$, where present, is independently $C_1$-$C_3$ alkyl, $C_1$-$C_3$ haloalkyl, $C_1$-$C_3$ alkyl-OH, —CN, $C_1$-$C_3$ alkyl-CN, —O($C_1$-$C_3$ alkyl), —O($C_1$-$C_3$ haloalkyl), halo, hydroxy, oxo, —$CO_2$H, —C(O)NH($C_1$-$C_3$ alkyl), —C(O)NH($C_1$-$C_3$ haloalkyl), —C(O)O($C_1$-$C_3$ alkyl), —$SO_2$—($C_1$-$C_3$ alkyl), —$SO_2$—NH($C_1$-$C_3$ alkyl), —$SO_2$—N($C_1$-$C_3$ alkyl)$_2$, —C(O)($C_1$-$C_3$ alkyl), —($C_1$-$C_3$ alkylene)-C(O)N($C_1$-$C_3$ alkyl)$_2$, —($C_1$-$C_3$ alkylene)-C(O)NH($C_1$-$C_3$ alkyl), $C_3$-$C_6$ cycloalkyl, 5- to 6-membered heterocyclyl, 5- to 6-membered heteroaryl, —($C_1$-$C_3$ alkylene)-(5- to 6-membered heterocyclyl), —($C_1$-$C_3$ alkylene)-(5- to 6-membered heteroaryl), —C(O)-(5- to 6-membered heterocyclyl), —C(O)-(5- to 6-membered heteroaryl), or $C_6$-$C_{10}$ aryl, wherein each cycloalkyl, heterocyclyl, heteroaryl, or aryl group is optionally substituted by 1-5 $R^{11}$ groups.

In some embodiments, $R^{10}$ is $C_1$-$C_6$ alkyl. In some embodiments, $R^{10}$ is $C_1$-$C_3$ alkyl. In some embodiments, $R^{10}$ is methyl, ethyl, n-propyl, or isopropyl. In some embodiments, $R^{10}$ is methyl, ethyl, or isopropyl. In some embodiments, $R^{10}$ is —$CH_3$. In some embodiments, $R^{10}$ is —$CH_2CH_3$. In some embodiments, $R^{10}$ is —$CH(CH_3)_2$.

In some embodiments, $R^{10}$ is $C_1$-$C_6$ haloalkyl. In some embodiments, $R^{10}$ is $C_1$-$C_6$ haloalkyl containing 1-7 halogen atoms. In some embodiments, $R^{10}$ is $C_1$-$C_3$ haloalkyl. In some embodiments, $R^{10}$ is $C_1$-$C_3$ haloalkyl containing 1-7 halogen atoms. In some embodiments, $R^{10}$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{10}$ is —$CF_3$, —$CCl_3$, —$CF_2Cl$, —$CFCl_2$, —$CHF_2$, —$CH_2F$, —$CHCl_2$, —CHFCl, —$CH_2CF_3$, —$CH_2CCl_3$, —$CH_2CH_2F$, or —$CH_2CH_2Cl$. In some embodiments, $R^{10}$ is —$CF_3$, —$CHF_2$, or —$CH_2CF_3$. In some embodiments, $R^{10}$ is —$CF_3$. In some embodiments, $R^{10}$ is —$CHF_2$. In some embodiments, $R^{10}$ is —$CH_2CF_3$.

In some embodiments, $R^{10}$ is $C_1$-$C_6$ alkyl-OH. In some embodiments, $R^{10}$ is $C_1$-$C_3$ alkyl-OH. In some embodiments, $R^{10}$ is —$CH_2OH$, —$CH_2CH_2OH$, —$CH_2CH_2CH_2OH$, or —$C(CH_3)_2OH$. In some embodiments, $R^{10}$ is —$CH_2OH$.

In some embodiments, $R^{10}$ is —CN.

In some embodiments, $R^{10}$ is $C_1$-$C_6$ alkyl-CN. In some embodiments, $R^{10}$ is $C_1$-$C_3$ alkyl-CN. In some embodiments, $R^{10}$ is —$CH_2CN$, —$CH_2CH_2CN$, —$CH_2CH_2CH_2CN$, or —$C(CH_3)_2CN$. In some embodiments, $R^{10}$ is —$CH_2CN$.

In some embodiments, $R^{10}$ is —O($C_1$-$C_6$ alkyl). In some embodiments, $R^{10}$ is —O($C_1$-$C_3$ alkyl). In some embodiments, $R^{10}$ is —$OCH_3$, —$OCH_2CH_3$, —$OCH_2CH_2CH_3$, or —$OCH(CH_3)_2$. In some embodiments, $R^{10}$ is —$OCH_3$.

In some embodiments, $R^{10}$ is —O($C_1$-$C_6$ haloalkyl). In some embodiments, $R^{10}$ is —O($C_1$-$C_6$ haloalkyl) containing 1-7 halogen atoms. In some embodiments, $R^{10}$ is —O($C_1$-$C_3$ haloalkyl). In some embodiments, $R^{10}$ is —O($C_1$-$C_3$ haloalkyl) containing 1-7 halogen atoms. In some embodiments, $R^{10}$ is —O($C_1$-$C_3$ haloalkyl) containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{10}$ is —$OCF_3$, —$OCCl_3$, —$OCF_2Cl$, —$OCFCl_2$, —$OCHF_2$, —$OCH_2F$, —$OCHCl_2$, —OCHFCl, —$OCH_2CF_3$, —$OCH_2CCl_3$, —$OCH_2CH_2F$, or —$OCH_2CH_2Cl$. In some embodiments, $R^{10}$ is —$OCF_3$.

In some embodiments, $R^{10}$ is halo. In some embodiments, $R^{10}$ is chloro, fluoro, or bromo.

In some embodiments, $R^{10}$ is chloro or fluoro. In some embodiments, $R^{10}$ is bromo or fluoro. In some embodiments, $R^{10}$ is fluoro. In some embodiments, $R^{10}$ is bromo.

In some embodiments, $R^{10}$ is hydroxy.

In some embodiments, $R^{10}$ is oxo.

In some embodiments, $R^{10}$ is —$CO_2H$.

In some embodiments, $R^{10}$ is —C(O)NH($C_1$-$C_6$ alkyl). In some embodiments, $R^{10}$ is —C(O)NH($C_1$-$C_3$ alkyl). In some embodiments, $R^{10}$ is —C(O)NH($CH_3$), —C(O)NH($CH_2CH_3$), —C(O)NH($CH_2CH_2CH_3$), or —C(O)NH($CH(CH_3)_2$). In some embodiments, $R^{10}$ is —C(O)NH($CH_3$).

In some embodiments, $R^{10}$ is —C(O)N($C_1$-$C_6$ alkyl)$_2$. In some embodiments, the two $C_1$-$C_6$ alkyl groups are the same. In other embodiments, the two $C_1$-$C_6$ alkyl groups are different. In some embodiments, $R^{10}$ is —C(O)N($C_1$-$C_3$ alkyl)$_2$. In some embodiments, $R^{10}$ is —C(O)N$(CH_3)_2$, —C(O)N$(CH_2CH_3)_2$, —C(O)N$(CH_2CH_2CH_3)_2$, or —C(O)N$(CH(CH_3)_2)_2$. In some embodiments, $R^{10}$ is —C(O)N$(CH_3)(CH_2CH_3)$, —C(O)N$(CH_3)(CH_2CH_2CH_3)$, —C(O)N$(CH_3)(CH(CH_3)_2)$, —C(O)N$(CH_2CH_3)(CH_2CH_2CH_3)$, or —C(O)N$(CH_2CH_3)(CH(CH_3)_2)$. In some embodiments, $R^{10}$ is —C(O)N$(CH_3)_2$.

In some embodiments, $R^{10}$ is —C(O)NH($C_1$-$C_6$ haloalkyl). In some embodiments, $R^{10}$ is —C(O)NH($C_1$-$C_6$ haloalkyl) containing 1-7 halogen atoms. In some embodiments, $R^{10}$ is —C(O)NH($C_1$-$C_3$ haloalkyl). In some embodiments, $R^{10}$ is —C(O)NH($C_1$-$C_3$ haloalkyl) containing 1-7 halogen atoms. In some embodiments, $R^{10}$ is —C(O)NH($C_1$-$C_3$ haloalkyl) containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{10}$ is —C(O)NH($CF_3$), —C(O)NH($CHF_2$), —C(O)NH($CCl_3$), —C(O)NH($CF_2Cl$), —C(O)NH($CFCl_2$), —C(O)NH($CH_2F$), —C(O)NH($CHCl_2$), or —C(O)NH(CHFCl). In some embodiments, $R^{10}$ is —C(O)NH($CF_3$).

In some embodiments, $R^{10}$ is —C(O)O($C_1$-$C_6$ alkyl). In some embodiments, $R^{10}$ is —C(O)O($C_1$-$C_3$ alkyl). In some embodiments, $R^{10}$ is —C(O)O($CH_3$), —C(O)O($CH_2CH_3$), —C(O)O($CH_2CH_2CH_3$), or —C(O)O($CH(CH_3)_2$). In some embodiments, $R^{10}$ is —C(O)O($CH_3$).

In some embodiments, $R^{10}$ is —$SO_2$—($C_1$-$C_6$ alkyl). In some embodiments, $R^{10}$ is —$SO_2$—($C_1$-$C_3$ alkyl). In some embodiments, $R^{10}$ is —$SO_2$—($CH_3$), —$SO_2$—($CH_2CH_3$), —$SO_2$—($CH_2CH_2CH_3$), or —$SO_2$—($CH(CH_3)_2$). In some embodiments, $R^{10}$ is —$SO_2$—($CH_3$).

In some embodiments, $R^{10}$ is —$SO_2$—NH($C_1$-$C_6$ alkyl). In some embodiments, $R^{10}$ is —$SO_2$—NH($C_1$-$C_3$ alkyl). In some embodiments, $R^{10}$ is —$SO_2$—NH($CH_3$), —$SO_2$—NH($CH_2CH_3$), —$SO_2$—NH($CH_2CH_2CH_3$), or —$SO_2$—NH($CH(CH_3)_2$). In some embodiments, $R^{10}$ is —$SO_2$—NH($CH_3$). In some embodiments, $R^{10}$ is —$SO_2$—N($C_1$-$C_6$ alkyl)$_2$. In some embodiments, the two $C_1$-$C_6$ alkyl groups are the same. In other embodiments, the two $C_1$-$C_6$ alkyl groups are different. In some embodiments, $R^{10}$ is —$SO_2$—N($C_1$-$C_3$ alkyl)$_2$. In some embodiments, $R^{10}$ is —$SO_2$—N$(CH_3)_2$, —$SO_2$—N$(CH_2CH_3)_2$, —$SO_2$—N$(CH_2CH_2CH_3)_2$, or —$SO_2$—N$(CH(CH_3)_2)_2$. In some embodiments, $R^{10}$ is —$SO_2$—N$(CH_3)(CH_2CH_3)$, —$SO_2$—N$(CH_3)(CH_2CH_2CH_3)$, —$SO_2$—N$(CH_3)(CH(CH_3)_2)$, —$SO_2$—N$(CH_2CH_3)(CH_2CH_2CH_3)$, or —$SO_2$—N$(CH_2CH_3)(CH(CH_3)_2)$. In some embodiments, $R^{10}$ is —$SO_2$—N$(CH_3)_2$.

In some embodiments, $R^{10}$ is —$C(O)(C_1$-$C_6$ alkyl). In some embodiments, $R^{10}$ is —$C(O)(C_1$-$C_3$ alkyl). In some embodiments, $R^{10}$ is —$C(O)(CH_3)$, —$C(O)(CH_2CH_3)$, —$C(O)(CH_2CH_2CH_3)$, or —$C(O)(CH(CH_3)_2)$. In some embodiments, $R^{10}$ is —$C(O)(CH_3)$.

In some embodiments, $R^{10}$ is —($C_1$-$C_6$ alkylene)-C(O)N($C_1$-$C_6$ alkyl)$_2$. In some embodiments, the two $C_1$-$C_6$ alkyl groups are the same. In other embodiments, the two $C_1$-$C_6$ alkyl groups are different. In some embodiments, $R^{10}$ is —($C_1$-$C_3$ alkylene)-C(O)N($C_1$-$C_3$ alkyl)$_2$. In some embodiments, $R^{10}$ is —($CH_2$)—C(O)N($C_1$-$C_3$ alkyl)$_2$, —($CH_2CH_2$)—C(O)N($C_1$-$C_3$ alkyl)$_2$, or —($CH_2CH_2CH_2$)—C(O)N($C_1$-$C_3$ alkyl)$_2$. In some embodiments, $R^{10}$ is —($CH_2$)—$C(O)N(CH_3)_2$, —($CH_2$)—$C(O)N(CH_2CH_3)_2$, —($CH_2$)—$C(O)N(CH_2CH_2CH_3)_2$, —($CH_2$)—$C(O)N(CH(CH_3)_2)_2$, —($CH_2$)—$C(O)N(CH_3)(CH_2CH_3)$, —($CH_2$)—$C(O)N(CH_3)(CH_2CH_2CH_3)_2$, —($CH_2$)—$C(O)N(CH_3)(CH(CH_3)_2)$, —($CH_2CH_2$)—$C(O)N(CH_3)_2$, —($CH_2CH_2$)—$C(O)N(CH_2CH_3)_2$, —($CH_2CH_2$)—$C(O)N(CH_2CH_2CH_3)_2$, —($CH_2CH_2$)—$C(O)N(CH(CH_3)_2)_2$, —($CH_2CH_2$)—$C(O)N(CH_3)(CH_2CH_3)$, —($CH_2CH_2$)—$C(O)N(CH_3)(CH_2CH_2CH_3)_2$, or —($CH_2CH_2$)—$C(O)N(CH_3)(CH(CH_3)_2)$. In some embodiments, $R^{10}$ is —($CH_2$)—$C(O)N(CH_3)_2$.

In some embodiments, $R^{10}$ is —($C_1$-$C_6$ alkylene)-C(O)NH($C_1$-$C_6$ alkyl). In some embodiments, $R^{10}$ is —($C_1$-$C_3$ alkylene)-C(O)NH($C_1$-$C_3$ alkyl). In some embodiments, $R^{10}$ is —($CH_2$)—C(O)NH($C_1$-$C_3$ alkyl), —($CH_2CH_2$)—C(O)NH($C_1$-$C_3$ alkyl), or —($CH_2CH_2CH_2$)—C(O)NH($C_1$-$C_3$ alkyl). In some embodiments, $R^{10}$ is —($CH_2$)—$C(O)NH(CH_3)$, —($CH_2$)—$C(O)NH(CH_2CH_3)$, —($CH_2$)—$C(O)NH(CH_2CH_2CH_3)$, —($CH_2$)—$C(O)NH(CH(CH_3)_2)$, —($CH_2CH_2$)—$C(O)NH(CH_3)$, —($CH_2CH_2$)—$C(O)NH(CH_2CH_3)$, —($CH_2CH_2$)—$C(O)NH(CH_2CH_2CH_3)$, or —($CH_2CH_2$)—$C(O)NH(CH(CH_3)_2)$. In some embodiments, $R^{10}$ is —($CH_2$)—$C(O)NH(CH_3)$.

In some embodiments, $R^{10}$ is $C_3$-$C_6$ cycloalkyl optionally substituted with 1-5 $R^{11}$ groups. In some embodiments, $R^{10}$ is $C_3$-$C_5$ cycloalkyl optionally substituted with 1-5 $R^{11}$ groups. In some embodiments, $R^{10}$ is cyclopropyl, cyclobutyl, or cyclopentyl, each of which is optionally substituted with 1-5 $R^{11}$ groups. In some embodiments, $R^{10}$ is cyclopropyl or cyclobutyl, each of which is optionally substituted with 1-5 $R^{11}$ groups. In some embodiments, $R^{10}$ is cyclopropyl optionally substituted with 1-5 $R^{11}$ groups. In some embodiments, $R^{10}$ is cyclobutyl optionally substituted with 1-5 $R^{11}$ groups. In some embodiments, the cycloalkyl group is substituted by 1-5 $R^{11}$ groups. In some embodiments, the cycloalkyl is substituted by one $R^{11}$ group. In some embodiments, the cycloalkyl is substituted by two $R^{11}$ groups. In some embodiments, the cycloalkyl is substituted by three $R^{11}$ groups. In some embodiments, the cycloalkyl is substituted by four $R^{11}$ groups. In some embodiments, the cycloalkyl is substituted by five $R^{11}$ groups. In some embodiments, the cycloalkyl is unsubstituted.

In some embodiments, $R^{10}$ is 5- to 6-membered heterocyclyl optionally substituted by 1-5 $R^{11}$ groups. In some embodiments, $R^{10}$ is 5-membered heterocyclyl optionally substituted by 1-5 $R^{11}$ groups. In some embodiments, $R^{10}$ is 6-membered heterocyclyl optionally substituted by 1-5 $R^{11}$ groups. In some embodiments, the heterocyclyl contains 1-3 heteroatoms selected from the group consisting of N, O, and S. In some embodiments, the heterocyclyl contains 1-3 heteroatoms selected from the group consisting of N and O. In some embodiments, the heterocyclyl contains one nitrogen atom. In some embodiments, the heterocyclyl contains two nitrogen atoms. In some embodiments, the heterocyclyl contains one oxygen atom. In some embodiments, the heterocyclyl contains two oxygen atoms. In some embodiments, the heterocyclyl contains one oxygen atom and one nitrogen atom. In some embodiments, the heterocyclyl is substituted by 1-5 $R^{11}$ groups. In some embodiments, the heterocyclyl is substituted by one $R^{11}$ group. In some embodiments, the heterocyclyl is substituted by two $R^{11}$ groups. In some embodiments, the heterocyclyl is substituted by three $R^{11}$ groups. In some embodiments, the heterocyclyl is substituted by four $R^{11}$ groups. In some embodiments, the heterocyclyl is substituted by five $R^{11}$ groups. In some embodiments, the heterocyclyl is unsubstituted. In some embodiments, the heterocyclyl is piperazinyl, piperidinyl, pyrrolidinyl, morpholinyl, dioxanyl, tetrahydropyranyl, or tetrahydrofuranyl, each of which is optionally substituted by 1-5 $R^{11}$ groups. In some embodiments, $R^{10}$ is

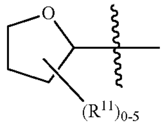
or
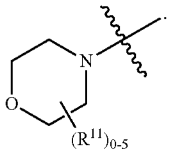

In some embodiments, $R^{10}$ is 5- to 6-membered heteroaryl optionally substituted by 1-5 $R^{11}$ groups. In some embodiments, $R^{10}$ is 5-membered heteroaryl optionally substituted by 1-5 $R^{11}$ groups. In some embodiments, $R^{10}$ is 6-membered heteroaryl optionally substituted by 1-5 $R^{11}$ groups. In some embodiments, the heteroaryl contains 1-3 heteroatoms selected from the group consisting of N, O, and S. In some embodiments, the heteroaryl contains 1-3 heteroatoms selected from the group consisting of N and O. In some embodiments, the heteroaryl contains one nitrogen atom. In some embodiments, the heteroaryl contains two nitrogen atoms. In some embodiments, the heteroaryl contains one oxygen atom. In some embodiments, the heteroaryl contains two oxygen atoms. In some embodiments, the heteroaryl contains one oxygen atom and one nitrogen atom. In some embodiments, the heteroaryl contains one oxygen atom and two nitrogen atoms. In some embodiments, the heteroaryl is substituted by 1-5 $R^{11}$ groups. In some embodiments, the heteroaryl is substituted by one $R^{11}$ group. In some embodiments, the heteroaryl is substituted by two $R^{11}$ groups. In some embodiments, the heteroaryl is substituted by three $R^{11}$ groups. In some embodiments, the heteroaryl is substituted by four $R^{11}$ groups. In some embodiments, the heteroaryl is substituted by five $R^{11}$ groups. In some embodiments, the heteroaryl is unsubstituted. In some embodiments, the heteroaryl is pyridinyl, pyrimidinyl, pyrazinyl, pyridazinyl, triazinyl, imidazolyl, pyrazolyl, oxazolyl, isoxazolyl, oxadiazolyl, or triazolyl, each of which is optionally substituted by 1-5 $R^{11}$ groups. In some embodiments, $R^{10}$ is

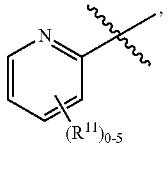
,
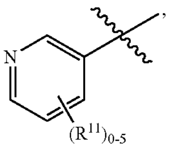
,
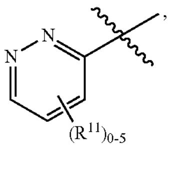
,

-continued

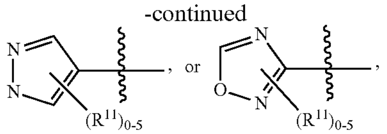

(wherein the nitrogen atom is bound to H if not substituted by $R^{11}$ if needed to complete the valency of the nitrogen atom.

In some embodiments, $R^{10}$ is —($C_1$-$C_6$ alkylene)-(5- to 6-membered heterocyclyl), wherein the heterocyclyl is optionally substituted by 1-5 $R^{11}$ groups. In some embodiments, $R^{10}$ is —($C_1$-$C_3$ alkylene)-(5- to 6-membered heterocyclyl), wherein the heterocyclyl is optionally substituted by 1-5 $R^{11}$ groups. In some embodiments, $R^{10}$ is —($C_1$-$C_3$ alkylene)-(5-membered heterocyclyl), wherein the heterocyclyl is optionally substituted by 1-5 $R^{11}$ groups. In some embodiments, $R^{10}$ is —($C_1$-$C_3$ alkylene)-(6-membered heterocyclyl), wherein the heterocyclyl is optionally substituted by 1-5 $R^{11}$ groups. In some embodiments, $R^{10}$ is —($CH_2$)-(5- to 6-membered heterocyclyl), wherein the heterocyclyl is optionally substituted by 1-5 $R^{11}$ groups. In some embodiments, $R^{10}$ is —($CH_2CH_2$)-(5- to 6-membered heterocyclyl), wherein the heterocyclyl is optionally substituted by 1-5 $R^{11}$ groups. In some embodiments, the heterocyclyl contains 1-3 heteroatoms selected from the group consisting of N, O, and S. In some embodiments, the heterocyclyl contains 1-3 heteroatoms selected from the group consisting of N and O. In some embodiments, the heterocyclyl contains one nitrogen atom. In some embodiments, the heterocyclyl contains two nitrogen atoms. In some embodiments, the heterocyclyl contains one oxygen atom. In some embodiments, the heterocyclyl contains two oxygen atoms. In some embodiments, the heterocyclyl contains one oxygen atom and one nitrogen atom. In some embodiments, the heterocyclyl is substituted by 1-5 $R^{11}$ groups. In some embodiments, the heterocyclyl is substituted by one $R^{11}$ group. In some embodiments, the heterocyclyl is substituted by two $R^{11}$ groups. In some embodiments, the heterocyclyl is substituted by three $R^{11}$ groups. In some embodiments, the heterocyclyl is substituted by four $R^{11}$ groups. In some embodiments, the heterocyclyl is substituted by five $R^{11}$ groups. In some embodiments, the heterocyclyl is unsubstituted. In some embodiments, the heterocyclyl is piperazinyl, piperidinyl, pyrrolidinyl, morpholinyl, dioxanyl, tetrahydropyranyl, or tetrahydrofuranyl, each of which is optionally substituted by 1-5 $R^{11}$ groups.

In some embodiments, $R^{10}$ is —($C_1$-$C_6$ alkylene)-(5- to 6-membered heteroaryl) optionally substituted by 1-5 $R^{11}$ groups. In some embodiments, $R^{10}$ is —($C_1$-$C_3$ alkylene)-(5- to 6-membered heteroaryl), wherein the heteroaryl is optionally substituted by 1-5 $R^{11}$ groups. In some embodiments, $R^{10}$ is —($C_1$-$C_3$ alkylene)-(5-membered heteroaryl), wherein the heteroaryl is optionally substituted by 1-5 $R^{11}$ groups. In some embodiments, $R^{10}$ is —($C_1$-$C_3$ alkylene)-(6-membered heteroaryl), wherein the heteroaryl is optionally substituted by 1-5 $R^{11}$ groups. In some embodiments, $R^{10}$ is —($CH_2$)-(5- to 6-membered heteroaryl), wherein the heterocyclyl is optionally substituted by 1-5 $R^{11}$ groups. In some embodiments, $R^{10}$ is —($CH_2CH_2$)-(5- to 6-membered heteroaryl), wherein the heteroaryl is optionally substituted by 1-5 $R^{11}$ groups. In some embodiments, the heteroaryl contains 1-3 heteroatoms selected from the group consisting of N, O, and S. In some embodiments, the heteroaryl contains 1-3 heteroatoms selected from the group consisting of N and O. In some embodiments, the heteroaryl contains one nitrogen atom. In some embodiments, the heteroaryl contains two nitrogen atoms. In some embodiments, the heteroaryl contains one oxygen atom. In some embodiments, the heteroaryl contains two oxygen atoms. In some embodiments, the heteroaryl contains one oxygen atom and one nitrogen atom. In some embodiments, the heteroaryl contains one oxygen atom and two nitrogen atoms. In some embodiments, the heteroaryl is substituted by 1-5 $R^{11}$ groups. In some embodiments, the heteroaryl is substituted by one $R^{11}$ group. In some embodiments, the heteroaryl is substituted by two $R^{11}$ groups. In some embodiments, the heteroaryl is substituted by three $R^{11}$ groups. In some embodiments, the heteroaryl is substituted by four $R^{11}$ groups. In some embodiments, the heteroaryl is substituted by five $R^{11}$ groups. In some embodiments, the heteroaryl is unsubstituted. In some embodiments, the heteroaryl is pyridinyl, pyrimidinyl, pyrazinyl, pyridazinyl, triazinyl, imidazolyl, pyrazolyl, oxazolyl, isoxazolyl, oxadiazolyl, or triazolyl, each of which is optionally substituted by 1-5 $R^{11}$ groups.

In some embodiments, $R^{10}$ is —C(O)-(5- to 6-membered heterocyclyl), wherein the heterocyclyl is optionally substituted by 1-5 $R^{11}$ groups. In some embodiments, $R^{10}$ is —C(O)-(5-membered heterocyclyl), wherein the heterocyclyl is optionally substituted by 1-5 $R^{11}$ groups. In some embodiments, $R^{10}$ is —C(O)-(6-membered heterocyclyl), wherein the heterocyclyl is optionally substituted by 1-5 $R^{11}$ groups. In some embodiments, the heterocyclyl contains 1-3 heteroatoms selected from the group consisting of N, O, and S. In some embodiments, the heterocyclyl contains 1-3 heteroatoms selected from the group consisting of N and O. In some embodiments, the heterocyclyl contains one nitrogen atom. In some embodiments, the heterocyclyl contains two nitrogen atoms. In some embodiments, the heterocyclyl contains one oxygen atom. In some embodiments, the heterocyclyl contains two oxygen atoms. In some embodiments, the heterocyclyl contains one oxygen atom and one nitrogen atom. In some embodiments, the heterocyclyl is substituted by 1-5 $R^{11}$ groups. In some embodiments, the heterocyclyl is substituted by one $R^{11}$ group. In some embodiments, the heterocyclyl is substituted by two $R^{11}$ groups. In some embodiments, the heterocyclyl is substituted by three $R^{11}$ groups. In some embodiments, the heterocyclyl is substituted by four $R^{11}$ groups. In some embodiments, the heterocyclyl is substituted by five $R^{11}$ groups. In some embodiments, the heterocyclyl is unsubstituted. In some embodiments, the heterocyclyl is piperazinyl, piperidinyl, pyrrolidinyl, morpholinyl, dioxanyl, tetrahydropyranyl, or tetrahydrofuranyl, each of which is optionally substituted by 1-5 $R^{11}$ groups. In some embodiments, $R^{10}$ is

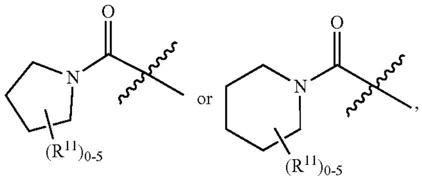

In some embodiments, $R^{10}$ is —C(O)-(5- to 6-membered heteroaryl), wherein the heteroaryl is optionally substituted by 1-5 $R^{11}$ groups. In some embodiments, $R^{10}$ is —C(O)-(5-membered heteroaryl), wherein the heteroaryl is optionally substituted by 1-5 $R^{11}$ groups. In some embodiments, $R^{10}$ is —C(O)-(6-membered heteroaryl), wherein the heteroaryl is optionally substituted by 1-5 $R^{11}$ groups. In some embodiments, the heteroaryl contains 1-3 heteroatoms selected from the group consisting of N, O, and S. In some embodiments, the heteroaryl contains 1-3 heteroatoms selected from the group consisting of N and O. In some embodiments, the heteroaryl contains one nitrogen atom. In some embodiments, the heteroaryl contains two nitrogen atoms. In some embodiments, the heteroaryl contains one oxygen atom. In some embodiments, the heteroaryl contains two oxygen atoms. In some embodiments, the heteroaryl contains one oxygen atom and one nitrogen atom. In some embodiments, the heteroaryl is substituted by 1-5 $R^{11}$ groups. In some embodiments, the heteroaryl is substituted by one $R^{11}$ group. In some embodiments, the heteroaryl is substituted by two $R^{11}$ groups. In some embodiments, the heteroaryl is substituted by three $R^{11}$ groups. In some embodiments, the heteroaryl is substituted by four $R^{11}$ groups. In some embodiments, the heteroaryl is substituted by five $R^{11}$ groups. In some embodiments, the heteroaryl is unsubstituted. In some embodiments, the heteroaryl is pyridinyl, pyrimidinyl, pyrazinyl, pyridazinyl, triazinyl, imidazolyl, pyrazolyl, oxazolyl, isoxazolyl, oxadiazolyl, or triazolyl, each of which is optionally substituted by 1-5 $R^{11}$ groups.

In some embodiments, $R^{10}$ is $C_6$-$C_{10}$ aryl optionally substituted by 1-5 $R^{11}$ groups. In some embodiments, $R^{10}$ is $C_6$ aryl optionally substituted by 1-5 $R^{11}$ groups. In some embodiments, the aryl is substituted by 1-5 $R^{11}$ groups. In some embodiments, the aryl is substituted by one $R^{11}$ group. In some embodiments, the aryl is substituted by two $R^{11}$ groups. In some embodiments, the aryl is substituted by three $R^{11}$ groups. In some embodiments, the aryl is substituted by four $R^{11}$ groups. In some embodiments, the aryl is substituted by five $R^{11}$ groups. In some embodiments, the aryl is unsubstituted. In some embodiments, $R^{10}$ is phenyl optionally substituted by 1-5 $R^{11}$ groups.

In some embodiments, each $R^{10}$ is independently $-CH_3$, $-CH_2CH_3$, $-CH(CH_3)_2$, $-CF_3$, $-CHF_2$, $-CH_2CF_3$, $-CH_2OH$, $-CN$, $-CH_2CN$, $-OCH_3$, $-OCF_3$, Br, F, hydroxy, oxo, $-CO_2H$, $-C(O)NH(CH_3)$, $C(O)N(CH_3)_2$, $-C(O)NH(CF_3)$, $-C(O)OCH_3$, $-SO_2CH_3$, $-SO_2NH(CH_3)$, $-SO_2N(CH_3)_2$, $-C(O)CH_3$, $-(CH_2)-C(O)N(CH_3)_2$, $-(CH_2)-C(O)NH(CH_3)$,

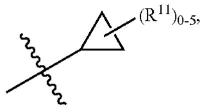
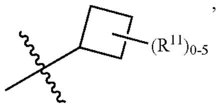
,
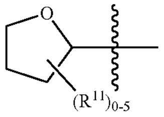
,
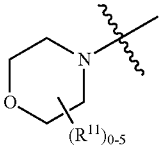
,
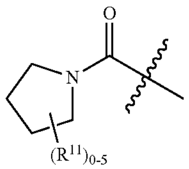
,
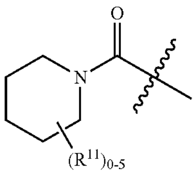
,
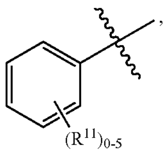
,
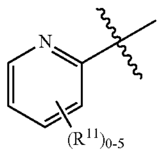
, -continued

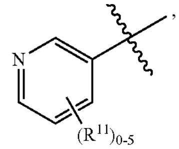
,
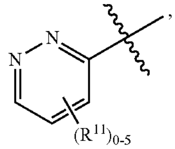
,
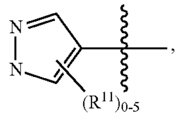
, or
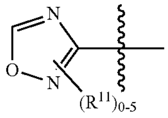
.

In some embodiments, two $R^{10}$ groups attached to the same carbon atom are taken together with the carbon atom to which they are attached to form a spiro $C_3$-$C_6$ cycloalkyl or a spiro 4- to 6-membered heterocyclyl, each of which is optionally substituted by 1-5 $R^{11}$ groups.

In some embodiments, two $R^{10}$ groups attached to the same carbon atom are taken together with the carbon atom to which they are attached to form a spiro $C_3$-$C_6$ cycloalkyl optionally substituted by 1-5 $R^{11}$ groups. In some embodiments, two $R^{10}$ groups attached to the same carbon atom are taken together with the carbon atom to which they are attached to form a spiro $C_3$-$C_5$ cycloalkyl optionally substituted by 1-5 $R^{11}$ groups. In some embodiments, the cycloalkyl is cyclopropyl, cyclobutyl, or cyclopentyl, each of which is optionally substituted with 1-5 $R^{11}$ groups. In some embodiments, two $R^{10}$ groups attached to the same carbon atom are taken together with the carbon atom to which they are attached to form a spiro cyclopropyl or cyclobutyl, each of which is optionally substituted with 1-5 $R^{11}$ groups. In some embodiments, two $R^{10}$ groups attached to the same carbon atom are taken together with the carbon atom to which they are attached to form a spiro cyclopropyl optionally substituted with 1-5 $R^{11}$ groups. In some embodiments, two $R^{10}$ groups attached to the same carbon atom are taken together with the carbon atom to which they are attached to form a spiro cyclobutyl optionally substituted with 1-5 $R^{11}$ groups. In some embodiments, the cycloalkyl group is substituted by 1-5 $R^{11}$ groups. In some embodiments, the cycloalkyl is substituted by one $R^{11}$ group. In some embodiments, the cycloalkyl is substituted by two $R^{11}$ groups. In some embodiments, the cycloalkyl is substituted by three $R^{11}$ groups. In some embodiments, the cycloalkyl is substituted by four $R^{11}$ groups. In some embodiments, the cycloalkyl is substituted by five $R^{11}$ groups. In some embodiments, the cycloalkyl is unsubstituted.

In some embodiments, two $R^{10}$ groups attached to the same carbon atom are taken together with the carbon atom to which they are attached to form a spiro 4- to 6-membered heterocyclyl optionally substituted by 1-5 $R^{11}$ groups. In some embodiments, two $R^{10}$ groups attached to the same carbon atom are taken together with the carbon atom to which they are attached to form a spiro 4-membered heterocyclyl optionally substituted by 1-5 $R^{11}$ groups. In some embodiments, two $R^{10}$ groups attached to the same carbon atom are taken together with the carbon atom to which they are attached to form a spiro 5-membered heterocyclyl optionally substituted by 1-5 $R^{11}$ groups. In some embodiments, two $R^{10}$ groups attached to the same carbon atom are taken together with the carbon atom to which they are attached to form a spiro 6-membered heterocyclyl optionally substituted by 1-5 $R^{11}$ groups. In some embodiments, the heterocyclyl contains 1-3 heteroatoms selected from the group consisting of N, O, and S. In some embodiments, the heterocyclyl contains 1-3 heteroatoms selected from the group consisting of N and O. In some embodiments, the heterocyclyl contains one nitrogen atom. In some embodiments, the heterocyclyl contains two nitrogen atoms. In some embodiments, the heterocyclyl contains one oxygen atom. In some embodiments, the heterocyclyl contains two oxygen atoms. In some embodiments, the heterocyclyl contains one oxygen atom and one nitrogen atom. In some embodiments, the heterocyclyl is substituted by 1-5 $R^{11}$ groups. In some embodiments, the heterocyclyl is substituted by one $R^{11}$ group. In some embodiments, the heterocyclyl is substituted by two $R^{11}$ groups. In some embodiments, the heterocyclyl is substituted by three $R^{11}$ groups. In some embodiments, the heterocyclyl is substituted by four $R^{11}$ groups. In some embodiments, the heterocyclyl is substituted by five $R^{11}$ groups. In some embodiments, the heterocyclyl is unsubstituted. In some embodiments, the heterocyclyl is azetidinyl, piperazinyl, piperidinyl, pyrrolidinyl, morpholinyl, dioxanyl, tetrahydropyranyl, or tetrahydrofuranyl, each of which is optionally substituted by 1-5 $R^{11}$ groups. In some embodiments, the heterocyclyl is substituted by at least one $R^{11}$ group, wherein the $R^{11}$ group is oxo. In some embodiments, two $R^{10}$ groups attached to the same carbon atom are taken together with the carbon atom to which they are attached to form

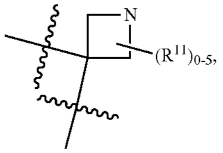
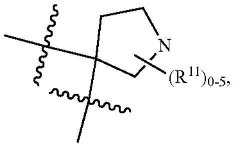
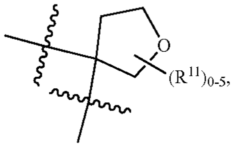
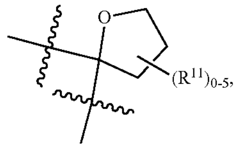
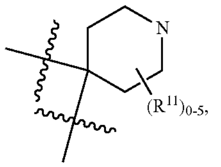
or
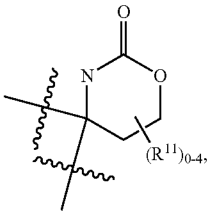

wherein the nitrogen atoms of the heterocyclyl groups are bound to H when not substituted by $R^{11}$.

In some embodiments, two $R^{10}$ groups attached to the same carbon atom are taken together with the carbon atom to which they are attached to form

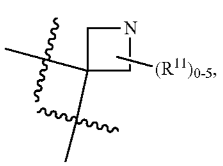
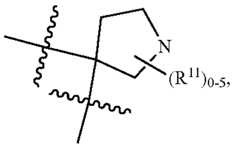
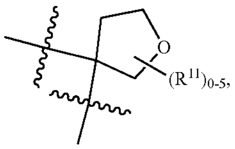
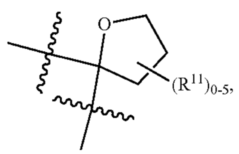

-continued

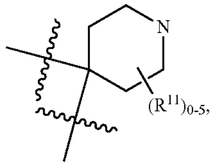
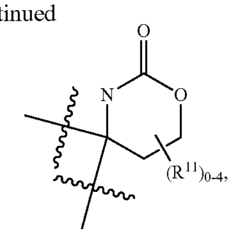
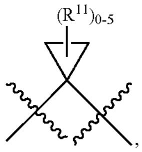
, or
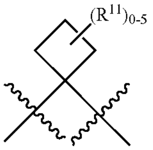
, wherein the nitrogen atoms of the heterocyclyl groups are bound to H when not substituted by $R^{11}$.

In some embodiments, each $R^{11}$ is independently $C_1$-$C_6$ alkyl, hydroxy, oxo, or —C(O)($C_1$-$C_6$ alkyl). In some embodiments, each $R^{11}$ is independently $C_1$-$C_3$ alkyl, hydroxy, oxo, or —C(O)($C_1$-$C_3$ alkyl). In some embodiments, each $R^{11}$ is independently —$CH_3$, hydroxy, oxo, or —C(O)$CH_3$.

In some embodiments, $R^{11}$ is $C_1$-$C_6$ alkyl. In some embodiments, $R^{11}$ is $C_1$-$C_3$ alkyl. In some embodiments, $R^{11}$ is methyl, ethyl, n-propyl, or isopropyl. In some embodiments, $R^{11}$ is methyl, ethyl, or isopropyl. In some embodiments, $R^{11}$ is —$CH_3$.

In some embodiments, $R^{11}$ is hydroxyl.

In some embodiments, $R^{11}$ is oxo.

In some embodiments, $R^{11}$ is —C(O)($C_1$-$C_6$ alkyl). In some embodiments, $R^{11}$ is —C(O)($C_1$-$C_3$ alkyl). In some embodiments, $R^{11}$ is —C(O)$CH_3$, —C(O)$CH_2CH_3$, —C(O)$CH_2CH_2CH_3$, or —C(O)$CH(CH_3)_2$. In some embodiments, $R^{11}$ is —C(O)$CH_3$.

In some embodiments, $R^{12}$ is H, $C_1$-$C_6$ alkyl, or $C_1$-$C_6$ haloalkyl. In some embodiments, $R^{12}$ is H, $C_1$-$C_3$ alkyl, or $C_1$-$C_3$ haloalkyl. In some embodiments, $R^{12}$ is H, —$CH_3$, or —$CF_3$.

In some embodiments, $R^{12}$ is H.

In some embodiments, $R^{12}$ is $C_1$-$C_6$ alkyl. In some embodiments, $R^{12}$ is $C_1$-$C_3$ alkyl. In some embodiments, $R^{12}$ is methyl, ethyl, n-propyl, or isopropyl. In some embodiments, $R^{12}$ is methyl, ethyl, or isopropyl. In some embodiments, $R^{12}$ is —$CH_3$.

In some embodiments, $R^{12}$ is $C_1$-$C_6$ haloalkyl. In some embodiments, $R^{12}$ is $C_1$-$C_6$ haloalkyl containing 1-7 halogen atoms. In some embodiments, $R^{12}$ is $C_1$-$C_3$ haloalkyl. In some embodiments, $R^{12}$ is $C_1$-$C_3$ haloalkyl containing 1-7 halogen atoms. In some embodiments, $R^{12}$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{12}$ is —$CF_3$, —$CCl_3$, —$CF_2Cl$, —$CFCl_2$, —$CHF_2$, —$CH_2F$, —$CHCl_2$, or —CHFCl. In some embodiments, $R^{12}$ is —$CF_3$.

In some embodiments, when $R^6$ and $R^7$ are taken together with the nitrogen atom to which they are attached to form a 4- to 10-membered monocyclic or fused bicyclic heterocyclyl optionally containing 1-2 additional heteroatoms selected from the group consisting of N, S, and O, $R^{12}$ is $C_1$-$C_6$ alkylene which connects to the 4- to 10-membered monocyclic or fused bicyclic heterocyclyl to form a 7- to 14-membered fused bicyclic or tricyclic heterocyclyl, each of which heterocyclyl is optionally substituted by 1-5 $R^{10}$ groups. In some embodiments, $R^6$ and $R^7$ are taken together with the nitrogen atom to which they are attached to form a 5- to 6-membered monocyclic heterocyclyl, and $R^{12}$ is —$CH_2$— which connects to the 5- to 6-membered monocyclic heterocyclyl to form

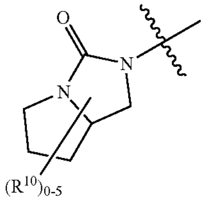

or

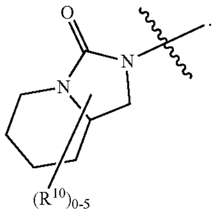

In some embodiments, when $R^6$ and $R^7$ are taken together with the nitrogen atom to which they are attached to form a 4- to 10-membered monocyclic or fused bicyclic heterocyclyl optionally containing 1-2 additional heteroatoms selected from the group consisting of N, S, and O, $R^{12}$ is $C_1$-$C_3$ alkylene which connects to the 4- to 10-membered monocyclic or fused bicyclic heterocyclyl to form a 7- to 14-membered fused bicyclic or tricyclic heterocyclyl, each of which heterocyclyl is optionally substituted by 1-5 $R^{10}$ groups. In some embodiments, when $R^6$ and $R^7$ are taken together with the nitrogen atom to which they are attached to form a 4- to 10-membered monocyclic or fused bicyclic heterocyclyl optionally containing 1-2 additional heteroatoms selected from the group consisting of N, S, and O, $R^{12}$ is $C_1$-$C_2$ alkylene which connects to the 4- to 10-membered monocyclic or fused bicyclic heterocyclyl to form a 7- to 14-membered fused bicyclic or tricyclic heterocyclyl, each of which heterocyclyl is optionally substituted by 1-5 $R^{10}$ groups. In some embodiments, when $R^6$ and $R^7$ are taken together with the nitrogen atom to which they are attached to form a 4- to 10-membered monocyclic or fused bicyclic heterocyclyl optionally containing 1-2 additional heteroatoms selected from the group consisting of N, S, and O, $R^{12}$ is methylene which connects to the 4- to 10-membered monocyclic or fused bicyclic heterocyclyl to form a 7- to 14-membered fused bicyclic or tricyclic heterocyclyl, each of which heterocyclyl is optionally substituted by 1-5 $R^{10}$ groups.

In some embodiments, when $R^6$ and $R^7$ are taken together with the nitrogen atom to which they are attached to form a 4- to 10-membered monocyclic heterocyclyl optionally containing 1-2 additional heteroatoms selected from the group consisting of N, S, and O, $R^{12}$ is methylene which connects to the 4- to 10-membered monocyclic heterocyclyl to form a 7- to 13-membered fused bicyclic heterocyclyl optionally substituted by 1-5 $R^{10}$ groups. In some embodiments, when $R^6$ and $R^7$ are taken together with the nitrogen atom to which they are attached to form a 5- to 6-membered monocyclic heterocyclyl, and $R^{12}$ is —$CH_2$— which connects to the 5- to 6-membered monocyclic heterocyclyl to form a 8- to 9-membered fused bicyclic heterocyclyl optionally substituted by 1-5 $R^{10}$ groups. In some embodiments, $R^6$ and $R^7$ are taken together with the nitrogen atom to which they are attached to form a 5-membered monocyclic heterocyclyl and $R^{12}$ is —$CH_2$— which connects to the 5-membered monocyclic heterocyclyl to form

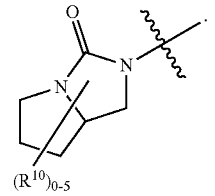

In some embodiments, $R^6$ and $R^7$ are taken together with the nitrogen atom to which they are attached to form a 6-membered monocyclic heterocyclyl and $R^{12}$ is —$CH_2$— which connects to the 6-membered monocyclic heterocyclyl to form

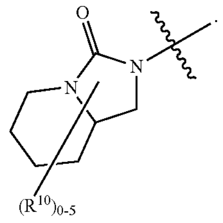

In some embodiments, when $R^6$ and $R^7$ are taken together with the nitrogen atom to which they are attached to form a 4- to 10-membered fused bicyclic heterocyclyl optionally containing 1-2 additional heteroatoms selected from the group consisting of N, S, and O, $R^{12}$ is $C_1$-$C_3$ alkylene which connects to the 4- to 10-membered fused bicyclic heterocyclyl to form a 7- to 14-membered fused tricyclic heterocyclyl optionally substituted by 1-5 $R^{10}$ groups. In some embodiments, when $R^6$ and $R^7$ are taken together with the nitrogen atom to which they are attached to form a 4- to 10-membered fused bicyclic heterocyclyl optionally containing 1-2 additional heteroatoms selected from the group consisting of N, S, and O, $R^{12}$ is methylene which connects to the 4- to 10-membered fused bicyclic heterocyclyl to form a 7- to 13-membered fused tricyclic heterocyclyl optionally substituted by 1-5 $R^{10}$ groups.

In some embodiments, each $R^{13}$ is independently H, $C_1$-$C_3$ alkyl, $C_1$-$C_3$ alkyl-OH, or $C_1$-$C_3$ haloalkyl. In some embodiments, each $R^{13}$ is independently H, $C_1$-$C_2$ alkyl, $C_1$-$C_2$ alkyl-OH, or $C_1$-$C_2$ haloalkyl. In some embodiments, each $R^{13}$ is independently H, —$CH_3$, —$CH_2OH$, or —$CF_3$.

In some embodiments, each $R^{13}$ is independently H. In some embodiments, one $R^{13}$ is H and the other $R^{13}$ is $C_1$-$C_3$ alkyl. In some embodiments, one $R^{13}$ is H and the other $R^{13}$ is $C_1$-$C_2$ alkyl. In some embodiments, one $R^{13}$ is H and the other $R^{13}$ is methyl. In some embodiments, one $R^{13}$ is H and the other $R^{13}$ is ethyl. In some embodiments, one $R^{13}$ is H and the other $R^{13}$ is $C_1$-$C_3$ haloalkyl. In some embodiments, one $R^{13}$ is H and the other $R^{13}$ is $C_1$-$C_2$ haloalkyl. In some embodiments, one $R^{13}$ is H and the other $R^{13}$ is $C_1$ haloalkyl. In some embodiments, one $R^{13}$ is H and the other $R^{13}$ is —$CF_3$. In some embodiments, each $R^{13}$ is H.

In some embodiments, $R^{13}$ is $C_1$-$C_3$ alkyl. In some embodiments, $R^{13}$ is $C_1$-$C_2$ alkyl. In some embodiments, $R^{13}$ is methyl, ethyl, n-propyl, or isopropyl. In some embodiments, $R^{13}$ is methyl or ethyl. In some embodiments, $R^{13}$ is —$CH_3$.

In some embodiments, $R^{13}$ is $C_1$-$C_3$ alkyl-OH. In some embodiments, $R^{13}$ is $C_1$-$C_2$ alkyl-OH. In some embodiments, $R^{13}$ is —$CH_2OH$, —$CH_2CH_2OH$, or —$CH_2CH_2CH_2OH$. In some embodiments, $R^{13}$ is —$CH_2OH$.

In some embodiments, $R^{13}$ is $C_1$-$C_3$ haloalkyl. In some embodiments, $R^{13}$ is $C_1$-$C_3$ haloalkyl containing 1-5 halogen atoms. In some embodiments, $R^{13}$ is $C_1$-$C_2$ haloalkyl. In some embodiments, $R^{13}$ is $C_1$-$C_2$ haloalkyl containing 1-3 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{13}$ is —$CF_3$, —$CCl_3$, —$CF_2Cl$, —$CFCl_2$, —$CHF_2$, —$CH_2F$, —$CHCl_2$, or —$CHFCl$. In some embodiments, $R^{13}$ is —$CF_3$.

TABLE 1

| Representative Compounds of Formula (I) | |
|---|---|
| Cmpd No. | Structure |
| 1 | 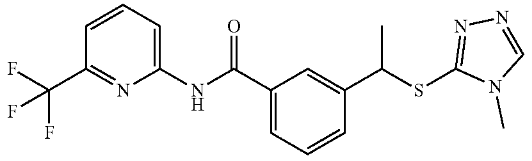 [SMILES: CC(Sc1nncn1C)c1cccc(C(=O)Nc2cccc(C(F)(F)F)n2)c1] |
| 2 | 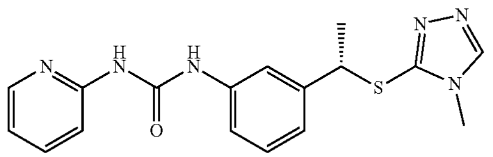 [SMILES: C[C@H](Sc1nncn1C)c1cccc(NC(=O)Nc2ccccn2)c1] |
| 3 | 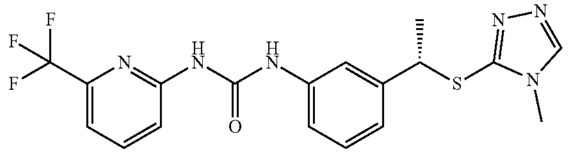 [SMILES: C[C@H](Sc1nncn1C)c1cccc(NC(=O)Nc2cccc(C(F)(F)F)n2)c1] |
| 4 | 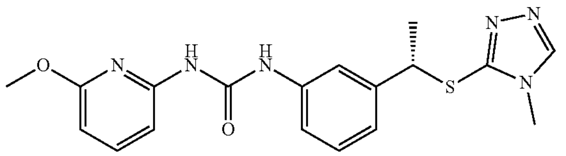 [SMILES: COc1cccc(NC(=O)Nc2cccc([C@H](C)Sc3nncn3C)c2)n1] |
| 5 | 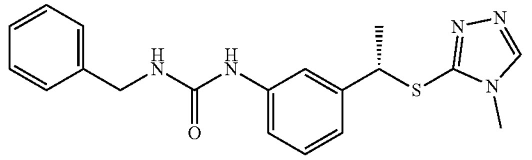 [SMILES: C[C@H](Sc1nncn1C)c1cccc(NC(=O)NCc2ccccc2)c1] |
| 6 | 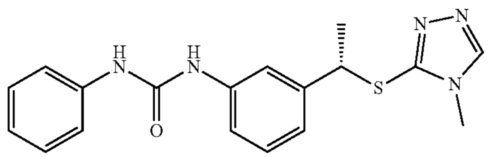 [SMILES: C[C@H](Sc1nncn1C)c1cccc(NC(=O)Nc2ccccc2)c1] |
| 7 | 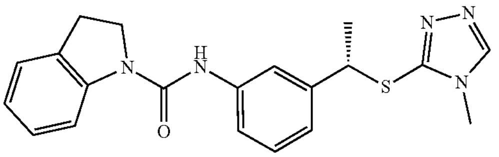 [SMILES: C[C@H](Sc1nncn1C)c1cccc(NC(=O)N2CCc3ccccc32)c1] |

TABLE 1-continued
| Representative Compounds of Formula (I) | |
|---|---|
| Cmpd No. | Structure |
| 8 | 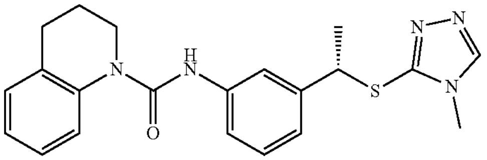 |
| 9 | 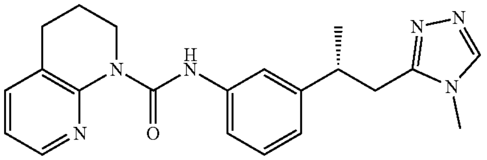 [SMILES: C[C@H](Cc1nncn1C)c1cccc(NC(=O)N2CCCc3cccnc32)c1] |
| 10 | 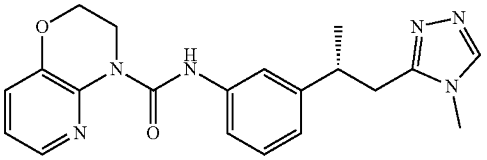 |
| 11 | 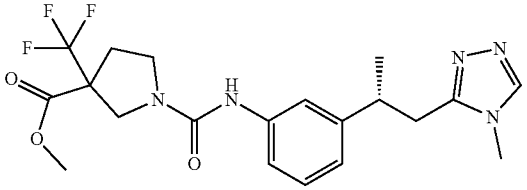 [SMILES: COC(=O)C1(C(F)(F)F)CCN(C(=O)Nc2cccc([C@H](C)Cc3nncn3C)c2)C1] |
| 12 | 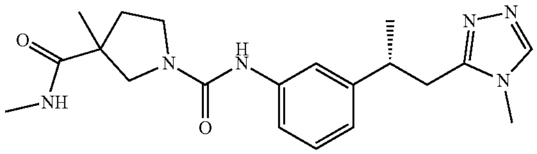 [SMILES: CNC(=O)C1(C)CCN(C(=O)Nc2cccc([C@H](C)Cc3nncn3C)c2)C1] |
| 13 | 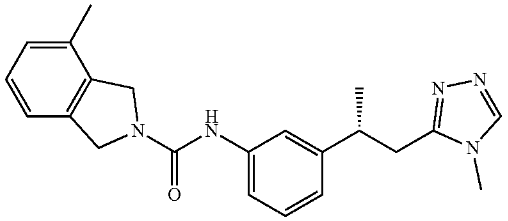 [SMILES: Cc1cccc2c1CN(C(=O)Nc1cccc([C@H](C)Cc3nncn3C)c1)C2] |
| 14 | 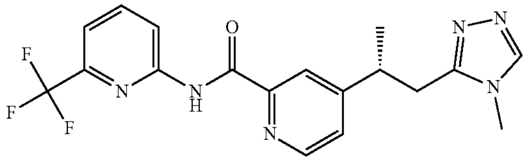 [SMILES: C[C@H](Cc1nncn1C)c1ccnc(C(=O)Nc2cccc(C(F)(F)F)n2)c1] |
| 15 | 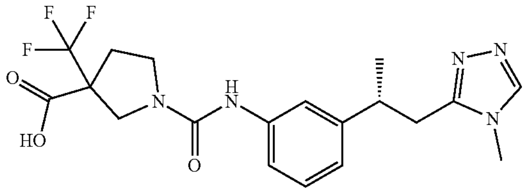 [SMILES: C[C@H](Cc1nncn1C)c1cccc(NC(=O)N2CCC(C(=O)O)(C(F)(F)F)C2)c1] |

TABLE 1-continued
| Representative Compounds of Formula (I) | |
|---|---|
| Cmpd No. | Structure |
| 16 | 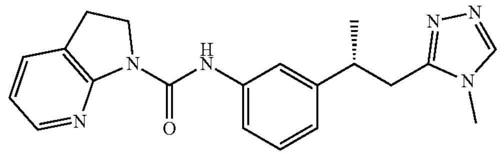 [SMILES: C[C@H](Cc1nncn1C)c1cccc(NC(=O)N2CCc3cccnc32)c1] |
| 17 | 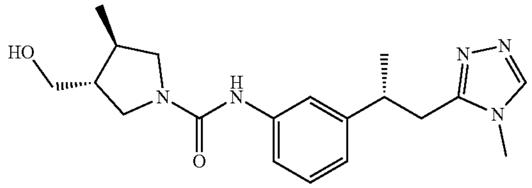 [SMILES: C[C@H](Cc1nncn1C)c1cccc(NC(=O)N2C[C@H](CO)[C@@H](C)C2)c1] |
| 18 | 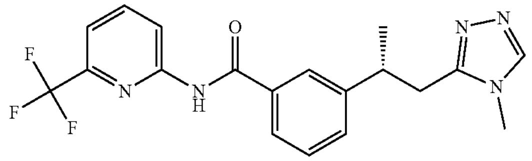 |
| 19 | 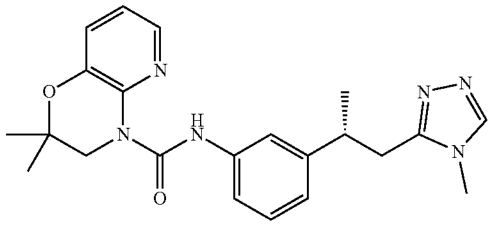 [SMILES: C[C@H](Cc1nncn1C)c1cccc(NC(=O)N2CC(C)(C)Oc3cccnc32)c1] |
| 20 | 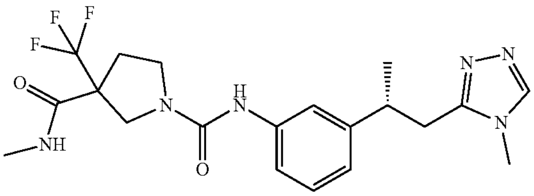 [SMILES: CNC(=O)C1(C(F)(F)F)CCN(C(=O)Nc2cccc([C@H](C)Cc3nncn3C)c2)C1] |
| 21 | 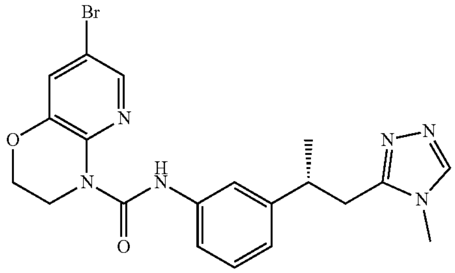 [SMILES: C[C@H](Cc1nncn1C)c1cccc(NC(=O)N2CCOc3cc(Br)cnc32)c1] |
| 22 | 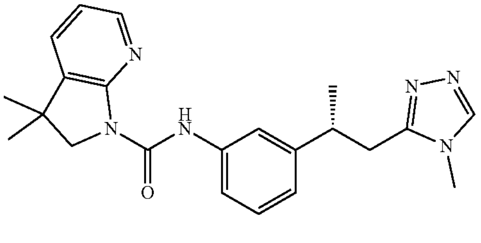 [SMILES: C[C@H](Cc1nncn1C)c1cccc(NC(=O)N2CC(C)(C)c3cccnc32)c1] |

TABLE 1-continued
| Representative Compounds of Formula (I) | |
|---|---|
| Cmpd No. | Structure |
| 23 | 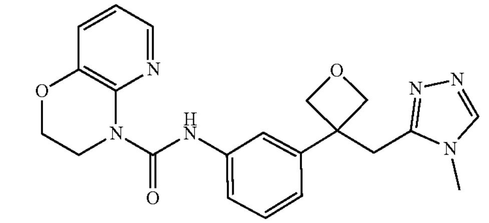 [SMILES: Cn1cnnc1CC1(c2cccc(NC(=O)N3CCOc4cccnc43)c2)COC1] |
| 24 | 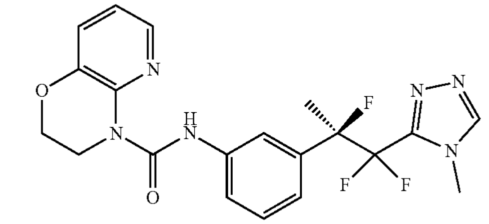 [SMILES: Cn1cnnc1C(F)(F)[C@](C)(F)c1cccc(NC(=O)N2CCOc3cccnc32)c1] |
| 25 | 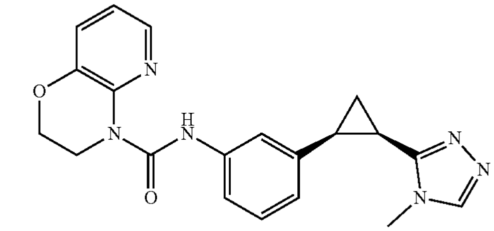 [SMILES: Cn1cnnc1[C@@H]1C[C@@H]1c1cccc(NC(=O)N2CCOc3cccnc32)c1] |
| 26 | 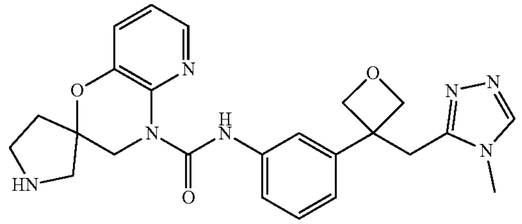 [SMILES: Cn1cnnc1CC1(c2cccc(NC(=O)N3CC4(CCNC4)Oc4cccnc43)c2)COC1] |
| 27 | 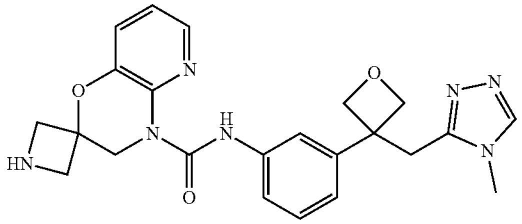 [SMILES: Cn1cnnc1CC1(c2cccc(NC(=O)N3CC4(CNC4)Oc4cccnc43)c2)COC1] |
| 28 | 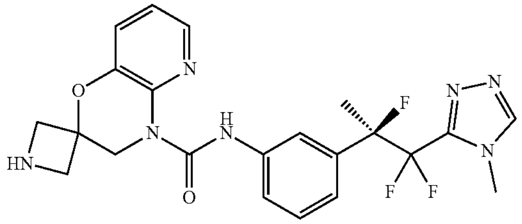 [SMILES: Cn1cnnc1C(F)(F)[C@](C)(F)c1cccc(NC(=O)N2CC3(CNC3)Oc3cccnc32)c1] |

TABLE 1-continued
| Representative Compounds of Formula (I) | |
|---|---|
| Cmpd No. | Structure |
| 29 | 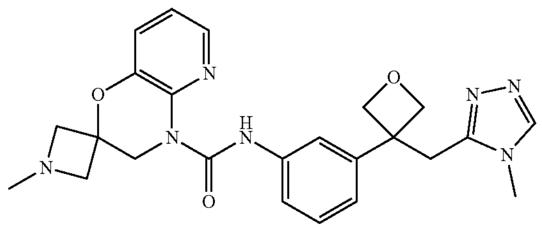 [SMILES: CN1CC2(C1)CN(C(=O)Nc1cccc(C3(Cc4nncn4C)COC3)c1)c1ncccc1O2] |
| 30 | 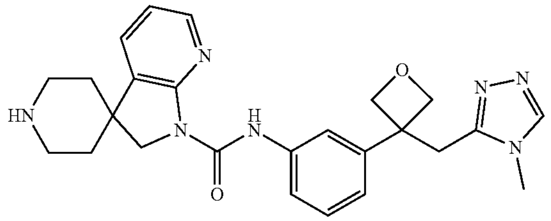 [SMILES: Cn1cnnc1CC1(c2cccc(NC(=O)N3CC4(CCNCC4)c4cccnc43)c2)COC1] |
| 31 | 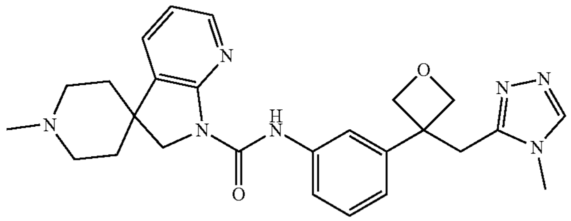 [SMILES: CN1CCC2(CC1)CN(C(=O)Nc1cccc(C3(Cc4nncn4C)COC3)c1)c1ncccc12] |
| 32 | 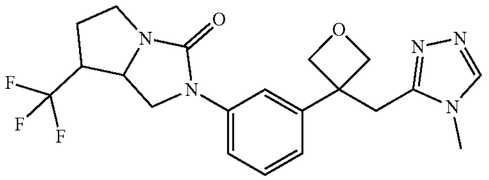 [SMILES: Cn1cnnc1CC1(c2cccc(N3CC4C(C(F)(F)F)CCN4C3=O)c2)COC1] |
| 33 | 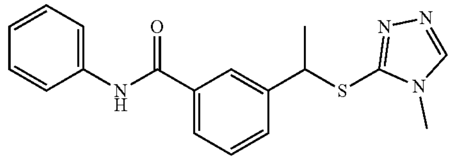 |
| 34 | 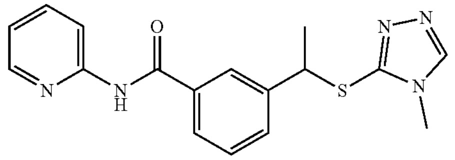 |
| 35 | 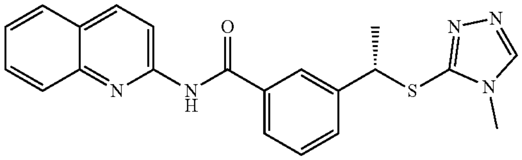 [SMILES: C[C@H](Sc1nncn1C)c1cccc(C(=O)Nc2ccc3ccccc3n2)c1] |

TABLE 1-continued
| Representative Compounds of Formula (I) | |
|---|---|
| Cmpd No. | Structure |
| 36 | 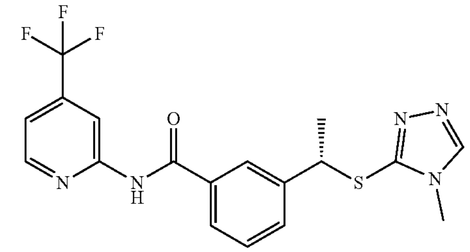 [SMILES: C[C@H](Sc1nncn1C)c1cccc(C(=O)Nc2cc(C(F)(F)F)ccn2)c1] |
| 37 | 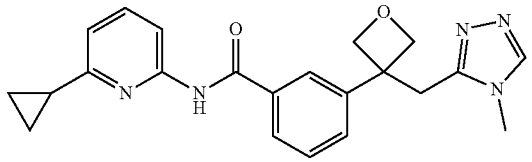 [SMILES: Cn1cnnc1CC1(c2cccc(C(=O)Nc3cccc(C4CC4)n3)c2)COC1] |
| 38 | 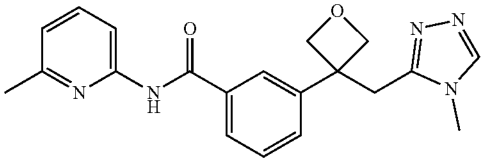 [SMILES: Cc1cccc(NC(=O)c2cccc(C3(Cc4nncn4C)COC3)c2)n1] |
| 39 | 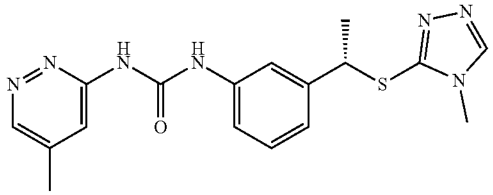 [SMILES: Cc1cnnc(NC(=O)Nc2cccc([C@H](C)Sc3nncn3C)c2)c1] |
| 40 | 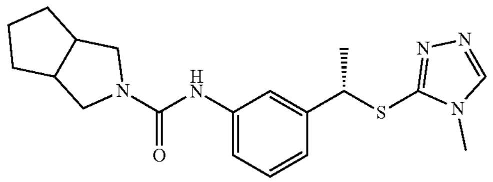 [SMILES: C[C@H](Sc1nncn1C)c1cccc(NC(=O)N2CC3CCCC3C2)c1] |
| 41 | 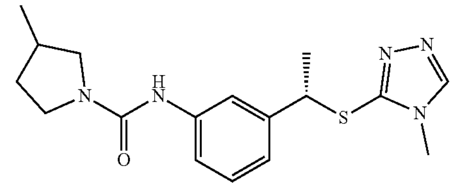 [SMILES: CC1CCN(C(=O)Nc2cccc([C@H](C)Sc3nncn3C)c2)C1] |
| 42 | 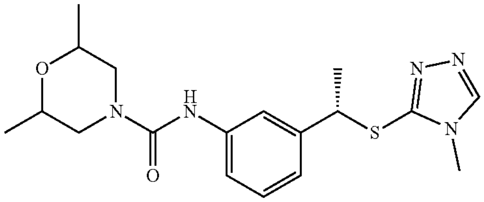 [SMILES: CC1CN(C(=O)Nc2cccc([C@H](C)Sc3nncn3C)c2)CC(C)O1] |

TABLE 1-continued
Representative Compounds of Formula (I)
| Cmpd No. | Structure |
|---|---|
| 43 | 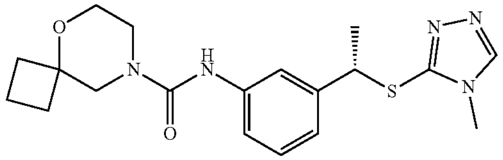 [SMILES: C[C@H](Sc1nncn1C)c1cccc(NC(=O)N2CCOC3(CCC3)C2)c1] |
| 44 | 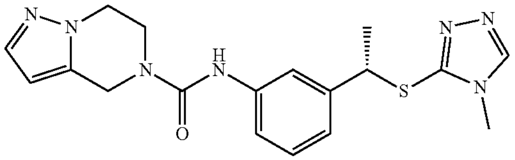 [SMILES: C[C@H](Sc1nncn1C)c1cccc(NC(=O)N2CCn3nccc3C2)c1] |
| 45 | 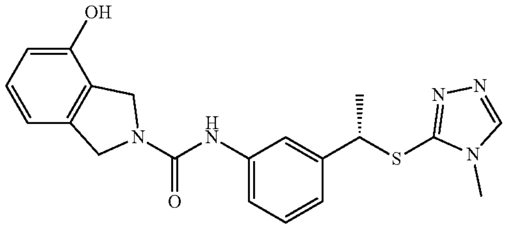 [SMILES: C[C@H](Sc1nncn1C)c1cccc(NC(=O)N2Cc3cccc(O)c3C2)c1] |
| 46 | 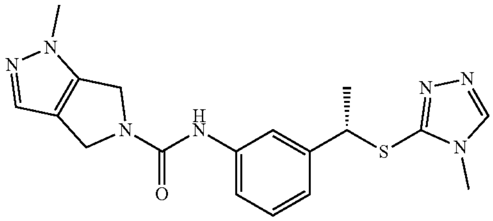 [SMILES: C[C@H](Sc1nncn1C)c1cccc(NC(=O)N2Cc3cnn(C)c3C2)c1] |
| 47 | 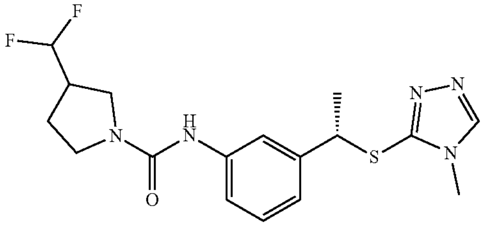 [SMILES: C[C@H](Sc1nncn1C)c1cccc(NC(=O)N2CCC(C(F)F)C2)c1] |
| 48 | 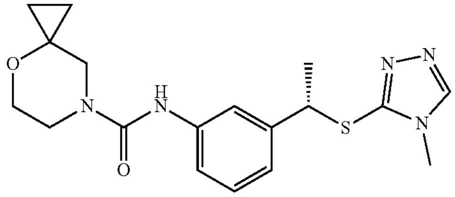 [SMILES: C[C@H](Sc1nncn1C)c1cccc(NC(=O)N2CCOC3(CC3)C2)c1] |
| 49 | 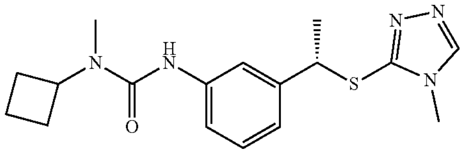 [SMILES: C[C@H](Sc1nncn1C)c1cccc(NC(=O)N(C)C2CCC2)c1] |

TABLE 1-continued
| Representative Compounds of Formula (I) | |
|---|---|
| Cmpd No. | Structure |
| 50 | 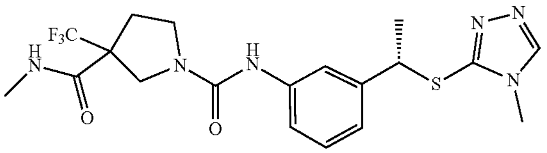 [SMILES: CNC(=O)C1(C(F)(F)F)CCN(C(=O)Nc2cccc([C@H](C)Sc3nncn3C)c2)C1] |
| 51 | 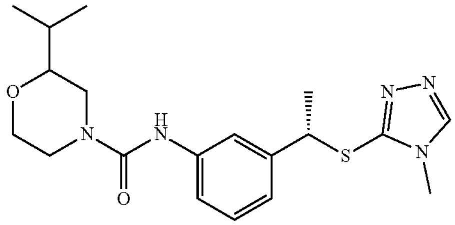 [SMILES: CC(C)C1CN(C(=O)Nc2cccc([C@H](C)Sc3nncn3C)c2)CCO1] |
| 52 | 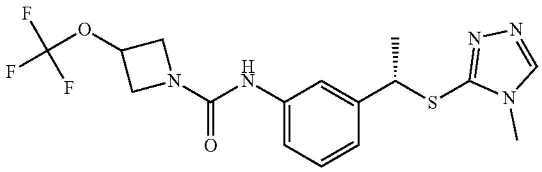 [SMILES: C[C@H](Sc1nncn1C)c1cccc(NC(=O)N2CC(OC(F)(F)F)C2)c1] |
| 53 | 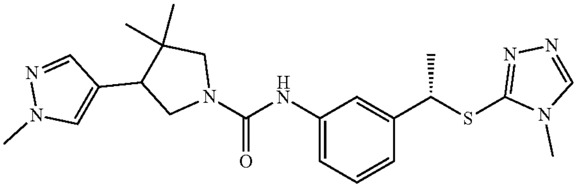 [SMILES: C[C@H](Sc1nncn1C)c1cccc(NC(=O)N2CC(c3cnn(C)c3)C(C)(C)C2)c1] |
| 54 | 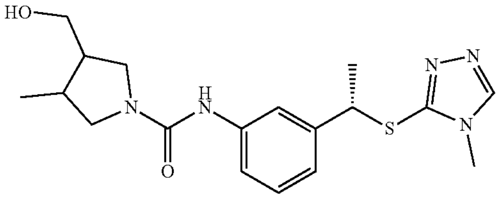 [SMILES: CC1CN(C(=O)Nc2cccc([C@H](C)Sc3nncn3C)c2)CC1CO] |
| 121 | 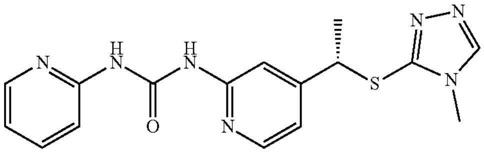 |
| 122 | 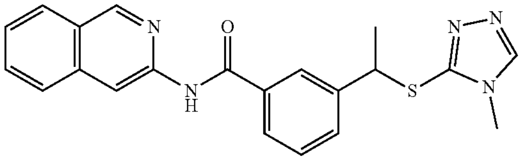 [SMILES: CC(Sc1nncn1C)c1cccc(C(=O)Nc2cc3ccccc3cn2)c1] |
| 123 | 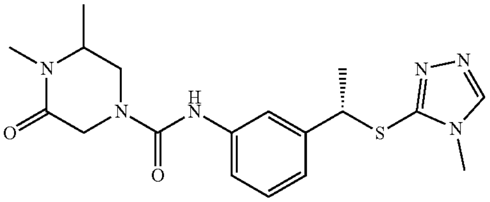 [SMILES: CC1CN(C(=O)Nc2cccc([C@H](C)Sc3nncn3C)c2)CC(=O)N1C] |

TABLE 1-continued
| Representative Compounds of Formula (I) | |
|---|---|
| Cmpd No. | Structure |
| 124 | 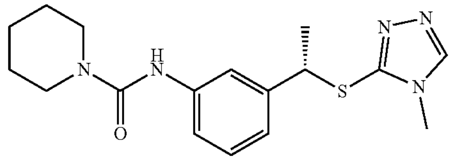 [SMILES: C[C@H](Sc1nncn1C)c1cccc(NC(=O)N2CCCCC2)c1] |
| 125 | 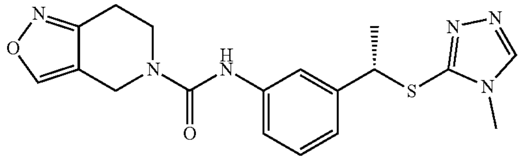 [SMILES: C[C@H](Sc1nncn1C)c1cccc(NC(=O)N2CCc3nocc3C2)c1] |
| 126 | 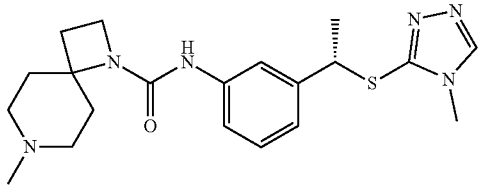 [SMILES: C[C@H](Sc1nncn1C)c1cccc(NC(=O)N2CCC23CCN(C)CC3)c1] |
| 127 | 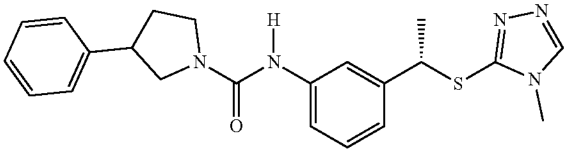 [SMILES: C[C@H](Sc1nncn1C)c1cccc(NC(=O)N2CCC(c3ccccc3)C2)c1] |
| 128 | 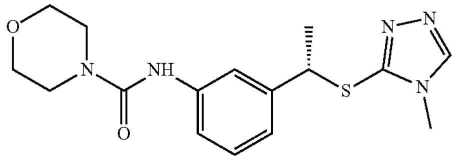 [SMILES: C[C@H](Sc1nncn1C)c1cccc(NC(=O)N2CCOCC2)c1] |
| 129 | 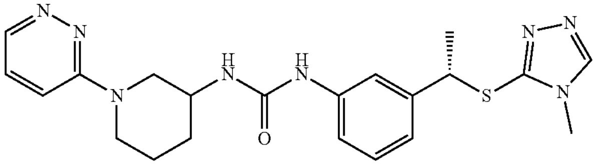 [SMILES: C[C@H](Sc1nncn1C)c1cccc(NC(=O)NC2CCCN(c3cccnn3)C2)c1] |
| 130 | 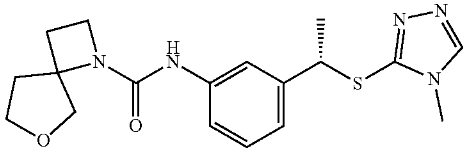 [SMILES: C[C@H](Sc1nncn1C)c1cccc(NC(=O)N2CCC23CCOC3)c1] |
| 131 | 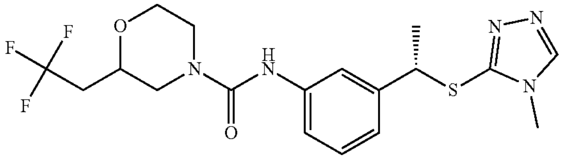 [SMILES: C[C@H](Sc1nncn1C)c1cccc(NC(=O)N2CCOC(CC(F)(F)F)C2)c1] |
| 132 | 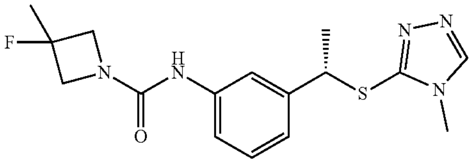 [SMILES: C[C@H](Sc1nncn1C)c1cccc(NC(=O)N2CC(C)(F)C2)c1] |

TABLE 1-continued
| Representative Compounds of Formula (I) | |
|---|---|
| Cmpd No. | Structure |
| 133 | 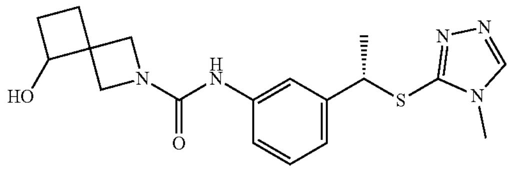 [SMILES: C[C@H](Sc1nncn1C)c1cccc(NC(=O)N2CC3(CCC3O)C2)c1] |
| 134 | 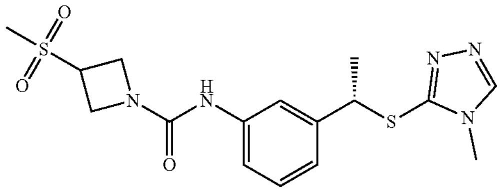 [SMILES: C[C@H](Sc1nncn1C)c1cccc(NC(=O)N2CC(S(C)(=O)=O)C2)c1] |
| 135 | 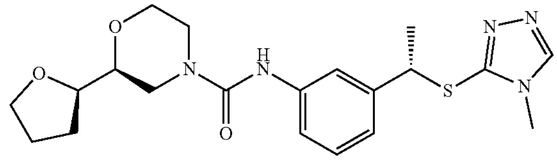 [SMILES: C[C@H](Sc1nncn1C)c1cccc(NC(=O)N2CCO[C@H]([C@H]3CCCO3)C2)c1] |
| 136 | 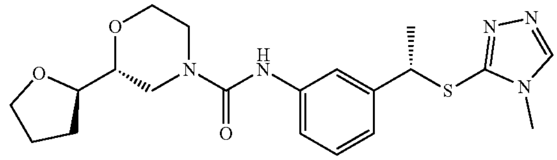 [SMILES: C[C@H](Sc1nncn1C)c1cccc(NC(=O)N2CCO[C@@H]([C@H]3CCCO3)C2)c1] |
| 137 | 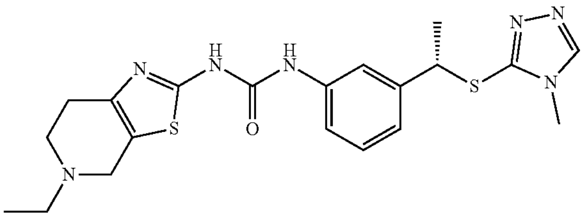 [SMILES: CCN1CCc2nc(NC(=O)Nc3cccc([C@H](C)Sc4nncn4C)c3)sc2C1] |
| 138 | 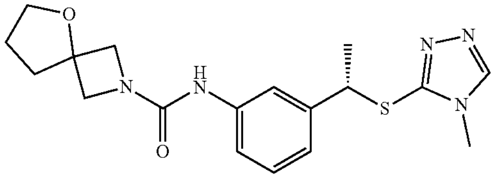 [SMILES: C[C@H](Sc1nncn1C)c1cccc(NC(=O)N2CC3(CCCO3)C2)c1] |
| 139 | 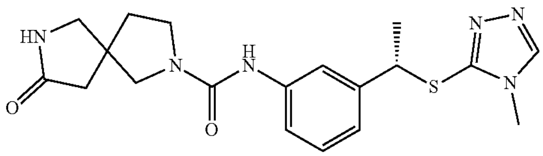 [SMILES: C[C@H](Sc1nncn1C)c1cccc(NC(=O)N2CCC3(CNC(=O)C3)C2)c1] |
| 140 | 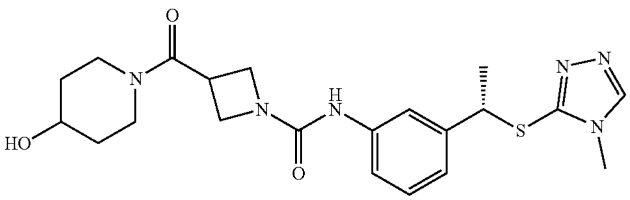 [SMILES: C[C@H](Sc1nncn1C)c1cccc(NC(=O)N2CC(C(=O)N3CCC(O)CC3)C2)c1] |

TABLE 1-continued
| Representative Compounds of Formula (I) | |
|---|---|
| Cmpd No. | Structure |
| 141 | 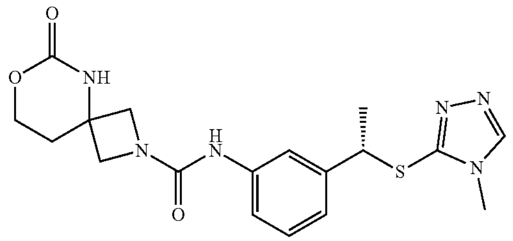 [SMILES: C[C@H](Sc1nncn1C)c1cccc(NC(=O)N2CC3(CCOC(=O)N3)C2)c1] |
| 142 | 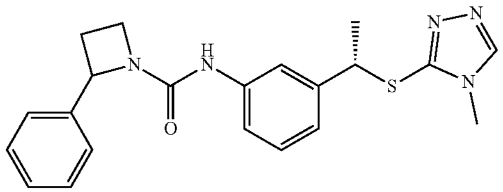 [SMILES: C[C@H](Sc1nncn1C)c1cccc(NC(=O)N2CCC2c2ccccc2)c1] |
| 143 | 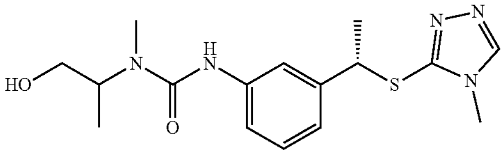 [SMILES: CC(CO)N(C)C(=O)Nc1cccc([C@H](C)Sc2nncn2C)c1] |
| 144 | 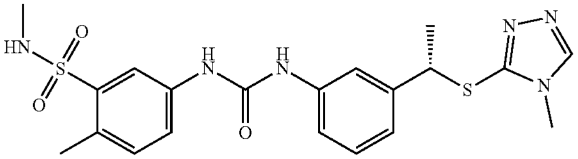 [SMILES: CNS(=O)(=O)c1cc(NC(=O)Nc2cccc([C@H](C)Sc3nncn3C)c2)ccc1C] |
| 145 | 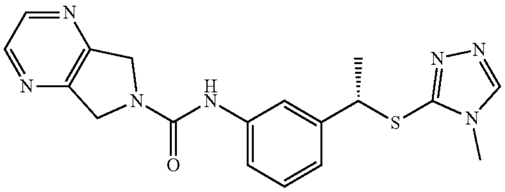 [SMILES: C[C@H](Sc1nncn1C)c1cccc(NC(=O)N2Cc3nccnc3C2)c1] |
| 146 | 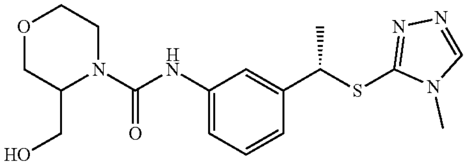 [SMILES: C[C@H](Sc1nncn1C)c1cccc(NC(=O)N2CCOCC2CO)c1] |
| 147 | 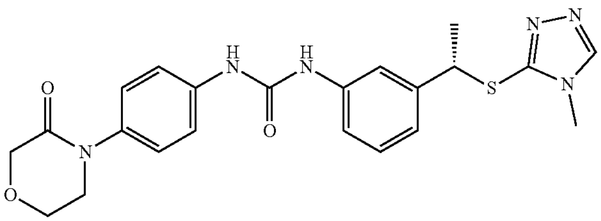 [SMILES: C[C@H](Sc1nncn1C)c1cccc(NC(=O)Nc2ccc(N3CCOCC3=O)cc2)c1] |

TABLE 1-continued
| Representative Compounds of Formula (I) | |
|---|---|
| Cmpd No. | Structure |
| 148 | 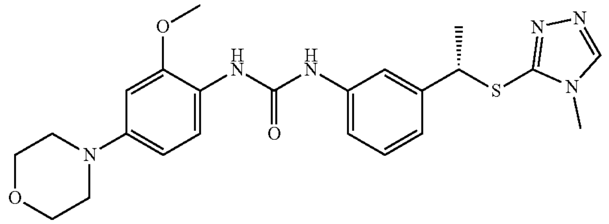 [SMILES: COc1cc(N2CCOCC2)ccc1NC(=O)Nc1cccc([C@H](C)Sc2nncn2C)c1] |
| 149 | 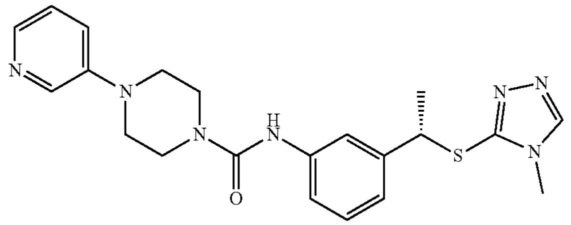 [SMILES: C[C@H](Sc1nncn1C)c1cccc(NC(=O)N2CCN(c3cccnc3)CC2)c1] |
| 150 | 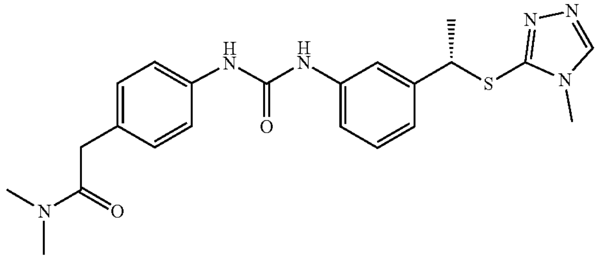 [SMILES: C[C@H](Sc1nncn1C)c1cccc(NC(=O)Nc2ccc(CC(=O)N(C)C)cc2)c1] |
| 151 | 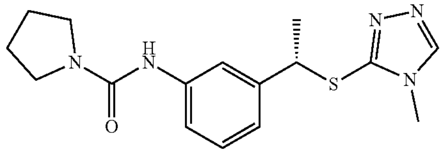 [SMILES: C[C@H](Sc1nncn1C)c1cccc(NC(=O)N2CCCC2)c1] |
| 152 | 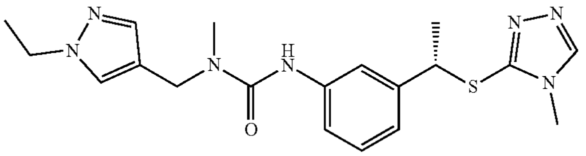 [SMILES: CCn1cc(CN(C)C(=O)Nc2cccc([C@H](C)Sc3nncn3C)c2)cn1] |
| 153 | 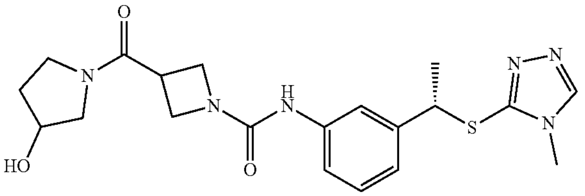 [SMILES: C[C@H](Sc1nncn1C)c1cccc(NC(=O)N2CC(C(=O)N3CCC(O)C3)C2)c1] |
| 154 | 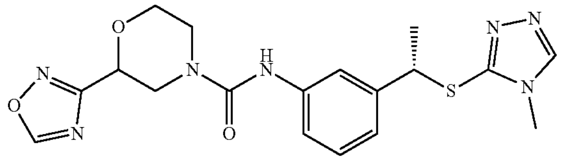 [SMILES: C[C@H](Sc1nncn1C)c1cccc(NC(=O)N2CCOC(c3ncon3)C2)c1] |

TABLE 1-continued
| Representative Compounds of Formula (I) | |
|---|---|
| Cmpd No. | Structure |
| 155 | 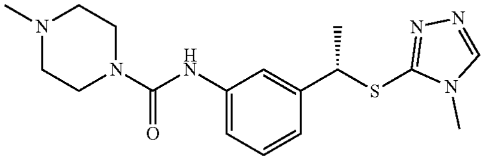 [SMILES: C[C@H](Sc1nncn1C)c1cccc(NC(=O)N2CCN(C)CC2)c1] |
| 156 | 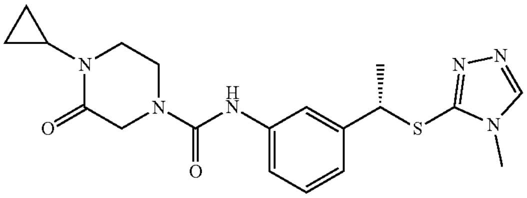 [SMILES: C[C@H](Sc1nncn1C)c1cccc(NC(=O)N2CCN(C3CC3)C(=O)C2)c1] |
| 157 | 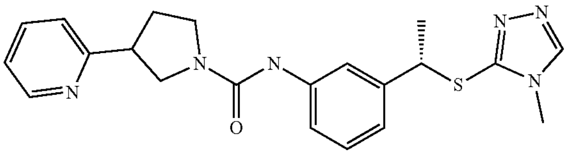 |
| 158 | 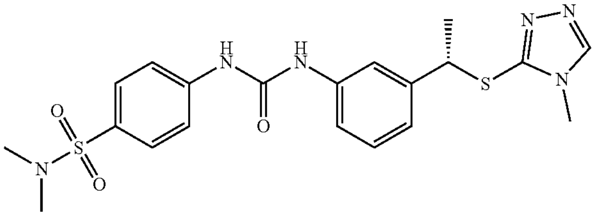 [SMILES: C[C@H](Sc1nncn1C)c1cccc(NC(=O)Nc2ccc(S(=O)(=O)N(C)C)cc2)c1] |
| 159 | 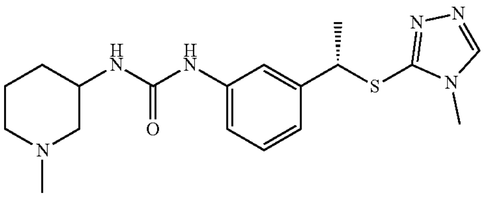 [SMILES: C[C@H](Sc1nncn1C)c1cccc(NC(=O)NC2CCCN(C)C2)c1] |
| 160 | 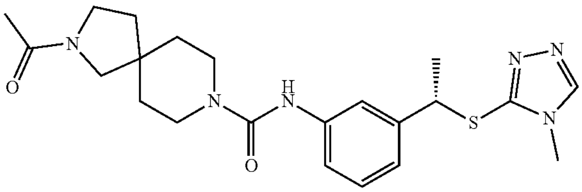 [SMILES: CC(=O)N1CCC2(CCN(C(=O)Nc3cccc([C@H](C)Sc4nncn4C)c3)CC2)C1] |
| 161 | 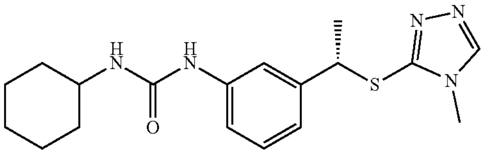 [SMILES: C[C@H](Sc1nncn1C)c1cccc(NC(=O)NC2CCCCC2)c1] |
| 162 | 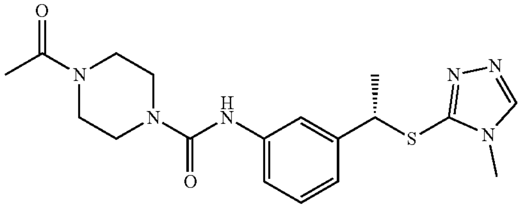 [SMILES: CC(=O)N1CCN(C(=O)Nc2cccc([C@H](C)Sc3nncn3C)c2)CC1] |

TABLE 1-continued

Representative Compounds of Formula (I)

| Cmpd No. | Structure |
| --- | --- |
| 163 | 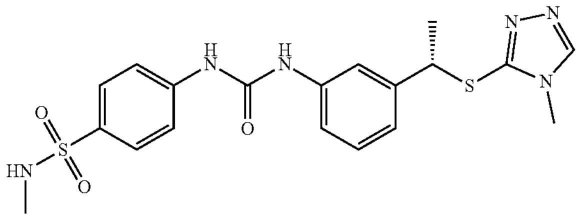 [SMILES: CNS(=O)(=O)c1ccc(NC(=O)Nc2cccc([C@H](C)Sc3nncn3C)c2)cc1] |
| 164 | 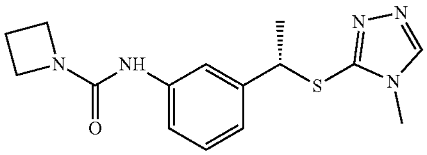 [SMILES: C[C@H](Sc1nncn1C)c1cccc(NC(=O)N2CCC2)c1] |
| 165 | 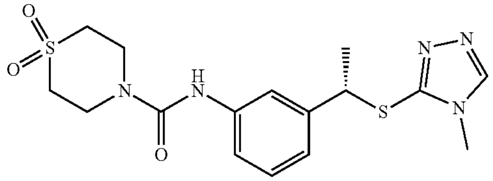 [SMILES: C[C@H](Sc1nncn1C)c1cccc(NC(=O)N2CCS(=O)(=O)CC2)c1] |
| 166 | 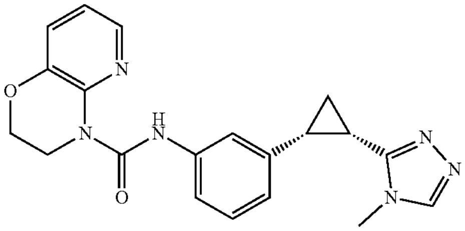 [SMILES: Cn1cnnc1[C@H]1C[C@H]1c1cccc(NC(=O)N2CCOc3cccnc32)c1] |

In some embodiments, provided is a compound selected from Compounds Nos. 1-54 and 121-166 in Table 1, or a tautomer thereof, or a pharmaceutically acceptable salt thereof.

In another aspect, provided is a compound of Formula (II):

(II)

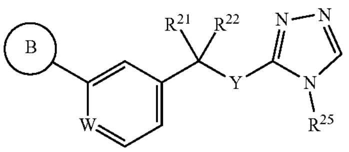

or a tautomer thereof, or a pharmaceutically acceptable salt thereof, wherein:

$R^{21}$ and $R^{22}$ are independently H, $C_1$-$C_6$ alkyl, halo, $C_1$-$C_6$ haloalkyl, or $C_3$-$C_6$ cycloalkyl, provided that $R^{21}$ and $R^{22}$ are not halo when Y is S or a bond;

or $R^{2'}$ and $R^{22}$ are taken together with the carbon atom to which they are attached to form

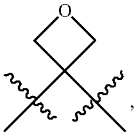 , 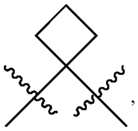 , or 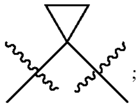 ;

Y is $CR^{23}R^{24}$, S, or a bond;

$R^{23}$ and $R^{24}$ are independently H, halo, $C_1$-$C_6$ alkyl, or $C_1$-$C_6$ haloalkyl;

or $R^{21}$ and $R^{23}$ are taken together with the carbon atoms to which they are attached to form the moiety

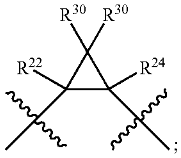 ;

$R^{25}$ is $C_1$-$C_6$ alkyl, $C_1$-$C_6$ haloalkyl, or $C_3$-$C_6$ cycloalkyl;

W is CH or N;

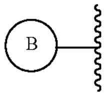

is selected from the group consisting of

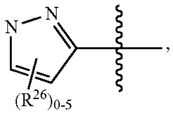, 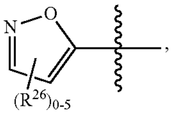, 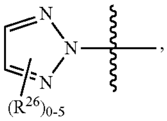, 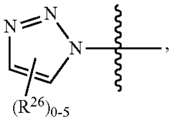, 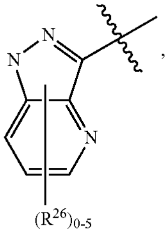, and 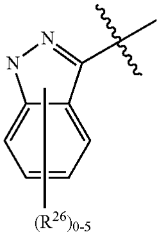, wherein the nitrogen atoms, where necessary to complete the valency, are bound to H when not substituted by $R^{26}$;

each $R^{26}$ is independently $C_1$-$C_6$ alkyl, $C_1$-$C_6$ haloalkyl, $C_1$-$C_6$ alkyl-OH, $C_1$-$C_6$ alkyl-CN, —$(CR^{28}R^{29})_p$-(4- to 6-membered heterocyclyl), —$(CR^{28}R^{29})_p$-(5- to 6-membered heteroaryl), —$(CR^{28}R^{29})_p$—($C_6$-$C_{10}$ aryl), or —$(CR^{28}R^{29})_p$—($C_3$-$C_6$ cycloalkyl), wherein each cycloalkyl, heterocyclyl, heteroaryl, or aryl group is optionally substituted by 1-5 $R^{27}$ groups; each $R^{27}$ is independently $C_1$-$C_6$ alkyl, $C_1$-$C_6$ alkyl-OH, $C_1$-$C_6$ haloalkyl, $C_1$-$C_6$ alkyl-CN, —CN, halo, hydroxy, —O—($C_1$-$C_6$ alkyl), —O($C_1$-$C_6$ haloalkyl), oxo, —C(O)$NH_2$, —C(O)NH($C_1$-$C_6$ alkyl), —C(O)N($C_1$-$C_6$ alkyl)$_2$, —C(O)NH($C_1$-$C_6$ haloalkyl), —$CO_2$H, —C(O)O($C_1$-$C_6$ alkyl), —$SO_2$—($C_1$-$C_6$ alkyl), —$SO_2$—NH($C_1$-$C_6$ alkyl), —$SO_2$—N($C_1$-$C_6$ alkyl)$_2$, —C(O)($C_1$-$C_6$ alkyl), —($C_1$-$C_6$ alkylene)-C(O)N($C_1$-$C_6$ alkyl)$_2$, or —($C_1$-$C_6$ alkylene)-C(O)NH($C_1$-$C_6$ alkyl);

p is zero or one;

$R^{28}$ and $R^{29}$ are independently H, $C_1$-$C_6$ alkyl, or $C_1$-$C_6$ haloalkyl; and each $R^{30}$ is independently H, $C_1$-$C_3$ alkyl, $C_1$-$C_3$ haloalkyl, or $C_1$-$C_3$ alkyl-OH.

In some embodiments,

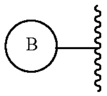

(i.e., the Ring B moiety) is selected from the group consisting of

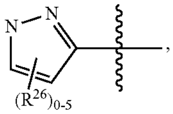, 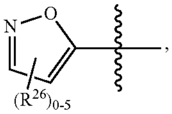, 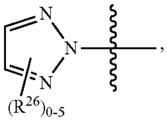,

-continued

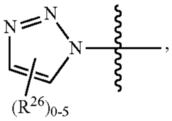, 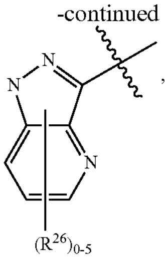, and 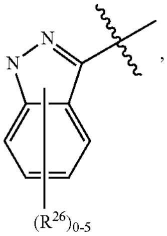, wherein the nitrogen atoms, where necessary to complete the valency, are bound to H when not substituted by $R^{26}$. In some embodiments, the Ring B moiety is

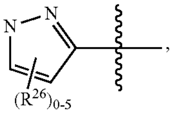, wherein the nitrogen atoms, where necessary to complete the valency, are bound to H when not substituted by $R^{26}$. In some embodiments, the Ring B moiety is

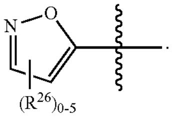.

In some embodiments, the Ring B moiety is

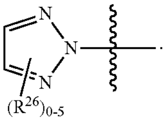.

In some embodiments, the Ring B moiety is

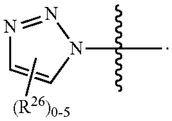.

In some embodiments, the Ring B moiety is

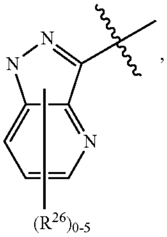, wherein the nitrogen atoms, where necessary to complete the valency, are bound to H when not substituted by $R^{26}$. In some embodiments, the Ring B moiety is

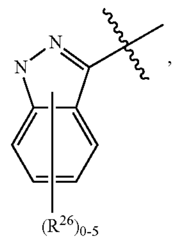

wherein the nitrogen atoms, where necessary to complete the valency, are bound to H when not substituted by $R^{26}$. In some embodiments, the Ring B moiety is substituted by 1-5 $R^{26}$ groups. In some embodiments, the Ring B moiety is substituted by one $R^{26}$ group. In some embodiments, the Ring B moiety is substituted by two $R^{26}$ groups. In some embodiments, the Ring B moiety is substituted by three $R^{26}$ groups. In some embodiments, the Ring B moiety is substituted by four $R^{26}$ groups. In some embodiments, the Ring B moiety is substituted by five $R^{26}$ groups. In some embodiments, the Ring B moiety is unsubstituted.

In some embodiments, $R^{21}$ and $R^{22}$ are independently H, $C_1$-$C_6$ alkyl, halo, $C_1$-$C_6$ haloalkyl, or $C_3$-$C_6$ cycloalkyl. In some embodiments, $R^{21}$ and $R^{22}$ are independently H, $C_1$-$C_3$ alkyl, halo, $C_1$-$C_3$ haloalkyl, or $C_3$-$C_5$ cycloalkyl. In some embodiments, $R^{21}$ and $R^{22}$ are independently H, —$CH_3$, F, —$CF_3$, or cyclobutyl.

In some embodiments, $R^{21}$ is H.

In some embodiments, $R^{21}$ is $C_1$-$C_6$ alkyl. In some embodiments, $R^{21}$ is $C_1$-$C_3$ alkyl. In some embodiments, $R^{21}$ is methyl, ethyl, n-propyl, or isopropyl. In some embodiments, $R^{21}$ is —$CH_3$.

In some embodiments, $R^{21}$ is halo. In some embodiments, $R^{21}$ is chloro, fluoro, or bromo. In some embodiments, $R^{21}$ is chloro or fluoro. In some embodiments, $R^{21}$ is fluoro.

In some embodiments, $R^{21}$ is $C_1$-$C_6$ haloalkyl. In some embodiments, $R^{21}$ is $C_1$-$C_6$ haloalkyl containing 1-7 halogen atoms. In some embodiments, $R^{21}$ is $C_1$-$C_3$ haloalkyl. In some embodiments, $R^{21}$ is $C_1$-$C_3$ haloalkyl containing 1-7 halogen atoms. In some embodiments, $R^{21}$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{21}$ is —$CF_3$, —$CCl_3$, —$CF_2Cl$, —$CFCl_2$, —$CHF_2$, —$CH_2F$, —$CHCl_2$, or —CHFCl. In some embodiments, $R^{21}$ is —$CF_3$.

In some embodiments, $R^{21}$ is $C_3$-$C_6$ cycloalkyl. In some embodiments, $R^{21}$ is $C_3$-$C_5$ cycloalkyl. In some embodiments, $R^{21}$ is $C_3$-$C_4$ cycloalkyl. In some embodiments, $R^{21}$ is cyclopropyl, cyclobutyl, or cyclopentyl. In some embodiments, $R^{21}$ is cyclopropyl. In some embodiments, $R^{21}$ is cyclobutyl.

In some embodiments, $R^{22}$ is H.

In some embodiments, $R^{22}$ is $C_1$-$C_6$ alkyl. In some embodiments, $R^{22}$ is $C_1$-$C_3$ alkyl. In some embodiments, $R^{22}$ is methyl, ethyl, n-propyl, or isopropyl. In some embodiments, $R^{22}$ is —$CH_3$.

In some embodiments, $R^{22}$ is halo. In some embodiments, $R^{22}$ is chloro, fluoro, or bromo. In some embodiments, $R^{22}$ is chloro or fluoro. In some embodiments, $R^{22}$ is fluoro.

In some embodiments, one of $R^{21}$ and $R^{22}$ is halo provided that Y is $CR^{23}R^{24}$. In some embodiments, $R^{21}$ is halo provided that Y is $CR^{23}R^{24}$. In some embodiments, $R^{22}$ is halo provided that Y is $CR^{23}R^{24}$. In some embodiments, $R^{21}$ and $R^{22}$ are each halo provided that Y is $CR^{23}R^{24}$.

In some embodiments, $R^{22}$ is $C_1$-$C_6$ haloalkyl. In some embodiments, $R^{22}$ is $C_1$-$C_6$ haloalkyl containing 1-7 halogen atoms. In some embodiments, $R^{22}$ is $C_1$-$C_3$ haloalkyl. In some embodiments, $R^{22}$ is $C_1$-$C_3$ haloalkyl containing 1-7 halogen atoms. In some embodiments, $R^{22}$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{22}$ is —$CF_3$, —$CCl_3$, —$CF_2Cl$, —$CFCl_2$, —$CHF_2$, —$CH_2F$, —$CHCl_2$, or —CHFCl. In some embodiments, $R^{22}$ is —$CF_3$.

In some embodiments, $R^{22}$ is $C_3$-$C_6$ cycloalkyl. In some embodiments, $R^{22}$ is $C_3$-$C_5$ cycloalkyl. In some embodiments, $R^{22}$ is $C_3$-$C_4$ cycloalkyl. In some embodiments, $R^{22}$ is cyclopropyl, cyclobutyl, or cyclopentyl. In some embodiments, $R^{22}$ is cyclopropyl. In some embodiments, $R^{22}$ is cyclobutyl.

In some embodiments, $R^{21}$ is H and $R^{22}$ is $C_1$-$C_6$ alkyl. In some embodiments, $R^{21}$ is H and $R^{22}$ is $C_1$-$C_3$ alkyl. In some embodiments, $R^{21}$ is H and $R^{22}$ is methyl, ethyl, n-propyl, or isopropyl. In some embodiments, $R^{21}$ is H and $R^{22}$ is methyl. In some embodiments, $R^{21}$ and $R^{22}$ are each H. In some embodiments, $R^{21}$ is H and $R^{22}$ is $C_3$-$C_6$ cycloalkyl. In some embodiments, $R^{21}$ is H and $R^{22}$ is $C_3$-$C_5$ cycloalkyl. In some embodiments, $R^{21}$ is H and $R^{22}$ is cyclopropyl, cyclobutyl, or cyclopentyl. In some embodiments, $R^{21}$ is H and $R^{22}$ is cyclobutyl. In some embodiments, $R^{22}$ is H and $R^{21}$ is $C_1$-$C_6$ alkyl. In some embodiments, $R^{22}$ is H and $R^{21}$ is $C_1$-$C_3$ alkyl. In some embodiments, $R^{22}$ is H and $R^{21}$ is methyl, ethyl, n-propyl, or isopropyl. In some embodiments, $R^{22}$ is H and $R^{21}$ is methyl. In some embodiments, $R^{22}$ is H and $R^{21}$ is $C_3$-$C_6$ cycloalkyl. In some embodiments, $R^{22}$ is H and $R^{21}$ is $C_3$-$C_5$ cycloalkyl. In some embodiments, $R^{22}$ is H and $R^{21}$ is cyclopropyl, cyclobutyl, or cyclopentyl. In some embodiments, $R^{22}$ is H and $R^{21}$ is cyclobutyl.

In some embodiments, $R^{21}$ is halo, and $R^{22}$ is $C_1$-$C_6$ alkyl. In some embodiments, $R^{21}$ is halo (such as chloro, fluoro, or bromo), and $R^{22}$ is $C_1$-$C_3$ alkyl (such as methyl, ethyl, n-propyl, or isopropyl). In some embodiments, $R^{21}$ is fluoro and $R^{22}$ is methyl.

In some embodiments, $R^{22}$ is halo, and $R^{21}$ is $C_1$-$C_6$ alkyl. In some embodiments, $R^{22}$ is halo (such as chloro, fluoro, or bromo), and $R^{21}$ is $C_1$-$C_3$ alkyl (such as methyl, ethyl, n-propyl, or isopropyl). In some embodiments, $R^{22}$ is fluoro and $R^{21}$ is methyl.

In some embodiments, $R^{21}$ and $R^{22}$ are taken together with the carbon atom to which they are attached to form

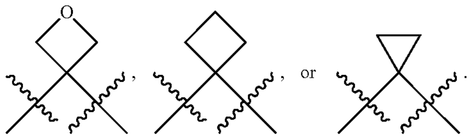 [SMILES: *C1(*)COC1 ; *C1(*)CCC1 ; *C1(*)CC1]

In some embodiments, $R^{21}$ and $R^{22}$ are taken together with the carbon atom to which they are attached to form

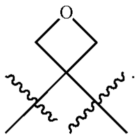 [SMILES: *C1(*)COC1]

In some embodiments, $R^{21}$ and $R^{22}$ are taken together with the carbon atom to which they are attached to form

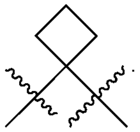 [SMILES: *C1(*)CCC1]

In some embodiments, $R^{21}$ and $R^{22}$ are taken together with the carbon atom to which they are attached to form

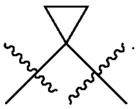 [SMILES: *C1(*)CC1]

In some embodiments, Y is $CR^{23}R^{24}$. In some embodiments, Y is S. In some embodiments, Y is a bond. When Y is S or a bond, neither $R^{21}$ nor $R^{22}$ is halo.

In some embodiments, $R^{23}$ and $R^{24}$ are independently H, $C_1$-$C_6$ alkyl, halo, or $C_1$-$C_6$ haloalkyl. In some embodiments, $R^{23}$ and $R^{24}$ are independently H, halo, $C_1$-$C_3$ alkyl, or $C_1$-$C_3$ haloalkyl. In some embodiments, $R^{23}$ and $R^{24}$ are independently H, F, —$CH_3$, or —$CF_3$.

In some embodiments, $R^{23}$ is H.

In some embodiments, $R^{23}$ is $C_1$-$C_6$ alkyl. In some embodiments, $R^{23}$ is $C_1$-$C_3$ alkyl. In some embodiments, $R^{23}$ is methyl, ethyl, n-propyl, or isopropyl. In some embodiments, $R^{23}$ is —$CH_3$.

In some embodiments, $R^{23}$ is halo. In some embodiments, $R^{23}$ is chloro, fluoro, or bromo. In some embodiments, $R^{23}$ is chloro or fluoro. In some embodiments, $R^{23}$ is fluoro.

In some embodiments, $R^{23}$ is $C_1$-$C_6$ haloalkyl. In some embodiments, $R^{23}$ is $C_1$-$C_6$ haloalkyl containing 1-7 halogen atoms. In some embodiments, $R^{23}$ is $C_1$-$C_3$ haloalkyl. In some embodiments, $R^{23}$ is $C_1$-$C_3$ haloalkyl containing 1-7 halogen atoms. In some embodiments, $R^{23}$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{23}$ is —$CF_3$, —$CCl_3$, —$CF_2Cl$, —$CFCl_2$, —$CHF_2$, —$CH_2F$, —$CHCl_2$, or —CHFCl. In some embodiments, $R^{23}$ is —$CF_3$.

In some embodiments, $R^{24}$ is H.

In some embodiments, $R^{24}$ is $C_1$-$C_6$ alkyl. In some embodiments, $R^{24}$ is $C_1$-$C_3$ alkyl. In some embodiments, $R^{24}$ is methyl, ethyl, n-propyl, or isopropyl. In some embodiments, $R^{24}$ is —$CH_3$.

In some embodiments, $R^{24}$ is halo. In some embodiments, $R^{24}$ is chloro, fluoro, or bromo. In some embodiments, $R^{24}$ is chloro or fluoro. In some embodiments, $R^{24}$ is fluoro.

In some embodiments, $R^{24}$ is $C_1$-$C_6$ haloalkyl. In some embodiments, $R^{24}$ is $C_1$-$C_6$ haloalkyl containing 1-7 halogen atoms. In some embodiments, $R^{24}$ is $C_1$-$C_3$ haloalkyl. In some embodiments, $R^{24}$ is $C_1$-$C_3$ haloalkyl containing 1-7 halogen atoms. In some embodiments, $R^{24}$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{24}$ is —$CF_3$, —$CCl_3$, —$CF_2Cl$, —$CFCl_2$, —$CHF_2$, —$CH_2F$, —$CHCl_2$, or —CHFCl. In some embodiments, $R^{24}$ is —$CF_3$.

In some embodiments, $R^{23}$ and $R^{24}$ are each H. In some embodiments, $R^{23}$ is H and $R^{24}$ is $C_1$-$C_6$ alkyl. In some embodiments, $R^{23}$ is H and $R^{24}$ is $C_1$-$C_3$ alkyl. In some embodiments, $R^{23}$ is H and $R^{24}$ is methyl. In some embodiments, $R^{24}$ is H and $R^{23}$ is $C_1$-$C_6$ alkyl. In some embodiments, $R^{24}$ is H and $R^{23}$ is $C_1$-$C_3$ alkyl. In some embodiments, $R^{24}$ is H and $R^{23}$ is methyl.

In some embodiments, $R^{23}$ and $R^{24}$ are each independently halo. In some embodiments, $R^{23}$ is fluoro, and $R^{24}$ is fluoro, chloro, or bromo. In some embodiments, $R^{24}$ is fluoro, and $R^{23}$ is fluoro, chloro, or bromo. In some embodiments, $R^{23}$ and $R^{24}$ are each fluoro.

In some embodiments, $R^{21}$ and $R^{23}$ are taken together with the carbon atoms to which they are attached to form the moiety

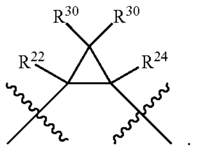

In some embodiments, $R^{22}$ is H, $C_1$-$C_6$ alkyl, halo, or $C_1$-$C_6$ haloalkyl; $R^{24}$ is H, $C_1$-$C_6$ alkyl, halo, or $C_1$-$C_6$ haloalkyl; and each $R^{30}$ is independently H, $C_1$-$C_3$ alkyl, $C_1$-$C_3$ haloalkyl, or $C_1$-$C_3$ alkyl-OH. In some embodiments, $R^{22}$ is H, $C_1$-$C_3$ alkyl, halo, or $C_1$-$C_3$ haloalkyl; $R^{24}$ is H, $C_1$-$C_3$ alkyl, halo, or $C_1$-$C_3$ haloalkyl; and each $R^{30}$ is independently H, $C_1$-$C_2$ alkyl, $C_1$-$C_2$ haloalkyl, or $C_1$-$C_2$ alkyl-OH. In some embodiments, $R^{22}$ is H, —$CH_3$, F, or —$CF_3$; $R^{24}$ is H, —$CH_3$, F, or —$CF_3$; and each $R^{30}$ is independently H, —$CH_3$, —$CF_3$, or —$CH_2OH$. In some embodiments, $R^{22}$ and $R^{24}$ are each H; and each $R^{30}$ is H.

In some embodiments, W is CH. In some embodiments, W is N.

In some embodiments, $R^{25}$ is $C_1$-$C_6$ alkyl, $C_1$-$C_6$ haloalkyl, or $C_3$-$C_6$ cycloalkyl. In some embodiments, $R^{25}$ is $C_1$-$C_3$ alkyl, $C_1$-$C_3$ haloalkyl, or $C_3$-$C_4$ cycloalkyl. In some embodiments, $R^{25}$ is —$CH_3$, —$CHF_2$, or cyclopropyl.

In some embodiments, $R^{25}$ is $C_1$-$C_6$ alkyl. In some embodiments, $R^{25}$ is $C_1$-$C_3$ alkyl. In some embodiments, $R^{25}$ is methyl, ethyl, n-propyl, or isopropyl. In some embodiments, $R^{25}$ is —$CH_3$.

In some embodiments, $R^{25}$ is $C_1$-$C_6$ haloalkyl. In some embodiments, $R^{25}$ is $C_1$-$C_6$ haloalkyl containing 1-7 halogen atoms. In some embodiments, $R^{25}$ is $C_1$-$C_3$ haloalkyl. In some embodiments, $R^{25}$ is $C_1$-$C_3$ haloalkyl containing 1-7 halogen atoms. In some embodiments, $R^{25}$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{25}$ is $-CF_3$, $-CCl_3$, $-CF_2Cl$, $-CFCl_2$, $-CHF_2$, $-CH_2F$, $-CHCl_2$, or $-CHFCl$. In some embodiments, $R^{25}$ is $-CHF_2$.

In some embodiments, $R^{25}$ is $C_3$-$C_6$ cycloalkyl. In some embodiments, $R^{25}$ is $C_3$-$C_5$ cycloalkyl. In some embodiments, $R^{25}$ is $C_3$-$C_4$ cycloalkyl. In some embodiments, $R^{25}$ is cyclopropyl, cyclobutyl, or cyclopentyl. In some embodiments, $R^{25}$ is cyclopropyl.

In some embodiments, each $R^{26}$ is independently $C_1$-$C_6$ alkyl, $C_1$-$C_6$ haloalkyl, $C_1$-$C_6$ alkyl-OH, $C_1$-$C_6$ alkyl-CN, $-(CR^{28}R^{29})_p$-(4- to 6-membered heterocyclyl), $-(CR^{28}R^{29})_p$-(5- to 6-membered heteroaryl), $-(CR^{28}R^{29})_p-(C_6$-$C_{10}$ aryl), or $-(CR^{28}R^{29})_p-(C_3$-$C_6$ cycloalkyl), wherein each cycloalkyl, heterocyclyl, heteroaryl, or aryl group is optionally substituted by 1-5 $R^{27}$ groups. In some embodiments, each $R^{26}$ is independently $C_1$-$C_3$ alkyl, $C_1$-$C_3$ haloalkyl, $C_1$-$C_3$ alkyl-OH, $C_1$-$C_3$ alkyl-CN, $-(CR^{28}R^{29})_p$-(4- to 6-membered heterocyclyl), $-(CR^{28}R^{29})_p$-(5- to 6-membered heteroaryl), $-(CR^{28}R^{29})_p-(C_6$-$C_{10}$ aryl), or $-(CR^{28}R^{29})_p-(C_3$-$C_6$ cycloalkyl), wherein each heterocyclyl, heteroaryl, aryl, or cycloalkyl group is optionally substituted by 1-5 $R^{27}$ groups.

In some embodiments, $R^{26}$ is $C_1$-$C_6$ alkyl. In some embodiments, $R^{26}$ is $C_1$-$C_3$ alkyl. In some embodiments, $R^{26}$ is methyl, ethyl, n-propyl, or isopropyl. In some embodiments, $R^{26}$ is $-CH_3$.

In some embodiments, $R^{26}$ is $C_1$-$C_6$ haloalkyl. In some embodiments, $R^{26}$ is $C_1$-$C_6$ haloalkyl containing 1-7 halogen atoms. In some embodiments, $R^{26}$ is $C_1$-$C_3$ haloalkyl. In some embodiments, $R^{26}$ is $C_1$-$C_3$ haloalkyl containing 1-7 halogen atoms. In some embodiments, $R^{26}$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{26}$ is $-CF_3$, $-CCl_3$, $-CF_2Cl$, $-CFCl_2$, $-CHF_2$, $-CH_2F$, $-CHCl_2$, or $-CHFCl$. In some embodiments, $R^{26}$ is $-CF_3$.

In some embodiments, $R^{26}$ is $C_1$-$C_6$ alkyl-OH. In some embodiments, $R^{26}$ is $C_1$-$C_3$ alkyl-OH. In some embodiments, $R^{26}$ is $-CH_2OH$, $-CH_2CH_2OH$, $-CH_2CH_2CH_2OH$, or $-C(CH_3)_2OH$. In some embodiments, $R^{26}$ is $-CH_2OH$.

In some embodiments, $R^{26}$ is $C_1$-$C_6$ alkyl-CN. In some embodiments, $R^{26}$ is $C_1$-$C_3$ alkyl-CN. In some embodiments, $R^{26}$ is $-CH_2CN$, $-CH_2CH_2CN$, $-CH_2CH_2CH_2CN$, or $-C(CH_3)_2CN$. In some embodiments, $R^{26}$ is $-CH_2CN$.

In some embodiments, $R^{26}$ is $-(CR^{28}R^{29})_p$-(4- to 6-membered heterocyclyl), wherein the heterocyclyl is optionally substituted by 1-5 $R^{27}$ groups. In some embodiments, p is zero and $R^{26}$ is 4- to 6-membered heterocyclyl optionally substituted by 1-5 $R^{27}$ groups. In some embodiments, p is one and $R^{26}$ is $-CR^{28}R^{29}$-(4- to 6-membered heterocyclyl), wherein the heterocyclyl is optionally substituted by 1-5 $R^{27}$ groups. In some embodiments, the heterocyclyl contains 1-3 nitrogen atoms. In some embodiments, the heterocyclyl contains one nitrogen atom. In some embodiments, the heterocyclyl contains two nitrogen atoms. In some embodiments, the heterocyclyl contains 1-2 nitrogen atoms and one sulfur atom. In some embodiments, the heterocyclyl contains two nitrogen atoms and one sulfur atom. In some embodiments, the heterocyclyl contains 1-2 nitrogen atoms and one oxygen atoms. In some embodiments, the heterocyclyl contains one nitrogen atom and one oxygen atom. In some embodiments, the heterocyclyl contains one oxygen atom. In some embodiments, the heterocyclyl contains one sulfur atom. In some embodiments, the heterocyclyl is substituted by 1-5 $R^{27}$ groups. In some embodiments, the heterocyclyl is substituted by one $R^{27}$ group. In some embodiments, the heterocyclyl is substituted by two $R^{27}$ groups. In some embodiments, the heterocyclyl is substituted by three $R^{27}$ groups. In some embodiments, the heterocyclyl is substituted by four $R^{27}$ groups. In some embodiments, the heterocyclyl is substituted by five $R^{27}$ groups. In some embodiments, the heterocyclyl is unsubstituted. In some embodiments, the heterocyclyl is azetidinyl, pyrrolidinyl, piperidinyl, piperazinyl, oxetanyl, tetrahydrofuranyl, or morpholinyl. In some embodiments, $R^{26}$ is

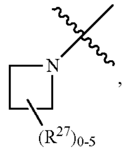,
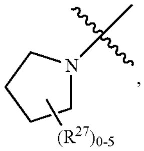,
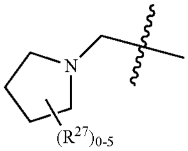, or
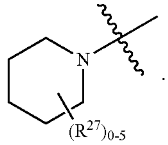.

In some embodiments, $R^{26}$ is $-(CR^{28}R^{29})_p$-(5- to 6-membered heteroaryl), wherein the heteroaryl is optionally substituted by 1-5 $R^{27}$ groups. In some embodiments, p is zero and $R^{26}$ is 5- to 6-membered heteroaryl optionally substituted by 1-5 $R^{27}$ groups. In some embodiments, p is one and $R^{26}$ is $-CR^{28}R^{29}$-(5- to 6-membered heteroaryl), wherein the heteroaryl is optionally substituted by 1-5 $R^{27}$ groups. In some embodiments, the heteroaryl contains 1-3 nitrogen atoms. In some embodiments, the heteroaryl contains one nitrogen atom. In some embodiments, the heteroaryl contains two nitrogen atoms. In some embodiments, the heteroaryl contains 1-2 nitrogen atoms and one sulfur atom. In some embodiments, the heteroaryl contains two nitrogen atoms and one sulfur atom. In some embodiments, the heteroaryl contains 1-2 nitrogen atoms and one oxygen atoms. In some embodiments, the heteroaryl contains one nitrogen atom and one oxygen atom. In some embodiments, the heteroaryl contains one oxygen atom. In some embodiments, the heteroaryl contains one sulfur atom. In some embodiments, the heteroaryl is substituted by 1-5 $R^{27}$ groups. In some embodiments, the heteroaryl is substituted by one $R^{27}$ group. In some embodiments, the heteroaryl is substituted by two $R^{27}$ groups. In some embodiments, the heteroaryl is substituted by three $R^{27}$ groups. In some embodiments, the heteroaryl is substituted by four $R^{27}$ groups. In some embodiments, the heteroaryl is substituted by five $R^{27}$ groups. In some embodiments, the heteroaryl is unsubstituted. In some embodiments, the heteroaryl is pyridinyl, pyrazinyl, pyrimidinyl, pyridazinyl, triazinyl, furanyl, pyrrolyl, imidazolyl, pyrazolyl, oxazolyl, or thiazolyl. In some embodiments, $R^{26}$ is

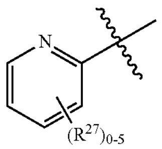 or 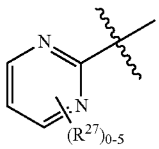 .

In some embodiments, $R^{26}$ is $—(CR^{28}R^{29})_p—(C_6\text{-}C_{10}$ aryl), wherein the aryl is optionally substituted by 1-5 $R^{27}$ groups. In some embodiments, p is zero and $R^{26}$ is $C_6\text{-}C_{10}$ aryl, wherein the aryl is optionally substituted by 1-5 $R^{27}$ groups. In some embodiments, p is one and $R^{26}$ is $—CR^{28}R^{29}—(C_6\text{-}C_{10}$ aryl), wherein the aryl is optionally substituted by 1-5 $R^{27}$ groups. In some embodiments, $R^{26}$ is $—(CR^{28}R^{29})_p—(C_6$ aryl), wherein the aryl is optionally substituted by 1-5 $R^{27}$ groups. In some embodiments, p is zero and $R^{26}$ is $C_6$ aryl, wherein the aryl is optionally substituted by 1-5 $R^{27}$ groups. In some embodiments, the aryl is a monocyclic aromatic ring. In some embodiments, the aryl is a fused bicyclic ring. In some embodiments, the aryl contains an aromatic ring fused to a second aromatic ring. In some embodiments, the aryl contains an aromatic ring fused to a saturated or partially unsaturated ring. In some embodiments, the aryl is substituted by 1-5 $R^{27}$ groups. In some embodiments, the aryl is substituted by one $R^{27}$ group. In some embodiments, the aryl is substituted by two $R^{27}$ groups. In some embodiments, the aryl is substituted by three $R^{27}$ groups. In some embodiments, the aryl is substituted by four $R^{27}$ groups. In some embodiments, the aryl is substituted by five $R^{27}$ groups. In some embodiments, the aryl is unsubstituted. In some embodiments, the aryl is phenyl. In some embodiments, $R^{26}$ is

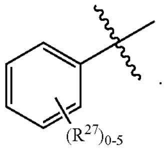 .

In some embodiments, $R^{26}$ is $—(CR^{28}R^{29})P—(C_3\text{-}C_6$ cycloalkyl), wherein the cycloalkyl is optionally substituted by 1-5 $R^{27}$ groups. In some embodiments, p is zero and $R^{26}$ is $C_3\text{-}C_6$ cycloalkyl optionally substituted by 1-5 $R^{27}$ groups. In some embodiments, p is one and $R^{26}$ is $—CR^{28}R^{29}—(C_3\text{-}C_6$ cycloalkyl), wherein the cycloalkyl is optionally substituted by 1-5 $R^{27}$ groups. In some embodiments, the cycloalkyl is substituted by 1-5 $R^{27}$ groups. In some embodiments, the cycloalkyl is substituted by one $R^{27}$ group. In some embodiments, the cycloalkyl is substituted by two $R^{27}$ groups. In some embodiments, the cycloalkyl is substituted by three $R^{27}$ groups. In some embodiments, the cycloalkyl is substituted by four $R^{27}$ groups. In some embodiments, the cycloalkyl is substituted by five $R^{27}$ groups. In some embodiments, the cycloalkyl is unsubstituted. In some embodiments, the cycloalkyl is cyclopropyl, cyclobutyl, cyclopentyl, or cyclohexyl. In some embodiments, the cycloalkyl is cyclobutyl or cyclopentyl. In some embodiments, $R^{26}$ is

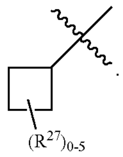 .

In some embodiments, each $R^{26}$ is independently $—CH_3$, $—CF_3$, $—CH_2OH$, $—CH_2CN$,

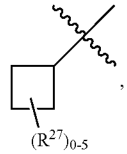 , 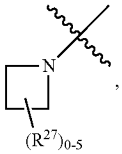 , 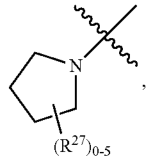 ,

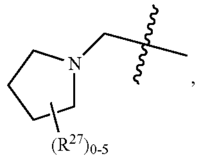 , 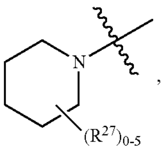 , 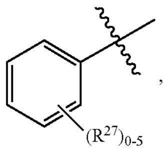 ,

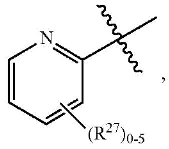 , or 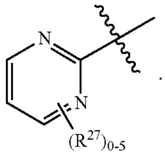 .

In some embodiments, p is zero. In some embodiments, p is one.

In some embodiments, $R^{28}$ and $R^{29}$ are independently H, $C_1\text{-}C_6$ alkyl, or $C_1\text{-}C_6$ haloalkyl. In some embodiments, $R^{28}$ and $R^{29}$ are independently H, $C_1\text{-}C_3$ alkyl, or $C_1\text{-}C_3$ haloalkyl. In some embodiments, $R^{28}$ and $R^{29}$ are independently H, $—CH_3$, or $—CF_3$.

In some embodiments, $R^{28}$ is H. In some embodiments, $R^{29}$ is H. In some embodiments, $R^{28}$ and $R^{29}$ are both H. In some embodiments, one of $R^{28}$ and $R^{29}$ is H, and the other is $C_1\text{-}C_6$ alkyl or $C_1\text{-}C_6$ haloalkyl. In some embodiments, one of $R^{28}$ and $R^{29}$ is H, and the other is $C_1\text{-}C_3$ alkyl or $C_1\text{-}C_3$ haloalkyl. In some embodiments, one of $R^{28}$ and $R^{29}$ is H, and the other is $—CH_3$ or $—CF_3$.

In some embodiments, $R^{28}$ and $R^{29}$ are independently $C_1\text{-}C_6$ alkyl. In some embodiments, $R^{28}$ and $R^{29}$ are independently $C_1\text{-}C_3$ alkyl. In some embodiments, $R^{28}$ and $R^{29}$ are independently methyl, ethyl, n-propyl, or isopropyl. In some embodiments, $R^{28}$ and $R^{29}$ are independently $—CH_3$. In some embodiments, $R^{28}$ and $R^{29}$ are both $—CH_3$.

In some embodiments, $R^{28}$ and $R^{29}$ are independently $C_1\text{-}C_6$ haloalkyl. In some embodiments, $R^{28}$ and $R^{29}$ are independently $C_1\text{-}C_6$ haloalkyl containing 1-7 halogen atoms. In some embodiments, $R^{28}$ and $R^{29}$ are independently $C_1\text{-}C_3$ haloalkyl. In some embodiments, $R^{28}$ and $R^{29}$ are independently $C_1\text{-}C_3$ haloalkyl containing 1-7 halogen atoms. In some embodiments, $R^{28}$ and $R^{29}$ are independently $C_1\text{-}C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{28}$ and $R^{29}$ are independently —$CF_3$, —$CCl_3$, —$CF_2Cl$, —$CFCl_2$, —$CHF_2$, —$CH_2F$, —$CHCl_2$, or —CHFCl. In some embodiments, $R^{28}$ and $R^{29}$ are independently —$CF_3$. In some embodiments, $R^{28}$ and $R^{29}$ are both —$CF_3$.

In some embodiments, each $R^{27}$ is independently $C_1$-$C_6$ alkyl, $C_1$-$C_6$ alkyl-OH, $C_1$-$C_6$ haloalkyl, $C_1$-$C_6$ alkyl-CN, —CN, halo, hydroxy, —O—($C_1$-$C_6$ alkyl), —O($C_1$-$C_6$ haloalkyl), oxo, —C(O)$NH_2$, —C(O)NH($C_1$-$C_6$ alkyl), —C(O)N($C_1$-$C_6$ alkyl)$_2$, —C(O)NH($C_1$-$C_6$ haloalkyl), —$CO_2H$, —C(O)O($C_1$-$C_6$ alkyl), —$SO_2$—($C_1$-$C_6$ alkyl), —$SO_2$—NH($C_1$-$C_6$ alkyl), —$SO_2$—N($C_1$-$C_6$ alkyl)$_2$, —C(O)($C_1$-$C_6$ alkyl), —($C_1$-$C_6$ alkylene)-C(O)N($C_1$-$C_6$ alkyl)$_2$, or —($C_1$-$C_6$ alkylene)-C(O)NH($C_1$-$C_6$ alkyl). In some embodiments, each $R^{27}$ is independently $C_1$-$C_3$ alkyl, $C_1$-$C_3$ alkyl-OH, $C_1$-$C_3$ haloalkyl, $C_1$-$C_3$ alkyl-CN, —CN, halo, hydroxy, —O—($C_1$-$C_3$ alkyl), —O($C_1$-$C_3$ haloalkyl), oxo, —C(O)$NH_2$, —C(O)NH($C_1$-$C_3$ alkyl), —C(O)NH($C_1$-$C_3$ haloalkyl), —C(O)N($C_1$-$C_3$ alkyl)$_2$, —$CO_2H$, —C(O)O($C_1$-$C_3$ alkyl), —$SO_2$—($C_1$-$C_3$ alkyl), —$SO_2$—NH($C_1$-$C_3$ alkyl), —$SO_2$—N($C_1$-$C_3$ alkyl)$_2$, —C(O)($C_1$-$C_3$ alkyl), —($C_1$-$C_3$ alkylene)-C(O)N($C_1$-$C_3$ alkyl)$_2$, or —($C_1$-$C_3$ alkylene)-C(O)NH($C_1$-$C_3$ alkyl). In some embodiments, each $R^{27}$ is independently —$CH_3$, —$CH_2OH$, —$CF_3$, —$CH_2CN$, —CN, F, Cl, hydroxy, —$OCH_3$, —$OCF_3$, oxo, —C(O)$NH_2$, —C(O)NH($CH_3$), —C(O)NH($CF_3$), —C(O)N($CH_3$)$_2$, —$CO_2H$, —C(O)$OCH_3$, —$SO_2$—($CH_3$), —$SO_2$—NH($CH_3$), —$SO_2$—N($CH_3$)$_2$, —C(O)($CH_3$), —($CH_2$)—C(O)N($CH_3$)$_2$, or —($CH_2$)—C(O)NH($CH_3$).

In some embodiments, $R^{27}$ is $C_1$-$C_6$ alkyl. In some embodiments, $R^{27}$ is $C_1$-$C_3$ alkyl. In some embodiments, $R^{27}$ is methyl, ethyl, n-propyl, or isopropyl. In some embodiments, $R^{27}$ is —$CH_3$.

In some embodiments, $R^{27}$ is $C_1$-$C_6$ alkyl-OH. In some embodiments, $R^{27}$ is $C_1$-$C_3$ alkyl-OH. In some embodiments, $R^{27}$ is —$CH_2OH$, —$CH_2CH_2OH$, —$CH_2CH_2CH_2OH$, or —C($CH_3$)$_2$OH. In some embodiments, $R^{27}$ is —$CH_2OH$.

In some embodiments, $R^{27}$ is —CN.

In some embodiments, $R^{27}$ is $C_1$-$C_6$ alkyl-CN. In some embodiments, $R^{27}$ is $C_1$-$C_3$ alkyl-CN. In some embodiments, $R^{27}$ is —$CH_2CN$, —$CH_2CH_2CN$, —$CH_2CH_2CH_2CN$, or —C($CH_3$)$_2$CN. In some embodiments, $R^{27}$ is —$CH_2CN$.

In some embodiments, $R^{27}$ is halo. In some embodiments, $R^{27}$ is chloro, fluoro, or bromo. In some embodiments, $R^{27}$ is chloro or fluoro. In some embodiments, $R^{27}$ is fluoro. In some embodiments, $R^{27}$ is chloro.

In some embodiments, $R^{27}$ is $C_1$-$C_6$ haloalkyl. In some embodiments, $R^{27}$ is $C_1$-$C_6$ haloalkyl containing 1-7 halogen atoms. In some embodiments, $R^{27}$ is $C_1$-$C_3$ haloalkyl. In some embodiments, $R^{27}$ is $C_1$-$C_3$ haloalkyl containing 1-7 halogen atoms. In some embodiments, $R^{27}$ is $C_1$-$C_3$ haloalkyl containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{27}$ is —$CF_3$, —$CCl_3$, —$CF_2Cl$, —$CFCl_2$, —$CHF_2$, —$CH_2F$, —$CHCl_2$, —CHFCl, —$CH_2CF_3$, —$CH_2CCl_3$, —$CH_2CH_2F$, or —$CH_2CH_2Cl$. In some embodiments, $R^{27}$ is —$CF_3$ or —$CHF_2$. In some embodiments, $R^{27}$ is —$CF_3$.

In some embodiments, $R^{27}$ is hydroxy.

In some embodiments, $R^{27}$ is —O($C_1$-$C_6$ alkyl). In some embodiments, $R^{27}$ is —O($C_1$-$C_3$ alkyl). In some embodiments, $R^{27}$ is —$OCH_3$, —$OCH_2CH_3$, —$OCH_2CH_2CH_3$, or —OCH($CH_3$)$_2$. In some embodiments, $R^{27}$ is —$OCH_3$.

In some embodiments, $R^{27}$ is —O($C_1$-$C_6$ haloalkyl). In some embodiments, $R^{27}$ is —O($C_1$-$C_6$ haloalkyl) containing 1-7 halogen atoms. In some embodiments, $R^{27}$ is —O($C_1$-$C_3$ haloalkyl). In some embodiments, $R^{27}$ is —O($C_1$-$C_3$ haloalkyl) containing 1-7 halogen atoms. In some embodiments, $R^{27}$ is —O($C_1$-$C_3$ haloalkyl) containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{27}$ is —$OCF_3$, —$OCCl_3$, —$OCF_2Cl$, —$OCFCl_2$, —$OCHF_2$, —$OCH_2F$, —$OCHCl_2$, —OCHFCl, —$OCH_2CF_3$, —$OCH_2CCl_3$, —$OCH_2CH_2F$, or —$OCH_2CH_2Cl$. In some embodiments, $R^{27}$ is —$OCF_3$.

In some embodiments, $R^{27}$ is oxo.

In some embodiments, $R^{27}$ is —C(O)$NH_2$.

In some embodiments, $R^{27}$ is —C(O)NH($C_1$-$C_6$ alkyl). In some embodiments, $R^{27}$ is —C(O)NH($C_1$-$C_3$ alkyl). In some embodiments, $R^{27}$ is —C(O)NH($CH_3$), —C(O)NH($CH_2CH_3$), —C(O)NH($CH_2CH_2CH_3$), or —C(O)NH(CH($CH_3$)$_2$). In some embodiments, $R^{27}$ is —C(O)NH($CH_3$).

In some embodiments, $R^{27}$ is —C(O)N($C_1$-$C_6$ alkyl)$_2$. In some embodiments, the two $C_1$-$C_6$ alkyl groups are the same. In other embodiments, the two $C_1$-$C_6$ alkyl groups are different. In some embodiments, $R^{27}$ is —C(O)N($C_1$-$C_3$ alkyl)$_2$. In some embodiments, $R^{27}$ is —C(O)N($CH_3$)$_2$, —C(O)N($CH_2CH_3$)$_2$, —C(O)N($CH_2CH_2CH_3$)$_2$, or —C(O)N(CH($CH_3$)$_2$)$_2$. In some embodiments, $R^{27}$ is —C(O)N($CH_3$)($CH_2CH_3$), —C(O)N($CH_3$)($CH_2CH_2CH_3$), —C(O)N($CH_3$)(CH($CH_3$)$_2$), —C(O)N($CH_2CH_3$)($CH_2CH_2CH_3$), or —C(O)N($CH_2CH_3$)(CH($CH_3$)$_2$). In some embodiments, $R^{27}$ is —C(O)N($CH_3$)$_2$.

In some embodiments, $R^{27}$ is —$CO_2H$.

In some embodiments, $R^{27}$ is —C(O)NH($C_1$-$C_6$ haloalkyl). In some embodiments, $R^{27}$ is —C(O)NH($C_1$-$C_6$ haloalkyl) containing 1-7 halogen atoms. In some embodiments, $R^{27}$ is —C(O)NH($C_1$-$C_3$ haloalkyl). In some embodiments, $R^{27}$ is —C(O)NH($C_1$-$C_3$ haloalkyl) containing 1-7 halogen atoms. In some embodiments, $R^{27}$ is —C(O)NH($C_1$-$C_3$ haloalkyl) containing 1-5 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{27}$ is —C(O)NH($CF_3$), —C(O)NH($CHF_2$), —C(O)NH($CCl_3$), —C(O)NH($CF_2Cl$), —C(O)NH($CFCl_2$), —C(O)NH($CH_2F$), —C(O)NH($CHCl_2$), or —C(O)NH(CHFCl). In some embodiments, $R^{27}$ is —C(O)NH($CF_3$).

In some embodiments, $R^{27}$ is —C(O)O($C_1$-$C_6$ alkyl). In some embodiments, $R^{27}$ is —C(O)O($C_1$-$C_3$ alkyl). In some embodiments, $R^{27}$ is —C(O)O($CH_3$), —C(O)O($CH_2CH_3$), —C(O)O($CH_2CH_2CH_3$), or —C(O)O(CH($CH_3$)$_2$). In some embodiments, $R^{27}$ is —C(O)O($CH_3$).

In some embodiments, $R^{27}$ is —$SO_2$—($C_1$-$C_6$ alkyl). In some embodiments, $R^{27}$ is —$SO_2$—($C_1$-$C_3$ alkyl). In some embodiments, $R^{27}$ is —$SO_2$—($CH_3$), —$SO_2$—($CH_2CH_3$), —$SO_2$—($CH_2CH_2CH_3$), or —$SO_2$—($CH(CH_3)_2$). In some embodiments, $R^{27}$ is —$SO_2$—($CH_3$).

In some embodiments, $R^{27}$ is —$SO_2$—NH($C_1$-$C_6$ alkyl). In some embodiments, $R^{27}$ is —$SO_2$—NH($C_1$-$C_3$ alkyl). In some embodiments, $R^{27}$ is —$SO_2$—NH($CH_3$), —$SO_2$—NH($CH_2CH_3$), —$SO_2$—NH($CH_2CH_2CH_3$), or —$SO_2$—NH($CH(CH_3)_2$). In some embodiments, $R^{27}$ is —$SO_2$—NH($CH_3$).

In some embodiments, $R^{27}$ is —$SO_2$—N($C_1$-$C_6$ alkyl)$_2$. In some embodiments, the two $C_1$-$C_6$ alkyl groups are the same. In other embodiments, the two $C_1$-$C_6$ alkyl groups are different. In some embodiments, $R^{27}$ is —$SO_2$—N($C_1$-$C_3$ alkyl)$_2$. In some embodiments, $R^{27}$ is —$SO_2$—N$(CH_3)_2$, —$SO_2$—N$(CH_2CH_3)_2$, —$SO_2$—N$(CH_2CH_2CH_3)_2$, or —$SO_2$—N$(CH(CH_3)_2)_2$. In some embodiments, $R^{27}$ is —$SO_2$—N($CH_3$)($CH_2CH_3$), —$SO_2$—N($CH_3$)($CH_2CH_2CH_3$), —$SO_2$—N($CH_3$)($CH(CH_3)_2$), —$SO_2$—N($CH_2CH_3$)($CH_2CH_2CH_3$), or —$SO_2$—N($CH_2CH_3$)($CH(CH_3)_2$). In some embodiments, $R^{27}$ is —$SO_2$—N$(CH_3)_2$.

In some embodiments, $R^{27}$ is —C(O)($C_1$-$C_6$ alkyl). In some embodiments, $R^{27}$ is —C(O)($C_1$-$C_3$ alkyl). In some embodiments, $R^{27}$ is —C(O)($CH_3$), —C(O)($CH_2CH_3$), —C(O)($CH_2CH_2CH_3$), or —C(O)($CH(CH_3)_2$). In some embodiments, $R^{27}$ is —C(O)($CH_3$).

In some embodiments, $R^{27}$ is —($C_1$-$C_6$ alkylene)-C(O)N($C_1$-$C_6$ alkyl)$_2$. In some embodiments, the two $C_1$-$C_6$ alkyl groups are the same. In other embodiments, the two $C_1$-$C_6$ alkyl groups are different. In some embodiments, $R^{27}$ is —($C_1$-$C_3$ alkylene)-C(O)N($C_1$-$C_3$ alkyl)$_2$. In some embodiments, $R^{27}$ is —($CH_2$)—C(O)N($C_1$-$C_3$ alkyl)$_2$, —($CH_2CH_2$)—C(O)N($C_1$-$C_3$ alkyl)$_2$, or —($CH_2CH_2CH_2$)—C(O)N($C_1$-$C_3$ alkyl)$_2$. In some embodiments, $R^{27}$ is —($CH_2$)—C(O)N$(CH_3)_2$, —($CH_2$)—C(O)N$(CH_2CH_3)_2$, —($CH_2$)—C(O)N$(CH_2CH_2CH_3)_2$, —($CH_2$)—C(O)N$(CH(CH_3)_2)_2$, —($CH_2$)—C(O)N($CH_3$)($CH_2CH_3$), —($CH_2$)—C(O)N($CH_3$)$(CH_2CH_2CH_3)_2$, —($CH_2$)—C(O)N($CH_3$)($CH(CH_3)_2$), —($CH_2CH_2$)—C(O)N$(CH_3)_2$, —($CH_2CH_2$)—C(O)N$(CH_2CH_3)_2$, —($CH_2CH_2$)—C(O)N$(CH_2CH_2CH_3)_2$, —($CH_2CH_2$)—C(O)N$(CH(CH_3)_2)_2$, —($CH_2CH_2$)—C(O)N($CH_3$)($CH_2CH_3$), —($CH_2CH_2$)—C(O)N($CH_3$)$(CH_2CH_2CH_3)_2$, or —($CH_2CH_2$)—C(O)N($CH_3$)($CH(CH_3)_2$). In some embodiments, $R^{27}$ is —($CH_2$)—C(O)N$(CH_3)_2$.

In some embodiments, $R^{27}$ is —($C_1$-$C_6$ alkylene)-C(O)NH($C_1$-$C_6$ alkyl). In some embodiments, $R^{27}$ is —($C_1$-$C_3$ alkylene)-C(O)NH($C_1$-$C_3$ alkyl). In some embodiments, $R^{27}$ is —($CH_2$)—C(O)NH($C_1$-$C_3$ alkyl), —($CH_2CH_2$)—C(O)NH($C_1$-$C_3$ alkyl), or —($CH_2CH_2CH_2$)—C(O)NH($C_1$-$C_3$ alkyl). In some embodiments, $R^{27}$ is —($CH_2$)—C(O)NH($CH_3$), —($CH_2$)—C(O)NH($CH_2CH_3$), —($CH_2$)—C(O)NH($CH_2CH_2CH_3$), —($CH_2$)—C(O)NH($CH(CH_3)_2$), —($CH_2CH_2$)—C(O)NH($CH_3$), —($CH_2CH_2$)—C(O)NH($CH_2CH_3$), —($CH_2CH_2$)—C(O)NH($CH_2CH_2CH_3$), or —($CH_2CH_2$)—C(O)NH($CH(CH_3)_2$). In some embodiments, $R^{27}$ is —($CH_2$)—C(O)NH($CH_3$).

In some embodiments, each $R^{30}$ is independently H, $C_1$-$C_3$ alkyl, $C_1$-$C_3$ alkyl-OH, or $C_1$-$C_3$ haloalkyl. In some embodiments, each $R^{30}$ is independently H, $C_1$-$C_2$ alkyl, $C_1$-$C_2$ alkyl-OH, or $C_1$-$C_2$ haloalkyl. In some embodiments, each $R^{30}$ is independently H, —$CH_3$, —$CH_2OH$, or —$CF_3$.

In some embodiments, each $R^{30}$ is independently H. In some embodiments, one $R^{30}$ is H and the other $R^{30}$ is $C_1$-$C_3$ alkyl. In some embodiments, one $R^{30}$ is H and the other $R^{30}$ is $C_1$-$C_2$ alkyl. In some embodiments, one $R^{30}$ is H and the other $R^{30}$ is methyl. In some embodiments, one $R^{30}$ is H and the other $R^{30}$ is ethyl. In some embodiments, one $R^{30}$ is H and the other $R^{30}$ is $C_1$-$C_3$ haloalkyl. In some embodiments, one $R^{30}$ is H and the other $R^{30}$ is $C_1$-$C_2$ haloalkyl. In some embodiments, one $R^{30}$ is H and the other $R^{30}$ is $C_1$ haloalkyl. In some embodiments, one $R^{30}$ is H and the other $R^{30}$ is —$CF_3$. In some embodiments, each $R^{30}$ is H.

In some embodiments, $R^{30}$ is $C_1$-$C_3$ alkyl. In some embodiments, $R^{30}$ is $C_1$-$C_2$ alkyl. In some embodiments, $R^{30}$ is methyl, ethyl, n-propyl, or isopropyl. In some embodiments, $R^{30}$ is methyl or ethyl. In some embodiments, $R^{30}$ is —$CH_3$.

In some embodiments, $R^{30}$ is $C_1$-$C_3$ alkyl-OH. In some embodiments, $R^{30}$ is $C_1$-$C_2$ alkyl-OH. In some embodiments, $R^{30}$ is —$CH_2OH$, —$CH_2CH_2OH$, or —$CH_2CH_2CH_2OH$. In some embodiments, $R^{30}$ is —$CH_2OH$.

In some embodiments, $R^{30}$ is $C_1$-$C_3$ haloalkyl. In some embodiments, $R^{30}$ is $C_1$-$C_3$ haloalkyl containing 1-5 halogen atoms. In some embodiments, $R^{30}$ is $C_1$-$C_2$ haloalkyl. In some embodiments, $R^{30}$ is $C_1$-$C_2$ haloalkyl containing 1-3 halogen atoms. In some embodiments, the halogen atoms are independently selected from the group consisting of chloro, bromo, and fluoro atoms. In some embodiments, the halogen atoms are independently selected from the group consisting of chloro and fluoro atoms. In some embodiments, the halogen atoms are all fluoro atoms. In some embodiments, the halogen atoms are a combination of chloro and fluoro atoms. In some embodiments, $R^{30}$ is —$CF_3$, —$CCl_3$, —$CF_2Cl$, —$CFCl_2$, —$CHF_2$, —$CH_2F$, —$CHCl_2$, or —$CHFCl$. In some embodiments, $R^{30}$ is —$CF_3$.

In some embodiments, the compound of Formula (II) is a compound of Formula (II-A):

(II-A)

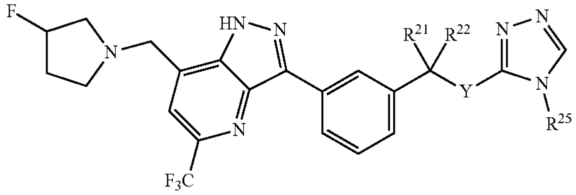

or a tautomer thereof, or a pharmaceutically acceptable salt of thereof, wherein $R^{21}$, $R^{22}$, and $R^{25}$ are as defined for the compound of Formula (II).

TABLE 2
| Representative Compounds of Formula (II) | |
|---|---|
| Cmpd No. | Structure |
| 55 | 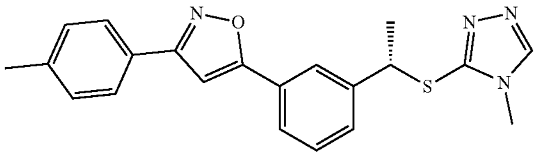 [SMILES: Cc1ccc(-c2cc(-c3cccc([C@H](C)Sc4nncn4C)c3)on2)cc1] |
| 56 | 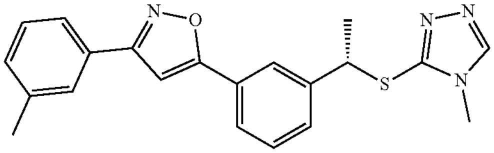 [SMILES: Cc1cccc(-c2cc(-c3cccc([C@H](C)Sc4nncn4C)c3)on2)c1] |
| 57 | 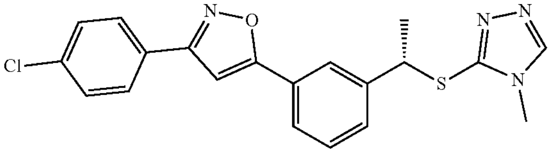 [SMILES: C[C@H](Sc1nncn1C)c1cccc(-c2cc(-c3ccc(Cl)cc3)no2)c1] |
| 58 | 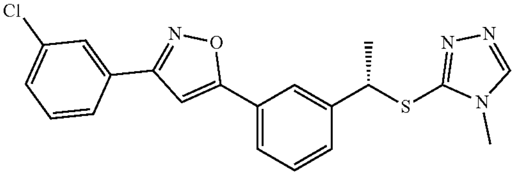 [SMILES: C[C@H](Sc1nncn1C)c1cccc(-c2cc(-c3cccc(Cl)c3)no2)c1] |
| 59 | 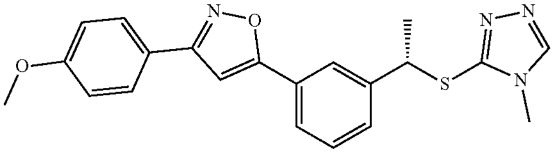 [SMILES: COc1ccc(-c2cc(-c3cccc([C@H](C)Sc4nncn4C)c3)on2)cc1] |
| 60 | 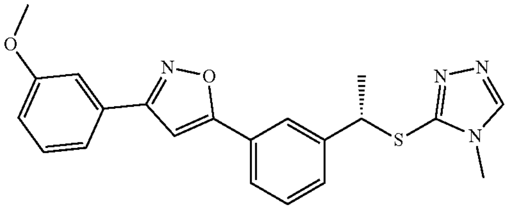 [SMILES: COc1cccc(-c2cc(-c3cccc([C@H](C)Sc4nncn4C)c3)on2)c1] |
| 61 | 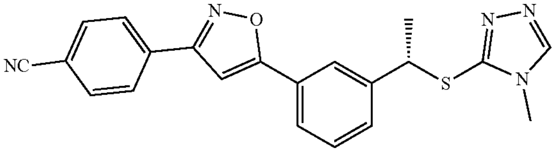 [SMILES: C[C@H](Sc1nncn1C)c1cccc(-c2cc(-c3ccc(C#N)cc3)no2)c1] |
| 62 | 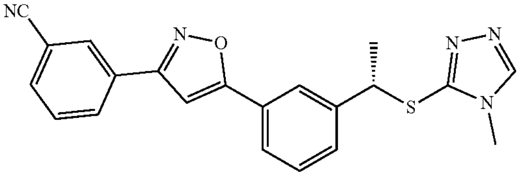 [SMILES: C[C@H](Sc1nncn1C)c1cccc(-c2cc(-c3cccc(C#N)c3)no2)c1] |

TABLE 2-continued
| Representative Compounds of Formula (II) | |
|---|---|
| Cmpd No. | Structure |
| 63 | 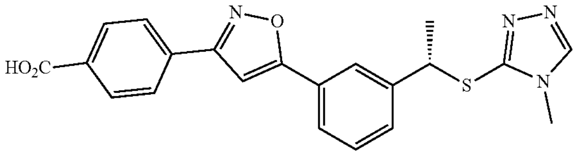 [SMILES: C[C@H](Sc1nncn1C)c1cccc(-c2cc(-c3ccc(C(=O)O)cc3)no2)c1] |
| 64 | 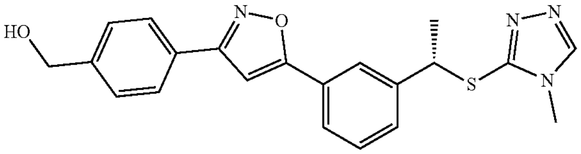 [SMILES: C[C@H](Sc1nncn1C)c1cccc(-c2cc(-c3ccc(CO)cc3)no2)c1] |
| 65 | 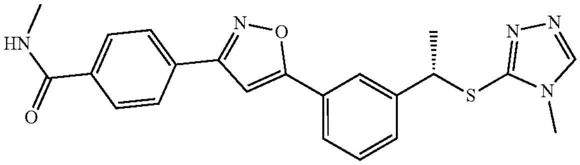 [SMILES: CNC(=O)c1ccc(-c2cc(-c3cccc([C@H](C)Sc4nncn4C)c3)on2)cc1] |
| 66 | 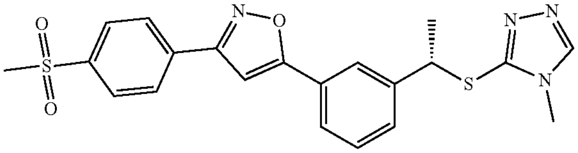 [SMILES: C[C@H](Sc1nncn1C)c1cccc(-c2cc(-c3ccc(S(C)(=O)=O)cc3)no2)c1] |
| 67 | 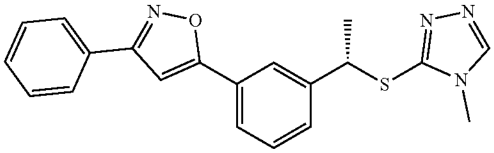 [SMILES: C[C@H](Sc1nncn1C)c1cccc(-c2cc(-c3ccccc3)no2)c1] |
| 68 | 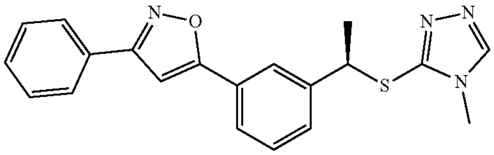 [SMILES: C[C@@H](Sc1nncn1C)c1cccc(-c2cc(-c3ccccc3)no2)c1] |
| 69 | 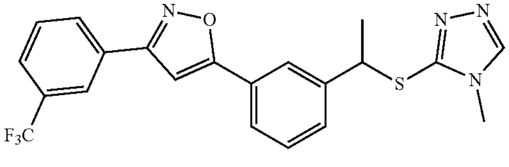 [SMILES: CC(Sc1nncn1C)c1cccc(-c2cc(-c3cccc(C(F)(F)F)c3)no2)c1] |
| 70 | 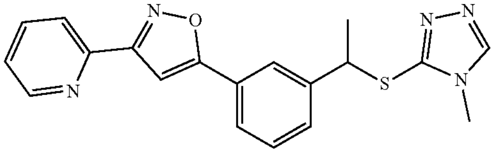 |
| 71 | 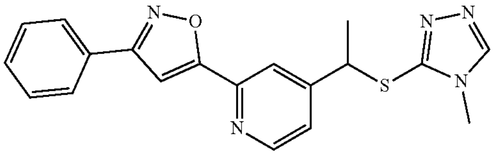 [SMILES: CC(Sc1nncn1C)c1ccnc(-c2cc(-c3ccccc3)no2)c1] |

TABLE 2-continued
| Representative Compounds of Formula (II) | |
|---|---|
| Cmpd No. | Structure |
| 72 | 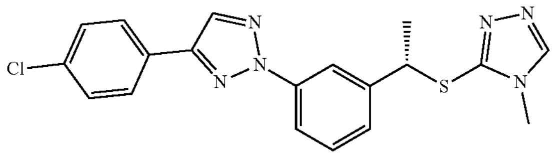 [SMILES: C[C@H](Sc1nncn1C)c1cccc(-n2ncc(-c3ccc(Cl)cc3)n2)c1] |
| 73 | 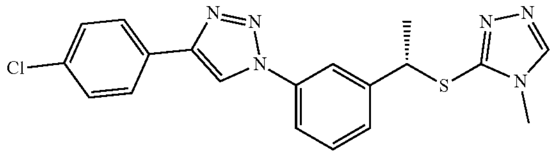 [SMILES: C[C@H](Sc1nncn1C)c1cccc(-n2cc(-c3ccc(Cl)cc3)nn2)c1] |
| 74 | 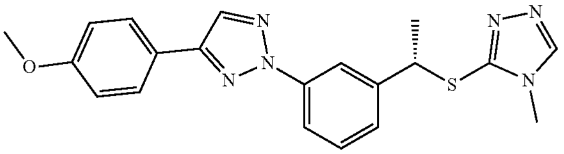 [SMILES: COc1ccc(-c2cnn(-c3cccc([C@H](C)Sc4nncn4C)c3)n2)cc1] |
| 75 | 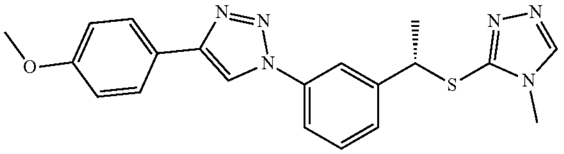 [SMILES: COc1ccc(-c2cn(-c3cccc([C@H](C)Sc4nncn4C)c3)nn2)cc1] |
| 76 | 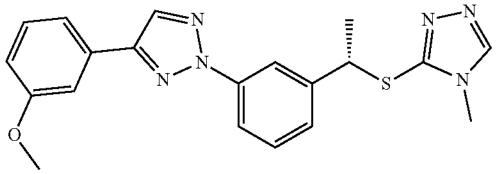 [SMILES: COc1cccc(-c2cnn(-c3cccc([C@H](C)Sc4nncn4C)c3)n2)c1] |
| 77 | 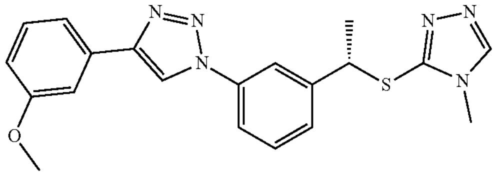 [SMILES: COc1cccc(-c2cn(-c3cccc([C@H](C)Sc4nncn4C)c3)nn2)c1] |
| 78 | 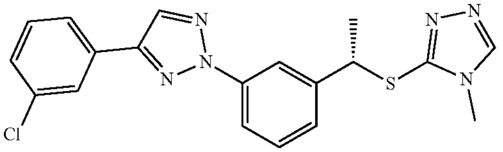 [SMILES: C[C@H](Sc1nncn1C)c1cccc(-n2ncc(-c3cccc(Cl)c3)n2)c1] |
| 79 | 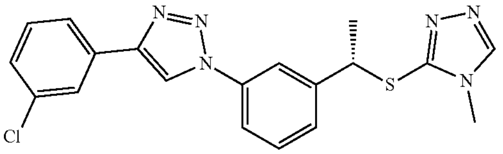 [SMILES: C[C@H](Sc1nncn1C)c1cccc(-n2cc(-c3cccc(Cl)c3)nn2)c1] |
| 80 | 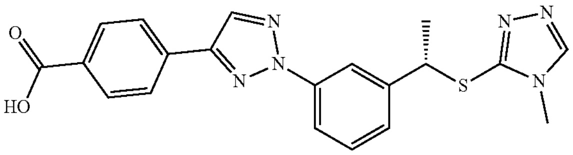 [SMILES: C[C@H](Sc1nncn1C)c1cccc(-n2ncc(-c3ccc(C(=O)O)cc3)n2)c1] |

TABLE 2-continued
| Representative Compounds of Formula (II) | |
|---|---|
| Cmpd No. | Structure |
| 81 | 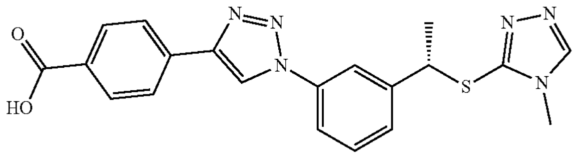 [SMILES: C[C@H](Sc1nncn1C)c1cccc(-n2cc(-c3ccc(C(=O)O)cc3)nn2)c1] |
| 82 | 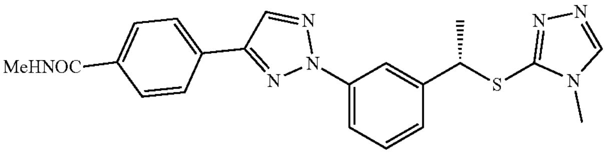 |
| 83 | 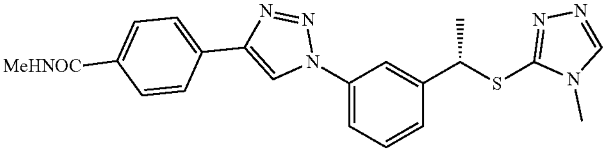 |
| 84 | 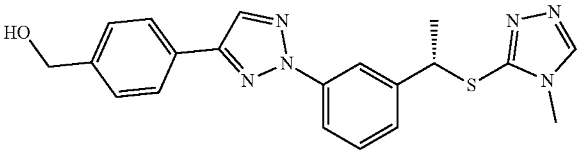 [SMILES: C[C@H](Sc1nncn1C)c1cccc(-n2ncc(-c3ccc(CO)cc3)n2)c1] |
| 85 | 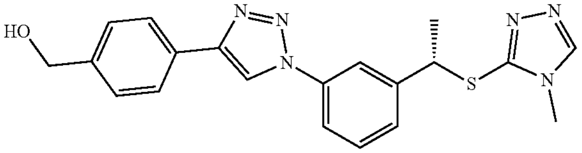 [SMILES: C[C@H](Sc1nncn1C)c1cccc(-n2cc(-c3ccc(CO)cc3)nn2)c1] |
| 86 | 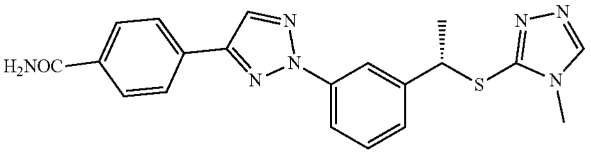 [SMILES: C[C@H](Sc1nncn1C)c1cccc(-n2ncc(-c3ccc(C(N)=O)cc3)n2)c1] |
| 87 | 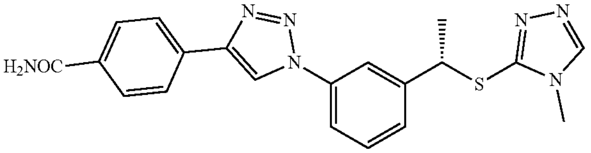 [SMILES: C[C@H](Sc1nncn1C)c1cccc(-n2cc(-c3ccc(C(N)=O)cc3)nn2)c1] |
| 88 | 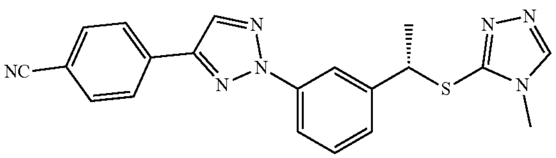 [SMILES: C[C@H](Sc1nncn1C)c1cccc(-n2ncc(-c3ccc(C#N)cc3)n2)c1] |
| 89 | 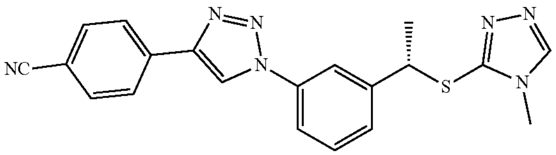 [SMILES: C[C@H](Sc1nncn1C)c1cccc(-n2cc(-c3ccc(C#N)cc3)nn2)c1] |

TABLE 2-continued
Representative Compounds of Formula (II)
| Cmpd No. | Structure |
| --- | --- |
| 90 | 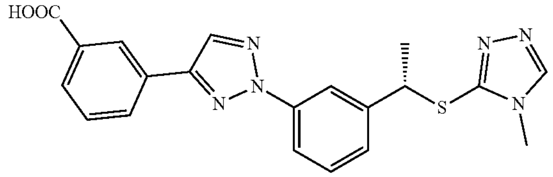 [SMILES: C[C@H](Sc1nncn1C)c1cccc(-n2ncc(-c3cccc(C(=O)O)c3)n2)c1] |
| 91 | 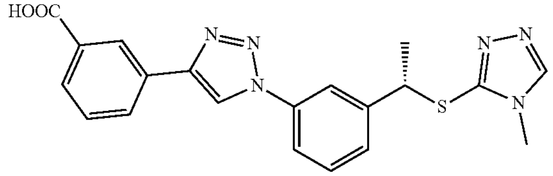 [SMILES: C[C@H](Sc1nncn1C)c1cccc(-n2cc(-c3cccc(C(=O)O)c3)nn2)c1] |
| 92 | 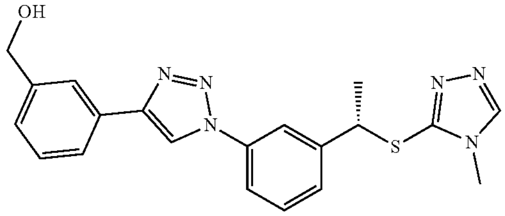 [SMILES: C[C@H](Sc1nncn1C)c1cccc(-n2cc(-c3cccc(CO)c3)nn2)c1] |
| 93 | 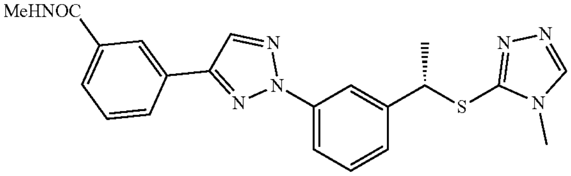 |
| 94 | 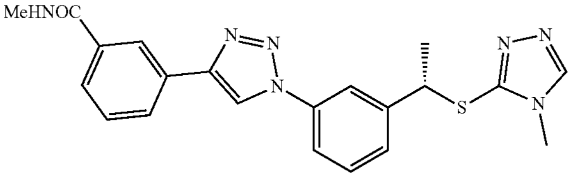 |
| 95 | 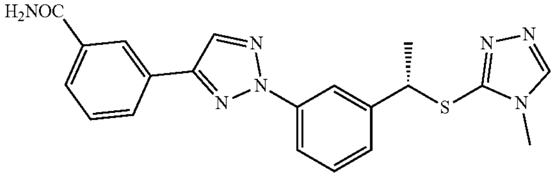 [SMILES: C[C@H](Sc1nncn1C)c1cccc(-n2ncc(-c3cccc(C(N)=O)c3)n2)c1] |
| 96 | 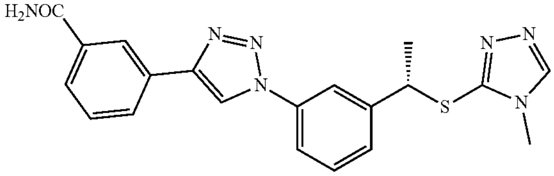 [SMILES: C[C@H](Sc1nncn1C)c1cccc(-n2cc(-c3cccc(C(N)=O)c3)nn2)c1] |
| 97 | 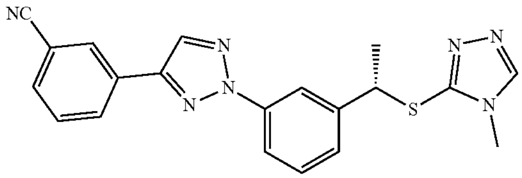 [SMILES: C[C@H](Sc1nncn1C)c1cccc(-n2ncc(-c3cccc(C#N)c3)n2)c1] |

TABLE 2-continued
| Representative Compounds of Formula (II) | |
|---|---|
| Cmpd No. | Structure |
| 98 | 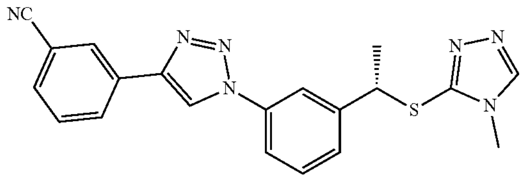 [SMILES: C[C@H](Sc1nncn1C)c1cccc(-n2cc(-c3cccc(C#N)c3)nn2)c1] |
| 99 | 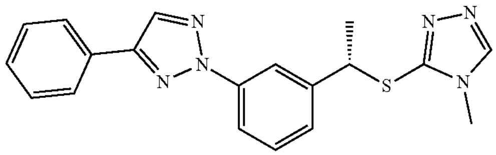 [SMILES: C[C@H](Sc1nncn1C)c1cccc(-n2ncc(-c3ccccc3)n2)c1] |
| 100 | 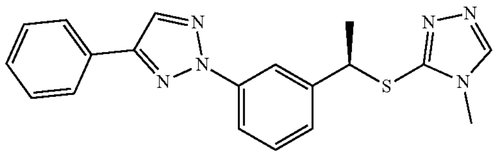 [SMILES: C[C@@H](Sc1nncn1C)c1cccc(-n2ncc(-c3ccccc3)n2)c1] |
| 101 | 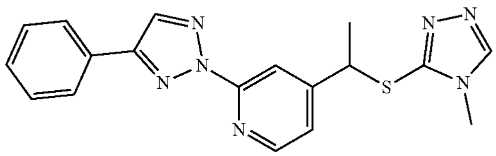 [SMILES: CC(Sc1nncn1C)c1ccnc(-n2ncc(-c3ccccc3)n2)c1] |
| 102 | 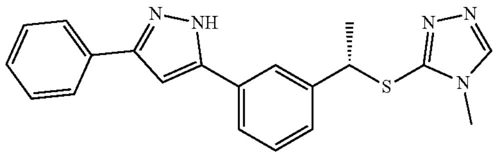 [SMILES: C[C@H](Sc1nncn1C)c1cccc(-c2cc(-c3ccccc3)n[nH]2)c1] |
| 103 | 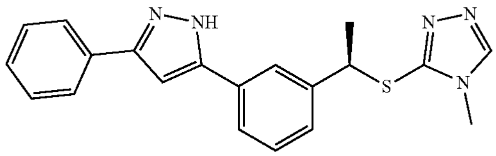 [SMILES: C[C@@H](Sc1nncn1C)c1cccc(-c2cc(-c3ccccc3)n[nH]2)c1] |
| 104 | 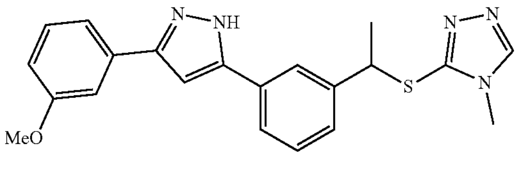 [SMILES: COc1cccc(-c2cc(-c3cccc(C(C)Sc4nncn4C)c3)[nH]n2)c1] |
| 105 | 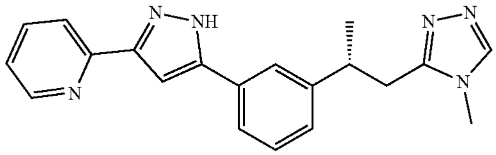 [SMILES: C[C@H](Cc1nncn1C)c1cccc(-c2cc(-c3ccccn3)n[nH]2)c1] |
| 106 | 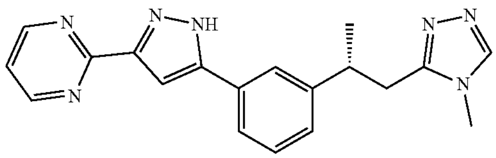 [SMILES: C[C@H](Cc1nncn1C)c1cccc(-c2cc(-c3ncccn3)n[nH]2)c1] |

TABLE 2-continued
| Representative Compounds of Formula (II) | |
|---|---|
| Cmpd No. | Structure |
| 107 | 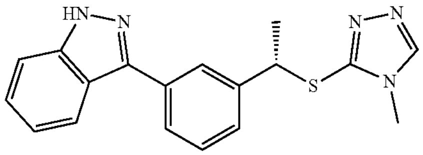 [SMILES: C[C@H](Sc1nncn1C)c1cccc(-c2n[nH]c3ccccc23)c1] |
| 108 | 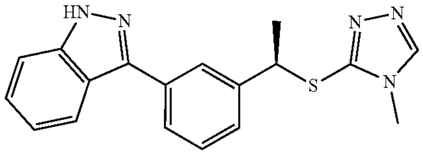 [SMILES: C[C@@H](Sc1nncn1C)c1cccc(-c2n[nH]c3ccccc23)c1] |
| 109 | 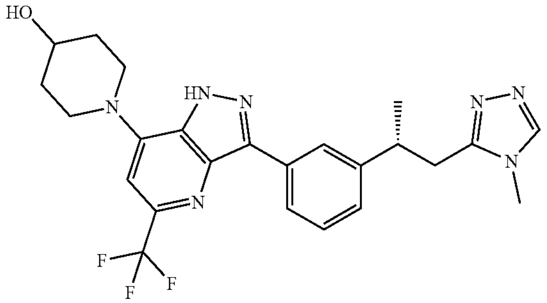 [SMILES: C[C@H](Cc1nncn1C)c1cccc(-c2n[nH]c3c(N4CCC(O)CC4)cc(C(F)(F)F)nc23)c1] |
| 110 | 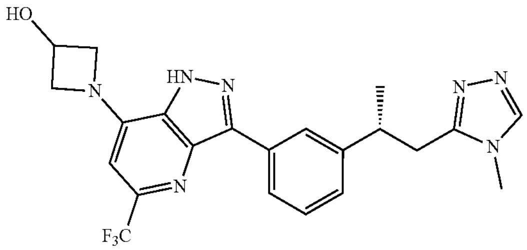 [SMILES: C[C@H](Cc1nncn1C)c1cccc(-c2n[nH]c3c(N4CC(O)C4)cc(C(F)(F)F)nc23)c1] |
| 111 | 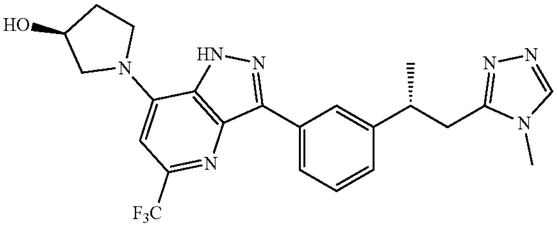 [SMILES: C[C@H](Cc1nncn1C)c1cccc(-c2n[nH]c3c(N4CC[C@H](O)C4)cc(C(F)(F)F)nc23)c1] |
| 112 | 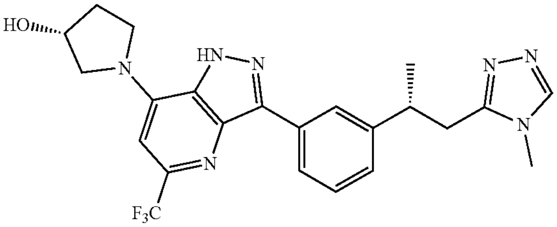 [SMILES: C[C@H](Cc1nncn1C)c1cccc(-c2n[nH]c3c(N4CC[C@@H](O)C4)cc(C(F)(F)F)nc23)c1] |

TABLE 2-continued
| Representative Compounds of Formula (II) | |
|---|---|
| Cmpd No. | Structure |
| 113 | 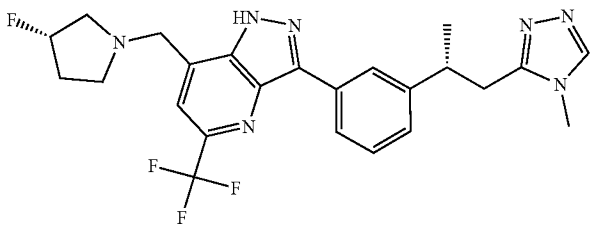 [SMILES: C[C@H](Cc1nncn1C)c1cccc(-c2n[nH]c3c(CN4CC[C@H](F)C4)cc(C(F)(F)F)nc23)c1] |
| 114 | 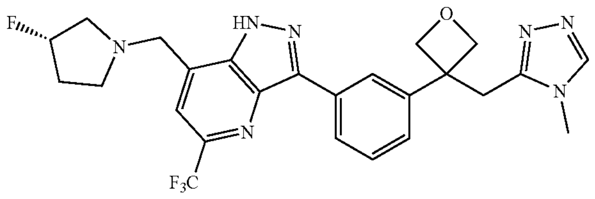 [SMILES: Cn1cnnc1CC1(c2cccc(-c3n[nH]c4c(CN5CC[C@H](F)C5)cc(C(F)(F)F)nc34)c2)COC1] |
| 115 | 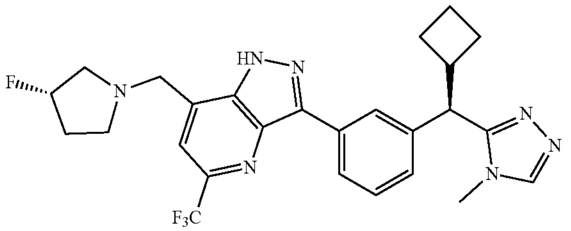 [SMILES: Cn1cnnc1[C@@H](c1cccc(-c2n[nH]c3c(CN4CC[C@H](F)C4)cc(C(F)(F)F)nc23)c1)C1CCC1] |
| 116 | 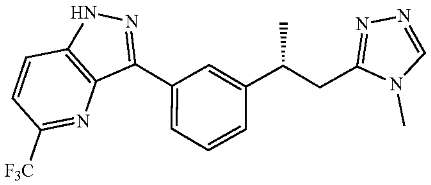 [SMILES: C[C@H](Cc1nncn1C)c1cccc(-c2n[nH]c3ccc(C(F)(F)F)nc23)c1] |
| 117 | 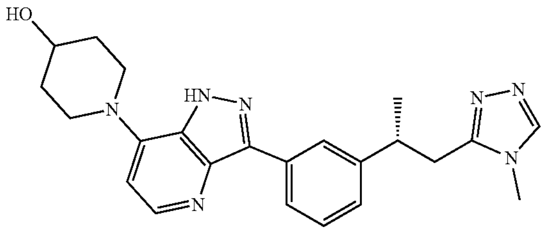 [SMILES: C[C@H](Cc1nncn1C)c1cccc(-c2n[nH]c3c(N4CCC(O)CC4)ccnc23)c1] |
| 118 | 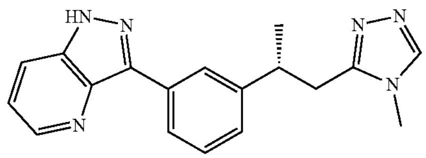 |
| 119 | 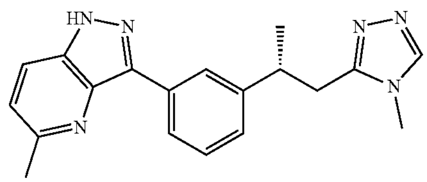 [SMILES: Cc1ccc2[nH]nc(-c3cccc([C@H](C)Cc4nncn4C)c3)c2n1] |

TABLE 2-continued

| Representative Compounds of Formula (II) | |
|---|---|
| Cmpd No. | Structure |
| 120 | 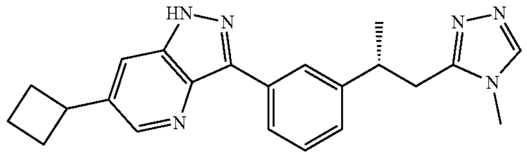 [SMILES: C[C@H](Cc1nncn1C)c1cccc(-c2n[nH]c3cc(C4CCC4)cnc23)c1] |
| 167 | 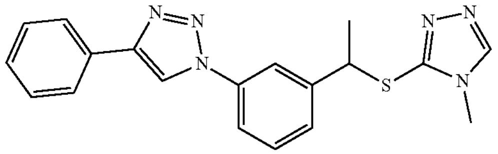 [SMILES: CC(Sc1nncn1C)c1cccc(-n2cc(-c3ccccc3)nn2)c1] |

In some embodiments, provided is a compound selected from Compounds Nos. 55-120 and 167 in Table 2, or a tautomer thereof, or a pharmaceutically acceptable salt thereof.

In one aspect, provided herein are methods of preparing the compounds of Formula (I) described herein. In another aspect, provided herein are intermediate compounds for preparing the compounds of Formula (I). In one aspect, provided herein are methods of preparing the compounds of Formula (II) described herein. In another aspect, provided herein are intermediate compounds for preparing the compounds of Formula (II). Also provided herein are compounds which are assay probes, and which are optionally tagged with, for example, a fluorescent label. In a further aspect, provided herein is a method for assaying inhibition of Cbl-b. In one variation, provided herein is a method for assaying inhibition of Cbl-b comprising pre-incubating Cbl-b with an assay probe, such as an assay probe tagged with a fluorescent label, followed by exposing the Cbl-b/assay probe mixture to a candidate compound, and then determining whether and to what extent the assay probe is displaced by the candidate compound using, for example, FRET signal detection.

The schemes below describe methods of synthesizing the compounds disclosed herein. Mixtures of stereoisomers produced during synthesis, such as racemic mixtures of final compounds, can be separated into the respective enantiomers using common chromatography methods such as supercritical fluid chromatography (SFC) in combination with chiral stationary phases, chiral column chromatography, or other methods known in the art.

Scheme I.

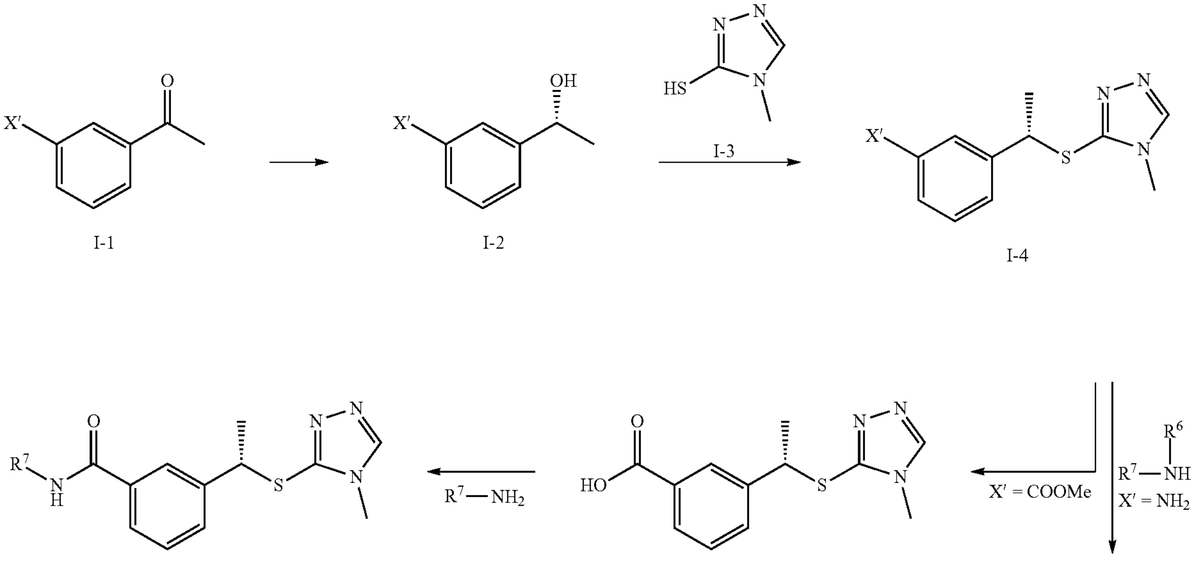

-continued

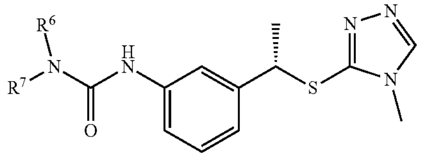

I-7 wherein $R^6$ and $R^7$ are as defined for the compound of Formula (I); and X' is methyl ester or $NH_2$.

Compounds of Formula (I), wherein X is S, can be synthesized as outlined in Scheme I. Benzophenone I-1 is reduced enantioselectively with a suitable catalyst, such as the CBS reagent, to afford enantioenriched alcohols I-2. The triazole can be installed through Mitsunobu reaction to provide intermediate I-4. When X' is ester, hydrolysis to the acid provides acid I-5, which is then coupled to amines with a dehydrating reagent such as HATU or T3P to provide amides I-6. When X' is an amine, ureas I-7 can be formed by coupling with a bis-electrophile such as p-$NO_2$PhOC(O)Cl.

Scheme II.

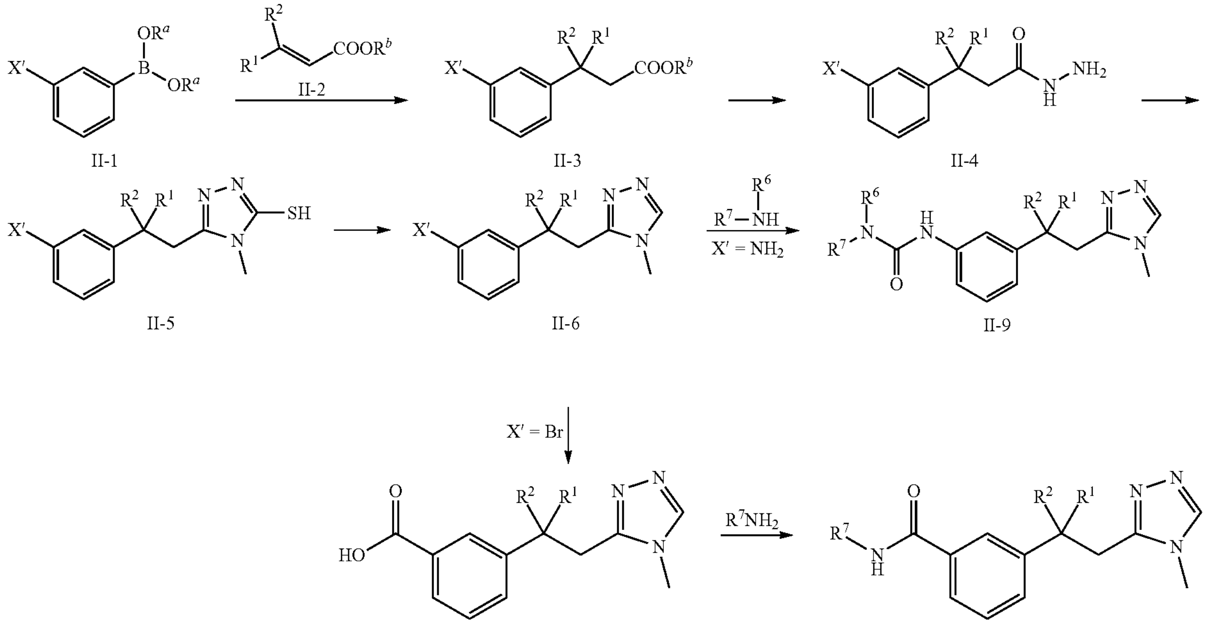

II-1, II-2, II-3, II-4, II-5, II-6, II-9, II-7, II-8 wherein $R^1$, $R^2$, $R^6$, and $R^7$ are as defined for the compound of Formula (I); X' is Br or $NH_2$; and $R^a$ and $R^b$ are suitable protecting groups.

Compounds of the Formula (I), wherein X is carbon, can be synthesized as outlined in Scheme II. Coupling of boronic esters II-1 with alkenes II-2 under rhodium catalysis affords (oxetane) esters 11-3. A triazole is assembled by hydrazide formation, cyclization, and desulphurization, to provide triazoles 11-6. When X' is bromine, palladium-catalyzed carbonylation and hydrolysis affords acid II-7, which is coupled to amines to provide amides II-8. When X' is an amine, ureas II-9 are formed by coupling with a bis-electrophile such as p-$NO_2$PhOC(O)Cl.

Scheme III.

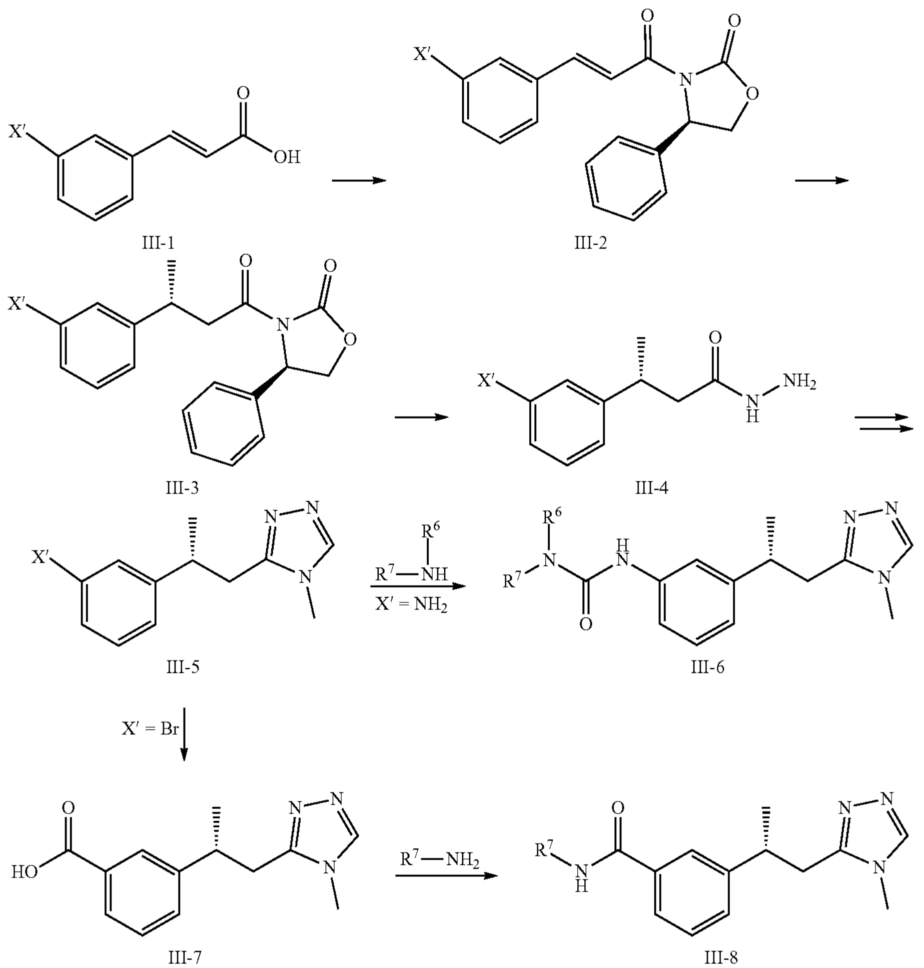

III-1 III-2 III-3 III-4 III-5 III-6 III-7 III-8 wherein $R^6$ and $R^7$ are as defined for the compound of Formula (I); and X' is Br or $NH_2$.

Compounds of Formula (I), wherein $R^1$ is methyl and X is $CH_2$, can be assembled as illustrated in Scheme III. Substituted cinnamic acids III-1 are coupled to Evans chiral auxiliary to form imides III-2. Conjugate addition of $LiMe_2Cu$ affords enantio-enriched intermediates III-3. The chiral auxiliary is displaced with hydrazine to afford hydrazide III-4, which is then elaborated to triazole III-5 as in Scheme I. Formation of amides III-7 and ureas III-8 can be realized as in Scheme II.

Scheme IV.

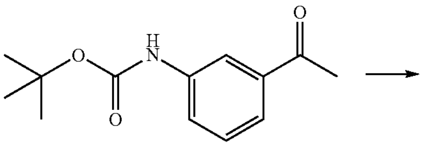

IV-1

-continued

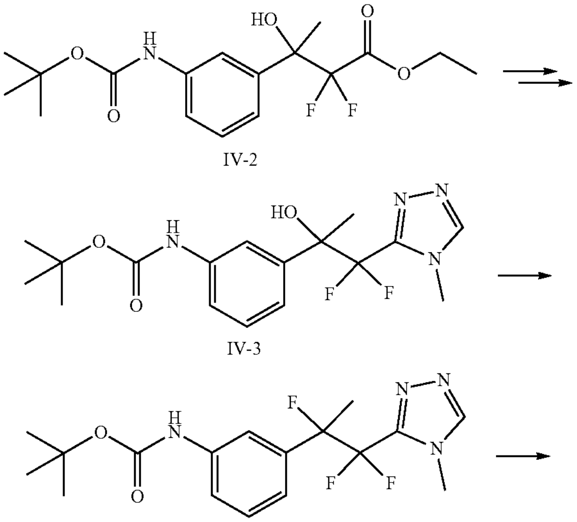

IV-2 IV-3 IV-4

-continued

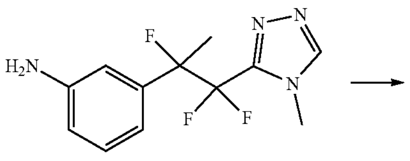

IV-5

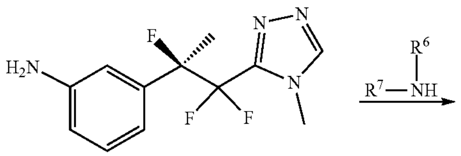

IV-6

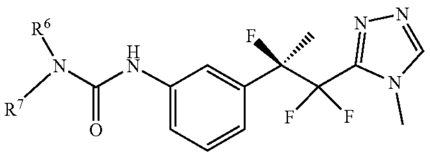

IV-7 wherein $R^6$ and $R^7$ are as defined for the compound of Formula (I).

Fluorinated compounds of formula IV-7 can be synthesized as illustrated in Scheme IV. Addition of ethyl 2-bromo-2,2-difluoro-acetate to acetphonone IV-1 under the action of Zn metal affords hydroxy ester IV-2. The ester is elaborated to a triazole IV-3 as in Scheme II. The hydroxy group is fluorinated with a reagent such as DAST to afford trifluoro IV-4. After Boc deprotection with acid, the enantiomers were resolved by chiral IPLC to afford enantiopure IV-6, which is converted to ureas IV-7 as in Scheme I.

Scheme V.

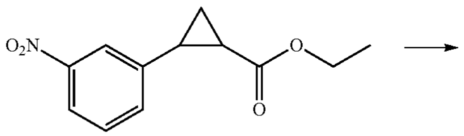

V-1

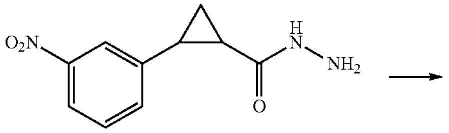

V-2

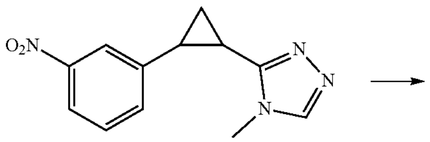

V-3

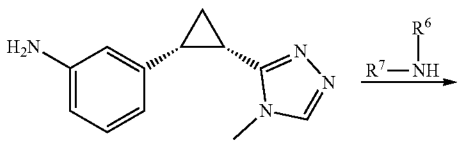

V-4

-continued

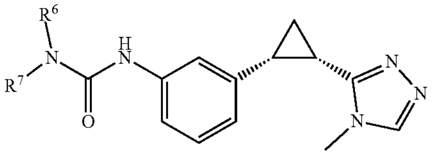

V-5 wherein $R^6$ and $R^7$ are as defined for the compound of Formula (I).

Compounds of formula V-5 can be synthesized as illustrated in Scheme V. Cyclopropyl ester V-1 is converted to hydrazide V-2, then to triazole V-3. Following reduction of the nitro to the amine, resolution by chiral chromatography affords intermediate V-4, which is elaborated to V-5 as in Scheme I.

Scheme VI.

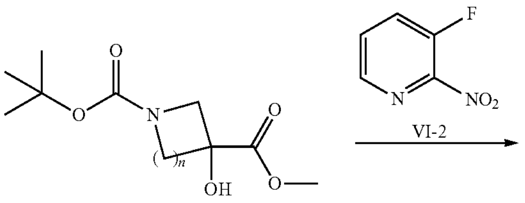

VI-1

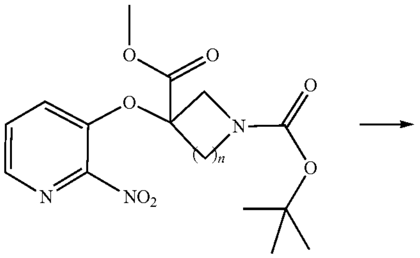

VI-3

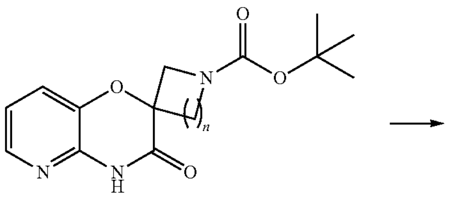

VI-4

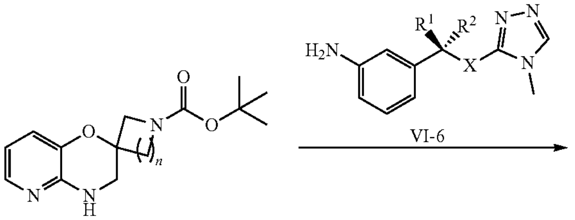

VI-5

-continued

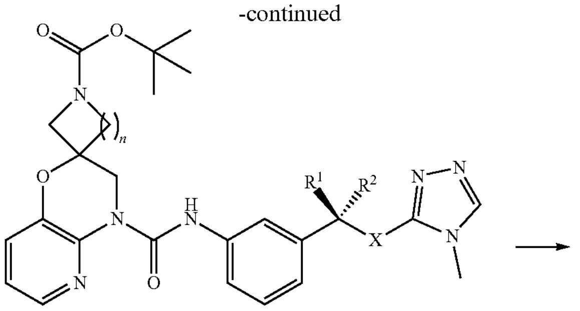

VI-7

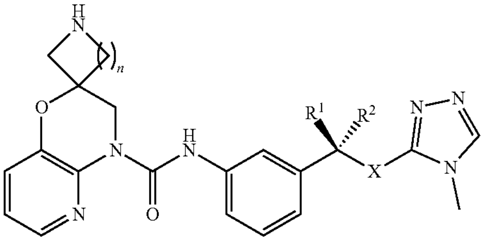

VI-8 wherein $R^1$, $R^2$, X and n are as defined for the compound of Formula (I).

Compounds of formula VI-8 can be synthesized as illustrated in Scheme VI. Hydroxy-esters VI-1 are condensed with nitro-fluoropyridine VI-2 with a strong base, such as NaH. Nitro reduction with Fe(0) proceeds with concomitant lactam formation affording intermediates VI-4. Reduction of the lactam with $BH_3$ THF affords amines VI-5. Urea Examples VI-8 are completed by coupling to aniline intermediates VI-6 as in Scheme I.

Scheme VII.

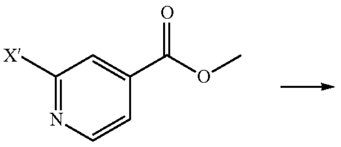

VII-1

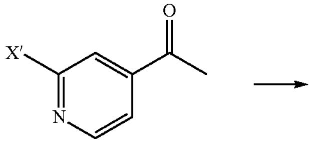

VII-2

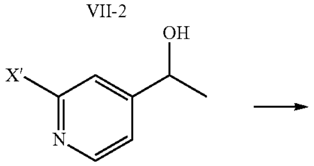

VII-3

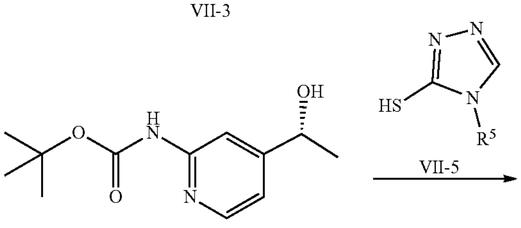

VII-4

-continued

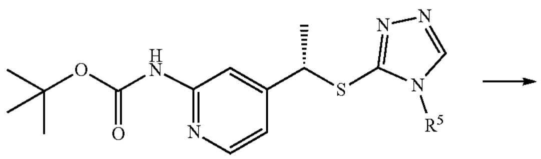

VII-6

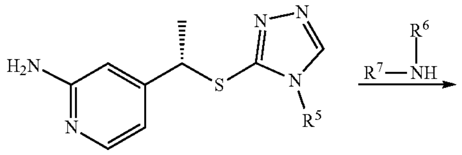

VII-7

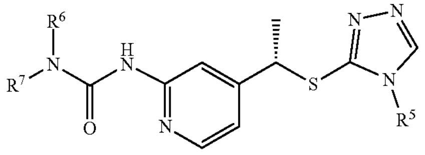

VII-8 wherein $R^5$, $R^6$, and $R^7$ are as defined for the compound of Formula (I); and X' is NHBoc or OMe.

Compounds of the formula VII-8 can be synthesized as illustrated in Scheme VII. Esters VII-1 are converted to methyl ketones VII-2 by Weinreb amide formation and methyl Grignard addition. When X is NHBoc, the ketone is reduced with $NaBH_4$ and the resulting alcohol VII-3 is resolved by enzymatic acylation to afford enantiopure alcohol VII-4. Urea Examples VIII-8 are completed as described in Scheme I.

Scheme VIII.

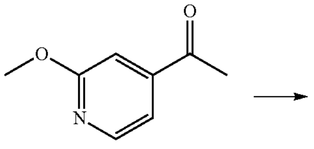

VIII-2

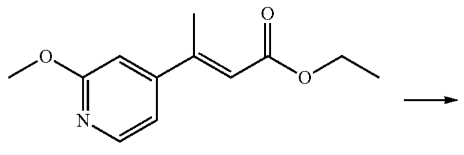

VIII-1

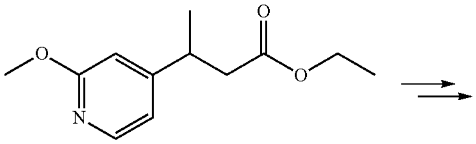

VIII-2

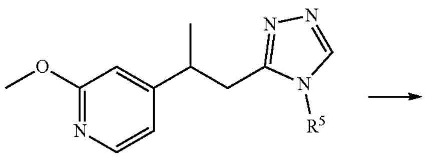

VIII-3

-continued

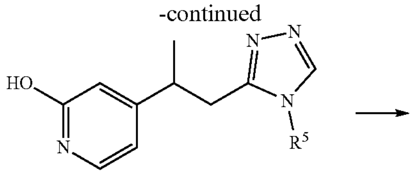

VIII-4

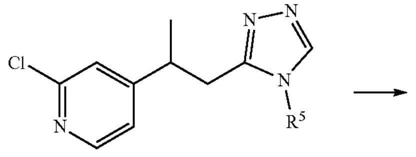

VIII-5

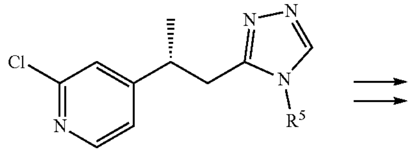

VIII-6

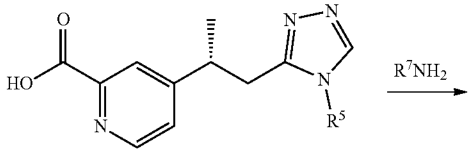

VIII-7

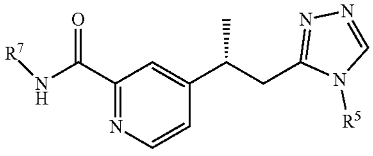

VIII-8 wherein $R^5$ and $R^7$ are as defined for the compound of Formula (I).

Compounds of the formula VIII-8 can be synthesized as illustrated in Scheme VIII. Ketone VIII-2 is homologated with HWE reagent to ester VIII-1. Reduction with $H_2$ and Pd·C followed by triazole formation affords intermediate VIII-3. The methoxy group is converted to a chlorine by hydrolysis and chlorination with $POCl_3$. After resolution by chiral chromatography, the chlorine is converted to an acid by palladium-catalyzed carbonylation and ester hydrolysis to provide acid VIII-7. Example compounds are completed as in Scheme I Scheme IX.

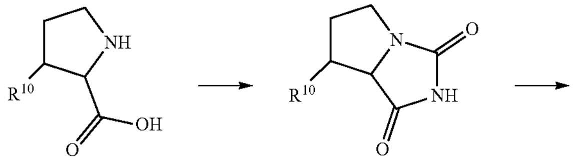

IX-1 IX-2

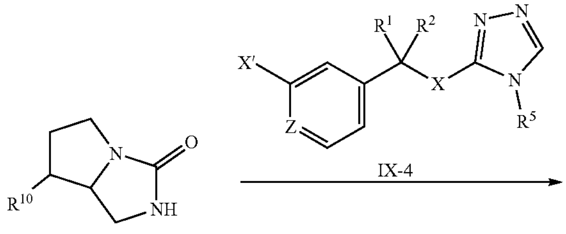

IX-3

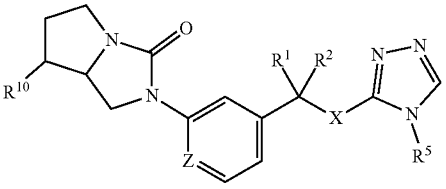

IX-5 wherein $R^1$, $R^2$, $R^5$, $R^{10}$, X, and Z are as defined for the compound of Formula (I); and X' is chlorine or bromine.

Compounds IX-5 can be synthesized as illustrated in Scheme IX. Substituted IX-1 is converted into hydantoin IX-2 with potassium cyanate, followed by reduction to urea IX-3. Example compounds IX-5 are completed by palladium-catalyzed coupling with a halogen IX-4.

Scheme X.

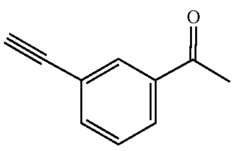

X-1

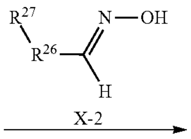

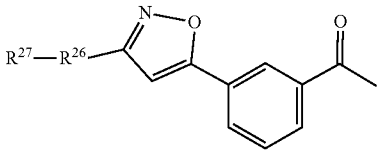

X-3

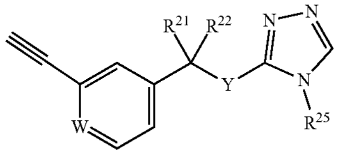

X-4

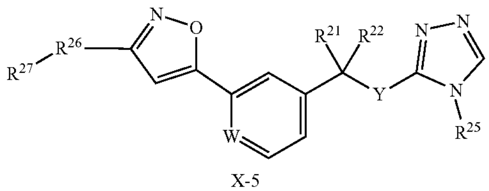

X-5 wherein $R^{21}$, $R^{22}$, $R^{25}$, $R^{26}$, $R^{27}$, W, and Y are as defined for the compound of Formula (II).

Oxazole compounds X-5 can be synthesized as illustrated in Scheme X. Alkynes X-1 are treated with a nitrile oxide, generated in situ by oxidation of oximes X-2, to provide oxazoles X-3, the ketone of which is then elaborated as in Scheme I to provide compounds of the formula X-5. Alternatively, elaborated intermediates X-4 may be treated with a nitrile oxide, generated in situ by oxidation of oximes X-2, to provide oxazoles X-5.

Scheme XI.

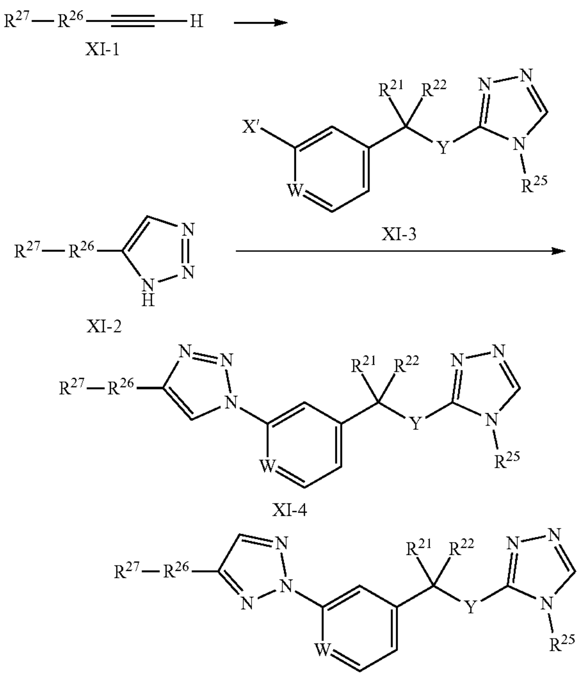

XI-1

XI-3

XI-2

XI-4

XI-5 wherein $R^{21}$, $R^{22}$, $R^{25}$, $R^{26}$, $R^{27}$, W, and Y are as defined for the compound of Formula (II); and X' is chlorine or bromine.

Compounds XI-4 and XI-5 can be synthesized as illustrated in Scheme XI. Terminal acetylene compounds XI-1 are converted to 1,2,3-triazoles by reaction with TMS-$N_3$. Subsequent palladium-catalyzed coupling with halo intermediates XI-3 provides compound of formula XI-4 and XI-5.

Scheme XII.

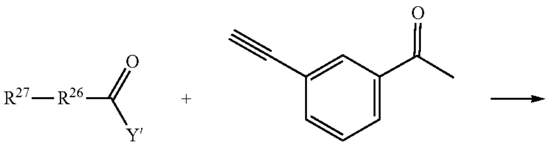

XII-1 XII-2

-continued

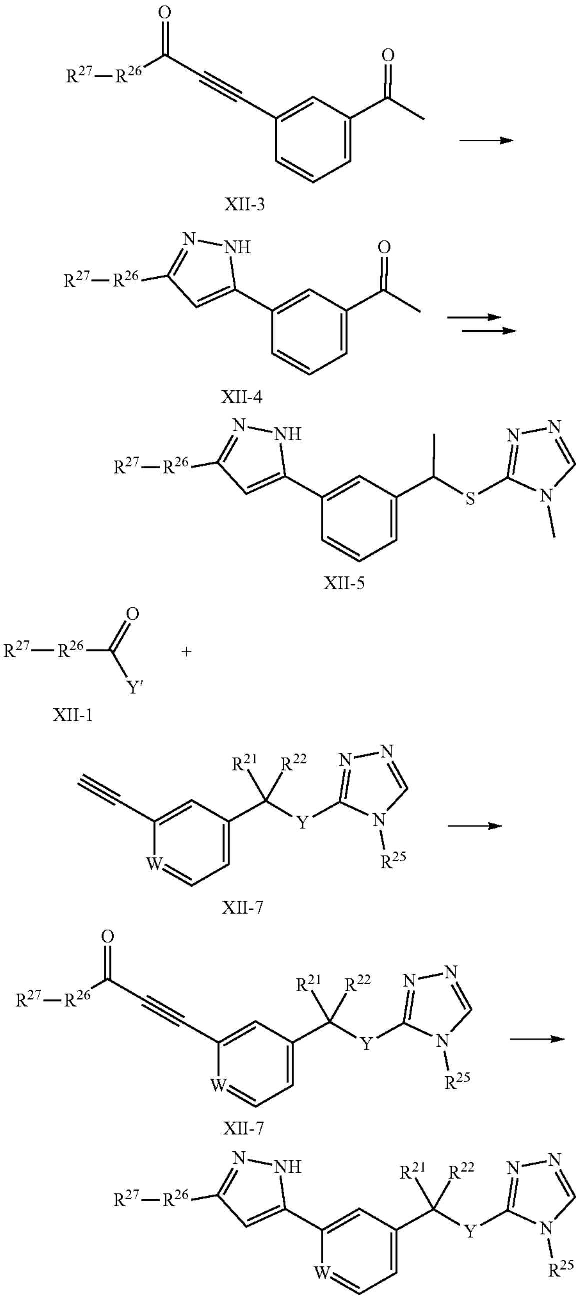

XII-3

XII-4

XII-5

XII-1

XII-7

XII-7

XII-8 wherein $R^{21}$, $R^{22}$, $R^{25}$, $R^{26}$, $R^{27}$, W, and Y are as defined for the compound of Formula (II); and Y' is Cl or NMe(OMe).

Pyrazole examples can be synthesized as illustrated in Scheme XII. In some embodiments, an acid chloride XII-1 (Y' is Cl) is coupled to a terminal alkyne XII-2 under palladium catalysis to afford yne-ones XII-3. Treatment with hydrazine affords pyrazoles XII-4. The remaining ketone is then elaborated to Examples XII-5 as illustrated in Scheme I. In other embodiments, elaborated alkynes such as XII-7 are deprotonated with a strong base such as n-BuLi and treated with Weinreb amides XII-1 (Y' is NMe(OMe)) to afford yne-ones XII-7, which are converted to pyrazoles XII-8 with hydrazine.

Scheme XIII.

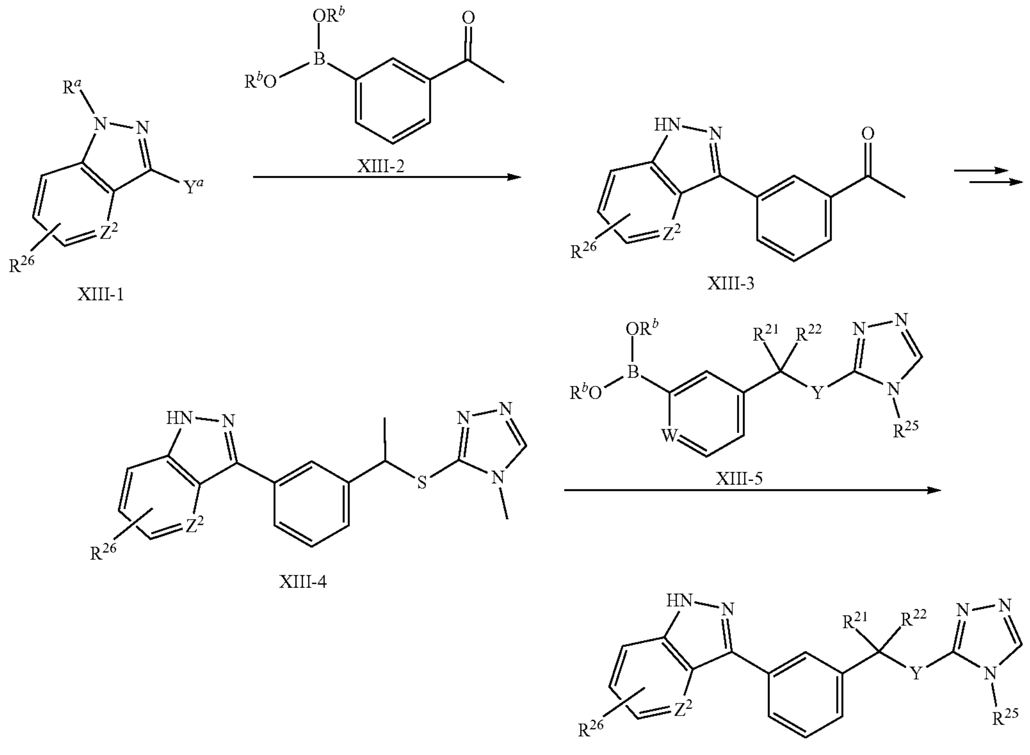

XIII-1

XIII-2

XIII-3

XIII-4

XIII-5

XIII-6 wherein $R^{21}$, $R^{22}$, $R^{25}$, $R^{26}$, W, and Y are as defined for the compound of Formula (II); $Z^2$ is CH or N; $Y^a$ is Br or I; and $R^a$ and $R^b$ are suitable protecting groups.

Benzopyrazole analogs can be assembled as illustrated in Scheme XIII. In some embodiments, protected benzopyrazole compounds XIII-1 are coupled to boronic acids or esters XIII-2 under palladium catalysis. The protecting group is either removed in the coupling or in a separate step. The ketone is elaborated to triazole XIII-4 as illustrated in Scheme I. In other embodiments, protected benzopyrazole compounds XIII-1 are coupled to elaborated cores XIII-5 under palladium catalysis. The protecting group is either removed in the coupling or in a separate step to afford compounds of formula XIII-6.

Scheme XIV.

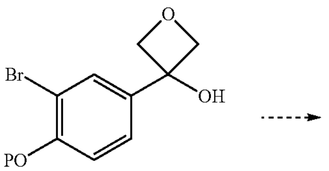

XIV-1

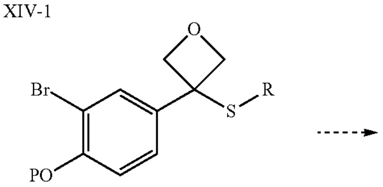

XIV-2

-continued

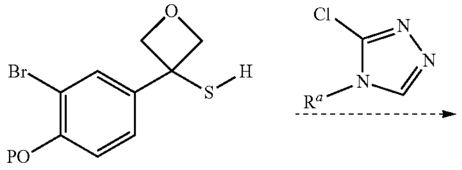

XIV-3

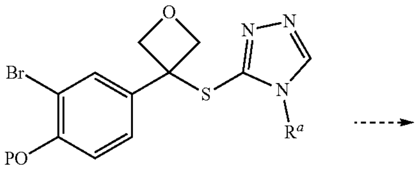

XIV-4

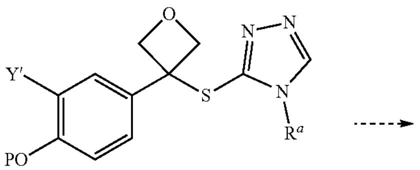

XIV-5

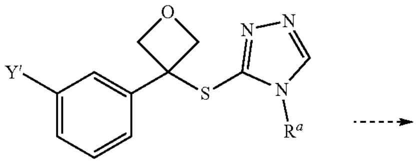

XIV-6

-continued

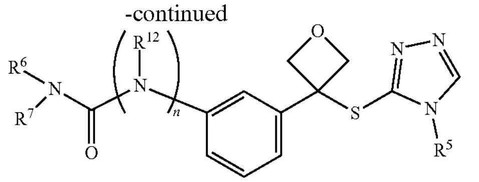

XIV-7

XIV-4

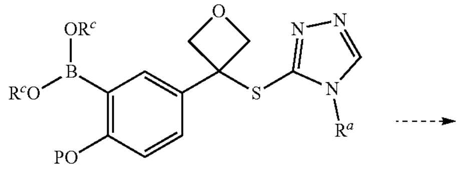

XIV-8

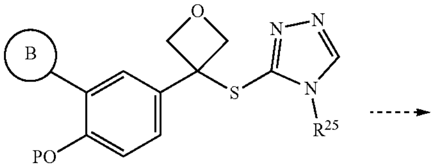

XIV-9

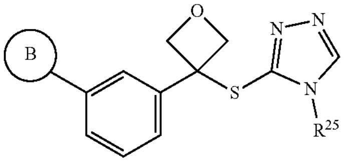

XIV-10 wherein $R^6$, $R^7$, and $R^2$ are as defined for the compound of Formula (I); $R^a$ is $R^5$ as defined for the compound of Formula (I) or $R^{25}$ as defined for the compound of Formula (II); Y' is $COOR^b$ or $NH_2$; $R^b$ and P are suitable protecting groups; and the Ring B moiety is as defined for the compound of Formula (II).

Scheme XIV outlines a synthesis for compounds of the general formula XIV-8 and XIV-9. The alcohol of XIV-1 is converted to a sulfide (XIV-3) by displacement with a thiol source such as tritylSH (Croft, Rosemary A. et al., Chemistry—A European Journal, 24(4), 818-821; 2018). The triazole is installed by $S_nAr$ displacement with a triazoyl chloride to afford XIV-4. The bromine is then elaborated to either an ester or amine XIV-5. The protecting group is then removed under the action of Ni catalysis (Correa, Arkaitz et al., Journal of the American Chemical Society, 136(3), 1062-1069; 2014) to intermediate XIV-6, which is elaborated to compounds XIV-7 as in Scheme III. In some embodiments, intermediate XIV-4 is converted to a heterocycle XIV-9 through intermediate XIV-8 as in Scheme XIII, then the OP group reduced as described above to provide compounds of the formula XIV-10.

Compounds 10, 19, 26-30, 113, and 122 display $IC_{50}$ values of less than 0.1 µM in the Cbl-b inhibition assay of Biological Example 1A, and in one embodiment are used for the pharmaceutical compositions and in the methods as disclosed herein. Compounds 2, 3, 9, 13, 14, 16, 20-25, 31, 45, 74, 88, 95, 99, 102, 105-107, 109-112, and 116 display $IC_{50}$ values between 0.1 µM and less than 1 µM in the Cbl-b inhibition assay of Biological Example 1A, and in one embodiment are used for the pharmaceutical compositions and in the methods as disclosed herein. Compounds 11, 15, 17, 32, 36, 39, 40, 46, 50, 55-62, 64, 65, 67, 69, 72, 73, 75-79, 82, 84, 86, 87, 89, 90, 93, 96, 97, 104, 108, 117-120, and 167 display $IC_{50}$ values of between 1 µM and less than 5 µM in the Cbl-b inhibition assay of Biological Example 1A, and in one embodiment are used for the pharmaceutical compositions and in the methods as disclosed herein. Compounds 1, 4-8, 12, 18, 33-35, 37, 38, 41-44, 47-49, 51-54, 63, 66, 68, 70, 71, 80, 81, 83, 85, 91, 92, 94, 98, 100, 101, 103, and 122-166 display $IC_{50}$ values of 5 µM or greater in the Cbl-b inhibition assay of Biological Example 1A, and in one embodiment are used for the pharmaceutical compositions and in the methods as disclosed herein.

In various embodiments, and as further described herein, compounds as provided herein (as well as compositions comprising compounds described herein, and methods using the compounds or compositions) have $IC_{50}$ values of less than 0.1 µM, between 0.1 µM and less than 1 µM, between 1 µM and less than 5 µM, or 5 µM or greater, as determined by the Cbl-b inhibition assay of Biological Example 1A. In a further embodiment, and as further described herein, compounds as provided herein (as well as compositions comprising compounds described herein, and methods using the compounds or compositions) have $IC_{50}$ values of less than 0.1 µM, as determined by the Cbl-b inhibition assay of Biological Example 1A. In a further embodiment, and as further described herein, compounds as provided herein (as well as compositions comprising compounds described herein, and methods using the compounds or compositions) have $IC_{50}$ values of between 0.1 µM and less than 1 µM, as determined by the Cbl-b inhibition assay of Biological Example 1A. In a further embodiment, and as further described herein, compounds as provided herein (as well as compositions comprising compounds described herein, and methods using the compounds or compositions) have $IC_{50}$ values of between 1 µM and less than 5 µM, as determined by the Cbl-b inhibition assay of Biological Example 1A. In a further embodiment, and as further described herein, compounds as provided herein (as well as compositions comprising compounds described herein, and methods using the compounds or compositions) have $IC_{50}$ values of 5 µM or greater, as determined by the Cbl-b inhibition assay of Biological Example 1A.

Compounds 114 and 115 display $IC_{50}$ values of less than 0.1 µM in the Cbl-b inhibition assay of Biological Example 1B, and in one embodiment are used for the pharmaceutical compositions and in the methods as disclosed herein.

In various embodiments, and as further described herein, compounds as provided herein (as well as compositions comprising compounds described herein, and methods using the compounds or compositions) have $IC_{50}$ values of less than 0.1 µM, between 0.1 µM and less than 1 µM, between 1 µM and less than 5 µM, or 5 µM or greater, as determined by the Cbl-b inhibition assay of Biological Example 1B. In a further embodiment, and as further described herein, compounds as provided herein (as well as compositions comprising compounds described herein, and methods using the compounds or compositions) have $IC_{50}$ values of less than 0.1 µM, as determined by the Cbl-b inhibition assay of Biological Example 1B. In a further embodiment, and as further described herein, compounds as provided herein (as well as compositions comprising compounds described herein, and methods using the compounds or compositions) have $IC_{50}$ values of between 0.1 µM and less than 1 µM, as determined by the Cbl-b inhibition assay of Biological Example 1B. In a further embodiment, and as further described herein, compounds as provided herein (as well as compositions comprising compounds described herein, and methods using the compounds or compositions) have $IC_{50}$ values of between 1 µM and less than 5 µM, as determined by the Cbl-b inhibition assay of Biological Example 1B. In a further embodiment, and as further described herein, compounds as provided herein (as well as compositions comprising compounds described herein, and methods using the compounds or compositions) have $IC_{50}$ values of 5 μM or greater, as determined by the Cbl-b inhibition assay of Biological Example 1B.

III. Use and Methods

Provided herein are methods for modulating activity of an immune cell (e.g., a T-cell, a B-cell, or a NK-cell) such as by contacting the immune cell with an effective amount of a Cbl-b inhibitor described herein or a composition thereof. Also provided are in vitro methods of producing said immune cells with modulated activity, referred to herein as "modified immune cells," wherein said modified immune cells can be administered to an individual in need thereof (e.g., an individual having cancer) by ex vivo methods. Further provided are in vivo methods of modulating a response in an individual in need thereof (e.g., an individual with cancer), wherein the method comprises administration of an effective amount of a Cbl-b inhibitor described herein or a composition thereof. Moreover, this disclosure provides in vitro methods of producing an expanded population of lymphocytes after in vivo lympho-conditioning in an individual with cancer, wherein the lympho-conditioning occurs as a result of administration of an effective amount of a Cbl-b inhibitor described herein or a composition thereof to the individual. The expanded population of lymphocytes can then be administered to the individual with cancer. In some embodiments, the modified immune cells or the expanded population of lymphocytes are produced from a biological sample comprising immune cells obtained from the individual, such as a blood sample comprising peripheral blood mononuclear cells or a tumor biopsy comprising tumor infiltrating lymphocytes (TTLs).

Additionally, provided are Cbl-b inhibitors for use as therapeutic active substances. A Cbl-b inhibitor for use in treating or preventing a disease or condition associated with Cbl-b activity is provided. Also, a Cbl-b inhibitor for use in treating cancer is provided. Further provided is the use of a Cbl-b inhibitor in the manufacture of a medicament for treating or preventing a disease or condition associated with Cbl-b activity. Also provided is the use of a Cbl-b inhibitor in the manufacture of a medicament for treating cancer.

Moreover, this disclosure provides treatment methods, medicaments, and uses comprising a Cbl-b inhibitor as part of a combination therapy for treating cancer involving one or more of an immune checkpoint inhibitor, an antineoplastic agent, and radiation therapy.

In some embodiments of the treatment methods, medicaments, and uses of this disclosure, the cancer is a hematologic cancer such as lymphoma, a leukemia, or a myeloma. In other embodiments of the treatment methods, medicaments, and uses of this disclosure, the cancer is a non-hematologic cancer such as a sarcoma, a carcinoma, or a melanoma.

Hematologic cancers include, but are not limited to, one or more leukemias such as B-cell acute lymphoid leukemia ("BALL"), T-cell acute lymphoid leukemia ("TALL"), acute lymphoid leukemia (ALL); one or more chronic leukemias including, but not limited to, chronic myelogenous leukemia (CML) and chronic lymphocytic leukemia (CLL); additional hematologic cancers or hematologic conditions including, but not limited to, B-cell prolymphocytic leukemia, blastic plasmacytoid dendritic cell neoplasm, Burkitt's lymphoma, diffuse large B-cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia," which are a diverse collection of hematological conditions united by ineffective production (or dysplasia) of myeloid blood cells.

Non-hematologic cancers include, but are not limited to, a neuroblastoma, renal cell carcinoma, colon cancer, colorectal cancer, breast cancer, epithelial squamous cell cancer, melanoma, stomach cancer, brain cancer, lung cancer (e.g., NSCLC), pancreatic cancer, cervical cancer, ovarian cancer, liver cancer, bladder cancer, prostate cancer, testicular cancer, thyroid cancer, uterine cancer, adrenal cancer, and head and neck cancer.

In some aspects, the effectiveness of administration of a Cbl-b inhibitor in the treatment of a disease or disorder such as cancer is measured by assessing clinical outcome, such as reduction in tumor size or number of tumors, and/or survival. In certain embodiments, "treating cancer" comprises assessing a patient's response to the treatment regimen according to the Response Evaluation Criteria in Solid Tumors (RECIST version 1.1) as described (see, e.g., Eisenhauer et al., Eur J Cancer, 45:228-247, 2009; and Nishino et al., Am J Roentgenol, 195: 281-289, 2010). Response criteria to determine objective anti-tumor responses per RECIST 1.1 include complete response (CR); partial response (PR); progressive disease (PD); and stable disease (SD).

A. Isolation and Processing of Cells

Provided are methods for the preparation and processing of immune cells produced (e.g., modified immune cells) and used in the methods herein. As used herein, the term "modified immune cells" refers to immune cells or a cell population comprising the immune cells which have been cultured, incubated, and/or have been contacted with an effective amount of a Cbl-b inhibitor to modulate the activity of said immune cells. In some embodiments, the modified immune cells can be used for immunotherapy, such as in connection with adoptive immunotherapy methods.

1. Samples

In some embodiments, the immune cells to be modified or cell populations comprising the immune cells to be modified are isolated from a sample, such as a biological sample, e.g., one obtained from or derived from an individual (e.g., a human). In some embodiments, the individual from which the immune cell is isolated is one having a particular disease or condition (e.g., cancer) or in need of a cell therapy or to which cell therapy will be administered. The individual, in some embodiments, is a human in need of a particular therapeutic intervention, such as the adoptive cell therapy for which immune cells are being isolated, processed, and/or modified. Accordingly, the cells isolated from the individual, in some embodiments, are primary cells (e.g., primary human cells). As used herein, the term "primary cells" refers to cells isolated directly from mammalian biological fluid or tissue (e.g., human biological fluid or tissue).

In some embodiments, the immune cells to be modified are hematopoietic cells, multipotent stem cells, myeloid progenitor cells, lymphoid progenitor cells, T-cells, B-cells, and/or NK-cells. As used herein, the term "hematopoietic cells" includes hematopoietic stem cells and hematopoietic progenitor cells. In some embodiments, the immune cells to be modified are present in a heterogeneous cell population or a composition comprising a heterogeneous cell population. For example, the immune cells to be modified may be hematopoietic cells present in a heterogeneous cell population comprising cells such as differentiated cells derived from a tissue or organ. In some embodiments, the immune cells to be modified are present in a homogenous cell population or a composition comprising a homogenous cell population. For example, the immune cells to be modified may be hematopoietic cells present in a homogenous cell population comprising only hematopoietic cells. In some embodiments, the immune cells to be modified or cell populations comprising the immune cells to be modified include one or more subsets of immune cells. For example, one or more subsets of immune cells may be CD4+ cells, CD8+ cells and subpopulations thereof, such as those defined by function, activation state, maturity, potential for differentiation, expansion, localization, persistence capacities, surface marker profile, cytokine secretion profile, and/or degree of differentiation.

In some embodiments, biological samples described herein include tissue, fluid, and other samples taken directly from the individual, as well as samples resulting from one or more processing steps, such as separation, centrifugation, genetic engineering (e.g., transduction with a viral vector encoding a recombinant chimeric receptor), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine, sweat, and tissue and organ samples (e.g., sample from a tissue or organ containing a tumor), including processed samples derived therefrom. In some embodiments, the biological sample is a biological fluid sample or a biological tissue sample. In some embodiments, the biological sample is a biological tissue sample. In some aspects, the biological sample from which the immune cells are derived or isolated is blood or a blood-derived sample, or is derived from an apheresis or leukapheresis product.

Exemplary biological samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Biological samples include, in the context of cell therapy (e.g., adoptive cell therapy) samples from autologous sources (i.e., obtained from or derived from the individual in need of cell therapy) and allogeneic sources (i.e., obtained from or derived from an individual or source other than the individual in need of cell therapy).

In some embodiments, the immune cells to be modified or a cell population comprising the immune cells to be modified are derived from a cell line (e.g., a T-cell line, a B-cell line, a NK-cell line, etc.). In some embodiments, the immune cells to be modified or a cell population comprising the immune cells to be modified are obtained from a xenogeneic source, such as from mouse, rat, non-human primate, or pig.

2. Cell Processing and Separation

In some embodiments, isolation of the immune cells to be modified includes one or more preparation and/or cell separation steps. The one or more cell separation steps can be non-affinity based separation or affinity based separation. As an example, non-affinity based separation can be centrifugation of a composition comprising the immune cells to be modified. In some embodiments, the non-affinity based separation methods include density-based cell separation methods, such as the preparation of white blood cells from peripheral blood by lysing the red blood cells and centrifugation through a Percoll or Ficoll gradient. Affinity based separation methods can include contacting a composition comprising the immune cells to be modified with antibody-coated beads. Antibody-coated beads contemplated herein include, but are not limited to, magnetic beads (e.g., Dynabeads® marketed by Life Technologies, Carlsbad, CA; MACS® microbeads marketed by Miltenyi Biotec Inc., Auburn, CA; or EasySep™ Direct RapidSpheres™ marketed by Stemcell Technologies, Vancouver, BC, Canada) coated with an antibody that binds to a marker expressed on the surface of the immune cell to be modified. In some embodiments, specific subpopulations of T-cells, such as cells positive for or otherwise expressing high levels of one or more surface markers, e.g., CD4+, CD8+, etc., are isolated by positive or negative selection techniques. Positive selection can be based on a technique in which the target cells (e.g., immune cells to be modified) have bound to a reagent and are retained for further use. For example, T-cells that are CD3+ can be positively selected using magnetic beads conjugated to anti-CD3 antibodies (e.g., MACS® CD3 human microbeads). Negative selection can be based on a technique in which the targets cells (e.g., immune cells to be modified) that have not bound to a reagent are retained. For example, total human primary T-cells can be isolated from peripheral blood mononuclear cells (PMBCs) utilizing negative selection, wherein a cocktail of antibodies against surface markers CD14, CD15, CD16, CD19, CD34, CD36, CD56, CD123, and CD235a are incubated in a sample comprising the PBMCs before passing the sample by magnetic beads for removal of cells expressing those surface markers and retaining the remaining cells in the sample for subsequent processing. In some embodiments, the immune cells or a cell population comprising the immune cells to be modified are washed, centrifuged, and/or incubated in the presence of one or more reagents, for example, to remove unwanted components, enrich for desired components, and/or lyse or remove cells sensitive to particular reagents. In some examples, the immune cells are separated based on one or more property, such as density, adherent properties, size, sensitivity, and/or resistance to particular components. Cell separation steps do not require 100% enrichment or removal of particular cells. In some embodiments, positive selection of or enrichment for immune cells of a particular type (e.g., CD4+ T-cells) refers to increasing the number or percentage of such cells. In some embodiments, removal, or depletion of cells of a particular type that are not of interest such as by negative selection, refers to decreasing the number or percentage of such cells.

In some embodiments, immune cells or a cell population comprising the immune cells are obtained from the circulating blood of an individual, e.g., by apheresis or leukapheresis. In some aspects, a sample comprising the immune cells to be modified contains lymphocytes, including T-cells, B-cells, and NK-cells, as well as monocytes, granulocytes, red blood cells, and/or platelets, and in some aspects contains cells other than red blood cells and platelets.

In some embodiments, the blood cells collected from the individual are washed such as to remove the plasma fraction and to place the cell population comprising the immune cells to be modified in an appropriate buffer or media for subsequent processing steps. In some embodiments, the cell population comprising the immune cells to be modified is washed with phosphate buffered saline. In some embodiments, the wash solution lacks calcium and/or magnesium. In some aspects, a washing step is accomplished by a semi-automated "flow-through" centrifuge. In some aspects, a washing step is accomplished by tangential flow filtration. In some embodiments, the immune cells to be modified or cell population containing the immune cells to be modified are resuspended in a variety of suitable buffers after washing, such as, for example, calcium and/or magnesium free phosphate buffered saline. In some embodiments, components of a blood cell sample are removed and the immune cells to be modified or a cell population comprising the immune cells to be modified are directly resuspended in a suitable cell culture medium.

Representative methods for processing and/or separating immune cells, such as hematopoietic cells, from samples containing a cell population containing said hematopoietic cells (e.g., samples comprising PBMCs) are described in Biological Example 2 and Biological Example 3 herein. Methods and techniques for processing and/or separating immune cells such as hematopoietic cells, multipotent stem cells, myeloid progenitor cells, lymphoid progenitor cells, T-cells, B-cells, and/or NK-cells are well known in the art. See for example, U.S. Patent Application No. 2017/0037369; U.S. Patent Application No. 2012/0148553; U.S. Pat. Nos. 6,461,645; 6,352,694; and 7,776,562.

3. Incubation and Treatment

Provided herein are methods for modulating the activity of an immune cell, such as the processed, and/or separated immune cells described above, by contacting the immune cell with an effective amount of a Cbl-b inhibitor described herein. Also provided herein are modified immune cells produced by any of the methods described herein such as by culturing a cell population containing an immune cell (e.g., the processed and/or separated immune cells described above) in the presence of an effective amount of a Cbl-b inhibitor to modulate the activity of the immune cell and thereby produce the modified immune cell.

In some embodiments, the immune cells to be modified (e.g., the processed and/or separated immune cells described above) are incubated and/or cultured in a suitable culture medium prior to contacting said immune cells with a Cbl-b inhibitor provided herein. In some embodiments, the immune cells to be modified are incubated and/or cultured in a suitable culture medium simultaneously to contacting said immune cells with a Cbl-b inhibitor provided herein.

The processed and/or separated immune cells to be modified or cell population comprising the immune cells to be modified can be differentiated and/or expanded in vitro. In some embodiments, the immune cells to be modified are hematopoietic cells, multipotent stem cells, myeloid progenitor cells, lymphoid progenitor cells, T-cells, B-cells, and/or NK-cells. In some embodiments, the immune cell to be modified is incubated in a suitable cell culture medium comprising a Cbl-b inhibitor described herein before differentiation and/or expansion of the immune cell. In some embodiments, the immune cell to be modified is incubated in a suitable cell culture medium comprising a Cbl-b inhibitor described herein after differentiation and/or expansion of the immune cell. The immune cells become modified (i.e., modified immune cells) upon contact with a Cbl-b inhibitor provided herein in an effective amount to modulate the activity of said immune cells. In some embodiments, the immune cell to be modified is not differentiated and/or expanded in vitro and is therefore the same cell type as the modified immune cell that has been contacted with a Cbl-b inhibitor. For example, a T-cell can be incubated in a suitable medium comprising a Cbl-b inhibitor without differentiation of the T-cell. In other embodiments, the immune cell to be modified is differentiated and/or expanded in vitro and is therefore a different cell type than the modified immune cell that has been contacted with a Cbl-b inhibitor. For example, a hematopoietic cell can be incubated in a suitable medium comprising a Cbl-b inhibitor as well as other agents that drive differentiation of the hematopoietic cell into a mature hematopoietic cell. Accordingly, in some aspects of the embodiments herein, the modified immune cells are hematopoietic cells, multipotent stem cells, myeloid progenitor cells, lymphoid progenitor cells, T-cells, B-cells, and/or NK-cells. Methods for expansion and/or differentiation of immune cells are well known in the art. See, for example, International Patent Application No. WO 2017/037083.

An effective amount of a Cbl-b inhibitor is the amount or concentration of the Cbl-b inhibitor that is sufficient to modulate the activity of the immune cell as compared to a reference sample. The reference sample may be immune cells that have not been contacted with the Cbl-b inhibitor. In some embodiments, the concentration of a Cbl-b inhibitor added to a composition (e.g., cell culture medium) comprising the immune cells to be modified is from about 1 pM to about 100 μM, about 5 pM to about 100 μM, about 10 pM to about 100 μM, about 20 pM to about 100 μM, about 40 pM to about 100 μM, about 60 pM to about 100 μM, about 80 pM to about 100 μM, about 1 nM to about 100 μM, about 3 nM to about 100 μM, about 10 nM to about 100 μM, about 15 nM to about 100 μM, about 20 nM to about 100 μM, about 40 nM to about 100 μM, about 60 nM to about 100 μM, about 80 nM to about 100 μM, about 0.1 μM to about 100 μM, about 0.1 μM to about 90 μM, about 0.1 μM to about 80 μM, about 0.1 μM to about 70 μM, about 0.1 μM to about 60 μM, about 0.1 μM to about 50 μM, about 0.1 μM to about 40 μM, about 0.1 μM to about 30 μM, about 0.1 μM to about 20 μM, about 0.1 μM to about 10 μM, about 0.2 μM to about 10 μM, or about 0.3 μM to about 8 μM. In some embodiments, the concentration of a Cbl-b inhibitor added to a composition (e.g., cell culture medium) comprising the immune cells to be modified is about 1 pM, about 2 pM, about 3 pM, about 4 pM, about 5 pM, about 10 pM, about 20 pM, about 30 pM, about 40 pM, about 50 pM, about 60 pM, about 70 pM, about 80 pM, about 90 pM, about 1 nM, about 3 nM, about 5 nM, about 10 nM, about 20 nM, about 40 nM, about 50 nM, about 80 nM, about 0.1 μM, about 0.2 μM, about 0.3 μM, about 0.4 μM, about 0.5 μM, about 1 μM, about 5 μM, about 10 μM, about 15 μM, about 20 μM, about 25 μM, about 30 μM, about 40 μM, about 50 μM, about 60 μM, about 70 μM, about 80 μM, about 90 μM, or about 100 μM. In some embodiments, the concentration of a Cbl-b inhibitor added to a composition (e.g., cell culture medium) comprising the immune cells to be modified is about 0.3 μM, about 1 μM, or about 4 μM. In some embodiments, the concentration of a Cbl-b inhibitor added to a composition (e.g., cell culture medium) comprising the immune cells to be modified is about 1 μM or about 8 μM.

The effective amount of a Cbl-b inhibitor is in contact with the immune cells for a sufficient time to modulate the activity of the immune cell as compared to a reference sample. The reference sample may be immune cells that have not been contacted with the Cbl-b inhibitor, but are incubated for the same length of time as the composition (e.g., cell culture medium) comprising the immune cells and the Cbl-b inhibitor. In some embodiments, the Cbl-b inhibitor is in contact and/or is incubated with the immune cells from about 1 minute to about 1 hour, about 5 minutes to about 1 hour, about 10 minutes to about 1 hour, about 15 minutes to about 1 hour, about 20 minutes to about 1 hour, about 30 minutes to about 1 hour, about 45 minutes to about 1 hour, about 1 hour to about 2 hours, about 1 hour to about 4 hours, about 1 hour to about 6 hours, about 1 hour to about 8 hours, about 1 hour to about 12 hours, about 1 hour to about 24 hours, about 2 hours to about 24 hours, about 6 hours to about 7 hours, about 6 hours to about 24 hours, about 8 hours to about 24 hours, about 10 hours to about 24 hours, about 15 hours to about 24 hours, about 20 hours to about 24 hours, about 12 hours to about 48 hours, about 24 hours to about 48 hours, or about 36 hours to about 48 hours. In some embodiments, the Cbl-b inhibitor is in contact and/or is incubated with the immune cells for about 1 minute, about 5 minutes, about 10 minutes, about 15 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours. In some embodiments, the Cbl-b inhibitor is in contact and/or is incubated with the immune cells from about 1 day to about 7 days, about 2 days to about 7 days, about 3 days to about 7 days, about 4 days to about 7 days, about 5 days to about 7 days, or about 6 days to about 7 days. In some embodiments, the Cbl-b inhibitor is in contact and/or is incubated with the immune cells from about 7 days to about 14 days, about 14 days to about 21 days, or about 21 days to about 28 days. In some embodiments, the Cbl-b inhibitor is in contact and/or is incubated with the immune cells for about 1 day, about 2 days, about 3 days, about 4 days, about 5 days, about 6 days, about 7 days, about 8 days, about 9 days, about 10 days, about 11 days, about 12 days, about 13 days or about 14 days.

In some embodiments, the immune cells or a cell population comprising the immune cells are incubated under a suitable condition to induce proliferation, expansion, activation, and/or survival of the immune cells. Suitable conditions during incubation include, but are not limited to, use of one or more medium of cell culture medium, temperature, incubation time, the presence of a stimulating agent (e.g., anti-CD3 and/or anti-CD28 antibody), and the presence of any other beneficial agents, such as growth factors, cytokines, chemokines, and/or recombinant soluble receptors.

In some embodiments, a suitable condition to induce proliferation, expansion, activation, and/or survival of the immune cells includes the provision of stimulating conditions comprising agents that are capable of activating the immune cell (e.g., NK-cell). For example, a suitable condition to induce proliferation, expansion, activation, and/or survival of a T-cell includes the provision of stimulating conditions and/or agents that are capable of activating intracellular signaling in the T-cell. Full activation of T-cells generally requires the recognition of antigen by the T-cell receptor, referred to herein as "TCR" (signal one) as well as recognition of costimulators such as CD28 (signal two). In some aspects, one or more agents turn on or initiate a TCR complex-mediated intracellular signaling cascade in a T-cell. For example, a first agent can bind to a component of the TCR complex in order to activate the T-cell and a second agent can bind to a costimulatory molecule on the surface of the T-cell to thereby stimulate the activated T-cell. In some embodiments, the first agent stimulated a TCR/CD3 complex-associated signal in the T-cell by specifically binding to CD3 (e.g., an anti-CD3 antibody). In a further embodiment, the co-stimulatory molecule on the surface of the T-cell may be CD28 and the second agent specifically binds to CD28 (e.g., anti-CD28 antibody). Such agents include, but are not limited to, antibodies, divalent antibody fragments, and binding molecules such as those specific for a TCR complex component (e.g., anti-CD3 antibody) and/or those specific for costimulatory receptor (e.g., anti-CD28 antibody). In some embodiments, an agent that specifically binds to CD3 is an anti-CD3 antibody, a divalent antibody fragment of an anti-CD3 antibody (e.g., (Fab)2' fragment or a divalent scFv fragment), a monovalent antibody fragment of an anti-CD3 antibody (e.g., a Fab fragment, a Fv fragment, or a scFv fragment), or a CD3 binding molecule (e.g., an aptamer). In some embodiments, an agent that specifically binds to CD28 is an anti-CD28 antibody, a divalent antibody fragment of an anti-CD28 antibody (e.g., (Fab)2' fragment or a divalent scFv fragment), a monovalent antibody fragment of an anti-CD28 antibody (e.g., a Fab fragment, a Fv fragment, or a scFv fragment), and a CD28 binding molecule (e.g., an aptamer). The one or more agents provided herein (e.g., anti-CD3 antibody and anti-CD28 antibody) for example, can be bound to a solid support such as a bead, or cross-linked with an anti-Fc antibody. In some embodiments, the expansion method step may further comprise the step of adding anti-CD3 antibody and/or anti-CD28 antibody to the culture medium. In some embodiments, the stimulating agents added to the cell culture medium include one or more cytokines such as, but not limited to, one or more of IL-2, IL-7, IL-15, and IL-21. For example, IL-2 can be added at a concentration of at least about 10 units/mL to a cell culture medium comprising the immune cells and agents such as anti-CD3 antibodies and/or anti-CD28 antibodies.

In some embodiments, a suitable condition to induce proliferation, expansion, activation, and/or survival of a T-cell includes the provision of stimulating conditions or agents which are capable of activating intracellular signaling through the T-cell receptor (TCR) complex, and a Cbl-b inhibitor as described herein. In some embodiments, the immune cells or a cell population comprising the immune cells are incubated with a first agent that stimulates a TCR/CD3 complex-associated signal in the T-cell by specifically binding to CD3 (e.g., an anti-CD3 antibody). In a further embodiment, the immune cells or a cell population comprising the immune cells are incubated with a first agent that stimulates a TCR/CD3 complex-associated signal in the T-cell by specifically binding to CD3 (e.g., an anti-CD3 antibody), with a second agent that binds to the co-stimulatory molecule CD28 (e.g., an anti-CD28 antibody), and with a Cbl-b inhibitor at a concentration of about 1 pM to about 100 μM (e.g., about 0.3 μM, about 1 μM, or about 4 μM). In some embodiments, a suitable condition to induce proliferation, expansion, activation, and/or survival of a T-cell when in the presence of a Cbl-b inhibitor does not require stimulation through a co-stimulatory molecule (e.g., CD28). Contacting T-cells with a Cbl-b inhibitor or a composition thereof can bypass the need for co-stimulation required for T-cells to enter into an activated state. In some embodiments, the immune cells or a cell population comprising the immune cells are incubated with a first agent that stimulates a TCR/CD3 complex-associated signal in the T-cell by specifically binding to CD3 (e.g., an anti-CD3 antibody) and with a Cbl-b inhibitor at a concentration of about 0.001 μM to about 1,000 μM, about 0.01 μM to about 100 μM, about 0.1 μM to about 10 μM, or about 0.1 μM to about 50 μM (e.g., about 1 μM or about 8 μM).

In some embodiments of the methods for modulating activity of an immune cell, the immune cell is a T-cell and modulating activity of the T-cell comprises increased T-cell activation and/or increased T-cell proliferation. T-cells contemplated in embodiments herein may be in a tolerant state even in the presence of an activating agent that binds to a component of the TCR complex, such as an anti-CD3 antibody, as well as in the presence of a stimulating agent that binds a co-stimulatory molecule, such as an anti-CD28 antibody. In some embodiments, the method of modulating activity of a T-cell comprises contacting the T-cell with an effective amount of a Cbl-b inhibitor or a composition thereof in the presence of an anti-CD3 antibody in combination with an anti-CD28 antibody. In some embodiments, the method of modulating activity of a T-cell comprises contacting the T-cell with an effective amount of a Cbl-b inhibitor or a composition thereof, wherein the T-cell previously has been in contact with an anti-CD3 antibody in combination with an anti-CD28 antibody. In some embodiments, stimulation via the co-stimulatory CD28 molecule is not required for modulating the activity of the T-cell (e.g., increasing T-cell activation and/or increasing T-cell proliferation). In some embodiments, the method of modulating activity of a T-cell comprises contacting the T-cell with an effective amount of a Cbl-b inhibitor or a composition thereof in the presence of an anti-CD3 antibody alone. In some embodiments, the method of modulating activity of a T-cell comprises contacting the T-cell with an effective amount of a Cbl-b inhibitor or a composition thereof, wherein the T-cell has previously been in contact with one or more agents that activate the T-cell (e.g., an anti-CD3 antibody), wherein said agents do not include an agent that stimulates the CD28 co-stimulatory molecule (e.g., an anti-CD28 antibody).

In some embodiments, the immune cell is a T-cell and modulating activity of the T-cell comprises enhanced T-cell activation and/or enhanced T-cell proliferation. For example, T-cells contemplated in embodiments herein may be in an activated state such as when in the presence of agents that activate the T-cells (e.g., anti-CD3 antibody), and in some further embodiments, in the presence of agents that stimulate the T-cells (e.g., anti-CD28 antibody). Contacting T-cells with a Cbl-b inhibitor or composition thereof can lower the threshold required for activation and therefore enhance activation and/or proliferation of T-cells that are in the presence of an activating agent (e.g., an anti-CD3 antibody) and in some further embodiments, a stimulating agent (e.g., an anti-CD28 antibody). In some embodiments, the method of modulating activity of a T-cell comprises contacting the T-cell with an effective amount of a Cbl-b inhibitor or a composition thereof in the presence of an anti-CD3 antibody in combination with an anti-CD28 antibody. In some embodiments, the method of modulating activity of a T-cell comprises contacting the T-cell with an effective amount of a Cbl-b inhibitor or a composition thereof, wherein the T-cell has previously been in contact with an anti-CD3 antibody in combination with an anti-CD28 antibody. In some embodiments, stimulation via the co-stimulatory CD28 molecule is not required for modulating the activity of the T-cell (e.g., enhancing T-cell activation and/or enhancing T-cell proliferation). In some embodiments, the method of modulating activity of a T-cell comprises contacting the T-cell with an effective amount of a Cbl-b inhibitor or a composition thereof in the presence of an anti-CD3 antibody alone. In some embodiments, the method of modulating activity of a T-cell comprises contacting the T-cell with an effective amount of a Cbl-b inhibitor or a composition thereof, wherein the T-cell has previously been in contact with one or more agents that activate the T-cell (e.g., anti-CD3 antibody).

In some embodiments, the immune cell is a T-cell and modulating activity of the T-cell comprises decreased T-cell dysfunction including decreased T-cell exhaustion, decreased T-cell tolerance, and/or decreased T-cell anergy. General principles of T-cell dysfunction are well known in the art (see, e.g., Schietinger et al., Trends Immunol., 35: 51-60, 2014). Immune tolerance is a process that is part of the normal function of the immune system. Antigen-specific immune tolerance is characterized by a decrease in responsiveness to an antigen, which is induced by previous exposure to that antigen. When specific lymphocytes (e.g., T-cells) encounter antigens, the lymphocytes may be activated, leading to an antigen-specific immune response, or the lymphocytes (e.g., T-cells) may be inactivated or eliminated, leading instead to antigen-specific immune tolerance. In some aspects, tolerance can be caused by clonal anergy, peripheral clonal deletion, suppression of T-cells, and/or other forms of antigen-specific tolerance. In some embodiments, tolerance may result from or be characterized by the induction of anergy. In some aspects, anergy can result from exposure of T-cells to an antigen in the absence of costimulation. Prolonged antigen recognition by the TCR alone, in the absence of the co-stimulatory signal, may lead to anergy (i.e., functional unresponsiveness). Anergic T-cells may be refractory to subsequent antigenic challenge, and may be capable of suppressing other immune responses. Generally, in the natural setting, tolerance is involved in non-reactivity or nonproductive reactivity to self-antigens. In some cases, however, tolerance to a "non-self" antigen can be induced. Thus, in some aspects, the same mechanisms by which mature T-cells that recognize self-antigens in peripheral tissues become incapable of subsequently responding to these antigens also may regulate unresponsiveness to foreign or "non-self" antigens such as those expressed by cancer cells. Accordingly, T-cells contemplated in embodiments herein may be in a tolerant state even in the presence of stimulatory agents such as agents that bind to a co-stimulatory molecule such as CD28. Contacting T-cells with a Cbl-b inhibitor provided herein or a composition thereof can bypass aspects of T-cell dysfunction such as T-cell tolerance, T-cell anergy, and/or T-cell exhaustion. In some embodiments, the method of modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof. In some embodiments of the methods herein, modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof in the presence of an anti-CD3 antibody in combination with an anti-CD28 antibody. In some embodiments of the methods herein, the method of modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof, wherein the T-cell previously has been in contact with an anti-CD3 antibody in combination with an anti-CD28 antibody. In some embodiments, stimulation via the co-stimulatory CD28 molecule is not required for modulating the activity of the T-cell (e.g., decreasing T-cell tolerance, decreasing T-cell anergy, and/or decreasing T-cell exhaustion). In some embodiments of the methods herein, the method of modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof in the presence of an anti-CD3 antibody alone. In some embodiments, the method of modulating activity of a T-cell (e.g., decreasing T-cell tolerance, decreasing T-cell anergy, and/or decreasing T-cell exhaustion) comprises contacting the T-cell with an effective amount of a Cbl-b inhibitor or a composition thereof, wherein the T-cell has previously been in contact with one or more agents that activate the T-cell, such as an anti-CD3 antibody alone.

T-cell activation and T-cell tolerance are tightly controlled processes regulating the immune response. Accordingly, provided herein are methods of modulating activity of the T-cell, wherein modulating activity of the T-cell comprises increased T-cell activation, increased T-cell proliferation, decreased T-cell exhaustion, and/or decreased T-cell tolerance. In some embodiments, the method of modulating activity of a T-cell (e.g., increased T-cell activation, increased T-cell proliferation, decreased T-cell exhaustion, and/or decreased T-cell tolerance) comprises contacting the T-cell with an effective amount of a Cbl-b inhibitor or a composition thereof. In some embodiments of the methods herein, modulating activity of a T-cell (e.g., increasing T-cell activation, increasing T-cell proliferation, decreasing T-cell exhaustion, and/or decreasing T-cell tolerance) comprises contacting the T-cell with an effective amount of a Cbl-b inhibitor or a composition thereof in the presence of an anti-CD3 antibody in combination with an anti-CD28 antibody. In some embodiments of the methods herein, the method of modulating activity of a T-cell (e.g., increasing T-cell activation, increasing T-cell proliferation, decreasing T-cell exhaustion, and/or decreasing T-cell tolerance) comprises contacting the T-cell with an effective amount of a Cbl-b inhibitor or a composition thereof, wherein the T-cell previously has been in contact with an anti-CD3 antibody in combination with an anti-CD28 antibody. In some embodiments, stimulation via the co-stimulatory CD28 molecule is not required for modulating the activity of the T-cell (e.g., increasing T-cell activation, increasing T-cell proliferation, decreasing T-cell exhaustion, and/or decreasing T-cell tolerance). In some embodiments of the methods herein, the method of modulating activity of a T-cell (e.g., increasing T-cell activation, increasing T-cell proliferation, decreasing T-cell exhaustion, and/or decreasing T-cell tolerance) comprises contacting the T-cell with an effective amount of a Cbl-b inhibitor provided herein or a composition thereof in the presence of an anti-CD3 antibody alone. In some embodiments, the method of modulating activity of a T-cell (e.g., increasing T-cell activation, increasing T-cell proliferation, decreasing T-cell exhaustion, and/or decreasing T-cell tolerance) comprises contacting the T-cell with an effective amount of a Cbl-b inhibitor or a composition thereof, wherein the T-cell has previously been in contact with one or more agents that activate the T-cell (e.g., an anti-CD3 antibody).

In some embodiments of the methods herein, increased T-cell activation comprises increased production of one or more cytokines from T-cells or surrounding immune cells in the activated T-cell microenvironment (e.g., myeloid cells). In some embodiments, the one or more cytokines include, but are not limited to, IFN-γ, IL-10, IL-2, IL-4, IL-5, IL-6, IL-13, IL-18, TNFα, and GM-CSF. In some embodiments, the cytokine is one or more of IL-2, IFN-γ, TNFα, and GM-CSF. In some embodiments, the cytokine is a chemokine. In some embodiments, the one or more chemokines include, but are not limited to, IP-10, Eotaxin, GRO alpha, RANTES, MIP-1α, MIP-1β, MIP-2, MCP-1, and MCP-3. Increased expression of cytokines can be measured by ELISA.

In some embodiments of the methods herein, increased T-cell activation comprises increased cell surface expression of one or more T-cell activation markers. In some embodiments, the one or more T-cell activation markers include, but are not limited to, CD25, CD44, CD62L, CD69, CD152 (CTLA4), CD154, CD137, and CD279. In some embodiments, the T-cell activation marker is one or more of, CD25, CD69, and CTLA4. Increased expression of cell surface markers can be measured by FACS.

Methods for experimentally determining increased T-cell activation, increased T-cell proliferation, decreased T-cell exhaustion, and/or decreased T-cell tolerance are well known in the art. In some embodiments, representative methods of determining T-cell activation can be found in Biological Example 2 provided herein. In some embodiments, representative in vitro and in vivo methods of determining increased T-cell activation, increased T-cell proliferation, decreased T-cell exhaustion, and/or decreased T-cell tolerance can be found in Biological Example 3 provided herein.

In some embodiments of the methods for modulating activity of an immune cell, the immune cell is a B-cell and modulating activity of the B-cell comprises increased B-cell activation. In some embodiments, increased B-cell activation comprises increased cell surface expression of one or more B-cell activation markers. In some embodiments, the one or more B-cell activation markers include, but are not limited to, CD69, CD86, and MHIC class II (e.g., HLA-DR). In some embodiments, the B-cell activation marker is CD69. Increased expression of cell surface markers can be measured by FACS. In some embodiments, increased B-cell activation comprises increased activation of proteins in signaling pathways such as those mediated by ERK, INK, and Syk. Increased activation of said proteins can be detected by measurement of levels of phosphorylation on the proteins using reagents such as anti-phospho antibodies available in the art.

In some embodiments of the methods for modulating activity of an immune cell, the immune cell is a NK-cell and modulating activity of the NK-cell comprises increased NK-cell activation. In some embodiments, increased NK-cell activation comprises secretion of one or more cytokines. In some embodiments, the one or more cytokines include, but are not limited to, IFN-γ, TNFα, and MIP-1β. Increased expression of cytokines can be measured by ELISA. In some embodiments, increased NK-cell activation comprises increased cell surface expression of one or more NK-cell activation markers. In some embodiments, the one or more NK-cell activation markers include, but are not limited to, CD69, and CD107a. Increased expression of cell surface markers can be measured by FACS. In some embodiments, increased NK-cell activation comprises increased killing of target cells such as tumor cells, including primary tumor cells, and cell line derived tumor cells such as the K562 cell line.

Methods for experimentally determining increased B-cell activation and NK-cell activation are well known in the art (see, e.g., Fauriat et al., Blood, 115: 2167-76, 2010; Beano et al., J. Transl. Med. 6:25, 2008; Claus et al., J. Immunol. Methods, 341: 154-64, 2009; and Fujisaki et al., Cancer Res. 69: 4010-4017, 2009). In some embodiments, representative methods of determining B-cell activation can be found in Biological Example 3 provided herein. In some embodiments, representative methods of determining NK-cell activation can be found in Biological Example 3 provided herein.

Modulation of activity of an immune cell, such as a T-cell, a B-cell, or a NK-cell can be measured by determining a baseline value for a parameter of interest (e.g., cytokine secretion). For example, T-cell activation, such as in a sample obtained from in vitro experiments of cells contacted with a Cbl-b inhibitor, can be measured before contacting or administering said Cbl-b inhibitor to determine a baseline value. A reference value then is obtained for T-cell activation after contacting or administering said Cbl-b inhibitor. The reference value is compared to the baseline value in order to determine the amount of T-cell activation due to contact or administration of the Cbl-b inhibitor or composition thereof. For example, in some embodiments, immune cell (e.g., T-cell) activation is increased by at least 0.1-fold in a sample as compared to a baseline value, wherein the baseline value is obtained before contacting the immune cell (e.g., T-cell) with a Cbl-b inhibitor or a composition thereof. In some embodiments, immune cell (e.g., T-cell) activation is increased by at least about 0.1-fold, about 0.2-fold, about 0.3-fold, about 0.4-fold, about 0.5-fold, about 0.6-fold, about 0.7-fold, about 0.8-fold, about 0.9-fold, about 1-fold, about 2-fold, about 4-fold, about 6-fold, about 8-fold, about 10-fold, about 20-fold, about 30-fold about 40-fold, about 50-fold, about 75-fold, or about 100-fold over a baseline value (e.g., about 0.1-fold to about 100-fold, or about 1-fold to about 100-fold). Immune cell activation can be assessed by measuring biological markers of activation such as increased cytokine secretion, increased cell surface expression of activation markers (e.g., cell surface markers), or increased phosphorylation of proteins in a downstream signaling pathway. The fold over baseline value that indicates immune cell activation can be determined for the parameter being tested and the conditions under which the immune cells are treated. For example, for measuring T-cell activation, a baseline value can be obtained from T-cells stimulated with anti-CD3 antibody in combination with anti-CD28 antibody, wherein the cells are not incubated with a Cbl-b inhibitor. A reference value is then obtained from T-cells stimulated with anti-CD3 antibody in combination with anti-CD28 antibody, wherein the T-cells have been or are in contact with a Cbl-b inhibitor. A positive response for immune cell activation can then be determined by the obtained reference value. Similar reference value measurements can be obtained and compared to a baseline value for assessing T-cell activation, T-cell proliferation, T-cell exhaustion, T-cell tolerance, B-cell activation, and/or NK-cell activation. Measurements for these parameters can be obtained utilizing techniques well known in the art, as well as the techniques provided in Biological Examples 2 and 3.

The terms "baseline" or "baseline value" as used herein can refer to a measurement or characterization before administration of a therapeutic agent as disclosed herein (e.g., a composition comprising a Cbl-b inhibitor as described herein) or at the beginning of administration of the therapeutic agent. The baseline value can be compared to a reference value in order to determine the increase or decrease of an immune cell function (e.g., increasing T-cell activation, increasing T-cell proliferation, decreasing T-cell exhaustion, and/or decreasing T-cell tolerance). The terms "reference" or "reference value" as used herein can refer to a measurement or characterization after administration of the therapeutic agent as disclosed herein (e.g., a composition comprising a Cbl-b inhibitor as described herein). The reference value can be measured one or more times during an experimental time course, dosage regimen, or treatment cycle, or at the completion of the experimental time course, dosage regimen, or treatment cycle. A "reference value" can be an absolute value, a relative value, a value that has an upper and/or lower limit, a range of values, an average value, a median value, a mean value, or a value as compared to a baseline value. Similarly, a "baseline value" can be an absolute value, a relative value, a value that has an upper and/or lower limit, a range of values, an average value, a median value, a mean value, or a value as compared to a reference value. The reference value and/or baseline value can be obtained from one sample (e.g., one sample obtained from an individual), from two different samples (e.g., a sample obtained from two different individuals) or from a group of samples (e.g., samples obtained from a group of two, three, four, five, or more individuals).

In some embodiments, a positive response for T-cell activation as measured by cytokine secretion (e.g., IL-2 secretion) by T-cells stimulated with anti-CD3 antibody in combination with anti-CD28 antibody in the presence of a Cbl-b inhibitor is at least 2.5-fold over the baseline value for cytokine secretion (e.g., IL-2 secretion) obtained from T-cells stimulated with anti-CD3 antibody in combination with anti-CD28 antibody in the absence of a Cbl-b inhibitor. In some embodiments, a positive response for T-cell activation as measured by surface marker expression (e.g., CD25 surface marker staining) by T-cells stimulated with anti-CD3 antibody in combination with anti-CD28 antibody in the presence of a Cbl-b inhibitor is at least 1.3-fold over the baseline value for surface marker expression (e.g., CD25 surface marker staining) obtained from T-cells stimulated with anti-CD3 antibody in combination with anti-CD28 antibody in the absence of a Cbl-b inhibitor. In some embodiments, a baseline value can be obtained from T-cells stimulated with anti-CD3 antibody alone, wherein the cells are not incubated with a Cbl-b inhibitor. In some embodiments, a positive response for T-cell activation as measured by cytokine secretion (e.g., IL-2 secretion) by T-cells stimulated with anti-CD3 antibody alone in the presence of a Cbl-b inhibitor is at least 0.1-fold over the baseline value for cytokine secretion (e.g., IL-2 secretion) obtained from T-cells stimulated with anti-CD3 antibody alone in the absence of a Cbl-b inhibitor. In some embodiments, a positive response for T-cell activation as measured by surface marker expression (e.g., CD25 surface marker staining) by T-cells stimulated with anti-CD3 antibody alone in the presence of a Cbl-b inhibitor is at least 0.6-fold over the baseline value for surface marker expression (e.g., CD25 surface marker staining) obtained from T-cells stimulated with anti-CD3 antibody alone in the absence of a Cbl-b inhibitor.

In some aspects, provided herein are methods of producing a modified immune cell, comprising culturing a cell population containing an immune cell in the presence of an effective amount of a Cbl-b inhibitor provided herein or a composition thereof to modulate the activity of the immune cell, thereby producing the modified immune cell. In some embodiments, the immune cell is a T-cell, a B-cell, or a natural killer (NK) cell.

In some embodiments of the methods for producing a modified immune cell, the immune cell that is to be modified is a cell selected from the group consisting of a hematopoietic cell, a multipotent stem cell, a myeloid progenitor cell, a lymphoid progenitor cell, a T-cell, a B-cell, and a NK-cell. In some embodiments, the method further comprises culturing the immune cell with stimulating agents such as cytokines or antibodies that bind to activating proteins expressed by the immune cell (e.g., an anti-CD3 antibody and/or an anti-CD28 antibody). In some embodiments, the immune cell that is to be modified is in a cell population containing the immune cell, wherein the cell population is obtained as a sample from an individual. In some embodiments, the immune cell that is to be modified is in a cell population containing the immune cell, wherein the cell population is obtained from culturing a biological sample (e.g., blood sample, bone marrow sample, etc.) from an individual. In some embodiments, the immune cell is modified by contacting the cell population containing the immune cell with a Cbl-b inhibitor or composition thereof thereby producing a modified immune cell. In some embodiments, the modified immune cell is a cell selected from the group consisting of a hematopoietic cell, a multipotent stem cell, a myeloid progenitor cell, a lymphoid progenitor cell, a T-cell, a B-cell, and a NK-cell. In some embodiments, the immune cell is the same cell type as the modified immune cell. For example, the immune cell can be an inactive T-cell and the modified immune cell can be an activated T-cell. In some embodiments, the immune cell is a different cell type than the modified immune cell. For example, the immune cell can be a hematopoietic stem cell and the modified immune cell can be an NK-cell that has differentiated from the hematopoietic stem cell. In some embodiments of the method of producing the modified immune cell, the method further comprises recovering the modified immune cell. In some embodiments, the cell population containing the immune cell, the immune cell or the modified immune cell is from an individual (e.g., a human). In some embodiments, the immune cell or modified immune cell is a human immune cell or human modified immune cell, respectively.

Further provided herein are modified immune cells produced by any of the methods described herein such as culturing a cell population containing an immune cell in the presence of an effective amount of a Cbl-b inhibitor to modulate the activity of the immune cell and thereby produce the modified immune cell.

In some embodiments, the Cbl-b inhibitors provided herein are cell membrane permeable. Accordingly, in some embodiments, a modified immune cell provided herein can comprise a Cbl-b inhibitor described herein such as in the cytoplasm of the modified immune cell.

In some aspects, provided herein is an isolated modified immune cell, wherein the modified immune cell has been contacted or is in contact with a Cbl-b inhibitor described herein or a composition thereof. In some embodiments, the modified immune cell is a T-cell, a B-cell, or a natural killer (NK) cell. In some embodiments, the modified immune cell is a hematopoietic cell, a multipotent stem cell, a myeloid progenitor cell, a lymphoid progenitor cell, a T-cell, a B-cell, or a NK-cell.

In some embodiments of the isolated modified immune cell, the modified immune cell is a T-cell, and the T-cell exhibits increased T-cell activation, increased T-cell proliferation, decreased T-cell exhaustion, and/or decreased T-cell tolerance. In some embodiments, increased T-cell activation comprises increased production of one or more cytokines from T-cells or surrounding immune cells in the activated T-cell microenvironment (e.g., myeloid cells). In some embodiments, the one or more cytokines include, but are not limited to IFN-γ, IL-1β, IL-2, IL-4, IL-5, IL-6, IL-13, IL-18, TNFα, and GM-CSF. In some embodiments, the one or more cytokines is one or more selected from the group consisting of IL-2, IFN-γ, TNFα, and GM-CSF. In some embodiments, the cytokine is a chemokine. In some embodiments, the one or more chemokines include, but are not limited to IP-10, Eotaxin, GRO alpha, RANTES, MIP-1α, MIP-1β, MIP-2, MCP-1, and MCP-3. In some embodiments, increased T-cell activation comprises increased cell surface expression of one or more T-cell activation markers. In some embodiments, the one or more T-cell activation markers include, but are not limited to CD25, CD44, CD62L, CD69, CD152 (CTLA4), CD154, CD137, and CD279. In some embodiments, the one or more T-cell activation markers include, but are not limited to CD25, CD69, and CTLA4. In some embodiments, the T-cell activation markers are CD25 and/or CD69. In some embodiments, the T-cell has been or is in contact with an anti-CD3 antibody. In some embodiments, the T-cell has been or is in contact with an anti-CD3 antibody in combination with an anti-CD28 antibody.

In some embodiments of the isolated modified immune cell, the modified immune cell is a NK-cell, and the NK-cell exhibits increased NK-cell activation. In some embodiments, increased NK-cell activation comprises increased secretion of one or more cytokines (e.g., IFN-γ, TNFα, and/or MIP-1β). In some embodiments, increased NK-cell activation comprises increased cell surface expression of one or more NK-cell activation markers (e.g., CD69 and/or CD107a).

In some embodiments of the isolated modified immune cell, the modified immune cell is a B-cell, and the B-cell exhibits increased B-cell activation. In some embodiments, increased B-cell activation comprises increased cell surface expression of one or more B-cell activation markers (e.g., CD69, CD86, and/or HLA-DR).

In some of any embodiments of the methods or modified immune cells provided herein, the immune cell or modified immune cell is a mammalian cell (e.g., human cell). In some embodiments, the immune cell or modified immune cell is a human cell.

In some aspects, incubation is carried out in accordance with techniques such as those described in U.S. Pat. No. 6,040,177; Klebanoff et al., J Immunother., 35: 651-660, 2012; Terakura et al., Blood, 119: 72-82, 2012; and Wang et al., J Immunother., 35: 689-701, 2012.

The immune cells to be modified or modified immune cells provided herein can be engineered to express a recombinant chimeric receptor such as a chimeric antigen receptor (CAR). In some embodiments, the CAR comprises from its N-terminus to C-terminus an extracellular ligand-binding domain, a transmembrane domain, an intracellular costimulatory domain, and an activating cytoplasmic signaling domain. In some embodiments, the CAR comprises from its N-terminus to C-terminus an extracellular ligand-binding domain, a transmembrane domain, and an activating cytoplasmic signaling domain. The immune cells can be engineered to express the recombinant chimeric receptor (e.g., CAR) before, during, or after contact with a Cbl-b inhibitor provided herein. In some embodiments, an immune cell to be modified is a T-cell (e.g., a $CD4^+$ T-cell or a $CD8^+$ T-cell). In a further embodiment, the T-cell comprises a recombinant chimeric receptor such as a CAR. In some embodiments, the modified immune cell is a modified T-cell (e.g., a $CD4^+$ T-cell or a $CD8^+$ T-cell). In a further embodiment, the modified T-cell comprises a recombinant chimeric receptor such as a CAR. Methods for producing immune cells expressing recombinant chimeric receptors are well known in the art such as by the introduction of a nucleic acid encoding the recombinant chimeric receptor (e.g., CAR) to an immune cell (e.g., T-cell) via a vector (e.g., viral vector). See, for example, see International Patent Application No. WO 2017/096329 and U.S. Publication No. 2017/0204372.

In particular, this disclosure provides methods of producing an expanded population of lymphocytes, the method comprising (a) obtaining a biological sample comprising lymphocytes from an individual with cancer, wherein the individual has received or is receiving an effective amount of a Cbl-b inhibitor as a monotherapy or as part of a combination therapy, and (b) culturing the lymphocytes in cell culture medium comprising at least one T-cell growth factor to produce an expanded population of lymphocytes. In certain embodiments, the lymphocytes are tumor infiltrating lymphocytes (TILs). In certain embodiments, the lymphocytes are peripheral blood mononuclear cells (PBMCs). In certain embodiments, the at least one T-cell growth factor comprises one or more of the group consisting of IL-2, IL-7, IL-15, and IL-21, optionally wherein the at least one T-cell growth factor comprises IL-2. In some embodiments, the cell culture medium further comprises an anti-CD3 antibody, or both an anti-CD3 antibody and an anti-CD28 antibody. In some embodiments, the cell culture medium further comprises the Cbl-b inhibitor. In some embodiments, the cell culture medium further comprises irradiated feeder cells. In some embodiments, the individual is a human patient. Also provided by this disclosure are compositions comprising the expanded population of TILs produced by the aforementioned methods, and a physiologically acceptable buffer.

In some embodiments, methods for isolation and processing of immune cells to be modified or which have been modified (i.e., modified immune cells) include steps for freezing (e.g., cryopreserving) the cells, either before or after isolation, incubation (e.g., incubation with a Cbl-b inhibitor), and/or engineering (e.g., introduction of a nucleic acid encoding a recombinant chimeric receptor to the immune cell). A variety of freezing solutions and parameters known in the art may be used.

B. Adoptive Cell Therapy

The modified immune cells, such as an expanded population of lymphocytes, or compositions thereof produced by the methods described herein, can be used as a therapeutic agent in methods of treatment of an individual in need thereof, such as an individual having cancer. Such methods of treatment include adoptive cell therapy. In some embodiments, the method of treatment includes isolating cells from an individual, preparing, processing, culturing, and/or engineering them, as described herein, and re-introducing them into the same individual, before or after cryopreservation. In some embodiments, the method of treatment includes isolating cells from an individual, preparing, processing, culturing, and/or engineering them, as described herein, and re-introducing them into a different individual, before or after cryopreservation.

Accordingly, in some aspects, provided herein is a method of modulating the immune response in an individual, the method comprising administering an effective amount of a modified immune cell described herein or a composition thereof to an individual in need thereof (e.g., an individual with a T-cell dysfunction disorder). In some embodiments, the individual has a cancer. In some embodiments, provided herein is a method of treating a cancer responsive to inhibition of Cbl-b activity, the method comprising administering an effective amount of a modified immune cell described herein or a composition thereof to an individual having the cancer responsive to inhibition of Cbl-b activity. In some embodiments, provided herein is a method of inhibiting abnormal cell proliferation, the method comprising administering an effective amount of a modified immune cell described herein or a composition thereof to an individual in need thereof. The term "abnormal cell proliferation" as used herein includes hyperplasia or cancer cell proliferation. The cancer cell may be derived from a hematologic cancer or a non-hematologic cancer. In some embodiments, the cancer is a hematologic cancer, such as lymphoma, a leukemia, or a myeloma. In other embodiments, the cancer cell is derived from a non-hematologic cancer, such as a sarcoma, a carcinoma, or a melanoma.

In certain embodiments, an individual in need of treatment, such as an individual having cancer or a T-cell dysfunction disorder, is administered a composition comprising the modified immune cells provided herein at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

The modified immune cells and compositions thereof are administered using standard administration techniques, formulations, and/or devices. Provided are formulations and devices, such as syringes and vials, for storage and administration of the compositions. Formulations or pharmaceutical compositions comprising the modified immune cells include those for intravenous, intraperitoneal, subcutaneous, or intramuscular administration. In some embodiments, the modified immune cells are administered parenterally. The term "parenteral," as used herein, includes, but is not limited to, intravenous, intramuscular, subcutaneous, and intraperitoneal administration. In some embodiments, the cell populations are administered to a subject using peripheral systemic delivery by intravenous, intraperitoneal, or subcutaneous injections. Compositions of the modified immune cells can be provided as sterile liquid preparations, e.g., isotonic aqueous solutions, suspensions, emulsions, dispersions, or viscous compositions, which may in some aspects be buffered to a selected pH. Viscous compositions can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, and liquid polyethylene glycol) and suitable mixtures thereof. Sterile injectable solutions can be prepared by incorporating the modified immune cells in a solvent, such as in admixture with a suitable carrier, diluent, or excipient such as sterile water, physiological saline, glucose, dextrose, or the like.

In some embodiments, the modified immune cells are co-administered with one or more additional therapeutic agents or in connection with another therapeutic intervention, either simultaneously or sequentially in any order. For instance, in some therapeutic regimens of this disclosure, both the modified immune cells and a Cbl-b inhibitor are administered to a mammalian subject in need thereof, wherein the Cbl-b inhibitor is a compound of Formula (I), (II), (II-A), or any variation thereof. In some embodiments, the Cbl-b inhibitor is a compound of Table 1 or a compound of Table 2. Thus, in some embodiments the therapeutic regimens comprise both adoptive cell therapy and chemotherapy.

After the modified immune cells are administered to an individual (e.g., a human), the biological activity of the modified immune cell populations can be measured by methods known in the art. Parameters to assess include specific binding of modified immune cell or other immune cell to antigen, in vivo (e.g., by imaging) or ex vivo (e.g., by ELISA or flow cytometry). In some embodiments, the ability of modified immune cells to destroy target cells can be measured using a cytotoxicity assay (see, e.g., Kochenderfer et al., J. Immunotherapy, 32: 689-702, 2009; and Herman et al., J. Immunological Methods, 285: 25-40, 2004). In some embodiments, the biological activity of the modified immune cells also can be measured by assaying expression and/or secretion of certain cytokines, such as IL-2 and IFNγ.

C. Administration of Cbl-b Inhibitor

In some aspects, a Cbl-b inhibitor or composition thereof can be administered directly to an individual to modulate an immune response, treat a disease or condition (e.g., cancer and/or abnormal cell proliferation), and/or inhibit Cbl-b activity in the individual. The Cbl-b inhibitor may be a compound of Table 1, a compound of Table 2, a tautomer thereof, or a pharmaceutically acceptable salt thereof.

In some embodiments, provided herein is a method of modulating the immune response, the method comprising administering an effective amount of a Cbl-b inhibitor provided herein or a composition thereof to an individual to modulate the immune response in the individual. In some embodiments, the individual has a cancer such as a hematologic cancer or non-hematological cancer described herein.

In some embodiments, provided herein is a method of treating cancer responsive to inhibition of Cbl-b activity, the method comprising administering an effective amount of a Cbl-b inhibitor provided herein or a composition thereof to an individual to treat the cancer responsive to inhibition of Cbl-b activity. In some embodiments, the cancer is a hematologic cancer or non-hematological cancer such as one described herein.

In some embodiments, provided herein is a method of inhibiting abnormal cell proliferation (e.g., hyperplasia), the method comprising administering an effective amount of a Cbl-b inhibitor provided herein or a composition thereof to an individual to inhibit abnormal cell proliferation in the individual.

In some embodiments, provided herein is a method of inhibiting Cbl-b activity, the method comprising administering an effective amount of a Cbl-b inhibitor provided herein or a composition thereof to an individual to inhibit Cbl-b activity in the individual.

In some embodiments, such as in the modulation of an immune response in an individual in need thereof (e.g., an individual with a T-cell dysfunction disorder), treatment of a disease or condition in an individual (e.g., an individual cancer and/or abnormal cell proliferation), and/or inhibition of Cbl-b activity in an individual, the appropriate dosage of an active agent, will depend on the type of condition, disease, or disorder to be treated, as defined above, the severity and course of the condition, disease, or disorder, whether the agent is administered for preventive or therapeutic purposes, previous therapy, the subject's clinical history and response to the Cbl-b inhibitor, and the discretion of the attending physician.

The Cbl-b inhibitor or composition thereof is suitably administered to the individual at one time or over a series of treatments. In some embodiments, the treatment includes multiple administrations of the Cbl-b inhibitor or composition, wherein the interval between administrations may vary. For example, the interval between the first administration and the second administration is about one month, and the intervals between the subsequent administrations are about three months. In some embodiments, a Cbl-b inhibitor described herein is administered at a flat dose. In some embodiments, a Cbl-b inhibitor described herein is administered to an individual at a fixed dose based on the individual's weight (e.g., mg/kg).

In some aspects of this disclosure, the cancer is a hematologic cancer. For example, the hematologic cancer may be a lymphoma, a leukemia, or a myeloma. In other aspects of this disclosure, the cancer is a non-hematologic cancer. In particular, the non-hematologic cancer may be a carcinoma, a sarcoma, or a melanoma.

In some embodiments, the Cbl-b inhibitor is co-administered with one or more additional therapeutic agents or in connection with another therapeutic intervention, either simultaneously or sequentially in any order. For instance, in some therapeutic regimens of this disclosure, both the Cbl-b inhibitor and modified immune cells are administered to a mammalian subject in need thereof, wherein the Cbl-b inhibitor is a compound of Formula (I), (II), (II-A), or any variation thereof. Thus, in some embodiments the therapeutic regimens comprise both adoptive cell therapy and chemotherapy.

In some embodiments, the effectiveness of Cbl-b inhibitor administration in the methods herein (e.g., method of modulating an immune response in an individual) can be assessed by measuring the biological activity of immune cells present in a sample (e.g., blood sample) isolated from the treated individual. For example, the ability of immune cells isolated from the individual after treatment with a Cbl-b inhibitor to destroy target cells in a cytotoxicity assay may be measured to assess treatment efficacy. In some embodiments, the biological activity of immune cells present in a sample (e.g., blood sample) can be measured by assaying expression and/or secretion of certain cytokines, such as IL-2 and IFNγ.

This disclosure provides methods of treating cancer, comprising administering to an individual with cancer an effective amount of a Cbl-b inhibitor, and administering to the individual an effective amount of an additional therapeutic agent. Also provided are methods of treating an individual with cancer, comprising administering to the individual an effective amount of a Cbl-b inhibitor; and administering to the individual an effective amount of an additional therapeutic agent. Additionally, this disclosure provides methods of increasing an anti-cancer immune response, comprising administering to an individual with cancer an effective amount of a Cbl-b inhibitor, and administering to the individual an effective amount of an additional therapeutic agent. Further provided are methods of treating cancer, comprising administering to an individual with cancer an effective amount of a Cbl-b inhibitor, wherein the individual has received or is receiving an effective amount of an additional therapeutic agent.

In some embodiments of the methods of the preceding paragraph, the Cbl-b inhibitor and the additional therapeutic agent are administered consecutively in either order. As used herein, the terms "consecutively," "serially," and "sequentially" refer to administration of a Cbl-b inhibitor after an additional therapeutic agent, or administration of the additional therapeutic agent after the Cbl-b inhibitor. For instance, consecutive administration may involve administration of the Cbl-b inhibitor in the absence of the additional therapeutic agent during an induction phase (primary therapy), which is followed by a post-induction treatment phase comprising administration of the additional therapeutic agent. The methods may further comprise a maintenance phase comprising administration of the Cbl-b inhibitor or the additional therapeutic agent. Alternatively, consecutive administration may involve administration of the additional therapeutic agent in the absence of the Cbl-b inhibitor during an induction phase (primary therapy), which is followed by a post-induction treatment phase comprising administration of the Cbl-b inhibitor. The methods may further comprise a maintenance phase comprising administration of the Cbl-b inhibitor or the additional therapeutic agent.

In some embodiments of the combination therapy methods, the Cbl-b inhibitor and the additional therapeutic agent are administered concurrently. As used herein, the terms "concurrently," "simultaneously," and "in parallel" refer to administration of a Cbl-b inhibitor and an additional therapeutic agent during the same doctor visit or during the same phase of treatment. For instance, both the Cbl-b inhibitor and the additional therapeutic agent may be administered during one or more of an induction phase, a treatment phase, and a maintenance phase. However, concurrent administration does not require that the Cbl-b inhibitor and the additional therapeutic agent be present together in a single formulation or pharmaceutical composition, or that the Cbl-b inhibitor and the additional therapeutic agent be administered at precisely the same time.

1. Combination Therapy Comprising a Cbl-b Inhibitor and an Immune Checkpoint Inhibitor In some embodiments of the combination therapy methods of this disclosure, the additional therapeutic agent comprises an immune checkpoint inhibitor. The term "immune checkpoint" refers to a signaling pathway that prevents activation of immune cells, while the term "immune checkpoint inhibitor" refers to a compound that impedes the immune checkpoint to remove the brake on activation of immune cells. In some embodiments, the immune checkpoint inhibitor is an antagonist of at least one inhibitory checkpoint molecule. In certain embodiments, the inhibitory checkpoint molecule is selected from the group consisting of PD-1 (CD279), PD-L1 (CD274), CTLA-4 (CD125), LAG3 (CD223), PVR (CD155), PVRL2 (CD112), PVRL3 (CD113), TIGIT, TIM3 (CD366), and VISTA. In certain embodiments, the immune checkpoint inhibitor is an antagonist of at least one inhibitory checkpoint molecule selected from the group consisting of PD-1 (CD279), PD-L1 (CD274), and CTLA-4 (CD152).

PD-1 refers to programmed cell death protein 1 (PD-1). PD-1 antagonists suitable for the treatment methods, medicaments, and uses of this disclosure include any chemical compound or biological molecule that blocks binding of PD-L1 expressed on a cancer cell or antigen presenting cell to PD-1 expressed on a lymphocyte (T-cell, B-cell, and/or NK-cell). Alternative names or synonyms for PD-1 and its ligand include CD279, PDCD1, PD1, and SLEB2 for PD-1; and CD274, PDCD1L1, PDL1, B7H1, B7-4, and B7-H for programmed cell death 1 ligand 1 (PD-L1). In some embodiments in which a human subject is being treated, the PD-1 antagonist blocks binding of human PD-L1 to human PD-1. The amino acid sequence of the mature form of human PD-1 is set forth as residues 21-288 in NCBI Locus No. NP_005009. The amino acid sequence of the mature form of human PD-L1 is set forth as residues 19-290 in NCBI Locus No. NP_054862.

CTLA-4 refers to cytotoxic T-lymphocyte associated protein 4. CTLA-4 antagonists suitable for the treatment methods, medicaments, and uses of this disclosure include any chemical compound or biological molecule that blocks binding of CTLA-4 expressed on a lymphocyte (T-cell, B-cell, and/or NK-cell) to a ligand (CD80 and/or CD86) expressed on an antigen presenting cell. Alternative names or synonyms for CTLA-4 include CD152, CTLA4, ALPS5, CELIAC3, GRD4, GSE, and IDDM12. In some embodiments in which a human subject is being treated, the CTLA-4 antagonist blocks binding of human CTLA-4 to a human ligand. The amino acid sequence of the mature form of human CTLA-4 is set forth as residues 36-223 in NCBI Locus No. NP_005205.

LAG3 refers to lymphocyte activating gene 3 protein. LAG3 antagonists suitable for the treatment methods, medicaments, and uses of this disclosure include any chemical compound or biological molecule that blocks binding of LAG3 expressed on a lymphocyte (T-cell, B-cell, and/or NK-cell) to a ligand (MHC class II) expressed on an antigen presenting cell. LAG3 is also known as CD223. In some embodiments in which a human subject is being treated, the LAG3 antagonist blocks binding of human LAG3 to a human ligand. The amino acid sequence of the mature form of human LAG3 is set forth as residues 23-525 in NCBI Locus No. NP_002277.

PVR refers to poliovirus receptor. PVR antagonists suitable for the treatment methods, medicaments, and uses of this disclosure include any chemical compound or biological molecule that blocks binding of PVR expressed on a cancer cell or an antigen presenting cell to TIGIT expressed on a lymphocyte (T-cell, B-cell, and/or NK-cell). Alternative names or synonyms for PVR include CD155, PVS, HVED, NECL5, nectin-like protein 5, and TAGE4. In some embodiments in which a human subject is being treated, the PVR antagonist blocks binding of human PVR to human TIGIT. There are multiple isoforms of human PVR. The amino acid sequence of alpha isoform of human PVR is set forth in NCBI Locus No. NP_006496. The amino acid sequence of beta isoform of human PVR is set forth in NCBI Locus No. NP_001129240. The amino acid sequence of gamma isoform of human PVR is set forth in NCBI Locus No. NP_001129241. The amino acid sequence of delta isoform of human PVR is set forth in NCBI Locus No. NP_001129242.

PVRL2 refers to poliovirus receptor related 2. PVRL2 antagonists suitable for the treatment methods, medicaments, and uses of this disclosure include any chemical compound or biological molecule that blocks binding of PVRL2 expressed on a cancer cell or an antigen presenting cell to TIGIT expressed on a lymphocyte (T-cell, B-cell, and/or NK-cell). Alternative names or synonyms for PVRL2 include CD112, NECTIN2, HVEB, herpesvirus entry mediator B, PRR2, and PVRR2. In some embodiments in which a human subject is being treated, the PVRL2 antagonist blocks binding of human PVRL2 to human TIGIT. The amino acid sequence of the alpha isoform of human PVRL2 is set forth in NCBI Locus No. NP_002847. The amino acid sequence of the delta isoform of human PVRL2 is set forth in NCBI Locus No. NP_001036189.

PVRL3 refers to poliovirus receptor related 3. PVRL3 antagonists suitable for the treatment methods, medicaments, and uses of this disclosure include any chemical compound or biological molecule that blocks binding of PVRL3 expressed on a cancer cell or an antigen presenting cell to TIGIT expressed on a lymphocyte (T-cell, B-cell, and/or NK-cell). Alternative names or synonyms for PVRL3 include CD113, NECTIN3, PRR3, and PVRR3. In some embodiments in which a human subject is being treated, the PVRL3 antagonist blocks binding of human PVRL3 to human TIGIT. The amino acid sequence of isoform 1 of human PVRL3 is set forth in NCBI Locus No. NP_056295. The amino acid sequence of isoform 2 of human PVRL3 is set forth in NCBI Locus No. NP_001230215. The amino acid sequence of isoform 3 of human PVRL3 is set forth in NCBI Locus No. NP_001230217.

TIGIT refers to T-cell immunoreceptor with Ig and ITIM domains protein. TIGIT antagonists suitable for the treatment methods, medicaments, and uses of this disclosure include any chemical compound or biological molecule that blocks binding of TIGIT expressed on a lymphocyte (T-cell, B-cell, or NK-cell) to a ligand (CD112, CD113, and/or CD155) expressed on a cancer cell or an antigen presenting cell. Alternative names or synonyms for TIGIT include VSIG9, V-set and immunoglobulin domain containing 9, VSTM3, V-set and transmembrane domain containing 3, and Washington University cell adhesion molecule (WUCAM). In some embodiments in which a human subject is being treated, the TIGIT antagonist blocks binding of human TIGIT to a human ligand. The amino acid sequence of the mature form of human TIGIT is set forth as residues 22-244 in NCBI Locus No.: NP_776160.

TIM3 refers to T-cell immunoglobulin and mucin-domain containing-3 protein. TIM3 antagonists suitable for the treatment methods, medicaments, and uses of this disclosure include any chemical compound or biological molecule that blocks binding of TIM3 expressed on a lymphocyte (T-cell, B-cell, or NK-cell) to a ligand (galectin-9 phosphatidylserine) expressed on an antigen presenting cell. Alternative names or synonyms for TIM3 include CD366, HAVCR2, hepatitis A virus cellular receptor 2, KIM3, and SPTCL. In some embodiments in which a human subject is being treated, the TIM3 antagonist blocks binding of human TIM3 to a human ligand. The amino acid sequence of the mature form of human TIM3 is set forth as residues 22-301 in NCBI Locus No. NP_116171.

VISTA refers to V-domain Ig suppressor of T-cell activation. VISTA antagonists suitable for the treatment methods, medicaments, and uses of this disclosure include any chemical compound or biological molecule that blocks binding of VISTA expressed on a lymphocyte (T-cell, B-cell, and/or NK-cell) to a ligand expressed on a cancer cell or an antigen presenting cell. Alternative names or synonyms for VISTA include VSIR, V-set immunoregulatory receptor, PD-1H, B7H5, GI24, PP2135, SISP1, and Dies1. In some embodiments in which a human subject is being treated, the VISTA antagonist blocks binding of human VISTA to a human ligand. The amino acid sequence of the mature form of human VISTA is set forth as residues 33-311 in NCBI Locus No.: NP_071436.

The immune checkpoint inhibitor may be a biological molecule. For instance, the immune checkpoint inhibitor may comprise an antibody or antigen-binding fragment thereof. The antibody or fragment may be a monoclonal antibody (mAb), a human antibody, a humanized antibody, or a chimeric antibody, and may include a human constant region. In some embodiments the human constant region is selected from the group consisting of IgG1, IgG2, IgG3, and IgG4 constant regions, and in certain embodiments, the human constant region is an IgG1 or IgG4 constant region. In some embodiments, the antibody or fragment is a bispecific antibody. In some embodiments, the antigen-binding fragment comprises one of the group consisting of Fab, Fab'-SH, $F(ab')_2$, scFv, and Fv fragments.

In some embodiments, the at least one inhibitory checkpoint molecule comprises PD-1. In certain embodiments, the immune checkpoint inhibitor is selected from the group consisting of pembrolizumab, nivolumab, cemiplimab, and biosimilars thereof. In one embodiment, the anti-PD-1 antibody is pembrolizumab (MK-3475 marketed as KEYTRUDA® by Merck & Co.). In one embodiment, the anti-PD-1 antibody is nivolumab (BMS-936558 or MDX-1106, marketed as OPDIVO® by Bristol-Myers Squibb). In one embodiment, the anti-PD-1 antibody is cemiplimab (REGN2810, Regeneron). In some embodiments, the immune checkpoint inhibitor is a variant of pembrolizumab, nivolumab, or cemiplimab.

In some embodiments, the at least one inhibitory checkpoint molecule comprises PD-L1. In certain embodiments, the immune checkpoint inhibitor is selected from the group consisting of atezolizumab, avelumab, durvalumab, and biosimilars thereof. In one embodiment, the anti-PD-L1 antibody is atezolizumab (marketed as TECENTRIQ® by Genentech, Inc.). In one embodiment, the anti-PD-L1 antibody is avelumab (marketed as BAVENCIO® by EMD Serono, Inc. and Pfizer, Inc.). In one embodiment, the anti-PD-L1 antibody is durvalumab (MEDI4736 marketed as IMFINZI® by AstraZeneca). In some embodiments, the immune checkpoint inhibitor is a variant of atezolizumab, avelumab, or durvalumab.

In some embodiments, the at least one inhibitory checkpoint molecule comprises CTLA-4. In certain embodiments, the immune checkpoint inhibitor is selected from the group consisting of ipilimumab, tremelimumab, and biosimilars thereof. In one embodiment, the anti-CTLA4 antibody is ipilimumab (MDX-010 or BMS-734016, marketed as YERVOY® by Bristol-Myers Squibb). In one embodiment, the anti-CTLA4 antibody is tremelimumab (ticilimumab, CP-675,206, developed by AstraZeneca). In some embodiments, the immune checkpoint inhibitor is a variant of ipilimumab, or tremelimumab.

In some embodiments, the monoclonal antibody is a "variant" antibody which comprises heavy chain and light chain sequences that are identical to those in the "reference" antibody, except for having three, two, or one conservative amino acid substitutions at positions that are located outside of the light chain CDRs and/or six, five, four, three, two, or one conservative amino acid substitutions that are located outside of the heavy chain CDRs (e.g., the variant positions are located in the framework regions or the constant region). In other words, the reference antibody and the variant antibody comprise identical CDR sequences, but differ from each other due to having a conservative amino acid substitution at no more than three or six other positions in their full length light and heavy chain sequences, respectively. A variant antibody is substantially the same as a reference antibody with respect to the following properties: binding affinity to the inhibitory checkpoint molecule and ability to block the binding of the inhibitory checkpoint molecule to its ligand.

In other embodiments, the immune checkpoint inhibitor may comprise an immunoadhesin comprising the inhibitory checkpoint molecule binding domain of one of its ligands fused to a constant region such as an Fc region of an immunoglobulin molecule.

As used herein the term "biosimilar" refers to a biological product that is similar to but without clinically meaningful differences in safety and effectiveness from a Federal Drug Administration (FDA)-approved reference product. For instance, there may be differences between a biosimilar product and a reference product in clinically inactive components (e.g., differences in excipients of the formulations, minor differences in glycosylation, etc.). Clinically meaningful characteristics can be assessed through pharmacokinetic and pharmacodynamic studies. In some embodiments, the biosimilar product is an interchangeable product as determined by the FDA.

2. Combination Therapy Comprising a Cbl-b Inhibitor and an Antineoplastic Agent

In some embodiments of the combination therapy methods of this disclosure, the additional therapeutic agent comprises an antineoplastic agent. As used herein, the terms "anti-neoplastic agent" and "antineoplastic agent" refer to a therapeutic agent classified according to the Anatomical Therapeutic Chemical Classification System (ATC) code L01 developed by the World Health Organization. In certain embodiments, the antineoplastic agent is classified as one of the group consisting of a cytotoxic antibiotic (ATC code L01D), a plant alkaloid (ATC code L01C), an antimetabolite (ATC code L01B), an alkylating agent (ATC code L01A), and other antineoplastic agent (ATC code L01X). In some embodiments, the antineoplastic agent is a small molecule drug (e.g., cancer chemotherapeutic agent) as opposed to a biological molecule.

A cytotoxic antibiotic is a suitable antineoplastic agent for the treatment methods, medicaments and uses of this disclosure. In some embodiments, the cytotoxic antibiotic is selected from the group consisting of ixabepilone, mitomycin, plicamycin, bleomycin, pixantrone, amrubicin, valrubicin, pirarubicin, mitoxantrone, idarubicin, zorubicin, aclarubicin, epirubicin, daunorubicin, doxorubicin, and dactinomycin.

A plant alkaloid is a suitable antineoplastic agent for the treatment methods, medicaments, and uses of this disclosure. In some embodiments, the plant alkaloid is selected from the group consisting of trabectedin, cabazitaxel, paclitaxel poliglumex, docetaxel, paclitaxel, demecolcine, teniposide, etoposide, vintafolide, vinflunine, vinorelbine, vindesine, vincristine, and vinblastine.

An antimetabolite is a suitable antineoplastic agent for the treatment methods, medicaments, and uses of this disclosure. In some embodiments, the antimetabolite is a pyrimidine analog, a purine analog, or a folic acid analog. In some embodiments, the antimetabolite is selected from the group consisting of floxuridine, trifluridine, tegafur, fluorouracil, decitabine, azacitidine, capecitabine, gemcitabine, carmofur, tegafur, fluorouracil, cytarabine, nelarabine, clofarabine, fludarabine, cladribine, tioguanine, mercaptopurine, pralatrexate, pemetrexed, raltitrexed, and methotrexate.

An alkylating agent is a suitable antineoplastic agent for the treatment methods, medicaments, and uses of this disclosure. In some embodiments, the alkylating agent is selected from the group consisting of dacarbazine, temozolomide, pipobroman, mitobronitol, etoglucid, uracil mustard, ranimustine, nimustine, fotemustine, streptozocin, semustine, lomustine, carmustine, carboquone, triaziquone, thiotepa, mannosulfan, treosulfan, busulfan, bendamustine, prednimustine, trofosfamide, ifosfamide, mechlorethamine, melphalan, chlorambucil, and cyclophosphamide.

In other embodiments, the antineoplastic agent comprises another antineoplastic agent selected from the group consisting of a platinum compound (ATC Code L01XA), a methylhydrazine (ATC Code L01XB), a sensitizer (ATC Code L01XD), a protein kinase inhibitor (ATC Code L01XE), and an other agent (ATC Code L01XA).

A platinum compound is a suitable antineoplastic agent for the treatment methods, medicaments and uses of this disclosure. In some embodiments, the platinum compound is selected from the group consisting of cisplatin, carboplatin, oxaliplatin, satraplatin, and polyplatillen.

3. Combination Therapy Comprising a Cbl-b Inhibitor and Radiation Therapy

This disclosure provides methods of treating cancer comprising administering to an individual with cancer an effective amount of a Cbl-b inhibitor, and administering to the individual an effective amount of radiation therapy. Also provided are methods of treating an individual with cancer, comprising administering to the individual an effective amount of a Cbl-b, and administering to the individual an effective amount of radiation therapy. Additionally, this disclosure provides methods of increasing an anti-cancer immune response, comprising administering to an individual with cancer an effective amount of a Cbl-b inhibitor, and administering to the individual an effective amount of radiation therapy. Further provided are methods of treating cancer, comprising administering to an individual with cancer an effective amount of a Cbl-b inhibitor, wherein the individual has received or is receiving an effective amount of radiation therapy.

In some embodiments, the radiation therapy is external beam radiation therapy. In other embodiments, the radiation therapy is internal radiation therapy. In some embodiments, the radiation therapy is ablative radiation therapy.

In some embodiments, the combination therapy regimen of this disclosure comprises administration of a Cbl-b inhibitor, radiation therapy, and one or both of an immune checkpoint inhibitor and an antineoplastic agent.

IV. Compositions, Formulations and Routes of Administration

Pharmaceutical compositions of any of the compounds disclosed herein, or a salt or solvate thereof, are embraced by this disclosure. Thus, the disclosure includes pharmaceutical compositions comprising a Cbl-b inhibitor, wherein the Cbl-B inhibitor is a compound of Formula (I), (II), or (II-A), or any variation thereof disclosed herein, or a pharmaceutically acceptable salt or solvate thereof, or tautomers thereof, or stereoisomers or mixtures of stereoisomers thereof, and a pharmaceutically acceptable excipient, such as a pharmaceutically acceptable vehicle or pharmaceutically acceptable carrier. In some embodiments, the compound is a compound selected from Compound Nos. 1-54 and 121-166 in Table 1, or a pharmaceutically acceptable salt or solvate thereof, or tautomers thereof, or stereoisomers or mixtures of stereoisomers thereof. In some embodiments, the compound is a compound selected from Compound Nos. 55-120 and 167 in Table 2, or a pharmaceutically acceptable salt or solvate thereof, or tautomers thereof, or stereoisomers or mixtures of stereoisomers thereof. In one aspect, the pharmaceutically acceptable salt is an acid addition salt, such as a salt formed with an inorganic acid or an organic acid. In some embodiments, the Cbl-b inhibitor is a compound of Table 1 or Table 2, a tautomer thereof, or a salt thereof.

The compounds and compositions disclosed herein may be administered in any suitable form and by any suitable route that will provide sufficient levels of the compounds for treatment of the disease or disorder. In some embodiments, the Cbl-b inhibitor and/or the additional therapeutic agent are administered by enteral administration. In certain embodiments, the enteral administration is oral administration. In other embodiments, the Cbl-b inhibitor and/or the additional therapeutic agent are administered by parenteral administration. In certain embodiments, the parenteral administration is intratumoral injection. In certain embodiments, the parenteral administration is by a route selected from the group consisting of intravenous, intraperitoneal, and subcutaneous.

Suitable routes of administration include oral administration, enteral administration, parenteral administration including subcutaneous injection, intravenous injection, intraarterial injection, intramuscular injection, intrasternal injection, intraperitoneal injection, intralesional injection, intraarticular injection, intratumoral injection, or infusion techniques. The compounds and compositions also can be administered sublingually, by mucosal administration, by buccal administration, subcutaneously, by spinal administration, by epidural administration, by administration to cerebral ventricles, by inhalation (e.g., as mists or sprays), nasal administration, vaginal administration, rectal administration, topical administration, or transdermal administration, or by sustained release or extended release mechanisms. The compounds and compositions can be administered in unit dosage formulations containing conventional pharmaceutically acceptable carriers, excipients, adjuvants, and vehicles as desired. The compounds and compositions may be administered directly to a specific or affected organ or tissue. The compounds can be mixed with pharmaceutically acceptable carriers, excipients, adjuvants, and vehicles to form compositions appropriate for the desired route of administration. In some embodiments, the compounds can be mixed with one or both of an antigen and an adjuvant. In some embodiments, the antigen is a cancer antigen.

In certain embodiments disclosed herein, especially those embodiments where a formulation is used for injection or other parenteral administration, including the routes listed herein, but also including any other route of administration described herein (such as oral, enteric, gastric, etc.), the formulations and preparations used in the methods are sterile. Sterile pharmaceutical formulations are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art. A "sterile" formulation is aseptic, or free or essentially free from all living microorganisms and their spores. Examples of methods of sterilization of pharmaceutical formulations include, but are not limited to, sterile filtration through sterile filtration membranes, exposure to radiation such as gamma radiation, and heat sterilization.

Oral administration is advantageous due to its ease of implementation and patient compliance. If a patient has difficulty swallowing, introduction of medicine via feeding tube, feeding syringe, or gastrostomy can be employed in order to accomplish enteric administration. The active compound, and, if present, other co-administered agents, can be enterally administered in any other pharmaceutically acceptable excipient suitable for formulation for administration via feeding tube, feeding syringe, or gastrostomy.

Intravenous administration also can be used advantageously, for delivery of the compounds or compositions to the bloodstream as quickly as possible and to circumvent the need for absorption from the gastrointestinal tract.

The compounds and compositions described for use herein can be administered in solid form, in liquid form, in aerosol form, or in the form of tablets, pills, caplets, capsules (such as hard gelatin capsules or soft elastic gelatin capsules), powder mixtures, granules, injectables, solutions, suppositories, enemas, colonic irrigations, emulsions, dispersions, food premixes, cachets, troches, lozenges, gums, ointments, cataplasms (poultices), pastes, powders, dressings, creams, patches, aerosols (e.g., nasal spray or inhalers), gels, suspensions (e.g., aqueous or non-aqueous liquid suspensions, oil-in-water emulsions or water-in-oil liquid emulsions), elixirs, or in other forms suitable for the route of administration. The compounds and compositions also can be administered in liposome formulations. The compounds also can be administered as prodrugs, where the prodrug undergoes transformation in the treated subject to a therapeutically effective form.

In addition, pharmaceutical formulations may contain preservatives, solubilizers, stabilizers, re-wetting agents, emulgators, sweeteners, dyes, adjusters, and salts for the adjustment of osmotic pressure, buffers, coating agents, or antioxidants. Formulations comprising the compound also may contain other substances that have valuable therapeutic properties. Pharmaceutical formulations may be prepared by known pharmaceutical methods. Additional formulations and methods of administration are known in the art. Suitable formulations can be found, e.g., in Remington: The Science and Practice of Pharmacy, Lippincott Williams & Wilkins, 21st ed. (2005), which is incorporated herein by reference.

Injectable preparations, for example, sterile injectable aqueous or oleaginous suspensions, may be formulated according to methods known in the art using suitable dispersing or wetting agents and suspending agents. The sterile injectable preparation also may be a sterile injectable solution or suspension in a parenterally acceptable diluent or solvent, for example, as a solution in propylene glycol. Among the acceptable vehicles and solvents that may be employed are water, saline, Ringer's solution, and isotonic sodium chloride solution. In addition, sterile, fixed oils are conventionally employed as a solvent or suspending medium. For this purpose, any bland fixed oil may be employed including synthetic mono or di-glycerides. In addition, fatty acids such as oleic acid may be used in the preparation of injectables.

Solid dosage forms for oral administration may include capsules, tablets, pills, powders, and granules. In such solid dosage forms, the active compound may be admixed with at least one inert diluent such as sucrose, lactose, talc, or starch. Such dosage forms also may comprise additional excipient substances other than inert diluents, e.g., lubricating agents such as magnesium stearate. In the case of capsules, tablets, and pills, the dosage forms also may comprise buffering agents. Tablets and pills additionally can be prepared with enteric coatings. Acceptable excipients for gel capsules with a soft shell are, for instance, plant oils, wax, fats, semisolid and liquid poly-ols, and so on.

Liquid dosage forms for oral administration may include pharmaceutically acceptable emulsions, solutions, suspensions, syrups, and elixirs containing inert diluents commonly used in the art, such as water. Such compositions also may comprise additional agents, such as wetting agents, emulsifying and suspending agents, cyclodextrins, and sweetening, flavoring, and perfuming agents. Alternatively, the compound also may be administered in neat form if suitable.

The compounds and compositions also can be administered in the form of liposomes. As is known in the art, liposomes are generally derived from phospholipids or other lipid substances. Liposomes are formed by mono or multilamellar hydrated liquid crystals that are dispersed in an aqueous medium. Any physiologically acceptable and metabolizable lipid capable of forming liposomes can be used. The compositions of this disclosure in liposome form can contain stabilizers, preservatives, excipients, and the like, in addition to a compound as disclosed herein. Useful lipids include the phospholipids and phosphatidyl cholines (lecithins), both natural and synthetic. Methods to form liposomes are known in the art. See, for example, Gregoriadis, G. Ed., Liposome Technology, Third Edition: Liposome Technology: Liposome Preparation and Related Techniques, CRC Press, Boca Raton, Florida (2006); and Prescott, Ed., Methods in Cell Biology, Volume XIV, Academic Press, New York, N.W., p. 33 et seq (1976).

The amount of active ingredient that may be combined with the carrier materials to produce a single dosage form can vary depending upon the patient to whom the active ingredient is administered and the particular mode of administration. It will be understood, however, that the specific dose level for any particular patient will depend upon a variety of factors including the specific compound employed; the age, body weight, body area, body mass index (BMI), general health, sex, and diet of the patient; the time of administration and route of administration used; the rate of excretion; and the drug combination, if any, used. The compounds can be administered in a unit dosage formulation. The pharmaceutical unit dosage chosen is fabricated and administered to provide sufficient concentration of drug in the patient, subject, or individual.

Although the compounds for use as described herein can be administered as the sole active pharmaceutical agent, they also can be used in combination with one or more other agents. When additional active agents are used in combination with the compounds for use as described herein, the additional active agents may generally be employed in therapeutic amounts as indicated in the Physicians' Desk Reference (PDR) 71st Edition (2017), which is incorporated herein by reference, or such therapeutically useful amounts as would be known to one of ordinary skill in the art, or as are determined empirically for each patient.

Combinations of two or more of the compounds and compositions disclosed herein also can be used. The two or more compounds or compositions can be mixed together shortly before administration and administered together. The two or more compounds or compositions can be administered simultaneously, either by the same route of administration or by different routes of administration. The two or more compounds or compositions can be administered consecutively, either by the same route of administration or by different routes of administration. In one embodiment, a kit form can contain two or more compounds or compositions as individual compounds or compositions, with printed or electronic instructions for administration either as a mixture of compounds or compositions, as separate compounds or compositions administered simultaneously, or as separate compounds or compositions administered consecutively. Where three or more compounds or compositions are administered, they can be administered as a mixture of compounds or compositions, as separate compounds or compositions administered simultaneously, as separate compounds or compositions administered consecutively, as separate compounds or compositions where two or more may be administered simultaneously with the remainder administered consecutively before or after the simultaneous administration, or any other possible combination of mixed administration, simultaneous administration, and consecutive administration.

A compound as disclosed herein may in one aspect be in a purified form and compositions comprising a compound in purified forms are disclosed herein. Compositions comprising a compound as disclosed herein or a salt thereof are provided, such as compositions of substantially pure compounds. In some embodiments, a composition containing a compound as disclosed herein or a salt thereof is in substantially pure form. In one variation, "substantially pure" refers to a composition that contains no more than 35% impurity, wherein the impurity denotes a compound other than the compound (or compounds, if combinations of compounds are used) to be administered in the composition, or a salt or solvate of the compound (or compounds, if combinations are used). The weight of any added vehicle, carrier, or excipient is excluded from such a calculation, and the added vehicle, carrier, or excipient is not considered as an impurity. For example, a composition of a substantially pure compound selected from a compound of Table 1 or Table 2 refers to a composition that contains no more than 35% impurity, wherein the impurity denotes a compound other than the compound or a salt or solvate thereof. In one variation, a composition of substantially pure compound or a salt or solvate thereof is provided wherein the composition contains no more than 25% impurity. In another variation, a composition of substantially pure compound or a salt or solvate thereof is provided wherein the composition contains no more than 20% impurity. In still another variation, a composition of substantially pure compound or a salt or solvate thereof is provided wherein the composition contains no more than 10% impurity. In a further variation, a composition of substantially pure compound or a salt or solvate thereof is provided wherein the composition contains no more than 5% impurity. In another variation, a composition of substantially pure compound or a salt or solvate thereof is provided wherein the composition contains no more than 3% impurity. In still another variation, a composition of substantially pure compound or a salt or solvate thereof is provided wherein the composition contains no more than 1% impurity. In a further variation, a composition of substantially pure compound or a salt or solvate thereof is provided wherein the composition contains no more than 0.5% impurity. In yet other variations, a composition of substantially pure compound means that the composition contains no more than 15%, no more than 10%, no more than 5%, no more than 3%, or no more than 1% impurity. An impurity may be the compound in a stereochemical form different from the desired stereochemical form. For instance, a composition of substantially pure (S)-compound means that the composition contains no more than 15%, no more than 10%, no more than 5%, no more than 3%, or no more than 1% of the (R)-form of the compound. Alternatively, as used herein, "enantiomeric excess (ee)" refers to a dimensionless mol ratio describing the purity of chiral substances that contain, for example, a single stereogenic center. For instance, an enantiomeric excess of zero would indicate a racemic (e.g., 50:50 mixture of enantiomers, or no excess of one enantiomer over the other). By way of further example, an enantiomeric excess of ninety-nine would indicate a nearly stereopure enantiomeric compound (i.e., large excess of one enantiomer over the other). The percentage enantiomeric excess, % ee=([(R)-compound]−[(S)-compound])/([(R)-compound]+[(S)-compound])×100, where the (R)-compound>(S)-compound; or % ee=([(S)-compound]−[(R)-compound])/([(S)-compound]+[(R)-compound])×100, where the (S)-compound>(R)-compound. Moreover, as used herein, "diastereomeric excess (de)" refers to a dimensionless mol ratio describing the purity of chiral substances that contain more than one stereogenic center. For example, a diastereomeric excess of zero would indicate an equimolar mixture of diastereoisomers. By way of further example, diastereomeric excess of ninety-nine would indicate a nearly stereopure diastereomeric compound (i.e., large excess of one diastereomer over the other). Diastereomeric excess may be calculated via a similar method to ee. As would be appreciated by a person of skill, de is usually reported as percent de (% de). % de may be calculated in a similar manner to % ee.

In some aspects, provided herein are compositions comprising a cell population containing a modified immune cell such as those described herein or produced by the methods disclosed herein. In some embodiments, the composition comprises a cell population containing a modified immune cell that has been in contact or is in contact with a Cbl-b inhibitor described herein or a composition thereof. In some embodiments, the modified immune cell has been or is in contact with an anti-CD3 antibody alone. In some embodiments, the modified immune cell has been or is in contact with an anti-CD3 antibody in combination with an anti-CD28 antibody. The provided compositions comprising a cell population containing a modified immune cell described herein may further comprise a pharmaceutically acceptable excipient.

In some aspects, also provided herein is a cell culture composition comprising a cell population containing an immune cell and a Cbl-b inhibitor described herein. In some embodiments, the immune cell is a cell selected from the group consisting of a hematopoietic cell, a multipotent stem cell, a myeloid progenitor cell, a lymphoid progenitor cell, a T-cell, a B-cell, and a NK-cell. In some embodiments, the cell culture composition further comprises an anti-CD3 antibody. In some embodiments, the cell culture composition further comprises an anti-CD3 antibody in combination with an anti-CD28 antibody. Methods for culturing cell compositions containing immune cells are well known in the art and are contemplated herein.

A modified immune cell or compositions as described herein, e.g., a composition comprising a cell population containing the modified immune cell or a pharmaceutical composition, can be provided in a suitable container. Suitable containers include, for example, bottles, vials (e.g., dual chamber vials), syringes (e.g., single or dual chamber syringes), bags (e.g., an intravenous bag), and tubes (e.g., test tubes). The container may be formed from a variety of materials such as glass or plastic.

In some embodiments, a composition comprising a cell population containing a modified immune cell as described herein (e.g., a cell culture composition) is provided in a culture vessel. A culture vessel as provided herein includes, but is not limited to, a tube (e.g., a test tube), a dish (e.g., a tissue culture dish), a bag, a multiwell plate (e.g., a 6-well tissue culture plate), and a flask (e.g., a cell culture flask).

Also provided are the compositions as described herein for any use described herein. In some embodiments, the compositions as described herein are for preparation of a medicament for treating or preventing a disease or condition associated with Cbl-b activity. In some embodiments, the compositions as described herein are for preparation of a medicament for treating cancer.

V. Articles of Manufacture or Kits

Also provided are articles of manufacture comprising any of the compounds, pharmaceutical compositions, cells, modified immune cells, cell populations, cell compositions, cell cultures, or cell culture compositions described herein. The articles of manufacture include suitable containers or packaging materials for the compounds, pharmaceutical compositions, cells, modified immune cells, cell populations, cell compositions, cell cultures, or cell culture compositions. Examples of a suitable container include, but are not limited to, a bottle, a vial, a syringe, an intravenous bag, or a tube. For cells, modified immune cells, cell populations, cell compositions, cell cultures, or cell culture compositions, a suitable container can be a culture vessel, including, but not limited to, a tube, a dish, a bag, a multiwell plate, or a flask.

Also provided are kits comprising any of the compounds, pharmaceutical compositions, cells, modified immune cells, cell populations, cell compositions, cell cultures, or cell culture compositions described herein. The kits can contain the compounds, pharmaceutical compositions, cells, modified immune cells, cell populations, cell compositions, cell cultures, or cell culture compositions in suitable containers or packaging materials, including, but not limited to, a bottle, a vial, a syringe, an intravenous bag, or a tube. The kits can contain cells, modified immune cells, cell populations, cell compositions, cell cultures, or cell culture compositions in a culture vessel, including, but not limited to, a tube, a dish, a bag, a multiwell plate, or a flask. The kits can comprise the compounds, pharmaceutical compositions, cells, modified immune cells, cell populations, cell compositions, cell cultures, or cell culture compositions for administration to an individual in single-dose form or in multiple-dose form. The kits can further comprise instructions or a label for administering the compounds, pharmaceutical compositions, cells, modified immune cells, cell populations, cell compositions, cell cultures, or cell culture compositions to an individual according to any of the methods disclosed herein. The kits can further comprise equipment for administering the compounds, pharmaceutical compositions, cells, modified immune cells, cell populations, cell compositions, cell cultures, or cell culture compositions to an individual, including, but not limited to, needles, syringes, tubing, or intravenous bags. The kits can further comprise instructions for producing any of the compounds, pharmaceutical compositions, cells, modified immune cells, cell populations, cell compositions, cell cultures, or cell culture compositions disclosed herein.

This disclosure will be more fully understood by reference to the following examples. They should not, however, be construed as limiting the scope of this disclosure. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

General Work-Up Procedure

General Workup Procedure: Aqueous solutions were extracted with EtOAc or DCM 2-3 times. The combined organic extract was dried over anhydrous sodium sulfate or anhydrous magnesium sulfate, or was washed with brine or saturated ammonium chloride aqueous solution before drying, filtration, and concentration under vacuum.

Purification Procedures

Chromatography A refers to purification over silica gel, typically in pre-packed cartridges, eluting with mixtures of EtOAc in hexanes or petroleum ether; Chromatography B refers to elution with mixtures of MeOH in DCM; Chromatography C refers to use of C18 reverse-phase silica gel, eluting with mixtures of acetonitrile in water. Compounds drawn without stereochemistry were tested as racemic or diasteromeric mixtures. Abbreviations used in the Examples include the following: CBS: Corey-Bakshi-Shibata catalyst; DIAD: diisopropyl azodicarboxylate; EDC: N-Ethyl-N-(3-dimethylaminopropyl)carbodiimide hydrochloride; HATU: 1-[bis(dimethylamino)methylene]-1H-1,2,3-triazolo[4,5-b] pyridinium 3-oxide hexafluorophosphate; HWE: Horner-Wadsworth-Emmons; Xantphos: 4,5-Bis(diphenylphosphino)-9,9-dimethylxanthene; THF: tetrahydrofuran; EtOAc; ethyl acetate; DCM: dichloromethane; MeOH: methanol; dppf: 1,1'-ferrocenediyl-bis(diphenylphosphine); DAST: (diethylamino)sulfur trifluoride; T3P: propylphosphonic anhydride; TFA: trifluoroacetic acid; DIPEA: N,N-diisopropylethylamine; X-Phos: 2-dicyclohexylphosphino-2',4',6'-triisopropylbiphenyl; DMF: dimethylformamide; DMA: dimethylacetamide; NMP: N-methyl-2-pyrrolidone.

Example A: 3-(1-((4-methyl-4H-1,2,4-triazol-3-yl) thio)ethyl)benzoic acid

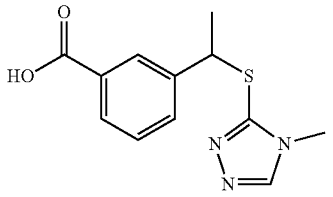 [SMILES: CC(Sc1nncn1C)c1cccc(C(=O)O)c1]

Step 1: methyl 3-[1-[(4-methyl-1,2,4-triazol-3-yl)sulfanyl]ethyl]benzoate. To a solution of 4-methyl-4H-1,2,4-triazole-3-thiol (1.30 g, 11.1 mmol), methyl 3-[(1R)-1-hydroxyethyl]benzoate (511.2 mg, 2.84 mmol) and $PPh_3$ (resin bound, 1.6 mmol/g, 7.40 g, 11.1 mmol) in THE (55 mL) was added DIAD (2.29 g, 11.1 mmol) dropwise at room temperature. The mixture was stirred at the same temperature for 2 h. After the reaction was completed, the resulting mixture was filtered. The residue was purified by Chromatography B to afford the title compound (0.700 g, 45%).

Step 2: 3-[1-[(4-methyl-4H-1,2,4-triazol-3-yl)sulfanyl] ethyl]benzoic acid. To a solution of methyl 3-[1-[(4-methyl-1,2,4-triazol-3-yl)sulfanyl]ethyl]benzoate (700 mg, 2.51 mmol) in THF/water (13/3.5 mL) was added LiOH (116 mg, 2.77 mmol). The mixture was stirred at room temperature for 4 h. After the reaction was completed, the reaction was quenched with HCl (2 N, 1.38 mL, 2.77 mmol) and evaporated to dryness to afford the crude title compound, which was used without purification.

Example B: 3-[(1S)-1-[(4-methyl-4H-1,2,4-triazol-3-yl)sulfanyl]ethyl]benzoic acid

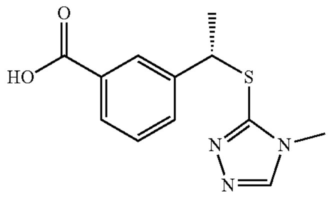 [SMILES: C[C@H](Sc1nncn1C)c1cccc(C(=O)O)c1]

Step 1: methyl 3-[(1R)-1-hydroxyethyl]benzoate. To a solution of $BH_3$ $Me_2S$ (3 mL, 2 M in THF) and (S)-(−)-2-methyl-CBS-oxazaborolidine (6 mL, 1 M) in toluene (6 mL) was added a solution of methyl 3-acetylbenzoate (1.0 g, 5.61 mmol) in THE (12 mL) dropwise at −70° C. under nitrogen. The resulting solution was stirred at−70 to −40° C. for 3 h under nitrogen. After the reaction was completed, the reaction mixture was quenched by the addition of saturated $NH_4Cl$ aqueous solution. General Workup Procedure followed by Chromatography A afforded the title compound (566 mg, 56%). MS (ESI) calculated for ($C_{10}H_{12}O_3$) $[M+H]^+$, 181.1; found, 181.0.

Step 2: 3-[(1S)-1-[(4-methyl-4H-1,2,4-triazol-3-yl)sulfanyl]ethyl]benzoate. To a solution of 4-methyl-4H-1,2,4-triazole-3-thiol (800 mg, 6.95 mmol), methyl 3-[(1R)-1-hydroxyethyl]benzoate (511.2 mg, 2.84 mmol) and $PPh_3$ (1.75 g, 6.67 mmol) in THF (10 mL) was added DIAD (1.35 g, 6.68 mmol) dropwise at 0° C. The mixture was stirred at room temperature for 3 h. After the reaction was completed, the resulting mixture was concentrated under vacuum. The residue was purified by Chromatography B to afford the title compound (750 mg, 39%). MS (ESI) calculated for ($C_{13}H_{15}N_3O_2S$) $[M+H]^+$, 278.1; found, 278.0.

Step 3: 3-[(1S)-1-[(4-methyl-4H-1,2,4-triazol-3-yl)sulfanyl]ethyl]benzoic acid. To a solution of methyl 3-[(1S)-1-[(4-methyl-4H-1,2,4-triazol-3-yl)sulfanyl]ethyl]benzoate (740 mg, 2.67 mmol) in methanol/water (10/2 mL) was added LiOH (192 mg, 8.02 mmol). The mixture was stirred at room temperature for 3 h. The organic solvent was removed under vacuum and the residue was diluted with water. The aqueous phase was acidified to pH 3~4 by HCl (1 N) General Workup Procedure was followed. The residue was purified by Chromatography C to afford the title compound (383 mg, 30%). $^1H$ NMR (400 MHz, DMSO-$d_6$) δ 13.03 (s, 1H), 8.53 (s, 1H), 7.89-7.80 (m, 2H), 7.55 (dt, J=7.8, 1.6 Hz, 1H), 7.44 (t, J=7.6 Hz, 1H), 4.77 (q, J=7.0 Hz, 1H), 3.35 (s, 3H), 1.67 (d, J=7.0 Hz, 3H). MS (ESI) calculated for ($C_{12}H_{14}N_3O_2S$) $[M+H]^+$, 264.1; found, 264.1.

Example C: 3-(1-(4-methyl-4H-1,2,4-triazol-3-yl-thio)ethyl)aniline

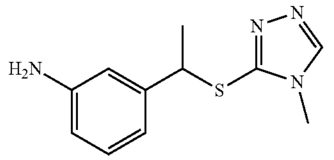 [SMILES: CC(Sc1nncn1C)c1cccc(N)c1]

Step 1: 4-methyl-3-(1-(3-nitrophenyl)ethylthio)-4H-1,2,4-triazole. A mixture of 1-(3-nitrophenyl)ethanol (10.0 g, 59.88 mmol), 4-methyl-4H-1,2,4-triazole-3-thiol (8.3 g, 71.86 mmol) and triphenylphosphine (31.0 g, 119.8 mmol) in THE (200 mL) was cooled 0° C. and diisopropyl diazene-1,2-dicarboxylate (24 g, 119.76 mmol) was added dropwise. The mixture was allowed to warm to about 25° C. for about 3 h. The mixture was quenched by the addition of water (150 mL) and following General Workup Procedure, the resulting crude residue was purified by flash chromatography to afford the title compound (6.4 g, 40%). $^1H$ NMR (400 MHz, DMSO-$d_6$) δ 8.54 (s, 1H), 8.14-8.11 (m, 2H), 7.81-7.79 (m, 1H), 7.64-7.60 (m, 1H), 4.88 (q, J=6.8 Hz, 1H), 3.40 (s, 3H), 1.71 (d, J=6.8 Hz, 3H).

Step 2: 3-(1-(4-methyl-4H-1,2,4-triazol-3-ylthio)ethyl) aniline. To a stirred solution of 4-methyl-3-[[1-(3-nitrophenyl)ethyl]sulfanyl]-4H-1,2,4-triazole (6.4 g, 24.24 mmol) and ammonium chloride (7.8 g, 145.46 mmol) in ethanol (80 mL) and water (40 mL) was added iron powder (4.1 g, 72.72 mmol) in portions at about 25° C. The mixture was heated at about 80° C. for 5 h. The iron powder was filtered off and the collected filtrate was concentrated to afford the title compound (5.8 g, crude), which was used without purification. MS (ESI) calc'd for ($C_{11}H_{14}N_4S$) $[M+H]^+$, 235.1; found, 235.1. $^1H$ NMR (400 MHz, DMSO-$d_6$) δ 8.54 (s, 1H), 6.96-6.92 (m, 1H), 6.53 (s, 1H), 6.48-6.40 (m, 2H), 5.15 (br, 2H), 4.48 (q, J=6.8 Hz, 1H), 3.38 (s, 1H), 1.58 (d, J=7.2 Hz, 3H).

Example D: (S)-3-(1-(4-methyl-4H-1,2,4-triazol-3-ylthio)ethyl)aniline

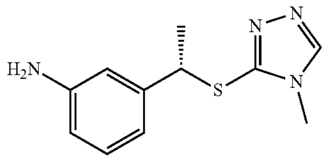 [SMILES: C[C@H](Sc1nncn1C)c1cccc(N)c1]

Step 1: (R)-1-(3-nitrophenyl)ethanol. To a solution of (S)-(−)-2-methyl-CBS-oxazaborolidine (12.1 mL, 12.1 mmol) in anhydrous toluene (300 mL) was added borane-N,N-diethylaniline complex (21.7 g, 133 mmol) at 30° C. under nitrogen atmosphere and the mixture was stirred for 20 min. Then, a solution of 1-(3-nitrophenyl)ethanone (20.0 g, 121 mmol) in toluene (200 mL) was added dropwise slowly over 5 h while maintaining the internal temperature at 30° C. The resulting mixture was stirred for another 30 min. The reaction was quenched by the addition of a hydrochloric acid solution (4 N in methanol, 50 mL) and then diluted with water (150 mL). Following General Workup Procedure, the resulting residue was purified by trituration with 10% EtOAc in petroleum ether to afford the title compound (15.0 g, 74%). MS (ESI) calculated for ($C_8H_9NO_3$) $[M+H]^+$, 168.1; found, 168.1.

Step 2: (S)-4-methyl-3-(1-(3-nitrophenyl)ethylthio)-4H-1,2,4-triazole. To a stirred solution of (R)-1-(3-nitrophenyl) ethanol (7.00 g, 41.9 mmol), 4-methyl-4H-1,2,4-triazole-3-thiol (5.78 g, 50.3 mmol) and triphenylphosphine (16.47 g, 62.9 mmol) in THF (100 mL) was added diisopropyl azodicarboxylate (12.70 g, 62.9 mmol) dropwise at 0° C. The resulting mixture was warmed to room temperature and stirred for 1.5 h. The reaction mixture was diluted with water (80 mL), followed by the General Workup Procedure, and the resulting residue was purified by Chromatography B to afford the title compound (8.90 g, 80%). MS (ESI) calculated for ($C_{11}H_{12}N_4O_2S$) $[M+H]^+$, 265.1; found, 265.0.

Step 3: (S)-3-(1-(4-methyl-4H-1,2,4-triazol-3-ylthio) ethyl)aniline. To a solution of (S)-4-methyl-3-(1-(3-nitrophenyl)ethylthio)-4H-1,2,4-triazole (8.9 g, 33.7 mmol) in ethanol (150 mL) was added ammonium chloride (10.7 g, 202.2 mmol) and iron powder (5.7 g, 101.1 mmol). The resulting mixture was stirred at 80° C. overnight and then was filtered through a Celite pad. The filtrate was concentrated under vacuum to give a crude solid which was re-suspended in EtOAc (100 mL) and methanol (5 mL). The precipitate was filtered off, and the filtrate was concentrated to give the title compound (7.8 g, crude), which was used without purification. The analytical sample was obtained by Chromatography C. MS (ESI) calculated for ($C_{11}H_{14}N_4S$) $[M+H]^+$, 235.1; found, 235.1. $^1H$ NMR (300 MHz, Chloroform-d) δ 8.13 (s, 1H), 7.08 (t, J=7.8 Hz, 1H), 6.71-6.58 (m, 2H), 6.56-6.49 (m, 1H), 4.63 (q, J=7.2 Hz, 1H), 3.51 (s, 2H), 3.26 (s, 3H), 1.78 (d, J=7.2 Hz, 3H).

Example E: (R)-3-(1-(4-methyl-4h-1,2,4-triazol-3-yl)propan-2-yl)aniline

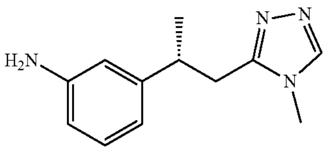 [SMILES: C[C@H](Cc1nncn1C)c1cccc(N)c1]

Step 1: (R,E)-3-(3-(3-nitrophenyl)acryloyl)-4-phenyloxazolidin-2-one. A mixture of (E)-3-(3-nitrophenyl)acrylic acid (500.0 g, 2.59 mol) and $SOCl_2$ (2.5 L) was heated at 80° C. for 2 h. Then the mixture was concentrated to afford (E)-3-(3-nitrophenyl)acryloyl chloride. In another three-necked flask was placed a solution of (R)-4-phenyloxazolidin-2-one (422.4 g, 2.59 mol) in anhydrous THF (1.0 L). Then lithium bis(trimethylsilyl)amide (3.1 L, 3.10 mol, 1 M in THF) was added dropwise to above solution at −70° C. under nitrogen atmosphere. After stirring at −70° C. for 30 min, a solution of (E)-3-(3-nitrophenyl)acryloyl chloride in anhydrous THE (1 L) was added dropwise to above mixture at −70° C. The mixture was warmed to 0° C. in 1 h. The reaction was quenched with saturated ammonium chloride aqueous solution at 0° C. General Workup Procedure followed by Chromatography A afforded the title compound (480.0 g, 55%). MS (ESI) calc'd for ($C_{18}H_{14}N_2O_5$) $[M+H]^+$, 339.1; found, 339.1.

Step 2: (R)-3-((R)-3-(3-nitrophenyl)butanoyl)-4-phenyloxazolidin-2-one. To a suspension of $CuBr{\cdot}Me_2S$ (314.9 g, 1.54 mol) in anhydrous THF (1.0 L) was added MeMgBr (1.0 L, 3.00 mol, 3 M in 2-methylTHF) dropwise with stirring at −40° C. under nitrogen atmosphere. The mixture was allowed to warm to −30~−20° C. for 40 min. Then The mixture was cooled to −40° C., and to this was added $BF_3{\cdot}Et_2O$ (200.3 g, 1.54 mol) dropwise with stirring at −40° C. Then the mixture was warmed to −30~−20° C. over 40 min. The mixture was cooled to −40° C. again, to this was added a suspension of (R,E)-3-(3-(3-nitrophenyl)acryloyl)-4-phenyloxazolidin-2-one (350.0 g, 1.03 mol) in anhydrous THF (1.0 L) slowly with stirring at −40~−30° C. The mixture was allowed to warm to −20° C. for 2 h. The reaction was then quenched by saturated aqueous ammonium chloride solution. Following General Workup Procedure, the resulting crude product was precipitated by the addition of petroleum ether. The solids were collected by filtration, then triturated with methanol to afford the title compound (210.0 g, 57%). MS (ESI) calc'd for ($C_{19}H_{18}N_2O_5$) $[M+H]^+$, 355.1; found, 355.1.

Step 3: (R)-3-(3-nitrophenyl)butanehydrazide. To a solution of (R)-3-((R)-3-(3-nitrophenyl)butanoyl)-4-phenyloxazolidin-2-one (160.0 g, 451.52 mmol) in THE (1.5 L) was added hydrazine hydrate (56.5 g, 903 mmol, 80%) dropwise at 0° C. The mixture was stirred at rt for 16 h. The mixture was concentrated. The residue was diluted with water, followed by General Workup Procedure to afford the title compound (160.0 g, crude). MS (ESI) calc'd for ($C_{10}H_{13}N_3O_3$) $[M+H]^+$, 224.1; found, 224.1.

Step 4: (R,E)-N,N-dimethyl-N'-(3-(3-nitrophenyl)butanoyl)formohydrazonamide. To a stirred solution of (R)-3-(3-nitrophenyl)butanehydrazide (160.0 g, 716 mmol, crude) in DCM (1.5 L) was added dimethylformamide dimethyl acetal (170.8 g, 1.43 mol) at rt. The mixture was heated at 50° C. for 2 h. The mixture was concentrated to afford the title compound (160.0 g, crude). MS (ESI) calc'd for ($C_{13}H_{18}N_4O_3$) $[M+H]^+$, 279.1; found, 279.2.

Step 5: (R)-4-methyl-3-(2-(3-nitrophenyl)propyl)-4H-1,2,4-triazole. To a stirred solution of (R,E)-N,N-dimethyl-N-(3-(3-nitrophenyl)butanoyl)formohydrazonamide (160.0 g, 0.40 mol, crude) in acetic acid (2.0 L) was added methylamine (2.0 L, 4.00 mol, 2 M in THF) at 0~10° C. The mixture heated at 90° C. for 3 h. Then, the mixture was concentrated. The residue was diluted with water and basified with $Na_2CO_3$ (aqueous) to pH 7-8. Following General Workup Procedure, the resulting residue was purified by flash column chromatography with 0-10% methanol in EtOAc to afford the title compound (58.0 g, 41% over three steps). MS (ESI) calc'd for ($C_{12}H_{14}N_4O_2$) $[M+H]^+$, 247.1; found, 247.2.

Step 6: (R)-3-(1-(4-methyl-4H-1,2,4-triazol-3-yl)propan-2-yl)aniline. To a solution of (R)-4-methyl-3-(2-(3-nitrophenyl)propyl)-4H-1,2,4-triazole (58.0 g, 235 mmol) in ethanol (600.0 mL) was added palladium on carbon (6.0 g) at rt under nitrogen atmosphere. Then the mixture was stirred at rt for 16 h under a hydrogen atmosphere. The mixture was filtered. The filtrate was concentrated. The title compound (43.0 g, 84%) was obtained using standard flash chromatography purification methods. MS (ESI) calc'd for ($C_{12}H_{16}N_4$) $[M+H]^+$, 217.1; found, 217.0.

Example F: 3-(3-((4-methyl-4H-1,2,4-triazol-3-yl)methyl)oxetan-3-yl)aniline

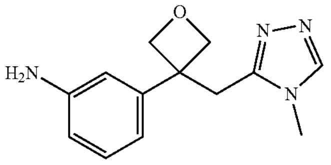 [SMILES: Cn1cnnc1CC1(c2cccc(N)c2)COC1]

Step 1: ethyl 2-(3-(3-nitrophenyl)oxetan-3-yl)acetate. Aqueous KOH (133.0 mL, 0.20 mol) was added to a suspension of chloro(1,5-cyclooctadiene)rhodium(I) dimer (3.2 g, 6.5 mmol) in dioxane (100 mL) and the mixture was stirred for 30 min. 3-nitrophenylboronic acid (32.6 g, 0.20 mol) and successively ethyl 2-(oxetan-3-ylidene)acetate (WO 2017/107907) (18.6 g, 0.13 mol) in dioxane (40 mL) were added and the mixture was stirred at rt for 16 h under nitrogen. The reaction was quenched by the addition of HCl (1 N) to pH=6~7. General Workup Procedure followed by Chromatography A afforded the title compound (25.6 g, 74%). MS (ESI) calculated for ($C_{13}H_{15}NO_5$) $[M+H]^+$, 266.1; found, 266.0.

Step 2: 2-(3-(3-nitrophenyl)oxetan-3-yl)acetohydrazide. A mixture of ethyl 2-(3-(3-nitrophenyl)oxetan-3-yl)acetate (20.0 g, 75.4 mmol) in ethanol (100 mL) and hydrazine hydrate (20 mL) was stirred at 80° C. for 16 h. The solvent was removed under vacuum. The residue was triturated with EtOAc/petroleum ether (1/10) to afford the title compound (25.0 g, crude), which was used without purification. MS (ESI) calculated for ($C_{11}H_{13}N_3O_4$) $[M+H]^+$, 252.1; found, 252.2.

Step 3: N-methyl-2-(2-(3-(3-nitrophenyl)oxetan-3-yl)acetyl)hydrazinecarbothioamide. To a solution of 2-(3-(3-nitrophenyl)oxetan-3-yl)acetohydrazide (10.0 g, 39.8 mmol) in THF (100 mL) was added isothiocyanatomethane (5.8 g, 79.7 mmol). The solution was stirred at rt for 4 h. The solvent was removed under vacuum. The residue was purified by Chromatography B to afford the title compound (10.0 g, 78%). MS (ESI) calculated for ($C_{13}H_{16}N_4O_4S$) $[M+H]^+$, 325.1; found, 325.2.

Step 4: 4-methyl-5-((3-(3-nitrophenyl)oxetan-3-yl)methyl)-4H-1,2,4-triazole-3-thiol. A mixture of N-methyl-2-(2-(3-(3-nitrophenyl)oxetan-3-yl)acetyl)hydrazinecarbothioamide (10.0 g, 30.8 mmol) in sodium hydroxide (308 mL, 1 M) was stirred at rt for 16 h. The reaction was diluted with water. The pH value of the solution was adjusted to 5 with HCl (1 N). The solids were collected by filtration to afford the title compound (7.0 g), which was used without purification. MS (ESI) calculated for ($C_{13}H_{14}N_4O_3S$) $[M+1]^+$, 307.1; found, 307.1.

Step 5: 4-methyl-3-((3-(3-nitrophenyl)oxetan-3-yl)methyl)-4H-1,2,4-triazole. To a solution of 4-methyl-5-((3-(3-nitrophenyl)oxetan-3-yl)methyl)-4H-1,2,4-triazole-3-thiol (7.0 g, 22.8 mmol) in water (30 mL) was added $NaNO_2$ (15.8 g, 228.8 mmol). This was followed by the addition of $HNO_3$ (228.8 mL, 1 M) dropwise with stirring at 0° C. and the mixture was stirred for another 1 h at 0° C. The mixture was basified by saturated aqueous sodium bicarbonate solution, and then extracted with EtOAc (200 mL×3). The combined organic layers were washed with brine, dried, and concentrated to afford the title compound (6 g, crude), which was used without purification. MS (ESI) calculated for ($C_{13}H_{14}N_4O_3$) $[M+H]^+$, 275.1; found, 274.9.

Step 6: 3-(3-((4-methyl-4H-1,2,4-triazol-3-yl)methyl)oxetan-3-yl)aniline. To a solution of 4-methyl-3-((3-(3-nitrophenyl)oxetan-3-yl)methyl)-4H-1,2,4-triazole (10 g, 36.5 mmol) in methanol (100 mL) was added Pd/C (dry, 4 g). The solution was stirred at rt for 16 h under hydrogen (2 atm). When the reaction was completed, the solids were filtered out. The filtrate was concentrated. The residue was purified by Chromatography C to afford the title compound (4.7 g, 53%). MS (ESI) calculated for ($C_{13}H_{16}N_4O$) $[M+H]^+$, 245.1; found, 245.0. $^1H$ NMR (300 MHz, DMSO-$d_6$) δ 8.19 (s, 1H), 6.92-6.87 (m, 1H), 6.40 (J=8.1 Hz, 1H), 6.05 (s, 1H), 5.94 (J=7.5 Hz, 1H), 5.00 (s, 2H), 4.90-4.84 (m, 2H), 4.79-4.74 (m, 2H), 3.38 (s, 2H), 2.83 (s, 3H).

Example G: (R)-3-(1,1,2-trifluoro-1-(4-methyl-4H-1,2,4-triazol-3-yl)propan-2-yl)aniline

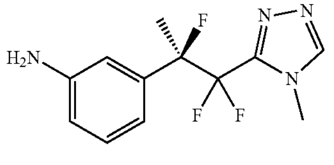 [SMILES: Cn1cnnc1C(F)(F)[C@](C)(F)c1cccc(N)c1]

Step 1: ethyl 3-(3-((tert-butoxycarbonyl)amino)phenyl)-2,2-difluoro-3-hydroxybutanoate. To a solution of Zn (231.9 g, 3.55 mol, 4.5 equiv) and ethyl 2-bromo-2,2-difluoroacetate (20.0 g, 98.5 mmol, 12.6 mL, 0.1 equiv) in THF (1.6 L) was added diisobutylaluminum hydride (1.00 M, 39.4 mL, 0.04 equiv) at 30° C. Then the mixture was stirred at 30° C. for 1 h. Then tert-butyl (3-acetylphenyl)carbamate (200.0 g, 791 mmol, 29.2 mL, 0.802 equiv) and ethyl 2-bromo-2,2-difluoro-acetate (200.0 g, 985 mmol, 126.5 mL, 1.2 equiv)

in THF (400 mL) were added dropwise at 40° C. and stirred at 40° C. for 3 h. Five batches were combined to work up. The mixture was filtered and the filtrate was poured into saturated $NH_4Cl$. The filtrate was extracted with EtOAc (5 L×3). The organic layers were combined and concentrated to give the crude product. The crude product was purified by Chromatography A to give the title compound (700.0 g, 1.95 mol, 39.5% yield).

Step 2: tert-butyl (3-(3,3-difluoro-4-hydrazinyl-2-hydroxy-4-oxobutan-2-yl)phenyl)carbamate. To a solution of ethyl 3-(3-((tert-butoxycarbonyl)amino)phenyl)-2,2-difluoro-3-hydroxybutanoate (385.0 g, 1.07 mol, 1.0 equiv) in EtOH (1.50 L) was added $NH_2NH_2·H_2O$ (273.6 g, 5.36 mol, 265.6 mL, 98.0% purity, 5.0 equiv). Then The mixture was stirred at 25° C. for 16 h. The mixture was concentrated to give the title compound (370.0 g, crude) which was used in the next step without purification.

Step 3: tert-butyl (3-(3,3-difluoro-2-hydroxy-4-(2-(methylcarbamothioyl)hydrazinyl)-4-oxobutan-2-yl)phenyl)carbamate. To a solution of tert-butyl (3-(3,3-difluoro-4-hydrazinyl-2-hydroxy-4-oxobutan-2-yl)phenyl)carbamate (370.0 g, 1.07 mol, 1.0 equiv) in THF (1.50 L) was added methylimino(thioxo)methane (156.6 g, 2.14 mol, 146.4 mL, 2.0 equiv). Then the mixture was stirred at 70° C. for 2 h. The mixture was concentrated to give the crude product (450.0 g, crude), which was used without purification.

Step 4: tert-butyl (3-(1,1-difluoro-2-hydroxy-1-(5-mercapto-4-methyl-4H-1,2,4-triazol-3-yl)propan-2-yl)phenyl) carbamate. A solution of tert-butyl (3-(3,3-difluoro-2-hydroxy-4-(2-(methylcarbamothioyl)hydrazinyl)-4-oxobutan-2-yl)phenyl)carbamate (450.0 g, 1.08 mol, 1.0 equiv) in NaOH (1.00 M, 4.50 L, 4.2 equiv) was stirred at 50° C. for 2 h. The mixture was poured into HCl (0.50 M, 1.50 L) and filtered. The filter cake was collected to give the crude product (430.0 g), which was used without purification.

Step 5: tert-butyl (3-(1,1-difluoro-2-hydroxy-1-(4-methyl-4H-1,2,4-triazol-3-yl)propan-2-yl)phenyl)carbamate. To a solution of tert-butyl (3-(1,1-difluoro-2-hydroxy-1-(5-mercapto-4-methyl-4H-1,2,4-triazol-3-yl)propan-2-yl) phenyl)carbamate (214.0 g, 534.4 mmol, 1.0 equiv) in methylene chloride (1.50 L) was added a solution of $H_2O_2$ (181.7 g, 1.60 mol, 154.0 mL, 30.0% purity, 3.0 equiv) in AcOH (48.1 g, 801.6 mmol, 45.8 mL, 1.5 equiv) dropwise at 35° C. Then the reaction was stirred at 35° C. for 1 h. Two batches were combined to work up. The mixture was poured into saturated sodium carbonate and extracted with methylene chloride. The organic layers were combined and concentrated to give the crude product. The crude product was purified by Chromatography A to afford the title compound (200 g).

Step 6: tert-butyl (3-(1,1,2-trifluoro-1-(4-methyl-4H-1,2,4-triazol-3-yl)propan-2-yl)phenyl)carbamate. To a solution of tert-butyl (3-(1,1-difluoro-2-hydroxy-1-(4-methyl-4H-1,2,4-triazol-3-yl)propan-2-yl)phenyl)carbamate (115.0 g, 312.1 mmol, 1.0 equiv) in methylene chloride (550 mL) was added DAST (150.9 g, 936.5 mmol, 123.7 mL, 3.0 equiv). Then the mixture was stirred at 25° C. for 30 min. The mixture was poured into saturated $NaHCO_3$ and extracted with methylene chloride. The organic layers were combined and concentrated to give the crude product. The crude product was purified by MPLC (Petroleum ether/EtOAc 2/1-1/1) to give the title compound (90.0 g, 39% yield).

Step 7: (R)-3-(1,1,2-trifluoro-1-(4-methyl-4H-1,2,4-triazol-3-yl)propan-2-yl)aniline. A solution of tert-butyl (3-(1,1,2-trifluoro-1-(4-methyl-4H-1,2,4-triazol-3-yl)propan-2-yl)phenyl)carbamate (90.0 g, 241.7 mmol, 1.0 equiv) in HCl/EtOAc (4.00 M, 500.0 mL, 8.23 equiv) was stirred at 25° C. for 16 h. The mixture was filtered. The filter cake was poured into saturated $NaHCO_3$ and extracted with EtOAc. The organic layers were combined and concentrated to give the racemic title compound (66.0 g, 231.0 mmol, 95.0% yield, 94.6% purity). The racemic product was separated by chiral SFC to afford the title compound (33.4 g): $^1H$ NMR (400 MHz, DMSO-$d_6$) δ: 8.58 (s, 1H), 7.01 (t, J=8.0 Hz, 1H), 6.51-6.63 (m, 2H), 6.35 (d, J=8.0 Hz, 1H), 5.23 (br s, 2H), 3.29 (s, 3H), 1.84 (d, J=24.0 Hz, 3H).

Example H: 3-((1R,2S)-2-(4-methyl-4H-1,2,4-triazol-3-yl)cyclopropyl)aniline and 3-((1S,2R)-2-(4-methyl-4H-1,2,4-triazol-3-yl)cyclopropyl)aniline

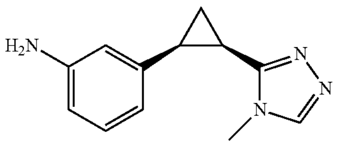

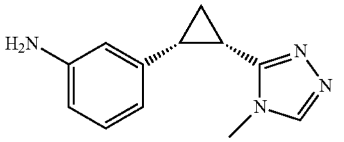

Step 1: cis-2-(3-nitrophenyl)cyclopropanecarbohydrazide. To a solution of cis-ethyl 2-(3-nitrophenyl)cyclopropanecarboxylate (Valente, S. et al., Eur. J. Org. Chem. 2015, 94, 163-174) (4.0 g, 17.0 mmol) in ethanol (40 mL) was added hydrazine hydrate (4 mL, 80%). The mixture was stirred at 80° C. for 48 h. The solvent was removed by vacuum to afford the title compound (3.0 g, crude), which was used without purification. MS (ESI) calculated for ($C_{10}H_{11}N_3O_3$) $[M+H]^+$, 222.1; found, 221.9.

Step 2: (E)-N,N-dimethyl-N'-((cis)-2-(3-nitrophenyl)cyclopropane-1-carbonyl)-formohydrazonamide. To a solution of cis-2-(3-nitrophenyl)cyclopropanecarbohydrazide (1.5 g, 6.8 mmol) in DCM (50 mL) was added DMF-DMA (1.5 mL) and stirred at rt for 3 h. The solvent was removed to afford the title compound (1.5 g, crude), which was used without purification. MS (ESI) calculated for ($C_{13}H_{16}N_4O_3$) $[M+H]^+$, 277.1; found, 276.9.

Step 3: 4-methyl-3-(cis-2-(3-nitrophenyl)cyclopropyl)-4H-1,2,4-triazole. To a solution of (E)-N,N-dimethyl-N-(cis-2-(3-nitrophenyl)cyclopropanecarbonyl)formohydrazonamide (500 mg, 1.81 mmol) in acetic acid (10 mL) was added methylamine (10 mL, 2 mol/L in THF). The mixture was stirred at 90° C. for 3 h before concentration. The residue was diluted with water, and then alkalized with aqueous $NaHCO_3$ and extracted with EtOAc. The organic layers were combined, washed with brine, dried, and filtered. The filtrate was evaporated under vacuum. The residue was purified by Chromatography B to afford the title compound (100 mg, 23%). MS (ESI) calculated for ($C_{12}H_{12}N_4O_2$) $[M+H]^+$, 245.1; found, 245.2.

Step 4: 3-((1R,2S)-2-(4-methyl-4H-1,2,4-triazol-3-yl)cyclopropyl)aniline and 3-((1S,2R)-2-(4-methyl-4H-1,2,4-triazol-3-yl)cyclopropyl)aniline. To a solution of 4-methyl-3-(cis-2-(3-nitrophenyl)cyclopropyl)-4H-1,2,4-triazole (600.0 mg, 2.46 mmol) in ethanol/water (10/5 mL) were added Fe powder (413.0 mg, 7.38 mmol) and $NH_4Cl$ (652.0 mg, 12.20 mmol). The mixture was stirred at 70° C. for 3 h. The solids were filtered off by filtration. The filtrate was evaporated under vacuum. The residue was purified by Chromatography B to afford the racemic title compound (300.0 mg, 57%). The racemic mixture (500.0 mg, 0.36 mmol) was separated by chiral-SFC (Chiralpak AD-H, $CO_2$-methanol) to afford 3-((1R,2S)-2-(4-methyl-4H-1,2,4-triazol-3-yl)cyclopropyl) aniline (130.0 mg) with a shorter retention time on chiral SFC as a white solid and 3-((1S,2R)-2-(4-methyl-4H-1,2,4-triazol-3-yl)cyclopropyl)aniline (140.0 mg) with a longer retention time on chiral SFC as a white solid. [0397]3-((1R, 2S)-2-(4-methyl-4H-1,2,4-triazol-3-yl)cyclopropyl)aniline. $^1$H NMR (300 MHz, $CDCl_3$) δ 7.86 (s, 1H), 6.92-6.87 (m, 1H), 6.42-6.39 (m, 2H), 6.38-6.16 (m, 1H), 3.33 (s, 3H), 2.49-2.41 (m, 1H), 2.28-2.21 (m, 1H), 2.06-2.00 (m, 1H), 1.66-1.59 (m, 1H). MS (ESI) calculated for ($C_{12}H_{14}N_4$) $[M+H]^+$, 215.1; found, 215.0. [0398]3-((1S,2R)-2-(4-methyl-4H-1,2,4-triazol-3-yl)cyclopropyl)aniline. $^1$H NMR (300 MHz, $CDCl_3$) δ 7.85 (s, 1H), 6.92-6.86 (m, 1H), 6.42-6.37 (m, 2H), 6.35-6.16 (m, 1H), 3.32 (s, 3H), 2.49-2.41 (m, 1H), 2.28-2.20 (m, 1H), 2.06-2.00 (m, 1H), 1.66-1.58 (m, 1H). MS (ESI) calculated for ($C_{12}H_{14}N_4$) $[M+H]^+$, 215.1; found, 215.0.

Example I: tert-butyl 3',4'-dihydrospiro[azetidine-3, 2'-pyrido[3,2-b][1,4]oxazine]-1-carboxylate

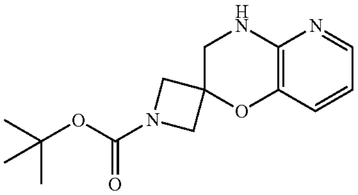 [SMILES: CC(C)(C)OC(=O)N1CC2(CNc3ncccc3O2)C1]

Step 1: 1-(tert-butyl) 3-methyl 3-((2-nitropyridin-3-yl) oxy)azetidine-1,3-dicarboxylate. To a stirred mixture of 1-(tert-butyl) 3-methyl 3-hydroxyazetidine-1,3-dicarboxylate (3.7 g, 16.01 mmol) and 3-fluoro-2-nitropyridine (2.4 g, 16.81 mmol) in THE (50 mL) was sequentially added NaH (768 mg, 19.21 mmol) and 15-crown-5 (1.5 mL) at 0° C. The mixture was warmed to 15° C. and stirred for 20 h. The reaction was quenched by the addition of $H_2O$. General Workup Procedure followed by Chromatography A afforded the title compound (4.2 g, 74%). MS (ESI) calculated for ($C_{15}H_{19}N_3O_7$) $[M+1]^+$, 354.1; found, 354.0.

Step 2: tert-butyl 3'-oxo-3',4'-dihydrospiro[azetidine-3,2'-pyrido[3,2-b][1,4]oxazine]-1-carboxylate. To a solution of 1-(tert-butyl) 3-methyl 3-((2-nitropyridin-3-yl)oxy)azetidine-1,3-dicarboxylate (4.2 g, 11.89 mmol) in acetic acid (80 mL) was added Fe powder (3.3 g, 59.47 mmol). The mixture was stirred at 50° C. for 1.5 h under nitrogen. The reaction mixture was filtered, and the filtrate was concentrated under vacuum. The residue was diluted with water and basified with saturated sodium carbonate. General Workup Procedure followed by Chromatography A afforded the title compound (1.5 g, 43%). MS (ESI) calculated for ($C_{14}H_{17}N_3O_4$) $[M+1]^+$, 292.1; found, 292.0.

Step 3: tert-butyl 3',4'-dihydrospiro[azetidine-3,2'-pyrido [3,2-b][1,4]oxazine]-1-carboxylate. To a stirred solution of tert-butyl 3'-oxo-3',4'-dihydrospiro[azetidine-3,2'-pyrido[3, 2-b][1,4]oxazine]-1-carboxylate (1.1 g, 3.78 mmol) in THE (20 mL) was added $BH_3$ THF (11 mL, 11.00 mmol) at room temperature. The solution was stirred at 70° C. for 3 h under nitrogen. The reaction was quenched by the addition of methanol and concentrated to give a residue which was purified by Chromatography B to afford the title compound (240 mg, 23%). $^1$H NMR (400 MHz, Chloroform-d) δ 7.72 (dd, J=5.2, 1.6 Hz, 1H), 7.07 (dd, J=8.0, 1.6 Hz, 1H), 6.63 (dd, J=8.0, 5.2 Hz, 1H), 5.11 (s, 1H), 4.04 (d, J=9.6 Hz, 2H), 3.94 (dd, J=9.6, 1.2 Hz, 2H), 3.60 (d, J=2.0 Hz, 2H), 1.47 (s, 9H). MS (ESI) calculated for ($C_{14}H_{19}N_3O_3$) $[M+1]^+$, 278.1; found, 278.1.

Example J: tert-butyl 3,4-dihydrospiro[pyrido[3,2-b] [1,4]oxazine-2,3'-pyrrolidine]-1'-carboxylate

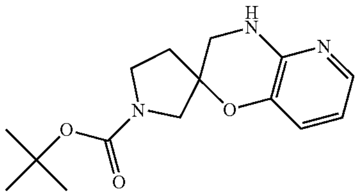 [SMILES: CC(C)(C)OC(=O)N1CCC2(CNc3ncccc3O2)C1]

Step 1: 1-(tert-butyl) 3-methyl 3-((2-nitropyridin-3-yl) oxy)pyrrolidine-1,3-dicarboxylate. To a stirred mixture of 1-(tert-butyl) 3-methyl 3-hydroxypyrrolidine-1,3-dicarboxylate (3.0 g, 12.24 mmol) and 3-fluoro-2-nitropyridine (1.8 g, 12.85 mmol) were reacted under the conditions of Example I, Step 1 to afford the title compound (3.7 g, 82%). MS (ESI) calculated for ($C_{16}H_{21}N_3O_7$) $[M+1]^+$, 368.1; found, 368.0.

Step 2: tert-butyl 3-oxo-3,4-dihydrospiro[pyrido[3,2-b] [1,4]oxazine-2,3'-pyrrolidine]-1'-carboxylate. This compound was prepared from 1-(tert-butyl) 3-methyl 3-((2-nitropyridin-3-yl)oxy)pyrrolidine-1,3-dicarboxylate following the procedure of Example I, Step 2 to afford the title compound (2.3 g, 75%). MS (ESI) calculated for ($C_{15}H_{19}N_3O_4$) $[M+1]^+$, 306.1; found, 306.0.

Step 3: tert-butyl 3,4-dihydrospiro[pyrido[3,2-b][1,4] oxazine-2,3'-pyrrolidine]-1'-carboxylate. This compound was prepared from tert-butyl 3-oxo-3,4-dihydrospiro[pyrido [3,2-b][1,4]oxazine-2,3'-pyrrolidine]-1'-carboxylate following the procedure of Example I, Step 3. (250 mg, 34%). $^1$H NMR (300 MHz, Chloroform-d) δ 7.72 (d, J=5.1 Hz, 1H), 7.02 (d, J=7.8 Hz, 1H), 6.72-6.53 (m, 1H), 5.43-5.17 (m, 1H), 3.71-3.31 (m, 6H), 2.21-1.85 (m, 2H), 1.48 (s, 9H). MS (ESI) calculated for ($C_{15}H_{21}N_3O_3$) $[M+1]^+$, 292.2; found, 292.2.

Example K: 3-(3-((4-methyl-4H-1,2,4-triazol-3-yl) methyl)oxetan-3-yl)benzoic acid

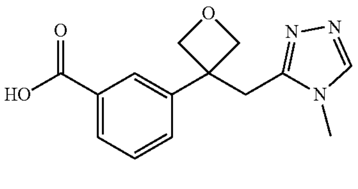 [SMILES: Cn1cnnc1CC1(c2cccc(C(=O)O)c2)COC1]

Step 1: ethyl 3-(3-((4-methyl-4H-1,2,4-triazol-3-yl) methyl)oxetan-3-yl)benzoate. A solution of 3-((3-(3-bromophenyl)oxetan-3-yl)methyl)-4-methyl-4H-1,2,4-triazole (1.0 g, 3.24 mmol), [1,1'-bis(diphenylphosphino)ferrocene] dichloropalladium(II) (1.19 g, 1.62 mmol) and triethylamine (0.90 mL, 6.49 mmol) in toluene and ethanol (1:1 v/v, 34 mL) was exposed to carbon monoxide (1 atm) and stirred at 78° C. for 2 h. Chromatography B afforded the title compound (0.811 g, 83.0%).

Step 2: 3-(3-((4-methyl-4H-1,2,4-triazol-3-yl)methyl)oxetan-3-yl)benzoic acid. The procedure of Example A Step 2 was followed using ethyl 3-(3-((4-methyl-4H-1,2,4-triazol-3-yl)methyl)oxetan-3-yl)benzoate to afford the crude title compound. LCMS: $C_{14}H_{15}N_3O_3$ requires: 273, found: m/z=274 $[M+H]^+$.

Example L: phenyl (S)-(3-(1-((4-methyl-4H-1,2,4-triazol-3-yl)thio)ethyl)phenyl)carbamate

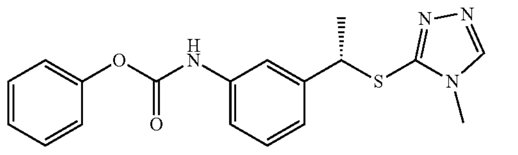 [SMILES: C[C@H](Sc1nncn1C)c1cccc(NC(=O)Oc2ccccc2)c1]

To a solution of 3-[(1S)-1-[(4-methyl-4H-1,2,4-triazol-3-yl)sulfanyl]ethyl]aniline (4.7 g, 20 mmol) in N,N-dimethylacetamide (100 mL) were added phenyl chloroformate (4.7 g, 90 mmol) and pyridine (3.1 g, 39 mmol). The reaction mixture was stirred at room temperature for 2 h. General Workup Procedure followed by Chromatography A afforded the title compound (6.2 g, 87%). MS (ESI) calc'd for $(C_{18}H_{18}N_4O_2S)$ $[M+1]^+$, 355.1; found, 355.1. $^1$H NMR (300 MHz, DMSO-$d_6$) δ 10.26 (s, 1H), 8.54 (s, 1H), 7.53 (s, 1H), 7.46-7.38 (m, 3H), 7.29-7.21 (m, 4H), 6.96 (d, J=7.5 Hz, 1H), 4.63 (q, J=6.9 Hz, 1H), 3.37 (s, 3H), 1.62 (d, J=6.9 Hz, 3H).

Example M: 3-((3-(3-bromophenyl)oxetan-3-yl)methyl)-4-methyl-4H-1,2,4-triazole

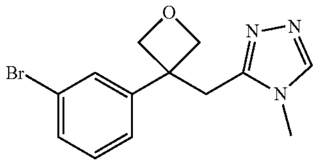 [SMILES: Cn1cnnc1CC1(c2cccc(Br)c2)COC1]

Step 1: ethyl 2-(3-(3-bromophenyl)oxetan-3-yl)acetate. To a solution of chloro(1,5-cyclooctadiene)rhodium(I) dimer (47.1 g, 95.5 mmol, 0.05 equiv) in dioxane (1160 mL) was added a solution of KOH (17 M, 168.6 mL, 1.50 equiv). Ethyl 2-(oxetan-3-ylidene)acetate (WO 2017/107907) (271.5 g, 1.91 mol, 1.00 equiv) and (3-bromophenyl)boronic acid (498.6 g, 2.48 mol, 1.3 equiv) were added to the mixture at 25-45° C. Then the reaction mixture was stirred at 25° C. for 16 h. The reaction mixture was poured into $H_2O$ (1 L). General Workup Procedure followed by Chromatography A afforded the title compound (468.2 g, 1.47 mol, 76.8% yield).

Step 2: 2-(3-(3-bromophenyl)oxetan-3-yl)acetohydrazide. To a solution of ethyl 2-(3-(3-bromophenyl)oxetan-3-yl)acetate (50.0 g, 156.7 mmol, 1 equiv) in EtOH (250 mL) was added $N_2H_4 \cdot H_2O$ (91.64 g, 1.56 mol, 88.9 mL, 85% in water, 9.93 equiv). The reaction mixture was stirred at 80° C. for 26 h. The reaction mixture was concentrated and diluted with $H_2O$ (100 mL). General Workup Procedure afforded the crude title compound, which was used without purification.

Step 3: 2-(2-(3-(3-bromophenyl)oxetan-3-yl)acetyl)-N-methylhydrazine-1-carbothioamide. To a solution of 2-(3-(3-bromophenyl)oxetan-3-yl)acetohydrazide (58.5 g, 205.16 mmol, 1 equiv) in THE (292 mL) was added methyl isothiocyanate (30.0 g, 410.33 mmol, 28.04 mL, 2 equiv), and the reaction mixture was stirred at 70° C. for 2 h. The reaction mixture was concentrated to give the crude product, which was used without purification.

Step 4: 5-((3-(3-bromophenyl)oxetan-3-yl)methyl)-4-methyl-4H-1,2,4-triazole-3-thiol. A solution of 2-(2-(3-(3-bromophenyl)oxetan-3-yl)acetyl)-N-methylhydrazine-1-carbothioamide (80.0 g, 223.3 mmol, 1.00 equiv) in NaOH (1 M, 800 mL, 3.58 equiv) was stirred at 50° C. for 2 h. The reaction mixture was poured into HCl (1 M, 800 mL) and filtered. The filter cake was collected to give the crude product, which was used without purification.

Step 5: 3-((3-(3-bromophenyl)oxetan-3-yl)methyl)-4-methyl-4H-1,2,4-triazole. To a solution of 5-((3-(3-bromophenyl)oxetan-3-yl)methyl)-4-methyl-4H-1,2,4-triazole-3-thiol (105 g, 308.6 mmol, 1.00 equiv) in DCM (520 mL) was added a solution of $H_2O_2$ (99.84 g, 880.5 mmol, 84.61 mL, 30% in water, 2.85 equiv) in AcOH (27.8 g, 462.9 mmol, 26.47 mL, 1.50 equiv) to the mixture at 0-25° C. Then the reaction mixture was stirred at 25° C. for 22 h. The reaction mixture was poured into saturated $Na_2SO_3$ solution (500 mL) and saturated $Na_2CO_3$ solution (500 mL) and extracted with DCM (300 mL×4). The organic phase was washed with brine (200 mL×2), dried, filtered, and concentrated. Chromatography C afforded the title compound (17.4 g, 56.01 mmol, 18.15% yield, 99.2% purity). LCMS: $C_{13}H_{14}BrN_3O$ requires: 307, found: m/z=308 $[M+H]^+$. $^1$H NMR (400 MHz, chloroform-d) δ 7.89 (s, 1H), 7.38 (dd, J=0.8, 8.0 Hz, 1H), 7.13 (t, J=8.0 Hz, 1H), 6.98 (t, J=2.0 Hz, 1H), 6.70 (d, J=7.6 Hz, 1H), 5.09 (d, J=8.0 Hz, 2H), 5.01 (d, J=6.4 Hz, 2H), 3.51 (s, 2H), 2.83 (s, 3H).

Example N: (R)-3-(2-(3-bromophenyl)propyl)-4-methyl-4H-1,2,4-triazole

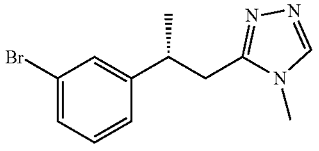 [SMILES: C[C@H](Cc1nncn1C)c1cccc(Br)c1]

Step 1: (4R)-3-[(2E)-3-(3-bromophenyl)prop-2-enoyl]-4-phenyl-1,3-oxazolidin-2-one. In a three-necked flask was placed a solution of (4R)-4-phenyl-1,3-oxazolidin-2-one (215.0 g, 1.32 mol) in anhydrous THE (1.0 L). Lithium bis(trimethylsilyl)amide (1.53 L, 1.53 mol, 1 M in THF) was added dropwise to the above solution at −70° C. under nitrogen atmosphere. The mixture was stirred for 30 mins at −70° C. A solution of (E)-3-(3-bromophenyl)acryloyl chloride (Raffa, D., et al. *Eur. J. Med. Chem.* 2013, 427-435.)) in dry THE (1 L) was added dropwise to above mixture at −70° C. The mixture was stirred at −70~−20° C. for 1 h. The reaction was quenched by saturated aqueous ammonium chloride solution at 0° C. The mixture was extracted with EtOAc twice. The organic layers were dried, filtered, and concentrated. The residue was purified by trituration with petroleum ether/EtOAc (1/5) to afford the title compound (310 g, 33%). MS (ESI) calculated for $(C_{18}H_{14}BrNO_3)$ $[M+H]^+$, 372.0; found, 371.8.

Step 2: (4R)-3-[(3R)-3-(3-bromophenyl)butanoyl]-4-phenyl-1,3-oxazolidin-2-one. To a suspension of CuBr·$Me_2S$ (128.0 g, 0.62 mol) in anhydrous THE (1 L) was added MeMgBr (420 mL, 1.26 mol, 3 M in 2-methyl THF) dropwise with stirring at −40° C. under nitrogen atmosphere. Then the mixture was allowed to warm to −30~−20° C. for 40 minutes. Then the mixture was cooled to −40° C., and to this mixture was added $BF_3 \cdot Et_2O$ (88.7 g, 0.62 mol) dropwise with stirring at −40° C. Then the mixture was slowly warmed to −30~−20° C. over 40 minutes. The mixture was cooled to −40° C. again and treated with a solution of (4R)-3-[(2E)-3-(3-bromophenyl)prop-2-enoyl]-4-phenyl-1,3-oxazolidin-2-one (155.0 g, 0.42 mol) in THF (0.5 L) slowly with stirring at −40~−30° C. The mixture was allowed to warm to ~−20° C. for 2 h. The reaction was quenched with $NH_4Cl$ (sat. aq.). General Workup Procedure followed by recrystallization with methyl t-butyl ether and petroleum ether afforded the title compound (100.0 g, 62%). MS (ESI) calculated for ($C_{19}H_{18}BrNO_3$) $[M+H]^+$, 388.1; found, 387.9.

Step 3: (3R)-3-(3-bromophenyl)butanehydrazide. To a solution of (4R)-3-[(3R)-3-(3-bromophenyl)butanoyl]-4-phenyl-1,3-oxazolidin-2-one (77.0 g, 198.3 mmol) in THF (800 mL) was added $NH_2NH_2 \cdot H_2O$ (33 mL, 80%) dropwise at 0° C. The mixture was stirred at rt for 16 h. The mixture was concentrated. General Workup Procedure followed by Chromatography A afforded the title compound (51.0 g, 99%). MS (ESI) calculated for ($C_{10}H_{13}BrN_2O$) $[M+H]^+$, 257.0; found, 257.1.

Step 4: 5-[(2R)-2-(3-bromophenyl)propyl]-4-methyl-4H-1,2,4-triazole-3-thiol. To a solution of (3R)-3-(3-bromophenyl)butanehydrazide (46.0 g, 178.9 mmol) in THF (500 mL) was added isothiocyanatomethane (13.0 g, 177.8 mmol). The mixture was stirred at rt for 16 h. The mixture was concentrated. The residue was treated with sodium hydroxide (aq., 1 M) and stirred at rt for 16 h. The mixture was acidified by HCl (2 N) to pH 3, followed by the General Workup Procedure to afford the title compound (55.2 g, crude). MS (ESI) calculated for ($C_{12}H_{14}BrN_3S$) $[M+H]^+$, 312.0; found, 311.9.

Step 5: 3-[(2R)-2-(3-bromophenyl)propyl]-4-methyl-4H-1,2,4-triazole. To a solution of 5-[(2R)-2-(3-bromophenyl)propyl]-4-methyl-4H-1,2,4-triazole-3-thiol (55.2 g, 177 mmol) in methylene chloride (600 mL) and acetic acid (300 mL) was added $H_2O_2$ (200 mL, 1.76 mol, 30% in water) dropwise with stirring at 0° C. The mixture was stirred at this temperature for 1 h before being concentrated. The residue was dissolved in water and basified by NaOH (aq.) to pH 10. General Workup Procedure followed by purification on $SiO_2$ with 0-10% methanol in EtOAc afforded the title compound (23.9 g, 48%). MS (ESI) calculated for ($C_{12}H_{14}BrN_3$) $[M+H]^+$, 280.0; found, 280.0. $^1H$ NMR (300 MHz, DMSO-$d_6$) δ 8.27 (s, 1H), 7.47 (d, J=1.8 Hz, 1H), 7.37 (d, J=7.2 Hz, 1H), 7.33-7.14 (m, 2H), 3.45 (s, 3H), 3.28-3.21 (m, 1H), 2.96 (d, J=7.5 Hz, 2H), 1.24 (d, J=6.9 Hz, 3H).

Example O (S)-4-(1-((4-methyl-4H-1,2,4-triazol-3-yl)thio)ethyl)pyridin-2-amine

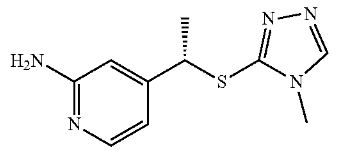 [SMILES: C[C@H](Sc1nncn1C)c1ccnc(N)c1]

Step 1: methyl 2-((tert-butoxycarbonyl)amino)isonicotinate. To a mixture of methyl 2-aminoisonicotinate (200 g, 1.32 mol) and di-tert-butyl dicarbonate (430.0 g, 1.97 mol) in t-BuOH (800 mL) and acetone (2400 mL) was added N,N-dimethylpyridin-4-amine (9.6 g, 78.6 mmol) in portions. The mixture was stirred at room temperature for 16 h and diluted with hexane (600 mL). The mixture was cooled to 0° C., the precipitated product was collected and dried to give the title compound (239.0 g, 72%). MS (ESI) calculated for ($C_{12}H_{16}N_2O_4$) $[M+H]^+$, 253.1; found, 253.1.

Step 2: 2-((tert-butoxycarbonyl)amino)isonicotinic acid. To a solution of methyl 2-((tert-butoxycarbonyl)amino)isonicotinate (239.0 g, 0.95 mol) in tetrahydrofuran (2400 mL) was added a solution of lithium hydroxide (45.6 g, 1.9 mol) in water (600 mL). The mixture was stirred at room temperature overnight, and then diluted with water (1500 mL). Most of the solvent was removed under reduced pressure. The pH value of the mixture was adjusted to 3 with citric acid (saturated). The precipitated product was collected and dried to give the title compound (253.0 g, crude). MS (ESI) calculated for ($C_{11}H_{14}N_2O_4$) $[M-1]^+$, 237.1; found, 237.0.

Step 3: tert-butyl (4-(methoxy(methyl)carbamoyl)pyridin-2-yl)carbamate. To a mixture of 2-((tert-butoxycarbonyl)amino)isonicotinic acid (253.0 g, 1.06 mol), N,O-dimethylhydroxylamine hydrochloride (103.1 g, 1.06 mol) and N,N-diisopropylethylamine (548.9 g, 4.25 mol) in dry N,N-dimethylformamide (3 L) was added HATU (484.8 g, 1.28 mol) at 0° C. The mixture was stirred at room temperature for 1 h. General Workup Procedure followed by trituration with EtOAc/petroleum ether (1:9) afforded the title compound (236.0 g, 88% over two steps). MS (ESI) calculated for ($C_{13}H_{19}N_3O_4$) $[M+H]^+$, 282.1; found, 282.1.

Step 4: tert-butyl (4-acetylpyridin-2-yl)carbamate. To a stirred solution of tert-butyl (4-(methoxy(methyl)carbamoyl)pyridin-2-yl)carbamate (236.0 g, 0.84 mol) in anhydrous tetrahydrofuran (3 L) was added MeMgBr (840 mL, 2.52 mol, 3 M in tetrahydrofuran) dropwise at 0° C. under nitrogen. The mixture was stirred at 0° C. for 1 h, and then quenched with aqueous ammonium chloride (saturated) carefully. General Workup Procedure followed by trituration with EtOAc:petroleum ether (1:8) afforded the title compound (160.0 g, 80%). MS (ESI) calculated for ($C_{12}H_{16}N_2O_3$) $[M+H]^+$, 237.1; found, 237.1.

Step 5: tert-butyl (4-(1-hydroxyethyl)pyridin-2-yl)carbamate. To a solution of tert-butyl (4-acetylpyridin-2-yl)carbamate (140.0 g, 0.59 mol) in methanol (1400 mL) was added sodium borohydride (27.1 g, 0.71 mol) in portions at 0° C. The mixture was stirred at 0° C. for 1.5 h and quenched with water. Most of the solvent (methanol) was removed under reduced pressure. General Workup Procedure followed by Chromatography A afforded the title compound (139.0 g, 98%). MS (ESI) calculated for ($C_{12}H_{18}N_2O_3$) $[M+H]^+$, 239.1; found, 239.1.

Step 6: (R)-1-(2-((tert-butoxycarbonyl)amino)pyridin-4-yl)ethyl acetate and tert-butyl (S)-(4-(1-hydroxyethyl)pyridin-2-yl)carbamate. To a mixture of tert-butyl (4-(1-hydroxyethyl)pyridin-2-yl)carbamate (40.0 g, 0.17 mol) and vinyl acetate (144.6 g, 1.68 mol) in diisopropyl ether (2 L) was added Novozym 435 (4.0 g, 10% w/w). The resulting mixture was stirred at 35° C. for 16 h. The mixture was filtered and the filtrate was evaporated in vacuo. The residue was purified by Chromatography A to afford (R)-1-(2-((tert-butoxy-carbonyl)amino)pyridin-4-yl)ethyl acetate (23.0 g) and tert-butyl (S)-(4-(1-hydroxyethyl)pyridin-2-yl)carbamate (19.0 g, ee=98.8%).

(R)-1-(2-((tert-butoxycarbonyl)amino)pyridin-4-yl)ethyl acetate. MS (ESI) calculated for ($C_{14}H_{20}N_2O_4$) $[M+H]^+$, 281.1; found, 281.1. $^1H$ NMR (300 MHz, DMSO-$d_6$) δ 9.79 (s, 1H), 8.20 (dd, $J_1$=5.1 Hz, $J_2$=0.6 Hz, 1H), 7.77 (dt, $J_1$=1.5 Hz, $J_2$=0.6 Hz, 1H), 6.99 (dd, $J_1$=5.1 Hz, $J_2$=1.5 Hz, 1H), 5.78-5.65 (m, 1H), 2.08 (s, 3H), 1.53-1.40 (m, 12H).

tert-butyl (S)-(4-(1-hydroxyethyl)pyridin-2-yl)carbamate: MS (ESI) calculated for ($C_{12}H_{18}N_2O_3$) $[M+H]^+$, 239.1; found, 239.1. $^1H$ NMR (300 MHz, DMSO-$d_6$) δ 9.65 (s, 1H), 8.14 (dd, $J_1$=5.1 Hz, $J_2$=0.9 Hz, 1H), 7.82 (dt, J=1.5 Hz, 0.9 Hz, 1H), 6.97 (dd, $J_1$=5.4 Hz, $J_2$=1.5 Hz, 1H), 5.36 (d, J=4.3 Hz, 1H), 4.77-4.63 (m, 1H), 1.48 (s, 9H), 1.31 (d, J=6.6 Hz, 3H).

Step 7: tert-butyl (R)-(4-(1-hydroxyethyl)pyridin-2-yl) carbamate. To a solution of (R)-1-(2-((tert-butoxycarbonyl) amino)pyridin-4-yl)ethyl acetate (23 g, 82.1 mmol) in methanol (250 mL) was added potassium carbonate (22.6 g, 164 mmol) at 20° C. The mixture was stirred at room temperature for 1.5 h. The solid was filtered off, and the filtrate was evaporated in vacuo. The residue was purified by Chromatography A to afford the title compound (17.8 g, ee=100%, 91%). MS (ESI) calculated for ($C_{12}H_{18}N_2O_3$) $[M+H]^+$, 239.1; found, 239.1. $^1H$ NMR (300 MHz, DMSO-$d_6$) δ 9.66 (s, 1H), 8.14 (dd, $J_1$=5.1 Hz, $J_2$=0.9 Hz, 1H), 7.83 (dt, $J_1$=1.5 Hz, $J_2$=0.9 Hz, 1H), 6.97 (ddd, $J_1$=5.1 Hz, $J_2$=1.5 Hz, $J_3$=0.6 Hz, 1H), 5.36 (d, J=4.5 Hz, 1H), 4.76-4.61 (m, 1H), 1.48 (s, 9H), 1.31 (d, J=6.6 Hz, 3H).

Step 8: tert-butyl (S)-(4-(1-((4-methyl-4H-1,2,4-triazol-3-yl)thio)ethyl)pyridin-2-yl)carbamate. To a mixture of tert-butyl (R)-(4-(1-hydroxyethyl)pyridin-2-yl)carbamate (7.8 g, 32.78 mmol), 4-methyl-4H-1,2,4-triazole-3-thiol (4.52 g, 39.33 mmol) and triphenylphosphine (12.9 g, 49.16 mmol) in dry tetrahydrofuran (200 mL) was added diisopropyl azodicarboxylate (9.9 g, 49.16 mmol) at 0° C. under nitrogen. The mixture was stirred at room temperature for 16 h. General Workup Procedure followed by Chromatography B afforded the title compound (9.5 g, 86%). MS (ESI) calculated for ($C_{15}H_{21}N_5O_2S$) $[M+H]^+$, 336.1; found, 336.0. $^1H$ NMR (300 MHz, DMSO-$d_6$) δ 9.80 (s, 1H), 8.56 (s, 1H), 8.21-8.13 (m, 1H), 7.82-7.71 (m, 1H), 6.95 (dd, $J_1$=5.1 Hz, $J_2$=1.5 Hz, 1H), 4.66 (q, J=7.2 Hz, 1H), 3.45 (s, 3H), 1.63 (d, J=7.2 Hz, 3H), 1.49 (s, 9H).

Step 9: (S)-4-(1-((4-methyl-4H-1,2,4-triazol-3-yl)thio) ethyl)pyridin-2-amine HCl salt. A mixture of tert-butyl (S)-(4-(1-((4-methyl-4H-1,2,4-triazol-3-yl)thio)ethyl)pyridin-2-yl)carbamate (9.5 g, 28.35 mol) in hydrochloric acid/1,4-dioxane (4 M, 40 mL) was stirred at room temperature for 6 h and evaporated in vacuo to afford the title compound (5.3 g, crude), which was used without purification. MS (ESI) calculated for ($C_{10}H_{13}N_5S$) $[M+H]^+$, 236.1; found, 236.1. $^1H$ NMR (300 MHz, Methanol-$d_4$) δ 9.78 (s, 1H), 7.87 (dd, $J_1$=6.9 Hz, $J_2$=0.6 Hz, 1H), 7.18-7.04 (m, 2H), 5.02-4.92 (m, 1H), 3.87 (s, 3H), 1.82 (d, J=7.2 Hz, 3H).

Example 1: 3-(1-((4-methyl-4H-1,2,4-triazol-3-yl) thio)ethyl)-N-(6-(trifluoromethyl)pyridin-2-yl)benzamide

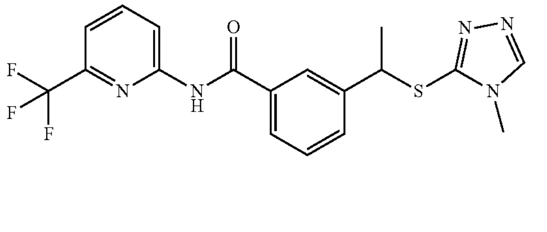 [SMILES: CC(Sc1nncn1C)c1cccc(C(=O)Nc2cccc(C(F)(F)F)n2)c1]

A mixture of 3-[1-[(4-methyl-1,2,4-triazol-3-yl)sulfanyl] ethyl]benzoic acid (0.0500 g, 0.190 mmol) and 6-(trifluoromethyl)pyridin-2-amine (0.0369 g, 0.228 mmol) was dissolved in EtOAc (0.94 mL) and treated with pyridine (0.0496 g, 0.627 mmol) and propylphosphonic anhydride (50% wt solution in EtOAc, 0.226 mL, 0.380 mmol). The reaction mixture was stirred at room temperature for 14 h and quenched with sat. sodium bicarbonate. General Workup Procedure followed by chromatography A afforded the title compound (0.0491 g, 63.0%). $^1H$ NMR (500 MHz, Chloroform-d) δ 8.64 (s, 1H), 8.59 (d, J=8.5 Hz, 1H), 8.08 (s, 1H), 7.98-7.91 (m, 2H), 7.80 (dt, J=7.4, 1.4 Hz, 1H), 7.50 (dt, J=7.7, 1.4 Hz, 1H), 7.47 (d, J=7.4 Hz, 1H), 7.43 (t, J=7.7 Hz, 1H), 4.93 (q, J=7.1 Hz, 1H), 3.36 (s, 3H), 1.85 (d, J=7.1 Hz, 3H). LCMS: $C_{18}H_{16}F_3N_5OS$ requires: 407, found: m/z=408 $[M+H]^+$.

Example 2: (S)-1-(3-(1-((4-methyl-4H-1,2,4-triazol-3-yl)thio)ethyl)phenyl)-3-(pyridin-2-yl)urea

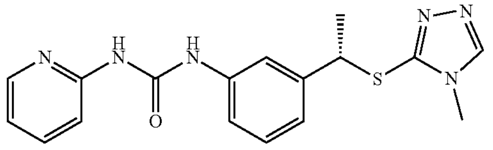 [SMILES: C[C@H](Sc1nncn1C)c1cccc(NC(=O)Nc2ccccn2)c1]

A mixture of 3-[(1S)-1-[(4-methyl-1,2,4-triazol-3-yl)sulfanyl]ethyl]aniline (0.0300 g, 0.128 mmol) and diisopropylethylamine (0.0267 mL, 0.154 mmol) in DCM (0.64 mL) was added to a solution of triphosgene (0.0141 g, 0.0474 mmol) in DCM (0.64 mL) dropwise at room temperature. After a further 5 min of stirring, a solution of 2-aminopyridine (0.0120 g, 0.128 mmol) in DCM (0.64 mL) with diisopropylethylamine (0.0267 mL, 0.154 mmol) was added in one portion at room temperature. The reaction mixture was stirred at room temperature for 72 h. Chromatography B gave the title compound. Yield: 0.0260 g (57.0%). $^1H$ NMR (500 MHz, DMSO-$d_6$) δ 10.49 (s, 1H), 9.43 (s, 1H), 8.55 (s, 1H), 8.30 (dd, J=5.1, 1.9 Hz, 1H), 7.76 (ddd, J=8.8, 7.3, 2.0 Hz, 1H), 7.51 (d, J=8.4 Hz, 1H), 7.48-7.39 (m, 2H), 7.25 (dd, J=8.9, 7.5 Hz, 1H), 7.03 (dd, J=7.2, 5.1 Hz, 1H), 6.95 (dt, J=7.4, 1.4 Hz, 1H), 4.66 (q, J=6.9 Hz, 1H), 3.37 (s, 3H), 1.66 (d, J=7.0 Hz, 3H). LCMS: $C_{17}H_{18}N_6OS$ requires: 354, found: m/z=355 $[M+H]^+$.

Example 3: (S)-1-(3-(1-((4-methyl-4H-1,2,4-triazol-3-yl)thio)ethyl)phenyl)-3-(6-(trifluoromethyl)pyridin-2-yl)urea

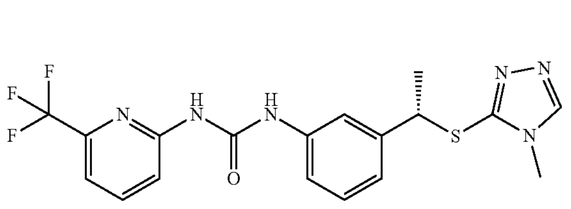 [SMILES: C[C@H](Sc1nncn1C)c1cccc(NC(=O)Nc2cccc(C(F)(F)F)n2)c1]

A solution of 6-(trifluoromethyl)pyridin-2-amine (0.0311 g, 0.192 mmol) and pyridine (0.0464 mL, 0.576 mmol) in dimethylacetamide (0.64 mL) was treated with phenyl chloroformate (0.0249 mL, 0.192 mmol) at 0° C. The reaction mixture was stirred at room temperature for 1 h and treated with 3-[(1S)-1-[(4-methyl-1,2,4-triazol-3-yl)sulfanyl]ethyl]

aniline (0.0300 g, 0.128 mmol). The reaction mixture was stirred at 90° C. for 15 h. Chromatography B followed by Chromatography C gave the title compound. Yield: 0.0086 g (15%). $^1$H NMR (500 MHz, DMSO-$d_6$) δ 10.49 (s, 1H), 9.43 (s, 1H), 8.55 (s, 1H), 8.30 (dd, J=5.1, 1.9 Hz, 1H), 7.76 (ddd, J=8.8, 7.3, 2.0 Hz, 1H), 7.51 (d, J=8.4 Hz, 1H), 7.48-7.39 (m, 1H), 7.25 (dd, J=8.9, 7.5 Hz, 1H), 7.03 (dd, J=7.2, 5.1 Hz, 1H), 6.95 (dt, J=7.4, 1.4 Hz, 1H), 4.66 (q, J=6.9 Hz, 1H), 3.37 (s, 3H), 1.66 (d, J=7.0 Hz, 3H). LCMS: $C_{18}H_{17}F_3N_6OS$ requires: 422, found: m/z=423 $[M+H]^+$.

Example 4: (S)-1-(6-methoxypyridin-2-yl)-3-(3-(1-((4-methyl-4H-1,2,4-triazol-3-yl)thio)ethyl)phenyl)urea

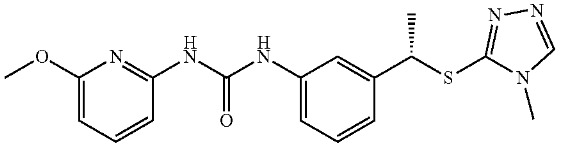 [SMILES: COc1cccc(NC(=O)Nc2cccc([C@H](C)Sc3nncn3C)c2)n1]

A mixture of 3-[(1S)-1-[(4-methyl-1,2,4-triazol-3-yl)sulfanyl]ethyl]aniline (0.0300 g, 0.128 mmol) and diisopropylethylamine (0.0267 mL, 0.154 mmol) in DCM (0.64 mL) was added to a solution of triphosgene (0.0141 g, 0.0474 mmol) in DCM (0.64 mL) dropwise at room temperature. After a further 5 min of stirring, a solution of 2-amino-6-methoxypyridine (0.0162 g, 0.128 mmol) in DCM (0.64 mL) with diisopropylethylamine (0.0267 mL, 0.154 mmol) was added in one portion at room temperature. The reaction mixture was stirred at room temperature for 72 h. Chromatography B gave the title compound. Yield: 0.0309 g (62.8%). $^1$H NMR (500 MHz, DMSO-$d_6$) δ 9.84 (s, 1H), 9.23 (s, 1H), 8.55 (s, 1H), 7.66 (t, J=8.0 Hz, 1H), 7.49-7.37 (m, 2H), 7.29-7.16 (m, 2H), 6.95 (dt, J=7.7, 1.3 Hz, 1H), 6.44 (d, J=8.0 Hz, 1H), 4.65 (q, J=6.9 Hz, 1H), 3.89 (s, 3H), 3.37 (s, 3H), 1.64 (d, J=6.9 Hz, 3H). LCMS: $C_{18}H_{20}N_6O_2S$ requires: 384, found: m/z=385 $[M+H]^+$.

Example 5: (S)-1-benzyl-3-(3-(1-((4-methyl-4H-1,2,4-triazol-3-yl)thio)ethyl)phenyl)urea

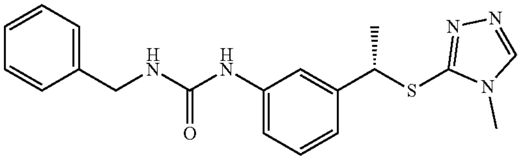 [SMILES: C[C@H](Sc1nncn1C)c1cccc(NC(=O)NCc2ccccc2)c1]

A solution of (S)-3-(1-(4-methyl-4H-1,2,4-triazol-3-ylthio)ethyl)aniline (30.0 mg, 0.128 mmol) in DCM (0.64 mL) was treated with benzyl isocyanate (27.3 mg, 0.205 mmol). The mixture was stirred overnight at room temperature. Chromatography B gave the title compound (26.6 mg, 56%). $^1$H NMR (500 MHz, DMSO-$d_6$) δ 8.60 (s, 1H), 8.55 (s, 1H), 7.39 (t, J=2.0 Hz, 1H), 7.36-7.28 (m, 5H), 7.29-7.21 (m, 1H), 7.16 (t, J=7.9 Hz, 1H), 6.85-6.79 (m, 1H), 6.61 (t, J=5.9 Hz, 1H), 4.60 (q, J=6.9 Hz, 1H), 4.30 (d, J=5.9 Hz, 2H), 3.37 (s, 3H), 1.62 (d, J=6.9 Hz, 3H). LCMS: $C_{19}H_{21}N_5OS$ requires: 367, found: m/z=368 $[M+H]^+$.

Example 6: (S)-1-(3-(1-((4-methyl-4H-1,2,4-triazol-3-yl)thio)ethyl)phenyl)-3-phenylurea

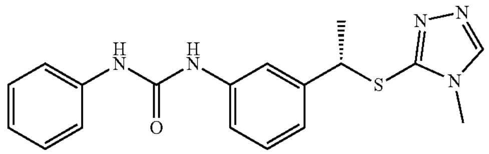 [SMILES: C[C@H](Sc1nncn1C)c1cccc(NC(=O)Nc2ccccc2)c1]

The procedure for Example 5 was followed using phenyl isocyanate to give the title compound (44.7 mg, 99%). $^1$H NMR (500 MHz, DMSO-$d_6$) δ 8.70 (s, 1H), 8.65 (s, 1H), 8.56 (s, 1H), 7.47-7.43 (m, 2H), 7.42 (t, J=2.0 Hz, 1H), 7.36 (dd, J=7.6, 2.1 Hz, 1H), 7.31-7.26 (m, 2H), 7.21 (t, J=7.8 Hz, 1H), 7.02-6.93 (m, 1H), 6.89 (dt, J=7.7, 1.2 Hz, 1H), 4.64 (q, J=6.9 Hz, 1H), 3.38 (s, 3H), 1.64 (d, J=6.9 Hz, 3H). LCMS: $C_{18}H_{19}N_5OS$ requires: 353, found: m/z=354 $[M+H]^+$.

Example 7: (S)—N-(3-(1-((4-methyl-4H-1,2,4-triazol-3-yl)thio)ethyl)phenyl)indoline-1-carboxamide

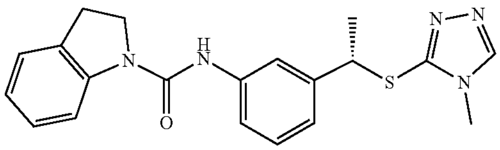 [SMILES: C[C@H](Sc1nncn1C)c1cccc(NC(=O)N2CCc3ccccc32)c1]

The procedure for Example 2 was followed using indoline to give the title compound (38.5 mg, 79%). $^1$H NMR (500 MHz, DMSO-$d_6$) δ 8.57 (s, 1H), 8.54 (s, 1H), 7.87 (d, J=7.7 Hz, 1H), 7.58 (t, J=2.0 Hz, 1H), 7.51 (ddd, J=8.1, 2.2, 1.0 Hz, 1H), 7.26-7.16 (m, 2H), 7.16-7.09 (m, 1H), 6.97-6.87 (m, 2H), 4.64 (q, J=6.9 Hz, 1H), 4.13 (t, J=8.6 Hz, 2H), 3.40 (s, 3H), 3.18 (t, J=8.6 Hz, 2H), 1.65 (d, J=6.9 Hz, 3H). LCMS: $C_{20}H_{21}N_5OS$ requires: 379, found: m/z=380 $[M+H]^+$.

Example 8: (S)—N-(3-(1-((4-methyl-4H-1,2,4-triazol-3-yl)thio)ethyl)phenyl)-3,4-dihydroquinoline-1(2H)-carboxamide

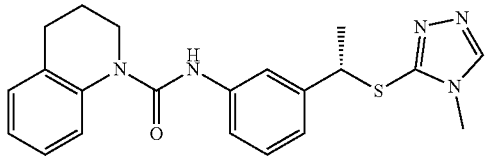 [SMILES: C[C@H](Sc1nncn1C)c1cccc(NC(=O)N2CCCc3ccccc32)c1]

The procedure for Example 2 was followed using 1,2,3,4-tetrahydroquinoline to give the title compound (39.7 mg, 79%). $^1$H NMR (500 MHz, DMSO-$d_6$) δ 8.87 (s, 1H), 8.56 (s, 1H), 7.48 (t, J=2.0 Hz, 1H), 7.41 (ddd, J=8.1, 2.2, 1.0 Hz, 1H), 7.34 (dd, J=8.2, 1.1 Hz, 1H), 7.19 (t, J=7.9 Hz, 1H), 7.17-7.10 (m, 2H), 6.98 (td, J=7.4, 1.2 Hz, 1H), 6.89 (dt, J=7.7, 1.3 Hz, 1H), 4.61 (q, J=6.9 Hz, 1H), 3.74-3.65 (m, 2H), 3.39 (s, 3H), 2.75 (t, J=6.6 Hz, 2H), 1.90 (p, J=6.6 Hz, 2H), 1.62 (d, J=6.9 Hz, 3H). LCMS: $C_{21}H_{23}N_5OS$ requires: 393, found: m/z=394 $[M+H]^+$.

Example 9: (R)—N-(3-(1-(4-methyl-4H-1,2,4-triazol-3-yl)propan-2-yl)phenyl)-3,4-dihydro-1,8-naphthyridine-1(2H)-carboxamide

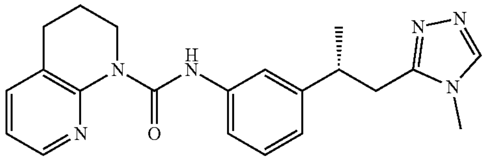

The procedure for Example 2 was followed using (R)-3-(1-(4-methyl-4H-1,2,4-triazol-3-yl)propan-2-yl)aniline and 1,2,3,4-tetrahydro-1,8-naphthyridine to give the title compound (63.1 mg, 73%). $^1$H NMR (500 MHz, DMSO-$d_6$) δ 13.16 (s, 1H), 9.11 (s, 1H), 8.29 (dd, J=4.9, 1.9 Hz, 1H), 7.68 (dd, J=7.4, 1.8 Hz, 1H), 7.49 (t, J=2.0 Hz, 1H), 7.46-7.42 (m, 1H), 7.25 (t, J=7.8 Hz, 1H), 7.08 (dd, J=7.4, 5.0 Hz, 1H), 6.95 (dt, J=7.7, 1.3 Hz, 1H), 4.00-3.86 (m, 2H), 3.65 (s, 3H), 3.29 (dd, J=14.3, 7.3 Hz, 1H), 3.23 (dd, J=7.4, 4.7 Hz, 2H), 2.85 (t, J=6.3 Hz, 2H), 1.90 (p, J=6.2 Hz, 2H), 1.33 (d, J=6.6 Hz, 3H). LCMS: $C_{21}H_{24}N_6O$ requires: 376, found: m/z=377 $[M+H]^+$.

Example 10: (R)—N-(3-(1-(4-methyl-4H-1,2,4-triazol-3-yl)propan-2-yl)phenyl)-2,3-dihydro-4H-pyrido[3,2-b][1,4]oxazine-4-carboxamide

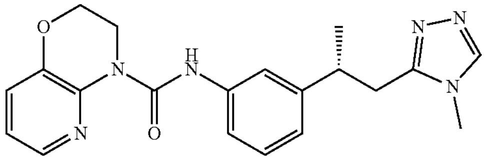

The procedure for Example 9 was followed using 3,4-dihydro-2H-pyrido[3,2-b][1,4]oxazine to give the title compound (33.8 mg, 64%). $^1$H NMR (500 MHz, DMSO-$d_6$) δ 12.71 (s, 1H), 8.97 (s, 1H), 8.06 (dd, J=4.8, 1.6 Hz, 1H), 7.49-7.44 (m, 2H), 7.43 (dd, J=8.0, 1.6 Hz, 1H), 7.26 (t, J=7.8 Hz, 1H), 7.12 (dd, J=8.0, 4.8 Hz, 1H), 6.97 (dt, J=7.7, 1.3 Hz, 1H), 4.29 (dd, J=5.2, 3.8 Hz, 2H), 4.06 (dd, J=5.4, 3.8 Hz, 2H), 3.62 (s, 3H), 3.28 (p, J=7.0 Hz, 1H), 3.26-3.13 (m, 2H), 1.33 (d, J=6.8 Hz, 3H). LCMS: $C_{20}H_{22}N_6O_2$ requires: 378, found: m/z=379 $[M+H]^+$.

Example 11: Methyl 1-((3-((R)-1-(4-methyl-4H-1,2,4-triazol-3-yl)propan-2-yl)phenyl)carbamoyl)-3-(trifluoromethyl)pyrrolidine-3-carboxylate

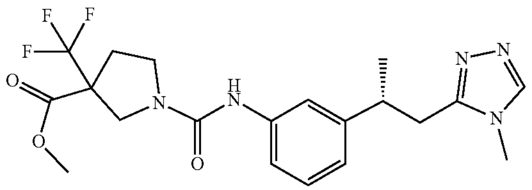 [SMILES: COC(=O)C1(C(F)(F)F)CCN(C(=O)Nc2cccc([C@H](C)Cc3nncn3C)c2)C1]

The procedure for Example 9 was followed using methyl 3-(trifluoromethyl)pyrrolidine-3-carboxylate hydrochloride to give the title compound (24.7 mg, 12%). $^1$H NMR (500 MHz, DMSO-$d_6$) δ 8.82 (s, 1H), 8.34 (s, 1H), 7.46-7.32 (m, 2H), 7.16 (t, J=7.9 Hz, 1H), 6.85 (dt, J=7.6, 1.3 Hz, 1H), 4.03 (d, J=11.7 Hz, 1H), 3.81 (s, 4H), 3.60 (d, J=8.7 Hz, 1H), 3.55 (d, J=2.3 Hz, 3H), 3.51 (d, J=8.4 Hz, 1H), 3.20 (p, J=7.0 Hz, 1H), 3.09 (m, 2H), 2.62-2.56 (m, 1H), 2.45-2.36 (m, 1H), 1.28 (d, J=6.8 Hz, 3H). LCMS: $C_{20}H_{24}F_3N_5O_3$ requires: 439, found: m/z=440 $[M+H]^+$.

Example 12: $N^3$,3-dimethyl-N'-(3-((R)-1-(4-methyl-4H-1,2,4-triazol-3-yl)propan-2-yl)phenyl)pyrrolidine-1,3-dicarboxamide

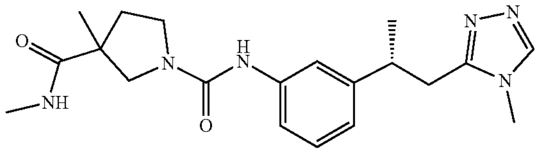 [SMILES: CNC(=O)C1(C)CCN(C(=O)Nc2cccc([C@H](C)Cc3nncn3C)c2)C1]

The procedure for Example 9 was followed using N,3-dimethylpyrrolidine-3-carboxamide to give the title compound (2.1 mg, 4%). $^1$H NMR (500 MHz, DMSO-$d_6$) δ 8.28 (s, 1H), 8.07 (s, 1H), 7.75 (d, J=4.9 Hz, 1H), 7.46-7.34 (m, 2H), 7.11 (t, J=7.8 Hz, 1H), 6.79 (dt, J=7.5, 1.3 Hz, 1H), 3.74 (d, J=10.3 Hz, 1H), 3.41 (s, 3H), 3.21 (dd, J=10.4, 1.6 Hz, 1H), 3.15 (q, J=7.1 Hz, 1H), 3.11-3.03 (m, 2H), 2.92 (d, J=7.4 Hz, 2H), 2.61 (d, J=4.5 Hz, 3H), 2.23 (dt, J=12.5, 7.5 Hz, 1H), 1.77 (ddd, J=12.7, 7.4, 5.8 Hz, 1H), 1.26-1.17 (m, 6H). LCMS: $C_{20}H_{28}N_6O_2$ requires: 384, found: m/z=385 $[M+H]^+$.

Example 13: (R)-4-methyl-N-(3-(1-(4-methyl-4H-1,2,4-triazol-3-yl)propan-2-yl)phenyl)isoindoline-2-carboxamide

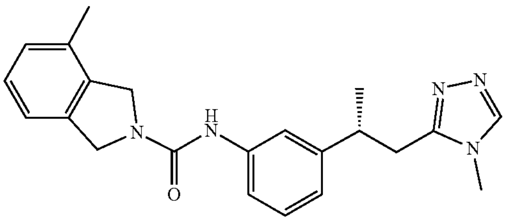 [SMILES: Cc1cccc2c1CN(C(=O)Nc1cccc([C@H](C)Cc3nncn3C)c1)C2]

The procedure for Example 9 was followed using 4-methylisoindoline to give the title compound (27.6 mg, 64%). $^1$H NMR (500 MHz, DMSO-$d_6$) δ 8.58 (s, 1H), 8.33 (s, 1H), 7.53-7.39 (m, 2H), 7.23 (t, J=7.5 Hz, 1H), 7.20-7.15 (m, 2H), 7.12 (d, J=7.4 Hz, 1H), 6.85 (dt, J=7.6, 1.3 Hz, 1H), 4.77 (s, 2H), 4.72 (s, 2H), 3.50 (s, 3H), 3.20 (p, J=7.1 Hz, 1H), 3.04 (dd, J=7.5, 1.5 Hz, 2H), 2.28 (s, 3H), 1.29 (d, J=6.9 Hz, 3H). LCMS: $C_{22}H_{25}N_5O$ requires: 375, found: m/z=376 $[M+H]^+$.

Example 14: 4-[(2R)-1-(4-methyl-4H-1,2,4-triazol-3-yl)propan-2-yl]-N-[6-(trifluoromethyl)pyridin-2-yl]pyridine-2-carboxamide

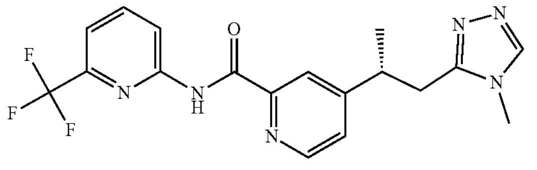 [SMILES: C[C@H](Cc1nncn1C)c1ccnc(C(=O)Nc2cccc(C(F)(F)F)n2)c1]

Step 1: N,2-dimethoxy-N-methylisonicotinamide. To a solution of 2-methoxyisonicotinic acid (50.0 g, 326.0 mmol) in N,N-dimethylformamide (1000 mL) was added N,O-dimethylhydroxylamine hydrochloride (63.8 g, 654.0 mmol), N,N-diisopropylethylamine (211.0 g, 1630 mmol), and HATU (248.0 g, 653.0 mmol). The resulting mixture was stirred at room temperature for 2 h. General Workup Procedure followed by Chromatography A afforded the title compound (58.3 g, 91%). MS (ESI) calculated for ($C_9H_{12}N_2O_3$) $[M+H]^+$, 197.1; found, 197.2.

Step 2: 1-(2-methoxypyridin-4-yl)ethanone. To a solution of N,2-dimethoxy-N-methylisonicotinamide (120.0 g, 612.0 mmol) in tetrahydrofuran (2000 mL) was added methylmagnesium bromide (109.0 g, 918.0 mmol) at 0° C. under $N_2$. The resulting mixture was stirred at 0° C. for 3 h. The reaction mixture was quenched by the addition of saturated aqueous ammonium chloride solution at 0° C. General Workup Procedure followed by Chromatography A afforded the title compound (74.5 g, 81%). MS (ESI) calculated for ($C_8H_9NO_2$) $[M+H]^+$, 152.1; found, 152.1. $^1H$ NMR (300 MHz, DMSO-$d_6$) δ 8.38-8.36 (m, 1H), 7.40-7.38 (m, 1H), 7.27-7.25 (m, 1H), 3.92 (s, 3H), 2.61 (s, 3H).

Step 3: (E)-ethyl 3-(2-methoxypyridin-4-yl)but-2-enoate. To a solution of ethyl 2-(diethoxyphosphoryl)acetate (131.0 g, 582.0 mmol) in tetrahydrofuran (2000 mL) was added potassium tert-butoxide (65.2 g, 582.0 mmol) at 0° C. under $N_2$. The reaction mixture was stirred at 0° C. for 30 min. Then 1-(2-methoxypyridin-4-yl)ethanone (22.0 g, 145.0 mmol) was added slowly to the above mixture at 0° C. The resulting mixture was stirred at room temperature for 16 h. General Workup Procedure followed by Chromatography A afforded the title compound (39.0 g). MS (ESI) calculated for ($C_{12}H_{15}NO_3$) $[M+H]^+$, 222.1; found, 222.0.

Step 4: ethyl 3-(2-methoxypyridin-4-yl)butanoate. To a solution of (E)-ethyl 3-(2-methoxypyridin-4-yl)but-2-enoate (55.0 g, 248.0 mmol) in methanol (1000 mL) was added Pd/C (5.5 g, dry) at room temperature under nitrogen. The resulting mixture was stirred at room temperature for 12 h under $H_2$. The resulting mixture was filtered and the filtrate was evaporated in vacuo to afford the title compound (56.0 g, crude), which was used without purification. MS (ESI) calculated for ($C_{12}H_{17}NO_3$) $[M+H]^+$, 224.1; found, 223.9.

Step 5: 3-(2-methoxypyridin-4-yl)butanehydrazide. To a solution of ethyl 3-(2-methoxypyridin-4-yl)butanoate (50.0 g, 224.0 mmol) in ethanol (500 mL) was added hydrazine hydrate (140 g, 80%). The resulting mixture was stirred at 95° C. for 48 h. The solvent was evaporated in vacuo to afford the title compound (42.0 g, crude), which was used without purification. MS (ESI) calculated for ($C_{10}H_{15}N_3O_2$) $[M+H]^+$, 210.1; found, 210.2.

Step 6: (E)-N'-(3-(2-methoxypyridin-4-yl)butanoyl)-N,N-dimethylformohydrazonamide. To a solution of 3-(2-methoxypyridin-4-yl)butanehydrazide (20.0 g, 95.50 mmol) in dichloromethane (500 mL) was added N,N-dimethylformamide dimethyl acetal (34.2 g, 287.0 mmol). The resulting mixture was stirred at 55° C. for 2 h. The resulting mixture was evaporated in vacuo. The residue was purified by Chromatography B to afford the title compound (19.0 g, 75%). MS (ESI) calculated for ($C_{13}H_{20}N_4O_2$) $[M+H]^+$, 265.2; found, 265.0.

Step 7: 2-methoxy-4-(1-(4-methyl-4H-1,2,4-triazol-3-yl)propan-2-yl)pyridine. To a solution of (E)-N-(3-(2-methoxypyridin-4-yl)butanoyl)-N,N-dimethylformohydrazonamide (7.0 g, 26.50 mmol) in acetic acid (133 mL) was added methylamine in tetrahydrofuran (133 mL, 2 mol/L). The resulting mixture was stirred at 90° C. for 3 h. The reaction mixture was evaporated in vacuo. The residue was alkalized with aqueous sodium bicarbonate to pH 8-9. General Workup Procedure followed by flash column chromatography with 0-5% methanol in EtOAc afforded the title compound (2.9 g, 47%). MS (ESI) calculated for ($C_{12}H_{16}N_4O$) $[M+H]^+$, 233.1; found, 233.0. $^1H$ NMR (300 MHz, DMSO-$d_6$) δ 8.31 (s, 1H), 8.07-8.05 (m, 1H), 6.93-6.92 (m, 1H), 6.73-6.72 (m, 1H), 3.82 (s, 3H), 3.52 (s, 3H), 3.32-3.14 (m, 1H), 3.04-2.92 (m, 2H), 1.28 (d, J=6.8 Hz, 3H).

Step 8: 4-(1-(4-methyl-4H-1,2,4-triazol-3-yl)propan-2-yl)pyridin-2-ol. To a solution of 2-methoxy-4-(1-(4-methyl-4H-1,2,4-triazol-3-yl)propan-2-yl)pyridine (10.0 g, 43.10 mmol) in acetic acid (170 mL) was added hydrogen bromide (170 mL, 40%) at room temperature. The resulting mixture was stirred at 90° C. for 12 h. The mixture was evaporated in vacuo and the residue was alkalized with aqueous ammonium hydroxide to pH 8-9. General Workup Procedure afforded the title compound (15.0 g, crude), which was used without purification. MS (ESI) calculated for ($C_{11}H_{14}N_4O$) $[M+H]^+$, 219.1; found, 218.9.

Step 9: 2-chloro-4-(1-(4-methyl-4H-1,2,4-triazol-3-yl)propan-2-yl)pyridine. To a solution of 4-(1-(4-methyl-4H-1,2,4-triazol-3-yl)propan-2-yl)pyridin-2-ol (30 g, crude) in acetonitrile (300 mL) was added phosphoryl trichloride (300 mL) at room temperature. The resulting mixture was stirred at 90° C. for 5 h. The solvent was evaporated under reduced pressure and the residue was alkalized with aqueous sodium bicarbonate to pH 7-8, and then extracted with dichloromethane. The combined organic layer was washed with brine, dried over sodium sulfate, and filtered. The filtrate was evaporated in vacuo. Purification by chromatography afforded the title compound (13.0 g, 40%). MS (ESI) calculated for ($C_{11}H_{13}ClN_4$) $[M+1]^+$, 237.1; found, 237.3.

Step 10: (S)-2-chloro-4-(1-(4-methyl-4H-1,2,4-triazol-3-yl)propan-2-yl)pyridine and (R)-2-chloro-4-(1-(4-methyl-4H-1,2,4-triazol-3-yl)propan-2-yl)pyridine. The racemic 2-chloro-4-(1-(4-methyl-4H-1,2,4-triazol-3-yl)propan-2-yl)pyridine (12.5 g) was separated by Prep-Chiral-SFC with the following conditions: [Column: Lux 5u Cellulose-4, AXIA Packed; Mobile Phase A: $CO_2$ 65%, Mobile Phase B: MeOH 35%] to afford (S)-2-chloro-4-(1-(4-methyl-4H-1,2,4-triazol-3-yl)propan-2-yl)pyridine (4.8 g, 76%) and (R)-2-chloro-4-(1-(4-methyl-4H-1,2,4-triazol-3-yl)propan-2-yl)pyridine as a yellow solid.

(S)-2-chloro-4-(1-(4-methyl-4H-1,2,4-triazol-3-yl)propan-2-yl)pyridine: MS (ESI) calculated for ($C_{11}H_{13}ClN_4$) $[M+1]^+$, 237.1; found, 236.9. $^1H$ NMR (400 MHz, DMSO-$d_6$) δ 8.31-8.29 (m, 2H), 7.48 (s, 1H), 7.37-7.35 (m, 1H), 3.54 (s, 3H), 3.36-3.31 (m, 1H), 3.09-3.02 (m, 2H), 1.27 (d, J=6.8 Hz, 3H).

(R)-2-chloro-4-(1-(4-methyl-4H-1,2,4-triazol-3-yl)propan-2-yl)pyridine: MS (ESI) calculated for ($C_{11}H_{13}ClN_4$) $[M+1]^+$, 237.1; found, 236.9. $^1H$ NMR (400 MHz, DMSO- $d_6$) δ 8.31-8.29 (m, 2H), 7.48 (s, 1H), 7.37-7.35 (m, 1H), 3.54 (s, 3H), 3.36-3.30 (m, 1H), 3.05-3.02 (m, 2H), 1.27 (d, J=6.8 Hz, 3H).

Step 11: Methyl (R)-4-(1-(4-methyl-4H-1,2,4-triazol-3-yl)propan-2-yl)picolinate. To a solution of (R)-2-chloro-4-(1-(4-methyl-4H-1,2,4-triazol-3-yl)propan-2-yl)pyridine (1.0 g, 4.22 mmol) in methanol (15 mL) was added TEA (1.08 g, 10.67 mmol), Pd(dppf)$Cl_2$ (260 mg, 0.36 mmol) under nitrogen. The mixture was stirred at 120° C. for 16 h under CO (40 atm). After the reaction was completed, the solids were filtered out and the organic phase was concentrated under vacuum. The residue was purified by Chromatography B to afford the title compound (400 mg, 36%). MS (ESI) calculated for ($C_{13}H_{16}N_4O_2$) $[M+1]^+$, 261.1; found, 260.9.

Step 12: 4-[(2R)-1-(4-methyl-4H-1,2,4-triazol-3-yl)propan-2-yl]-N-[6-(trifluoromethyl)pyridin-2-yl]pyridine-2-carboxamide. To a solution of 6-(trifluoromethyl)pyridin-2-amine (155.6 mg, 0.96 mmol) in tetrahydrofuran (2 mL) was added $AlMe_3$ (2 M in hexane, 1.5 mL). The mixture was stirred at room temperature for 15 min. Then a solution of methyl (R)-4-(1-(4-methyl-4H-1,2,4-triazol-3-yl)propan-2-yl)picolinate (250 mg, 0.96 mmol) in tetrahydrofuran (1 mL) was added to the above mixture. The resulting mixture was stirred at 60° C. for 16 h under nitrogen. After the reaction was completed, the reaction mixture was quenched by saturated $NH_4Cl$ aqueous solution. General Workup Procedure followed by Chromatography B afforded the title compound (62.7 mg, 17%). MS (ESI) calculated for ($C_{18}H_{17}F_3N_6O$) $[M+1]^+$, 391.1; found, 390.9. $^1$H NMR (300 MHz, DMSO-$d_6$) δ 10.65 (s, 1H), 8.67 (d, J=5.1 Hz, 1H), 8.55 (d, J=8.4 Hz, 1H), 8.31 (s, 1H), 8.28-8.14 (m, 2H), 7.76-7.66 (m, 2H), 3.56-3.43 (m, 1H), 3.34 (s, 3H), 3.20-3.05 (m, 2H), 1.36 (d, J=6.9 Hz, 3H).

Example 15: 1-((3-((R)-1-(4-methyl-4H-1,2,4-triazol-3-yl)propan-2-yl)phenyl)carbamoyl)-3-(trifluoromethyl)pyrrolidine-3-carboxylic acid

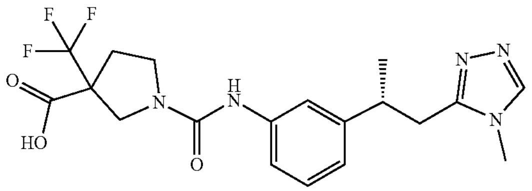 [SMILES: C[C@H](Cc1nncn1C)c1cccc(NC(=O)N2CCC(C(=O)O)(C(F)(F)F)C2)c1]

The procedure of Example A, Step 2 was followed using methyl 1-((3-((R)-1-(4-methyl-4H-1,2,4-triazol-3-yl)propan-2-yl)phenyl)carbamoyl)-3-(trifluoromethyl)pyrrolidine-3-carboxylate to give the crude title compound. $^1$H NMR (500 MHz, DMSO-$d_6$) δ 14.09 (s, 1H), 8.88 (s, 1H), 8.32 (s, 1H), 7.41 (t, J=1.9 Hz, 1H), 7.35 (ddd, J=8.1, 2.2, 1.0 Hz, 1H), 7.16 (t, J=7.8 Hz, 1H), 6.85 (dd, J=7.7, 1.4 Hz, 1H), 4.01 (d, J=11.4 Hz, 1H), 3.75 (dd, J=11.5, 1.7 Hz, 1H), 3.57 (s, 3H), 3.49 (q, J=8.5 Hz, 1H), 3.20 (p, J=7.0 Hz, 1H), 3.17-3.04 (m, 2H), 2.52-2.48 (m, 2H), 2.33 (dd, J=13.2, 7.8 Hz, 1H), 1.28 (d, J=6.8 Hz, 3H). LCMS: $C_{19}H_{22}F_3N_5O_3$ requires: 425, found: m/z=424 $[M-H]^+$.

Example 16: (R)—N-(3-(1-(4-methyl-4H-1,2,4-triazol-3-yl)propan-2-yl)phenyl)-2,3-dihydro-1H-pyrrolo[2,3-b]pyridine-1-carboxamide

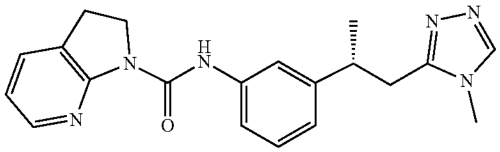 [SMILES: C[C@H](Cc1nncn1C)c1cccc(NC(=O)N2CCc3cccnc32)c1]

The procedure of Example 9 was followed using 2,3-dihydro-1H-pyrrolo[2,3-b]pyridine to give the title compound (22.5 mg, 45%). $^1$H NMR (500 MHz, DMSO-$d_6$) δ 11.41 (s, 1H), 9.20 (s, 1H), 8.13 (dd, J=5.4, 1.5 Hz, 1H), 7.68 (dq, J=7.4, 1.5 Hz, 1H), 7.52-7.38 (m, 2H), 7.27 (t, J=7.7 Hz, 1H), 7.02-6.91 (m, 2H), 4.04 (dd, J=9.2, 8.0 Hz, 2H), 3.68 (s, 3H), 3.37-3.20 (m, 3H), 3.19-3.04 (m, 2H), 1.33 (d, J=6.4 Hz, 3H). LCMS: $C_{20}H_{22}N_6O$ requires: 362, found: m/z=363 $[M+H]^+$.

Example 17: (3R*,4R*)-3-(hydroxymethyl)-4-methyl-N-(3-((R)-1-(4-methyl-4H-1,2,4-triazol-3-yl)propan-2-yl)phenyl)pyrrolidine-1-carboxamide

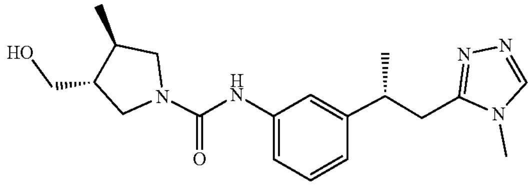 [SMILES: C[C@H](Cc1nncn1C)c1cccc(NC(=O)N2C[C@H](CO)[C@@H](C)C2)c1]

The procedure of Example 9 was followed using (trans-4-methylpyrrolidin-3-yl)methanol to give the title compound (27.2 mg, 55%). $^1$H NMR (500 MHz, DMSO-$d_6$) δ 8.99 (s, 1H), 8.06 (s, 1H), 7.42 (dt, J=8.7, 2.0 Hz, 1H), 7.36 (dd, J=8.3, 2.1 Hz, 1H), 7.14 (td, J=7.8, 5.4 Hz, 1H), 6.82 (t, J=7.9 Hz, 1H), 3.64 (ddd, J=9.9, 7.4, 2.2 Hz, 1H), 3.61-3.57 (m, 1H), 3.59 (s, 3H), 3.55 (dt, J=10.7, 4.1 Hz, 1H), 3.37 (dd, J=10.8, 7.0 Hz, 1H), 3.25-3.07 (m, 4H), 2.93 (ddd, J=10.3, 8.5, 1.8 Hz, 1H), 2.00 (p, J=7.8 Hz, 1H), 1.89 (dp, J=13.3, 4.6 Hz, 1H), 1.29 (d, J=6.6 Hz, 3H), 1.02 (d, J=6.5 Hz, 3H). LCMS: $C_{19}H_{27}N_5O_2$ requires: 357, found: m/z=358 $[M+H]^+$.

Example 18: (R)-3-(1-(4-methyl-4H-1,2,4-triazol-3-yl)propan-2-yl)-N-(6-(trifluoromethyl)pyridin-2-yl)benzamide

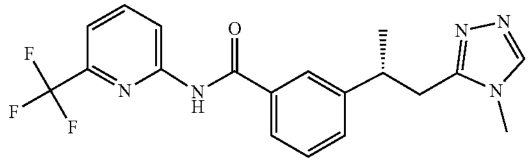 [SMILES: C[C@H](Cc1nncn1C)c1cccc(C(=O)Nc2cccc(C(F)(F)F)n2)c1]

Step 1: (R)-methyl 3-(1-(4-methyl-4H-1,2,4-triazol-3-yl)propan-2-yl)benzoate. To a solution of 3-[(2R)-2-(3-bromophenyl)propyl]-4-methyl-4H-1,2,4-triazole (2.0 g, 7.14 mmol) in methanol (30 mL) was added TEA (2.2 g, 21.74 mmol) and Pd(dppf)$Cl_2$ (522.4 mg, 0.71 mmol). The reaction mixture was stirred at 120° C. for 16 h under CO (40 atm). After the reaction was completed, the reaction mixture was cooled to room temperature and then concentrated under vacuum. The residue was purified by Chromatography B to afford the title compound (1.2 g, 64%). MS (ESI) calculated for ($C_{14}H_{17}N_3O_2$) $[M+1]^+$, 260.1; found, 259.9.

Step 2: 3-[(2R)-1-(4-methyl-4H-1,2,4-triazol-3-yl)propan-2-yl]benzoic acid. To a solution of (R)-methyl 3-(1-(4-methyl-4H-1,2,4-triazol-3-yl)propan-2-yl)benzoate (2.5 g, 9.64 mmol) in THF/$H_2O$ (25/3 mL) was added lithium hydroxide (350 mg, 14.61 mmol). The mixture was stirred at room temperature for 2 h. After the reaction was completed, the mixture was concentrated under vacuum. The pH value of the solution was adjusted to 6-7 with hydrogen chloride (1 N). The residue was purified by Chromatography B to afford 3-[(2R)-1-(4-methyl-4H-1,2,4-triazol-3-yl)propan-2-yl]benzoic acid (1.7 g, 72%). MS (ESI) calculated for ($C_{13}H_{15}N_3O_2$) $[M+1]^+$, 246.1; found, 245.9. $^1H$ NMR (300 MHz, DMSO-$d_6$) δ 12.95 (s, 1H), 8.28 (s, 1H), 7.83-7.77 (m, 2H), 7.52 (d, J=7.8 Hz, 1H), 7.43-7.39 (m, 1H), 3.44 (s, 3H), 3.40-3.28 (m, 1H), 2.99 (d, J=7.5 Hz, 2H), 1.29 (d, J=6.9 Hz, 3H).

Step 3: 3-[(2R)-1-(4-methyl-4H-1,2,4-triazol-3-yl)propan-2-yl]benzamide. To a solution of 3-[(2R)-1-(4-methyl-4H-1,2,4-triazol-3-yl)propan-2-yl]benzoic acid (140.0 mg, 0.57 mmol) in N,N-dimethylformamide (2 mL) were added DIPEA (735.3 mg, 5.69 mmol), $NH_4Cl$ (91.6 mg, 1.71 mmol), and HATU (433.5 mg, 1.14 mmol). The resulting mixture was stirred at room temperature for 1 h. General Workup Procedure followed by Chromatography B afforded the title compound (110 mg, 79%). MS (ESI) calculated for ($C_{13}H_{16}N_4O$) $[M+1]^+$, 245.1; found, 244.9.

Step 4: 3-[(2R)-1-(4-methyl-4H-1,2,4-triazol-3-yl)propan-2-yl]-N-[6-(trifluoromethyl)pyridin-2-yl]benzamide. To a solution of 3-[(2R)-1-(4-methyl-4H-1,2,4-triazol-3-yl)propan-2-yl]benzamide (200.0 mg, 0.82 mmol) in 1,4-dioxane (3 mL) were added 2-bromo-6-(trifluoromethyl)pyridine (185.0 mg, 0.82 mmol), $Cs_2CO_3$ (534.0 mg, 1.64 mmol), X-phos (95.0 mg, 0.20 mmol), and Pd(dppf)$Cl_2$ (47.2 mg, 0.06 mmol). The resulting mixture was stirred at 100° C. for 16 h. After the reaction was completed, the mixture was cooled to room temperature and then filtered. The filtrate was concentrated under vacuum. The residue was purified by Chromatography B and Chromatography C to afford the title compound (52.9 mg, 16%). MS (ESI) calculated for ($C_{19}H_{18}F_3N_5O$) $[M+1]^+$, 390.1; found, 389.9. $^1H$ NMR (300 MHz, DMSO-$d_6$) δ 11.20 (s, 1H), 8.47 (d, J=8.4 Hz, 1H), 8.32 (s, 1H), 8.11 (t, J=8.4 Hz, 1H), 8.03 (s, 1H), 7.87 (d, J=7.5 Hz, 1H), 7.66 (d, J=7.5 Hz, 1H), 7.46-7.40 (m, 2H), 3.48 (s, 3H), 3.40-3.33 (m, 1H), 3.06 (d, J=7.2 Hz, 2H), 1.33 (d, J=6.9 Hz, 3H).

Example 19: (R)-2,2-dimethyl-N-(3-(1-(4-methyl-4H-1,2,4-triazol-3-yl)propan-2-yl)phenyl)-2,3-dihydro-4H-pyrido[3,2-b][1,4]oxazine-4-carboxamide

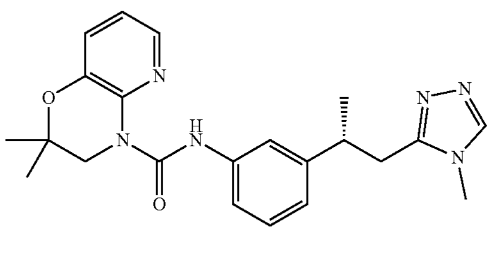 [SMILES: C[C@H](Cc1nncn1C)c1cccc(NC(=O)N2CC(C)(C)Oc3cccnc32)c1]

The procedure of Example 9 was followed using 2,2-dimethyl-2H,3H,4H-pyrido[3,2-b][1,4]oxazine to give the title compound (4.8 mg, 8.5%). $^1H$ NMR (500 MHz, DMSO-$d_6$) δ 12.60 (s, 1H), 9.03 (s, 1H), 8.07 (dd, J=4.8, 1.6 Hz, 1H), 7.50-7.45 (m, 2H), 7.40 (dd, J=8.0, 1.5 Hz, 1H), 7.27 (t, J=7.8 Hz, 1H), 7.14 (dd, J=8.0, 4.8 Hz, 1H), 6.98 (dt, J=7.7, 1.3 Hz, 1H), 3.89 (s, 2H), 3.64 (s, 3H), 3.30 (h, J=6.7 Hz, 1H), 3.26-3.14 (m, 2H), 1.33 (d, J=6.0 Hz, 9H). LCMS: $C_{22}H_{26}N_6O_2$ requires: 406, found: m/z=407 $[M+H]^+$.

Example 20: $N^3$-methyl-$N^1$-(3-((R)-1-(4-methyl-4H-1,2,4-triazol-3-yl)propan-2-yl)phenyl)-3-(trifluoromethyl)pyrrolidine-1,3-dicarboxamide

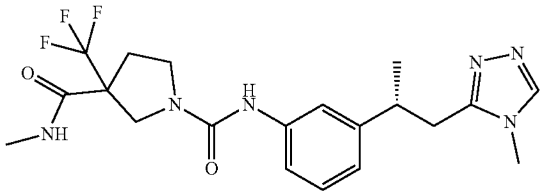 [SMILES: CNC(=O)C1(C(F)(F)F)CCN(C(=O)Nc2cccc([C@H](C)Cc3nncn3C)c2)C1]

The procedure of Example 9 was followed using N-methyl-3-(trifluoromethyl)pyrrolidine-3-carboxamide hydrochloride to give the title compound (12.2 mg, 20%). $^1H$ NMR (500 MHz, DMSO-$d_6$) δ 8.81 (s, 1H), 8.29 (d, J=15.1 Hz, 2H), 7.42-7.32 (m, 2H), 7.15 (t, J=7.9 Hz, 1H), 6.84 (dt, J=7.5, 1.3 Hz, 1H), 4.09 (d, J=11.4 Hz, 1H), 3.70 (dd, J=11.5, 1.4 Hz, 1H), 3.59-3.50 (m, 1H), 3.55 (s, 3H), 3.40 (q, J=8.3 Hz, 1H), 3.20 (h, J=7.0 Hz, 1H), 3.15-3.02 (m, 2H), 2.68 (d, J=4.4 Hz, 3H), 2.63-2.54 (m, 1H), 2.38-2.30 (m, 1H), 1.28 (d, J=6.9 Hz, 3H). LCMS: $C_{20}H_{25}F_3N_6O_2$ requires: 438, found: m/z=439 $[M+H]^+$.

Example 21: (R)-7-bromo-N-(3-(1-(4-methyl-4H-1,2,4-triazol-3-yl)propan-2-yl)phenyl)-2,3-dihydro-4H-pyrido[3,2-b][1,4]oxazine-4-carboxamide

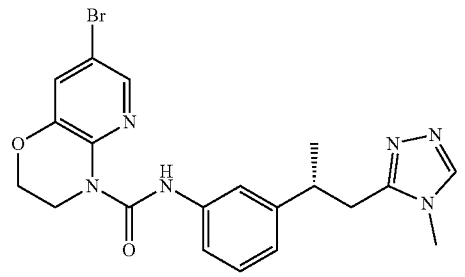 [SMILES: C[C@H](Cc1nncn1C)c1cccc(NC(=O)N2CCOc3cc(Br)cnc32)c1]

The procedure of Example 9 was followed using 7-bromo-3,4-dihydro-2H-pyrido[3,2-b]-1,4-oxazine to give the title compound (207 mg, 20%). $^1H$ NMR (500 MHz, DMSO-$d_6$) δ 12.21 (s, 1H), 8.28 (s, 1H), 8.22 (d, J=2.1 Hz, 1H), 7.72 (d, J=2.1 Hz, 1H), 7.49 (ddd, J=8.1, 2.2, 1.0 Hz, 1H), 7.43 (t, J=1.9 Hz, 1H), 7.25 (t, J=7.8 Hz, 1H), 6.96 (dt, J=7.7, 1.3 Hz, 1H), 4.32 (dd, J=5.2, 3.9 Hz, 2H), 4.06 (dd, J=5.6, 3.8 Hz, 2H), 3.43 (s, 3H), 3.24 (h, J=7.0 Hz, 1H), 3.04-2.92 (m, 2H), 1.29 (d, J=6.9 Hz, 3H). LCMS: $C_{20}H_{21}BrN_6O_2$ requires: 456, found: m/z=457 $[M+H]^+$.

Example 22: (R)-3,3-dimethyl-N-(3-(1-(4-methyl-4H-1,2,4-triazol-3-yl)propan-2-yl)phenyl)-2,3-dihydro-1H-pyrrolo[2,3-b]pyridine-1-carboxamide

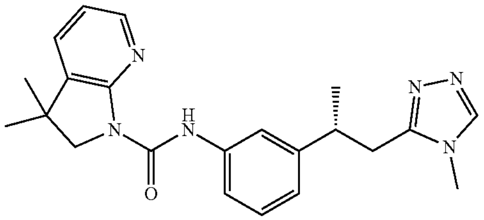 [SMILES: C[C@H](Cc1nncn1C)c1cccc(NC(=O)N2CC(C)(C)c3cccnc32)c1]

The procedure of Example 9 was followed using 3,3-dimethyl-1H,2H,3H-pyrrolo[2,3-b]pyridine to give the title compound (62.5 mg, 35%). $^1$H NMR (500 MHz, DMSO-$d_6$) δ 11.31 (s, 1H), 8.20 (s, 1H), 8.11 (dd, J=5.2, 1.6 Hz, 1H), 7.67 (dd, J=7.3, 1.6 Hz, 1H), 7.41-7.32 (m, 2H), 7.17 (t, J=7.8 Hz, 1H), 6.96 (dd, J=7.3, 5.2 Hz, 1H), 6.87 (dt, J=7.7, 1.3 Hz, 1H), 3.73 (s, 2H), 3.36 (s, 3H), 3.18 (p, J=7.1 Hz, 1H), 2.90 (d, J=7.4 Hz, 2H), 1.27 (s, 6H), 1.21 (d, J=7.0 Hz, 3H). LCMS: $C_{22}H_{26}N_6O$ requires: 390, found: m/z=391 [M+H]$^+$.

Example 23: N-(3-(3-((4-methyl-4H-1,2,4-triazol-3-yl)methyl)oxetan-3-yl)phenyl)-2,3-dihydro-4H-pyrido[3,2-b][1,4]oxazine-4-carboxamide

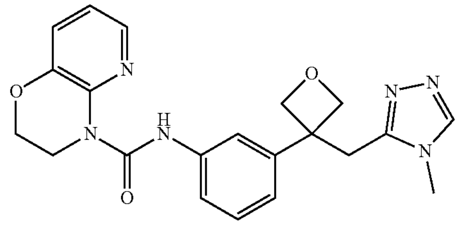 [SMILES: Cn1cnnc1CC1(c2cccc(NC(=O)N3CCOc4cccnc43)c2)COC1]

The procedure of Example 3 was followed using 3-{3-[(4-methyl-4H-1,2,4-triazol-3-yl)methyl]oxetan-3-yl}aniline and 2H,3H,4H-pyrido[3,2-b][1,4]oxazine to give the title compound (12.8 mg, 4.3%). $^1$H NMR (500 MHz, DMSO-$d_6$) δ 12.70 (s, 1H), 8.66 (s, 1H), 8.06 (dd, J=4.8, 1.6 Hz, 1H), 7.51-7.38 (m, 2H), 7.27 (t, J=7.9 Hz, 1H), 7.17 (t, J=2.0 Hz, 1H), 7.12 (dd, J=8.0, 4.9 Hz, 1H), 6.66 (dt, J=7.7, 1.3 Hz, 1H), 4.92 (d, J=6.0 Hz, 2H), 4.87 (d, J=6.2 Hz, 2H), 4.29 (dd, J=5.3, 3.7 Hz, 2H), 4.05 (dd, J=5.3, 3.8 Hz, 2H), 3.60 (s, 2H), 3.01 (s, 3H). LCMS: $C_{21}H_{22}N_6O_3$ requires: 406, found: m/z=407 [M+H]$^+$.

Example 24: (R)—N-(3-(1,1,2-trifluoro-1-(4-methyl-4H-1,2,4-triazol-3-yl)propan-2-yl)phenyl)-2,3-dihydro-4H-pyrido[3,2-b][1,4]oxazine-4-carboxamide

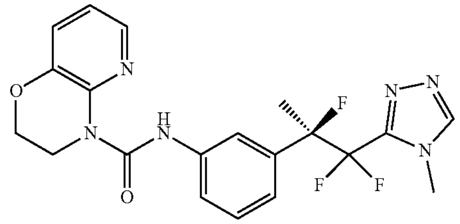 [SMILES: Cn1cnnc1C(F)(F)[C@](C)(F)c1cccc(NC(=O)N2CCOc3cccnc32)c1]

The procedure of Example 3 was followed using (R)-3-(1,1,2-trifluoro-1-(4-methyl-4H-1,2,4-triazol-3-yl)propan-2-yl)aniline and 2H,3H,4H-pyrido[3,2-b][1,4]oxazine to give the title compound (161 mg, 50%). $^1$H NMR (500 MHz, DMSO-$d_6$) δ 12.84 (s, 1H), 8.63 (s, 1H), 8.08 (dd, J=4.8, 1.6 Hz, 1H), 7.69-7.59 (m, 2H), 7.46-7.36 (m, 2H), 7.13 (dd, J=8.0, 4.8 Hz, 1H), 7.02 (d, J=7.9 Hz, 1H), 4.30 (dd, J=5.3, 3.8 Hz, 2H), 4.07 (dd, J=5.3, 3.8 Hz, 2H), 3.42 (s, 3H), 2.55 (s, 2H), 1.96 (d, J=24.2 Hz, 3H). LCMS: $C_{20}H_{19}F_3N_6O_2$ requires: 432, found: m/z=433 [M+H]$^+$.

Example 25: N-(3-((1S,2R)-2-(4-methyl-4H-1,2,4-triazol-3-yl)cyclopropyl)phenyl)-2,3-dihydro-4H-pyrido[3,2-b][1,4]oxazine-4-carboxamide

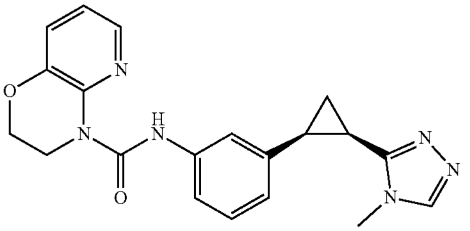 [SMILES: Cn1cnnc1[C@@H]1C[C@@H]1c1cccc(NC(=O)N2CCOc3cccnc32)c1]

The procedure of Example 10 was followed using 3-((1S,2R)-2-(4-methyl-4H-1,2,4-triazol-3-yl)cyclopropyl)aniline to give the title compound (90 mg, 66%). $^1$H NMR (500 MHz, DMSO-$d_6$) δ 12.66 (s, 1H), 8.86 (s, 1H), 8.06 (dd, J=4.8, 1.6 Hz, 1H), 7.41 (dd, J=8.0, 1.6 Hz, 1H), 7.37-7.27 (m, 2H), 7.18-7.04 (m, 2H), 6.71 (dt, J=7.8, 1.2 Hz, 1H), 4.28 (t, J=4.6 Hz, 2H), 4.11-3.94 (m, 2H), 3.64 (s, 3H), 2.88-2.79 (m, 1H), 2.76-2.65 (m, 1H), 2.01-1.91 (m, 1H), 1.77-1.66 (m, 1H); LCMS: $C_{20}H_{20}N_6O_2$ requires: 376, found: m/z=377 [M+H]$^+$.

Example 26: N-(3-(3-((4-methyl-4H-1,2,4-triazol-3-yl)methyl)oxetan-3-yl)phenyl)spiro[pyrido[3,2-b][1,4]oxazine-2,3'-pyrrolidine]-4(3H)-carboxamide

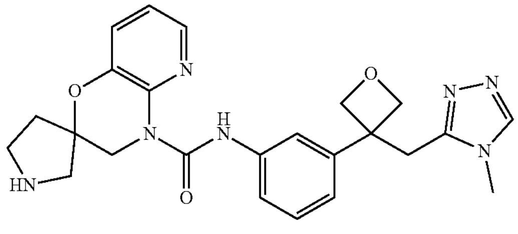 [SMILES: Cn1cnnc1CC1(c2cccc(NC(=O)N3CC4(CCNC4)Oc4cccnc43)c2)COC1]

Step 1: tert-butyl 4-((3-(3-((4-methyl-4H-1,2,4-triazol-3-yl)methyl)oxetan-3-yl)phenyl)carbamoyl)-3,4-dihydrospiro[pyrido[3,2-b][1,4]oxazine-2,3'-pyrrolidine]-1'-carboxylate. The procedure of Example 3 was followed using 3-{3-[(4-methyl-4H-1,2,4-triazol-3-yl)methyl]oxetan-3-yl}aniline and tert-butyl 3,4-dihydrospiro[pyrido[3,2-b][1,4]oxazine-2,3'-pyrrolidine]-1'-carboxylate to give the title compound (51.9 mg, 34%).

Step 2: N-(3-(3-((4-methyl-4H-1,2,4-triazol-3-yl)methyl)oxetan-3-yl)phenyl)spiro[pyrido[3,2-b][1,4]oxazine-2,3'-pyrrolidine]-4(3H)-carboxamide. A solution of tert-butyl 4-((3-(3-((4-methyl-4H-1,2,4-triazol-3-yl)methyl)oxetan-3-yl)phenyl)carbamoyl)-3,4-dihydrospiro[pyrido[3,2-b][1,4]

oxazine-2,3'-pyrrolidine]-1'-carboxylate (51.9 mg, 0.0924 mmol) in 1,1,1,3,3,3-hexafluoropropan-2-ol (1.82 mL) was heated to 120° C. for 24 h in a sealed tube. Chromatography C afforded the title compound (5.8 mg, 14%). $^1$H NMR (500 MHz, DMSO-$d_6$) δ 12.63 (d, J=14.1 Hz, 1H), 8.22 (d, J=7.5 Hz, 1H), 8.07 (dt, J=4.9, 1.8 Hz, 1H), 7.50 (t, J=6.1 Hz, 1H), 7.42 (ddd, J=8.4, 6.8, 1.6 Hz, 1H), 7.28-7.19 (m, 1H), 7.17-7.07 (m, 2H), 6.58 (dd, J=20.5, 7.8 Hz, 1H), 4.94 (dt, J=6.4, 3.3 Hz, 2H), 4.86 (dd, J=5.9, 4.4 Hz, 2H), 4.12 (t, J=14.0 Hz, 1H), 3.90 (dd, J=45.8, 13.5 Hz, 1H), 3.49 (d, J=2.3 Hz, 2H), 3.30 (s, 3H), 3.23-3.15 (m, 1H), 2.91 (s, 1H), 2.88 (s, 2H), 1.98-1.85 (m, 1H), 1.77 (t, J=6.9 Hz, 1H). LCMS: $C_{24}H_{27}N_7O_3$ requires: 461, found: m/z=462 $[M+H]^+$.

Example 27: N-(3-(3-((4-methyl-4H-1,2,4-triazol-3-yl)methyl)oxetan-3-yl)phenyl)spiro[azetidine-3,2'-pyrido[3,2-b][1,4]oxazine]-4'(3'H)-carboxamide

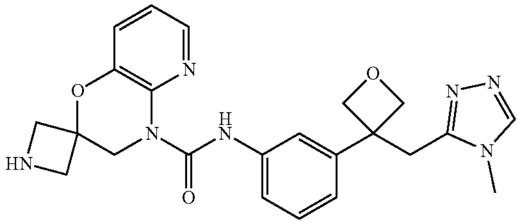 [SMILES: Cn1cnnc1CC1(c2cccc(NC(=O)N3CC4(CNC4)Oc4cccnc43)c2)COC1]

Step 1: tert-butyl 4'-((3-(3-((4-methyl-4H-1,2,4-triazol-3-yl)methyl)oxetan-3-yl)phenyl)carbamoyl)-3',4'-dihydrospiro[azetidine-3,2'-pyrido[3,2-b][1,4]oxazine]-1-carboxylate. The procedure of Example 3 was followed using 3-{3-[(4-methyl-4H-1,2,4-triazol-3-yl)methyl]oxetan-3-yl}aniline and tert-butyl 3',4'-dihydrospiro[azetidine-3,2'-pyrido[3,2-b][1,4]oxazine]-1-carboxylate to give the title compound (49.2 mg, 39%).

Step 2: N-(3-(3-((4-methyl-4H-1,2,4-triazol-3-yl)methyl)oxetan-3-yl)phenyl)spiro[azetidine-3,2'-pyrido[3,2-b][1,4]oxazine]-4'(3'H)-carboxamide. A solution of tert-butyl 4'-((3-(3-((4-methyl-4H-1,2,4-triazol-3-yl)methyl)oxetan-3-yl)phenyl)carbamoyl)-3',4'-dihydrospiro[azetidine-3,2'-pyrido[3,2-b][1,4]oxazine]-1-carboxylate (49.2 mg, 0.0898 mmol) in DCM (0.58 mL) and water (0.026 mL) was treated with TFA (0.138 mL, 1.80 mmol) at room temperature and stirred for 5 h. The mixture was concentrated to dryness and Chromatography C afforded the title compound (27.2 mg, 67%). $^1$H NMR (500 MHz, DMSO-$d_6$) δ 12.52 (s, 1H), 8.21 (s, 1H), 8.08 (dd, J=4.9, 1.5 Hz, 1H), 7.49 (ddd, J=8.0, 4.7, 1.7 Hz, 2H), 7.25 (t, J=7.9 Hz, 1H), 7.18-7.08 (m, 2H), 6.64-6.58 (m, 1H), 4.94 (d, J=6.0 Hz, 2H), 4.86 (d, J=6.0 Hz, 2H), 4.21 (s, 2H), 3.56 (d, J=8.9 Hz, 2H), 3.49 (s, 2H), 3.31 (s, 2H), 2.91 (s, 3H). LCMS: $C_{23}H_{25}N_7O_3$ requires: 447, found: m/z=448 $[M+H]^+$.

Example 28: (R)—N-(3-(1,1,2-trifluoro-1-(4-methyl-4H-1,2,4-triazol-3-yl)propan-2-yl)phenyl)spiro[azetidine-3,2'-pyrido[3,2-b][1,4]oxazine]-4'(3'H)-carboxamide

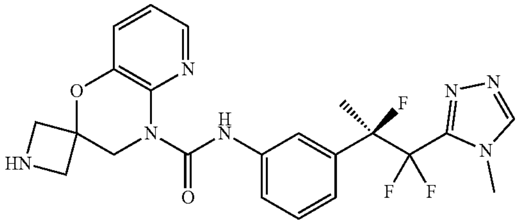 [SMILES: Cn1cnnc1C(F)(F)[C@](C)(F)c1cccc(NC(=O)N2CC3(CNC3)Oc3cccnc32)c1]

Step 1: tert-butyl (R)-4'-((3-(1,1,2-trifluoro-1-(4-methyl-4H-1,2,4-triazol-3-yl)propan-2-yl)phenyl)carbamoyl)-3',4'-dihydrospiro[azetidine-3,2'-pyrido[3,2-b][1,4]oxazine]-1-carboxylate. The procedure of Example 3 was followed using (R)-3-(1,1,2-trifluoro-1-(4-methyl-4H-1,2,4-triazol-3-yl)propan-2-yl)aniline and tert-butyl 3',4'-dihydrospiro[azetidine-3,2'-pyrido[3,2-b][1,4]oxazine]-1-carboxylate to give the title compound (113 mg, 55%).

Step 2: (R)—N-(3-(1,1,2-trifluoro-1-(4-methyl-4H-1,2,4-triazol-3-yl)propan-2-yl)phenyl)spiro[azetidine-3,2'-pyrido[3,2-b][1,4]oxazine]-4'(3'H)-carboxamide. The procedure of Example 27, Step 2 was followed using tert-butyl (R)-4'-((3-(1,1,2-trifluoro-1-(4-methyl-4H-1,2,4-triazol-3-yl)propan-2-yl)phenyl)carbamoyl)-3',4'-dihydrospiro[azetidine-3,2'-pyrido[3,2-b][1,4]oxazine]-1-carboxylate to afford the title compound (62.2 mg, 67%). $^1$H NMR (500 MHz, DMSO-$d_6$) δ 12.67 (s, 1H), 8.64 (s, 1H), 8.10 (dd, J=4.8, 1.6 Hz, 1H), 7.70-7.60 (m, 2H), 7.50 (dd, J=7.9, 1.5 Hz, 1H), 7.40 (t, J=7.9 Hz, 1H), 7.16 (dd, J=8.0, 4.8 Hz, 1H), 7.04 (d, J=8.0 Hz, 1H), 4.22 (s, 2H), 3.57 (d, J=8.8 Hz, 2H), 3.44 (s, 3H), 3.40 (d, J=9.5 Hz, 2H), 1.96 (d, J=24.4 Hz, 3H). LCMS: $C_{22}H_{22}F_3N_7O_2$ requires: 473, found: m/z=474 $[M+H]^+$.

Example 29: 1-methyl-N-(3-(3-((4-methyl-4H-1,2,4-triazol-3-yl)methyl)oxetan-3-yl)phenyl)spiro[azetidine-3,2'-pyrido[3,2-b][1,4]oxazine]-4'(3'H)-carboxamide

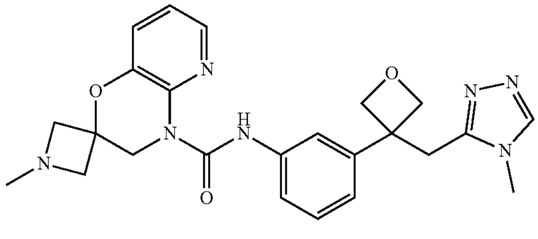 [SMILES: CN1CC2(C1)CN(C(=O)Nc1cccc(C3(Cc4nncn4C)COC3)c1)c1ncccc1O2]

A solution of N-(3-(3-((4-methyl-4H-1,2,4-triazol-3-yl)methyl)oxetan-3-yl)phenyl)spiro[azetidine-3,2'-pyrido[3,2-b][1,4]oxazine]-4'(3'H)-carboxamide (12.1 mg, 0.0270 mmol), formaldehyde (37% wt in water, 0.020 mL, 0.27 mmol) and sodium triacetoxyborohydride (22.9 mg, 0.108 mmol) in DCE (0.43 mL) was stirred for 2 h at room temperature. Solvent was evaporated and Chromatography C afforded the title compound (8.0 mg, 64%). $^1$H NMR (500 MHz, DMSO-$d_6$) δ 12.47 (s, 1H), 8.21 (s, 1H), 8.08 (dd, J=4.8, 1.6 Hz, 1H), 7.49 (td, J=7.9, 1.8 Hz, 2H), 7.25 (t, J=7.9 Hz, 1H), 7.16 (dd, J=8.0, 4.8 Hz, 1H), 7.10 (t, J=1.9 Hz, 1H), 6.64-6.58 (m, 1H), 4.94 (d, J=5.9 Hz, 2H), 4.86 (d, J=6.0 Hz, 2H), 4.17 (s, 3H), 3.49 (s, 2H), 3.44-3.38 (m, 2H), 3.30 (s, 2H), 3.06-3.00 (m, 2H), 2.91 (s, 2H), 2.35 (s, 3H). LCMS: $C_{24}H_{27}N_7O_3$ requires: 461, found: m/z=462 $[M+H]^+$.

Example 30: N-(3-(3-((4-methyl-4H-1,2,4-triazol-3-yl)methyl)oxetan-3-yl)phenyl)spiro[piperidine-4,3'-pyrrolo[2,3-b]pyridine]-1'(2'H)-carboxamide

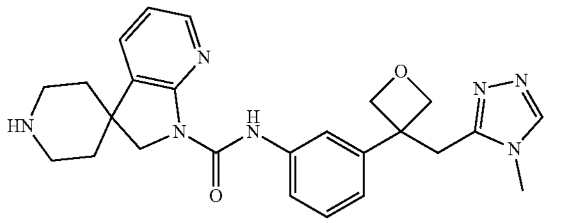 [SMILES: Cn1cnnc1CC1(c2cccc(NC(=O)N3CC4(CCNCC4)c4cccnc43)c2)COC1]

Step 1: tert-butyl 1'-((3-(3-((4-methyl-4H-1,2,4-triazol-3-yl)methyl)oxetan-3-yl)phenyl)carbamoyl)-1',2'-dihydrospiro[piperidine-4,3'-pyrrolo[2,3-b]pyridine]-1-carboxylate. The procedure of Example 3 was followed using 3-{3-[(4-methyl-4H-1,2,4-triazol-3-yl)methyl]oxetan-3-yl}aniline and tert-butyl 1',2'-dihydrospiro[piperidine-4,3'-pyrrolo[2,3-b]pyridine]-1-carboxylate to give the title compound (268 mg).

Step 2: N-(3-(3-((4-methyl-4H-1,2,4-triazol-3-yl)methyl)oxetan-3-yl)phenyl)spiro[piperidine-4,3'-pyrrolo[2,3-b]pyridine]-1'(2'H)-carboxamide. The procedure of Example 27, Step 2 was followed using tert-butyl 1'-((3-(3-((4-methyl-4H-1,2,4-triazol-3-yl)methyl)oxetan-3-yl)phenyl)carbamoyl)-1',2'-dihydrospiro[piperidine-4,3'-pyrrolo[2,3-b]pyridine]-1-carboxylate to afford the title compound (78.0 mg, 38% over two steps). $^1H$ NMR (500 MHz, DMSO-$d_6$) δ 11.38 (s, 1H), 8.23-8.16 (m, 2H), 7.72 (dd, J=7.4, 1.6 Hz, 1H), 7.52-7.43 (m, 1H), 7.25 (t, J=7.9 Hz, 1H), 7.11 (t, J=2.0 Hz, 1H), 7.05 (dd, J=7.4, 5.3 Hz, 1H), 6.59 (dt, J=7.7, 1.3 Hz, 1H), 4.94 (d, J=5.9 Hz, 2H), 4.85 (d, J=6.0 Hz, 2H), 3.95 (s, 2H), 3.49 (s, 2H), 3.04-2.97 (m, 2H), 2.90 (s, 3H), 2.78-2.70 (m, 2H), 1.78 (dt, J=12.8, 6.7 Hz, 2H), 1.65 (d, J=13.1 Hz, 2H). LCMS: $C_{25}H_{29}N_7O_2$ requires: 459, found: m/z=460 $[M+H]^+$.

Example 31: 1-methyl-N-(3-(3-((4-methyl-4H-1,2,4-triazol-3-yl)methyl)oxetan-3-yl)phenyl)spiro[piperidine-4,3'-pyrrolo[2,3-b]pyridine]-1'(2'H)-carboxamide

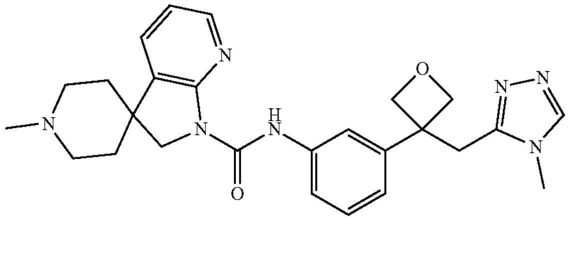 [SMILES: CN1CCC2(CC1)CN(C(=O)Nc1cccc(C3(Cc4nncn4C)COC3)c1)c1ncccc12]

The procedure of Example 29 was followed using N-(3-(3-((4-methyl-4H-1,2,4-triazol-3-yl)methyl)oxetan-3-yl)phenyl)spiro[piperidine-4,3'-pyrrolo[2,3-b]pyridine]-1'(2'H)-carboxamide to afford the title compound (27.5 mg, 44%). $^1H$ NMR (500 MHz, DMSO-$d_6$) δ 11.37 (s, 1H), 8.21 (s, 1H), 8.18 (dd, J=5.3, 1.6 Hz, 1H), 7.77 (dd, J=7.3, 1.5 Hz, 1H), 7.52-7.46 (m, 1H), 7.24 (t, J=7.9 Hz, 1H), 7.10 (t, J=2.0 Hz, 1H), 7.03 (dd, J=7.4, 5.3 Hz, 1H), 6.58 (dt, J=7.7, 1.3 Hz, 1H), 4.94 (d, J=6.0 Hz, 2H), 4.85 (d, J=6.1 Hz, 2H), 3.88 (s, 2H), 3.49 (s, 2H), 2.90 (s, 3H), 2.79-2.72 (m, 2H), 2.23 (s, 3H), 2.06-1.97 (m, 2H), 1.88 (td, J=12.8, 3.9 Hz, 2H), 1.64 (d, J=12.5 Hz, 2H). LCMS: $C_{26}H_{31}N_7O_2$ requires: 473, found: m/z=474 $[M+H]^+$.

Example 32: 2-(3-(3-((4-methyl-4H-1,2,4-triazol-3-yl)methyl)oxetan-3-yl)phenyl)-7-(trifluoromethyl)hexahydro-3H-pyrrolo[1,2-c]imidazol-3-one

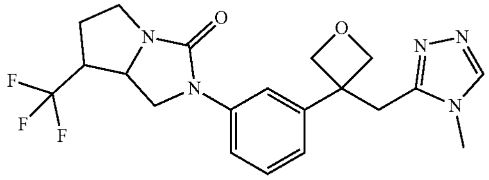 [SMILES: Cn1cnnc1CC1(c2cccc(N3CC4C(C(F)(F)F)CCN4C3=O)c2)COC1]

Step 1: 7-(trifluoromethyl)tetrahydro-1H-pyrrolo[1,2-c]imidazole-1,3(2H)-dione. A solution of 3-(trifluoromethyl)pyrrolidine-2-carboxylic acid (900 mg, 4.91 mmol) and potassium cyanate (478 mg, 5.90 mmol) in water (28.9 mL) was heated to 95° C. for 16 h. The mixture was cooled to room temperature, treated with HCl (2 N, 29.5 mL, 59.0 mmol) and stirred for 2 h at 95° C. Solvent was evaporated and Chromatography B afforded the title compound (490 mg, 47.9%).

Step 2: 7-(trifluoromethyl)hexahydro-3H-pyrrolo[1,2-c]imidazol-3-one. A solution of 7-(trifluoromethyl)tetrahydro-1H-pyrrolo[1,2-c]imidazole-1,3(2H)-dione (190 mg, 0.910 mmol) in THF (8.86 mL) was treated with a solution of lithium aluminum hydride (2 M in THF, 1.37 mL, 2.73 mmol) and stirred at 60° C. for 48 h. The reaction was quenched with sat. aq. Rochelle's salt. General Workup Procedure followed by Chromatography B afforded the title compound (13.9 mg, 7.9%).

Step 3: 2-(3-(3-((4-methyl-4H-1,2,4-triazol-3-yl)methyl)oxetan-3-yl)phenyl)-7-(trifluoromethyl)hexahydro-3H-pyrrolo[1,2-c]imidazol-3-one. A solution of 7-(trifluoromethyl)hexahydro-3H-pyrrolo[1,2-c]imidazol-3-one (13.9 mg, 0.0716 mmol), 3-{[3-(3-bromophenyl)oxetan-3-yl]methyl}-4-methyl-1,2,4-triazole (26.5 mg, 0.0859 mmol), cesium carbonate (46.7 mg, 0.143 mmol), palladium acetate (3.2 mg, 0.014 mmol), 4,5-Bis(diphenylphosphino)-9,9-dimethylxanthene (16.6 mg, 0.0286 mmol) in dioxane (0.55 mL) was stirred at 100° C. for 3 h. Solvent was removed and Chromatography C afforded the title compound (13.6 mg, 45%). $^1H$ NMR (500 MHz, DMSO-$d_6$) δ 8.20 (s, 1H), 7.61 (dd, J=8.3, 2.2 Hz, 1H), 7.24 (t, J=8.0 Hz, 1H), 7.04 (t, J=2.0 Hz, 1H), 6.60 (d, J=7.9 Hz, 1H), 4.93 (d, J=6.0 Hz, 2H), 4.84 (t, J=5.6 Hz, 2H), 4.02-3.92 (m, 2H), 3.86-3.80 (m, 1H), 3.70 (ddd, J=11.5, 8.7, 5.9 Hz, 1H), 3.47 (s, 2H), 3.19-3.04 (m, 2H), 2.89 (s, 3H), 2.18 (ddt, J=14.7, 9.0, 4.5 Hz, 1H), 2.01-1.93 (m, 1H). LCMS: $C_{20}H_{22}F_3N_5O_2$ requires: 421, found: m/z=422 $[M+H]^+$.

Example 33: 3-(1-((4-methyl-4H-1,2,4-triazol-3-yl)thio)ethyl)-N-phenylbenzamide

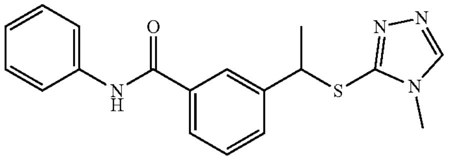 [SMILES: CC(Sc1nncn1C)c1cccc(C(=O)Nc2ccccc2)c1]

The procedure of Example 1 was followed using aniline to afford the title compound (0.0296 g, 46.0%). $^1$H NMR (500 MHz, Chloroform-d) δ 8.06 (s, 1H), 7.87 (s, 1H), 7.79-7.71 (m, 3H), 7.67 (t, J=1.8 Hz, 1H), 7.48 (dt, J=7.7, 1.5 Hz, 1H), 7.45-7.35 (m, 3H), 7.20-7.12 (m, 1H), 4.84 (q, J=7.1 Hz, 1H), 3.29 (s, 3H), 1.85 (d, J=7.1 Hz, 3H). LCMS: $C_{18}H_{18}N_4OS$ requires: 338, found: m/z=339 $[M+H]^+$.

Example 34: 3-(1-((4-methyl-4H-1,2,4-triazol-3-yl)thio)ethyl)-N-(pyridin-2-yl)benzamide

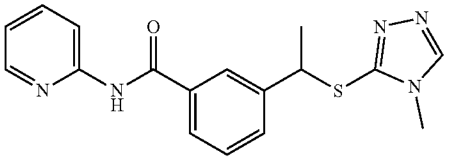 [SMILES: CC(Sc1nncn1C)c1cccc(C(=O)Nc2ccccn2)c1]

The procedure of Example 1 was followed using 2-aminopyridine to afford the title compound (0.0121 g, 18.7%). $^1$H NMR (500 MHz, DMSO-$d_6$) δ 10.86 (s, 1H), 8.56 (s, 1H), 8.41 (dd, J=4.9, 1.8 Hz, 1H), 8.19 (d, J=8.1 Hz, 1H), 8.03 (d, J=1.8 Hz, 1H), 7.94 (dt, J=7.3, 1.5 Hz, 1H), 7.87 (ddd, J=8.8, 7.5, 2.0 Hz, 1H), 7.51 (dt, J=7.6, 1.4 Hz, 1H), 7.45 (t, J=7.7 Hz, 1H), 7.22-7.16 (m, 1H), 4.78 (q, J=7.0 Hz, 1H), 3.39 (s, 3H), 1.72 (d, J=7.0 Hz, 3H). LCMS: $C_{17}H_{17}N_5OS$ requires: 339, found: m/z=340 $[M+H]^+$.

Example 35: (S)-3-(1-((4-methyl-4H-1,2,4-triazol-3-yl)thio)ethyl)-N-(quinolin-2-yl)benzamide

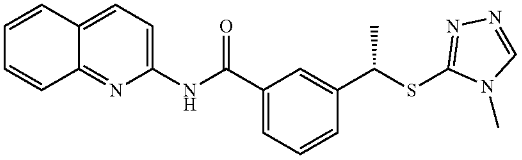 [SMILES: C[C@H](Sc1nncn1C)c1cccc(C(=O)Nc2ccc3ccccc3n2)c1]

The procedure of Example 1 was followed using 3-[(1S)-1-[(4-methyl-4H-1,2,4-triazol-3-yl)sulfanyl]ethyl]benzoic acid and quinolin-2-amine to afford the title compound (0.0020 g, 2.9%). $^1$H NMR (500 MHz, DMSO-$d_6$) 11.21 (s, 1H), 8.56 (s, 1H), 8.42 (d, J=9.0 Hz, 1H), 8.35 (d, J=8.9 Hz, 1H), 8.09 (d, J=1.9 Hz, 1H), 7.97 (dd, J=10.1, 8.4 Hz, 2H), 7.89 (d, J=8.3 Hz, 1H), 7.75 (ddd, J=8.4, 6.8, 1.5 Hz, 1H), 7.53 (dd, J=13.6, 7.0 Hz, 2H), 7.46 (t, J=7.6 Hz, 1H), 4.79 (q, J=7.1 Hz, 1H), 3.39 (s, 3H), 1.73 (d, J=7.0 Hz, 3H). LCMS: $C_{21}H_{19}N_5OS$ requires: 389, found: m/z=390 $[M+H]^+$.

Example 36: (S)-3-(1-((4-methyl-4H-1,2,4-triazol-3-yl)thio)ethyl)-N-(4-(trifluoromethyl)pyridin-2-yl)benzamide

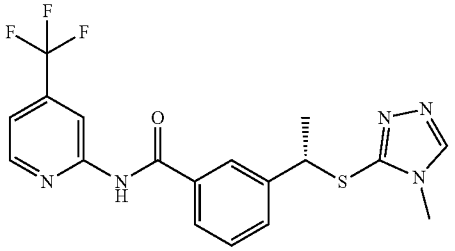 [SMILES: C[C@H](Sc1nncn1C)c1cccc(C(=O)Nc2cc(C(F)(F)F)ccn2)c1]

The procedure of Example 1 was followed using 3-[(1S)-1-[(4-methyl-4H-1,2,4-triazol-3-yl)sulfanyl]ethyl]benzoic acid and 4-(trifluoromethyl)pyridin-2-amine to afford the title compound (0.0106 g, 14.9%). $^1$H NMR (500 MHz, DMSO-$d_6$) 11.34 (s, 1H), 8.68 (d, J=5.2 Hz, 1H), 8.55 (d, J=13.1 Hz, 2H), 8.04 (s, 1H), 7.93 (dt, J=7.7, 1.4 Hz, 1H), 7.60-7.49 (m, 2H), 7.45 (t, J=7.7 Hz, 1H), 4.77 (q, J=7.0 Hz, 2H), 3.37 (s, 3H), 1.71 (d, J=7.0 Hz, 3H). LCMS: $C_{18}H_{16}F_3N_5OS$ requires: 407, found: m/z=408 $[M+H]^+$.

Example 37: N-(6-cyclopropylpyridin-2-yl)-3-(3-((4-methyl-4H-1,2,4-triazol-3-yl)methyl)oxetan-3-yl)benzamide

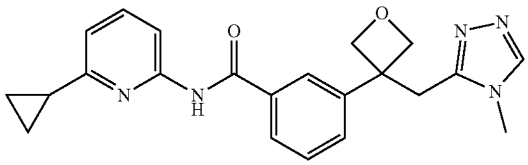 [SMILES: Cn1cnnc1CC1(c2cccc(C(=O)Nc3cccc(C4CC4)n3)c2)COC1]

The procedure of Example 1 was followed using 3-(3-((4-methyl-4H-1,2,4-triazol-3-yl)methyl)oxetan-3-yl)benzoic acid and 6-cyclopropylpyridin-2-amine to afford the title compound (0.0197 g, 31.9%). $^1$H NMR (500 MHz, DMSO-$d_6$) 10.50 (s, 1H), 8.21 (s, 1H), 7.90 (dd, J=8.2, 0.9 Hz, 1H), 7.84 (dt, J=7.8, 1.4 Hz, 1H), 7.76-7.65 (m, 2H), 7.39 (t, J=7.7 Hz, 1H), 7.09 (dt, J=7.6, 1.4 Hz, 1H), 7.00 (dd, J=7.6, 0.9 Hz, 1H), 4.96 (d, J=1.2 Hz, 4H), 3.54 (s, 2H), 2.93 (s, 3H), 2.12-2.05 (m, 1H), 1.00-0.90 (m, 4H). LCMS: $C_{22}H_{23}N_5O_2$ requires: 389, found: m/z=390 $[M+H]^+$.

Example 38: 3-(3-((4-methyl-4H-1,2,4-triazol-3-yl)methyl)oxetan-3-yl)-N-(6-methylpyridin-2-yl)benzamide

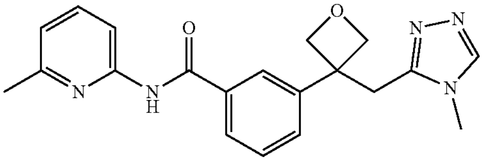 [SMILES: Cc1cccc(NC(=O)c2cccc(C3(Cc4nncn4C)COC3)c2)n1]

The procedure of Example 1 was followed using 6-methyl-2-pyridinamine and 3-(3-((4-methyl-4H-1,2,4-triazol-3-yl)methyl)oxetan-3-yl)benzoic acid to afford the title compound (15.8 mg, 22.9%). $^1$H NMR (500 MHz, DMSO-$d_6$) 10.79 (s, 1H), 8.21 (s, 1H), 8.03 (d, J=8.2 Hz, 1H), 7.85 (dt, J=7.9, 1.3 Hz, 1H), 7.79 (d, J=1.9 Hz, 1H), 7.73 (t, J=7.9 Hz, 1H), 7.39 (t, J=7.7 Hz, 1H), 7.10-7.01 (m, 2H), 4.97 (s, 4H), 3.55 (s, 2H), 2.91 (s, 3H), 2.47 (s, 3H). LCMS: $C_{20}H_{21}N_5O_2$ requires: 363, found: m/z=364 [M+H]$^+$.

Example 39: (S)-1-(3-(1-((4-methyl-4H-1,2,4-triazol-3-yl)thio)ethyl)phenyl)-3-(5-methylpyridazin-3-yl)urea

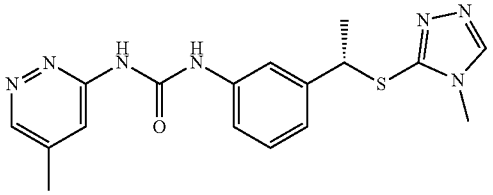 [SMILES: Cc1cnnc(NC(=O)Nc2cccc([C@H](C)Sc3nncn3C)c2)c1]

A mixture of phenyl (S)-(3-(1-((4-methyl-4H-1,2,4-triazol-3-yl)thio)ethyl)phenyl)carbamate (150 mg, 0.42 mmol) and 5-methylpyridazin-3-amine (92 mg, 0.84 mmol) in DMSO (2 mL) was stirred at 80° C. for 2 h. Purification by Chromatography C afforded the title compound (16.7 mg, 11%). MS (ESI) calc'd for ($C_{17}H_{19}N_7OS$) [M+1]$^+$, 370.1; found, 370.1. $^1$H NMR (300 MHz, DMSO-$d_6$) δ 9.87 (s, 1H), 9.68 (s, 1H), 8.76 (d, J=1.5 Hz, 1H), 8.55 (s, 1H), 7.86 (s, 1H), 7.47 (s, 1H), 7.40-7.37 (m, 1H), 7.25 (t, J=7.5 Hz, 1H), 6.97-6.94 (m, 1H), 4.65 (q, J=6.9 Hz, 1H), 3.37 (s, 3H), 2.32 (s, 3H), 1.67 (d, J=6.9 Hz, 3H).

Example 40: N-(3-((S)-1-((4-methyl-4H-1,2,4-triazol-3-yl)thio)ethyl)phenyl)hexahydrocyclopenta[c]pyrrole-2(1H)-carboxamide

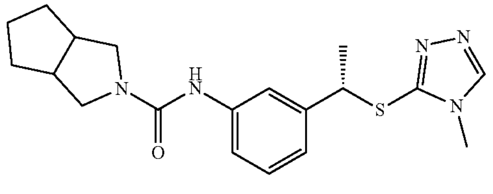 [SMILES: C[C@H](Sc1nncn1C)c1cccc(NC(=O)N2CC3CCCC3C2)c1]

The procedure for Example 39 was followed using (3aR,6aS)-octahydrocyclopenta[c]pyrrole to afford the title compound (20.8 mg, 26%). MS (ESI) calc'd for ($C_{19}H_{25}N_5OS$) [M+1]$^+$, 372.2; found, 372.2. $^1$H NMR (400 MHz, DMSO-$d_6$) δ 8.54 (s, 1H), 8.15 (s, 1H), 7.52 (t, J=2.0 Hz, 1H), 7.45-7.42 (m, 1H), 7.13 (t, J=8.0 Hz, 1H), 6.80 (d, J=8.0 Hz, 1H), 4.58-4.57 (m, 1H), 3.59-3.54 (m, 2H), 3.37 (s, 3H), 3.18-3.15 (m, 2H), 2.69-2.60 (m, 2H), 1.85-1.64 (m, 3H), 1.63-1.51 (m, 4H), 1.48-1.38 (m, 2H).

Example 41: 3-methyl-N-(3-((S)-1-((4-methyl-4H-1,2,4-triazol-3-yl)thio)ethyl)phenyl)pyrrolidine-1-carboxamide

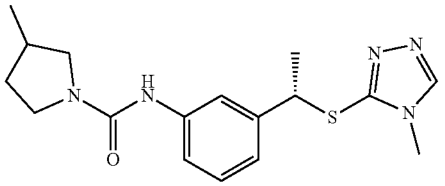 [SMILES: CC1CCN(C(=O)Nc2cccc([C@H](C)Sc3nncn3C)c2)C1]

The procedure for Example 39 was followed using 3-methylpyrrolidine to afford the title compound (23.0 mg, 39%). MS (ESI) calc'd for ($C_{17}H_{23}N_5OS$) [M+1]$^+$, 346.2; found, 346.1. $^1$H NMR (400 MHz, DMSO-$d_6$) δ 8.55 (s, 1H), 8.11 (s, 1H), 7.53 (s, 1H), 7.45 (d, J=8.0 Hz, 1H), 7.14-7.11 (m, 1H), 6.80 (d, J=7.2 Hz, 1H), 4.59-4.57 (m, 1H), 3.58-3.44 (m, 2H), 3.30-3.28 (m, 1H), 3.39 (s, 3H), 2.91-2.87 (m, 1H), 2.25-2.23 (m, 1H), 1.99-1.97 (m, 1H), 1.60 (d, J=6.4 Hz, 3H), 1.56-1.41 (m, 1H), 1.03 (d, J=6.0 Hz, 3H).

Example 42: 2,6-dimethyl-N-(3-((S)-1-((4-methyl-4H-1,2,4-triazol-3-yl)thio)ethyl)phenyl)morpholine-4-carboxamide

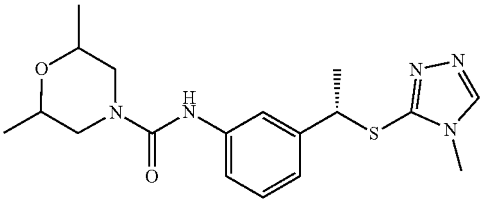 [SMILES: CC1CN(C(=O)Nc2cccc([C@H](C)Sc3nncn3C)c2)CC(C)O1]

The procedure for Example 39 was followed using 2,6-dimethylmorpholine to afford the title compound (26.9 mg, 32%). MS (ESI) calc'd for ($C_{18}H_{25}N_5O_2S$) [M+1]$^+$, 376.2; found, 376.2. $^1$H NMR (400 MHz, DMSO-$d_6$) δ 8.53 (s, 2H), 7.48-7.36 (m, 2H), 7.15 (t, J=7.6 Hz, 1H), 6.83 (d, J=7.6 Hz, 1H), 4.59 (q, J=7.0 Hz, 1H), 3.98-3.97 (m, 2H), 3.52-3.51 (m, 2H), 3.37 (s, 3H), 2.45-2.43 (m, 2H), 1.61 (d, J=6.9 Hz, 3H), 1.11 (d, J=6.2 Hz, 6H).

Example 43: (S)—N-(3-(1-((4-methyl-4H-1,2,4-triazol-3-yl)thio)ethyl)phenyl)-5-oxa-8-azaspiro[3.5]nonane-8-carboxamide

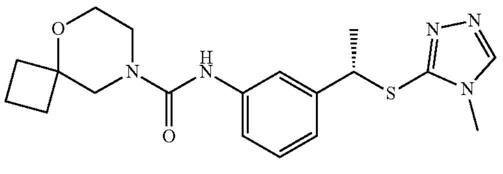 [SMILES: C[C@H](Sc1nncn1C)c1cccc(NC(=O)N2CCOC3(CCC3)C2)c1]

The procedure for Example 39 was followed using 5-oxa-8-azaspiro[3.5]nonane to afford the title compound (46.1 mg, 28%). MS (ESI) calc'd for ($C_{19}H_{25}N_5O_2S$) [M+1]$^+$, 388.2; found, 388.2. $^1$H NMR (300 MHz, DMSO-$d_6$) δ 8.57

(s, 1H), 8.54 (s, 1H), 7.48 (s, 1H), 7.44-7.40 (m, 1H), 7.17 (t, J=7.8 Hz, 1H), 6.85 (d, J=7.8 Hz, 1H), 4.61 (q, J=6.9 Hz, 1H), 3.55-3.53 (m, 2H), 3.51-3.49 (m, 2H), 3.48-3.47 (m, 2H), 3.36 (s, 3H), 3.43 (s, 2H), 1.96-1.93 (m, 2H), 1.84-1.65 (m, 2H), 1.62 (d, J=6.9 Hz, 3H).

Example 44: (S)—N-(3-(1-((4-methyl-4H-1,2,4-triazol-3-yl)thio)ethyl)phenyl)-6,7-dihydropyrazolo[1,5-a]pyrazine-5(4H)-carboxamide

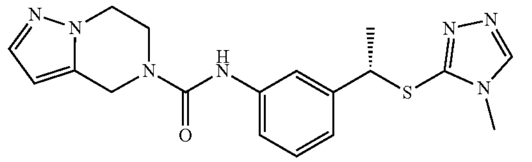 [SMILES: C[C@H](Sc1nncn1C)c1cccc(NC(=O)N2CCn3nccc3C2)c1]

The procedure for Example 39 was followed using 4,5,6,7-tetrahydropyrazolo[1,5-a]pyrazine to afford the title compound (21.4 mg, 25%). MS (ESI) calculated for ($C_{18}H_{21}N_7OS$) $[M+1]^+$, 384.2; found, 384.0. $^1H$ NMR (300 MHz, DMSO-$d_6$) δ 8.86 (s, 1H), 8.54 (s, 1H), 7.48-7.41 (m, 3H), 7.18 (t, J=7.8 Hz, 1H), 6.87 (d, J=7.8, 1H), 6.14 (d, J=1.8 Hz, 1H), 4.75 (br, 2H), 4.61 (q, J=6.9 Hz, 1H), 4.18-4.14 (m, 2H), 3.97-3.94 (m, 2H), 3.37 (s, 3H), 1.62 (d, J=6.9 Hz, 3H).

Example 45: (S)-4-hydroxy-N-(3-(1-((4-methyl-4H-1,2,4-triazol-3-yl)thio)ethyl)phenyl)isoindoline-2-carboxamide

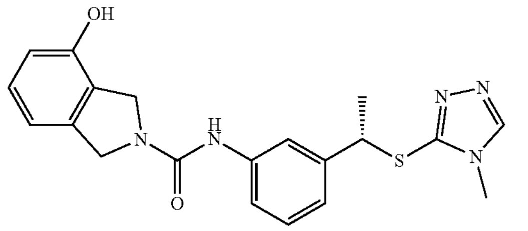 [SMILES: C[C@H](Sc1nncn1C)c1cccc(NC(=O)N2Cc3cccc(O)c3C2)c1]

The procedure for Example 39 was followed using isoindolin-4-ol to afford the title compound (36.0 mg, 40%). MS (ESI) calc'd for ($C_{20}H_{21}N_5O_2S$) $[M+1]^+$, 396.1; found, 396.2. $^1H$ NMR (400 MHz, DMSO-$d_6$) δ 9.78 (s, 1H), 8.54 (s, 1H), 8.39 (s, 1H), 7.60 (s, 1H), 7.58-7.51 (m, 1H), 7.15-7.11 (m, 2H), 6.84 (d, J=7.6 Hz, 1H), 6.78 (d, J=7.6 Hz, 1H), 6.72 (d, J=8.0 Hz, 1H), 4.78-4.69 (m, 2H), 4.68-4.57 (m, 3H), 3.38 (s, 3H), 1.63 (d, J=6.9 Hz, 3H).

Example 46: (S)-1-methyl-N-(3-(1-((4-methyl-4H-1,2,4-triazol-3-yl)thio)ethyl)phenyl)-4,6-dihydropyrrolo[3,4-c]pyrazole-5(1H)-carboxamide

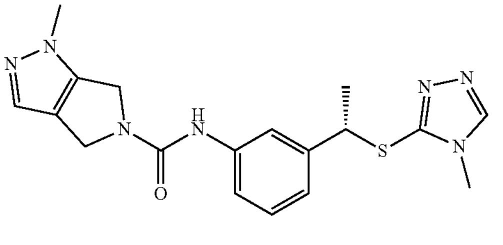 [SMILES: C[C@H](Sc1nncn1C)c1cccc(NC(=O)N2Cc3cnn(C)c3C2)c1]

The procedure for Example 39 was followed using 1-methyl-1,4,5,6-tetrahydropyrrolo[3,4-c]pyrazole to afford the title compound (18.5 mg, 22%). MS (ESI) calculated for ($C_{18}H_{21}N_7OS$) $[M+1]^+$, 384.2; found, 384.0. $^1H$ NMR (300 MHz, DMSO-$d_6$) δ 8.58 (s, 1H), 8.36 (s, 1H), 7.58 (s, 1H), 7.51 (d, J=8.1 Hz, 1H), 7.28 (s, 1H), 7.18 (t, J=7.8 Hz, 1H), 6.86 (d, J=4.2 Hz, 1H), 4.66-4.59 (m, 3H), 4.49-4.48 (m, 2H), 3.79 (s, 3H), 3.39 (s, 3H), 1.63 (d, J=6.9 Hz, 3H).

Example 47: 3-(difluoromethyl)-N-(3-((S)-1-((4-methyl-4H-1,2,4-triazol-3-yl)thio)ethyl)phenyl)pyrrolidine-1-carboxamide

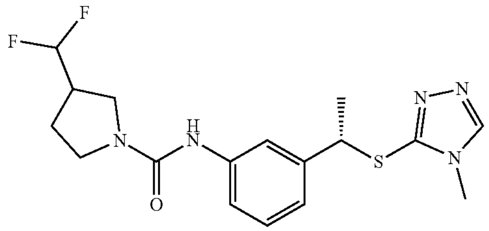 [SMILES: C[C@H](Sc1nncn1C)c1cccc(NC(=O)N2CCC(C(F)F)C2)c1]

The procedure for Example 39 was followed using 3-(difluoromethyl)pyrrolidine to afford the title compound (24.5 mg, 25%). MS (ESI) calc'd for ($C_{17}H_{21}F_2N_5OS$) $[M+1]^+$, 382.1; found, 382.1. $^1H$ NMR (400 MHz, DMSO-$d_6$) δ 8.54 (s, 1H), 8.26 (s, 1H), 7.52 (t, J=2.0 Hz, 1H), 7.46-7.44 (m, 1H), 7.14 (t, J=8.0 Hz, 1H), 6.82 (d, J=7.6 Hz, 1H), 6.32-5.97 (m, 1H), 4.58 (q, J=6.8 Hz, 1H), 3.58-3.51 (m, 2H), 3.45-3.33 (m, 5H), 2.80-2.70 (m, 1H), 2.05-2.02 (m, 1H), 1.90-1.87 (m, 1H), 1.61 (d, J=7.2 Hz, 3H).

Example 48: (S)—N-(3-(1-((4-methyl-4H-1,2,4-triazol-3-yl)thio)ethyl)phenyl)-4-oxa-7-azaspiro[2.5]octane-7-carboxamide

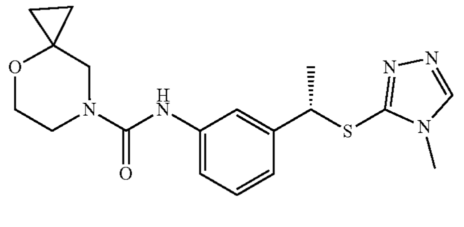 [SMILES: C[C@H](Sc1nncn1C)c1cccc(NC(=O)N2CCOC3(CC3)C2)c1]

The procedure for Example 39 was followed using 4-oxa-7-azaspiro[2.5]octane to afford the title compound (36.5 mg, 39%). MS (ESI) calc'd for ($C_{18}H_{23}N_5O_2S$) $[M+1]^+$, 374.2; found, 374.2. $^1H$ NMR (400 MHz, Chloroform-d) δ 8.07 (s, 1H), 7.43-7.36 (m, 1H), 7.20 (t, J=8.0 Hz, 1H), 7.10 (t, J=2.0 Hz, 1H), 6.97-6.90 (m, 1H), 6.73 (s, 1H), 4.67 (q, J=7.2 Hz, 1H), 3.81-3.76 (m, 2H), 3.57-3.55 (m, 2H), 3.46 (s, 2H), 3.27 (s, 3H), 1.76 (d, J=7.2 Hz, 3H), 0.86-0.83 (m, 2H), 0.71-0.65 (m, 2H).

Example 49: (S)-1-cyclobutyl-1-methyl-3-(3-(1-((4-methyl-4H-1,2,4-triazol-3-yl)thio)ethyl)phenyl)urea

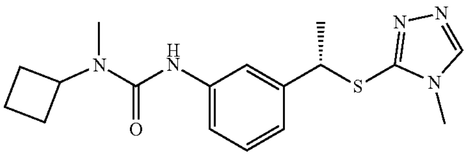 [SMILES: C[C@H](Sc1nncn1C)c1cccc(NC(=O)N(C)C2CCC2)c1]

The procedure for Example 39 was followed using N-methylcyclobutanamine to afford the title compound (36.2 mg, 37%). MS (ESI) calc'd for ($C_{17}H_{23}N_5OS$) $[M+1]^+$, 346.2; found, 346.2. $^1H$ NMR (400 MHz, Chloroform-d) δ 8.07 (s, 1H), 7.36 (d, J=8.0 Hz, 1H), 7.24-7.13 (m, 2H), 6.89 (d, J=7.6 Hz, 1H), 6.29 (s, 1H), 4.67 (q, J=7.0 Hz, 1H), 4.55-4.46 (m, 1H), 3.25 (s, 3H), 2.96 (s, 3H), 2.29-2.10 (m, 2H), 1.86-1.53 (m, 6H).

Example 50: $N^3$-methyl-$N^1$-(3-((S)-1-((4-methyl-4H-1,2,4-triazol-3-yl)thio)ethyl)phenyl)-3-(trifluoromethyl)pyrrolidine-1,3-dicarboxamide

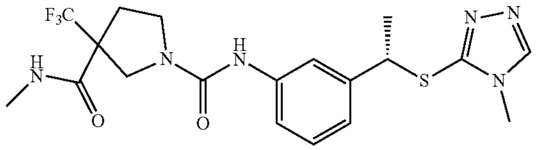 [SMILES: CNC(=O)C1(C(F)(F)F)CCN(C(=O)Nc2cccc([C@H](C)Sc3nncn3C)c2)C1]

The procedure for Example 39 was followed using N-methyl-3-(trifluoromethyl)pyrrolidine-3-carboxamide to afford the title compound (25.4 mg, 22%). MS (ESI) calc'd for ($C_{19}H_{23}F_3N_6O_2S$) $[M+1]^+$, 457.2; found, 457.2. $^1H$ NMR (400 MHz, Chloroform-d) δ 8.23 (s, 1H), 7.39 (d, J=8.0 Hz, 1H), 7.19-7.17 (m, 2H), 6.94 (d, J=7.6 Hz, 1H), 6.57-6.53 (m, 1H), 6.36 (br, 1H), 4.70-4.66 (m, 1H), 4.23-4.21 (m, 1H), 3.88-3.85 (m, 1H), 3.66-3.64 (m, 2H), 3.32 (s, 3H), 2.91 (s, 3H), 2.79-2.72 (m, 1H), 2.41-2.40 (m, 1H), 1.77 (d, J=7.2 Hz, 3H).

Example 51: 2-isopropyl-N-(3-((S)-1-((4-methyl-4H-1,2,4-triazol-3-yl)thio)ethyl)phenyl)morpholine-4-carboxamide

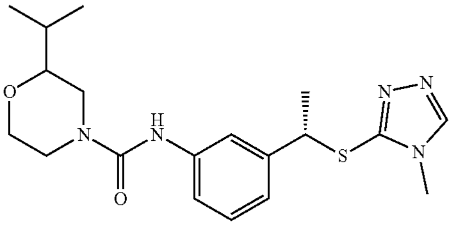 [SMILES: CC(C)C1CN(C(=O)Nc2cccc([C@H](C)Sc3nncn3C)c2)CCO1]

The procedure for Example 39 was followed using 2-isopropylmorpholine to afford the title compound (32.6 mg, 49%). MS (ESI) calc'd for ($C_{19}H_{27}N_5O_2S$) $[M+1]^+$,390.1; found, 390.0. $^1H$ NMR (300 MHz, DMSO-$d_6$) δ 8.57-8.53 (m, 2H), 7.46 (t, J=1.8 Hz, 1H), 7.40-7.37 (m, 1H), 7.17 (t, J=7.8 Hz, 1H), 6.93-6.81 (m, 1H), 4.62 (q, J=6.9 Hz, 1H), 4.02-3.86 (m, 3H), 3.52-3.42 (m, 1H), 3.39 (s, 3H), 3.06-3.04 (m, 1H), 2.97-2.79 (m, 1H), 2.65-2.60 (m, 1H), 1.68-1.59 (m, 4H), 0.95-0.90 (m, 6H).

Example 52: (S)—N-(3-(1-((4-methyl-4H-1,2,4-triazol-3-yl)thio)ethyl)phenyl)-3-(trifluoromethoxy)azetidine-1-carboxamide

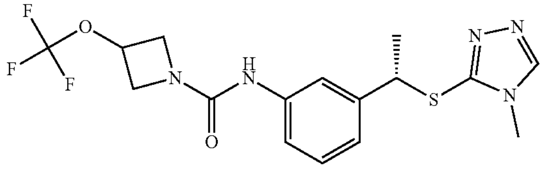 [SMILES: C[C@H](Sc1nncn1C)c1cccc(NC(=O)N2CC(OC(F)(F)F)C2)c1]

The procedure for Example 39 was followed using 3-(trifluoromethoxy)azetidine to afford the title compound (36.7 mg, 54%). MS (ESI) calc'd for ($C_{16}H_{18}F_3N_5O_2S$) $[M+1]^+$, 402.1; found, 402.1. $^1H$ NMR (400 MHz, Chloroform-d) δ 8.11 (s, 1H), 7.47 (d, J=8.0 Hz, 1H), 7.30-7.10 (m, 3H), 6.93 (d, J=7.6 Hz, 1H), 5.00-4.91 (m, 1H), 4.62 (q, J=7.2 Hz, 1H), 4.42-4.32 (m, 2H), 4.22-4.12 (m, 2H), 3.28 (s, 3H), 1.72 (d, J=7.2 Hz, 3H).

Example 53: 3,3-dimethyl-4-(1-methyl-1H-pyrazol-4-yl)-N-(3-((S)-1-((4-methyl-4H-1,2,4-triazol-3-yl)thio)ethyl)phenyl)pyrrolidine-1-carboxamide

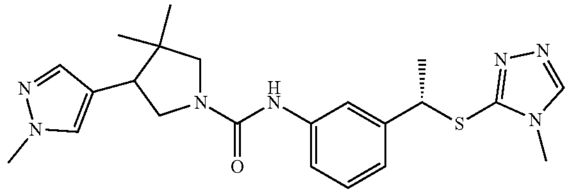 [SMILES: C[C@H](Sc1nncn1C)c1cccc(NC(=O)N2CC(c3cnn(C)c3)C(C)(C)C2)c1]

The procedure for Example 39 was followed using 4-(4,4-dimethylpyrrolidin-3-yl)-1-methyl-1H-pyrazole to afford the title compound (36.2 mg, 32%). MS (ESI) calc'd for ($C_{22}H_{29}N_7OS$) $[M+1]^+$, 440.2; found, 440.2. $^1H$ NMR (300 MHz, Chloroform-d) δ 8.08 (s, 1H), 7.44-7.41 (m, 1H), 7.36 (s, 1H), 7.23-7.15 (m, 3H), 6.88 (d, J=7.5 Hz, 1H), 6.38 (s, 1H), 4.65 (q, J=7.2 Hz, 1H), 3.89-3.85 (m, 4H), 3.64-3.61 (m, 1H), 3.46-3.44 (m, 1H), 3.35-3.30 (m, 4H), 3.08-3.09 (m, 1H), 1.78 (d, J=6.9 Hz, 3H), 1.13 (s, 3H), 0.86 (s, 3H).

Example 54: 3-(hydroxymethyl)-4-methyl-N-(3-((S)-1-((4-methyl-4H-1,2,4-triazol-3-yl)thio)ethyl)phenyl)pyrrolidine-1-carboxamide

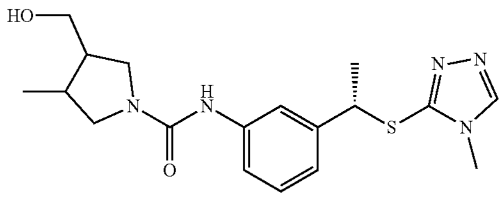 [SMILES: CC1CN(C(=O)Nc2cccc([C@H](C)Sc3nncn3C)c2)CC1CO]

The procedure for Example 39 was followed using (4-methylpyrrolidin-3-yl)methanol to afford the title compound (18.7 mg, 29%). MS (ESI) calc'd for ($C_{18}H_{25}N_5O_2S$) $[M+1]^+$, 376.2; found, 376.2. $^1H$ NMR (400 MHz, Chloroform-d) δ 8.18 (s, 1H), 7.42 (d, J=8.0 Hz, 1H), 7.23-7.14 (m, 2H), 6.90 (d, J=7.6 Hz, 1H), 6.46 (s, 1H), 4.66 (q, J=6.8 Hz, 1H), 3.84-3.71 (m, 3H), 3.65-3.61 (m, 1H), 3.41-3.37 (m, 1H), 3.28 (s, 3H), 3.08-3.04 (m, 1H), 2.20-2.09 (m, 2H), 1.77 (d, J=7.2 Hz, 3H), 1.12 (d, J=7.2 Hz, 3H).

Example 55: (S)-5-(3-(1-(4-methyl-4H-1,2,4-triazol-3-ylthio)ethyl)phenyl)-3-p-tolylisoxazole

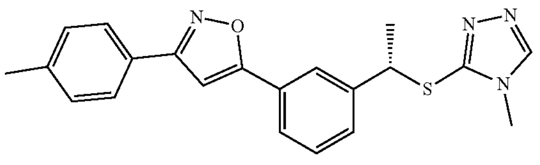 [SMILES: Cc1ccc(-c2cc(-c3cccc([C@H](C)Sc4nncn4C)c3)on2)cc1]

Step 1: (R)-1-(3-bromophenyl) ethanol. To a solution of 1-(3-bromophenyl)ethan-1-one (20.0 g, 100 mmol) and (S)-3,3-Diphenyl-1-methylpyrrolidino[1,2-c]-1,3,2-oxazaborole (10 mL, 10 mmol, 1 M in toluene) in toluene (200 mL) was added $BH_3 \cdot Me_2S$ (10 mL, 100 mmol, 10 M in THF) dropwise at 30° C. The mixture was stirred at 30° C. for 7 h, and then quenched by the addition of $H_2O$. General Workup Procedure followed by Chromatography A afforded the title compound (11.0 g, 54%). MS (ESI) calc'd for ($C_8H_9BrO$) $[M+H]^+$, 201.0; found, 201.0.

Step 2: (S)-3-(1-(3-bromophenyl)ethylthio)-4-methyl-4H-1,2,4-triazole. To a mixture of (R)-1-(3-bromophenyl) ethanol (20.0 g, 0.10 mol), 4-methyl-4H-1,2,4-triazole-3-thiol (12.1 g, 0.11 mmol) and triphenylphosphine (39.3 g, 0.15 mol) in THE (300 mL) was added diisopropyl azodicarboxylate (30.3 g, 0.15 mol) dropwise at 0° C. under nitrogen atmosphere. The mixture was stirred at 0° C. for 4 h. The reaction was quenched by the addition of $H_2O$. General Workup Procedure followed by Chromatography B afforded the title compound (17.3 g, 58%). MS (ESI) calc'd for ($C_{11}H_{12}BrN_3S$) $[M+H]^+$, 298.0; found, 298.0.

Step 3: (S)-4-methyl-3-(1-(3-((trimethylsilyl)ethynyl)phenyl)ethylthio)-4H-1,2,4-triazole. A Sonogashira coupling was performed following the procedure for Examples 72 and 73, Step 1 using (S)-3-(1-(3-bromophenyl)ethylthio)-4-methyl-4H-1,2,4-triazole (800 mg, 8.41 mmol) to afford the title compound (800 mg, 74%). MS (ESI) calc'd for ($C_{16}H_{21}N_3SSi$) $[M+H]^+$, 316.1; found, 316.1.

Step 4: (S)-3-(1-(3-ethynylphenyl)ethylthio)-4-methyl-4H-1,2,4-triazole. To a solution of (S)-4-methyl-3-(1-(3-((trimethylsilyl)ethynyl)phenyl)ethylthio)-4H-1,2,4-triazole (100 mg, 0.34 mmol) in methanol (2 mL) was added potassium carbonate (140 mg, 1.02 mmol). The mixture was stirred at room temperature for 2 h and then filtered. The filtrate was diluted with water. General Workup Procedure followed by Chromatography B afforded the title compound (46 mg, 56%). MS (ESI) calc'd for ($C_{13}H_{13}N_3S$) $[M+H]^+$, 244.1; found, 244.1.

Step 5: (S)-5-(3-(1-(4-methyl-4H-1,2,4-triazol-3-ylthio)ethyl)phenyl)-3-p-tolylisoxazole. To a solution of 4-methylbenzaldehyde oxime (167 mg, 1.23 mmol) in DMF (2 mL) was added NCS (165 mg, 1.23 mmol). The mixture was stirred at 60° C. for 1 h. Then TEA (187 mg, 1.85 mmol) and (S)-3-(1-(3-ethynylphenyl)ethylthio)-4-methyl-4H-1,2,4-triazole (150 mg, 0.62 mmol) were added to the above mixture at 0° C. The resulting mixture was stirred at room temperature for another 16 h. General Workup Procedure followed by Chromatography C afforded the title compound (23.7 mg, 10%). MS (ESI) calc'd for ($C_{21}H_{20}N_4OS$) $[M+Na]^+$, 399.1; found, $[M+Na]^+$, 399.0. $^1H$ NMR (400 MHz, Chloroform-d) δ 8.19 (s, 1H), 7.82-7.71 (m, 4H), 7.46-7.33 (m, 2H), 7.30-7.33 (m, 2H), 6.83 (s, 1H), 4.93-4.89 (m, 1H), 3.32 (s, 3H), 2.44 (s, 3H), 1.87 (d, J=7.2 Hz, 3H).

Example 56: 4-methyl-3-[[(1S)-1-[3-[3-(3-methylphenyl)-1,2-oxazol-5-yl]phenyl]ethyl]sulfanyl]-4H-1,2,4-triazole

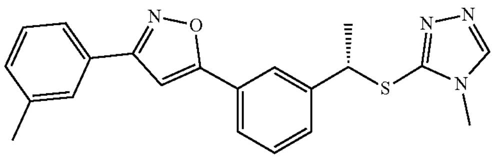 [SMILES: Cc1cccc(-c2cc(-c3cccc([C@H](C)Sc4nncn4C)c3)on2)c1]

Step 1: 3-methylbenzaldehyde oxime. To a solution of 3-methylbenzaldehyde (3.0 g, 25 mmol), $NH_2OH \cdot HCl$ (2.6 g, 38 mmol) in ethanol (30 mL) was added sodium acetate (3.1 g, 38 mmol). The mixture was stirred at reflux for 1.5 h, and then quenched by the addition of water. The aqueous layer was acidified to pH~6 by HCl (1 N) and extracted with DCM. The organic layers were dried over anhydrous sodium sulfate and filtered. The filtrate was concentrated under vacuum to afford the title compound (3.4 g, crude), which was used without purification. MS (ESI) calc'd for ($C_8H_9NO$) $[M+H]^+$, 136.1; found, 136.1.

Step 2: 4-methyl-3-[[(1S)-1-[3-[3-(3-methylphenyl)-1,2-oxazol-5-yl]phenyl]ethyl]sulfanyl]-4H-1,2,4-triazole. To a solution of 3-methylbenzaldehyde oxime (150 mg, 1.11 mmol) and 3-[[(1S)-1-(3-ethynylphenyl)ethyl]sulfanyl]-4-methyl-4H-1,2,4-triazole (180 mg, 0.74 mmol) in methanol (5 mL) and $H_2O$ (1 mL) was added [bis(trifluoroacetoxy)iodo]benzene (480 mg, 1.12 mmol) in three portions in 2 h. The mixture was stirred at room temperature for 2 h under nitrogen atmosphere. The reaction mixture was adjusted by TEA to pH~7 and then concentrated under vacuum. Chromatography C afforded the title compound (35.0 mg, 8%). MS (ESI) calc'd for ($C_{21}H_{20}N_4OS$) $[M+H]^+$, 377.1; found 377.1. $^1H$ NMR (400 MHz, DMSO-$d_6$) δ 8.54 (s, 1H), 7.85 (t, J=1.6 Hz, 1H), 7.83-7.80 (m, 1H), 7.76 (d, J=1.6 Hz, 1H), 7.75-7.69 (m, 1H), 7.63 (s, 1H), 7.51 (t, J=7.6 Hz, 1H), 7.48-7.41 (m, 2H), 7.35 (d, J=7.6 Hz, 1H), 4.81-4.76 (m, 1H), 3.38 (s, 3H), 2.41 (s, 3H), 1.73 (d, J=7.2 Hz, 3H).

Example 57: (S)-3-(4-chlorophenyl)-5-(3-(1-((4-methyl-4H-1,2,4-triazol-3-yl)thio)ethyl)phenyl)isoxazole

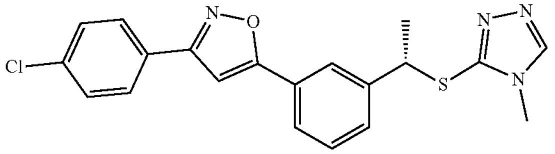 [SMILES: C[C@H](Sc1nncn1C)c1cccc(-c2cc(-c3ccc(Cl)cc3)no2)c1]

Step 1: 4-chlorobenzaldehyde oxime. Following the procedure of Example 56, using 4-chlorobenzaldehyde the title compound (20.0 mg, 8%) was obtained. MS (ESI) calc'd for ($C_{20}H_{17}ClN_4OS$) $[M+H]^+$, 396.9; found, 397.1, $[M+Na]^+$, 418.9. $^1H$ NMR (300 MHz, DMSO-$d_6$) δ 8.54 (s, 1H), 8.02-7.91 (m, 2H), 7.88-7.76 (m, 2H), 7.72-7.60 (m, 3H), 7.58-7.42 (m, 2H), 4.81-4.76 (m, 1H), 3.38 (s, 3H), 1.73 (d, J=7.2 Hz, 3H).

Example 58: 3-[[(1S)-1-[3-[3-(3-chlorophenyl)-1,2-oxazol-5-yl]phenyl]ethyl]sulfanyl]-4-methyl-4H-1,2,4-triazole

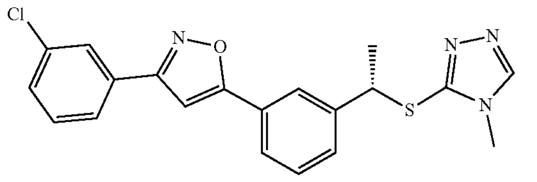 [SMILES: C[C@H](Sc1nncn1C)c1cccc(-c2cc(-c3cccc(Cl)c3)no2)c1]

Following the procedure of Example 56, using 3-chlorobenzaldehyde the title compound (35.0 mg, 9%) was obtained. MS (ESI) calc'd for ($C_{20}H_{17}ClN_4OS$) $[M+H]^+$, 397.0; found 397.0. $^1H$ NMR (400 MHz, DMSO-$d_6$) δ 8.54 (s, 1H), 7.98 (d, J=2.0 Hz, 1H), 7.95-7.88 (m, 1H), 7.85 (d, J=1.6 Hz, 1H), 7.83-7.79 (m, 1H), 7.74 (s, 1H), 7.65-7.57 (m, 2H), 7.51 (d, J=7.6 Hz, 1H), 7.48-7.45 (m, 1H), 4.79 (q, J=7.2 Hz, 1H), 3.38 (s, 3H), 1.73 (d, J=7.2 Hz, 3H).

Example 59: (S)-3-(4-methoxyphenyl)-5-(3-(1-((4-methyl-4H-1,2,4-triazol-3-yl)thio)ethyl)phenyl)isoxazole

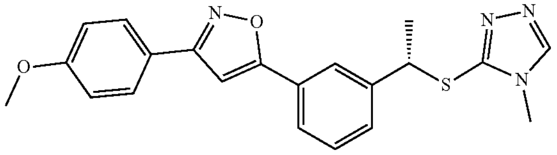 [SMILES: COc1ccc(-c2cc(-c3cccc([C@H](C)Sc4nncn4C)c3)on2)cc1]

Following the procedure of Example 56, using 4-methoxybenzaldehyde the title compound (35.2 mg, 15%) was obtained. MS (ESI) calc'd for ($C_{21}H_{20}N_4O_2S$) $[M+H]^+$, 393.1; found, 392.9. $^1H$ NMR (300 MHz, Chloroform-d) δ 8.14 (s, 1H), 7.89-7.77 (m, 2H), 7.80-7.68 (m, 2H), 7.48-7.31 (m, 2H), 7.08-6.97 (m, 2H), 6.80 (s, 1H), 4.89 (q, J=7.2 Hz, 1H), 3.90 (s, 3H), 3.31 (s, 3H), 1.88 (d, J=7.2 Hz, 3H).

Example 60: (S)-3-(3-methoxyphenyl)-5-(3-(1-((4-methyl-4H-1,2,4-triazol-3-yl)thio)ethyl)phenyl)isoxazole

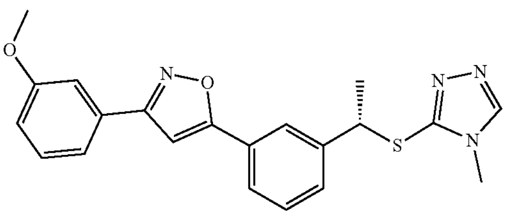 [SMILES: COc1cccc(-c2cc(-c3cccc([C@H](C)Sc4nncn4C)c3)on2)c1]

Following the procedure of Example 56, using 3-methoxybenzaldehyde the title compound (59.1 mg, 15%) was obtained. MS (ESI) calc'd for ($C_{21}H_{20}N_4O_2S$) $[M+H]^+$, 393.1; found, 393.1. $^1H$ NMR (400 MHz, DMSO-$d_6$) δ 8.54 (s, 1H), 7.87-7.77 (m, 2H), 7.67 (s, 1H), 7.56-7.42 (m, 5H), 7.12-7.09 (m, 1H), 4.81-4.76 (m, 1H), 3.86 (s, 3H), 3.38 (s, 3H), 1.73 (d, J=6.8 Hz, 3H).

Example 61: (S)-4-(5-(3-(1-(4-methyl-4H-1,2,4-triazol-3-ylthio)ethyl)phenyl)isoxazol-3-yl)benzonitrile

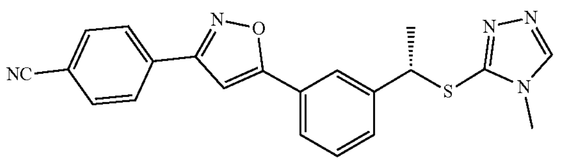 [SMILES: C[C@H](Sc1nncn1C)c1cccc(-c2cc(-c3ccc(C#N)cc3)no2)c1]

Following the procedure of Example 56, using 4-cyanobenzaldehyde the title compound (27.3 mg, 10%) was obtained. MS (ESI) calc'd for ($C_{21}H_{17}N_5OS$) $[M+H]^+$, 388.0; found, 388.0. $^1H$ NMR (300 MHz, DMSO-$d_6$) δ 8.54 (s, 1H), 8.18-8.02 (m, 4H), 7.89-7.75 (m, 3H), 7.59-7.43 (m, 2H), 4.81-4.76 (m, 1H), 3.38 (s, 3H), 1.73 (d, J=7.2 Hz, 3H).

Example 62: (S)-3-(5-(3-(1-(4-methyl-4H-1,2,4-triazol-3-ylthio)ethyl)phenyl)isoxazol-3-yl)benzonitrile

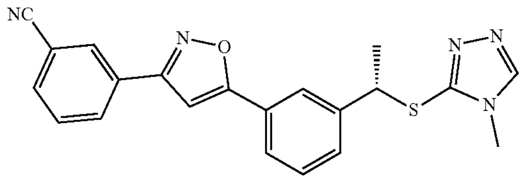 [SMILES: C[C@H](Sc1nncn1C)c1cccc(-c2cc(-c3cccc(C#N)c3)no2)c1]

Following the procedure of Example 56, using 3-cyanobenzaldehyde the title compound (43.2 mg, 16%) was obtained. MS (ESI) calc'd for ($C_{21}H_{17}N_5OS$) $[M+H]^+$, 388.1; found, 388.1. $^1H$ NMR (400 MHz, DMSO-$d_6$) δ 8.54 (s, 1H), 8.41-8.37 (m, 1H), 8.29-8.26 (m, 1H), 8.04-8.01 (m, 1H), 7.87-7.74 (m, 4H), 7.57-7.43 (m, 2H), 4.81-4.76 (m, 1H), 3.38 (s, 3H), 1.73 (d, J=7.2 Hz, 3H).

Example 63: 4-(5-{3-[(1S)-1-[(4-methyl-4H-1,2,4-triazol-3-yl)sulfanyl]ethyl]phenyl}-1,2-oxazol-3-yl)benzoic acid

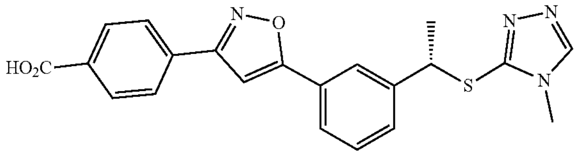 [SMILES: C[C@H](Sc1nncn1C)c1cccc(-c2cc(-c3ccc(C(=O)O)cc3)no2)c1]

Step 1: methyl 4-(5-[3-[(1S)-1-[(4-methyl-4H-1,2,4-triazol-3-yl)sulfanyl]ethyl]phenyl]-1,2-oxazol-3-yl)benzoate. Following the procedure of Example 56, using methyl 4-formylbenzoate the title compound (200 mg, 25%) was obtained. MS (ESI) calc'd for ($C_{22}H_{20}N_4O_3S$) $[M+H]^+$, 421.1; found 421.1. $^1H$ NMR (300 MHz, DMSO-$d_6$) δ 8.55 (s, 1H), 8.16-8.08 (m, 4H), 7.91-7.82 (m, 2H), 7.77 (s, 1H), 7.60-7.41 (m, 2H), 4.80 (d, J=7.2 Hz, 1H), 3.91 (s, 3H), 3.38 (s, 3H), 1.73 (d, J=7.2 Hz, 3H).

Step 2: 4-(5-{3-[(1S)-1-[(4-methyl-4H-1,2,4-triazol-3-yl)sulfanyl]ethyl]phenyl}-1,2-oxazol-3-yl)benzoic acid. To a solution of methyl 4-(5-[3-[(1S)-1-[(4-methyl-4H-1,2,4-triazol-3-yl)sulfanyl]ethyl]phenyl]-1,2-oxazol-3-yl)benzoate (100 mg, 0.24 mmol) in THE (1.5 mL) was added a solution of LiOH (11 mg, 0.48 mmol) in $H_2O$ (0.25 mL) dropwise at 0° C. The mixture was stirred at room temperature for 3 h. The reaction mixture was acidified by HCl (2 N) to pH~3. General Workup Procedure followed by Chromatography C afforded the title compound (60 mg, 62%). MS (ESI) calc'd for ($C_{21}H_{18}N_4O_3S$) $[M+H]^+$, 407.1; found 406.8. $^1H$ NMR (400 MHz, DMSO-$d_6$) δ 8.49 (s, 1H), 8.12-8.08 (m, 4H), 7.83-7.79 (m, 2H), 7.65 (s, 1H), 7.48-7.42 (m, 2H), 4.81-4.76 (m, 1H), 3.34 (s, 3H), 1.69 (d, J=7.2 Hz, 3H).

Example 64: (S)-(4-(5-(3-(1-(4-methyl-4H-1,2,4-triazol-3-ylthio)ethyl)phenyl)isoxazol-3-yl)phenyl)methanol

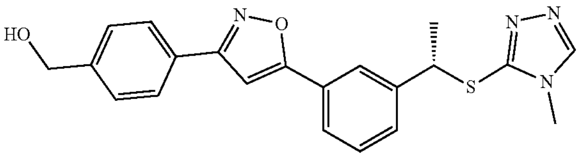 [SMILES: C[C@H](Sc1nncn1C)c1cccc(-c2cc(-c3ccc(CO)cc3)no2)c1]

To a solution of methyl 4-(5-[3-[(1S)-1-[(4-methyl-4H-1,2,4-triazol-3-yl)sulfanyl]ethyl]phenyl]-1,2-oxazol-3-yl)benzoate (50 mg, 0.12 mmol) in THE (3 mL) and methanol (1 mL) was added sodium borohydride (32 mg, 0.84 mmol). The mixture was stirred at 60° C. for 4 h before concentration under vacuum. Chromatography C afforded the title compound (20.7 mg, 44%). MS (ESI) calc'd for ($C_{21}H_{20}N_4O_2S$) $[M+H]^+$, 393.1; found, 392.9. $^1H$ NMR (400 MHz, DMSO-$d_6$) δ 8.53 (s, 1H), 7.93-7.77 (m, 4H), 7.62 (s, 1H), 7.55-7.41 (m, 4H), 5.32 (t, J=5.6 Hz, 1H), 4.81-4.76 (m, 1H), 4.58 (d, J=4.4 Hz, 2H), 3.38 (s, 3H), 1.73 (d, J=7.2 Hz, 3H).

Example 65: (S)—N-methyl-4-(5-(3-(1-(4-methyl-4H-1,2,4-triazol-3-ylthio)ethyl)phenyl)isoxazol-3-yl)benzamide

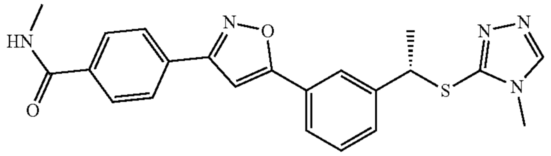 [SMILES: CNC(=O)c1ccc(-c2cc(-c3cccc([C@H](C)Sc4nncn4C)c3)on2)cc1]

To a mixture of $CH_3NH_2$·HCl (25 mg, 0.37 mmol) in DMF (3 mL) were added DIEA (143 mg, 1.11 mmol), (S)-4-(5-(3-(1-(4-methyl-4H-1,2,4-triazol-3-ylthio)ethyl)phenyl)isoxazol-3-yl)benzoic acid (150 mg, 0.37 mmol), EDCI (106 mg, 0.55 mmol), and hydroxybenzotriazole (75 mg, 0.55 mmol). The mixture was stirred at room temperature for 2 h. Chromatography C afforded the title compound (24.6 mg, 16%). MS (ESI) calc'd for ($C_{22}H_{21}N_5O_2S$) $[M+H]^+$, 420.1; found, 420.1. $^1H$ NMR (400 MHz, DMSO-$d_6$) δ 8.63-8.58 (m, 1H), 8.54 (s, 1H), 8.04-7.99 (m, 4H), 7.89-7.78 (m, 2H), 7.71 (s, 1H), 7.56-7.43 (m, 2H), 4.81-4.76 (m, 1H), 3.38 (s, 3H), 2.82 (d, J=4.4 Hz, 3H), 1.73 (d, J=7.2 Hz, 3H).

Example 66: ((S)-5-(3-(1-(4-methyl-4H-1,2,4-triazol-3-yl)thio)ethyl)phenyl)-3-(4-(methylsulfonyl)phenyl)isoxazole

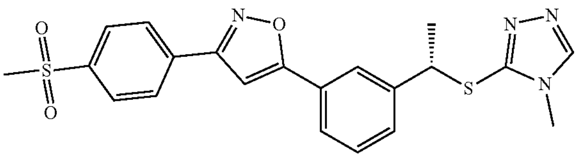 [SMILES: C[C@H](Sc1nncn1C)c1cccc(-c2cc(-c3ccc(S(C)(=O)=O)cc3)no2)c1]

Following the procedure of Example 56, using 4-(methylsulfonyl)benzaldehyde the title compound (21.1 mg, 10%) was obtained. MS (ESI) calc'd for ($C_{21}H_{20}N_4O_3S_2$) $[M+H]^+$, 441.1; found, 441.0. $^1H$ NMR (300 MHz, DMSO-$d_6$) δ 8.54 (s, 1H), 8.33-8.22 (m, 2H), 8.22-8.07 (m, 2H), 7.92-7.77 (m, 3H), 7.59-7.43 (m, 2H), 4.81-4.76 (m, 1H), 3.39 (s, 3H), 3.31 (s, 3H), 1.74 (d, J=7.2 Hz, 3H).

Examples 67 and 68: (S)-5-(3-(1-((4-methyl-4H-1,2,4-triazol-3-yl)thio)ethyl)phenyl)-3-phenylisoxazole and (R)-5-(3-(1-((4-methyl-4H-1,2,4-triazol-3-yl)thio)ethyl)phenyl)-3-phenylisoxazole

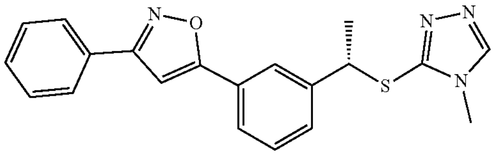

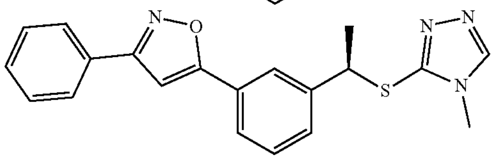

Step 1: 1-(3-(3-phenylisoxazol-5-yl)phenyl)ethan-1-one. The procedure of Example 55, Step 5 was followed using benzaldehyde oxime and 1-(3-ethynylphenyl)ethan-1-one to give the title compound (56 mg).

Step 2: 1-(3-(3-phenylisoxazol-5-yl)phenyl)ethan-1-ol. 1-(3-(3-phenylisoxazol-5-yl)phenyl)ethan-1-one (56 mg, 0.21 mmol) was dissolved in methanol (1 mL) at 0° C. Sodium borohydride (16 mg, 0.43 mmol) in methanol (0.5 mL) was added. Reaction was stirred for 1 h at 0° C. Water and DCM were added and the layers were separated. The crude product was extracted two more times with DCM and once with chloroform: isopropyl alcohol (2:1). The combined organic layers were dried over anhydrous sodium sulfate. After filtration and removal of solvent, the crude material was purified by silica gel column chromatography using a gradient of EtOAc in DCM to the title compound (52 mg, 93%).

Step 3: 5-(3-(1-((4-methyl-4H-1,2,4-triazol-3-yl)thio)ethyl)phenyl)-3-phenylisoxazole. The procedure of Example 55, Step 2 was followed using 1-(3-(3-phenylisoxazol-5-yl)phenyl)ethan-1-ol (52 mg, 0.20 mmol) to give the title compound (46 mg, 64%). $^1$H NMR (500 MHz, DMSO-$d_6$) δ 8.52 (s, 1H), 8.00-7.90 (m, 2H), 7.84 (d, J=1.8 Hz, 1H), 7.81 (dt, J=7.6, 1.5 Hz, 1H), 7.63 (s, 1H), 7.60-7.47 (m, 3H), 7.44 (dt, J=7.7, 1.5 Hz, 1H), 4.78 (q, J=7.0 Hz, 1H), 3.37 (s, 2H), 1.72 (d, J=7.0 Hz, 3H). MS (ESI) calc'd for ($C_{20}H_{18}N_4OS$) $[M+H]^+$, 363; found, 363.

Step 4: (S)-5-(3-(1-((4-methyl-4H-1,2,4-triazol-3-yl)thio)ethyl)phenyl)-3-phenylisoxazole and (R)-5-(3-(1-((4-methyl-4H-1,2,4-triazol-3-yl)thio)ethyl)phenyl)-3-phenylisoxazole. The racemic 5-(3-(1-((4-methyl-4H-1,2,4-triazol-3-yl)thio)ethyl)phenyl)-3-phenylisoxazole was SFC separated using an IG column and eluting with methanol:acetonitrile (7:3)—$CO_2$ to give (S)-5-(3-(1-((4-methyl-4H-1,2,4-triazol-3-yl)thio)ethyl)phenyl)-3-phenylisoxazole (14 mg, 0.039 mmol) and (R)-5-(3-(1-((4-methyl-4H-1,2,4-triazol-3-yl)thio)ethyl)phenyl)-3-phenylisoxazole (15 mg, 0.041 mmol).

(S)-5-(3-(1-((4-methyl-4H-1,2,4-triazol-3-yl)thio)ethyl)phenyl)-3-phenylisoxazole. $^1$H NMR (500 MHz, DMSO-$d_6$) δ 8.52 (s, 1H), 7.95-7.90 (m, 2H), 7.84 (t, J=1.8 Hz, 1H), 7.81 (dt, J=7.6, 1.4 Hz, 1H), 7.63 (s, 1H), 7.60-7.52 (m, 3H), 7.50 (t, J=7.7 Hz, 1H), 7.44 (dt, J=7.8, 1.5 Hz, 1H), 4.78 (q, J=7.0 Hz, 1H), 3.37 (s, 3H), 1.72 (d, J=7.0 Hz, 3H). MS (ESI) calc'd for ($C_{20}H_{18}N_4OS$) $[M+H]^+$, 363; found, 363.

(R)-5-(3-(1-((4-methyl-4H-1,2,4-triazol-3-yl)thio)ethyl)phenyl)-3-phenylisoxazole. $^1$H NMR (500 MHz, DMSO-$d_6$) δ 8.52 (s, 1H), 7.94-7.90 (m, 2H), 7.84 (t, J=1.8 Hz, 1H), 7.81 (dt, J=7.6, 1.4 Hz, 1H), 7.63 (s, 1H), 7.59-7.52 (m, 3H), 7.50 (t, J=7.6 Hz, 1H), 7.44 (dt, J=7.8, 1.5 Hz, 1H), 4.78 (q, J=7.0 Hz, 1H), 3.37 (s, 3H), 1.72 (d, J=7.0 Hz, 3H). MS (ESI) calc'd for ($C_{20}H_{18}N_4OS$) $[M+H]^+$, 363; found, 363.

Example 69: 5-(3-(1-((4-methyl-4H-1,2,4-triazol-3-yl)thio)ethyl)phenyl)-3-(3-(trifluoromethyl)phenyl)isoxazole

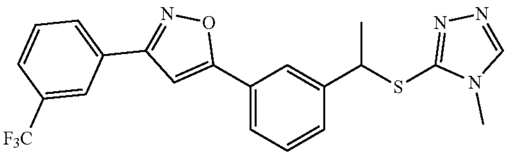 [SMILES: CC(Sc1nncn1C)c1cccc(-c2cc(-c3cccc(C(F)(F)F)c3)no2)c1]

Step 1: 1-(3-((trimethylsilyl)ethynyl)phenyl)ethan-1-one. The procedure of Example 55, Step 3 was followed using 1-(3-iodophenyl)ethan-1-one (200 μL, 1.4 mmol), and the title compound was obtained (199 mg, 64%).

Step 2: 1-(3-((trimethylsilyl)ethynyl)phenyl)ethan-1-ol. The ketone reduction was performed in a similar fashion to Examples 67 and 68, Step 2 to give the crude title compound, which was used without purification.

Step 3: 4-methyl-3-((1-(3-((trimethylsilyl)ethynyl)phenyl)ethyl)thio)-4H-1,2,4-triazole. A Mitsunobu reaction was performed following the procedure for Example 55, Step 2 to give the title compound (180 mg, 63% over 2 steps).

Step 4: 3-((1-(3-ethynylphenyl)ethyl)thio)-4-methyl-4H-1,2,4-triazole. Deprotection of the TMS group was performed following the procedure for Example 55, Step 4 to give 3-((1-(3-ethynylphenyl)ethyl)thio)-4-methyl-4H-1,2,4-triazole (139 mg, 100%).

Step 5: 5-(3-(1-((4-methyl-4H-1,2,4-triazol-3-yl)thio)ethyl)phenyl)-3-(3-(trifluoromethyl)phenyl)isoxazole. An isoxazole formation reaction was performed following the procedure for Example 55, Step 1 using 3-((1-(3-ethynylphenyl)ethyl)thio)-4-methyl-4H-1,2,4-triazole (30 mg, 0.12 mmol) and 3-(trifluoromethyl)benzaldehyde oxime (30 mg, 0.16 mmol) to give the title compound (15 mg, 29%). $^1$H NMR (500 MHz, DMSO-$d_6$) δ 8.54 (s, 1H), 8.27-8.21 (m, 2H), 7.92 (d, J=7.8 Hz, 1H), 7.86 (t, J=1.8 Hz, 1H), 7.84-7.77 (m, 3H), 7.52 (t, J=7.6 Hz, 1H), 7.46 (dt, J=7.9, 1.5 Hz, 1H), 4.79 (q, J=7.0 Hz, 1H), 3.37 (s, 3H), 1.72 (d, J=7.0 Hz, 3H). MS (ESI) calc'd for ($C_{21}H_{17}F_3N_4OS$) $[M+H]^+$, 431; found, 431.

Example 70: 5-(3-(1-((4-methyl-4H-1,2,4-triazol-3-yl)thio)ethyl)phenyl)-3-(pyridin-2-yl)isoxazole

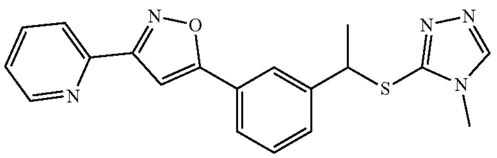 [SMILES: CC(Sc1nncn1C)c1cccc(-c2cc(-c3ccccn3)no2)c1]

Following the procedure for Example 55, Step 5 using 3-((1-(3-ethynylphenyl)ethyl)thio)-4-methyl-4H-1,2,4-triazole (17 mg, 0.069 mmol) and picolinaldehyde oxime (19 mg, 0.16 mmol) gave the title compound (13 mg, 51%). $^1$H NMR (500 MHz, DMSO-$d_6$) δ 8.75 (ddd, J=4.8, 1.8, 1.0 Hz, 1H), 8.52 (s, 1H), 8.07 (dt, J=7.9, 1.2 Hz, 1H), 7.99 (td, J=7.7, 1.8 Hz, 1H), 7.91-7.85 (m, 2H), 7.60 (s, 1H), 7.55 (ddd, J=7.5, 4.8, 1.2 Hz, 1H), 7.52-7.41 (m, 2H), 4.77 (q, J=6.9 Hz, 1H), 3.36 (s, 3H), 1.72 (d, J=7.0 Hz, 3H). MS (ESI) calc'd for ($C_{19}H_{17}N_5OS$) $[M+H]^+$, 364; found, 364.

Example 71: 5-(4-(1-((4-methyl-4H-1,2,4-triazol-3-yl)thio)ethyl)pyridin-2-yl)-3-phenylisoxazole

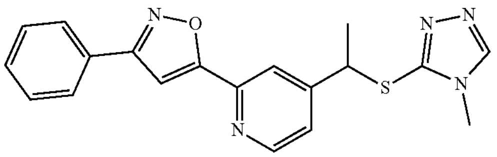

Step 1: 1-(2-((trimethylsilyl)ethynyl)pyridin-4-yl)ethan-1-one. Following the procedure for Example 55, Step 3 using 1-(2-chloropyridin-4-yl)ethan-1-one (502 mg, 3.2 mmol), the title compound was obtained (456 mg, 65%).

Step 2: 1-(2-ethynylpyridin-4-yl)ethan-1-ol. Ketone reduction following the procedure for Example 67 and 68, Step 2 gave the TMS deprotected title compound (78 mg, 25%).

Step 3: 2-ethynyl-4-(1-((4-methyl-4H-1,2,4-triazol-3-yl)thio)ethyl)pyridine. A Mitsunobu reaction was performed following the procedure for Example 55, Step 2 to give the title compound (92 mg, 71%).

Step 4: 5-(4-(1-((4-methyl-4H-1,2,4-triazol-3-yl)thio)ethyl)pyridin-2-yl)-3-phenylisoxazole. An isoxazole formation reaction was performed following the procedure for Example 55, Step 1 using 2-ethynyl-4-(1-((4-methyl-4H-1,2,4-triazol-3-yl)thio)ethyl)pyridine (35 mg, 0.14 mmol) and benzaldehyde oxime (41 μL, 0.38 mmol) to give 5-(4-(1-((4-methyl-4H-1,2,4-triazol-3-yl)thio)ethyl)pyridin-2-yl)-3-phenylisoxazole (20 mg, 38%). $^1$H NMR (500 MHz, DMSO-$d_6$) δ 8.65 (dd, J=5.0, 0.8 Hz, 1H), 8.54 (s, 1H), 7.97

(dd, J=7.4, 2.2 Hz, 2H), 7.93 (d, J=1.6 Hz, 1H), 7.70 (s, 1H), 7.54 (dq, J=4.7, 2.9, 2.3 Hz, 3H), 7.46 (dd, J=5.1, 1.7 Hz, 1H), 4.81 (q, J=7.1 Hz, 1H), 3.43 (s, 3H), 1.72 (d, J=7.1 Hz, 3H). MS (ESI) calc'd for ($C_{19}H_{17}N_5OS$) $[M+H]^+$, 364; found, 364.

Example 72 and 73: (S)-4-(4-chlorophenyl)-2-(3-(1-((4-methyl-4H-1,2,4-triazol-3-yl)thio)ethyl)phenyl)-2H-1,2,3-triazole and (S)-4-(4-chlorophenyl)-1-(3-(1-((4-methyl-4H-1,2,4-triazol-3-yl)thio)ethyl)phenyl)-1H-1,2,3-triazole

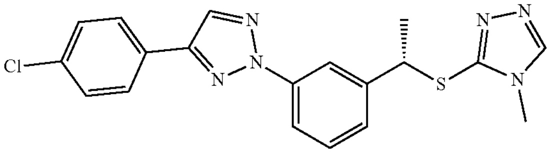

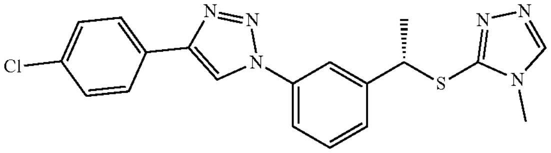

Step 1: [2-(4-chlorophenyl)ethynyl]trimethylsilane. A degassed solution of 1-bromo-4-chlorobenzene (5.0 g, 26.12 mmol), ethynyltrimethylsilane (3.9 g, 39.40 mmol), CuI (0.5 g, 2.61 mmol), and $Pd(PPh_3)_2Cl_2$ (1.8 g, 2.61 mmol) in TEA (100 mL) was stirred at 60° C. for 16 h under nitrogen atmosphere. The solids were filtered off and the filtrate was concentrated under vacuum. The residue was dissolved in EtOAc and washed with brine. The organic layer was dried over anhydrous sodium sulfate, filtered, and concentrated under vacuum. The residue was purified by Chromatography A to afford the title compound (4.0 g, 73%).

Step 2: 1-chloro-4-ethynylbenzene. TMS deprotection was performed following the procedure for Example 55, Step 4 to afford the title compound (2.4 g, 37%).

Step 3: 4-(4-chlorophenyl)-2H-1,2,3-triazole. A mixture of 1-chloro-4-ethynylbenzene (0.6 g, 4.4 mmol), $TMSN_3$ (5.0 g, 44 mmol), CuI (84 mg, 0.44) in MeOH (4 mL), and DMF (20 mL) was stirred at 100° C. for 16 h under nitrogen atmosphere. The mixture was diluted with EtOAc and washed with HCl (2 N). The organic layer was dried over anhydrous sodium sulfate, filtered, and concentrated under vacuum. The residue was purified by Chromatography C to afford the title compound (300 mg, 36%). MS (ESI) calc'd for ($C_8H_6ClN_3$) $[M+H]^+$, 180.0; found, 180.0.

Step 4: (S)-4-(4-chlorophenyl)-2-(3-(1-((4-methyl-4H-1,2,4-triazol-3-yl)thio)ethyl)phenyl)-2H-1,2,3-triazole and (S)-4-(4-chlorophenyl)-1-(3-(1-((4-methyl-4H-1,2,4-triazol-3-yl)thio)ethyl)phenyl)-1H-1,2,3-triazole. To a degassed solution of 4-(4-chlorophenyl)-2H-1,2,3-triazole (100 mg, 0.56 mmol) in DMSO (4 mL) were added 3-[[(1S)-1-(3-bromophenyl)ethyl]sulfanyl]-4-methyl-4H-1,2,4-triazole (200 mg, 0.67 mmol), (trans)-$N^1$,$N^2$-dimethylcyclohexane-1,2-diamine (16 mg, 0.11 mmol), potassium carbonate (193 mg, 1.40 mmol), and CuI (11 mg, 0.056 mmol). The mixture was stirred at 80° C. for 16 h under nitrogen atmosphere. General Workup Procedure followed by Chromatography C afforded (S)-4-(4-chlorophenyl)-2-(3-(1-(4-methyl-4H-1,2,4-triazol-3-ylthio)ethyl)phenyl)-2H-1,2,3-triazole (50 mg, 23%) and (S)-4-(4-chlorophenyl)-1-(3-(1-(4-methyl-4H-1,2,4-triazol-3-ylthio)ethyl)phenyl)-1H-1,2,3-triazole (30 mg, 14%).

(S)-4-(4-chlorophenyl)-2-(3-(1-(4-methyl-4H-1,2,4-triazol-3-ylthio)ethyl)phenyl)-2H-1,2,3-triazole: MS (ESI) calc'd for ($C_{19}H_{17}ClN_6S$) $[M+H]^+$, 397.1; found, 396.8. $^1H$ NMR (400 MHz, Chloroform-d) δ 8.22 (s, 1H), 8.11 (t, J=2.0 Hz, 1H), 8.08-8.00 (m, 2H), 7.90-7.82 (m, 2H), 7.51-7.43 (m, 2H), 7.42 (t, J=8.0 Hz, 1H), 7.26-7.24 (m, 1H), 4.94 (q, J=7.2 Hz, 1H), 3.37 (s, 3H), 1.89 (d, J=7.2 Hz, 3H).

(S)-4-(4-chlorophenyl)-1-(3-(1-(4-methyl-4H-1,2,4-triazol-3-ylthio)ethyl)phenyl)-1H-1,2,3-triazole: MS (ESI) calc'd for ($C_{19}H_{17}ClN_6S$) $[M+H]^+$, 397.1; found, 396.8. $^1H$ NMR (400 MHz, Chloroform-d) δ 8.22-8.21 (m, 2H), 7.93-7.84 (m, 2H), 7.78-7.68 (m, 2H), 7.54-7.40 (m, 4H), 5.00 (q, J=7.2 Hz, 1H), 3.42 (s, 3H), 1.88 (d, J=7.2 Hz, 3H).

Example 74 and 75: (S)-4-(4-methoxyphenyl)-2-(3-(1-((4-methyl-4H-1,2,4-triazol-3-yl)thio)ethyl)phenyl)-2H-1,2,3-triazole and (S)-4-(4-methoxyphenyl)-1-(3-(1-((4-methyl-4H-1,2,4-triazol-3-yl)thio)ethyl)phenyl)-1H-1,2,3-triazole

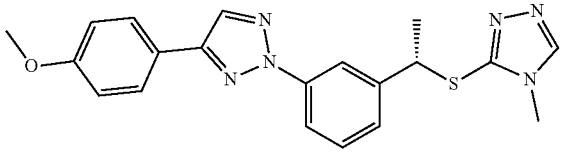

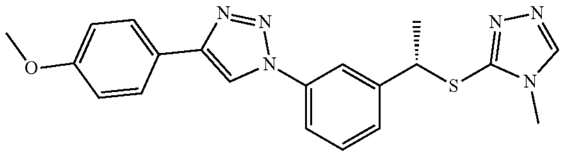

The synthesis was carried out starting with 1-bromo-4-methoxybenzene (5.0 g, 26.73 mmol), following Example 72 and 73, Steps 1 through 4 to afford the title compound (106.5 mg, 23%) and (S)-4-(1-(3-(1-(4-methyl-4H-1,2,4-triazol-3-ylthio)ethyl)phenyl)-1H-1,2,3-triazol-4-yl)benzamide (39.0 mg, 8%). [0546](S)-4-(4-methoxyphenyl)-2-(3-(1-((4-methyl-4H-1,2,4-triazol-3-yl)thio)ethyl)phenyl)-2H-1,2,3-triazole: MS (ESI) calc'd for ($C_{20}H_{20}N_6OS$) $[M+H]^+$, 393.1; found, 393.0. $^1H$ NMR (400 MHz, Chloroform-d) δ 8.17-8.07 (m, 2H), 8.07-7.98 (m, 2H), 7.89-7.81 (m, 2H), 7.39 (t, J=8.0 Hz, 1H), 7.21-7.19 (m, 1H), 7.07-6.98 (m, 2H), 4.90 (q, J=7.2 Hz, 1H), 3.89 (s, 3H), 3.33 (s, 3H), 1.89 (d, J=7.2 Hz, 3H).

(S)-4-(4-methoxyphenyl)-1-(3-(1-((4-methyl-4H-1,2,4-triazol-3-yl)thio)ethyl)phenyl)-1H-1,2,3-triazole: MS (ESI) calc'd for ($C_{20}H_{20}N_6OS$) $[M+H]^+$, 393.1; found, 393.0. $^1H$ NMR (400 MHz, Chloroform-d) δ 8.16 (s, 1H), 8.12 (s, 1H), 7.91-7.82 (m, 2H), 7.76-7.67 (m, 2H), 7.47 (t, J=8.0 Hz, 1H), 7.40-7.38 (m, 1H), 7.06-6.97 (m, 2H), 4.95 (q, J=7.2 Hz, 1H), 3.88 (s, 3H), 3.39 (s, 3H), 1.87 (d, J=7.2 Hz, 3H).

Example 76 and 77: (S)-4-(3-methoxyphenyl)-2-(3-(1-((4-methyl-4H-1,2,4-triazol-3-yl)thio)ethyl)phenyl)-2H-1,2,3-triazole and (S)-4-(3-methoxyphenyl)-1-(3-(1-((4-methyl-4H-1,2,4-triazol-3-yl)thio)ethyl)phenyl)-1H-1,2,3-triazole

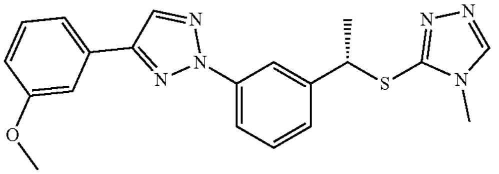

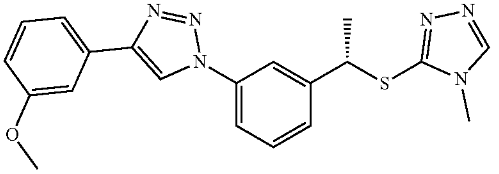

The synthesis was carried out starting with 1-bromo-3-methoxybenzene (10.0 g, 53.47 mmol), following Example 72 and 73, Steps 1 through 4 to afford 4-(3-methoxyphenyl)-2-[3-[(1S)-1-[(4-methyl-4H-1,2,4-triazol-3-yl)sulfanyl]ethyl]phenyl]-2H-1,2,3-triazole (80.2 mg, 18%) and 4-(3-methoxyphenyl)-1-{3-[(1S)-1-[(4-methyl-4H-1,2,4-triazol-3-yl)sulfanyl]ethyl]phenyl}-1H-1,2,3-triazole (32.5 mg, 7%). [0549](S)-4-(3-methoxyphenyl)-2-(3-(1-((4-methyl-4H-1,2,4-triazol-3-yl)thio)ethyl)phenyl)-2H-1,2,3-triazole: MS (ESI) calc'd for ($C_{20}H_{20}N_6OS$) $[M+H]^+$, 393.2; found, 393.0. $^1H$ NMR (300 MHz, DMSO-$d_6$) δ 8.66 (s, 1H), 8.54 (s, 1H), 8.00-7.97 (m, 2H), 7.60-7.54 (m, 3H), 7.52-7.47 (m, 1H), 7.44-7.36 (m, 1H), 7.05-7.01 (m, 1H), 4.84 (q, J=6.9 Hz, 1H), 3.86 (s, 3H), 3.39 (s, 3H), 1.72 (d, J=6.9 Hz, 3H).

(S)-4-(3-methoxyphenyl)-1-(3-(1-((4-methyl-4H-1,2,4-triazol-3-yl)thio)ethyl)phenyl)-1H-1,2,3-triazole: MS (ESI) calc'd for ($C_{20}H_{20}N_6OS$) $[M+H]^+$, 393.2; found, 393.0. $^1H$ NMR (300 MHz, DMSO-$d_6$) δ 9.33 (s, 1H), 8.55 (s, 1H), 7.93-7.92 (m, 1H), 7.87-7.84 (m, 1H), 7.63-7.51 (m, 3H), 7.45-7.40 (m, 2H), 6.99-7.95 (m, 1H), 4.82 (q, J=6.9 Hz, 1H), 3.85 (s, 3H), 3.41 (s, 3H), 1.74 (d, J=6.9 Hz, 3H).

Example 78 and 79: 4-(3-chlorophenyl)-2-[3-[(1S)-1-[(4-methyl-4H-1,2,4-triazol-3-yl)sulfanyl]ethyl]phenyl]-2H-1,2,3-triazole and 4-(3-chlorophenyl)-1-{3-[(1S)-1-[(4-methyl-4H-1,2,4-triazol-3-yl)sulfanyl]ethyl]phenyl}-1H-1,2,3-triazole

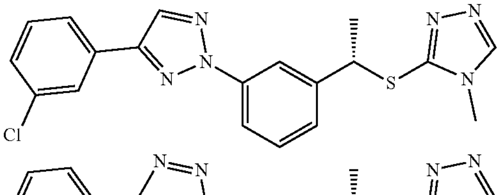

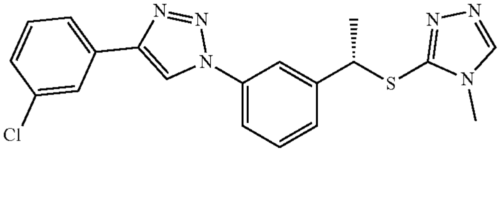

The synthesis was carried out starting with 1-bromo-3-chlorobenzene (5.0 g, 26.12 mmol), following Example 72 and 73, Steps 1 through 4 to afford 4-(3-chlorophenyl)-2-[3-[(1S)-1-[(4-methyl-4H-1,2,4-triazol-3-yl)sulfanyl]ethyl]phenyl]-2H-1,2,3-triazole (56.3 mg, 13%) and 4-(3-chlorophenyl)-1-{3-[(1S)-1-[(4-methyl-4H-1,2,4-triazol-3-yl)sulfanyl]ethyl]phenyl}-1H-1,2,3-triazole (36.7 mg, 8%).

4-(3-chlorophenyl)-2-[3-[(1S)-1-[(4-methyl-4H-1,2,4-triazol-3-yl)sulfanyl]ethyl]phenyl]-2H-1,2,3-triazole: MS (ESI) calc'd for ($C_{19}H_{17}ClN_6S$) $[M+H]^+$, 397.1; found, 396.9. $^1H$ NMR (300 MHz, DMSO-$d_6$) δ 8.73 (s, 1H), 8.56 (s, 1H), 8.08 (t, J=1.8 Hz, 1H), 8.02-7.97 (m, 3H), 7.60-7.50 (m, 3H), 7.38 (d, J=7.8 Hz, 1H), 4.85 (q, J=6.9 Hz, 1H), 3.40 (s, 3H), 1.73 (d, J=6.9 Hz, 3H).

4-(3-chlorophenyl)-1-{3-[(1S)-1-[(4-methyl-4H-1,2,4-triazol-3-yl)sulfanyl]ethyl]phenyl}-1H-1,2,3-triazole: MS (ESI) calc'd for ($C_{19}H_{17}ClN_6S$) $[M+H]^+$, 397.1; found, 396.9. $^1H$ NMR (300 MHz, DMSO-$d_6$) δ 9.43 (s, 1H), 8.55 (s, 1H), 8.00 (t, J=1.8 Hz, 1H), 7.96-7.93 (m, 2H), 7.87-7.84 (m, 1H), 7.60-7.53 (m, 2H), 7.48-7.42 (m, 2H), 4.82 (q, J=7.2 Hz, 1H), 3.41 (s, 3H), 1.74 (d, J=6.9 Hz, 3H).

Example 80: (S)-4-(2-(3-(1-(4-methyl-4H-1,2,4-triazol-3-ylthio)ethyl)phenyl)-2H-1,2,3-triazol-4-yl)benzoic acid

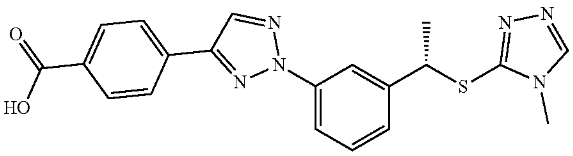 [SMILES: C[C@H](Sc1nncn1C)c1cccc(-n2ncc(-c3ccc(C(=O)O)cc3)n2)c1]

Steps 1-4: (S)-methyl 4-(2-(3-(1-(4-methyl-4H-1,2,4-triazol-3-ylthio)ethyl)phenyl)-2H-1,2,3-triazol-4-yl)benzoate and (S)-methyl 4-(1-(3-(1-(4-methyl-4H-1,2,4-triazol-3-ylthio)ethyl)phenyl)-1H-1,2,3-triazol-4-yl)benzoate. Following the procedure for Example 72 and 73, Steps 1 through 4 starting with methyl 4-bromobenzoate afforded (S)-methyl 4-(2-(3-(1-(4-methyl-4H-1,2,4-triazol-3-ylthio)ethyl)phenyl)-2H-1,2,3-triazol-4-yl)benzoate (1.2 g,) and (S)-methyl 4-(1-(3-(1-(4-methyl-4H-1,2,4-triazol-3-ylthio)ethyl)phenyl)-1H-1,2,3-triazol-4-yl)benzoate (800 mg).

Step-5: (S)-4-(2-(3-(1-(4-methyl-4H-1,2,4-triazol-3-ylthio)ethyl)phenyl)-2H-1,2,3-triazol-4-yl)benzoic acid. To a solution of (S)-methyl 4-(2-(3-(1-(4-methyl-4H-1,2,4-triazol-3-ylthio)ethyl)phenyl)-2H-1,2,3-triazol-4-yl)benzoate (100 mg, 0.24 mmol) in THF/$H_2O$ (1.8 mL/1.8 mL) was added LiOH (0.6 mL, 4 mol/L) at 0° C. The mixture was stirred at room temperature for 3 h. The reaction was diluted with $H_2O$ and acidified by concentrated HCl to pH ~4. General Workup Procedure followed by Chromatography C afforded the title compound (57.9 mg, 60%). MS (ESI) calc'd for ($C_{20}H_{18}N_6O_2S$) $[M+H]^+$, 407.1; found, 407.0. $^1H$ NMR (400 MHz, DMSO-$d_6$) δ 13.13 (s, 1H), 8.75 (s, 1H), 8.54 (s, 1H), 8.15-8.08 (m, 4H), 8.04-8.00 (m, 2H), 7.56-7.52 (m, 1H), 7.39 (d, J=8.0 Hz, 1H), 4.87-4.82 (m, 1H), 3.40 (s, 3H), 1.73 (d, J=7.2 Hz, 3H).

Example 81: (S)-4-(1-(3-(1-(4-methyl-4H-1,2,4-triazol-3-ylthio)ethyl)phenyl)-1H-1,2,3-triazol-4-yl)benzoic acid

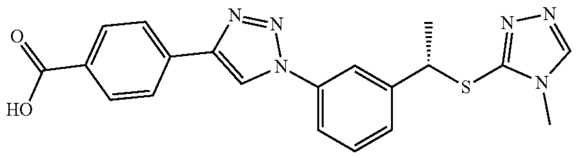 [SMILES: C[C@H](Sc1nncn1C)c1cccc(-n2cc(-c3ccc(C(=O)O)cc3)nn2)c1]

To a solution of (S)-methyl 4-(1-(3-(1-(4-methyl-4H-1,2,4-triazol-3-ylthio)ethyl)phenyl)-1H-1,2,3-triazol-4-yl)benzoate (100 mg, 0.24 mmol) in THF/MeOH (1.8 mL/1.8 mL) was added LiOH (0.6 mL, 4 mol/L) at 0° C. The resulting mixture was stirred at room temperature for 3 h. The reaction was diluted with $H_2O$, and then extracted with EtOAc. The combined organic layers were dried over anhydrous sodium sulfate, filtered, and concentrated under vacuum. The residue was further purified by Chromatography C to afford the title compound (63.0 mg, 65%). MS(ESI) calc'd for ($C_{20}H_{18}N_6O_2S$) $[M+H]^+$, 407.1; found, 407.0. $^1H$ NMR (300 MHz, DMSO-$d_6$) δ 13.05 (s, 1H), 9.46 (s, 1H), 8.55 (s, 1H), 8.10-8.08 (m, 4H), 7.96 (s, 1H), 7.89-7.86 (m, 1H), 7.59-7.56 (m, 1H), 7.45 (d, J=7.5 Hz, 1H), 4.86-4.81 (m, 1H), 3.42 (s, 3H), 1.75 (d, J=7.2 Hz, 3H).

Example 82: (S)—N-methyl-4-(2-(3-(1-(4-methyl-4H-1,2,4-triazol-3-ylthio)ethyl)phenyl)-2H-1,2,3-triazol-4-yl)benzamide

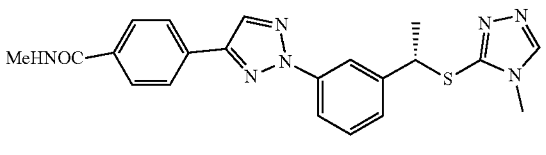

A solution of (S)-methyl 4-(2-(3-(1-(4-methyl-4H-1,2,4-triazol-3-ylthio)ethyl)phenyl)-2H-1,2,3-triazol-4-yl)benzoate (100 mg, 0.24 mmol) in $MeNH_2$ (5 mL, 2M in EtOH) was stirred at 70° C. for 16 h. The mixture was concentrated under vacuum. The residue was purified by Chromatography C to afford the title compound (57.5 mg, 58%). MS(ESI) calc'd for ($C_{21}H_{21}N_7OS$) $[M+H]^+$, 420.2; found, 420.2. $^1H$ NMR (400 MHz, DMSO-$d_6$) δ 8.72 (s, 1H), 8.56-8.54 (m, 2H), 8.11-8.09 (d, J=8.4 Hz, 2H), 8.03-7.98 (m, 4H), 7.56-7.52 (m, 1H), 7.39 (d, J=8.0 Hz, 1H), 4.88-4.82 (m, 1H), 3.40 (s, 3H), 2.82 (d, J=4.4 Hz, 3H), 1.73 (d, J=6.8 Hz, 3H).

Example 83: (S)—N-methyl-4-(1-(3-(1-(4-methyl-4H-1,2,4-triazol-3-ylthio)ethyl)phenyl)-1H-1,2,3-triazol-4-yl)benzamide

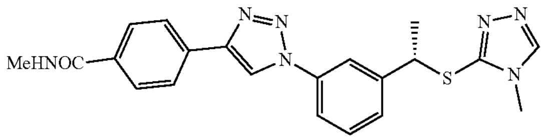

A solution of (S)-methyl 4-(1-(3-(1-(4-methyl-4H-1,2,4-triazol-3-ylthio)ethyl)phenyl)-1H-1,2,3-triazol-4-yl)benzoate (100 mg, 0.24 mmol) in $MeNH_2$ (5 mL, 2M in EtOH) was stirred at 70° C. for 16 h. The mixture was concentrated under vacuum. The residue was purified by Chromatography C to afford the title compound (60.0 mg, 60%). MS (ESI) calc'd for ($C_{21}H_{21}N_7OS$)$[M+H]^+$, 420.2; found, 419.9. $^1H$ NMR (300 MHz, DMSO-$d_6$) δ 9.41 (s, 1H), 8.55-8.51 (m, 2H), 8.05-7.95 (m, 5H), 7.88-7.86 (m, 1H), 7.60-7.55 (m, 1H), 7.44 (d, J=7.5 Hz, 1H), 4.87-4.80 (m, 1H), 3.42 (s, 3H), 2.82 (d, J=4.2 Hz, 3H), 1.74 (d, J=7.2 Hz, 3H).

Example 84: (S)-(4-(2-(3-(1-(4-methyl-4H-1,2,4-triazol-3-ylthio)ethyl)phenyl)-2H-1,2,3-triazol-4-yl)phenyl)methanol

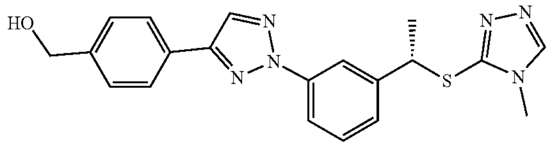 [SMILES: C[C@H](Sc1nncn1C)c1cccc(-n2ncc(-c3ccc(CO)cc3)n2)c1]

To a solution of (S)-methyl 4-(2-(3-(1-(4-methyl-4H-1,2,4-triazol-3-ylthio)ethyl)phenyl)-2H-1,2,3-triazol-4-yl)benzoate (100 mg, 0.24 mmolin THF/MeOH (5 mL/0.5 mL) was added $NaBH_4$ (63.3 mg, 1.67 mmol) at room temperature. The mixture was stirred at 60° C. for 16 h. General Workup Procedure followed by Chromatography C afforded the title compound (2.8 mg, 3%). MS(ESI) calc'd for ($C_{20}H_{20}N_6OS$) $[M+H]^+$, 393.1; found, 392.9. $^1H$ NMR (300 MHz, DMSO-$d_6$) δ 8.64 (s, 1H), 8.57 (s, 1H), 8.04-7.98 (m, 4H), 7.58-7.49 (m, 3H), 7.38 (d, J=7.5 Hz, 1H), 5.32 (s, 1H), 4.90-4.83 (m, 1H), 4.61 (s, 2H), 3.42 (s, 3H), 1.75 (d, J=6.9 Hz, 3H).

Example 85: (S)-(4-(1-(3-(1-(4-methyl-4H-1,2,4-triazol-3-ylthio)ethyl)phenyl)-1H-1,2,3-triazol-4-yl)phenyl)methanol

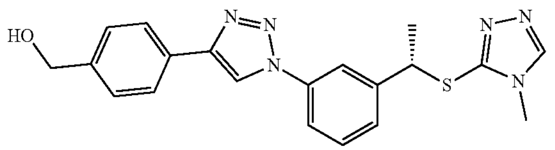 [SMILES: C[C@H](Sc1nncn1C)c1cccc(-n2cc(-c3ccc(CO)cc3)nn2)c1]

To a solution of (S)-methyl 4-(1-(3-(1-(4-methyl-4H-1,2,4-triazol-3-ylthio)ethyl)phenyl)-1H-1,2,3-triazol-4-yl)benzoate (100 mg, 0.24 mmol) in THF/MeOH (5 mL/0.5 mL) was added $NaBH_4$ (63 mg, 1.67 mmol) at room temperature. The resulting mixture was stirred at 60° C. for 16 h. General Workup Procedure followed by Chromatography C afforded the title compound (18.8 mg, 20%). MS(ESI) calc'd for ($C_{20}H_{20}N_6OS$) $[M+H]^+$, 393.1; found, 393.0. $^1H$ NMR (400 MHz, DMSO-$d_6$) δ 9.29 (s, 1H), 8.55 (s, 1H), 7.95-7.91 (m, 3H), 7.88-7.85 (m, 1H), 7.58-7.54 (m, 1H), 7.47-7.42 (m, 3H), 5.27 (s, 1H), 4.86-4.80 (m, 1H), 4.56 (s, 2H), 3.42 (s, 3H), 1.75 (d, J=6.8 Hz, 3H).

Example 86 and 87: (S)-4-(2-(3-(1-(4-methyl-4H-1,2,4-triazol-3-ylthio)ethyl)phenyl)-2H-1,2,3-triazol-4-yl)benzamide and (S)-4-(1-(3-(1-(4-methyl-4H-1,2,4-triazol-3-ylthio)ethyl)phenyl)-1H-1,2,3-triazol-4-yl)benzamide

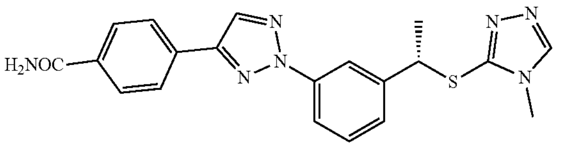

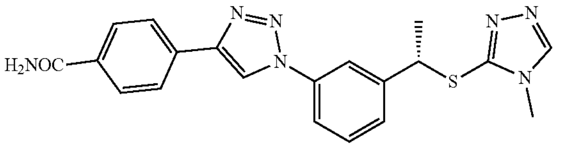

Step 1: 4-(2H-1,2,3-triazol-4-yl)benzamide. A mixture of methyl 4-(2H-1,2,3-triazol-4-yl)benzoate (100 mg, 0.49 mmol) in $NH_3$—$H_2O$ (5 mL, aq., 30%) was stirred at 70° C. for 16 h. The mixture was concentrated under vacuum to afford the title compound, which was used without purification. MS (ESI) calc'd for ($C_9H_8N_4O$) $[M+H]^+$, 189.1; found, 189.1.

Step 2: (S)-4-(2-(3-(1-(4-methyl-4H-1,2,4-triazol-3-ylthio)ethyl)phenyl)-2H-1,2,3-triazol-4-yl)benzamide and (S)-4-(1-(3-(1-(4-methyl-4H-1,2,4-triazol-3-ylthio)ethyl)phenyl)-1H-1,2,3-triazol-4-yl)benzamide. A degassed mixture of 4-(2H-1,2,3-triazol-4-yl)benzamide (200 mg, 1.06 mmol), 3-[[(1S)-1-(3-bromophenyl)ethyl]sulfanyl]-4-methyl-4H-1,2,4-triazole (378 mg, 1.27 mmol), trans-$N^1$,$N^2$-dimethylcyclohexane-1,2-diamine (30 mg, 0.21 mmol), potassium carbonate (366 mg, 2.65 mmol), and CuI (40 mg, 0.21 mmol) in DMSO (6 mL) was stirred at 80° C. for 16 h under nitrogen atmosphere. General Workup Procedure followed by Chromatography C afforded (S)-4-(2-(3-(1-(4-methyl-4H-1,2,4-triazol-3-ylthio)ethyl)phenyl)-2H-1,2,3-triazol-4-yl)benzamide (34.9 mg, 8%) and (S)-4-(1-(3-(1-(4-methyl-4H-1,2,4-triazol-3-ylthio)ethyl)phenyl)-1H-1,2,3-triazol-4-yl)benzamide (2.8 mg, 1%).

(S)-4-(2-(3-(1-(4-methyl-4H-1,2,4-triazol-3-ylthio)ethyl)phenyl)-2H-1,2,3-triazol-4-yl)benzamide: MS (ESI) calc'd for ($C_{20}H_{19}N_7OS$) $[M+H]^+$, 406.1; found, 405.9. $^1$H NMR (300 MHz, DMSO-$d_6$) δ 8.71 (s, 1H), 8.52 (s, 1H), 8.11-7.93 (m, 7H), 7.58-7.42 (m, 2H), 7.36 (d, J=7.8 Hz, 1H), 4.82 (q, J=6.9 Hz, 1H), 3.46 (s, 3H), 1.67 (d, J=6.9 Hz, 3H).

(S)-4-(1-(3-(1-(4-methyl-4H-1,2,4-triazol-3-ylthio)ethyl)phenyl)-1H-1,2,3-triazol-4-yl)benzamide: MS (ESI) calc'd for ($C_{20}H_{19}N_7OS$) $[M+H]^+$, 406.1; found, 405.9. $^1$H NMR (300 MHz, DMSO-$d_6$) δ 9.42 (s, 1H), 8.55 (s, 1H), 8.05-7.86 (m, 7H), 7.55 (t, J=7.8 Hz, 1H), 7.45-7.43 (m, 2H), 4.81 (q, J=6.9 Hz, 1H), 3.49 (s, 3H), 1.72 (d, J=6.9 Hz, 3H).

Example 88 and 89: (S)-4-(2-(3-(1-(4-methyl-4H-1,2,4-triazol-3-ylthio)ethyl)phenyl)-2H-1,2,3-triazol-4-yl)benzonitrile and (S)-4-(1-(3-(1-(4-methyl-4H-1,2,4-triazol-3-ylthio)ethyl)phenyl)-1H-1,2,3-triazol-4-yl)benzonitrile

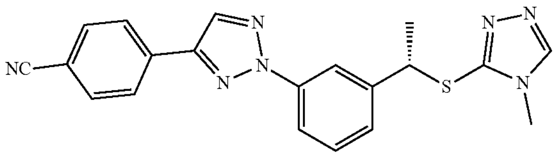

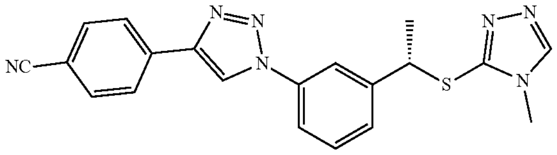

Step-1: 4-(2H-1,2,3-triazol-4-yl)benzonitrile. To a solution of 4-(2H-1,2,3-triazol-4-yl)benzamide (1.0 g, 5.31 mmol) in pyridine (15 mL) was added $POCl_3$ (4.0 g, 26.55 mmol). The mixture was stirred at room temperature for 16 h. General Workup Procedure followed by Chromatography C afforded the title compound (600 mg 69%). MS (ESI) calc'd for ($C_9H_6N_4$) $[M+H]^+$, 171.1; found, 170.9.

Step-2: (S)-4-(2-(3-(1-(4-methyl-4H-1,2,4-triazol-3-ylthio)ethyl)phenyl)-2H-1,2,3-triazol-4-yl)benzonitrile and (S)-4-(1-(3-(1-(4-methyl-4H-1,2,4-triazol-3-ylthio)ethyl)phenyl)-1H-1,2,3-triazol-4-yl)benzonitrile. To a solution of 4-(2H-1,2,3-triazol-4-yl)benzonitrile (200 mg, 1.18 mmol) in DMSO (100 mL) were added (S)-3-(1-(3-bromophenyl)ethylthio)-4-methyl-4H-1,2,4-triazole (421 mg, 1.41 mmol), CuI (89 mg, 0.47 mmol), potassium carbonate (406 mg, 2.94 mmol), and trans-$N^1$,$N^2$-dimethylcyclohexane-1,2-diamine (67 mg, 0.47 mmol). The mixture was stirred at 80° C. for 16 h under nitrogen atmosphere. General Workup Procedure followed by Chromatography C afforded (S)-4-(2-(3-(1-(4-methyl-4H-1,2,4-triazol-3-ylthio)ethyl)phenyl)-2H-1,2,3-triazol-4-yl)benzonitrile (129.0 mg, 28%) and (S)-4-(1-(3-(1-(4-methyl-4H-1,2,4-triazol-3-ylthio)ethyl)phenyl)-1H-1,2,3-triazol-4-yl)benzonitrile (70.2 mg, 15%).

(S)-4-(2-(3-(1-(4-methyl-4H-1,2,4-triazol-3-ylthio)ethyl)phenyl)-2H-1,2,3-triazol-4-yl)benzonitrile: MS (ESI) calc'd for ($C_{20}H_{17}N_7S$) $[M+H]^+$, 388.1; found, 388.0. $^1$H NMR (300 MHz, DMSO-$d_6$) δ 8.80 (s, 1H), 8.54 (s, 1H), 8.22-8.19 (m, 2H), 8.03-7.98 (m, 4H), 7.57-7.52 (m, 1H), 7.40 (d, J=7.8 Hz, 1H), 4.88-4.81 (m, 1H), 3.42 (s, 3H), 1.73 (d, J=7.2 Hz, 3H).

(S)-4-(1-(3-(1-(4-methyl-4H-1,2,4-triazol-3-ylthio)ethyl)phenyl)-1H-1,2,3-triazol-4-yl)benzonitrile: MS (ESI) calc'd for ($C_{20}H_{17}N_7S$) $[M+H]^+$, 388.1; found, 388.0. $^1$H NMR (300 MHz, DMSO-$d_6$) δ 9.52 (s, 1H), 8.56 (s, 1H), 8.16-8.13 (m, 2H), 8.02-7.94 (m, 2H), 7.88 (d, J=1.2 Hz, 1H), 7.85-7.84 (m, 1H), 7.61-7.56 (m, 1H), 7.49-7.44 (m, 1H), 4.87-4.80 (m, 1H), 3.42 (s, 3H), 1.74 (d, J=6.9 Hz, 3H).

Example 90 and 91: (S)-3-(2-(3-(1-(4-methyl-4H-1,2,4-triazol-3-ylthio)ethyl)phenyl)-2H-1,2,3-triazol-4-yl)benzoic acid and (S)-3-(1-(3-(1-(4-methyl-4H-1,2,4-triazol-3-ylthio)ethyl)phenyl)-1H-1,2,3-triazol-4-yl)benzoic acid

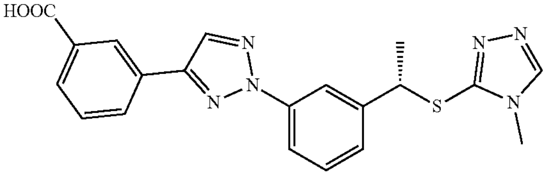

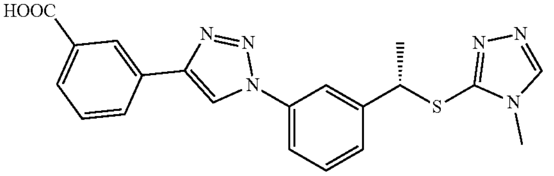

Steps 1-4: Methyl 3-(1-[3-[(1S)-1-[(4-methyl-4H-1,2,4-triazol-3-yl)sulfanyl]ethyl]phenyl]-1H-1,2,3-triazol-4-yl) benzoate and methyl 3-(2-[3-[(1S)-1-[(4-methyl-4H-1,2,4-triazol-3-yl)sulfanyl]ethyl]phenyl]-2H-1,2,3-triazol-4-yl) benzoate (mixture). Following Steps 1-4 of Example 80 starting with methyl 3-bromobenzoate afforded a mixture of methyl 3-(1-[3-[(1S)-1-[(4-methyl-4H-1,2,4-triazol-3-yl) sulfanyl]ethyl]phenyl]-1H-1,2,3-triazol-4-yl)benzoate and methyl 3-(2-[3-[(1S)-1-[(4-methyl-4H-1,2,4-triazol-3-yl) sulfanyl]ethyl]phenyl]-2H-1,2,3-triazol-4-yl)benzoate (1.1 g, 70%). MS (ESI) calc'd for ($C_{21}H_{20}N_6O_2S$) $[M+H]^+$, 421.1, found, 421.2.

Step 5: (S)-3-(2-(3-(1-(4-methyl-4H-1,2,4-triazol-3-ylthio)ethyl)phenyl)-2H-1,2,3-triazol-4-yl)benzoic acid and (S)-3-(1-(3-(1-(4-methyl-4H-1,2,4-triazol-3-ylthio)ethyl) phenyl)-1H-1,2,3-triazol-4-yl)benzoic acid. To a mixture of methyl 3-(1-[3-[(1S)-1-[(4-methyl-4H-1,2,4-triazol-3-yl) sulfanyl]ethyl]phenyl]-1H-1,2,3-triazol-4-yl)benzoate and methyl 3-(2-[3-[(1S)-1-[(4-methyl-4H-1,2,4-triazol-3-yl) sulfanyl]ethyl]phenyl]-2H-1,2,3-triazol-4-yl)benzoate (0.21 g, 0.50 mmol) in THE (3.75 mL) and MeOH (3.75 mL) was added a solution of LiOH (0.12 g, 5.00 mmol) in water (1.2 mL) at 0° C. The mixture was stirred at room temperature for 2 h. The mixture was acidified by HCl (2 N) to pH ~4 and extracted with EtOAc. The organic layers were dried over anhydrous sodium sulfate, filtered, and concentrated under vacuum. The residue was purified by Chromatography C to afford (S)-3-(2-(3-(1-(4-methyl-4H-1,2,4-triazol-3-ylthio) ethyl)phenyl)-2H-1,2,3-triazol-4-yl)benzoic acid (52.0 mg, 27%) and (S)-3-(1-(3-(1-(4-methyl-4H-1,2,4-triazol-3-ylthio)ethyl)phenyl)-1H-1,2,3-triazol-4-yl)benzoic acid (26.8 mg, 13%).

(S)-3-(2-(3-(1-(4-methyl-4H-1,2,4-triazol-3-ylthio)ethyl) phenyl)-2H-1,2,3-triazol-4-yl)benzoic acid: MS (ESI) calc'd for $C_{20}H_{18}N_6O_2S$) $[M+H]^+$, 407.1; found, 406.9. $^1H$ NMR (300 MHz, DMSO-$d_6$) δ 13.23 (s, 1H), 8.74 (s, 1H), 8.52 (s, 2H), 8.28-8.18 (m, 1H), 8.05-7.93 (m, 3H), 7.66 (t, J=7.8 Hz, 1H), 7.51 (t, J=7.8 Hz, 1H), 7.37-7.34 (m, 1H), 4.84 (q, J=6.9 Hz, 1H), 3.38 (s, 3H), 1.70 (d, J=6.9 Hz, 3H).

(S)-3-(1-(3-(1-(4-methyl-4H-1,2,4-triazol-3-ylthio)ethyl) phenyl)-1H-1,2,3-triazol-4-yl)benzoic acid: MS (ESI) calc'd for $C_{20}H_{18}N_6O_2S$) $[M+H]^+$, 407.1; found, 406.9. $^1H$ NMR (300 MHz, DMSO-$d_6$) δ 13.18 (s, 1H), 9.48 (s, 1H), 8.56-8.48 (m, 2H), 8.25-8.15 (m, 1H), 7.99-7.83 (m, 3H), 7.64 (t, J=7.8 Hz, 1H), 7.57 (t, J=7.8 Hz, 1H), 7.42 (d, J=7.8 Hz, 1H), 4.82 (q, J=7.2 Hz, 1H), 3.41 (s, 3H), 1.74 (d, J=7.2 Hz, 3H).

Example 92: (S)-(3-(1-(3-(1-(4-methyl-4H-1,2,4-triazol-3-ylthio)ethyl)phenyl)-1H-1,2,3-triazol-4-yl) phenyl)methanol

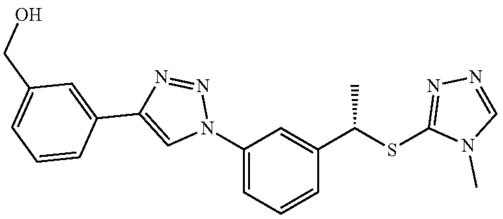 [SMILES: C[C@H](Sc1nncn1C)c1cccc(-n2cc(-c3cccc(CO)c3)nn2)c1]

To a mixture of (S)-methyl 3-(2-(3-(1-(4-methyl-4H-1,2,4-triazol-3-ylthio)ethyl)phenyl)-2H-1,2,3-triazol-4-yl)benzoate and (S)-methyl 3-(1-(3-(1-(4-methyl-4H-1,2,4-triazol-3-ylthio)ethyl)phenyl)-1H-1,2,3-triazol-4-yl)benzoate (150 mg, 0.36 mmol) (Step 4, Example 90 and 91) in THF/MeOH (8/1 mL) was added $NaBH_4$ (190 mg, 5.02 mmol). The mixture was stirred at 60° C. for 16 h and then quenched by the addition of water. General Workup Procedure followed by Chromatography C afforded the title compound (5.5 mg, 4%) along with (S)-(3-(2-(3-(1-(4-methyl-4H-1,2,4-triazol-3-ylthio)ethyl)phenyl)-2H-1,2,3-triazol-4-yl)phenyl)methanol (11.2 mg, 8%).

(S)-(3-(1-(3-(1-(4-methyl-4H-1,2,4-triazol-3-ylthio) ethyl)phenyl)-1H-1,2,3-triazol-4-yl)phenyl)methanol: MS (ESI) calc'd for ($C_{20}H_{20}N_6OS$) $[M+H]^+$, 393.1; found, 393.1. $^1H$ NMR (300 MHz, DMSO-$d_6$) δ 8.34 (s, 1H), 8.56 (s, 1H), 7.97-7.82 (m, 4H), 7.59-7.29 (m, 4H), 5.35-5.32 (m, 1H), 4.86-4.80 (m, 1H), 4.61-4.59 (m, 2H), 3.42 (s, 3H), 1.65 (d, J=7.5 Hz, 3H).

Example 93 and 94: (S)—N-methyl-3-(2-(3-(1-(4-methyl-4H-1,2,4-triazol-3-ylthio)ethyl)phenyl)-2H-1,2,3-triazol-4-yl)benzamide and (S)—N-methyl-3-(1-(3-(1-(4-methyl-4H-1,2,4-triazol-3-ylthio)ethyl) phenyl)-1H-1,2,3-triazol-4-yl)benzamide

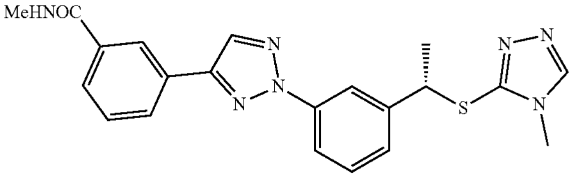

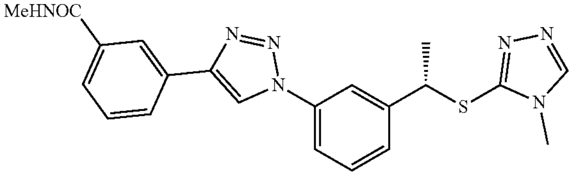

A mixture of (S)-methyl 3-(2-(3-(1-(4-methyl-4H-1,2,4-triazol-3-ylthio)ethyl)phenyl)-2H-1,2,3-triazol-4-yl)benzoate and (S)-methyl 3-(1-(3-(1-(4-methyl-4H-1,2,4-triazol-3-ylthio)ethyl)phenyl)-1H-1,2,3-triazol-4-yl)benzoate (100 mg, 0.24 mmol) (Step 4, Example 90 and 91) in $MeNH_2$ (10 mL, 2 M in EtOH) was stirred at 80° C. for 16 h. After the reaction was completed, the reaction mixture was concentrated under vacuum. The residue was purified by Chromatography C to afford (S)—N-methyl-3-(2-(3-(1-(4-methyl-4H-1,2,4-triazol-3-ylthio)ethyl)phenyl)-2H-1,2,3-triazol-4-yl)benzamide (62.3 mg, 62%) and (S)—N-methyl-3-(1-(3-(1-(4-methyl-4H-1,2,4-triazol-3-ylthio)ethyl)phenyl)-1H-1,2,3-triazol-4-yl)benzamide (16.1 mg, 13%).

(S)—N-methyl-3-(2-(3-(1-(4-methyl-4H-1,2,4-triazol-3-ylthio)ethyl)phenyl)-2H-1,2,3-triazol-4-yl)benzamide: MS (ESI) calc'd for ($C_{21}H_{21}N_7OS$) $[M+H]^+$, 420.2; found, 420.1. $^1H$ NMR (300 MHz, DMSO-$d_6$) δ 8.72 (s, 1H), 8.70-8.63 (s, 1H), 8.56 (s, 1H), 8.45 (s, 1H), 8.16-8.14 (m, 1H), 8.04-8.00 (m, 2H), 7.91 (d, J=7.8 Hz, 1H), 7.66-7.61 (m, 1H), 7.58-7.52 (m, 1H), 7.40-7.27 (m, 1H), 4.90-4.83 (m, 1H), 3.41 (s, 3H), 2.85 (d, J=4.5 Hz, 3H), 1.74 (d, J=7.2 Hz, 3H).

(S)—N-methyl-3-(1-(3-(1-(4-methyl-4H-1,2,4-triazol-3-ylthio)ethyl)phenyl)-1H-1,2,3-triazol-4-yl)benzamide: MS (ESI) calc'd for ($C_{21}H_{21}N_7OS$) $[M+H]^+$, 420.2; found, 420.1. $^1H$ NMR (300 MHz, DMSO-$d_6$) δ 9.41 (s, 1H), 8.60-8.56 (m, 2H), 8.44 (s, 1H), 8.09 (d, J=7.8 Hz, 1H), 7.97 (s, 1H), 7.91-7.82 (m, 2H), 7.63-7.54 (m, 2H), 7.43 (d, J=7.8 Hz, 1H), 4.87-4.80 (m, 1H), 3.42 (s, 3H), 2.83 (d, J=4.5 Hz, 3H), 1.75 (d, J=7.2 Hz, 3H).

Example 95 and 96: (S)-3-(2-(3-(1-(4-methyl-4H-1,2,4-triazol-3-ylthio)ethyl)phenyl)-2H-1,2,3-triazol-4-yl)benzamide and (S)-3-(1-(3-(1-(4-methyl-4H-1,2,4-triazol-3-ylthio)ethyl)phenyl)-1H-1,2,3-triazol-4-yl)benzamide

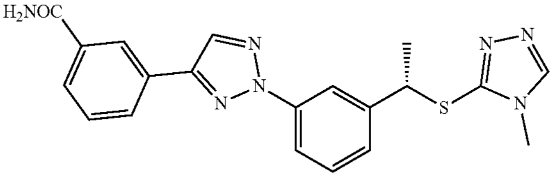

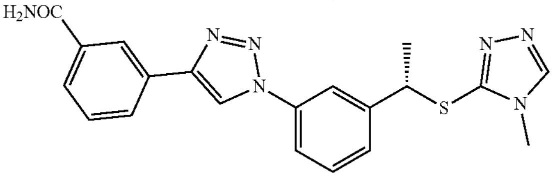

A mixture of methyl 3-(2-[3-[(1S)-1-[(4-methyl-4H-1,2,4-triazol-3-yl)sulfanyl]ethyl]phenyl]-2H-1,2,3-triazol-4-yl) benzoate and methyl 3-(1-[3-[(1S)-1-[(4-methyl-4H-1,2,4-triazol-3-yl)sulfanyl]ethyl]phenyl]-1H-1,2,3-triazol-4-yl) benzoate (200 mg, 0.47 mmol) (Step 4, Example 90 and 91) in $NH_3$ (10 mL, 7 M in MeOH) was stirred at 70° C. for 16 h. The mixture was concentrated under vacuum. The residue was purified by Chromatography C to afford (S)-3-(2-(3-(1-(4-methyl-4H-1,2,4-triazol-3-ylthio)ethyl)phenyl)-2H-1,2,3-triazol-4-yl)benzamide (23.0 mg, 24%) and (S)-3-(1-(3-(1-(4-methyl-4H-1,2,4-triazol-3-ylthio)ethyl)phenyl)-1H-1,2,3-triazol-4-yl)benzamide (29.5 mg, 30%).

(S)-3-(2-(3-(1-(4-methyl-4H-1,2,4-triazol-3-ylthio)ethyl)phenyl)-2H-1,2,3-triazol-4-yl)benzamide: MS (ESI) calc'd for ($C_{20}H_{19}N_7OS$) $[M+H]^+$, 406.1; found, 406.1. $^1H$ NMR (400 MHz, DMSO-$d_6$) δ 8.68 (s, 1H), 8.54 (s, 1H), 8.49 (t, J=2.0 Hz, 1H), 8.18-8.11 (m, 2H), 8.06-7.94 (m, 3H), 7.62

(t, J=7.6 Hz, 1H), 7.58-7.49 (m, 2H), 7.38 (d, J=8.0 Hz, 1H), 4.85 (q, J=6.8 Hz, 1H), 3.40 (s, 3H), 1.73 (d, J=7.2 Hz, 3H).

(S)-3-(1-(3-(1-(4-methyl-4H-1,2,4-triazol-3-ylthio)ethyl)phenyl)-1H-1,2,3-triazol-4-yl)benzamide: MS (ESI) calc'd for ($C_{20}H_{19}N_7OS$) $[M+H]^+$, 406.1; found, 406.1. $^1H$ NMR (400 MHz, DMSO-$d_6$) δ 9.40 (s, 1H), 8.55 (s, 1H), 8.47 (t, J=1.6 Hz, 1H), 8.14-8.06 (m, 2H), 7.97 (t, J=2.0 Hz, 1H), 7.93-7.85 (m, 2H), 7.58-7.42 (m, 4H), 4.83 (q, J=7.2 Hz, 1H), 3.41 (s, 3H), 1.74 (d, J=7.2 Hz, 3H).

Example 97 and 98: (S)-3-(2-(3-(1-(4-methyl-4H-1,2,4-triazol-3-ylthio)ethyl)phenyl)-2H-1,2,3-triazol-4-yl)benzonitrile and (S)-3-(1-(3-(1-(4-methyl-4H-1,2,4-triazol-3-ylthio)ethyl)phenyl)-1H-1,2,3-triazol-4-yl)benzonitrile

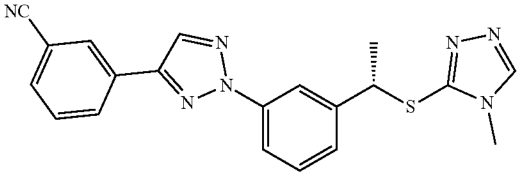

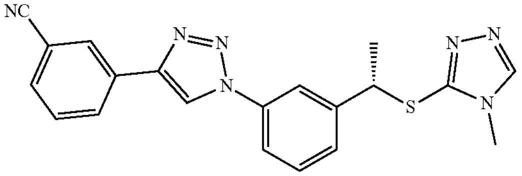

Step 1: 3-(2H-1,2,3-triazol-4-yl)benzamide. A mixture of methyl 3-(2H-1,2,3-triazol-4-yl)benzoate (900 mg, 4.44 mmol) (Step 3, Example 80) and ammonia (30 mL, 30% in water) was stirred for at room temperature for 16 h. The mixture was concentrated under vacuum. The residue was diluted with water and acidified by concentrated HCl to pH ~5. The solids were collected by filtration, then dried under vacuum to afford the title compound (700 mg, 84%). MS (ESI) calc'd for ($C_9H_8N_4O$) $[M+H]^+$, 189.1; found, 188.9. $^1H$ NMR (400 MHz, DMSO-$d_6$) δ 15.07 (s, 1H), 8.44-8.29 (m, 2H), 8.08 (s, 1H), 8.02-7.91 (m, 1H), 7.86-7.83 (m, 1H), 7.56-7.52 (m, 1H), 7.46 (s, 1H).

Step 2: 3-(2H-1,2,3-triazol-4-yl)benzonitrile. To a solution of 3-(2H-1,2,3-triazol-4-yl)benzamide (550 mg, 2.92 mmol) in pyridine (10 mL) was added phosphoryl trichloride (1.3 g, 8.76 mmol) slowly at 0° C. The mixture was stirred at room temperature for 16 h before concentration under vacuum. General Workup Procedure followed by Chromatography A afforded the title compound (280.0 mg, 56%). MS (ESI) calc'd for ($C_9H_6N_4$) $[M+H]^+$, 171.1; found, 170.8. $^1H$ NMR (300 MHz, DMSO-$d_6$) δ 15.50-15.18 (m, 1H), 8.80-8.05 (m, 3H), 7.92-7.56 (m, 2H).

Step 3: (S)-3-(2-(3-(1-(4-methyl-4H-1,2,4-triazol-3-ylthio)ethyl)phenyl)-2H-1,2,3-triazol-4-yl)benzonitrile and (S)-3-(1-(3-(1-(4-methyl-4H-1,2,4-triazol-3-ylthio)ethyl) phenyl)-1H-1,2,3-triazol-4-yl)benzonitrile. To a solution of 3-(2H-1,2,3-triazol-4-yl)benzonitrile (200 mg, 1.18 mmol) in DMSO (100 mL) were added (S)-3-(1-(3-bromophenyl) ethylthio)-4-methyl-4H-1,2,4-triazole (421 mg, 1.41 mmol), CuI (89 mg, 0.47 mmol), potassium carbonate (406 mg, 2.94 mmol), and trans-$N^1$,$N^2$-dimethylcyclohexane-1,2-diamine (67 mg, 0.47 mmol). The mixture was stirred at 80° C. for 16 h under nitrogen atmosphere. General Workup Procedure followed by Chromatography A afforded (S)-3-(2-(3-(1-(4- methyl-4H-1,2,4-triazol-3-ylthio)ethyl)phenyl)-2H-1,2,3-triazol-4-yl)benzonitrile (32.6 mg, 7%) and (S)-3-(1-(3-(1-(4-methyl-4H-1,2,4-triazol-3-ylthio)ethyl)phenyl)-1H-1,2,3-triazol-4-yl)benzonitrile (12.4 mg, 3%).

(S)-3-(2-(3-(1-(4-methyl-4H-1,2,4-triazol-3-ylthio)ethyl)phenyl)-2H-1,2,3-triazol-4-yl)benzonitrile: MS (ESI) calc'd for ($C_{20}H_{17}N_7S$) $[M+H]^+$, 388.1; found, 388.1. $^1H$ NMR (300 MHz, DMSO-$d_6$) δ 8.78 (s, 1H), 8.54 (s, 1H), 8.50-8.49 (m, 1H), 8.37-8.33 (m, 1H), 8.03-7.99 (m, 2H), 7.95-7.92 (m, 1H), 7.79-7.74 (m, 1H), 7.57-7.52 (m, 1H), 7.39 (d, J=7.8 Hz, 1H), 4.88-4.81 (m, 1H), 3.39 (s, 3H), 1.73 (d, J=6.9 Hz, 3H).

(S)-3-(1-(3-(1-(4-methyl-4H-1,2,4-triazol-3-ylthio)ethyl)phenyl)-1H-1,2,3-triazol-4-yl)benzonitrile: MS (ESI) calc'd for ($C_{20}H_{17}N_7S$) $[M+H]^+$, 388.1; found, 388.1. $^1H$ NMR (300 MHz, DMSO-$d_6$) δ 9.48 (s, 1H), 8.60 (s, 1H), 8.37 (s, 1H), 8.31 (d, J=7.8 Hz, 1H), 7.93 (s, 1H), 7.88-7.84 (m, 2H), 7.77-7.72 (s, 1H), 7.66-7.58 (m, 1H), 7.55-7.44 (m, 1H), 4.87-4.81 (m, 1H), 3.42 (s, 3H), 1.74 (d, J=6.9 Hz, 3H).

Example 99 and 100: (S)-2-(3-(1-((4-methyl-4H-1,2,4-triazol-3-yl)thio)ethyl)phenyl)-4-phenyl-2H-1,2,3-triazole and (R)-2-(3-(1-((4-methyl-4H-1,2,4-triazol-3-yl)thio)ethyl)phenyl)-4-phenyl-2H-1,2,3-triazole

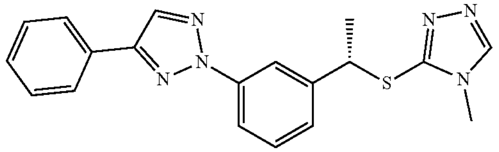

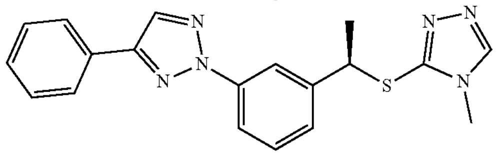

Step 1: 1-(3-(4-phenyl-2H-1,2,3-triazol-2-yl)phenyl)ethan-1-one and 1-(3-(4-phenyl-1H-1,2,3-triazol-1-yl)phenyl)ethan-1-one. DMSO (1 mL) was added to a mixture containing 4-phenyl-2H-1,2,3-triazole (100 mg, 0.69 mmol), Proline (16 mg, 0.14 mmol), and CuI (13 mg, 0.066 mmol) at room temperature. After purging the mixture with nitrogen, 1-(3-iodophenyl)ethan-1-one (115 μL, 0.83 mmol) and potassium carbonate (190 mg, 1.4 mmol) were added and the reaction was heated at 80° C. for three days. Water and DCM were added and the product was extracted with DCM three times. The combined organic layer was dried over anhydrous sodium sulfate, filtered, and concentrated. The crude material was purified on silica gel using a gradient of DCM in hexanes (0 to 100%), which eluted 1-(3-(4-phenyl-2H-1,2,3-triazol-2-yl)phenyl)ethan-1-one (42 mg, 0.16 mmol, 23%), followed by a gradient of EtOAc in DCM (0 to 40%) to give 1-(3-(4-phenyl-1H-1,2,3-triazol-1-yl)phenyl)ethan-1-one in 31 mg (0.12 mmol, 17%).

Step 2: 1-(3-(4-phenyl-2H-1,2,3-triazol-2-yl)phenyl)ethan-1-ol. 1-(3-(4-phenyl-2H-1,2,3-triazol-2-yl)phenyl)ethan-1-one was reduced following the procedure for Example 68 and 69, Step 2 to give the title compound (43 mg, 100%).

Step 3: 2-(3-(1-((4-methyl-4H-1,2,4-triazol-3-yl)thio)ethyl)phenyl)-4-phenyl-2H-1,2,3-triazole. A Mitsunobu reaction was performed following the procedure for Example 56, Step 2 to give the title compound (10 mg, 18%).

Step 4: (S)-2-(3-(1-((4-methyl-4H-1,2,4-triazol-3-yl)thio)ethyl)phenyl)-4-phenyl-2H-1,2,3-triazole and (R)-2-(3-(1-((4-methyl-4H-1,2,4-triazol-3-yl)thio)ethyl)phenyl)-4-phenyl-2H-1,2,3-triazole. The racemic 2-(3-(1-((4-methyl-4H-1,2,4-triazol-3-yl)thio)ethyl)phenyl)-4-phenyl-2H-1,2,3-triazole was SFC separated using a Chiralpak AD column and methanol-$CO_2$ to give (S)-2-(3-(1-((4-methyl-4H-1,2,4-triazol-3-yl)thio)ethyl)phenyl)-4-phenyl-2H-1,2,3-triazole (1.7 mg, 0.0047 mmol) and (R)-2-(3-(1-((4-methyl-4H-1,2,4-triazol-3-yl)thio)ethyl)phenyl)-4-phenyl-2H-1,2,3-triazole (1.6 mg, 0.0044 mmol).

(S)-2-(3-(1-((4-methyl-4H-1,2,4-triazol-3-yl)thio)ethyl)phenyl)-4-phenyl-2H-1,2,3-triazole: $^1H$ NMR (500 MHz, Methanol-$d_4$) δ 8.45 (s, 1H), 8.29 (s, 1H), 8.05-8.00 (m, 2H), 7.98-7.93 (m, 2H), 7.52-7.45 (m, 3H), 7.44-7.38 (m, 1H), 7.31 (dt, J=7.7, 1.4 Hz, 1H), 4.80 (q, J=7.1 Hz, 1H), 3.41 (s, 3H), 1.82 (d, J=7.1 Hz, 3H). MS (ESI) calc'd for ($C_{19}H_{18}N_6S$) $[M+H]^+$, 363; found, 363.

(R)-2-(3-(1-((4-methyl-4H-1,2,4-triazol-3-yl)thio)ethyl)phenyl)-4-phenyl-2H-1,2,3-triazole: $^1H$ NMR (500 MHz, Methanol-$d_4$) δ 8.43 (s, 1H), 8.29 (s, 1H), 8.06-8.00 (m, 2H), 7.98-7.93 (m, 2H), 7.52-7.45 (m, 3H), 7.44-7.38 (m, 1H), 7.31 (dt, J=7.8, 1.4 Hz, 1H), 4.80 (q, J=7.0 Hz, 1H), 3.41 (s, 3H), 1.82 (d, J=7.1 Hz, 3H). MS (ESI) calc'd for ($C_{19}H_{18}N_6S$) $[M+H]^+$, 363; found, 363.

Example 101: 4-(1-((4-methyl-4H-1,2,4-triazol-3-yl)thio)ethyl)-2-(4-phenyl-2H-1,2,3-triazol-2-yl)pyridine

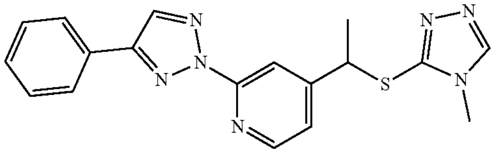 [SMILES: CC(Sc1nncn1C)c1ccnc(-n2ncc(-c3ccccc3)n2)c1]

Following Steps 1-3 in Example 99 and 100 using 1-(2-bromobpyridin-4-yl)ethan-1-one gave the title compound (11 mg, 0.031 mmol). $^1H$ NMR (500 MHz, DMSO-$d_6$) δ 8.69 (s, 1H), 8.54 (s, 1H), 8.51 (dd, J=5.1, 0.7 Hz, 1H), 8.03-7.96 (m, 2H), 7.58-7.50 (m, 3H), 7.49-7.43 (m, 2H), 4.87 (q, J=7.0 Hz, 1H), 3.44 (s, 3H), 1.72 (d, J=7.1 Hz, 3H). MS (ESI) calc'd for ($C_{18}H_{17}N_7S$) $[M+H]^+$, 364; found, 364.

Example 102 and 103: (S)-4-methyl-3-((1-(3-(3-phenyl-1H-pyrazol-5-yl)phenyl)ethyl)thio)-4H-1,2,4-triazole and (R)-4-methyl-3-((1-(3-(3-phenyl-1H-pyrazol-5-yl)phenyl)ethyl)thio)-4H-1,2,4-triazole

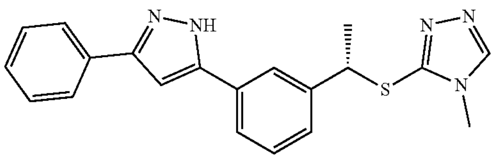

-continued

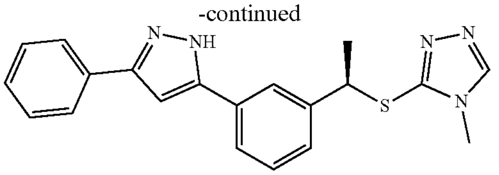

Step 1: 1-(3-(3-phenyl-1H-pyrazol-5-yl)phenyl)ethan-1-one. CuI (6.0 mg, 0.032 mmol), bis(triphenylphosphine) palladium(II) dichloride (7.5 mg, 0.011 mmol), 1-(3-ethynylphenyl)ethan-1-one (145 mg, 1.0 mmol), THF (5 mL), benzoyl chloride (174 μL, 1.5 mmol), and triethylamine (280 μL, 2.0 mmol) were all combined at room temperature and stirred for 4.5 h. Hydrazine hydrate (50%, 187 μL, 3.0 mmol) in acetonitrile (2 mL) was added at room temperature and the reaction was stirred for 16 h. The solvents were removed under reduced pressure. Water and DCM were added and the product was extracted three times with DCM, three times with EtOAc, and once with chloroform: isopropyl alcohol (2:1). The combined organic layers were dried over anhydrous sodium sulfate, filtered, and concentrated. Chromatography A afforded the title compound (33 mg, 12%).

Step 2: 1-(3-(3-phenyl-1H-pyrazol-5-yl)phenyl)ethan-1-ol. The ketone was reduced following the procedure for Example 67 and 68, Step 2 to give the title compound (30 mg, 91%).

Step 3: 4-methyl-3-((1-(3-(3-phenyl-1H-pyrazol-5-yl)phenyl)ethyl)thio)-4H-1,2,4-triazole. Following the procedure for Example 55, Step 2, the title compound was obtained (16 mg, 40%).

Step 4: (S)-4-methyl-3-((1-(3-(3-phenyl-1H-pyrazol-5-yl)phenyl)ethyl)thio)-4H-1,2,4-triazole and (R)-4-methyl-3-((1-(3-(3-phenyl-1H-pyrazol-5-yl)phenyl)ethyl)thio)-4H-1,2,4-triazole. Racemic 4-methyl-3-((1-(3-(3-phenyl-1H-pyrazol-5-yl)phenyl)ethyl)thio)-4H-1,2,4-triazole was SFC separated using an AD-H column and methanol-$CO_2$ to give (S)-4-methyl-3-((1-(3-(3-phenyl-1H-pyrazol-5-yl)phenyl)ethyl)thio)-4H-1,2,4-triazole (4.6 mg, 0.013 mmol) and (R)-4-methyl-3-((1-(3-(3-phenyl-1H-pyrazol-5-yl)phenyl)ethyl)thio)-4H-1,2,4-triazole (5.0 mg, 0.014 mmol).

(S)-4-methyl-3-((1-(3-(3-phenyl-1H-pyrazol-5-yl)phenyl)ethyl)thio)-4H-1,2,4-triazole: $^1$H NMR (500 MHz, DMSO-$d_6$) δ 13.37 (s, 1H), 8.53 (s, 1H), 7.89-7.70 (m, 4H), 7.57-7.20 (m, 5H), 7.18 (s, 1H), 4.72 (q, J=6.9 Hz, 1H), 3.36 (s, 3H), 1.72 (d, J=7.0 Hz, 3H). MS (ESI) calc'd for ($C_{20}H_{19}N_5S$) [M+H]$^+$, 362; found, 362.

(R)-4-methyl-3-((1-(3-(3-phenyl-1H-pyrazol-5-yl)phenyl)ethyl)thio)-4H-1,2,4-triazole: $^1$H NMR (500 MHz, DMSO-$d_6$) δ 13.36 (s, 1H), 8.52 (s, 1H), 7.88-7.72 (m, 4H), 7.58-7.20 (m, 5H), 7.17 (s, 1H), 4.71 (q, J=6.9 Hz, 1H), 3.35 (s, 3H), 1.71 (d, J=7.0 Hz, 3H). MS (ESI) calc'd for ($C_{20}H_{19}N_5S$) [M+H]$^+$, 362; found, 362.

Example 104: 3-((1-(3-(3-(3-methoxyphenyl)-1H-pyrazol-5-yl)phenyl)ethyl)thio)-4-methyl-4H-1,2,4-triazole

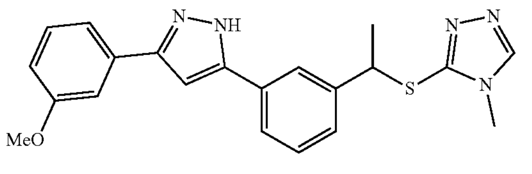 [SMILES: COc1cccc(-c2cc(-c3cccc(C(C)Sc4nncn4C)c3)[nH]n2)c1]

Step 1: 1-(3-ethynylphenyl)ethan-1-ol. Following the procedure for Example 67 and 68, Step 2 using 1-(3-ethynylphenyl)ethan-1-one (449 mg, 3.1 mmol), the title compound was obtained (416 mg, 92%).

Step 2: (1-(3-ethynylphenyl)ethoxy)triisopropylsilane. 1-(3-Ethynylphenyl)ethan-1-ol (363 mg, 2.5 mmol) was dissolved in DMF (3 mL) at room temperature. Imidazole (340 mg, 5.0 mmol) was added followed by triisopropylsilyl chloride (685 μL, 3.2 mmol). The reaction was stirred for 16 h. Water and hexanes were added and the product was extracted with hexanes three times. The combined organic layers were dried, filtered, and concentrated. Chromatography A afforded the title compound (519 mg, 69%).

Step 3: 1-(3-methoxyphenyl)-3-(3-(1-((triisopropylsilyl)oxy)ethyl)phenyl)prop-2-yn-1-one. To a THE (1 mL) solution of (1-(3-ethynylphenyl)ethoxy)triisopropylsilane (102 mg, 0.34 mmo) at room temperature was added CuI (2.5 mg, 0.013 mmol), bis(triphenylphosphine)palladium(II) dichloride (4.7 mg, 0.0067 mmol), and 3-methoxybenzoyl chloride (69 μL, 0.49 mmol). The mixture was purged with nitrogen and treated with triethylamine (92 μL, 0.66 mmol). The reaction mixture was stirred for 3 days. The crude mixture was pre-absorbed onto silica gel and purified using Chromatography A to afford the title compound (137 mg, 93%).

Step 4: 3-(3-methoxyphenyl)-5-(3-(1-((triisopropylsilyl)oxy)ethyl)phenyl)-1H-pyrazole. 1-(3-Methoxyphenyl)-3-(3-(1-((triisopropylsilyl)oxy)ethyl)phenyl)prop-2-yn-1-one (135 mg, 0.31 mmol) was dissolved in acetonitrile (1 mL) at room temperature. Hydrazine hydrate (50%, 60 μL, 1.1 mmol) was added and the reaction was stirred for 16 h. The reaction mixture was pre-absorbed onto silica gel and purified using Chromatography A to afford the title compound (160 mg, 100%).

Step 5: 1-(3-(3-(3-methoxyphenyl)-1H-pyrazol-5-yl)phenyl)ethan-1-ol. 3-(3-Methoxyphenyl)-5-(3-(1-((triisopropylsilyl)oxy)ethyl)phenyl)-1H-pyrazole (121 mg, 0.27 mmol) was dissolved in THE (1 mL) at room temperature. Tetrabutylammonium fluoride solution (1 M in THF, 0.33 mL, 0.33 mmol) was added and the reaction was stirred for 16 h. Solvents were removed and the crude material was purified using Chromatography A to afford the title compound (73 mg, 92%).

Step 6: 3-((1-(3-(3-(3-methoxyphenyl)-1H-pyrazol-5-yl)phenyl)ethyl)thio)-4-methyl-4H-1,2,4-triazole. A Mitsunobu reaction was performed following the procedure for Example 55, Step 2 to give the title compound (10 mg, 26%). $^1$H NMR (500 MHz, DMSO-$d_6$) δ 13.34 (s, 1H), 8.52 (s, 1H), 7.78 (s, 1H), 7.74 (br, 1H), 7.45-7.34 (m, 3H), 7.24 (br, 1H), 7.20 (s, 1H), 6.91 (br, 1H), 4.71 (q, J=7.0 Hz, 1H), 3.82 (s, 3H), 3.35 (s, 3H), 1.71 (d, J=7.0 Hz, 3H). MS (ESI) calc'd for ($C_{21}H_{21}N_5OS$) [M+H]$^+$, 392; found, 392.

Example 105: (R)-2-(5-(3-(1-(4-methyl-4H-1,2,4-triazol-3-yl)propan-2-yl)phenyl)-1H-pyrazol-3-yl)pyridine

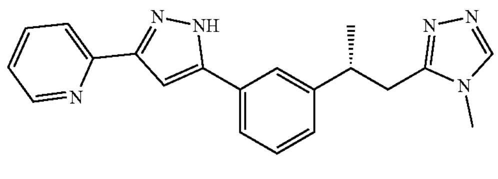 [SMILES: C[C@H](Cc1nncn1C)c1cccc(-c2cc(-c3ccccn3)n[nH]2)c1]

Step-1: N-methoxy-N-methylpyridine-2-carboxamide. To a mixture of methoxy(methyl)amine hydrochloride (792 mg, 8.12 mmol) and triethylamine (1.2 g, 12 mmol) in DMF (10 mL) were added pyridine-2-carboxylic acid (500 mg, 4.06 mmol), hydroxybenzotriazole (1.1 g, 8.1 mmol), and EDCI (1.5 g, 8.1 mmol). The mixture was stirred at room temperature for 2 h before being concentrated under vacuum. The crude residue was purified by Chromatography C to afford the title compound (150 mg, 22%). MS (ESI) calc'd for ($C_8H_{10}N_2O_2$) $[M+H]^+$, 167.0; found, 167.1.

Step 2: (R)-4-methyl-3-(2-(3-((trimethylsilyl)ethynyl) phenyl)propyl)-4H-1,2,4-triazole. A Sonogashira coupling was performed following the procedure for Example 72 and 73, Step 1 to afford the title compound (830 mg, 78%). MS (ESI) calc'd for ($C_{17}H_{23}N_3Si$) $[M+H]^+$, 298.1; found 298.0.

Step 3: (R)-3-(2-(3-ethynylphenyl)propyl)-4-methyl-4H-1,2,4-triazole. TMS group deprotection was performed following the procedure for Example 55, Step 4 to afford (R)-3-(2-(3-ethynylphenyl)propyl)-4-methyl-4H-1,2,4-triazole (480 mg, 76%). MS (ESI) calc'd for ($C_{14}H_{15}N_3$) $[M+H]^+$, 226.1; found 226.0.

Step 4: (R)-3-(3-(1-(4-methyl-4H-1,2,4-triazol-3-yl)propan-2-yl)phenyl)-1-(pyridin-2-yl)prop-2-yn-1-one. To a solution of (R)-3-(2-(3-ethynylphenyl)propyl)-4-methyl-4H-1,2,4-triazole (100 mg, 0.44 mmol) in THF (2 mL) was added n-BuLi (2.5 M in hexane, 0.23 mL, 0.58 mmol) at −50° C. under nitrogen atmosphere. The mixture was stirred at −50~−30° C. for 30 minutes. A solution of N-methoxy-N-methylpyridine-2-carboxamide (73 mg, 0.44 mmol) in THE (1 mL) was added slowly to the above mixture. The mixture was warmed to room temperature and stirred for 3 h under nitrogen atmosphere. The reaction was then quenched with saturated aqueous ammonium chloride solution. General Workup Procedure followed by Chromatography B afforded the title compound (88 mg, 60%). MS (ESI) calc'd for ($C_{20}H_{18}N_4O$) $[M+H]^+$, 331.1; found 331.0.

Step 5: (R)-2-(3-(3-(1-(4-methyl-4H-1,2,4-triazol-3-yl) propan-2-yl)phenyl)-1H-pyrazol-5-yl)pyridine. To a solution of (R)-3-(3-(1-(4-methyl-4H-1,2,4-triazol-3-yl)propan-2-yl)phenyl)-1-(pyridin-2-yl)prop-2-yn-1-one (88 mg, 0.27 mmol) in THE (1 mL) was added hydrazine (25 mg, 0.40 mmol, 80%). The mixture was stirred at 80° C. for 3 h. The reaction mixture was purified by Chromatography C to afford the title compound (13.4 mg, 15%). MS (ESI) calc'd for ($C_{20}H_{20}N_6$) $[M+H]^+$, 345.1; found 345.0. $^1H$ NMR (300 MHz, DMSO-$d_6$+$D_2O$) δ 8.64-8.56 (m, 1H), 8.26 (s, 1H), 8.04-7.90 (m, 2H), 7.74 (s, 1H), 7.66-7.58 (m, 1H), 7.35-7.20 (m, 4H), 3.49-3.35 (m, 3H), 3.35-3.27 (m, 1H), 3.02 (d, J=7.2 Hz, 2H), 1.31 (d, J=7.2 Hz, 3H).

Example 106: (R)-2-(3-(3-(1-(4-methyl-4H-1,2,4-triazol-3-yl)propan-2-yl)phenyl)-1H-pyrazol-5-yl) pyrimidine

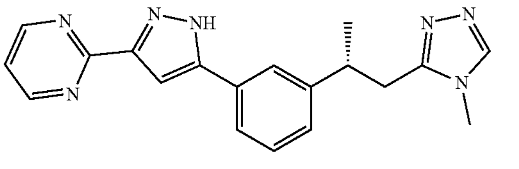 [SMILES: C[C@H](Cc1nncn1C)c1cccc(-c2cc(-c3ncccn3)n[nH]2)c1]

Step 1: N-methoxy-N-methylpyrimidine-2-carboxamide. A mixture of pyrimidine-2-carboxylic acid (500 mg, 4.03 mmol), imidazole (300 mg, 4.41 mmol), and 1,1'-carbonyldiimidazole (780 mg, 4.81 mmol) in MeCN (10 mL) was stirred at 50° C. for 2.5 h under nitrogen atmosphere. Then methoxy(methyl)amine hydrochloride (510 mg, 5.23 mmol) was added to the above mixture at room temperature. The mixture was stirred at room temperature for 16 h before being concentrated under vacuum. The residue was diluted with water and acidified to pH~6 by HCl (3 N), and then extracted with DCM. The combined organic layers were washed with saturated aqueous $NaHCO_3$ and brine, dried over anhydrous sodium sulfate, and concentrated under vacuum. The residue was purified by Chromatography A to afford the title compound (210.0 mg, 31%). MS (ESI) calc'd for ($C_7H_9N_3O_2$) $[M+H]^+$, 168.1; found, 168.0.

Step 2-3: (R)-2-(3-(3-(1-(4-methyl-4H-1,2,4-triazol-3-yl) propan-2-yl)phenyl)-1H-pyrazol-5-yl) pyrimidine. Following Step 9 and Step 10 for Example 105 using N-methoxy-N-methylpyrimidine-2-carboxamide, the title compound was obtained (30 mg, 0.077 mmol). MS (ESI) calc'd for ($C_{19}H_{19}N_7$) $[M+H]^+$, 346.2; found 346.1. $^1H$ NMR (300 MHz, DMSO-$d_6$+$D_2O$) δ 8.88 (d, J=4.8 Hz, 2H), 8.26 (s, 1H), 7.76 (s, 1H), 7.71-7.69 (m, 1H), 7.46-7.43 (m, 1H), 7.39 (s, 1H), 7.35-7.32 (m, 1H), 7.22-7.19 (m, 1H), 3.43 (s, 3H), 3.31-3.29 (m, 1H), 3.04-3.01 (m, 2H), 1.31 (d, J=6.9 Hz, 3H).

Example 107 and 108: (S)-3-(3-(1-((4-methyl-4H-1,2,4-triazol-3-yl)thio)ethyl)phenyl)-1H-indazole and (R)-3-(3-(1-((4-methyl-4H-1,2,4-triazol-3-yl)thio) ethyl)phenyl)-1H-indazole

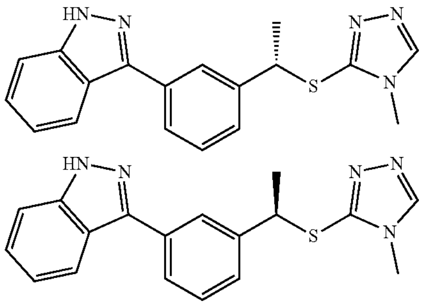

Step 1: 1-(3-(1H-indazol-3-yl)phenyl)ethan-1-one. (3-Acetylphenyl)boronic acid (196 mg, 1.2 mmol), tert-butyl 3-iodo-1H-indazole-1-carboxylate (344 mg, 1.0 mmol), sodium carbonate (287 mg, 2.7 mmol), tetrakis (triphenylphosphine)palladium(0) (115 mg, 0.099 mmol), and toluene (5 mL) were combined at room temperature. After purging the mixture with nitrogen, water (0.5 mL) was added and the mixture was heated at 80° C. for three days. More tetrakis(triphenylphosphine)palladium(0) (60 mg, 0.052 mmol) was added and the reaction was heated at 100° C. for 8 h. Water and EtOAc were added and the product was extracted with EtOAc three times. The crude product was absorbed onto silica gel and purified using a gradient of EtOAc in hexanes (0 to 50%) to afford the title compound (67 mg, 0.28 mmol, 28%).

Step 2: 1-(3-(1H-indazol-3-yl)phenyl)ethan-1-ol. The ketone reduction was performed following the procedure for Example 67 and 68, Step 2 to give the title compound (57 mg, 85%).

Step 3: 3-(3-(1-((4-methyl-4H-1,2,4-triazol-3-yl)thio) ethyl)phenyl)-1H-indazole. A Mitsunobu reaction was performed following the procedure for Example 55, Step 2 to give the title compound (31 mg, 0.092 mmol, 38%). MS (ESI) calc'd for ($C_{18}H_{17}N_5S$) $[M+H]^+$, 336; found 336.

Step 4: (S)-3-(3-(1-((4-methyl-4H-1,2,4-triazol-3-yl)thio)ethyl)phenyl)-1H-indazole and (R)-3-(3-(1-((4-methyl-4H-1,2,4-triazol-3-yl)thio)ethyl)phenyl)-1H-indazole. Racemic 3-(3-(1-((4-methyl-4H-1,2,4-triazol-3-yl)thio)ethyl)phenyl)-1H-indazole was SFC separated using a Chiralpak IA column and methanol-$CO_2$ to give (S)-3-(3-(1-((4-methyl-4H-1,2,4-triazol-3-yl)thio)ethyl)phenyl)-1H-indazole (11 mg, 0.032 mmol) and (R)-3-(3-(1-((4-methyl-4H-1,2,4-triazol-3-yl)thio)ethyl)phenyl)-1H-indazole (11 mg, 0.033 mmol).

(S)-3-(3-(1-((4-methyl-4H-1,2,4-triazol-3-yl)thio)ethyl)phenyl)-1H-indazole: $^1$H NMR (500 MHz, DMSO-$d_6$) δ 13.25 (s, 1H), 8.51 (s, 1H), 8.01 (d, J=8.2 Hz, 1H), 7.91-7.84 (m, 2H), 7.62-7.57 (m, 1H), 7.45 (t, J=7.7 Hz, 1H), 7.40 (ddd, J=8.2, 6.8, 1.0 Hz, 1H), 7.33 (dt, J=7.7, 1.5 Hz, 1H), 7.21 (ddd, J=7.9, 6.8, 0.9 Hz, 1H), 4.81 (q, J=6.9 Hz, 1H), 3.36 (s, 3H), 1.72 (d, J=7.0 Hz, 3H). MS (ESI) calc'd for ($C_{18}H_{17}N_5S$) [M+H]$^+$, 336; found 336.

(R)-3-(3-(1-((4-methyl-4H-1,2,4-triazol-3-yl)thio)ethyl)phenyl)-1H-indazole: $^1$H NMR (500 MHz, DMSO-$d_6$) δ 13.25 (s, 1H), 8.51 (s, 1H), 8.01 (d, J=8.2 Hz, 1H), 7.91-7.85 (m, 2H), 7.59 (dt, J=8.5, 0.9 Hz, 1H), 7.45 (t, J=7.7 Hz, 1H), 7.40 (ddd, J=8.2, 6.8, 1.0 Hz, 1H), 7.33 (dt, J=7.7, 1.4 Hz, 1H), 7.21 (ddd, J=7.8, 6.8, 0.9 Hz, 1H), 4.81 (q, J=7.0 Hz, 1H), 3.36 (s, 3H), 1.72 (d, J=7.0 Hz, 3H). MS (ESI) calc'd for ($C_{18}H_{17}N_5S$) [M+H]$^+$, 336; found 336.

Example 109: (R)-1-(3-(3-(1-(4-methyl-4H-1,2,4-triazol-3-yl)propan-2-yl)phenyl)-5-(trifluoromethyl)-1H-pyrazolo[4,3-b]pyridin-7-yl)piperidin-4-ol

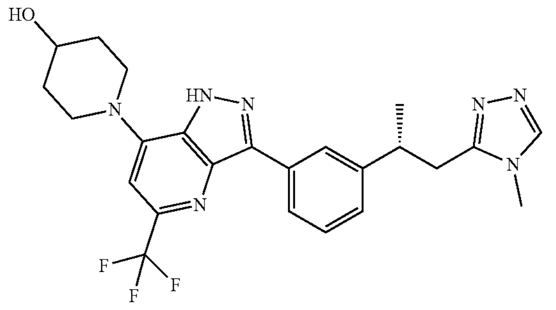 [SMILES: C[C@H](Cc1nncn1C)c1cccc(-c2n[nH]c3c(N4CCC(O)CC4)cc(C(F)(F)F)nc23)c1]

Step 1: (R)-4-methyl-3-(2-(3-(4,4,5,5-tetramethyl-1,3,2-dioxaborolan-2-yl)phenyl)propyl)-4H-1,2,4-triazole. To a degassed mixture of (R)-3-(2-(3-bromophenyl)propyl)-4-methyl-4H-1,2,4-triazole (2.0 g, 7.14 mmol), KOAc (1.4 g, 14 mmol), and $B_2Pin_2$ (3.6 g, 14 mmol) in dioxane (20 mL) was added Pd(dppf)$Cl_2$ (500 mg, 0.71 mmol). The resulting mixture was stirred at 80° C. for 16 h under nitrogen. The solvent was removed under vacuum. The crude residue was purified by Chromatography B to afford the title compound (1.1 g, 47%). MS (ESI) calculated for ($C_{18}H_{26}BN_3O_2$) [M+1]$^+$, 328.2; found, 328.0.

Step 2: 3-bromo-7-chloro-5-(trifluoromethyl)-1H-pyrazolo[4,3-b]pyridine. To a solution of 7-chloro-5-(trifluoromethyl)-1H-pyrazolo[4,3-b]pyridine (800 mg, 3.61 mol) in MeOH (15 mL) and $H_2O$ (15 mL) was added $Br_2$ (865.5 mg, 5.42 mmol) dropwise at 0° C. The resulting solution was stirred at 0° C. for 1 h. The reaction mixture was quenched by saturated $Na_2S_2O_3$ aqueous solution. General Workup Procedure followed by Chromatography B afforded the title compound (1.0 g, 92%). MS (ESI) calc'd for ($C_7H_2BrClF_3N_2$) [M+1]$^+$, 299.9/301.9; found, 300.0/302.0.

Step 3: 1-(3-bromo-5-(trifluoromethyl)-1H-pyrazolo[4,3-b]pyridin-7-yl)piperidin-4-ol. To a solution of 3-bromo-7-chloro-5-(trifluoromethyl)-1H-pyrazolo[4,3-b]pyridine (840 mg, 2.80 mmol) in ethanol (10 mL) were added piperidin-4-ol (1.4 g, 14 mmol) and DIEA (3.6 g, 28 mmol). The resulting solution was stirred at 100° C. for 16 h before concentration under vacuum. The residue was purified by Chromatography B to afford the title compound (600 mg, 59%). MS (ESI) calc'd for ($C_{12}H_{12}BrF_3N_4O$) [M+H]$^+$, 365.0/367.0; found, 365.0/367.0.

Step 4: tert-butyl 3-bromo-7-(4-((tert-butoxycarbonyl)oxy)piperidin-1-yl)-5-(trifluoromethyl)-1H-pyrazolo[4,3-b]pyridine-1-carboxylate. To a solution of 1-(3-bromo-5-(trifluoromethyl)-1H-pyrazolo[4,3-b]pyridin-7-yl)piperidin-4-ol (600 mg, 1.64 mmol) in THE (5 mL) were added triethylamine (831.3 mg, 8.22 mmol), DMAP (20.1 mg, 0.16 mmol), and $Boc_2O$ (1075.8 mg, 4.93 mmol). The resulting mixture was stirred at room temperature for 16 h. General Workup Procedure followed by Chromatography A afforded the title compound (200 mg, 21%). MS (ESI) calc'd for ($C_{22}H_{26}BrF_3N_4O_5$) [M+H]$^+$, 565.1/567.1; found, 565.0/567.0.

Step 5: tert-butyl (R)-7-(4-((tert-butoxycarbonyl)oxy)piperidin-1-yl)-3-(3-(1-(4-methyl-4H-1,2,4-triazol-3-yl)propan-2-yl)phenyl)-5-(trifluoromethyl)-1H-pyrazolo[4,3-b]pyridine-1-carboxylate. To a degassed solution of tert-butyl 3-bromo-7-(4-((tert-butoxycarbonyl)oxy)piperidin-1-yl)-5-(trifluoromethyl)-1H-pyrazolo[4,3-b]pyridine-1-carboxylate (150 mg, 0.27 mmol) and (R)-4-methyl-3-(2-(3-(4,4,5,5-tetramethyl-1,3,2-dioxaborolan-2-yl)phenyl)propyl)-4H-1,2,4-triazole (130.2 mg, 0.40 mmol) in dioxane (10 mL) and $H_2O$ (1 mL) were added Pd(dppf)$Cl_2$ (19.4 mg, 0.03 mmol) and $K_2CO_3$ (73.3 mg, 0.53 mmol). The mixture was stirred at 100° C. for 16 h under nitrogen atmosphere. General Workup Procedure followed by Chromatography B afforded the title compound (90 mg, 49%). MS (ESI) calc'd for ($C_{34}H_{42}F_3N_7O_5$) [M+H]$^+$, 686.3; found, 686.2.

Step 6: (R)-1-(3-(3-(1-(4-methyl-4H-1,2,4-triazol-3-yl)propan-2-yl)phenyl)-5-(trifluoromethyl)-1H-pyrazolo[4,3-b]pyridin-7-yl)piperidin-4-ol. A mixture of tert-butyl (R)-7-(4-((tert-butoxycarbonyl)oxy)piperidin-1-yl)-3-(3-(1-(4-methyl-4H-1,2,4-triazol-3-yl)propan-2-yl)phenyl)-5-(trifluoromethyl)-1H-pyrazolo[4,3-b]pyridine-1-carboxylate (90 mg, 0.13 mmol) in HCl (5 mL, 4 M in dioxane) was stirred at room temperature for 3 h. The mixture was concentrated under vacuum. The residue was purified by Chromatography C to afford the title compound (10.7 mg, 17%). MS (ESI) calc'd for ($C_{24}H_{26}F_3N_7O$) [M+H]$^+$, 486.2; found, 486.2. $^1$H NMR (300 MHz, DMSO-$d_6$+$D_2O$) δ 8.39-8.20 (m, 3H), 7.41 (t, J=7.8 Hz, 1H), 7.25 (d, J=7.8 Hz, 1H), 6.99 (br, 1H), 4.49 (br, 1H), 3.92-3.70 (m, 2H), 3.58-3.09 (m, 6H), 3.01 (d, J=7.5 Hz, 2H), 1.98-1.94 (m, 2H), 1.70-1.40 (m, 2H), 1.30 (d, J=6.9 Hz, 3H).

Example 110: (R)-1-(3-(3-(1-(4-methyl-4H-1,2,4-triazol-3-yl)propan-2-yl)phenyl)-5-(trifluoromethyl)-1H-pyrazolo[4,3-b]pyridin-7-yl)azetidin-3-ol

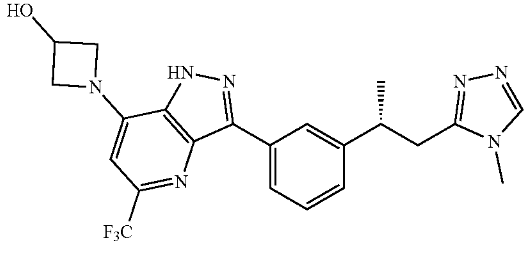 [SMILES: C[C@H](Cc1nncn1C)c1cccc(-c2n[nH]c3c(N4CC(O)C4)cc(C(F)(F)F)nc23)c1]

Step 1: 1-(3-bromo-5-(trifluoromethyl)-1H-pyrazolo[4,3-b]pyridin-7-yl)azetidin-3-ol. An $S_NAr$ reaction was performed following the procedure for Example 109, Step 3 using azetidin-3-ol to afford the title compound (200 mg). MS (ESI) calc'd for ($C_{10}H_8BrF_3N_4O$) $[M+H]^+$, 337.0/339.0; found, 337.0/339.0.

Step 2: tert-butyl 3-bromo-7-(3-((tert-butoxycarbonyl)oxy)azetidin-1-yl)-5-(trifluoromethyl)-1H-pyrazolo[4,3-b]pyridine-1-carboxylate. To a solution of 1-(5-(trifluoromethyl)-1H-pyrazolo[4,3-b]pyridin-7-yl)azetidin-3-ol (200 mg, 0.77 mmol) in DCM (5 mL) were added DMAP (9.5 mg, 0.08 mmol), DIEA (500.5 mg, 3.87 mmol), and $Boc_2O$ (507.1 mg, 2.32 mmol). The resulting solution was stirred at room temperature for 16 h before concentration under vacuum. The residue was purified by Chromatography A to afford the title compound (110 mg, 26%). MS (ESI) calc'd for ($C_{20}H_{24}BrF_3N_4O_5$) $[M+H]^+$, 537.1/539.1; found, 537.0/539.0.

Step 3: (R)-1-(3-(3-(1-(4-methyl-4H-1,2,4-triazol-3-yl)propan-2-yl)phenyl)-5-(trifluoromethyl)-1H-pyrazolo[4,3-b]pyridin-7-yl)azetidin-3-ol. To a degassed solution of tert-butyl 3-bromo-7-(3-((tert-butoxycarbonyl)oxy)azetidin-1-yl)-5-(trifluoromethyl)-1H-pyrazolo[4,3-b]pyridine-1-carboxylate (110 mg, 0.20 mmol) and (R)-4-methyl-3-(2-(3-(4,4,5,5-tetramethyl-1,3,2-dioxaborolan-2-yl)phenyl)propyl)-4H-1,2,4-triazole (100.5 mg, 0.31 mmol) in dioxane (10 mL) and $H_2O$ (1 mL) were added Pd(dppf)$Cl_2$ (15.0 mg, 0.02 mmol) and $K_2CO_3$ (56.6 mg, 0.41 mmol). The mixture was stirred at 100° C. for 16 h under nitrogen atmosphere. The resulting mixture was diluted with water and extracted with EtOAc. The combined organic layers were washed with brine, dried over anhydrous $Na_2SO_4$, and concentrated under reduced pressure. The crude residue was purified by reverse phase HPLC to afford (R)-1-(3-(3-(1-(4-methyl-4H-1,2,4-triazol-3-yl)propan-2-yl)phenyl)-5-(trifluoromethyl)-1H-pyrazolo[4,3-b]pyridin-7-yl)azetidin-3-ol (20.5 mg, 22%). MS (ESI) calc'd for ($C_{22}H_{22}F_3N_7O$) $[M+H]^+$, 458.2; found, 458.1. $^1H$ NMR (300 MHz, DMSO-$d_6$+$D_2O$) δ 8.32 (d, J=1.8 Hz, 1H), 8.29-8.17 (m, 2H), 7.43 (t, J=7.8 Hz, 1H), 7.32-7.17 (m, 1H), 6.45 (s, 1H), 4.74-4.51 (m, 3H), 4.19-4.02 (m, 2H), 3.45 (s, 3H), 3.35-3.33 (m, 1H), 3.02-3.01 (m, 2H), 1.33 (d, J=6.9 Hz, 3H).

Example 111: (S)-1-(3-(3-((R)-1-(4-methyl-4H-1,2,4-triazol-3-yl)propan-2-yl)phenyl)-5-(trifluoromethyl)-1H-pyrazolo[4,3-b]pyridin-7-yl)pyrrolidin-3-ol

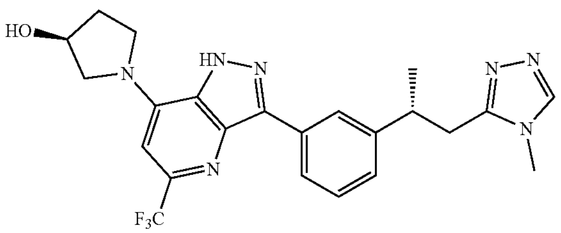 [SMILES: C[C@H](Cc1nncn1C)c1cccc(-c2n[nH]c3c(N4CC[C@H](O)C4)cc(C(F)(F)F)nc23)c1]

Step 1-4: (S)-1-(3-(3-((R)-1-(4-methyl-4H-1,2,4-triazol-3-yl)propan-2-yl)phenyl)-5-(trifluoromethyl)-1H-pyrazolo[4,3-b]pyridin-7-yl)pyrrolidin-3-ol. Following Steps 1 and 2 of Example 110 for the $S_NAr$ reaction using (S)-pyrrolidin-3-ol hydrochloride and Boc protection, then Steps 5 and 6 of Example 109 for the Suzuki coupling and Boc deprotection, afforded the title compound (44.0 mg). MS (ESI) calc'd for ($C_{23}H_{24}F_3N_7O$) $[M+H]^+$, 472.2; found, 471.8. $^1H$ NMR (400 MHz, DMSO-$d_6$) δ 13.51 (s, 1H), 8.38 (s, 1H), 8.31-8.27 (m, 2H), 7.44 (t, J=7.6 Hz, 1H), 7.27 (d, J=7.6 Hz, 1H), 6.51 (s, 1H), 5.15 (s, 1H), 4.49 (s, 1H), 3.87-3.66 (m, 4H), 3.47 (s, 3H), 3.36-3.33 (m, 1H), 3.03 (d, J=7.6 Hz, 2H), 2.13-2.08 (m, 1H), 2.02-1.99 (m, 1H), 1.35 (d, J=6.8 Hz, 3H).

Example 112: (R)-1-(3-(3-((R)-1-(4-methyl-4H-1,2,4-triazol-3-yl)propan-2-yl)phenyl)-5-(trifluoromethyl)-1H-pyrazolo[4,3-b]pyridin-7-yl)pyrrolidin-3-ol

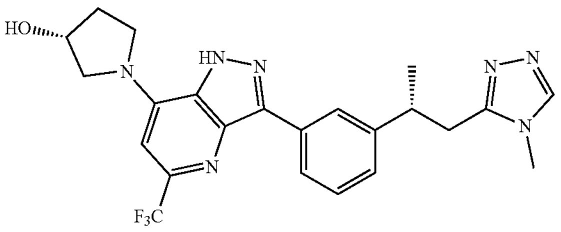 [SMILES: C[C@H](Cc1nncn1C)c1cccc(-c2n[nH]c3c(N4CC[C@@H](O)C4)cc(C(F)(F)F)nc23)c1]

Step 1-4: (R)-1-(3-(3-((R)-1-(4-methyl-4H-1,2,4-triazol-3-yl)propan-2-yl)phenyl)-5-(trifluoromethyl)-1H-pyrazolo[4,3-b]pyridin-7-yl)pyrrolidin-3-ol. Following Steps 1-4 of Example 111 starting with (R)-pyrrolidin-3-ol afforded the title compound (27.2 mg). MS (ESI) calc'd for ($C_{23}H_{24}F_3N_7O$) $[M+H]^+$, 472.2; found, 472.2. $^1H$ NMR (300 MHz, DMSO-$d_6$) δ 13.54 (br s, 1H), 8.38 (s, 1H), 8.31-8.20 (m, 2H), 7.44 (t, J=7.8 Hz, 1H), 7.25 (d, J=7.8 Hz, 1H), 6.49 (s, 1H), 5.15 (s, 1H), 4.49 (s, 1H), 3.98-3.62 (m, 4H), 3.47 (s, 3H), 3.35-3.23 (m, 1H), 3.03 (d, J=7.2 Hz, 2H), 2.13-2.03 (m, 2H), 1.34 (d, J=6.9 Hz, 3H).

Example 113: 3-[(2R)-2-[3-(7-[[(3S)-3-fluoropyrrolidin-1-yl]methyl]-5-(trifluoromethyl)-1H-pyrazolo[4,3-b]pyridin-3-yl)phenyl]propyl]-4-methyl-4H-1,2,4-triazole

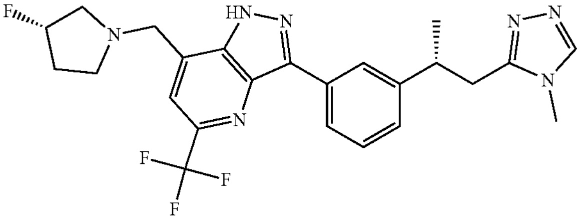 [SMILES: C[C@H](Cc1nncn1C)c1cccc(-c2n[nH]c3c(CN4CC[C@H](F)C4)cc(C(F)(F)F)nc23)c1]

Step 1: 7-chloro-5-(trifluoromethyl)-1-[[2-(trimethylsilyl)ethoxy]methyl]-1H-pyrazolo[4,3-b]pyridine. To a solution of 7-chloro-5-(trifluoromethyl)-1H-pyrazolo[4,3-b]pyridine (2.0 g, 9.0 mmol) and $K_2CO_3$ (2.5 g, 18 mmol) in dimethylformamide (20 mL) was added (2-(chloromethoxy)ethyl)trimethylsilane (1.9 g, 12 mmol). The resulting mixture was stirred at room temperature for 16 h. General Workup Procedure followed by Chromatography A afforded the title compound (2.6 g, 81%). MS (ESI) calc'd for ($C_{13}H_{17}ClF_3N_3OSi$) $[M+H]^+$, 352.1; found, 352.0.

Step 2: 7-ethenyl-5-(trifluoromethyl)-1-[[2-(trimethylsilyl)ethoxy]methyl]-1H-pyrazolo[4,3-b]pyridine. A degassed mixture of 7-chloro-5-(trifluoromethyl)-1-[[2-(trimethylsilyl)ethoxy]methyl]-1H-pyrazolo[4,3-b]pyridine (2.6 g, 7.4 mmol), potassium vinyltrifluoroborate (1.9 g, 14 mmol), Pd(dppf)$Cl_2$ (510 mg, 0.70 mmol), and $K_2CO_3$ (2.0 g, 14 mmol) in dioxane (30.0 mL) and $H_2O$ (3.0 mL) was heated at 100° C. for 16 h under nitrogen atmosphere. The solvent was removed under vacuum. The residue was purified by Chromatography A to afford the title compound (2.1 g, 82%). MS (ESI) calc'd for ($C_{15}H_{20}F_3N_3OSi$) $[M+H]^+$, 344.1; found, 344.0.

Step 3: 5-(trifluoromethyl)-1-[[2-(trimethylsilyl)ethoxy]methyl]-1H-pyrazolo[4,3-b]pyridine-7-carbaldehyde. To a mixture of 7-ethenyl-5-(trifluoromethyl)-1-[[2-(trimethylsilyl)ethoxy]methyl]-1H-pyrazolo[4,3-b]pyridine (2.1 g, 6.1 mmol) and $NaIO_4$ (2.6 g, 12 mmol) in dioxane (120 mL) and water (30.0 mL) was added $K_2OsO_4 2{\cdot}H_2O$ (80 mg, 0.22 mmol). The mixture was stirred at room temperature for 2 h. General Workup Procedure followed by Chromatography A afforded the title compound (2.1 g, 98%). MS (ESI) calc'd for ($C_{14}H_{18}F_3N_3O_2Si$) $[M+H]^+$, 346.1; found, 346.2.

Step 4: (S)-7-((3-fluoropyrrolidin-1-yl)methyl)-5-(trifluoromethyl)-1-((2-(trimethylsilyl)ethoxy)methyl)-1H-pyrazolo[4,3-b]pyridine. To a solution of 5-(trifluoromethyl)-1-[[2-(trimethylsilyl)ethoxy]methyl]-1H-pyrazolo[4,3-b]pyridine-7-carbaldehyde (2.1 g, 6.1 mmol) in DCM (20 mL) was added (3S)-3-fluoropyrrolidine (540.0 mg, 6.06 mmol), $NaBH(OAc)_3$ (2.5 g, 12 mmol) and HOAc (1 mL). The resulting mixture was stirred at room temperature for 16 h. The reaction mixture was quenched by the addition of saturated aqueous $NaHCO_3$ solution. General Workup Procedure followed by Chromatography C afforded the title compound (1.1 g, 43%). MS (ESI) calc'd for ($C_{18}H_{26}F_4N_4OSi$) $[M+H]^+$, 419.2; found, 419.4.

Step 5: (3S)-3-fluoro-1-[[5-(trifluoromethyl)-1H-pyrazolo[4,3-b]pyridin-7-yl]methyl]pyrrolidine. A mixture of (S)-7-((3-fluoropyrrolidin-1-yl)methyl)-5-(trifluoromethyl)-1-((2-(trimethylsilyl)ethoxy) methyl)-1H-pyrazolo[4,3-b]pyridine (1.1 g, 2.6 mmol) in HCl (4 M in dioxane, 20.0 mL) was stirred at room temperature for 16 h. The mixture was concentrated under vacuum and diluted with saturated aqueous $NaHCO_3$ solution. General Workup Procedure followed by Chromatography A afforded the title compound (600.0 mg, 79%). MS (ESI) calc'd for ($C_{12}H_{12}F_4N_4$) $[M+H]^+$, 289.1; found, 289.0.

Step 6: (3S)-1-[[3-bromo-5-(trifluoromethyl)-1H-pyrazolo[4,3-b]pyridin-7-yl]methyl]-3-fluoropyrrolidine. To a solution of (3S)-3-fluoro-1-[[5-(trifluoromethyl)-1H-pyrazolo[4,3-b]pyridin-7-yl]methyl]pyrrolidine (500 mg, 1.73 mmol) in methanol (5.0 mL) and $H_2O$ (5.0 mL) was added a solution of $Br_2$ (280 mg, 1.75 mmol) in methanol (2.0 mL) dropwise at 0° C. and stirred at 0° C. for 1 h. The reaction was quenched by addition of saturated aqueous $Na_2S_2O_3$ solution. General Workup Procedure followed by Chromatography A afforded the title compound (360.0 mg, 56%). MS (ESI) calc'd for ($C_{12}H_{11}BrF_4N_4$) $[M+H]^+$, 367.0; found, 367.1.

Step 7: (3S)-1-[[3-bromo-5-(trifluoromethyl)-1-[[2-(trimethylsilyl)ethoxy]methyl]-1H-pyrazolo[4,3-b]pyridin-7-yl]methyl]-3-fluoropyrrolidine. To a mixture of (3S)-1-[[3-bromo-5-(trifluoromethyl)-1H-pyrazolo[4,3-b]pyridin-7-yl]methyl]-3-fluoropyrrolidine (360 mg, 0.98 mmol) and $K_2CO_3$ (493 mg, 3.56 mmol) in DMF (5.0 mL) was added SEM-Cl (252 mg, 1.51 mmol). The resulting mixture was stirred at room temperature for 16 h. General Workup Procedure followed by Chromatography A afforded the title compound (310 mg, 63%). MS (ESI) calc'd for ($C_{18}H_{25}BrF_4N_4OSi$) $[M+H]^+$, 497.1; found, 497.1.

Step 8: 3-[(2R)-2-[3-(7-[[(3S)-3-fluoropyrrolidin-1-yl]methyl]-5-(trifluoromethyl)-1-[[2-(trimethylsilyl)ethoxy]methyl]-1H-pyrazolo[4,3-b]pyridin-3-yl)phenyl]propyl]-4-methyl-4H-1,2,4-triazole. A degassed mixture of (3S)-1-[[3-bromo-5-(trifluoromethyl)-1-[[2-(trimethylsilyl)ethoxy]methyl]-1H-pyrazolo[4,3-b]pyridin-7-yl]methyl]-3-fluoropyrrolidine (100.0 mg, 0.20 mmol), (R)-4-methyl-3-(2-(3-(4,4,5,5-tetramethyl-1,3,2-dioxaborolan-2-yl)phenyl)propyl)-4H-1,2,4-triazole (110.0 mg, 0.31 mmol), Pd(dppf)$Cl_2$ (30.0 mg, 0.04 mmol), and $K_2CO_3$ (62.0 mg, 0.45 mmol) in dioxane (2.0 mL) and $H_2O$ (0.2 mL) was heated at 100° C. for 16 h under nitrogen atmosphere. The solids were filtered off and the filtrate was concentrated under vacuum. The residue was purified by Chromatography B to afford the title compound (85.0 mg, 68%). MS (ESI) calc'd for ($C_{30}H_{39}F_4N_7OSi$) $[M+H]^+$, 618.3; found, 618.0.

Step 9: 3-[(2R)-2-[3-(7-[[(3S)-3-fluoropyrrolidin-1-yl]methyl]-5-(trifluoromethyl)-1H-pyrazolo[4,3-b]pyridin-3-yl)phenyl]propyl]-4-methyl-4H-1,2,4-triazole. A mixture of 3-[(2R)-2-[3-(7-[[(3S)-3-fluoropyrrolidin-1-yl]methyl]-5-(trifluoromethyl)-1-[[2-(trimethylsilyl)ethoxy]methyl]-1H-pyrazolo[4,3-b]pyridin-3-yl)phenyl]propyl]-4-methyl-4H-1,2,4-triazole (85.0 mg, 0.14 mmol) and HCl (4 M in dioxane, 5.0 mL) was stirred at room temperature for 6 h. The solvent was removed via concentration. The residue was treated with $NH_3$ (7 M in MeOH) and stirred at room temperature for 30 min before concentration under vacuum. The residue was purified by Chromatography C to afford the title compound (25.0 mg, 37%). MS (ESI) calc'd for ($C_{24}H_{25}F_4N_7$) $[M+H]^+$, 488.2; found, 488.1. $^1H$ NMR (400 MHz, Methanol-$d_4$) δ 8.45 (d, J=2.0 Hz, 1H), 8.37 (d, J=8.0 Hz, 1H), 8.22 (s, 1H), 7.76 (d, J=1.6 Hz, 1H), 7.41 (t, J=7.6 Hz, 1H), 7.21 (d, J=7.6 Hz, 1H), 5.29-5.14 (m, 1H), 4.18-4.10 (m, 2H), 3.41-3.37 (m, 4H), 3.22-3.09 (m, 2H), 2.98-2.83 (m, 3H), 2.61-2.56 (m, 1H), 2.30-2.21 (m, 1H), 2.13-2.05 (m, 1H), 1.49 (d, J=6.8 Hz, 3H).

Example 114: (S)-7-((3-fluoropyrrolidin-1-yl)methyl)-3-(3-(3-((4-methyl-4H-1,2,4-triazol-3-yl)methyl)oxetan-3-yl)phenyl)-5-(trifluoromethyl)-1H-pyrazolo[4,3-b]pyridine

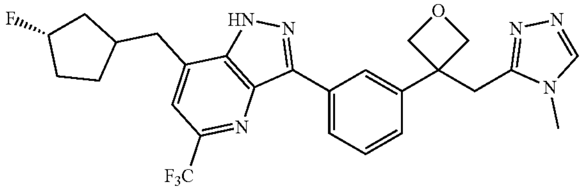 [SMILES: Cn1cnnc1CC1(c2cccc(-c3n[nH]c4c(CC5CC[C@H](F)C5)cc(C(F)(F)F)nc34)c2)COC1]

Step 1: 4-methyl-3-((3-(3-(4,4,5,5-tetramethyl-1,3,2-dioxaborolan-2-yl)phenyl)oxetan-3-yl)methyl)-4H-1,2,4-triazole. The reaction was performed in a similar manner as to Step 1 of Example 109 using 3-((3-(3-bromophenyl)oxetan-3-yl)methyl)-4-methyl-4H-1,2,4-triazole (500 mg, 1.62 mmol) to give the title compound (299 mg, 0.84 mmol, 52%).

Step 2: (S)-7-((3-fluoropyrrolidin-1-yl)methyl)-3-(3-(3-((4-methyl-4H-1,2,4-triazol-3-yl)methyl)oxetan-3-yl)phenyl)-5-(trifluoromethyl)-1-((2-(trimethylsilyl)ethoxy)methyl)-1H-pyrazolo[4,3-b]pyridine. A Suzuki reaction was performed following the procedure for Example 113, Step 8 to give the title compound (65 mg, 0.10 mmol).

Step 3: (S)-7-((3-fluoropyrrolidin-1-yl)methyl)-3-(3-(3-((4-methyl-4H-1,2,4-triazol-3-yl)methyl)oxetan-3-yl)phenyl)-5-(trifluoromethyl)-1H-pyrazolo[4,3-b]pyridine. (S)-7-((3-fluoropyrrolidin-1-yl)methyl)-3-(3-(3-((4-methyl-4H-1, 2,4-triazol-3-yl)methyl)oxetan-3-yl)phenyl)-5-(trifluoromethyl)-1-((2-(trimethylsilyl)ethoxy)methyl)-1H-pyrazolo[4,3-b]pyridine (65 mg, 0.10 mmol) was dissolved in DCM (1 mL) at room temperature. Trifluoroacetic acid (0.25 mL) was added and the reaction was stirred for 3 days. Sat. sodium bicarbonate solution was added and the product was extracted with DCM: methanol (4:1) four times. The combined organic layers were dried, filtered, and concentrated. Chromatography C gave the title compound (24 mg, 46%). $^1$H NMR (500 MHz, Acetonitrile-$d_3$) δ 11.92 (s, 1H), 8.44 (dt, J=7.8, 1.3 Hz, 1H), 8.08 (t, J=1.8 Hz, 1H), 7.85 (s, 1H), 7.69 (s, 1H), 7.44 (t, J=7.8 Hz, 1H), 6.97 (dt, J=7.7, 1.4 Hz, 1H), 5.24 (dddd, J=55.6, 6.6, 4.4, 1.9 Hz, 1H), 5.04 (q, J=6.1 Hz, 4H), 4.23-4.02 (m, 2H), 3.56 (s, 2H), 2.91 (s, 3H), 2.89-2.74 (m, 2H), 2.56 (td, J=8.5, 5.8 Hz, 1H), 2.34-2.18 (m, 1H), 2.09-1.97 (m, 1H). MS (ESI) calc'd for ($C_{25}H_{25}F_4N_7O$) [M+H]$^+$, 516; found, 516.

Example 115: 3-(3-((R)-cyclobutyl(4-methyl-4H-1,2,4-triazol-3-yl)methyl)phenyl)-7-(((S)-3-fluoropyrrolidin-1-yl)methyl)-5-(trifluoromethyl)-1H-pyrazolo[4,3-b]pyridine

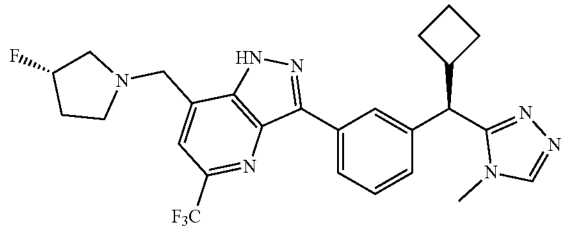 [SMILES: Cn1cnnc1[C@@H](c1cccc(-c2n[nH]c3c(CN4CC[C@H](F)C4)cc(C(F)(F)F)nc23)c1)C1CCC1]

Step 1: methyl 2-(3-bromophenyl)-2-cyclobutylacetate. To a mixture of methyl 2-(3-bromophenyl)acetate (10.0 g, 43.7 mmol) in DMF (100 mL) was added t-BuOK (6.4 g, 57 mmol) in portions at 0° C. and stirred at 0° C. for 30 min. Bromocyclobutane (7.1 g, 52 mmol) was added to the above solution dropwise at 0° C. The resulting mixture was stirred at room temperature for 16 h. The mixture was poured into saturated aqueous $NH_4Cl$ solution. General Workup Procedure followed by Chromatography A afforded the title compound (10.2 g, 82%). MS (ESI) calculated for ($C_{13}H_{15}BrO_2$) [M+1]$^+$, 283.0; found, 283.0.

Step 2: 2-(3-bromophenyl)-2-cyclobutylacetohydrazide. A mixture of methyl 2-(3-bromophenyl)-2-cyclobutylacetate (10.2 g, 36.0 mmol) in hydrazine (20 mL) and EtOH (80 mL) was stirred at 80° C. for 16 h. The solvents were removed under vacuum. General Workup Procedure afforded the title compound (10.5 g, crude), which was used without purification. MS (ESI) calculated for ($C_{12}H_{15}BrN_2O$) [M+1]$^+$, 283.0; found, 283.0.

Step 3: 5-[(3-bromophenyl)(cyclobutyl)methyl]-4-methyl-1,2,4-triazole-3-thiol. A mixture of 2-(3-bromophenyl)-2-cyclobutylacetohydrazide (10.5 g, 37.1 mmol) and MeNCS (3.30 g, 45.2 mmol) in THE (100 mL) was stirred at room temperature for 16 h. To the above mixture was added a solution of NaOH (8.0 g) in water (100 mL). The resulting mixture was stirred at 60° C. for 2 h. When the reaction was completed, the resulting mixture was acidified to pH ~4 by HCl (1 N). General Workup Procedure afforded the title compound (11.0 g, crude), which was used without purification. MS (ESI) calculated for ($C_{14}H_{16}BrN_3S$) [M+1]$^+$, 338.0; found, 338.0.

Step 4: 3-[(3-bromophenyl)(cyclobutyl)methyl]-4-methyl-1,2,4-triazole. To a solution of 5-[(3-bromophenyl)(cyclobutyl)methyl]-4-methyl-1,2,4-triazole-3-thiol (2.0 g, 5.9 mmol) in DCM (20.0 mL) were added acetic acid (4.0 mL) and $H_2O_2$ (3.4 g, 30 mmol) dropwise at room temperature. The reaction was stirred at room temperature for 1 h. The solvent was removed under vacuum and the residue was diluted with water. The aqueous solution was basified by saturated aqueous sodium bicarbonate solution and extracted with DCM. The combined organic layers were washed with brine, dried over anhydrous sodium sulfate, and concentrated under vacuum. Chromatography B afforded the title compound (1.3 g, 72%). MS (ESI) calculated for ($C_{14}H_{16}BrN_3$) [M+1]$^+$, 306.1; found, 306.2.

Step 5: 3-[(S)-(3-bromophenyl)(cyclobutyl)methyl]-4-methyl-1,2,4-triazole and 3-[(R)-(3-bromophenyl)(cyclobutyl)methyl]-4-methyl-1,2,4-triazole. The racemic compound of 3-((3-bromophenyl)(cyclobutyl)methyl)-4-methyl-4H-1,2,4-triazole (4.0 g) was separated by prep-chiral-SFC with the following conditions [Column: Lux 5u Cellulose-4, AXIA Packed, 2.12*25 cm, 5 μm; Mobile Phase A: $CO_2$, Mobile Phase B: MeOH (2 mM $NH_3$-MeOH)] to afford 3-[(S)-(3-bromophenyl)(cyclobutyl)methyl]-4-methyl-1,2,4-triazole (1.65 g) with a shorter retention time and 3-[(R)-(3-bromophenyl)(cyclobutyl)methyl]-4-methyl-1,2,4-triazole (1.68 g) with a longer retention time.

Step 6: (R)-3-(cyclobutyl(3-(4,4,5,5-tetramethyl-1,3,2-dioxaborolan-2-yl)phenyl)methyl)-4-methyl-4H-1,2,4-triazole. The reaction was performed in a similar manner as to Step 1 of Example 109 using 3-[(R)-(3-bromophenyl)(cyclobutyl)methyl]-4-methyl-1,2,4-triazole (99 mg, 0.32 mmol) to give the title compound (118 mg) as a mixture with the starting material, which was used as is in the next step.

Steps 7-8: 3-(3-((R)-cyclobutyl(4-methyl-4H-1,2,4-triazol-3-yl)methyl)phenyl)-7-(((S)-3-fluoropyrrolidin-1-yl)methyl)-5-(trifluoromethyl)-1H-pyrazolo[4,3-b]pyridine. A Suzuki reaction and subsequent SEM deprotection was performed following the procedures in Example 114, Step 2 and 3 to give the title compound (10 mg, 0.020 mmol). $^1$H NMR (500 MHz, Acetonitrile-$d_3$) δ 11.90 (s, 1H), 8.42 (d, J=7.9 Hz, 1H), 8.28 (d, J=1.8 Hz, 1H), 8.04 (s, 1H), 7.69 (s, 1H), 7.48 (t, J=7.7 Hz, 1H), 7.30 (d, J=7.6 Hz, 1H), 5.24 (d, J=54.3 Hz, 1H), 4.19-4.16 (m, 2H), 4.06 (d, J=15.0 Hz, 1H), 3.41 (s, 3H), 3.36 (dd, J=18.1, 8.6 Hz, 1H), 2.96-2.75 (m, 3H), 2.57 (q, J=8.2 Hz, 1H), 2.35-2.16 (m, 3H), 1.91-1.73 (m, 5H). MS (ESI) calc'd for ($C_{26}H_{27}F_4N_7$) [M+H]$^+$, 514; found, 514.

Example 116: (R)-3-(3-(1-(4-methyl-4H-1,2,4-triazol-3-yl)propan-2-yl)phenyl)-5-(trifluoromethyl)-1H-pyrazolo[4,3-b]pyridine

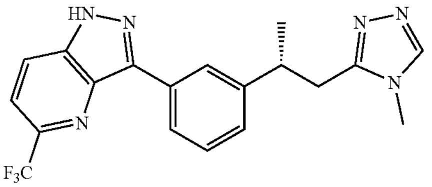 [SMILES: C[C@H](Cc1nncn1C)c1cccc(-c2n[nH]c3ccc(C(F)(F)F)nc23)c1]

Step 1: 2-methyl-6-(trifluoromethyl)pyridin-3-amine. To a degassed solution of 2-chloro-6-(trifluoromethyl)pyridin-3-amine (10 g, 50.88 mmol) and methylboronic acid (12.2 g, 204 mmol) in dioxane (200 mL) were added $Pd(PPh_3)_4$ (5.9 g, 5.1 mol) and $K_2CO_3$ (28.1 g, 204 mmol). The resulting solution was stirred at 100° C. for 16 h under nitrogen atmosphere. General Workup Procedure followed by Chromatography A afforded the title compound (7.7 g, 86%). MS (ESI) calc'd for ($C_7H_7F_3N_2$) $[M+H]^+$, 177.1; found, 177.0.

Step 2: N-(2-methyl-6-(trifluoromethyl)pyridin-3-yl)acetamide. To a solution of 2-methyl-6-(trifluoromethyl)pyridin-3-amine (7.6 g, 43 mol) and triethylamine (13.1 g, 129 mmol) in THE (100 mL) was added AcCl (6.8 g, 86 mmol) dropwise at 0° C. under nitrogen atmosphere. The resulting solution was stirred at room temperature for 2 h. General Workup Procedure followed by Chromatography A afforded the title compound (4.1 g, 43%). MS (ESI) calc'd for ($C_9H_9F_3N_2O$) $[M+H]^+$, 219.1; found, 219.0.

Step 3: 1-(5-(trifluoromethyl)-1H-pyrazolo[4,3-b]pyridin-1-yl)ethan-1-one. To a solution of N-(2-methyl-6-(trifluoromethyl)pyridin-3-yl)acetamide (4.1 g, 19 mmol) in toluene (50 mL) were added tert-butyl nitrite (3.1 g, 30 mmol), $Ac_2O$ (5.8 g, 56 mmol), and AcOK (2.2 g, 23 mmol). The resulting solution was stirred at 80° C. for 16 h. The reaction mixture was quenched by the addition of saturated aqueous $NaHCO_3$ solution. General Workup Procedure followed by Chromatography A afforded the title compound (2.5 g, 58%). MS (ESI) calc'd for ($C_9H_6F_3N_3O$) $[M+H]^+$, 230.0; found, 230.0.

Step 4: 5-(trifluoromethyl)-1H-pyrazolo[4,3-b]pyridine. To a solution of 1-(5-(trifluoromethyl)-1H-pyrazolo[4,3-b]pyridin-1-yl)ethan-1-one (2.5 g, 10 mmol) in THE (20 mL) and MeOH (5 mL) was added a solution of NaOH (1.3 g, 33 mmol) in $H_2O$ (2.5 mL) dropwise at 0° C. The resulting solution was stirred at room temperature for 2 h. General Workup Procedure afforded the crude title compound (2.0 g, 57%). MS (ESI) calc'd for ($C_7H_4F_3N_3$) $[M+H]^+$, 188.0; found, 188.0.

Step 5: 3-bromo-5-(trifluoromethyl)-1H-pyrazolo[4,3-b]pyridine. To a solution of 5-(trifluoromethyl)-1H-pyrazolo[4,3-b]pyridine (2.0 g, 11 mmol) in MeOH (15 mL) and $H_2O$ (15 mL) was added $Br_2$ (3.4 g, 21 mmol) dropwise at 0° C. The resulting solution was stirred at 0° C. for 1 h. The reaction mixture was quenched by saturated aqueous $NaS_2O_3$ solution. General Workup Procedure followed by Chromatography A afforded the title compound (2.0 g, 70%). MS (ESI) calc'd for ($C_7H_3BrF_3N_3$) $[M+H]^+$, 265.9/267.9; found, 266.0/268.0.

Steps 6-7: (R)-3-(3-(1-(4-methyl-4H-1,2,4-triazol-3-yl)propan-2-yl)phenyl)-5-(trifluoromethyl)-1H-pyrazolo[4,3-b]pyridine. Boc protection and Suzuki reactions were performed following Step 2 and 3 for Example 110 using tert-butyl 3-bromo-5-(trifluoromethyl)-1H-pyrazolo[4,3-b]pyridine-1-carboxylate (150 mg, 0.41 mmol) to afford (R)-3-(3-(1-(4-methyl-4H-1,2,4-triazol-3-yl)propan-2-yl)phenyl)-5-(trifluoromethyl)-1H-pyrazolo[4,3-b]pyridine (52.1 mg). MS (ESI) calc'd for ($C_{19}H_{17}F_3N_6$) $[M+H]^+$, 387.1; found, 387.1. $^1H$ NMR (300 MHz, DMSO-$d_6$) δ 13.89 (s, 1H), 8.48-8.18 (m, 4H), 7.90 (d, J=8.4 Hz, 1H), 7.48 (t, J=7.8 Hz, 1H), 7.35-7.31 (m, 1H), 3.51 (s, 3H), 3.06-3.04 (m, 1H), 3.05 (d, J=7.2 Hz, 2H), 1.37 (d, J=6.9 Hz, 3H).

Example 117: (R)-1-(3-(3-(1-(4-methyl-4H-1,2,4-triazol-3-yl)propan-2-yl)phenyl)-1H-pyrazolo[4,3-b]pyridin-7-yl)piperidin-4-ol

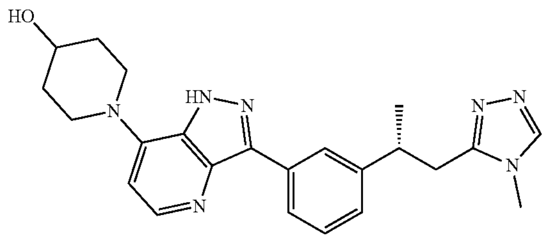 [SMILES: C[C@H](Cc1nncn1C)c1cccc(-c2n[nH]c3c(N4CCC(O)CC4)ccnc23)c1]

Step 1: 4-bromo-6-chloro-2-methylpyridin-3-amine. The bromination was carried out following Step 2 in Example 109 using 6-chloro-2-methylpyridin-3-amine (30 g, 0.21 mol) to afford the title compound (25 g, 54%). MS (ESI) calc'd for ($C_6H_6BrClN$) $[M+H]^+$, 220.9/222.9; found, 221.0/223.0.

Steps 2-3: 1-(7-bromo-5-chloro-1H-pyrazolo[4,3-b]pyridin-1-yl)ethan-1-one. Following Steps 2 and 3 of Example 116 afforded the title compound (2.7 g). MS (ESI) calc'd for ($C_8H_5BrClN_3O$) $[M+H]^+$, 273.9/275.9; found, 274.0/276.0.

Step 4: 1-(5-chloro-1H-pyrazolo[4,3-b]pyridin-7-yl)piperidin-4-ol. An $S_NAr$ reaction was performed following the procedure for Example 109, Step 3 to afford the title compound (2.3 g, 92%). MS (ESI) calc'd for ($C_{11}H_{13}ClN_4O$) $[M+H]^+$, 253.1/255.1; found, 253.0/255.0.

Step 5: 1-(1H-pyrazolo[4,3-b]pyridin-7-yl)piperidin-4-ol. To a solution of 1-(5-chloro-1H-pyrazolo[4,3-b]pyridin-7-yl)piperidin-4-ol (2.3 g, 9.10 mmol) in MeOH (30 mL) were added $NaHCO_3$ (764.6 mg, 9.10 mmol) and Pd/C (10%, 600 mg). The resulting solution was stirred at room temperature for 16 h under $H_2$ (2 atm). The solids were filtered off and the filtrate was concentrated under vacuum to afford the title compound (2.0 g, crude), which was used without purification. MS (ESI) calc'd for ($C_{11}H_{14}N_4O$) $[M+H]^+$, 219.1; found, 219.0.

Step 6: 1-(3-bromo-1H-pyrazolo[4,3-b]pyridin-7-yl)piperidin-4-ol. Bromination was performed following the procedure in Step 2 of Example 109 to afford the title compound (460 mg, 22%). MS (ESI) calc'd for ($C_{11}H_{13}BrN_4O$) $[M+H]^+$, 297.0/299.0; found, 297.0/299.0.

Steps 7-9: (R)-1-(3-(3-(1-(4-methyl-4H-1,2,4-triazol-3-yl)propan-2-yl)phenyl)-1H-pyrazolo[4,3-b]pyridin-7-yl)piperidin-4-ol. Following Steps 3-5 in Example 109 afforded the title compound (9.6 mg, 18%). MS (ESI) calc'd for ($C_{23}H_{27}N_7O$) $[M+H]^+$, 418.2; found, 418.2. $^1H$ NMR (300 MHz, DMSO-$d_6$+$D_2O$) δ 8.31-8.27 (m, 2H), 8.20-8.08 (m, 2H), 7.45 (t, J=8.1 Hz, 1H), 7.30-7.27 (m, 1H), 6.73-6.71 (m, 1H), 4.00-3.92 (m, 1H), 3.90-3.70 (m, 2H), 3.42 (s, 3H), 3.38-3.31 (m, 1H), 3.30-3.12 (m, 2H), 3.09-3.07 (m, 2H), 1.97-1.89 (m, 2H), 1.69-1.51 (m, 2H), 1.32 (d, J=6.9 Hz, 3H).

Example 118: (R)-3-(3-(1-(4-methyl-4H-1,2,4-triazol-3-yl)propan-2-yl)phenyl)-1H-pyrazolo[4,3-b]pyridine

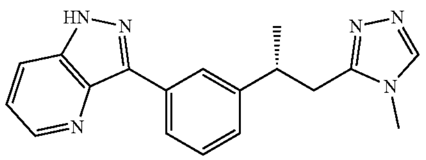 [SMILES: C[C@H](Cc1nncn1C)c1cccc(-c2n[nH]c3cccnc23)c1]

Step 1: tert-butyl 3-bromo-1H-pyrazolo[4,3-b]pyridine-1-carboxylate. Boc protection was performed following Step 2 of Example 110 using 3-bromo-1H-pyrazolo[4,3-b]pyridine (300.0 mg, 1.51 mmol) to afford the title compound (360.0 mg, 80%). MS (ESI) calc'd for ($C_{11}H_{12}BrN_3O_2$) $[M+H]^+$, 298.0; found, 298.0.

Steps 2-3: (R)-3-(3-(1-(4-methyl-4H-1,2,4-triazol-3-yl)propan-2-yl)phenyl)-1H-pyrazolo[4,3-b]pyridine. A Suzuki coupling and Boc deprotection was performed following Steps 5 and 6 in Example 109 to afford the title compound (22.7 mg, 15%). MS (ESI) calc'd for ($C_{18}H_{18}N_6$) $[M+1]^+$, 319.2; found, 319.1. $^1$H NMR (300 MHz, DMSO-$d_6$) δ 13.41 (s, 1H), 8.65-8.63 (m, 1H), 8.42-8.36 (m, 2H), 8.27 (s, 1H), 8.08-8.05 (m, 1H), 7.46-7.41 (m, 2H), 7.30-7.27 (m, 1H), 3.46 (s, 3H), 3.40-3.33 (m, 1H), 3.05 (d, J=7.5 Hz, 2H), 1.36 (d, J=6.9 Hz, 3H).

Example 119: (R)-5-methyl-3-(3-(1-(4-methyl-4H-1,2,4-triazol-3-yl)propan-2-yl)phenyl)-1H-pyrazolo[4,3-b]pyridine

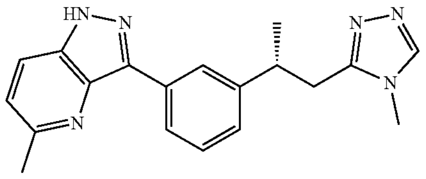 [SMILES: Cc1ccc2[nH]nc(-c3cccc([C@H](C)Cc4nncn4C)c3)c2n1]

Steps 1-5: (R)-5-methyl-3-(3-(1-(4-methyl-4H-1,2,4-triazol-3-yl)propan-2-yl)phenyl)-1H-pyrazolo[4,3-b]pyridine. Following Steps 2 to 7 in Example 116 starting with 2,6-dimethylpyridin-3-amine afforded the title compound (31.1 mg). MS (ESI) calc'd for ($C_{19}H_{20}N_6$) $[M+Na]^+$, 355.2; found, 354.8. $^1$H NMR (300 MHz, DMSO-$d_6$) δ 13.27 (s, 1H), 8.43-8.40 (m, 1H), 8.35 (s, 1H), 8.27 (s, 1H), 7.94 (d, J=8.7 Hz, 1H), 7.42 (t, J=7.5 Hz, 1H), 7.32-7.24 (m, 2H), 3.46 (s, 3H), 3.38-3.31 (m, 1H), 3.04 (d, J=7.5 Hz, 2H), 2.67 (s, 3H), 1.36 (d, J=6.9 Hz, 3H).

Example 120: (R)-6-cyclobutyl-3-(3-(1-(4-methyl-4H-1,2,4-triazol-3-yl)propan-2-yl)phenyl)-1H-pyrazolo[4,3-b]pyridine

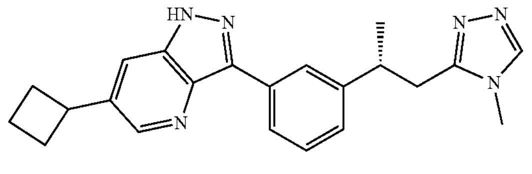 [SMILES: C[C@H](Cc1nncn1C)c1cccc(-c2n[nH]c3cc(C4CCC4)cnc23)c1]

Step 1: tert-butyl 6-bromo-1H-pyrazolo[4,3-b]pyridine-1-carboxylate. To a solution of 6-bromo-1H-pyrazolo[4,3-b]pyridine (3.0 g, 15.15 mmol) in DCM (50 mL) were added DMAP (186.0 mg, 1.52 mmol), $Boc_2O$ (4.0 g, 19 mmol), and triethylamine (3.08 g, 30.5 mmol). The resulting mixture was stirred at room temperature for 12 h before concentration under vacuum. The residue was purified by Chromatography A to afford the title compound (4.1 g, 91%). MS (ESI) calc'd for ($C_{11}H_{12}BrN_3O_2$) $[M+H]^+$, 298.0; found, 298.0.

Step 2: 6-cyclobutyl-1H-pyrazolo[4,3-b]pyridine. To a degassed solution of tert-butyl 6-bromo-1H-pyrazolo[4,3-b]pyridine-1-carboxylate (800.0 mg, 2.68 mmol) and Pd(dppf)$Cl_2$ (197.4 mg, 0.27 mmol) in THF (16.0 mL) was added cyclobutylzinc bromide (6.7 mL, 0.5 M in THF) dropwise at room temperature. The resulting mixture was stirred at 90° C. for 1 h under nitrogen atmosphere. General Workup Procedure followed by Chromatography A afforded the title compound (400.0 mg, 86%). MS (ESI) calc'd for ($C_{10}H_{11}N_3$) $[M+H]^+$, 174.1; found, 174.0.

Step 3: 3-bromo-6-cyclobutyl-1H-pyrazolo[4,3-b]pyridine. To a solution of 6-cyclobutyl-1H-pyrazolo[4,3-b]pyridine (360.0 mg, 2.08 mmol) in $CCl_4$ (20.0 mL) was added $Br_2$ (505.7 mg, 3.12 mmol). The resulting mixture was stirred at room temperature for 2 h. The reaction was quenched by the addition of saturated aqueous $Na_2S_2O_3$ solution and extracted with DCM. The combined organic layers were washed with brine, dried over anhydrous sodium sulfate, and concentrated under vacuum. The residue was purified by Chromatography B to afford the title compound (450.0 mg, 86%). MS (ESI) calc'd for ($C_{10}H_{10}BrN_3$) $[M+H]^+$, 252.0; found, 252.0.

Steps 4-5: (R)-6-cyclobutyl-3-(3-(1-(4-methyl-4H-1,2,4-triazol-3-yl)propan-2-yl)phenyl)-1H-pyrazolo[4,3-b]pyridine. Boc protection and Suzuki coupling was performed following the procedures in Steps 2 and 3 of Example 110 to afford the title compound (40.1 mg, 22%). MS (ESI) calc'd for ($C_{22}H_{24}N_6$) $[M+H]^+$, 373.2; found, 373.1. $^1$H NMR (400 MHz, DMSO-$d_6$) δ 13.26 (s, 1H), 8.54 (d, J=1.6 Hz, 1H), 8.38-8.34 (m, 2H), 8.26 (s, 1H), 7.81 (s, 1H), 7.42 (t, J=7.6 Hz, 1H), 7.27 (d, J=7.6 Hz, 1H), 3.78-3.74 (m, 1H), 3.45 (s, 3H), 3.39-3.36 (m, 1H), 3.03 (d, J=7.2 Hz, 2H), 2.43-2.37 (m, 2H), 2.28-2.18 (m, 2H), 2.09-1.02 (m, 1H), 1.91-1.82 (m, 1H), 1.35 (d, J=6.8 Hz, 3H).

Example 121: (S)-1-(4-(1-((4-methyl-4H-1,2,4-triazol-3-yl)thio)ethyl)pyridin-2-yl)-3-(pyridin-2-yl)urea

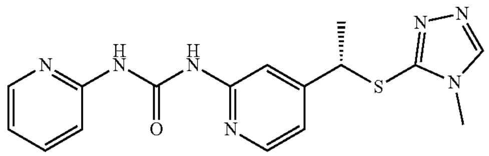

The procedure of Example 3 was followed using (S)-4-(1-((4-methyl-4H-1,2,4-triazol-3-yl)thio)ethyl)pyridin-2-amine and 2-aminopyridine to give the title compound (18.9 mg, 37%). $^1$H NMR (500 MHz, DMSO-$d_6$) δ 10.50 (s, 2H), 8.57 (s, 1H), 8.30 (dt, J=5.1, 1.4 Hz, 1H), 8.22 (d, J=5.3 Hz, 1H), 7.79 (ddd, J=9.0, 7.2, 1.9 Hz, 1H), 7.70 (s, 2H), 7.06 (ddd, J=7.2, 5.0, 1.1 Hz, 1H), 7.01 (dd, J=5.3, 1.6 Hz, 1H), 4.67 (q, J=7.0 Hz, 1H), 3.45 (s, 3H), 1.64 (d, J=7.0 Hz, 3H). LCMS: $C_{16}H_{17}N_7OS$ requires: 355, found: m/z=356 $[M+H]^+$.

Example 122: N-(isoquinolin-3-yl)-3-(1-((4-methyl-4H-1,2,4-triazol-3-yl)thio)ethyl)benzamide

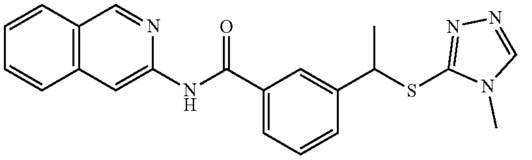 [SMILES: CC(Sc1nncn1C)c1cccc(C(=O)Nc2cc3ccccc3cn2)c1]

The procedure for Example O, Step 3 was followed to afford the title compound (58.6 mg, 39%). MS (ESI) calculated for ($C_{21}H_{19}N_5OS$) $[M+1]^+$, 390.1; found, 390.3. $^1H$ NMR (300 MHz, DMSO-$d_6$) δ 10.97 (s, 1H), 9.24 (s, 1H), 8.65 (s, 1H), 8.56 (s, 1H), 8.14-8.10 (m, 2H), 8.00-7.96 (m, 2H), 7.79-7.73 (m, 1H), 7.61-7.44 (m, 3H), 4.80 (q, J=6.9 Hz, 1H), 3.39 (s, 3H), 1.74 (d, J=6.9 Hz, 3H).

Example 123: 3,4-dimethyl-N-(3-((S)-1-((4-methyl-4H-1,2,4-triazol-3-yl)thio)ethyl)phenyl)-5-oxopiperazine-1-carboxamide

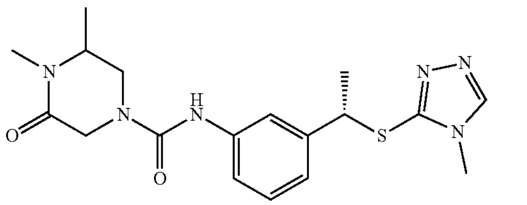 [SMILES: CC1CN(C(=O)Nc2cccc([C@H](C)Sc3nncn3C)c2)CC(=O)N1C]

The procedure for Example 39 was followed using 1,6-dimethylpiperazin-2-one to afford the title compound (22.6 mg, 34%). MS (ESI) calc'd for ($C_{18}H_{24}N_6O_2S$) $[M+1]^+$, 389.2; found, 389.0. $^1H$ NMR (300 MHz, Chloroform-d) δ 8.11-8.02 (m, 2H), 7.53-7.50 (m, 1H), 7.28-7.14 (m, 2H), 6.91 (d, J=7.8 Hz, 1H), 4.63-4.56 (m, 1H), 4.51-4.38 (m, 1H), 4.15-3.97 (m, 2H), 3.55-3.43 (m, 2H), 3.26 (s, 3H), 2.99 (s, 3H), 1.73 (d, J=7.2 Hz, 3H), 1.31 (d, J=6.3 Hz, 3H).

Example 124: (S)—N-(3-(1-((4-methyl-4H-1,2,4-triazol-3-yl)thio)ethyl)phenyl)piperidine-1-carboxamide

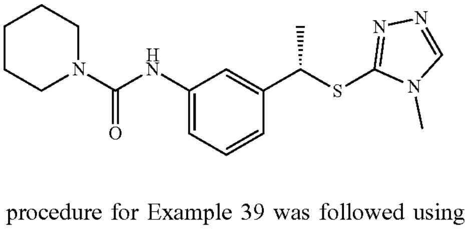

The procedure for Example 39 was followed using piperidine to afford the title compound (30 mg, 31%). MS (ESI) calc'd for ($C_{17}H_{23}N_5OS$) $[M+1]^+$, 346.2; found, 346.2. $^1H$ NMR (300 MHz, DMSO-$d_6$) δ 8.54 (s, 1H), 8.47 (s, 1H), 7.47 (t, J=1.8 Hz, 1H), 7.42-7.39 (m, 1H), 7.14 (t, J=7.8 Hz, 1H), 6.82 (dt, J=7.8, 1.2 Hz, 1H), 4.59 (q, J=6.9 Hz, 1H), 3.43-3.40 (m, 4H), 3.38 (s, 3H), 1.64-1.59 (m, 5H), 1.54-1.44 (m, 4H).

Example 125: (S)—N-(3-(1-((4-methyl-4H-1,2,4-triazol-3-yl)thio)ethyl)phenyl)-6,7-dihydroisoxazolo[4,3-c]pyridine-5(4H)-carboxamide

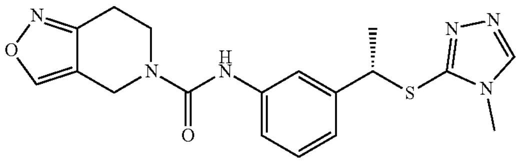 [SMILES: C[C@H](Sc1nncn1C)c1cccc(NC(=O)N2CCc3nocc3C2)c1]

The procedure for Example 39 was followed using 4,5,6,7-tetrahydroisoxazolo[4,3-c]pyridine to afford the title compound (28.5 mg, 44%). MS (ESI) calc'd for ($C_{18}H_{20}N_6O_2S$) $[M+1]^+$, 385.1; found, 385.0. $^1H$ NMR (300 MHz, Chloroform-d) δ 8.22 (s, 1H), 8.08 (s, 1H), 7.67 (s, 1H), 7.42-7.39 (m, 1H), 7.17 (t, J=7.8 Hz, 1H), 7.06 (s, 1H), 6.96 (d, J=7.8 Hz, 1H), 4.69-4.55 (m, 3H), 3.81 (t, J=5.7 Hz, 2H), 3.29 (s, 3H), 2.91 (t, J=5.7 Hz, 2H), 1.72 (d, J=7.2 Hz, 3H).

Example 126: (S)-7-methyl-N-(3-(1-((4-methyl-4H-1,2,4-triazol-3-yl)thio)ethyl)phenyl)-1,7-diazaspiro[3.5]nonane-1-carboxamide

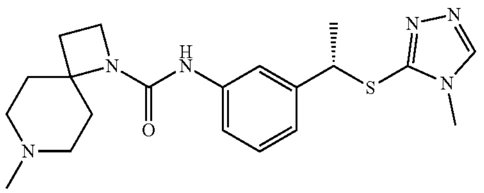 [SMILES: C[C@H](Sc1nncn1C)c1cccc(NC(=O)N2CCC23CCN(C)CC3)c1]

The procedure for Example 39 was followed using 7-methyl-1,7-diazaspiro[3.5]nonane to afford the title compound (23.0 mg, 34%). MS (ESI) calc'd for ($C_{20}H_{28}N_6OS$) $[M+1]^+$, 401.2; found, 401.0. $^1H$ NMR (300 MHz, Chloroform-d) δ 8.50 (s, 1H), 8.12 (s, 1H), 7.30 (d, J=7.2 Hz, 1H), 7.15 (d, J=7.8 Hz, 1H), 7.06 (s, 1H), 6.85 (d, J=7.8 Hz, 1H), 4.69-4.52 (m, 1H), 3.96 (t, J=7.5 Hz, 2H), 3.45 (s, 2H), 3.28 (s, 3H), 2.97-2.54 (m, 7H), 2.14-1.91 (m, 4H), 1.71 (d, J=6.9 Hz, 3H).

Example 127: N-(3-((S)-1-((4-methyl-4H-1,2,4-triazol-3-yl)thio)ethyl)phenyl)-3-phenylpyrrolidine-1-carboxamide

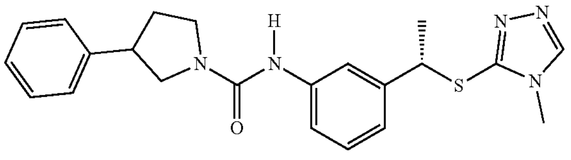 [SMILES: C[C@H](Sc1nncn1C)c1cccc(NC(=O)N2CCC(c3ccccc3)C2)c1]

The procedure for Example 39 was followed using 3-phenylpyrrolidine to afford the title compound (23.8 mg, 34%).

MS (ESI) calc'd for ($C_{22}H_{25}N_5OS$) $[M+1]^+$, 408.2; found, 408.2. $^1H$ NMR (400 MHz, DMSO-$d_6$) δ 8.54 (s, 1H), 8.21 (s, 1H), 7.54 (d, J=2.0 Hz, 1H), 7.47 (d, J=8.4 Hz, 1H), 7.37-7.34 (m, 4H), 7.28-7.22 (m, 1H), 7.15 (t, J=8.0 Hz, 1H), 6.82 (d, J=7.6 Hz, 1H), 4.63-4.54 (m, 1H), 3.88 (t, J=8.4 Hz, 1H), 3.64 (t, J=9.2 Hz, 1H), 3.50-3.39 (m, 2H), 3.37 (s, 3H), 3.32-3.30 (m, 1H), 2.35-2.21 (m, 1H), 2.09-1.93 (m, 1H), 1.61 (d, J=6.8 Hz, 3H).

Example 128: N-[3-[(1S)-1-[(4-methyl-4H-1,2,4-triazol-3-yl)sulfanyl]ethyl]phenyl]morpholine-4-carboxamide

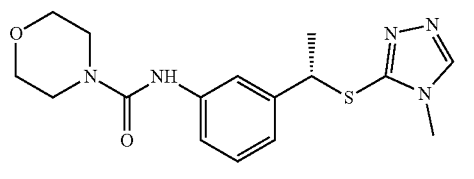 [SMILES: C[C@H](Sc1nncn1C)c1cccc(NC(=O)N2CCOCC2)c1]

The procedure for Example 39 was followed using morpholine to afford the title compound (35 mg, 36%). MS (ESI) calc'd for ($C_{16}H_{21}N_5O_2S$) $[M+1]^+$, 348.1; found, 348.0. $^1H$ NMR (300 MHz, DMSO-$d_6$) δ 8.57 (s, 1H), 8.54 (s, 1H), 7.47 (t, J=2.0 Hz, 1H), 7.41-7.39 (m, 1H), 7.16 (t, J=7.8 Hz, 1H), 6.84 (dt, J=7.8, 1.2 Hz, 1H), 4.60 (q, J=6.8 Hz, 1H), 3.63-3.59 (m, 4H), 3.44-3.40 (m, 7H), 1.61 (d, J=6.9 Hz, 3H).

Example 129: 1-(3-((S)-1-((4-methyl-4H-1,2,4-triazol-3-yl)thio)ethyl)phenyl)-3-(1-(pyridazin-3-yl)piperidin-3-yl)urea

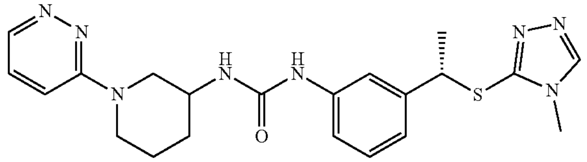 [SMILES: C[C@H](Sc1nncn1C)c1cccc(NC(=O)NC2CCCN(c3cccnn3)C2)c1]

The procedure for Example 39 was followed using 1-(pyridazin-3-yl)piperidin-3-amine to afford the title compound (31.6 mg, 42%). MS (ESI) calc'd for ($C_{21}H_{26}N_8OS$) $[M+1]^+$, 439.2; found, 439.2. $^1H$ NMR (400 MHz, Chloroform-d) δ 8.54-8.40 (m, 2H), 8.08 (d, J=3.2 Hz, 1H), 7.66 (d, J=8.4 Hz, 1H), 7.24-7.15 (m, 2H), 7.10-7.00 (m, 1H), 6.96-6.86 (m, 2H), 6.60 (s, 1H), 4.59-4.49 (m, 1H), 4.03-3.84 (m, 2H), 3.74-3.73 (m, 2H), 3.54-3.41 (m, 1H), 3.26 (s, 3H), 2.06-1.92 (m, 2H), 1.75-1.72 (m, 5H).

Example 130: N-(3-((S)-1-((4-methyl-4H-1,2,4-triazol-3-yl)thio)ethyl)phenyl)-6-oxa-1-azaspiro[3.4]octane-1-carboxamide

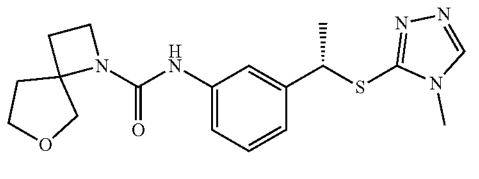 [SMILES: C[C@H](Sc1nncn1C)c1cccc(NC(=O)N2CCC23CCOC3)c1]

The procedure for Example 39 was followed using 6-oxa-1-azaspiro[3.4]octane to afford the title compound (47.2 mg, 75%). MS (ESI) calc'd for ($C_{18}H_{23}N_5O_2S$) $[M+1]^+$, 374.2; found, 374.2. $^1H$ NMR (300 MHz, DMSO-$d_6$) δ 8.55 (s, 1H), 8.16 (s, 1H), 7.50 (s, 1H), 7.47-7.35 (m, 1H), 7.17 (t, J=7.8 Hz, 1H), 6.84 (d, J=7.5 Hz, 1H), 4.59 (d, J=6.9 Hz, 1H), 4.05 (d, J=9.0 Hz, 1H), 3.95-3.92 (m, 3H), 3.84-3.69 (m, 2H), 3.39 (s, 3H), 2.55-2.54 (m, 1H), 2.32-2.30 (m, 2H), 2.07-1.92 (m, 1H), 1.62 (d, J=6.9 Hz, 3H).

Example 131: N-(3-((S)-1-((4-methyl-4H-1,2,4-triazol-3-yl)thio)ethyl)phenyl)-2-(2,2,2-trifluoroethyl)morpholine-4-carboxamide

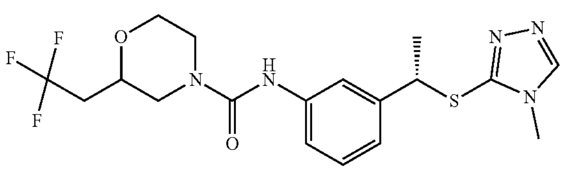 [SMILES: C[C@H](Sc1nncn1C)c1cccc(NC(=O)N2CCOC(CC(F)(F)F)C2)c1]

The procedure for Example 39 was followed using 2-(2,2,2-trifluoroethyl)morpholine to afford the title compound (32.2 mg, 18%). MS (ESI) calc'd for ($C_{18}H_{22}F_3N_5O_2S$) $[M+1]^+$, 430.1; found, 430.0. $^1H$ NMR (300 MHz, Chloroform-d) δ 8.09 (s, 1H), 7.50-7.38 (m, 2H), 7.20 (t, J=7.8 Hz, 1H), 7.11-7.03 (m, 1H), 6.99-6.90 (m, 1H), 4.62 (d, J=7.2 Hz, 1H), 4.16-4.06 (m, 1H), 4.00-3.86 (m, 2H), 3.85-3.74 (m, 1H), 3.69-3.54 (m, 1H), 3.30 (s, 3H), 3.17-3.02 (m, 1H), 2.84-2.73 (m, 1H), 2.52-2.21 (m, 2H), 1.73 (d, J=7.2 Hz, 3H).

Example 132: 3-fluoro-3-methyl-N-[3-[(1S)-1-[(4-methyl-4H-1,2,4-triazol-3-yl)sulfanyl]ethyl]phenyl]azetidine-1-carboxamide

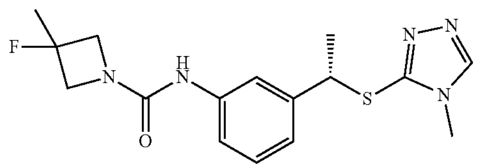 [SMILES: C[C@H](Sc1nncn1C)c1cccc(NC(=O)N2CC(C)(F)C2)c1]

The procedure for Example 39 was followed using 3-fluoro-3-methylazetidine to afford the title compound (2.6 mg, 4%). MS (ESI) calc'd for ($C_{16}H_{20}FN_5OS$) $[M+1]^+$, 350.1; found, 350.1. $^1H$ NMR (400 MHz, DMSO-$d_6$) δ 8.67 (s, 1H), 8.56 (s, 1H), 7.49-7.43 (m, 2H), 7.16 (t, J=7.6 Hz, 1H), 6.86-6.83 (m, 1H), 4.60 (q, J=6.8 Hz, 1H), 4.10-3.96 (m, 4H), 3.37 (s, 3H), 1.62-1.55 (m, 6H).

Example 133: 5-hydroxy-N-(3-((S)-1-((4-methyl-4H-1,2,4-triazol-3-yl)thio)ethyl)phenyl)-2-azaspiro[3.3]heptane-2-carboxamide

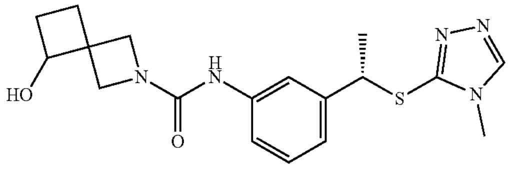 [SMILES: C[C@H](Sc1nncn1C)c1cccc(NC(=O)N2CC3(CCC3O)C2)c1]

The procedure for Example 39 was followed using 2-azaspiro[3.3]heptan-5-ol to afford the title compound (12.2 mg, 19%). MS (ESI) calc'd for ($C_{18}H_{23}N_5O_2S$) [M+1]$^+$, 374.2; found, 374.1. $^1$H NMR (400 MHz, Chloroform-d) δ 8.31 (s, 1H), 7.35 (s, 1H), 7.21-7.08 (m, 2H), 6.94 (t, J=7.2 Hz, 1H), 6.61 (s, 1H), 4.63 (d, J=8.0 Hz, 2H), 4.20 (s, 1H), 4.03-3.78 (m, 3H), 3.28 (s, 3H), 2.21-2.20 (m, 1H), 1.94-1.92 (m, 1H), 1.78-1.74 (m, 5H), 1.28-1.27 (m, 1H).

Example 134: 3-methanesulfonyl-N-[3-[(1S)-1-[(4-methyl-4H-1,2,4-triazol-3-yl)sulfanyl]ethyl]phenyl]azetidine-1-carboxamide

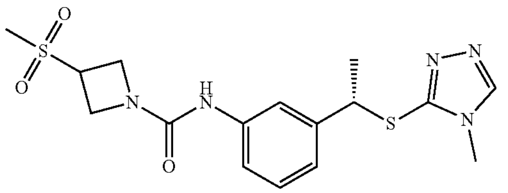 [SMILES: C[C@H](Sc1nncn1C)c1cccc(NC(=O)N2CC(S(C)(=O)=O)C2)c1]

The procedure for Example 39 was followed using 3-(methylsulfonyl)azetidine to afford the title compound (16.7 mg, 11%). MS (ESI) calc'd for ($C_{16}H_{21}N_5O_3S_2$) [M+1]$^+$, 396.1; found, 396.1. $^1$H NMR (400 MHz, DMSO-$d_6$) δ 8.71 (s, 1H), 8.55 (s, 1H), 7.47-7.42 (m, 2H), 7.20-7.14 (m, 1H), 6.87-6.84 (m, 1H), 4.60 (q, J=6.9 Hz, 1H), 4.29-4.21 (m, 3H), 4.14-4.10 (m, 2H), 3.37 (s, 3H), 3.04 (s, 3H), 1.61 (d, J=6.9 Hz, 3H).

Example 135 & 136: (S)—N-(3-((S)-1-((4-methyl-4H-1,2,4-triazol-3-yl)thio)ethyl)phenyl)-2-((R)-tetrahydrofuran-2-yl)morpholine-4-carboxamide and (R)—N-(3-((S)-1-((4-methyl-4H-1,2,4-triazol-3-yl)thio)ethyl)phenyl)-2-((R)-tetrahydrofuran-2-yl)morpholine-4-carboxamide

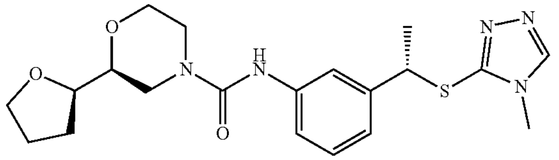

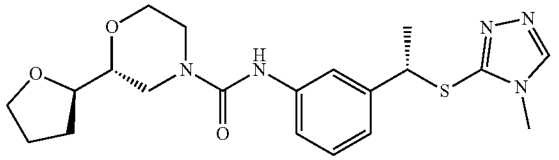

The procedure for Example 39 was followed using 2-(tetrahydrofuran-2-yl)morpholine to afford a mixture of N-(3-((S)-1-((4-methyl-4H-1,2,4-triazol-3-yl)thio)ethyl)phenyl)-2-(tetrahydrofuran-2-yl)morpholine-4-carboxamide (30 mg), which was separated by Chromatography C to afford (S)—N-(3-((S)-1-((4-methyl-4H-1,2,4-triazol-3-yl)thio)ethyl)phenyl)-2-((R)-tetrahydrofuran-2-yl)morpholine-4-carboxamide (8.6 mg, 12%) and (R)—N-(3-((S)-1-((4-methyl-4H-1,2,4-triazol-3-yl)thio)ethyl)phenyl)-2-((R)-tetrahydrofuran-2-yl)morpholine-4-carboxamide (3.9 mg, 5%).

(S)—N-(3-((S)-1-((4-methyl-4H-1,2,4-triazol-3-yl)thio)ethyl)phenyl)-2-((R)-tetrahydrofuran-2-yl)morpholine-4-carboxamide: MS (ESI) calc'd for ($C_{20}H_{27}N_5O_3S$) [M+1]$^+$, 418.2; found, 418.2. $^1$H NMR (300 MHz, Chloroform-d) δ 8.09 (s, 1H), 7.41 (d, J=8.1 Hz, 1H), 7.21 (t, J=7.8 Hz, 1H), 7.11 (s, 1H), 7.03-6.89 (m, 2H), 4.70-4.59 (m, 1H), 4.04-3.80 (m, 5H), 3.62 (t, J=11.2 Hz, 1H), 3.46 (s, 1H), 3.29 (s, 3H), 3.13 (t, J=11.7 Hz, 1H), 3.01-2.83 (m, 1H), 2.03-1.85 (m, 3H), 1.78-1.76 (m, 4H), 1.29-1.28 (m, 1H).

(R)—N-(3-((S)-1-((4-methyl-4H-1,2,4-triazol-3-yl)thio)ethyl)phenyl)-2-((R)-tetrahydrofuran-2-yl)morpholine-4-carboxamide: MS (ESI) calc'd for ($C_{20}H_{27}N_5O_3S$) [M+1]$^+$, 418.2; found, 418.2. $^1$H NMR (300 MHz, Chloroform-d) δ 8.09 (s, 1H), 7.40 (d, J=8.1 Hz, 1H), 7.24-7.09 (m, 2H), 7.01 (s, 1H), 6.92 (d, J=7.5 Hz, 1H), 4.73-4.59 (m, 1H), 4.07-3.73 (m, 6H), 3.70-3.53 (m, 1H), 3.36 (t, J=7.8 Hz, 1H), 3.27 (s, 3H), 3.17-3.04 (m, 1H), 3.00-2.90 (m, 1H), 2.11-2.01 (m, 1H), 2.01-1.82 (m, 3H), 1.77 (d, J=7.2 Hz, 3H).

Example 137: (S)-1-(5-ethyl-4,5,6,7-tetrahydrothiazolo[5,4-c]pyridin-2-yl)-3-(3-(1-((4-methyl-4H-1,2,4-triazol-3-yl)thio)ethyl)phenyl)urea

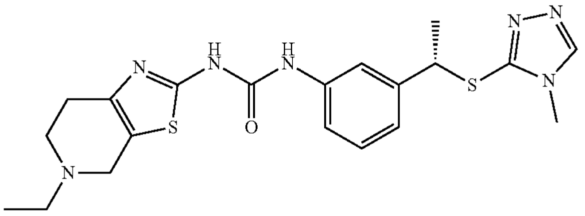 [SMILES: CCN1CCc2nc(NC(=O)Nc3cccc([C@H](C)Sc4nncn4C)c3)sc2C1]

The procedure for Example 39 was followed using 5-ethyl-4,5,6,7-tetrahydrothiazolo[5,4-c]pyridin-2-amine to afford the title compound (2.1 mg, 3%). MS (ESI) calc'd for ($C_{20}H_{25}N_7OS_2$) [M+1]$^+$, 444.2; found, 444.0. $^1$H NMR (300 MHz, DMSO-$d_6$) δ 9.09 (s, 1H), 8.52 (s, 1H), 8.14 (s, 1H), 7.40-7.33 (m, 2H), 7.22 (t, J=7.8 Hz, 1H), 6.95-6.89 (m, 1H), 4.68-4.57 (m, 1H), 3.51 (s, 2H), 3.35 (s, 3H), 2.75-2.72 (m, 2H), 2.63-2.52 (m, 4H), 1.62 (d, J=7.2 Hz, 3H), 1.06 (t, J=7.2 Hz, 3H).

Example 138: N-[3-[(1S)-1-[(4-methyl-4H-1,2,4-triazol-3-yl)sulfanyl]ethyl]phenyl]-5-oxa-2-azaspiro[3.4]octane-2-carboxamide

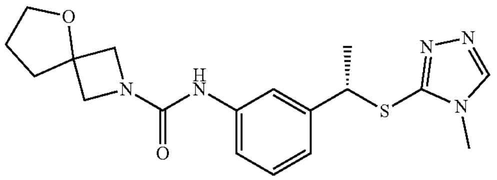 [SMILES: C[C@H](Sc1nncn1C)c1cccc(NC(=O)N2CC3(CCCO3)C2)c1]

The procedure for Example 39 was followed using 5-oxa-2-azaspiro[3.4]octane to afford the title compound (36.7 mg, 49%). MS (ESI) calc'd for ($C_{18}H_{23}N_5O_2S$) [M+1]$^+$, 374.2; found, 374.2. $^1$H NMR (400 MHz, DMSO-$d_6$) δ 8.53 (s, 2H), 7.49-7.43 (m, 2H), 7.15 (d, J=7.9 Hz, 1H), 6.84-6.81 (m, 1H), 4.58 (q, J=6.8 Hz, 1H), 3.94-3.90 (m, 4H), 3.75 (t, J=6.8 Hz, 2H), 3.35 (s, 3H), 2.08-2.03 (m, 2H), 1.89-1.80 (m, 2H), 1.60 (d, J=6.8 Hz, 3H).

Example 139: N-(3-((S)-1-((4-methyl-4H-1,2,4-triazol-3-yl)thio)ethyl)phenyl)-8-oxo-2,7-diazaspiro[4.4]nonane-2-carboxamide

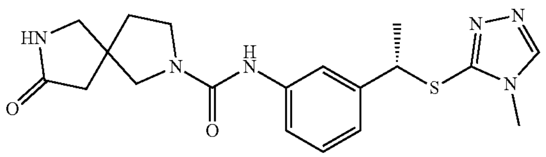 [SMILES: C[C@H](Sc1nncn1C)c1cccc(NC(=O)N2CCC3(CNC(=O)C3)C2)c1]

The procedure for Example 39 was followed using 2,7-diazaspiro[4.4]nonan-3-one to afford the title compound (43.1 mg, 64%). MS (ESI) calc'd for ($C_{19}H_{24}N_6O_2S$) $[M+1]^+$, 401.2; found, 401.2. $^1H$ NMR (300 MHz, DMSO-$d_6$+$D_2O$) δ 8.43 (s, 1H), 7.41 (t, J=1.8 Hz, 1H), 7.32-7.29 (m, 1H), 7.14 (d, J=7.8 Hz, 1H), 6.81 (s, 1H), 4.53 (q, J=6.9 Hz, 1H), 3.43-3.32 (m, 7H), 3.20-3.17 (m, 2H), 2.22 (s, 2H), 1.89 (t, J=7.2 Hz, 2H), 1.56 (d, J=6.9 Hz, 3H).

Example 140: (S)-3-(4-hydroxypiperidine-1-carbonyl)-N-(3-(1-((4-methyl-4H-1,2,4-triazol-3-yl)thio)ethyl)phenyl)azetidine-1-carboxamide

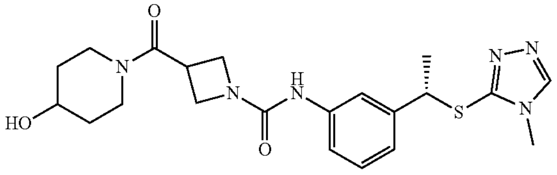 [SMILES: C[C@H](Sc1nncn1C)c1cccc(NC(=O)N2CC(C(=O)N3CCC(O)CC3)C2)c1]

The procedure for Example 39 was followed using azetidin-3-yl(4-hydroxypiperidin-1-yl)methanone to afford the title compound (31.0 mg, 41%). MS (ESI) calc'd for ($C_{21}H_{28}N_6O_3S$) $[M+1]^+$, 445.2; found, 445.1. $^1H$ NMR (300 MHz, Chloroform-d) δ 8.11 (s, 1H), 7.49-7.42 (m, 1H), 7.25-7.13 (m, 2H), 6.92 (d, J=7.8 Hz, 1H), 6.74 (d, J=7.8 Hz, 1H), 4.72-4.57 (m, 1H), 4.38-4.15 (m, 4H), 4.13-3.91 (m, 2H), 3.69-3.43 (m, 2H), 3.33 (s, 1H), 3.27 (s, 3H), 3.19-3.06 (m, 1H), 1.98-1.85 (m, 3H), 1.76 (d, J=7.2 Hz, 3H), 1.65-1.45 (m, 2H).

Example 141: (S)—N-(3-(1-((4-methyl-4H-1,2,4-triazol-3-yl)thio)ethyl)phenyl)-6-oxo-7-oxa-2,5-diazaspiro[3.5]nonane-2-carboxamide

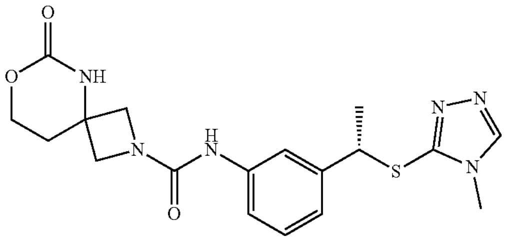 [SMILES: C[C@H](Sc1nncn1C)c1cccc(NC(=O)N2CC3(CCOC(=O)N3)C2)c1]

The procedure for Example 39 was followed using 7-oxa-2,5-diazaspiro[3.5]nonan-6-one to afford the title compound (8.3 mg, 12%). MS (ESI) calc'd for ($C_{18}H_{22}N_6O_3S$) $[M+1]^+$, 403.1; found, 403.0. $^1H$ NMR (400 MHz, Chloroform-d) δ 8.19 (s, 1H), 7.89-7.56 (m, 2H), 7.45 (d, J=8.0 Hz, 1H), 7.24-7.05 (m, 2H), 6.90 (d, J=7.6 Hz, 1H), 4.58-4.57 (m, 1H), 4.25-4.20 (m, 4H), 4.03-4.00 (m, 2H), 3.29 (s, 3H), 2.19-2.17 (m, 2H), 1.64 (d, J=6.4 Hz, 3H).

Example 142: N-(3-((S)-1-((4-methyl-4H-1,2,4-triazol-3-yl)thio)ethyl)phenyl)-2-phenylazetidine-1-carboxamide

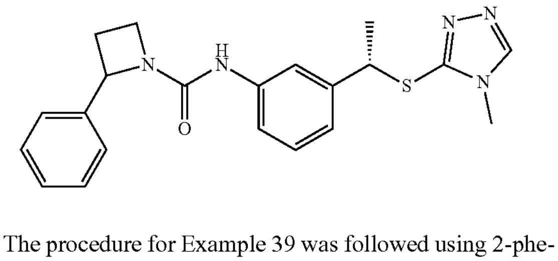

The procedure for Example 39 was followed using 2-phenylazetidine to afford the title compound (33.6 mg, 50%). MS (ESI) calc'd for ($C_{21}H_{23}N_5OS$) $[M+1]^+$, 394.2; found, 394.3. $^1H$ NMR (300 MHz, DMSO-$d_6$) δ 8.52 (s, 1H), 8.46 (s, 1H), 7.50 (q, J=1.8 Hz, 1H), 7.44-7.29 (m, 5H), 7.25-7.22 (m, 1H), 7.11 (t, J=7.8 Hz, 1H), 6.81 (d, J=7.8 Hz, 1H), 5.37-5.19 (m, 1H), 4.56 (d, J=6.9 Hz, 1H), 4.12-4.10 (m, 1H), 4.02 (d, J=7.8 Hz, 1H), 3.33 (s, 3H), 2.65-2.62 (m, 1H), 2.05-2.03 (m, 1H), 1.56 (d, J=6.9 Hz, 3H).

Example 143: 1-(1-hydroxypropan-2-yl)-1-methyl-3-(3-((S)-1-((4-methyl-4H-1,2,4-triazol-3-yl)thio)ethyl)phenyl)urea

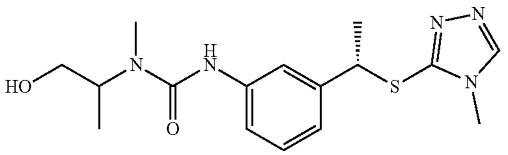 [SMILES: CC(CO)N(C)C(=O)Nc1cccc([C@H](C)Sc2nncn2C)c1]

The procedure for Example 39 was followed using 2-(methylamino)propan-1-ol to afford the title compound (10.9 mg, 18%). MS (ESI) calc'd for ($C_{16}H_{23}N_5O_2S$) $[M+1]^+$, 350.2; found, 350.0. $^1H$ NMR (300 MHz, Chloroform-d) δ 8.09 (d, J=6.3 Hz, 1H), 7.85-7.73 (m, 1H), 7.39-7.31 (m, 1H), 7.16 (t, J=7.8 Hz, 1H), 6.94-6.85 (m, 2H), 4.63-4.47 (m, 1H), 4.34-4.19 (m, 1H), 3.70-3.56 (m, 2H), 3.21 (d, J=5.7 Hz, 3H), 2.86 (s, 3H), 1.78-1.62 (m, 3H), 1.19-1.08 (m, 3H).

Example 144: (S)—N,2-dimethyl-5-(3-(3-(1-((4-methyl-4H-1,2,4-triazol-3-yl)thio)ethyl)phenyl)ureido)benzenesulfonamide

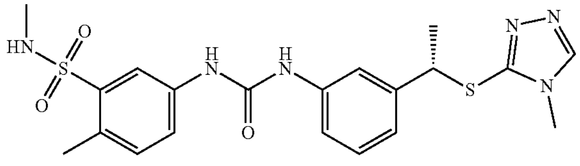 [SMILES: CNS(=O)(=O)c1cc(NC(=O)Nc2cccc([C@H](C)Sc3nncn3C)c2)ccc1C]

The procedure for Example 39 was followed using 5-amino-N,2-dimethylbenzenesulfonamide to afford the title compound (19.4 mg, 25%). MS (ESI) calc'd for ($C_{20}H_{24}N_6O_3S_2$) $[M+1]^+$, 461.1; found, 460.9. $^1H$ NMR (300 MHz, DMSO-$d_6$) δ 8.95 (s, 1H), 8.73 (s, 1H), 8.56 (s, 1H), 8.02 (s, 1H), 7.65-7.15 (m, 4H), 7.02-6.82 (m, 1H), 6.61-6.33 (m, 1H), 5.12 (s, 1H), 4.67-4.64 (m, 1H), 3.41 (s, 3H), 2.49 (s, 6H), 1.61 (d, J=6.9 Hz, 3H).

Example 145: (S)—N-(3-(1-((4-methyl-4H-1,2,4-triazol-3-yl)thio)ethyl)phenyl)-5,7-dihydro-6H-pyrrolo[3,4-b]pyrazine-6-carboxamide

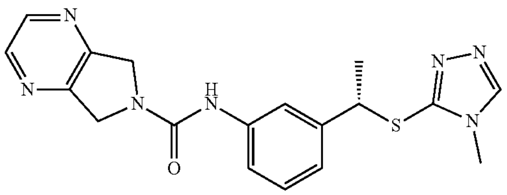 [SMILES: C[C@H](Sc1nncn1C)c1cccc(NC(=O)N2Cc3nccnc3C2)c1]

The procedure for Example 39 was followed using 6,7-dihydro-5H-pyrrolo[3,4-b]pyrazine to afford the title compound (23.7 mg, 37%). MS (ESI) calc'd for ($C_{18}H_{19}N_7OS$) $[M+1]^+$, 382.1; found, 382.0. $^1H$ NMR (300 MHz, DMSO-$d_6$) δ 8.55-8.49 (m, 4H), 7.59 (s, 1H), 7.53-7.44 (m, 1H), 7.17 (t, J=7.8 Hz, 1H), 6.87 (d, J=7.8 Hz, 1H), 4.82-4.80 (m, 4H), 4.59 (q, J=6.9 Hz, 1H), 3.36 (s, 3H), 1.62 (d, J=6.9 Hz, 3H).

Example 146: 3-(hydroxymethyl)-N-(3-((S)-1-((4-methyl-4H-1,2,4-triazol-3-yl)thio)ethyl)phenyl)morpholine-4-carboxamide

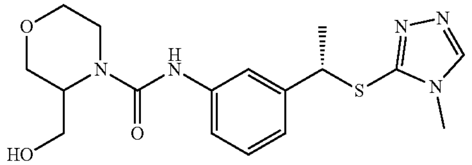 [SMILES: C[C@H](Sc1nncn1C)c1cccc(NC(=O)N2CCOCC2CO)c1]

The procedure for Example 39 was followed using morpholin-3-ylmethanol to afford the title compound (25.4 mg, 39%). MS (ESI) calc'd for ($C_{17}H_{23}N_5O_3S$) $[M+1]^+$, 378.2; found, 378.2. $^1H$ NMR (400 MHz, DMSO-$d_6$) δ 8.53 (s, 1H), 8.46 (s, 1H), 7.49-7.41 (m, 1H), 7.42-7.33 (m, 1H), 7.15 (t, J=8.0 Hz, 1H), 6.87-6.79 (m, 1H), 4.94 (t, J=5.2 Hz, 1H), 4.59 (d, J=6.8 Hz, 1H), 4.00-3.90 (m, 2H), 3.87-3.79 (m, 1H), 3.79-3.72 (m, 1H), 3.71-3.63 (m, 1H), 3.55-3.45 (m, 1H), 3.45-3.38 (m, 2H), 3.37 (s, 3H), 3.08-3.04 (m, 1H), 1.61 (d, J=6.9 Hz, 3H).

Example 147: (S)-1-(3-(1-(4-methyl-4H-1,2,4-triazol-3-ylthio)ethyl)phenyl)-3-(4-(3-oxomorpholino)phenyl)urea

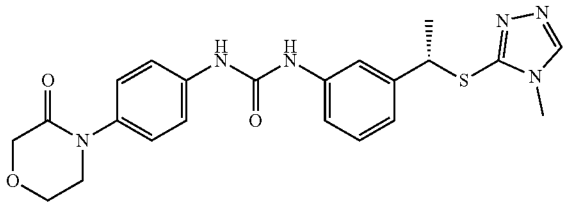 [SMILES: C[C@H](Sc1nncn1C)c1cccc(NC(=O)Nc2ccc(N3CCOCC3=O)cc2)c1]

The procedure for Example 39 was followed using 4-(4-aminophenyl)morpholin-3-one to afford the title compound (20.6 mg, 27%). MS (ESI) calc'd for ($C_{22}H_{24}N_6O_3S$) $[M+1]^+$, 453.2; found, 453.3. $^1H$ NMR (300 MHz, DMSO-$d_6$) δ 8.72 (s, 2H), 8.53 (s, 1H), 7.50-7.43 (m, 2H), 7.40 (s, 1H), 7.34 (d, J=8.1 Hz, 1H), 7.28-7.24 (m, 2H), 7.19 (t, J=7.8 Hz, 1H), 6.87 (d, J=7.5 Hz, 1H), 4.61 (q, J=6.9 Hz, 1H), 4.17 (s, 2H), 3.95 (t, J=5.1 Hz, 2H), 3.67 (t, J=5.1 Hz, 2H), 3.32 (s, 3H), 1.62 (d, J=6.9 Hz, 3H).

Example 148: (S)-1-(2-methoxy-4-morpholinophenyl)-3-(3-(1-((4-methyl-4H-1,2,4-triazol-3-yl)thio)ethyl)phenyl)urea

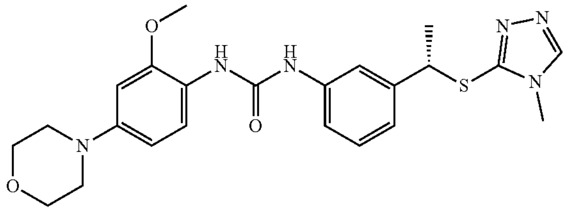 [SMILES: COc1cc(N2CCOCC2)ccc1NC(=O)Nc1cccc([C@H](C)Sc2nncn2C)c1]

The procedure for Example 39 was followed using 2-methoxy-4-morpholinoaniline to afford the title compound (33.8 mg, 42%). MS (ESI) calc'd for ($C_{23}H_{28}N_6O_3S$) $[M+1]^+$, 469.2; found, 469.3. $^1H$ NMR (400 MHz, DMSO-$d_6$) δ 9.18 (s, 1H), 8.54 (s, 1H), 7.96 (s, 1H), 7.88 (d, J=8.8 Hz, 1H), 7.40-7.31 (m, 2H), 7.19 (t, J=7.6 Hz, 1H), 6.86 (d, J=8.0 Hz, 1H), 6.64 (d, J=2.4 Hz, 1H), 6.49-6.41 (m, 1H), 4.67-4.57 (m, 1H), 3.86 (s, 3H), 3.77-3.70 (m, 4H), 3.38-3.34 (s, 3H), 3.10-3.02 (m, 4H), 1.63 (d, J=7.2 Hz, 3H).

Example 149: (S)—N-(3-(1-((4-methyl-4H-1,2,4-triazol-3-yl)thio)ethyl)phenyl)-4-(pyridin-3-yl)piperazine-1-carboxamide

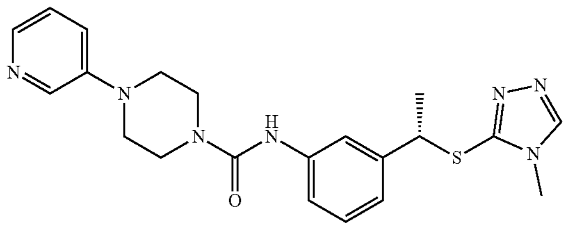 [SMILES: C[C@H](Sc1nncn1C)c1cccc(NC(=O)N2CCN(c3cccnc3)CC2)c1]

The procedure for Example 39 was followed using 1-(pyridin-2-yl)piperazine to afford the title compound (18.8 mg, 26%). MS (ESI) calc'd for ($C_{21}H_{25}N_7OS$) $[M+1]^+$, 424.2; found, 424.1. $^1H$ NMR (300 MHz, DMSO-$d_6$) δ 8.67 (s, 1H), 8.52 (s, 1H), 8.34 (d, J=2.7 Hz, 1H), 8.01 (d, J=4.8 Hz, 1H), 7.47 (s, 1H), 7.47-7.26 (m, 2H), 7.25-7.22 (m, 1H), 7.14 (t, J=7.8 Hz, 1H), 6.81 (d, J=7.5 Hz, 1H), 4.59 (q, J=6.9 Hz, 1H), 3.63-3.60 (m, 4H), 3.36 (s, 3H), 3.25-3.20 (m, 4H), 1.59 (d, J=6.9 Hz, 3H).

Example 150: (S)—N,N-dimethyl-2-(4-(3-(3-(1-((4-methyl-4H-1,2,4-triazol-3-yl)thio)ethyl)phenyl)ureido)phenyl)acetamide

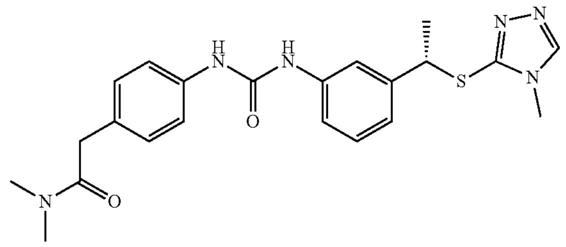 [SMILES: C[C@H](Sc1nncn1C)c1cccc(NC(=O)Nc2ccc(CC(=O)N(C)C)cc2)c1]

The procedure for Example 39 was followed using 2-(4-aminophenyl)-N,N-dimethylacetamide to afford the title compound (37.6 mg, 50%). MS (ESI) calc'd for ($C_{22}H_{26}N_6O_2S$) $[M+1]^+$, 439.2; found, 439.0. $^1H$ NMR (300 MHz, Chloroform-d) δ 8.77-8.61 (m, 2H), 8.27 (s, 1H), 7.62 (d, J=8.1 Hz, 1H), 7.48 (d, J=8.1 Hz, 2H), 7.24-7.13 (m, 3H), 6.92-6.90 (m, 2H), 4.56 (d, J=6.9 Hz, 1H), 3.72 (s, 2H), 3.30 (s, 3H), 3.06 (s, 3H), 2.99 (s, 3H), 1.77 (d, J=6.9 Hz, 3H).

Example 151: N-[3-[(1S)-1-[(4-methyl-4H-1,2,4-triazol-3-yl)sulfanyl]ethyl]phenyl]pyrrolidine-1-carboxamide

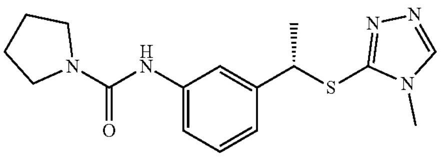 [SMILES: C[C@H](Sc1nncn1C)c1cccc(NC(=O)N2CCCC2)c1]

The procedure for Example 39 was followed using pyrrolidine to afford the title compound (22.3 mg, 16%). MS (ESI) calc'd for ($C_{16}H_{21}N_5OS$) $[M+1]^+$, 332.1; found, 332.2. $^1H$ NMR (300 MHz, Chloroform-d) δ 8.06 (s, 1H), 7.44-7.34 (m, 1H), 7.23-7.10 (m, 2H), 6.86 (d, J=7.8 Hz, 1H), 6.16 (s, 1H), 4.65 (q, J=7.2 Hz, 1H), 3.48-3.44 (m, 4H), 3.23 (s, 3H), 2.01-1.93 (m, 4H), 1.77 (d, J=6.9 Hz, 3H).

Example 152: (S)-1-((1-ethyl-1H-pyrazol-4-yl)methyl)-1-methyl-3-(3-(1-((4-methyl-4H-1,2,4-triazol-3-yl)thio)ethyl)phenyl)urea

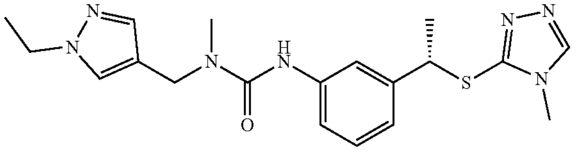 [SMILES: CCn1cc(CN(C)C(=O)Nc2cccc([C@H](C)Sc3nncn3C)c2)cn1]

The procedure for Example 39 was followed using 1-(1-ethyl-1H-pyrazol-4-yl)-N-methylmethanamine to afford the title compound (6.8 mg, 10%). MS (ESI) calc'd for ($C_{19}H_{25}N_7OS$) $[M+1]^+$, 400.2; found, 400.2. $^1H$ NMR (300 MHz, DMSO-$d_6$) δ 8.55 (s, 1H), 8.37 (s, 1H), 7.67 (s, 1H), 7.51 (d, J=2.1 Hz, 1H), 7.47-7.42 (m, 1H), 7.37 (d, J=0.9 Hz, 1H), 7.17 (t, J=7.8 Hz, 1H), 6.85 (d, J=7.5 Hz, 1H), 4.66-4.56 (m, 1H), 4.35 (s, 2H), 4.16-4.06 (m, 2H), 3.39 (s, 3H), 2.91 (s, 3H), 1.63 (d, J=6.9 Hz, 3H), 1.35 (t, J=7.2 Hz, 3H).

Example 153: 3-(3-hydroxypyrrolidine-1-carbonyl)-N-(3-((S)-1-((4-methyl-4H-1,2,4-triazol-3-yl)thio)ethyl)phenyl)azetidine-1-carboxamide

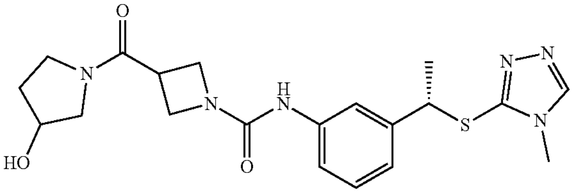 [SMILES: C[C@H](Sc1nncn1C)c1cccc(NC(=O)N2CC(C(=O)N3CCC(O)C3)C2)c1]

The procedure for Example 39 was followed using azetidin-3-yl(3-hydroxypyrrolidin-1-yl)methanone to afford the title compound (38.1 mg, 52%). MS (ESI) calc'd for ($C_{20}H_{26}N_6O_3S$) $[M+1]^+$, 431.2; found, 431.0. $^1H$ NMR (300 MHz, Chloroform-d) δ 8.13 (d, J=2.1 Hz, 1H), 7.53 (d, J=7.5 Hz, 1H), 7.48-7.37 (m, 1H), 7.19 (t, J=7.8 Hz, 1H), 7.06 (d, J=5.7 Hz, 1H), 6.94 (d, J=7.6 Hz, 1H), 4.68-4.47 (m, 2H), 4.40-4.11 (m, 4H), 3.77-3.33 (m, 5H), 3.26 (s, 3H), 2.09-2.08 (m, 2H), 2.03-1.94 (m, 1H), 1.77-1.69 (m, 3H).

Example 154: N-(3-((S)-1-((4-methyl-4H-1,2,4-triazol-3-yl)thio)ethyl)phenyl)-2-(1,2,4-oxadiazol-3-yl)morpholine-4-carboxamide

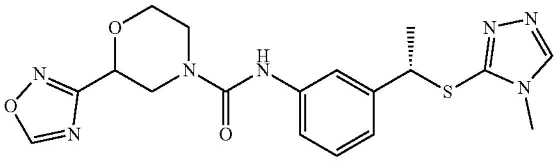 [SMILES: C[C@H](Sc1nncn1C)c1cccc(NC(=O)N2CCOC(c3ncon3)C2)c1]

The procedure for Example 39 was followed using 2-(1,2,4-oxadiazol-3-yl)morpholine to afford the title compound (44.3 mg, 63%). MS (ESI) calc'd for ($C_{18}H_{21}N_7O_3S$) $[M+1]^+$, 416.1; found, 416.2. $^1H$ NMR (300 MHz, DMSO-$d_6$) δ 9.71 (s, 1H), 8.73 (s, 1H), 8.55 (s, 1H), 7.50-7.39 (m, 2H), 7.18 (t, J=7.8 Hz, 1H), 6.91-6.84 (m, 1H), 4.87-4.81 (m, 1H), 4.61 (d, J=6.9 Hz, 1H), 4.26-4.24 (m, 1H), 3.99 (t, J=11.7 Hz, 2H), 3.72-3.70 (m, 1H), 3.38 (s, 3H), 3.33-3.09 (m, 2H), 1.63 (d, J=6.9 Hz, 3H).

Example 155: (S)-4-methyl-N-(3-(1-((4-methyl-4H-1,2,4-triazol-3-yl)thio)ethyl)phenyl)piperazine-1-carboxamide

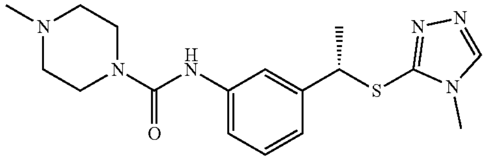 [SMILES: C[C@H](Sc1nncn1C)c1cccc(NC(=O)N2CCN(C)CC2)c1]

The procedure for Example 39 was followed using N-methyl piperazine to afford the title compound (20.0 mg, 13%). MS (ESI) calc'd for ($C_{17}H_{24}N_6OS$) $[M+1]^+$, 361.2; found, 361.2. $^1H$ NMR (400 MHz, DMSO-$d_6$) δ 8.54 (s, 2H), 7.46 (s, 1H), 7.40-7.38 (m, 1H), 7.14 (t, J=7.9 Hz, 1H), 6.82 (dt, J=7.6, 1.2 Hz, 1H), 4.59 (q, J=6.8 Hz, 1H), 3.45-3.42 (m, 4H), 3.32 (s, 3H), 2.34-2.32 (m, 4H), 2.21 (s, 3H), 1.61 (d, J=7.2 Hz, 3H).

Example 156: (S)-4-cyclopropyl-N-(3-(1-((4-methyl-4H-1,2,4-triazol-3-yl)thio)ethyl)phenyl)-3-oxopiperazine-1-carboxamide

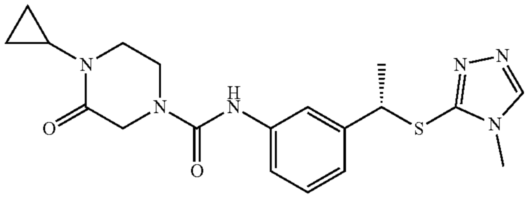 [SMILES: C[C@H](Sc1nncn1C)c1cccc(NC(=O)N2CCN(C3CC3)C(=O)C2)c1]

The procedure for Example 39 was followed using 1-cyclopropylpiperazin-2-one to afford the title compound (41.7 mg, 61%). MS (ESI) calc'd for ($C_{19}H_{24}N_6O_2S$) $[M+1]^+$, 401.2; found, 401.2. $^1H$ NMR (300 MHz, DMSO-$d_6$) δ 8.61 (s, 1H), 8.55 (s, 1H), 7.49 (d, J=1.8 Hz, 1H), 7.45-7.40 (m, 1H), 7.17 (t, J=7.8 Hz, 1H), 6.86 (d, J=7.5 Hz, 1H), 4.66-4.56 (m, 1H), 4.07 (s, 2H), 3.66 (t, J=5.4 Hz, 2H), 3.38 (s, 3H), 3.29 (d, J=5.4 Hz, 2H), 2.83-2.69 (m, 1H), 1.62 (d, J=7.2 Hz, 3H), 0.78-0.59 (m, 4H).

Example 157: N-(3-((S)-1-((4-methyl-4H-1,2,4-triazol-3-yl)thio)ethyl)phenyl)-3-(pyridin-2-yl)pyrrolidine-1-carboxamide

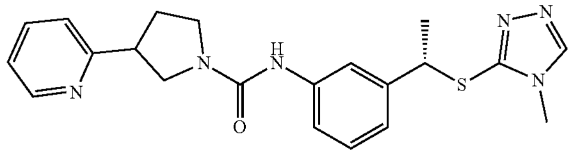 [SMILES: C[C@H](Sc1nncn1C)c1cccc(NC(=O)N2CCC(c3ccccn3)C2)c1]

The procedure for Example 39 was followed using 2-(pyrrolidin-3-yl)pyridine to afford the title compound (24.8 mg, 36%). MS (ESI) calc'd for ($C_{21}H_{24}N_6OS$) $[M+1]^+$, 409.2; found, 409.2. $^1H$ NMR (400 MHz, Chloroform-d) δ 8.62-8.56 (m, 1H), 8.08 (s, 1H), 7.76-7.65 (m, 1H), 7.40 (d, J=8.0 Hz, 1H), 7.27-7.15 (m, 4H), 6.88 (d, J=7.6 Hz, 1H), 6.27 (s, 1H), 4.71-4.62 (m, 1H), 3.96 (t, J=8.4 Hz, 1H), 3.83-3.74 (m, 2H), 3.72 (d, J=12.4 Hz, 1H), 3.60 (t, J=8.4 Hz, 1H), 3.25 (s, 3H), 2.47-2.38 (m, 1H), 2.38-2.25 (m, 1H), 1.79 (d, J=7.2 Hz, 3H).

Example 158: (S)—N,N-dimethyl-4-(3-(3-(1-((4-methyl-4H-1,2,4-triazol-3-yl)thio)ethyl)phenyl)ureido)benzenesulfonamide

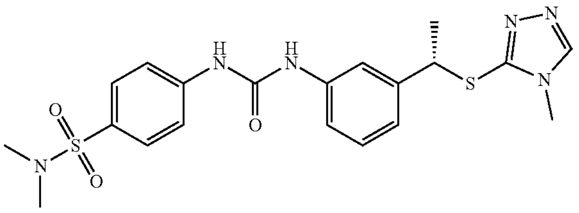 [SMILES: C[C@H](Sc1nncn1C)c1cccc(NC(=O)Nc2ccc(S(=O)(=O)N(C)C)cc2)c1]

The procedure for Example 2 was followed using 4-amino-N,N-dimethylbenzenesulfonamide to afford the title compound (84.9 mg, 43%). MS (ESI) calc'd for ($C_{20}H_{24}N_6O_3S_2$) $[M+1]^+$, 461.1; found, 461.1. $^1H$ NMR (300 MHz, DMSO-$d_6$) δ 9.21 (s, 1H), 8.88 (s, 1H), 8.55 (s, 1H), 7.77-7.62 (m, 4H), 7.47-7.35 (m, 2H), 7.26 (t, J=7.8 Hz, 1H), 6.93 (d, J=7.6 Hz, 1H), 4.65 (q, J=6.9 Hz, 1H), 3.39 (s, 3H), 2.58 (s, 6H), 1.65 (d, J=7.0 Hz, 3H).

Example 159: 1-(3-((S)-1-((4-methyl-4H-1,2,4-triazol-3-yl)thio)ethyl)phenyl)-3-(1-methylpiperidin-3-yl)urea

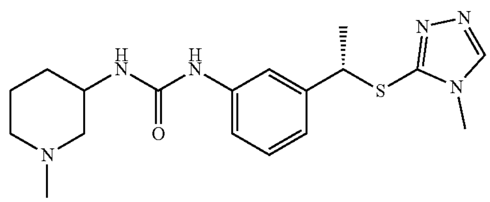 [SMILES: C[C@H](Sc1nncn1C)c1cccc(NC(=O)NC2CCCN(C)C2)c1]

The procedure for Example 2 was followed using 1-methylpiperidin-3-amine to afford the title compound (9.6 mg, 12%). MS (ESI) calc'd for ($C_{18}H_{26}N_6OS$) $[M+1]^+$, 375.2; found, 375.2. $^1H$ NMR (300 MHz, DMSO-$d_6$+$D_2O$) δ 8.49 (s, 1H), 7.35 (s, 1H), 7.20 (d, J=8.1 Hz, 1H), 7.11 (t, J=7.8 Hz, 1H), 6.78 (d, J=7.5 Hz, 1H), 4.56 (q, J=6.9 Hz, 1H), 3.33 (s, 3H), 2.98-2.92 (m, 1H), 2.77-2.70 (m, 1H), 2.49-2.40 (m, 5H), 1.90-1.89 (m, 1H), 1.77-1.65 (m, 2H), 1.58-1.56 (m, 1H), 1.56 (d, J=6.9 Hz, 3H), 1.38-1.30 (m, 1H).

Example 160: (S)-2-acetyl-N-(3-(1-((4-methyl-4H-1,2,4-triazol-3-yl)thio)ethyl)phenyl)-2,8-diazaspiro[4.5]decane-8-carboxamide

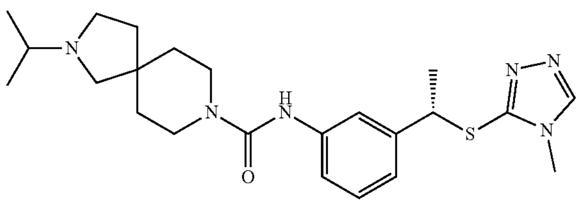 [SMILES: CC(C)N1CCC2(CCN(C(=O)Nc3cccc([C@H](C)Sc4nncn4C)c3)CC2)C1]

The procedure for Example 2 was followed using 1-(2,8-diazaspiro[4.5]decan-2-yl)ethan-1-one to afford the title compound (46.1 mg, 28%). MS (ESI) calc'd for ($C_{22}H_{30}N_6O_2S$) [M+1]$^+$, 443.2; found, 443.1. $^1$H NMR (300 MHz, DMSO-d$_6$) δ 8.54 (s, 1H), 8.52 (s, 1H), 7.46 (s, 1H), 7.41-7.38 (m, 1H), 7.14 (t, J=7.8 Hz, 1H), 6.83-6.80 (m, 1H), 4.56 (q, J=6.9 Hz, 1H), 3.55-3.42 (m, 4H), 3.33 (s, 3H), 3.32-3.30 (m, 3H), 3.20-3.19 (m, 1H), 1.93 (s, 3H), 1.83-1.73 (m, 2H), 1.60 (d, J=6.9 Hz, 3H), 1.53-1.40 (m, 4H).

Example 161: (S)-1-cyclohexyl-3-(3-(1-((4-methyl-4H-1,2,4-triazol-3-yl)thio)ethyl)phenyl)urea

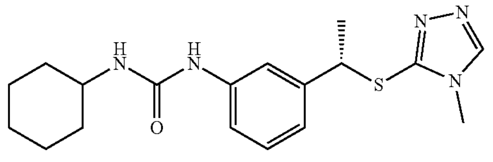 [SMILES: C[C@H](Sc1nncn1C)c1cccc(NC(=O)NC2CCCCC2)c1]

The procedure for Example 2 was followed using cyclohexylamine to afford the title compound (8.1 mg, 11%). MS (ESI) calc'd for ($C_{18}H_{25}N_5OS$) [M+1]$^+$, 360.2; found, 360.2. $^1$H NMR (300 MHz, DMSO-d$_6$) δ 8.54 (s, 1H), 8.34 (s, 1H), 7.34 (s, 1H), 7.26 (d, J=7.8 Hz, 1H), 7.13 (t, J=7.8 Hz, 1H), 6.79 (d, J=7.5 Hz, 1H), 6.06 (d, J=7.5 Hz, 1H), 4.58 (d, J=7.2 Hz, 1H), 3.33 (s, 3H), 1.81-1.78 (m, 2H), 1.61-1.59 (m, 6H), 1.33-1.14 (m, 6H).

Example 162: (S)-4-acetyl-N-(3-(1-(4-methyl-4H-1,2,4-triazol-3-ylthio)ethyl)phenyl)piperazine-1-carboxamide

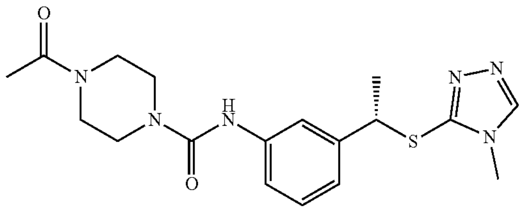 [SMILES: CC(=O)N1CCN(C(=O)Nc2cccc([C@H](C)Sc3nncn3C)c2)CC1]

The procedure for Example 2 was followed using N-acetylpiperazine to afford the title compound (8.4 mg, 11%). MS (ESI) calc'd for ($C_{18}H_{24}N_6O_2S$) [M+1]$^+$, 389.2; found, 389.2. $^1$H NMR (400 MHz, DMSO-d$_6$) δ 8.64 (s, 1H), 8.54 (s, 1H), 7.46 (t, J=2.0 Hz, 1H), 7.40 (d, J=7.8 Hz, 1H), 7.16 (t, J=7.8 Hz, 1H), 6.84 (d, J=7.8 Hz, 1H), 4.59 (q, J=6.9 Hz, 1H), 3.47-3.38 (m, 8H), 3.37 (s, 3H), 2.04 (s, 3H), 1.61 (d, J=6.9 Hz, 3H).

Example 163: (S)—N-methyl-4-(3-(3-(1-((4-methyl-4H-1,2,4-triazol-3-yl)thio)ethyl)phenyl)ureido)benzenesulfonamide

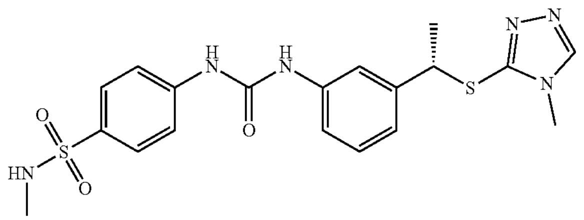 [SMILES: CNS(=O)(=O)c1ccc(NC(=O)Nc2cccc([C@H](C)Sc3nncn3C)c2)cc1]

The procedure for Example 2 was followed using 4-amino-N-methylbenzenesulfonamide to afford the title compound (75.3 mg, 40%). MS (ESI) calc'd for ($C_{19}H_{22}N_6O_3S_2$) [M+1]$^+$, 447.1; found, 447.1. $^1$H NMR (300 MHz, DMSO-d$_6$) δ 9.18 (s, 1H), 8.91 (s, 1H), 8.52 (s, 1H), 7.66-7.64 (m, 4H), 7.44 (t, J=2.1 Hz, 1H), 7.38-7.32 (m, 1H), 7.29-7.17 (m, 2H), 6.90 (d, J=7.8 Hz, 1H), 4.63-4.62 (m, 1H), 3.36 (s, 3H), 2.37 (d, J=5.1 Hz, 3H), 1.62 (d, J=6.9 Hz, 3H).

Example 164: (S)—N-(3-(1-(4-methyl-4H-1,2,4-triazol-3-ylthio)ethyl)phenyl)azetidine-1-carboxamide

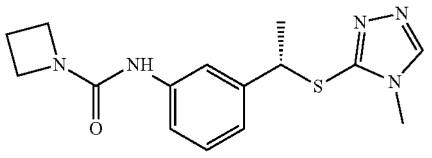 [SMILES: C[C@H](Sc1nncn1C)c1cccc(NC(=O)N2CCC2)c1]

The procedure for Example 2 was followed using azetidine to afford the title compound (14.1 mg, 21%). MS (ESI) calc'd for ($C_{15}H_{19}N_5OS$) [M+1]$^+$, 318.1; found, 318.0. $^1$H NMR (300 MHz, DMSO-d$_6$) δ 8.54 (s, 1H), 8.38 (s, 1H), 7.52-7.41 (m, 2H), 7.14 (t, J=7.8 Hz, 1H), 6.81 (d, J=7.8 Hz, 1H), 4.58 (q, J=6.9 Hz, 1H), 3.96-3.92 (m, 4H), 3.37 (s, 3H), 2.19-2.15 (m, 2H), 1.60 (d, J=6.9 Hz, 3H).

Example 165: (S)—N-(3-(1-((4-methyl-4H-1,2,4-triazol-3-yl)thio)ethyl)phenyl)thiomorpholine-4-carboxamide 1,1-dioxide

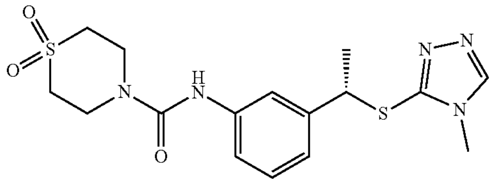 [SMILES: C[C@H](Sc1nncn1C)c1cccc(NC(=O)N2CCS(=O)(=O)CC2)c1]

The procedure for Example 2 was followed using thiomorpholine 1,1-dioxide to afford the title compound (4.2 mg, 5%). MS (ESI) calculated for ($C_{16}H_{21}N_5O_3S_2$) [M+1]$^+$, 396.1; found, 396.1. $^1$H NMR (300 MHz, DMSO-d$_6$) δ 8.83 (s, 1H), 8.54 (s, 1H), 7.46 (d, J=2.1 Hz, 1H), 7.40 (d, J=7.8 Hz, 1H), 7.18 (t, J=7.8 Hz, 1H), 6.87 (d, J=7.8 Hz, 1H), 4.61 (q, J=6.9 Hz, 1H), 3.90-3.88 (m, 4H), 3.38 (s, 3H), 3.19-3.18 (m, 4H), 1.61 (d, J=6.9 Hz, 3H).

Example 166: N-(3-((1R,2S)-2-(4-methyl-4H-1,2,4-triazol-3-yl)cyclopropyl)phenyl)-2,3-dihydro-4H-pyrido[3,2-b][1,4]oxazine-4-carboxamide

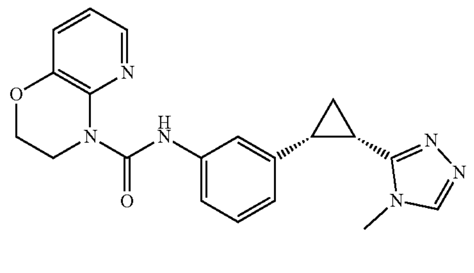 [SMILES: Cn1cnnc1[C@H]1C[C@H]1c1cccc(NC(=O)N2CCOc3cccnc32)c1]

The procedure of Example 10 was followed using 3-((1R,2S)-2-(4-methyl-4H-1,2,4-triazol-3-yl)cyclopropyl)aniline to give the title compound (66 mg, 61%). $^1$H NMR (500 MHz, DMSO-$d_6$) δ 12.66 (s, 1H), 8.76 (s, 1H), 8.06 (dd, J=4.8, 1.6 Hz, 1H), 7.41 (dd, J=8.0, 1.6 Hz, 1H), 7.35-7.31 (m, 1H), 7.29 (t, J=2.0 Hz, 1H), 7.14-7.07 (m, 2H), 6.73-6.66 (m, 1H), 4.28 (t, J=4.6 Hz, 2H), 4.04 (q, J=4.6 Hz, 2H), 3.61 (s, 3H), 2.80 (q, J=8.2 Hz, 1H), 2.67 (td, J=8.6, 6.0 Hz, 1H), 1.93 (p, J=6.2 Hz, 1H), 1.69 (td, J=8.5, 5.5 Hz, 1H). LCMS: $C_{20}H_{20}N_6O_2$ requires: 376, found: m/z=377 $[M+H]^+$.

Example 167: 1-(3-(1-((4-methyl-4H-1,2,4-triazol-3-yl)thio)ethyl)phenyl)-4-phenyl-1H-1,2,3-triazole

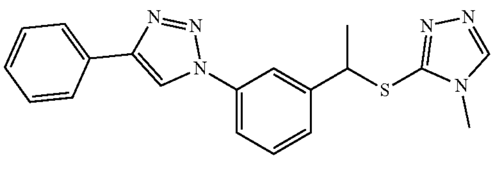 [SMILES: CC(Sc1nncn1C)c1cccc(-n2cc(-c3ccccc3)nn2)c1]

Step 1: 1-(3-(4-phenyl-1H-1,2,3-triazol-1-yl)phenyl)ethan-1-ol. The reduction of 1-(3-(4-phenyl-1H-1,2,3-triazol-1-yl)phenyl)ethan-1-one (29 mg, 0.11 mmol) was performed following the procedure for Example 67 and 68, Step 2 to give the title compound (23 mg, 78%).

Step 2: 1-(3-(1-((4-methyl-4H-1,2,4-triazol-3-yl)thio)ethyl)phenyl)-4-phenyl-1H-1,2,3-triazole. A Mitsunobu reaction was performed following the procedure for Example 55, Step 2 to give the title compound (17 mg, 54%). $^1$H NMR (500 MHz, DMSO-$d_6$) δ 9.30 (s, 1H), 8.53 (s, 1H), 8.00-7.89 (m, 2H), 7.85 (ddd, J=8.1, 2.3, 1.0 Hz, 1H), 7.53 (dt, J=24.1, 7.8 Hz, 3H), 7.46-7.32 (m, 2H), 4.81 (q, J=7.0 Hz, 1H), 3.40 (s, 3H), 1.73 (d, J=7.0 Hz, 3H). MS (ESI) calc'd for $(C_{19}H_{18}N_6S)$ $[M+H]^+$, 363; found, 363.

Example 168: (R)-6-cyclopropyl-5-(17-(5,5-difluoro-7,9-dimethyl-5H-5λ$^4$,6λ$^4$-dipyrrolo[1,2-c:2',1'-f][1,3,2]diazaborinin-3-yl)-15-oxo-5,8,11-trioxa-2,14-diazaheptadecyl)-N-(3-(1-(4-methyl-4H-1,2,4-triazol-3-yl)propan-2-yl)phenyl)picolinamide

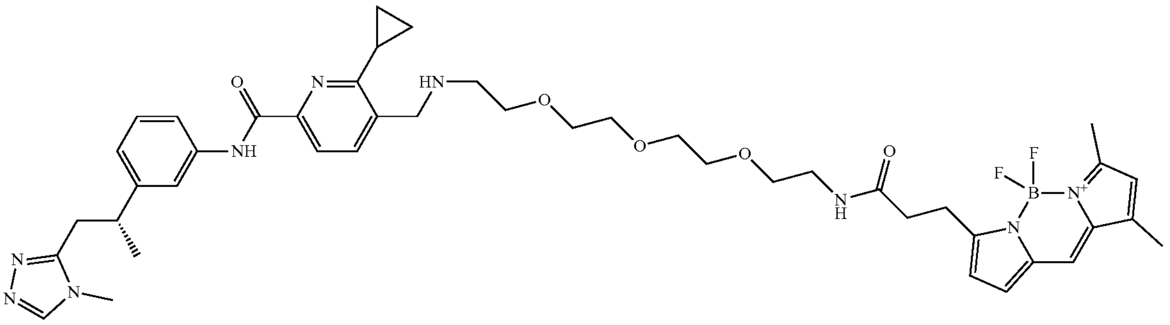

Step 1: Synthesis of methyl 6-cyclopropyl-5-(hydroxymethyl)pyridine-2-carboxylate. A mixture of methyl 6-chloro-5-(hydroxymethyl)pyridine-2-carboxylate (Gangadasu, B. et al., Tetrahedron 2006, 62, 8398-8403) (1.0 g, 5.0 mmol), potassium cyclopropyltrifluoroboranuide (2.1 g, 14.1 mmol), Pd(dppf)$Cl_2$ (770 mg, 1.05 mmol), and $K_3PO_4$ (3.8 g, 18.1 mmol) in toluene (40 mL) and water (4 mL) was heated to 100° C. for 16 h under nitrogen. The mixture was cooled to rt and then filtered. The filtrate was evaporated under vacuum. The residue was purified by Chromatography A to afford the title compound (834.0 mg, 81%). LCMS: $C_{11}H_{13}NO_3$ requires 207.2, found 207.9 $[M+H]^+$.

Step 2: Synthesis of 6-cyclopropyl-5-(hydroxymethyl)pyridine-2-carboxylic acid. A mixture of methyl 6-cyclopropyl-5-(hydroxymethyl)pyridine-2-carboxylate (170.0 mg, 0.82 mmol) and LiOH (45.0 mg, 1.88 mmol) in THE (6 mL) and water (2 mL) was stirred at rt for 3 h. The pH of the mixture was adjusted to ~5 with HCl (1 N). The mixture was evaporated under vacuum to afford the title compound (200.0 mg, crude), which was used without purification. MS (ESI) calculated for $(C_{10}H_{11}NO_3)$ $[M+H]^+$, 194.1, found, 193.9.

Step 3: Synthesis of 6-cyclopropyl-5-(hydroxymethyl)-N-[3-[(2R)-1-(4-methyl-4H-1,2,4-triazol-3-yl)propan-2-yl]phenyl]pyridine-2-carboxamide. To a mixture of 6-cyclopropyl-5-(hydroxymethyl)pyridine-2-carboxylic acid (200.0 mg, crude) in DMF (3 mL) were added DIEA (1 mL, 6.05 mmol), 3-[(2R)-1-(4-methyl-4H-1,2,4-triazol-3-yl)propan-2-yl]aniline (173.6 mg, 0.80 mmol), and HATU (883.0 mg, 2.32 mmol). The mixture was stirred at rt for 2 h. The mixture was purified by Chromatography C, then purified by Prep-HPLC to afford the title compound (31.6 mg, 10%). MS (ESI) calculated for $(C_{22}H_{25}N_5O_2)$ $[M+H]^+$, 392.2, found, 392.2.

Step 4: Synthesis of (R)-6-cyclopropyl-5-formyl-N-(3-(1-(4-methyl-4H-1,2,4-triazol-3-yl)propan-2-yl)phenyl)picolinamide. To a solution of (R)-6-cyclopropyl-5-(hydroxymethyl)-N-(3-(1-(4-methyl-4H-1,2,4-triazol-3-yl)propan-2-yl)phenyl)picolinamide (3.1 g, 7.9 mmol) in methylene chloride (30 mL) was added Dess-Martin reagent (4.0 g, 9.5 mmol) at 0° C. The mixture was stirred at 0° C. for 1 h, and then quenched by the addition of saturated aqueous $NaHCO_3$. The aqueous phase was extracted with EtOAc. The organic layers were combined, washed with brine, dried, and filtered. The filtrate was concentrated. The residue was purified by Chromatography B to afford the title compound (1.8 g, 58%). MS (ESI) calculated for $(C_{22}H_{23}N_5O_2)$ $[M+H]^+$, 390.2; found 390.2.

Step 5. Synthesis of (R)-5-(13-amino-5,8,11-trioxa-2-azatridecyl)-6-cyclopropyl-N-(3-(1-(4-methyl-4H-1,2,4-triazol-3-yl)propan-2-yl)phenyl)picolinamide. Sodium triacetoxyborohydride (0.05 g, 0.23 mmol) was added to a DCM (1.00 mL) solution containing tert-butyl N-(2-{2-[2-(2-aminoethoxy)ethoxy]ethoxy}ethyl)carbamate (45 mg, 0.15 mmol) (R)-6-cyclopropyl-5-formyl-N-(3-(1-(4-methyl-4H-1,2,4-triazol-3-yl)propan-2-yl)phenyl)picolinamide (60 mg, 0.15 mmol). The mixture was stirred at room temperature for 3 h. After concentration, the crude reaction mixture was purified by reverse phase preparative HPLC (Waters 5 mM CSH C18 column, 50×50 mm), eluting with acetonitrile in water with 0.1% TFA. The desired fractions were combined and concentrated to give tert-butyl (R)-(1-(2-cyclopropyl-6-((3-(1-(4-methyl-4H-1,2,4-triazol-3-yl)propan-2-yl)phenyl) carbamoyl)pyridin-3-yl)-5,8,11-trioxa-2-azatridecan-13-yl) carbamate, which was treated with DCM/TFA 1:1 solution at room temperature. After 1 h the reaction was concentrated to afford the title compound (51 mg); LCMS: $C_{30}H_{43}N_7O_4$ requires m/z=565, found 566 $[M+H]^+$.

Step 6. Synthesis of (R)-6-cyclopropyl-5-(17-(5,5-difluoro-7,9-dimethyl-5H-5λ$^4$,6λ$^4$-dipyrrolo[1,2-c:2',1'-f][1,3,2]diazaborinin-3-yl)-15-oxo-5,8,11-trioxa-2,14-diazaheptadecyl)-N-(3-(1-(4-methyl-4H-1,2,4-triazol-3-yl)propan-2-yl)phenyl)picolinamide. Triethylamine (0.01 mL, 6.08 mg, 0.06 mmol) was added to a DMF solution (1 mL) containing HATU (17 mg, 0.05 mmol) and 3-(5,5-difluoro-7,9-dimethyl-5H-5λ$^4$,6λ$^4$-dipyrrolo[1,2-c:2',1'-f][1,3,2]diazaborinin-3-yl)propanoic acid (9 mg, 0.03 mmol). After stirring for 5 min at room temperature, 5-(13-amino-5,8,11-trioxa-2-azatridecan-1-yl)-6-cyclopropyl-N-{3-[(2R)-1-(4-methyl-4H-1,2,4-triazol-3-yl)propan-2-yl]phenyl}pyridine-2-carboxamide (17 mg, 0.03 mmol) was added, and the resulting solution was stirred at rt for 4 h. The crude reaction mixture was purified by reverse phase preparative HPLC, eluting with acetonitrile in water with 0.1% TFA, to afford the title compound. $^1$H NMR (500 MHz, Methanol-$d_4$) δ 8.00 (s, 2H), 7.67 (t, J=2.0 Hz, 1H), 7.55-7.45 (m, 1H), 7.38 (s, 1H), 7.33 (t, J=7.9 Hz, 1H), 7.05 (d, J=7.7 Hz, 1H), 6.97 (d, J=4.0 Hz, 1H), 4.57 (s, 2H), 3.82 (dd, J=5.7, 4.2 Hz, 2H), 3.68 (hd, J=3.9, 2.6 Hz, 4H), 3.65-3.62 (m, 3H), 3.61 (s, 3H), 3.60-3.56 (m, 2H), 3.48 (t, J=5.6 Hz, 3H), 3.39 (q, J=6.2, 5.6 Hz, 3H), 3.34 (s, 4H), 3.18 (t, J=7.8 Hz, 3H), 2.59 (t, J=7.7 Hz, 2H), 2.47 (s, 3H), 2.35 (tt, J=8.3, 4.7 Hz, 1H), 2.24 (s, 3H), 1.46 (d, J=6.7 Hz, 3H), 1.37-1.28 (m, 2H), 1.19 (dt, J=8.2, 3.3 Hz, 3H); LCMS: $C_{44}H_{56}BF_2N_9O_5$ requires m/z=840, found 841 $[M+H]^+$.

BIOLOGICAL EXAMPLES

The following abbreviations apply: ACT (adoptive cell therapy); AUC (area under curve); Cmpd (compound); CP (cell proliferation); E/T (Effector:Target cell ratio); ID (identification); MFI (mean fluorescence intensity); mpk (milligram per kilogram); PBMC (peripheral blood mononuclear cells); TIL (tumor infiltrating lymphocyte); and Ub (ubiquitin).

Biological Example 1A: Evaluation of Cbl-b Inhibition by Candidate Cbl-b Inhibitors Candidate compounds isolated from screening assays were evaluated for their ability to bind and inhibit Cbl-b, an E3 ubiquitin-protein ligase.

Materials and Methods

Cbl-b Activity Assay

The ability of candidate compounds to inhibit Cbl-b activity was measured by monitoring the interaction of Cbl-b with UbcH5B-Ub in the presence of the candidate compound. A truncated variant of Cbl-b (UniProt number Q13191; SEQ ID NO:1) containing an Avitag at its N-terminus was co-expressed with BirA biotin ligase and purified using a standard protocol (see Dou et al., Nature Structural and Molecular Biology 8: 982-987, 2013; Avidity LLC).

```
Cbl-b amino acid residues 36-427:
                                                  (SEQ ID NO: 1)
PKQAAADRRTVEKTWKLMDKVVRLCQNPKLQLKNSPPYILDILPDTYQHL

RLILSKYDDNQKLAQLSENEYFKIYIDSLMKKSKRAIRLFKEGKERMYEE

QSQDRRNLTKLSLIFSHMLAEIKAIFPNGQFQGDNFRITKADAAEFWRKF

FGDKTIVPWKVFRQCLHEVHQISSGLEAMALKSTIDLTCNDYISVFEFDI

FTRLFQPWGSILRNWNFLAVTHPGYMAFLTYDEVKARLQKYSTKPGSYIF

RLSCTRLGQWAIGYVTGDGNILQTIPHNKPLFQALIDGSREGFYLYPDGR

SYNPDLTGLCEPTPHDHIKVTQEQYELYCEMGSTFQLCKICAENDKDVKI

EPCGHLMCTSCLTAWQESDGQGCPFCRCEIKGTEPIIVDPFD
```

Fluorescently labeled UbcH5B-Ub was prepared by conjugating ubiquitin (Ub), labeled at its N-terminus with Bodipy-Fluorescein, to UbcH5B, an E2 enzyme, harboring a cysteine to lysine mutation at position 85. This mutation is similar to a mutation that was previously reported (see Dou et al., Nature Structural and Molecular Biology 8: 982-987, 2013). Cbl-b activity assays were performed in a 384-well plate at room temperature in a 10 μL reaction volume by pre-incubating 12 nM Cbl-b (final concentration) in an assay buffer containing 50 mM HEPES pH 7.0, 100 mM NaCl, 0.01% Triton X-100, 0.01% BSA, and 1 mM DTT in the presence of a candidate compound in 1% DMSO (final concentration, High Conditions) for one hour. After incubation in the presence of the candidate compound, the plate was incubated for an additional 1.5 hours in the presence of 60 nM Src kinase with 1 mM ATP and 5 mM $MgCl_2$ (final concentrations). Alternatively, compounds were tested as described above with assay buffer containing 50 mM NaCl instead of 100 mM NaCl and 30 nM Src kinase instead of 60 nM Src kinase (Low Conditions). Src kinase was prepared as previously described (see Kobashigawa et al., Proc Natl Acad Sci USA, 108: 20579-20584, 2011). Following incubation, 2 μL of a mixture containing 1.5 μM fluorescently labeled UbcH5B-Ub, 15 nM Streptavidin-Terbium (Cisbio), 300 nM EDTA, and 0.01% BSA was added to the reaction, wherein the EDTA quenched the activity of the Src kinase. The plate was incubated for one hour. Following the one hour incubation, the plates were read for TR-FRET signal at 520/620 nm using Envision plate reader (Perkin Elmer). The presence of a FRET signal that indicated Cbl-b was not inhibited by the compound candidate. The absence of a FRET signal indicated Cbl-b was inhibited by the compound candidate and was therefore a Cbl-b inhibitor.

Results

The resulting data for the Cbl-b activity assays were analyzed using standard methods to report the $IC_{50}$ values of the tested compounds (Tables 3-4). The resulting data for the Cbl-b binding assay was solvent corrected and double-referenced prior to analysis. All data were globally fit to a steady-state affinity and kinetic binding model where applicable. Compounds were ranked into bins A through D as follows for $IC_{50}$: A indicates <0.1 μM, B indicates 0.1 μM≤$IC_{50}$<1 μM, C indicates 1 μM≤$IC_{50}$<5 μM, and D indicates 5 μM≤$IC_{50}$.

TABLE 3

| Cbl-b inhibition by tested compounds under low conditions | |
|---|---|
| Cmpd No. | Cbl-b activity $IC_{50}$ (μM) |
| 1 | D |
| 2 | B |
| 5 | D |
| 33 | D |
| 34 | D |
| 122 | A |

TABLE 4

| Cbl-b inhibition by tested compounds under high conditions | |
|---|---|
| Cmpd No. | Cbl-b activity $IC_{50}$ (μM) |
| 3 | B |
| 4 | D |
| 6 | D |
| 7 | D |
| 8 | D |
| 9 | B |
| 10 | A |
| 11 | C |
| 12 | D |
| 13 | B |
| 14 | B |
| 15 | C |
| 16 | B |
| 17 | C |
| 18 | D |
| 19 | A |
| 20 | B |
| 21 | B |
| 22 | B |
| 23 | B |
| 24 | B |
| 25 | B |
| 26 | A |
| 27 | A |
| 28 | A |
| 29 | A |
| 30 | A |
| 31 | B |
| 32 | C |
| 35 | D |
| 36 | C |
| 37 | D |
| 38 | D |
| 39 | C |
| 40 | C |
| 41 | D |
| 42 | D |
| 43 | D |
| 44 | D |
| 45 | B |
| 46 | C |
| 47 | D |
| 48 | D |
| 49 | D |
| 50 | C |
| 51 | D |
| 52 | D |
| 53 | D |
| 54 | D |
| 55 | C |
| 56 | C |
| 57 | C |
| 58 | C |
| 59 | C |

TABLE 4-continued

| Cbl-b inhibition by tested compounds under high conditions | |
|---|---|
| Cmpd No. | Cbl-b activity $IC_{50}$ (μM) |
| 60 | C |
| 61 | C |
| 62 | C |
| 63 | D |
| 64 | C |
| 65 | C |
| 66 | D |
| 67 | C |
| 68 | D |
| 69 | C |
| 70 | D |
| 71 | D |
| 72 | C |
| 73 | C |
| 74 | B |
| 75 | C |
| 76 | C |
| 77 | C |
| 78 | C |
| 79 | C |
| 80 | D |
| 81 | D |
| 82 | C |
| 83 | D |
| 84 | C |
| 85 | D |
| 86 | C |
| 87 | C |
| 88 | B |
| 89 | C |
| 90 | C |
| 91 | D |
| 92 | D |
| 93 | C |
| 94 | D |
| 95 | B |
| 96 | C |
| 97 | C |
| 98 | D |
| 99 | B |
| 100 | D |
| 101 | D |
| 102 | B |
| 103 | D |
| 104 | C |
| 105 | B |
| 106 | B |
| 107 | B |
| 108 | C |
| 109 | B |
| 110 | B |
| 111 | B |
| 112 | B |
| 113 | A |
| 116 | B |
| 117 | C |
| 118 | C |
| 119 | C |
| 120 | C |
| 121 | D |
| 123 | D |
| 124 | D |
| 125 | D |
| 126 | D |
| 127 | D |
| 128 | D |
| 129 | D |
| 130 | D |
| 131 | D |
| 132 | D |
| 133 | D |
| 134 | D |
| 135 | D |

TABLE 4-continued

| Cbl-b inhibition by tested compounds under high conditions | |
|---|---|
| Cmpd No. | Cbl-b activity $IC_{50}$ (μM) |
| 136 | D |
| 137 | D |
| 138 | D |
| 139 | D |
| 140 | D |
| 141 | D |
| 142 | D |
| 143 | D |
| 144 | D |
| 145 | D |
| 146 | D |
| 147 | D |
| 148 | D |
| 149 | D |
| 150 | D |
| 151 | D |
| 152 | D |
| 153 | D |
| 154 | D |
| 155 | D |
| 156 | D |
| 157 | D |
| 158 | D |
| 159 | D |
| 160 | D |
| 161 | D |
| 162 | D |
| 163 | D |
| 164 | D |
| 165 | D |
| 166 | D |
| 167 | C |

Biological Example 1B: Evaluation of Cbl-b Inhibition by Candidate Inhibitors Candidate compounds were evaluated for their ability to bind and inhibit Cbl-b, an E3 ubiquitin-protein ligase, as evidenced by their ability to displace a fluorophore-labeled probe (Example 168) bound to Cbl-b.

Materials and Methods

Cbl-b Displacement Assay (Cbl-b Inhibition Assay)

The ability of candidate compounds to displace a known inhibitor and thereby inhibit Cbl-b activity was measured by monitoring the interaction of Cbl-b with a fluorophore-labeled probe in the presence of the candidate compound. A truncated variant of Cbl-b (UniProt number Q13191; SEQ ID NO:1) containing an Avitag at its N-terminus was co-expressed with BirA biotin ligase and purified using a standard protocol (see Dou et al., Nature Structural and Molecular Biology, 8: 982-987, 2013; Avidity LLC).

```
Cbl-b amino acid residues 36-427:
                                      (SEQ ID NO: 1)
PKQAAADRRTVEKTWKLMDKVVRLCQNPKLQLKNSPPYILDILPDTYQHL

RLILSKYDDNQKLAQLSENEYFKIYIDSLMKKSKRAIRLFKEGKERMYEE

QSQDRRNLTKLSLIFSHMLAEIKAIFPNGQFQGDNFRITKADAAEFWRKF

FGDKTIVPWKVFRQCLHEVHQISSGLEAMALKSTIDLTCNDYISVFEFDI
```

-continued

```
FTRLFQPWGSILRNWNFLAVTHPGYMAFLTYDEVKARLQKYSTKPGSYIF

RLSCTRLGQWAIGYVTGDGNILQTIPHNKPLFQALIDGSREGFYLYPDGR

SYNPDLTGLCEPTPHDHIKVTQEQYELYCEMGSTFQLCKICAENDKDVKI

EPCGHLMCTSCLTAWQESDGQGCPFCRCEIKGTEPIIVDPFD
```

Fluorescently-labeled inhibitor probe was synthesized and tagged with BODIPY FL (Example 168). Cbl-b displacement assays were performed in a 384-well plate at room temperature in a 10 μL reaction volume by pre-incubating 0.125 nM Cbl-b (final concentration) in an assay buffer containing 20 mM HEPES pH 7.5, 150 mM NaCl, 0.01% Triton X-100, 0.01% BSA, and 0.5 mM TCEP in the presence of a candidate compound in 1% DMSO (final concentration) for one hour. After incubation in the presence of the candidate compound, the plate was incubated for an additional one hour in the presence of an approximate $EC_{40}$ binding saturation consisting of 150 nM fluorescently-labeled inhibitor probe and 2 nM Streptavidin-Terbium (Cisbio) (final concentrations). Following the one hour incubation, the plates were read for TR-FRET signal at 520/620 nm using an Envision plate reader (Perkin Elmer). The presence of a TR-FRET signal indicated that the probe was not displaced from Cbl-b by the compound candidate. The absence of a FRET signal indicated that the probe was displaced from Cbl-b by the compound candidate.

Compounds were ranked into bins A through D as follows for $IC_{50}$: A indicates <0.1 μM, B indicates 0.1 μM≤$IC_{50}$<1 μM, C indicates 1 μM≤$IC_{50}$<5 μM, and D indicates 5 μM≤$IC_{50}$. Data for tested compounds is shown in Table 5.

TABLE 5

| Cbl-b inhibition by tested compounds under displacement assay | |
|---|---|
| Cmpd No. | Cbl-b activity $IC_{50}$ (μM) |
| 114 | A |
| 115 | A |

Biological Example 2: Evaluation of T-cell Activation by Cbl-b Inhibitors

Loss of Cbl-b function in both T-cells and mice by genetic knockout of the cbl-b gene results in loss of the CD28 co-stimulation requirement for T-cell activation and T-cell resistance to anergy (see Bachmaier et al., Nature, 403: 211-216, 2000; and Jeon et al., Immunity, 21: 167-177, 2004). Cbl-b inhibitors described herein are evaluated for their ability to activate T-cells.

Materials and Methods

Purification and Assessment of Primary Human Total T-Cell Activation

Peripheral blood mononuclear cells (PBMC) are obtained either 1) by using Ficoll-Paque™ (GE Healthcare) for separation of peripheral blood hematopoietic cells from buffy coats of healthy human donors; or 2) directly from LeukoPak donations. Total human primary T-cells are isolated from the PMBCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a are incubated with the PBMCs before passing the samples by magnetic beads for removal of cells expressing those surface markers) or Stemcell Technologies Catalog #17951) to yield >95% CD3+ cells as assessed by flow cytometry. The cells are rested overnight at 37° C. in 5% $CO_2$. The Cbl-inhibitor is added to $1\times10^5$ cells per well and the plate is incubated for one hour at 37° C. in 5% $CO_2$ at various concentrations with a final DMSO concentration of <0.1%. For samples stimulated with anti-CD3 antibody and anti-CD28 antibody (anti-CD3/anti-CD28), the Cbl-b inhibitor concentrations tested are 1 μM and 0.3 μM. For samples stimulated with anti-CD3 antibody alone (anti-CD3), the Cbl-b inhibitor concentrations tested are 3 μM and 1 μM. Following incubation with the Cbl-b inhibitor, primary human total T-cells are stimulated with either plate bound anti-CD3 antibody (OKT3) alone or plate bound anti-CD3 antibody (OKT3) with soluble anti-CD28 antibody (28.2) (Life Technologies). To prepare plates with plate bound anti-CD3 antibody (OKT3), 96-well round bottom tissue culture plates are coated with 100 μL of anti-CD3 antibody (OKT3) at 10 μg/mL for 4 hours at 37° C. in 5% $CO_2$ in phosphate buffered saline (PBS). The plates are washed with PBS once prior to adding the cells with or without soluble anti-CD28 antibody (28.2) to each well at a final concentration of 5 μg/mL. Cells are stimulated for 48 hours prior to harvesting the cell free supernatant and staining the cell population for surface marker assessment by flow cytometry. Supernatants are analyzed for cytokine secretion, including IL-2 by ELISA (R&D Systems, Peprotech or Life Technologies) or Luminex multiplex kits (Procarta Life Technologies) following the manufacturer's protocol. Cells are stained with anti-CD25 antibody (BD Biosciences) to assess levels of surface marker of activation.

Results

Readouts are reported as fold change over baseline. Baseline for this study is the measurement obtained from total human T-cells stimulated with anti-CD3 antibody and with soluble anti-CD28 antibody, wherein the cells are not incubated with a Cbl-b inhibitor. For T-cells stimulated with anti-CD3/anti-CD28, changes greater than 2.5-fold over baseline for IL-2 secretion and greater than 1.3-fold over baseline for CD25 surface staining are considered significant and a positive response. For T-cells stimulated with anti-CD3 alone, changes greater than 0.1-fold over baseline for IL-2 secretion and greater than 0.6-fold over baseline for CD25 surface staining are considered significant and a positive response.

Biological Example 3: Evaluation of Immunomodulatory Effects of Cbl-b Inhibitors Cbl-b inhibitors identified from screening assays demonstrated the ability to activate total human T-cells in vitro as evidenced by enhanced IL-2 secretion and expression of the CD25 surface activation marker. Further in vitro studies are conducted to assess additional cytokine secretion by T-cells and expression of surface activation markers on T-cells. Additional immunomodulatory effects on T-cells contacted with the Cbl-b inhibitors described herein are assessed, such as the ability of a Cbl-b inhibitor to increase T-cell proliferation, decrease T-cell exhaustion, and decrease T-cell anergy. The ability of Cbl-b inhibitors, such as those described herein, to activate T-cells in vivo is also assessed. Other immunomodulatory effects by the Cbl-b inhibitors are assessed, such as the ability of Cbl-b inhibitors to activate B-cells and NK-cells.

Purification and Assessment of Primary Human Total T-Cell Activation

Peripheral blood mononuclear cells (PBMC) are obtained either 1) by using Ficoll-Paque™ (GE Healthcare) for separation of peripheral blood hematopoietic cells from buffy coats of healthy human donors; or 2) directly from LeukoPak donations. Total human primary T-cells are isolated from the PMBCs utilizing negative selection with commercial kits following the manufacturer's protocol (Miltenyi Biotec Catalog #130-096-535 (i.e., cocktail of antibodies against surface markers CD14, CD15, CD16, CD19, CD34, CD36, CD56, CD123, and CD235a are incubated with the PBMCs before passing the samples by magnetic beads for removal of cells expressing those surface markers) or Stemcell Technologies Catalog #17951) to yield >95% CD3+ cells as assessed by flow cytometry. For measurement of cell proliferation, cells are labeled with Cell Trace Violet (Invitrogen) following the manufacturer's protocol prior to activation by stimulation with anti-CD3 antibody alone or in combination with anti-CD28 antibody. The Cbl-b inhibitor is added to $1\times10^5$ cells per well at multiple concentrations (e.g., 10 μM, 1.11 μM, or 0.123 μM) with a final DMSO concentration of <0.1%. The plate is incubated for one hour at 37° C. in 5% $CO_2$. Following incubation with the Cbl-b inhibitor, primary human total T-cells are stimulated with either plate bound anti-CD3 antibody (OKT3) alone or plate bound anti-CD3 antibody (OKT3) with soluble anti-CD28 antibody (28.2) (Life Technologies). To prepare plates with plate bound anti-CD3 antibody (OKT3), 96-well round bottom tissue culture plates are coated with 100 μL of anti-CD3 antibody (OKT3) at 10 μg/mL for 4 hours at 37° C. in 5% $CO_2$ in phosphate buffered saline (PBS). The plates are washed with PBS prior to adding the cells with or without soluble anti-CD28 antibody (28.2) to each well at a final concentration of 5 μg/mL. Cells are stimulated for 48 hours prior to harvesting the cell free supernatant and staining the cell population for surface marker assessment by flow cytometry. Supernatants are analyzed for cytokine secretion (e.g., GM-CSF, IFNγ, and TNFα) by ELISA (R&D Systems, Peprotech or Life Technologies) or Luminex multiplex kits (Procarta Life Technologies) following the manufacturer's protocol. Cells are stained with anti-CD69 (BD Biosciences) to assess levels of surface markers of activation. Proliferation is measured by flow cytometry and data is analyzed with FlowJo v7.6.5 or v10. Readouts are reported as fold change over baseline. In some embodiments, baseline is the measurement obtained from total human T-cells stimulated with anti-CD3 antibody alone, wherein the cells are not incubated with a Cbl-b inhibitor. In some embodiments, baseline is the measurement obtained from total human T-cells stimulated with anti-CD3 antibody and anti-CD28 antibody, where the cells are not incubated with a Cbl-b inhibitor.

Cbl-b inhibitor effects on primary human T-cells are also evaluated in the context of an allogenic mixed lymphocyte reaction (MLR). Allogenic immature dendritic cells are generated under the following conditions. Peripheral blood mononuclear cells (PBMC) are obtained either 1) by using Ficoll-Paque™ (GE Healthcare) for separation of peripheral blood hematopoietic cells from buffy coats of healthy human donors; or 2) directly from LeukoPak donations. Monocytes are isolated from the PMBCs utilizing positive selection with a commercial kit following the manufacturer's protocol (Stemcell Technologies Catalog #17858) to yield >95%

CD14+ cells as assessed by flow cytometry. Monocytes are cultured with 30 ng/mL of recombinant human GM-CSF and 20 ng/mL of recombinant human IL-4 for seven days to generate immature dendritic cells. Monocytes and T-cells are either isolated fresh from peripheral blood or thawed from frozen stocks. Human T-cells are isolated, labeled with CFSE, and incubated with inhibitors as described above. The Cbl-b inhibitor is added to $1\times10^5$ T-cells in co-culture with $2\times10^3$ allogenic immature dendritic cells per well at multiple concentrations (e.g., 10 μM, or 1.11 μM) with a final DMSO concentration of <0.1% and incubated at 37° C. in 5% $CO_2$ for 5 days. Proliferation of the T-cells is evaluated by flow cytometry.

Cbl-b inhibitors are tested to determine their ability to induce or enhance secretion of cytokines from T-cells (e.g., GM-CSF, IFNγ, and TNFα) and/or surface expression of cell surface markers on T-cells (e.g., CD69) that is indicative of T-cell activation. Cbl-b inhibitors are also tested to determine their ability to induce or enhance T-cell proliferation. Cbl-b inhibitors are tested for their effects on T-cell activation in the presence of co-stimulation and where conditions are suboptimal for priming.

Human T-Cell In Vitro Models of T-Cell Exhaustion

T-cell exhaustion is characterized by cells having a poor effector response and a sustained level of inhibitory receptor expression that results in T-cell dysfunction in response to chronic infections and cancer. In vitro models of T-cell exhaustion include allogenic and autologous models. In an autologous model, myeloid cells and SEB (Staphylococcal enterotoxin B, Millipore) are used to stimulate anti-CD3 stimulated T-cells. Peripheral blood mononuclear cells (PBMC) are obtained either 1) by using Ficoll-Paque™ (GE Healthcare) for separation of peripheral blood hematopoietic cells from buffy coats of healthy human donors; or 2) directly from LeukoPak donations. Monocytes are isolated with commercial kits using negative selection with Stemcell Technologies EasySep Human Monocyte Enrichment Kit without CD16 Depletion (Catalog #19058) following the manufacturer's protocol. Isolated monocytes are cultured in complete media (e.g., RPMI 1640 with no additives, 10% HI FBS, 1× Glutamine and 1×P-mercaptoethanol) with 50 ng/mL recombinant human M-CSF (R&D System or Peprotech). Cells are plated at $2\times10^6$ cells per well (Day 0) and cultured for 5 days and are fed with fresh media and cytokines on Day 2. On Day 5 IFNγ is added at 100 ng/mL and the cells are incubated overnight. Primary human T-cells from the same donor are isolated from PBMCs with a commercial kit using negative selection (with Stemcell Technologies EasySep Human T-cell Isolation Kit (Catalog #17951) following the manufacturer's protocol. Purity is confirmed by surface marker detection by flow cytometry for CD4, CD8, CD45RA, CD45RO, CD19, CD14, CD56, and CD3 (BD Biosciences). $3\times10^6$ cells per/mL T-cells are stimulated with 10 μg/mL of plate bound anti-CD3 antibody (Clone UCHT-1) for 5 days. This is done in parallel with myeloid cell generation. On Day 6, $2.5\times10^4$ T-cells are added per well, $12.5\times10^3$ myeloid cells per well and SEB antigen (0.1 pg/mL) are added to wells of a round bottom 96-well plate. Test agents (e.g., Cbl-b inhibitor compounds) or controls (e.g., checkpoint neutralizing antibodies such as anti-PD1 antibody) are added to the wells at the indicated concentrations (e.g., 10 μM). Cells are cultured for 3 days at which point cell free supernatants are collected and assessed for secreted cytokines (e.g., GM-CSF, IFNγ, and IL-2) by ELISA (R&D Systems, Peprotech or Life Technologies) or Luminex multiplex kits (Procarta Life Technologies). The T-cells are stained for a panel of surface markers including checkpoint inhibitors (e.g., CTLA4) and evaluated by flow cytometry for Cbl-b inhibitor effects.

Cbl-b inhibitors are tested to determine their ability to induce or enhance secretion of cytokines from exhausted T-cells (e.g., GM-CSF, IFNγ, and IL-2) in the presence of myeloid cells, which is indicative of decreased T-cell exhaustion. Cbl-b inhibitors are also tested for their effects on checkpoint modulator expression levels following activation of exhausted T-cells.

Human T-Cell In Vitro Models of T-Cell Anergy

Peripheral blood mononuclear cells (PBMC) are obtained either 1) by using Ficoll-Paque™ (GE Healthcare) for separation of peripheral blood hematopoietic cells from buffy coats of healthy human donors; or 2) directly from LeukoPak donations. Total human primary T-cells are isolated from the PBMCs utilizing negative selection with commercial kits following the manufacturer's protocol (Miltenyi Catalog #130-096-535 (i.e., cocktail of antibodies against surface markers CD14, CD15, CD16, CD19, CD34, CD36, CD56, CD123, and CD235a are incubated with the PBMCs before passing the samples by magnetic beads for removal of cells expressing those surface markers) or Stemcell Technologies Catalog #17951) to yield >95% CD3+ cells assessed by flow cytometry. The cells are activated with immobilized anti-CD3 antibody (OKT3) and soluble anti-CD28 antibody (28.2) for two days at which time they are washed and allowed to rest for three days in the absence of stimulation. They are then treated with ionomycin (Sigma) for 18-24 hours to induce anergy. Following two washes to remove the ionomycin from the samples, Cbl-b inhibitor compounds are added to the cells at the indicated concentrations (e.g., 10, 1.11, and 0.37 μM) and incubated for one hour. The cells are then re-challenged with anti-CD3 antibody and anti-CD28 antibody for 24 hours at which point cell free supernatants are collected and assessed for cytokines (e.g., IFNγ) by ELISA (R&D Systems or Peprotech) or Luminex multiplex kits (Procarta Life Technologies) following the manufacturer's protocols.

Cbl-b inhibitors are tested to determine their ability to induce or enhance secretion of cytokines from anergic T-cells (e.g., IFNγ), which is indicative of decreased T-cell tolerance.

In Vivo Activity of Cbl-b Inhibitors

A method of determining the pharmacodynamic profile of Cbl-b inhibitors is performed by dosing strains of mice with competent immune systems such as C57BL/6 or BALB/c with a Cbl-b inhibitor. The Cbl-b inhibitor is dissolved in a suitable formulation and administered by one of various routes such as intravenous (IV), intraperitoneal (IP), subcutaneous (SC), or oral (PO), at a suitable dose level and frequency (e.g., twice per day BID or thrice per day TID) as informed by prior pharmacokinetic and tolerability studies. Following administration of the Cbl-b inhibitor, T-cells and indirectly other immune cells (e.g., via cytokine production) are stimulated in vivo by administration of an anti-CD3 antibody or antigen-binding fragment thereof in PBS at defined amounts such as 2 g or 10 g per animal by routes such as IV or IP (See Hirsh et al., J. Immunol., 1989; Ferran et al., Eur. J. Immunol., 1990). Additional study control arms include groups of mice treated with a vehicle formulation alone (i.e., formulation without the Cbl-b inhibitor and anti-CD3 antibody), a formulation containing the Cbl-b inhibitor alone, a formulation containing the anti-CD3 antibody alone, PBS alone, or combinations of these agents. The level of immune activation is then assessed by analysis of plasma cytokine levels and/or expression of activation markers on immune cells (e.g., T-cells). Blood or lymphoid organs (e.g., spleen) are collected at defined time points (e.g., 8 hours or 24 hours). Blood samples are processed to collect plasma for determination of cytokine levels using standard methods known in the art. Cytokines measured included IL-2, IFNγ, and TNFα. Additional blood samples and lymphoid tissues are processed for flow cytometric analysis of immune cells (e.g., T-cells) using standard methods to determine expression of cell type-specific markers and activation markers such as CD25 and/or CD69. Augmentation of immune stimulation by Cbl-b inhibitor administration is assessed by comparing the relative concentrations of cytokines in plasma, or the expression levels of activation markers on immune cells between appropriate groups (e.g., mice treated with Cbl-b inhibitor and 2 g anti-CD3 antibody versus mice treated with vehicle and 2 g anti-CD3 antibody).

Cbl-b inhibitors are tested to determine their ability to induce or enhance the level of cytokines (e.g., IL-2, IFNγ, and TNFα) in blood obtained from treated mice stimulated with an anti-CD3 antibody, which is indicative of modulation of the immune response. Cbl-b inhibitors are also tested to determine their ability to induce or enhance the expression of cell surface markers on T-cells (e.g., CD25 and/or CD69) isolated from treated mice stimulated with an anti-CD3 antibody, which is indicative of modulation of the immune response.

B Cell Activation Assay

Peripheral blood mononuclear cells (PBMC) are obtained either 1) by using Ficoll-Paque™ (GE Healthcare) for separation of peripheral blood hematopoietic cells from buffy coats of healthy human donors; or 2) directly from LeukoPak donations. Human primary B-cells are isolated from the PBMCs utilizing negative selection with commercial kits following the manufacturer's protocol (Stemcell Technologies Catalog #17954) to yield >95% CD20+ cells assessed by flow cytometry. Primary human B-cells are plated at 0.7-1×$10^5$ per well in a 96-well plate with Cbl-b inhibitors over a dose ranging from 10 μM to 1 nM and incubated at 37° C. in 5% $CO_2$, with a final DMSO concentration of <0.5%. Cells are stimulated with anti-IgM for 20 hours at 37° C. in 5% $CO_2$. Surface activation markers on mature $CD20^+$ $IgD^+$ B-cells are monitored by FACS using an anti-CD69 antibody (BD Biosciences).

Cbl-b inhibitors are tested to determine their ability to induce or enhance surface expression of cell surface markers on B-cells (e.g., CD69), which is indicative of B-cell activation.

Purification and Activation of Primary Human NK-Cells

Peripheral blood mononuclear cells (PBMC) are obtained either 1) by using Ficoll-Paque™ (GE Healthcare) for separation of peripheral blood hematopoietic cells from buffy coats of healthy human donors; or 2) directly from LeukoPak donations. Total human primary NK-cells are isolated from the PBMCs utilizing negative selection with commercial kits following the manufacturer's protocol (Miltenyi Catalog #130-092-657 or Stemcell Technologies Catalog #17955) to yield >92% CD56+, CD3− cells as assessed by flow cytometry. The cells are cultured overnight with IL-2 (60 ng/mL) at 37° C. in 5% $CO_2$. Cbl-b inhibitors are added one hour prior to stimulation and incubated at 37° C. in 5% $CO_2$ at a specific concentration (e.g., 10 μM, 1 μM, or 0.1 μM) with a final DMSO concentration of <0.1%. NK-cells are co-cultured with target cells that are engineered to have a red nucleus (K562 NucRed) measurable by flow cytometry. K562 NucRed cells are produced by transduction of K562 cells with IncuCyte NucLight Red Lentivirus reagent (Catalog #4476) and selected for 5 days. Clonal populations are isolated and expanded using standard tissue culture techniques, and individual clones are validated by comparison to wildtype K562 cells in NK-cell killing assays. The cells are mixed at the indicated ratios (e.g., 5:1, 1:1, or 1:5) of NK (effector cells) to K562 NucRed (target cells) for 6 hours. Cell free supernatants are collected and analyzed for cytokine secretion (e.g., TNFα, IFNγ, or MIP1β) by ELISA or Luminex multiplex kits following the manufacturer's protocol. IFNγ secretion is assessed using an R&D Systems ELISA kit (Catalog #DY285), TNFα secretion is assessed using an R&D Systems ELISA kit (Catalog #DY210), and MIP1β secretion is assessed using an R&D Systems ELISA kit (Catalog #DY271).

Biological Example 4: Evaluation of a Cbl-b Inhibitor in Combination With an Immune Checkpoint Inhibitor for Treating Cancer Tumor microenvironments exploit T-cell inhibitory pathways as a mechanism to evade anti-tumor immune responses. The use of immune checkpoint inhibitors such as inhibitors of PD-1, PD-L1, and CTLA-4 have resulted in strikingly efficacious and durable responses against some tumor types (Marshall and Djamgoz, Front Oncol, 8:315, 2018). However, the response to immune checkpoint inhibitor monotherapy is not universal and therefore benefits only a small subset of cancer patients (Lv et al., Journal for ImmunoTherapy of Cancer, 7:159, 2019). This example describes the evaluation of a combination therapy for treating cancer including an immune checkpoint inhibitor and a Cbl-b inhibitor.

In brief, combination therapies are tested in strains of mice with competent immune systems (e.g., C57BL/6 or BALB/c) in whom syngeneic tumors can be grown. Syngeneic murine tumor cells are injected subcutaneously: CT26 colon cancer cells in BALB/c mice; TC-1 lung cancer cells in C57BL/6 mice; or MC-38 colon cancer cells in C57BL/6 mice. Tumors are allowed to grow to up to 100-200 $mm^3$ at which time the animals are randomized and treatment is initiated. Alternatively, treatment is administered in a prophylactic setting within 1-3 days of tumor cell implant. The Cbl-b inhibitor is dissolved in a suitable formulation and administered at a suitable dose level and frequency as informed by prior pharmacokinetic and tolerability studies. The Cbl-b inhibitor formulation is administered orally (PO) or parenterally (e.g., IV, IP, SC, or intratumorally at one to three injection sites per tumor). The immune checkpoint inhibitor formulation is administered by IP injection every three days (e.g., Days 1, 4 and 7). In addition to the test group of mice who receive the combination therapy, the study includes control groups of mice who receive either the vehicle formulation alone, the Cbl-b inhibitor formulation alone, or the immune checkpoint inhibitor alone.

The level of response is evaluated by measuring tumor growth and comparing tumor growth in the test mice versus the control mice. The level of immune activation is assessed by collecting tumors for analysis of tumor infiltrating lymphocytes (TILs). TILs and lymphoid tissues are processed for flow cytometric analysis using standard methods to determine cell lineage, expression of cell type-specific markers, and expression of activation markers such as granzyme B, PD-1, TIM3, and LAG3. Augmentation of the anti-tumor immune response by the combination therapy is assessed by comparing the relative percentage of immune cell populations in the tumor, and the relative levels of expression of activation markers on immune cells in mice of the test and study groups.

Biological Example 5: Evaluation of a Cbl-b Inhibitor in Combination With an Anti-Neoplastic Agent for Treating Cancer Chemotherapy has been reported to have a positive immunologic effect on tumor infiltrating lymphocytes (Lazzari et al., Ther Adv Med Oncol, 10:1-12, 2018), with the balance of regulatory and effector immune cells influencing prognosis. In addition, chemotherapy is contemplated to increase the intratumoral T-cell repertoire by augmenting tumor antigen presentation. This example describes the evaluation of a combination therapy for treating cancer including an anti-neoplastic agent and a Cbl-b inhibitor.

In brief, combination therapies are tested in strains of mice with competent immune systems (e.g., C57BL/6 or BALB/c) in whom syngeneic tumors can be grown. Syngeneic murine tumor cells are injected subcutaneously: CT26 colon cancer cells in BALB/c mice; or TC-1 lung cancer cells in C57BL/6 mice. Tumors are allowed to grow up to about 120 $mm^3$ at which time the animals are randomized and treatment is initiated. The Cbl-b inhibitor is dissolved in a suitable formulation and administered at a suitable dose level and frequency as informed by prior pharmacokinetic and tolerability studies. The Cbl-b inhibitor formulation is administered orally (PO) or parenterally (e.g., IV, IP, SC, or intratumorally at one to three injection sites per tumor). The anti-neoplastic agent (e.g., gemcitabine and/or oxaliplatin) is administered by IP injection once every three or four days. In addition to the test group of mice who receive the combination therapy, the study includes control groups of mice who receive either the vehicle formulation alone, the Cbl-b inhibitor formulation alone, or the anti-neoplastic agent alone.

The level of response is evaluated by measuring tumor growth and comparing tumor growth in the test mice versus the control mice. The level of immune activation is assessed by collecting tumors for analysis of tumor infiltrating lymphocytes (TILs). TILs and lymphoid tissues are processed for flow cytometric analysis using standard methods to determine cell lineage, expression of cell type-specific markers and expression of activation markers such as granzyme B, PD-1, TIM3, and LAG3. Augmentation of the anti-tumor immune response by the combination therapy is assessed by comparing the relative percentage of immune cell populations in the tumor, and the relative levels of expression of activation markers on immune cells in mice of the test and study groups.

Biological Example 6: Evaluation of a Cbl-b Inhibitor in Combination With Radiation Therapy for Treating Cancer Ablative radiation therapy targeting local tumors limits damage to normal tissue and has the ability to enhance the diversity of the T-cell receptor repertoire by increasing the presence of tumor antigens (Lee et al., Blood, 114: 589-595, 2009). Radiotherapy at one site has been reported to lead to regression of distant site tumors that were not irradiated (Ngwa et al., Nat Rev Cancer, 18: 313-322, 2018). The systemic effect of a localized therapy is termed an “abscopal effect,” which in the context of radiation therapy is thought to involve the immune system. This example describes the evaluation of a combination therapy for treating cancer including radiation therapy and a Cbl-b inhibitor.

In brief, combination therapies are tested in strains of mice with competent immune systems (e.g., C57BL/6 or BALB/c) in whom syngeneic tumors can be grown. Syngeneic murine tumor cells are injected subcutaneously: CT26 colon cancer cells in BALB/c mice; or B16-F10 melanoma cells in C57BL/6 mice. Tumors are allowed to grow up to about 80 $mm^3$ at which time the animals are randomized and treatment is initiated. In some studies, tumor cells are implanted in both flanks and only one tumor is treated to assess the abscopal effect. The Cbl-b inhibitor is dissolved in a suitable formulation and administered at a suitable dose level and frequency as informed by prior pharmacokinetic and tolerability studies. The Cbl-b inhibitor formulation is administered orally (PO) or parenterally (e.g., IV, IP, SC, or intratumorally at one to three injection sites per tumor). Radiation therapy is administered once at a dose of 20 grays using an X-ray based focal beam irradiator. In addition to the test group of mice who receive the combination therapy, the study includes control groups of mice who receive either the vehicle formulation alone, the Cbl-b inhibitor formulation alone, or radiation therapy alone.

The level of response is evaluated by measuring tumor growth and comparing tumor growth in the test mice versus the control mice. The level of immune activation is assessed by collecting tumors for analysis of tumor infiltrating lymphocytes (TILs). TILs and lymphoid tissues are processed for flow cytometric analysis using standard methods to determine cell lineage, expression of cell type-specific markers, and expression of activation markers such as granzyme B, PD-1, TIM3, and LAG3. Augmentation of the anti-tumor immune response by the combination therapy is assessed by comparing the relative percentage of immune cell populations in the tumor, and the relative levels of expression of activation markers on immune cells in mice of the test and study groups.

Biological Example 7: Evaluation of a Cbl-B Inhibitor in Combination With Adoptive Cell Therapy for Treating Cancer Adoptive cell therapy (ACT) utilizing autologous tumor-specific T-cells leverages the natural function of T-cells to specifically recognize and eliminate target cells (Hinrichs and Rosenberg, Immunol Rev, 257: 56-71, 2014). Specificity of tumor infiltrating lymphocytes (TILs) is due to their ability to recognize tumor-associated antigens, including neoantigens derived from products of mutated genes. This example describes the evaluation of an in vivo lymphoconditioning program with a Cbl-b inhibitor prior to ex vivo expansion of TILs for treating cancer with ACT.

Strains of mice with competent immune systems (e.g., C57BL/6 or BALB/c) in whom syngeneic tumors can be grown are utilized. Syngeneic murine tumor cells are injected subcutaneously or intravenously: 4T1 breast cancer cells in BALB/c mice; RENCA kidney cancer cells in BALB/c mice; B16-F10 melanoma cells in C57BL/6 mice; 3LL lung cancer cells in C57BL/6 mice; or MC-38 colon cancer cells in C57BL/6 mice. Tumors are allowed to grow up to about 50-600 $mm^3$ at which time the animals are randomized and treatment is initiated. The Cbl-b inhibitor is dissolved in a suitable formulation and administered at a suitable dose level and frequency as informed by prior pharmacokinetic and tolerability studies. The Cbl-b inhibitor formulation is administered orally (PO) or parenterally (e.g., IV, IP, SC, or intratumorally at one to three injection sites per tumor). In addition to the test group of mice who receive the Cbl-b inhibitor prior to tumor harvest, a control group of mice will receive either the vehicle formulation alone or will be left untreated prior to tumor harvest. Tumor tissue is harvested either from the primary tumor or from tissues with metastases (e.g., lung). The tissues are minced and cultured in medium in the presence or absence of one or more exogenous T-cell growth factors (e.g., IL-2, IL-7, IL-15, and/or IL-21) under conditions suitable for expansion of TILs. Expansion of TILs is done in the presence or absence of the Cbl-b inhibitor. Expanded TILs are assessed for phenotype by flow cytometric analysis by measuring expression of markers for memory, effector, and stemness (e.g., CD95, TCF7, CD62L, CD44, etc.). Upon successful expansion of the TILs, tumor bearing mice are infused with TILs in the presence or absence of the Cbl-b inhibitor to assess the effect of lympho-conditioning and/or subsequent in vivo treatment on TIL engraftment and anti-tumor immune responses.

Anti-tumor efficacy of ACT is assessed through tumor measurements to determine the level of tumor growth inhibition by TILs.

The disclosures of all publications, patents, patent applications, and published patent applications referred to herein by an identifying citation are hereby incorporated herein by reference in their entirety.

Although aspects of the foregoing disclosure have been described in some detail by way of illustration and example for purposes of clarity of understanding, it is apparent to those skilled in the art that certain changes and modifications will be practiced. Therefore, the description and examples should not be construed as limiting the scope of the disclosure.

What is claimed is:

1. A compound of Formula (I)

(I)

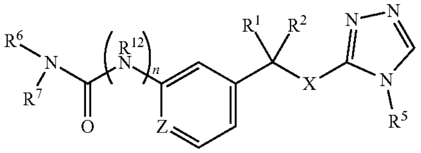

or a tautomer of the compound, or a pharmaceutically acceptable salt of the compound or the tautomer, wherein $R^1$ and $R^2$ are independently hydrogen, $C_1$-$C_6$ alkyl, halo, or $C_1$-$C_6$ haloalkyl, provided that when X is sulfur, $R^1$ and $R^2$ are not both hydrogen, and provided that $R^1$ and $R^2$ are not halo when X is sulfur or a bond; or $R^1$ and $R^2$ are taken together with the carbon atom to which they are attached to form

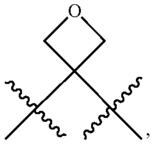, 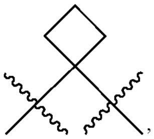, or 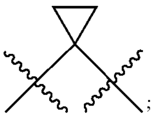;

X is $CR^3R^4$ or sulfur;

$R^3$ and $R^4$ are independently hydrogen, $C_1$-$C_6$ alkyl, halo, or $C_1$-$C_6$ haloalkyl; or $R^1$ and $R^3$ are taken together with the carbon atoms to which they are attached to form

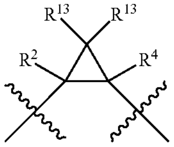;

$R^5$ is $C_1$-$C_6$ alkyl, $C_1$-$C_6$ haloalkyl, or $C_3$-$C_6$ cycloalkyl;

Z is CH or nitrogen;

n is zero or one;

$R^6$ is hydrogen, $C_1$-$C_6$ alkyl, or $C_1$-$C_6$ haloalkyl;

$R^7$ is $C_1$-$C_6$ alkyl-OH, —$(CR^8R^9)_m$-(5- to 10-membered monocyclic or fused bicyclic heteroaryl), —$(CR^8R^9)_m$-(4- to 10-membered monocyclic or fused bicyclic heterocyclyl), —$(CR^8R^9)_m$—($C_6$-$C_{10}$ aryl), or —$(CR^8R^9)_m$—($C_3$-$C_6$ cycloalkyl), wherein each heteroaryl, heterocyclyl, aryl, or cycloalkyl group is optionally substituted by one to five $R^{10}$ groups; or $R^6$ and $R^7$ are taken together with the nitrogen atom to which they are attached to form a 5- to 10-membered monocyclic or fused bicyclic heteroaryl, or a 4- to 10-membered monocyclic or fused bicyclic heterocyclyl, wherein each heteroaryl or heterocyclyl optionally contains one to two additional heteroatoms selected from the group consisting of nitrogen, sulfur, and oxygen, and wherein each heteroaryl or heterocyclyl is optionally substituted by one to five $R^{10}$ groups;

m is zero or one;

$R^8$ and $R^9$ are independently hydrogen, $C_1$-$C_6$ alkyl, or $C_1$-$C_6$ haloalkyl;

each $R^{10}$ is independently $C_1$-$C_6$ alkyl, $C_1$-$C_6$ haloalkyl, $C_1$-$C_6$ alkyl-OH, —CN, $C_1$-$C_6$ alkyl-CN, —O($C_1$-$C_6$ alkyl), —O($C_1$-$C_6$ haloalkyl), halo, hydroxy, oxo, —$CO_2$H, —C(O)NH($C_1$-$C_6$ alkyl), —C(O)N($C_1$-$C_6$ alkyl)$_2$, —C(O)NH($C_1$-$C_6$ haloalkyl), —C(O)O($C_1$-$C_6$ alkyl), —$SO_2$—($C_1$-$C_6$ alkyl), —$SO_2$—NH($C_1$-$C_6$ alkyl), —$SO_2$—$N(C_1$-$C_6$ alkyl$)_2$, —$C(O)(C_1$-$C_6$ alkyl), —$(C_1$-$C_6$ alkylene)-$C(O)N(C_1$-$C_6$ alkyl$)_2$, —$(C_1$-$C_6$ alkylene)-$C(O)NH(C_1$-$C_6$ alkyl), $C_3$-$C_6$ cycloalkyl, 5- to 6-membered heterocyclyl, 5- to 6-membered heteroaryl, —$(C_1$-$C_6$ alkylene)-(5- to 6-membered heterocyclyl), —$(C_1$-$C_6$ alkylene)-(5- to 6-membered heteroaryl), —C(O)-(5- to 6-membered heterocyclyl), —C(O)-(5- to 6-membered heteroaryl), or $C_6$-$C_{10}$ aryl, wherein each cycloalkyl, heterocyclyl, heteroaryl, or aryl group is optionally substituted by one to five $R^{11}$ groups; or two $R^{10}$ groups attached to the same carbon atom are taken together with the carbon atom to which they are attached to form a spiro $C_3$-$C_6$ cycloalkyl or a spiro 4- to 6-membered heterocyclyl, each of which is optionally substituted by one to five $R^{11}$ groups;

each $R^{11}$ is independently $C_1$-$C_6$ alkyl, hydroxy, oxo, or —$C(O)(C_1$-$C_6$ alkyl);

$R^{12}$ is hydrogen, $C_1$-$C_6$ alkyl, or $C_1$-$C_6$ haloalkyl;

or when $R^6$ and $R^7$ are taken together with the nitrogen atom to which they are attached to form a 4- to 10-membered monocyclic or fused bicyclic heterocyclyl optionally containing one to two additional heteroatoms selected from the group consisting of nitrogen, sulfur, and oxygen, $R^{12}$ is $C_1$-$C_6$ alkylene which connects to the 4- to 10-membered monocyclic or fused bicyclic heterocyclyl to form a 7- to 14-membered fused bicyclic or tricyclic heterocyclyl, wherein each heterocyclyl is optionally substituted by one to five $R^{10}$ groups; and each $R^{13}$ is independently hydrogen, $C_1$-$C_3$ alkyl, $C_1$-$C_3$ alkyl-OH, or $C_1$-$C_3$ haloalkyl.

2. The compound of claim 1, or a tautomer of the compound, or a pharmaceutically acceptable salt of the compound or the tautomer, wherein $R^1$ and $R^2$ are independently hydrogen, $C_1$-$C_3$ alkyl, halo, or $C_1$-$C_3$ haloalkyl.

3. The compound of claim 1, or a tautomer of the compound, or a pharmaceutically acceptable salt of the compound or the tautomer, wherein $R^1$ and $R^2$ are taken together with the carbon atom to which they are attached to form the group

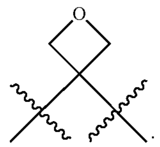 [SMILES: *C1(*)COC1]

4. The compound of claim 1, or a tautomer of the compound, or a pharmaceutically acceptable salt of the compound or the tautomer, wherein X is sulfur.

5. The compound of claim 1, or a tautomer of the compound, or a pharmaceutically acceptable salt of the compound or the tautomer, wherein X is $CR^3R^4$.

6. The compound of claim 1, or a tautomer of the compound, or a pharmaceutically acceptable salt of the compound or the tautomer, wherein $R^3$ and $R^4$ are independently hydrogen, halo, $C_1$-$C_3$ alkyl, or $C_1$-$C_3$ haloalkyl.

7. The compound of claim 5, or a tautomer of the compound, or a pharmaceutically acceptable salt of the compound or the tautomer, wherein $R^1$ and $R^3$ are taken together with the carbon atoms to which they are attached to form the moiety

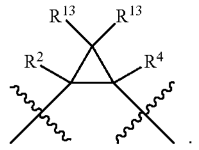

8. The compound of claim 7, or a tautomer of the compound, or a pharmaceutically acceptable salt of the compound or the tautomer, wherein $R^2$ is hydrogen, $C_1$-$C_3$ alkyl, halo, or $C_1$-$C_3$ haloalkyl;

$R^4$ is hydrogen, $C_1$-$C_3$ alkyl, halo, or $C_1$-$C_3$ haloalkyl; and each $R^{13}$ is independently hydrogen, $C_1$-$C_2$ alkyl, $C_1$-$C_2$ alkyl-OH, or $C_1$-$C_2$ haloalkyl.

9. The compound of claim 1, or a tautomer of the compound, or a pharmaceutically acceptable salt of the compound or the tautomer, wherein $R^5$ is $C_1$-$C_3$ alkyl, $C_1$-$C_3$ haloalkyl, or $C_3$-$C_4$ cycloalkyl.

10. The compound of claim 1, or a tautomer of the compound, or a pharmaceutically acceptable salt of the compound or the tautomer, wherein Z is CH.

11. The compound of claim 1, or a tautomer of the compound, or a pharmaceutically acceptable salt of the compound or the tautomer, wherein Z is nitrogen.

12. The compound of claim 1, or a tautomer of the compound, or a pharmaceutically acceptable salt of the compound or the tautomer, wherein n is zero.

13. The compound of claim 1, or a tautomer of the compound, or a pharmaceutically acceptable salt of the compound or the tautomer, wherein n is one.

14. The compound of claim 1, or a tautomer of the compound, or a pharmaceutically acceptable salt of the compound or the tautomer, wherein $R^6$ is hydrogen, $C_1$-$C_3$ alkyl, or $C_1$-$C_3$ haloalkyl.

15. The compound of claim 1, or a tautomer of the compound, or a pharmaceutically acceptable salt of the compound or the tautomer, wherein $R^7$ is $C_1$-$C_3$ alkyl-OH, —$(CR^8R^9)_m$-(5- to 6-membered monocyclic heteroaryl), —$(CR^8R^9)_m$-(8- to 10-membered fused bicyclic heteroaryl), —$(CR^8R^9)_m$-(4- to 6-membered monocyclic heterocyclyl), —$(CR^8R^9)_m$-(8- to 10-membered fused bicyclic heterocyclyl), —$(CR^8R^9)_m$—$(C_6$-$C_{10}$ aryl), or —$(CR^8R^9)_m$—$(C_3$-$C_6$ cycloalkyl), wherein each heteroaryl, heterocyclyl, aryl, or cycloalkyl group is optionally substituted with one to five $R^{10}$ groups.

16. The compound of claim 15, or a tautomer of the compound, or a pharmaceutically acceptable salt of the compound or the tautomer, wherein m is zero.

17. The compound of claim 15, or a tautomer of the compound, or a pharmaceutically acceptable salt of the compound or the tautomer, wherein m is one.

18. The compound of claim 17, or a tautomer of the compound, or a pharmaceutically acceptable salt of the compound or the tautomer, wherein $R^8$ and $R^9$ are independently hydrogen, $C_1$-$C_3$ alkyl, or $C_1$-$C_3$ haloalkyl.

19. The compound of claim 1, or a tautomer of the compound, or a pharmaceutically acceptable salt of the compound or the tautomer, wherein $R^6$ and $R^7$ are taken together with the nitrogen atom to which they are attached to form a 5- to 10-membered monocyclic or fused bicyclic heteroaryl, or a 4- to 10-membered monocyclic or fused bicyclic heterocyclyl, wherein each heteroaryl or heterocyclyl optionally contains one to two additional heteroatoms selected from the group consisting of nitrogen, sulfur, and oxygen, and wherein each heteroaryl or heterocyclyl is optionally substituted by one to five $R^{10}$ groups.

20. The compound of claim 15, or a tautomer of the compound, or a pharmaceutically acceptable salt of the compound or the tautomer, wherein each $R^{10}$, when present, is independently $C_1$-$C_3$ alkyl, $C_1$-$C_3$ haloalkyl, $C_1$-$C_3$ alkyl-OH, —CN, $C_1$-$C_3$ alkyl-CN, —O($C_1$-$C_3$ alkyl), —O($C_1$-$C_3$ haloalkyl), halo, hydroxy, oxo, —$CO_2$H, —C(O)NH($C_1$-$C_3$ alkyl), —C(O)NH($C_1$-$C_3$ haloalkyl), —C(O)O($C_1$-$C_3$ alkyl), —$SO_2$—($C_1$-$C_3$ alkyl), —$SO_2$—NH($C_1$-$C_3$ alkyl), —$SO_2$—N($C_1$-$C_3$ alkyl)$_2$, —C(O)($C_1$-$C_3$ alkyl), —($C_1$-$C_3$ alkylene)-C(O)N($C_1$-$C_3$ alkyl)$_2$, —($C_1$-$C_3$ alkylene)-C(O)NH($C_1$-$C_3$ alkyl), $C_3$-$C_6$ cycloalkyl, 5- to 6-membered heterocyclyl, 5- to 6-membered heteroaryl, —($C_1$-$C_3$ alkylene)-(5- to 6-membered heterocyclyl), —($C_1$-$C_3$ alkylene)-(5- to 6-membered heteroaryl), —C(O)-(5- to 6-membered heterocyclyl), —C(O)-(5- to 6-membered heteroaryl), or $C_6$-$C_{10}$ aryl, wherein each cycloalkyl, heterocyclyl, heteroaryl, or aryl group is optionally substituted with one to five $R^{11}$ groups; or two $R^{10}$ groups attached to the same carbon atom are taken together with the carbon atom to which they are attached to form a spiro $C_3$-$C_6$ cycloalkyl or a spiro 4- to 6-membered heterocyclyl, each of which is optionally substituted by one to five $R^{11}$ groups.

21. The compound of claim 20, or a tautomer of the compound, or a pharmaceutically acceptable salt of the compound or the tautomer, wherein each $R^{11}$, when present, is independently $C_1$-$C_3$ alkyl, hydroxy, oxo, or —C(O)($C_1$-$C_3$ alkyl).

22. The compound of claim 1, or a tautomer of the compound, or a pharmaceutically acceptable salt of the compound or the tautomer, wherein $R^{12}$ is hydrogen, $C_1$-$C_3$ alkyl, or $C_1$-$C_3$ haloalkyl.

23. The compound of claim 19, or a tautomer of the compound, or a pharmaceutically acceptable salt of the compound or the tautomer, wherein $R^6$ and $R^7$ are taken together with the nitrogen atom to which they are attached to form a 4- to 10-membered monocyclic or fused bicyclic heterocyclyl optionally containing one to two additional heteroatoms selected from the group consisting of nitrogen, sulfur, and oxygen, and $R^{12}$ is $C_1$-$C_6$ alkylene which connects to the 4- to 10-membered monocyclic or fused bicyclic heterocyclyl to form a 7- to 14-membered fused bicyclic or tricyclic heterocyclyl, wherein each heterocyclyl is optionally substituted with one to five $R^{10}$ groups.

24. A compound selected from

| Cmpd No. | Structure | Cmpd No. | Structure |
|---|---|---|---|
| 1 | 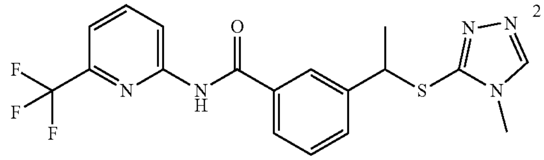 | 2 | 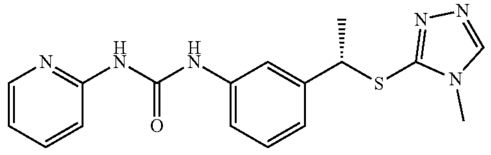 [SMILES: C[C@H](Sc1nncn1C)c1cccc(NC(=O)Nc2ccccn2)c1] |
| 3 | 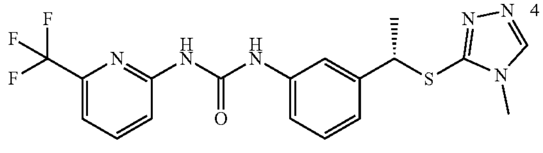 | 4 | 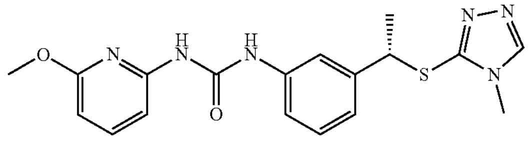 [SMILES: COc1cccc(NC(=O)Nc2cccc([C@H](C)Sc3nncn3C)c2)n1] |
| 5 | 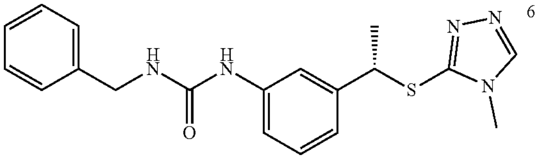 | 6 | 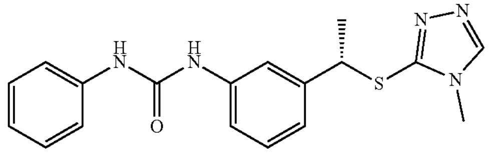 [SMILES: C[C@H](Sc1nncn1C)c1cccc(NC(=O)Nc2ccccc2)c1] |
| 7 | 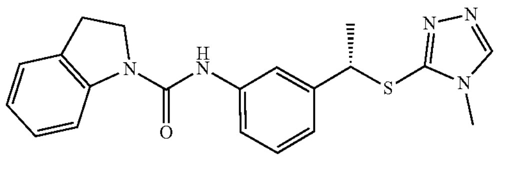 [SMILES: C[C@H](Sc1nncn1C)c1cccc(NC(=O)N2CCc3ccccc32)c1] | 8 | 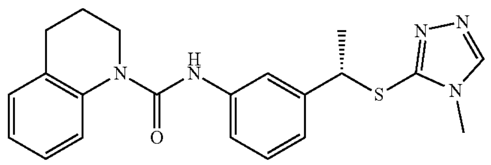 [SMILES: C[C@H](Sc1nncn1C)c1cccc(NC(=O)N2CCCc3ccccc32)c1] |
| 9 | 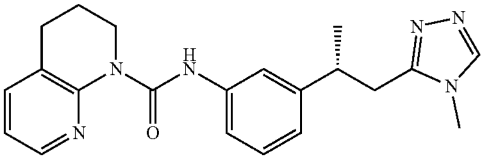 [SMILES: C[C@H](Cc1nncn1C)c1cccc(NC(=O)N2CCCc3cccnc32)c1] | 10 | 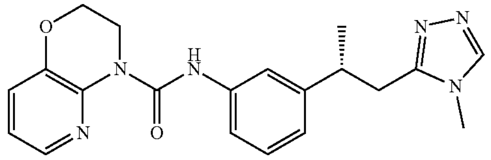 [SMILES: C[C@H](Cc1nncn1C)c1cccc(NC(=O)N2CCOc3cccnc32)c1] |

-continued
| Cmpd No. | Structure | Cmpd No. | Structure |
|---|---|---|---|
| 11 | 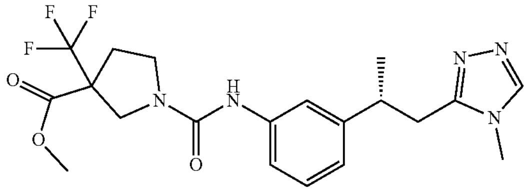 [SMILES: COC(=O)C1(C(F)(F)F)CCN(C(=O)Nc2cccc([C@H](C)Cc3nncn3C)c2)C1] | 12 | 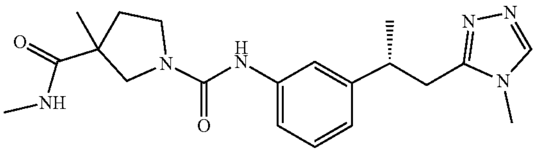 [SMILES: CNC(=O)C1(C)CCN(C(=O)Nc2cccc([C@H](C)Cc3nncn3C)c2)C1] |
| 13 | 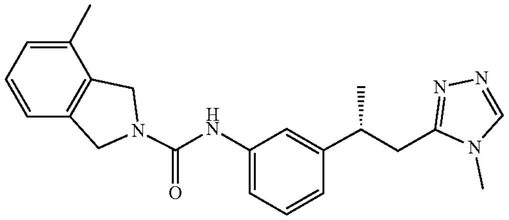 [SMILES: Cc1cccc2c1CN(C(=O)Nc1cccc([C@H](C)Cc3nncn3C)c1)C2] | 14 | 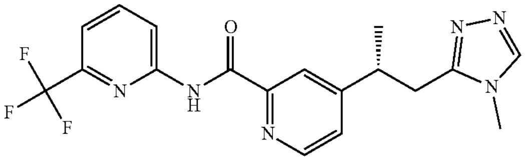 |
| 15 | 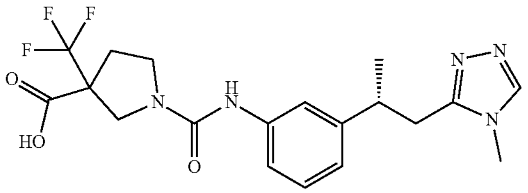 [SMILES: C[C@H](Cc1nncn1C)c1cccc(NC(=O)N2CCC(C(=O)O)(C(F)(F)F)C2)c1] | 16 | 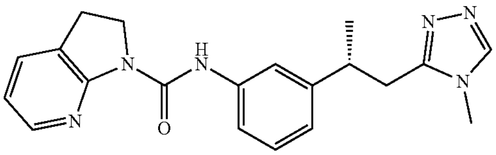 [SMILES: C[C@H](Cc1nncn1C)c1cccc(NC(=O)N2CCc3cccnc32)c1] |
| 17 | 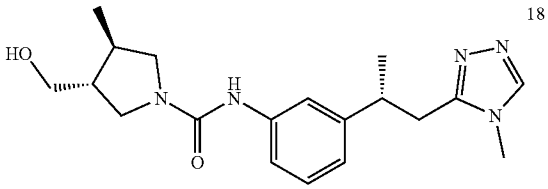 | 18 | 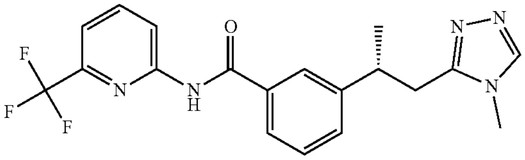 |
| 19 | 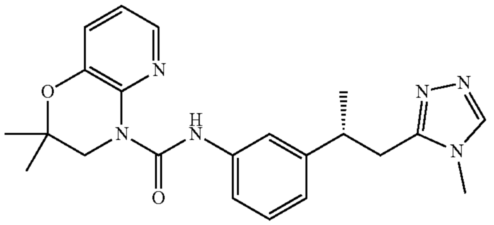 [SMILES: C[C@H](Cc1nncn1C)c1cccc(NC(=O)N2CC(C)(C)Oc3cccnc32)c1] | 20 | 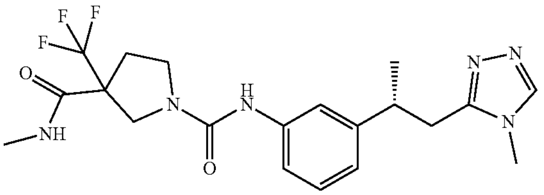 [SMILES: CNC(=O)C1(C(F)(F)F)CCN(C(=O)Nc2cccc([C@H](C)Cc3nncn3C)c2)C1] |
| 21 | 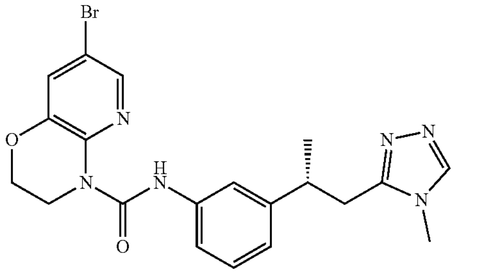 [SMILES: C[C@H](Cc1nncn1C)c1cccc(NC(=O)N2CCOc3cc(Br)cnc32)c1] | 22 | 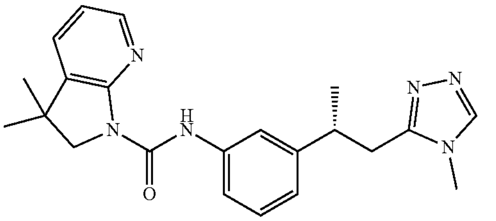 [SMILES: C[C@H](Cc1nncn1C)c1cccc(NC(=O)N2CC(C)(C)c3cccnc32)c1] |
| 23 | 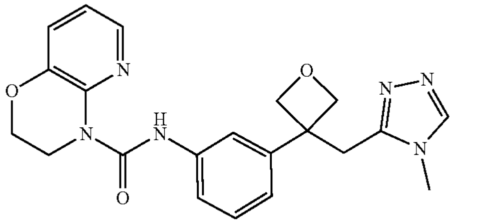 [SMILES: Cn1cnnc1CC1(c2cccc(NC(=O)N3CCOc4cccnc43)c2)COC1] | 24 | 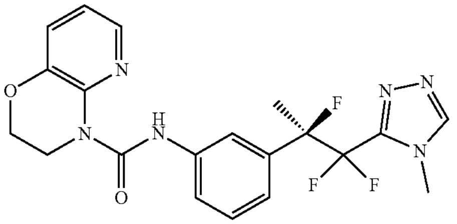 [SMILES: Cn1cnnc1C(F)(F)[C@](C)(F)c1cccc(NC(=O)N2CCOc3cccnc32)c1] |

-continued
| Cmpd No. | Structure | Cmpd No. | Structure |
|---|---|---|---|
| 25 | 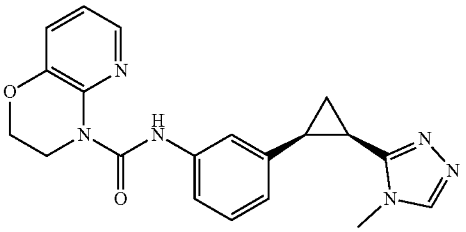 [SMILES: Cn1cnnc1[C@@H]1C[C@@H]1c1cccc(NC(=O)N2CCOc3cccnc32)c1] | 26 | 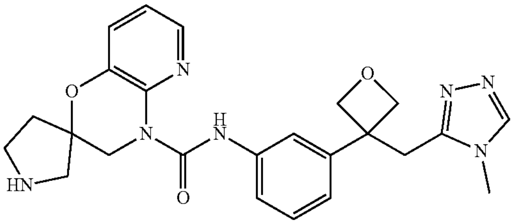 [SMILES: Cn1cnnc1CC1(c2cccc(NC(=O)N3CC4(CCNC4)Oc4cccnc43)c2)COC1] |
| 27 | 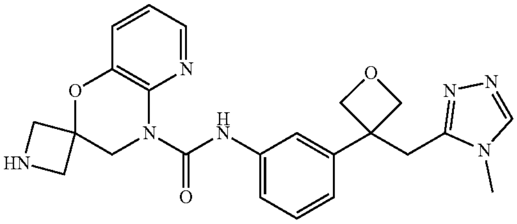 [SMILES: Cn1cnnc1CC1(c2cccc(NC(=O)N3CC4(CNC4)Oc4cccnc43)c2)COC1] | 28 | 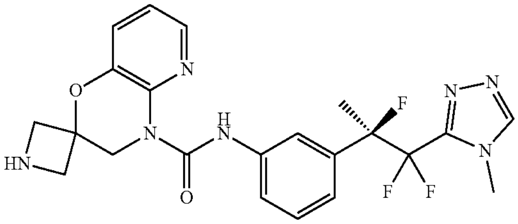 [SMILES: Cn1cnnc1C(F)(F)[C@](C)(F)c1cccc(NC(=O)N2CC3(CNC3)Oc3cccnc32)c1] |
| 29 | 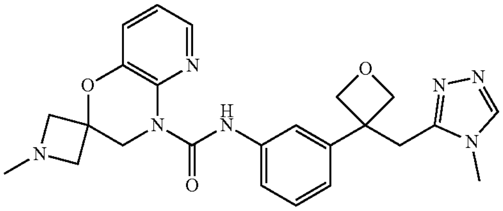 [SMILES: CN1CC2(C1)CN(C(=O)Nc1cccc(C3(Cc4nncn4C)COC3)c1)c1ncccc1O2] | 30 | 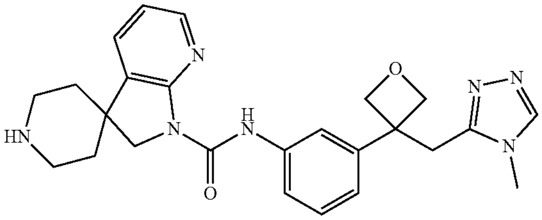 [SMILES: Cn1cnnc1CC1(c2cccc(NC(=O)N3CC4(CCNCC4)c4cccnc43)c2)COC1] |
| 31 | 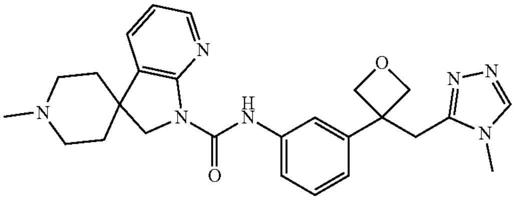 [SMILES: CN1CCC2(CC1)CN(C(=O)Nc1cccc(C3(Cc4nncn4C)COC3)c1)c1ncccc12] | 32 | 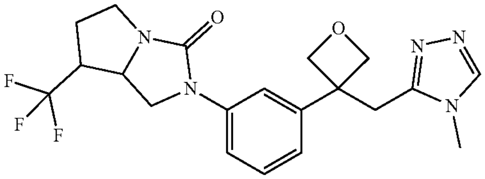 [SMILES: Cn1cnnc1CC1(c2cccc(N3CC4C(C(F)(F)F)CCN4C3=O)c2)COC1] |
| 33 | 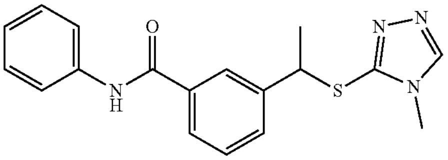 [SMILES: CC(Sc1nncn1C)c1cccc(C(=O)Nc2ccccc2)c1] | 34 | 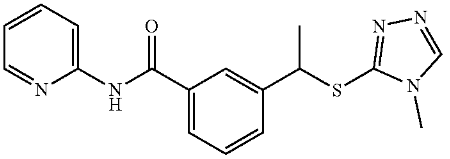 [SMILES: CC(Sc1nncn1C)c1cccc(C(=O)Nc2ccccn2)c1] |
| 35 | 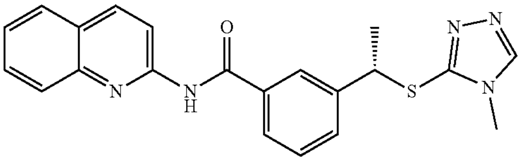 [SMILES: C[C@H](Sc1nncn1C)c1cccc(C(=O)Nc2ccc3ccccc3n2)c1] | 36 | 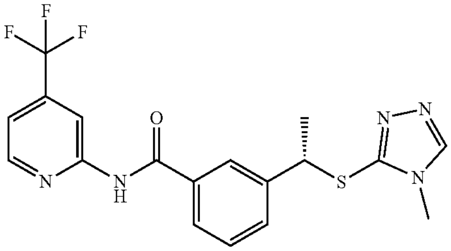 [SMILES: C[C@H](Sc1nncn1C)c1cccc(C(=O)Nc2cc(C(F)(F)F)ccn2)c1] |
| 37 | 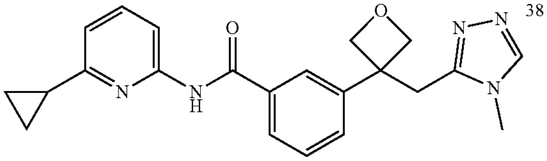 | 38 | 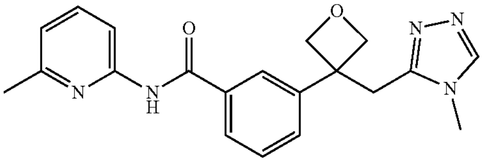 [SMILES: Cc1cccc(NC(=O)c2cccc(C3(Cc4nncn4C)COC3)c2)n1] |

-continued
| Cmpd No. | Structure | Cmpd No. | Structure |
|---|---|---|---|
| 39 | 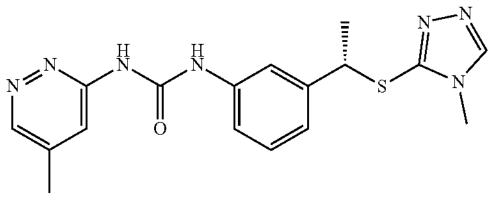 [SMILES: Cc1cnnc(NC(=O)Nc2cccc([C@H](C)Sc3nncn3C)c2)c1] | 40 | 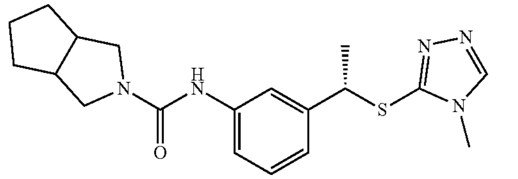 [SMILES: C[C@H](Sc1nncn1C)c1cccc(NC(=O)N2CC3CCCC3C2)c1] |
| 41 | 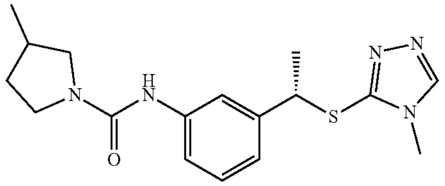 [SMILES: CC1CCN(C(=O)Nc2cccc([C@H](C)Sc3nncn3C)c2)C1] | 42 | 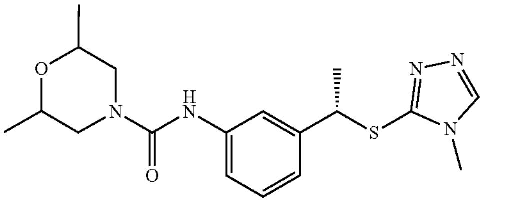 [SMILES: CC1CN(C(=O)Nc2cccc([C@H](C)Sc3nncn3C)c2)CC(C)O1] |
| 43 | 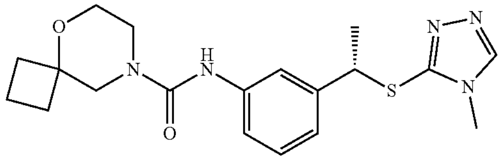 [SMILES: C[C@H](Sc1nncn1C)c1cccc(NC(=O)N2CCOC3(CCC3)C2)c1] | 44 | 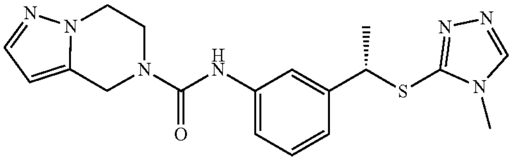 [SMILES: C[C@H](Sc1nncn1C)c1cccc(NC(=O)N2CCn3nccc3C2)c1] |
| 45 | 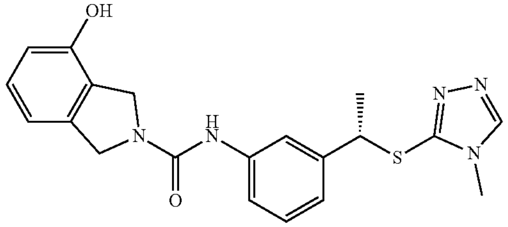 [SMILES: C[C@H](Sc1nncn1C)c1cccc(NC(=O)N2Cc3cccc(O)c3C2)c1] | 46 | 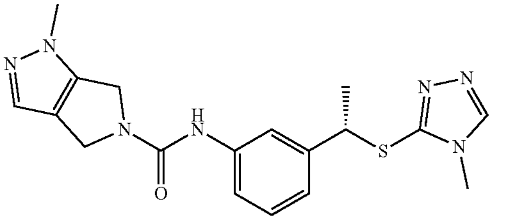 [SMILES: C[C@H](Sc1nncn1C)c1cccc(NC(=O)N2Cc3cnn(C)c3C2)c1] |
| 47 | 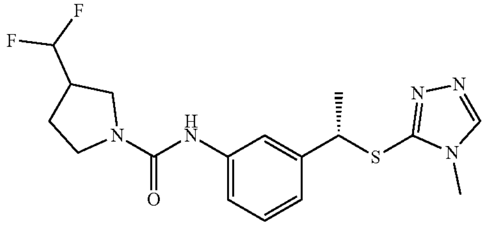 [SMILES: C[C@H](Sc1nncn1C)c1cccc(NC(=O)N2CCC(C(F)F)C2)c1] | 48 | 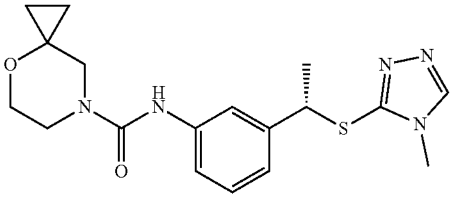 [SMILES: C[C@H](Sc1nncn1C)c1cccc(NC(=O)N2CCOC3(CC3)C2)c1] |
| 49 | 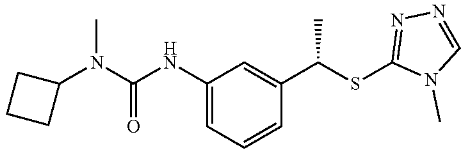 [SMILES: C[C@H](Sc1nncn1C)c1cccc(NC(=O)N(C)C2CCC2)c1] | 50 | 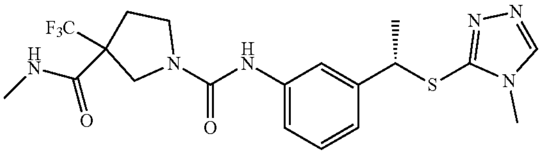 [SMILES: CNC(=O)C1(C(F)(F)F)CCN(C(=O)Nc2cccc([C@H](C)Sc3nncn3C)c2)C1] |
| 51 | 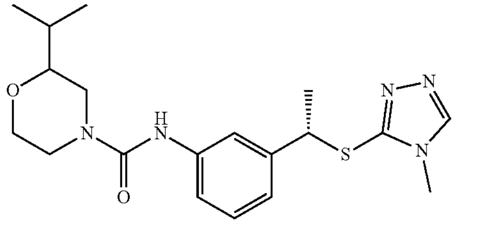 [SMILES: CC(C)C1CN(C(=O)Nc2cccc([C@H](C)Sc3nncn3C)c2)CCO1] | 52 | 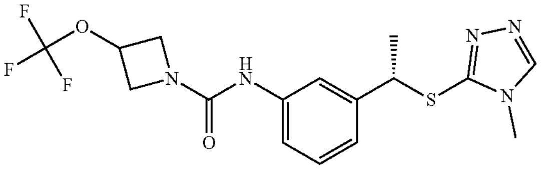 [SMILES: C[C@H](Sc1nncn1C)c1cccc(NC(=O)N2CC(OC(F)(F)F)C2)c1] |

-continued
| Cmpd No. | Structure | Cmpd No. | Structure |
|---|---|---|---|
| 53 | 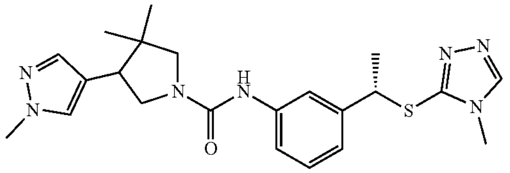 [SMILES: C[C@H](Sc1nncn1C)c1cccc(NC(=O)N2CC(c3cnn(C)c3)C(C)(C)C2)c1] | 54 | 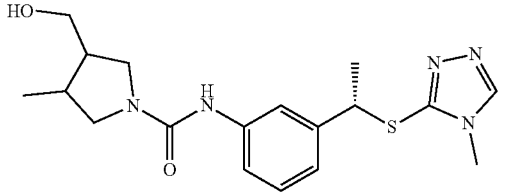 [SMILES: CC1CN(C(=O)Nc2cccc([C@H](C)Sc3nncn3C)c2)CC1CO] |
| 121 | 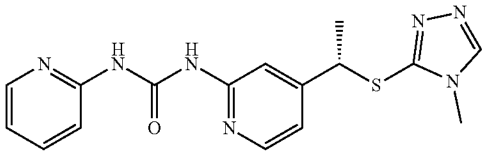 [SMILES: C[C@H](Sc1nncn1C)c1ccnc(NC(=O)Nc2ccccn2)c1] | 122 | 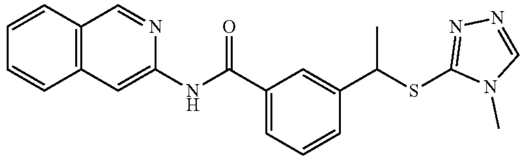 [SMILES: CC(Sc1nncn1C)c1cccc(C(=O)Nc2cc3ccccc3cn2)c1] |
| 123 | 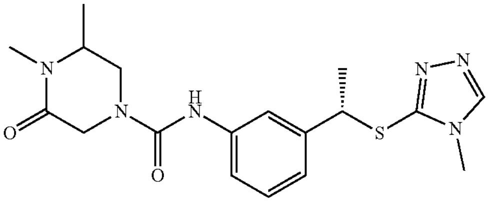 [SMILES: CC1CN(C(=O)Nc2cccc([C@H](C)Sc3nncn3C)c2)CC(=O)N1C] | 124 | 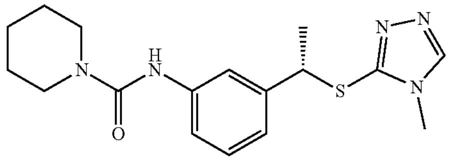 [SMILES: C[C@H](Sc1nncn1C)c1cccc(NC(=O)N2CCCCC2)c1] |
| 125 | 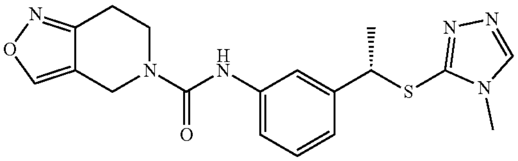 [SMILES: C[C@H](Sc1nncn1C)c1cccc(NC(=O)N2CCc3nocc3C2)c1] | 126 | 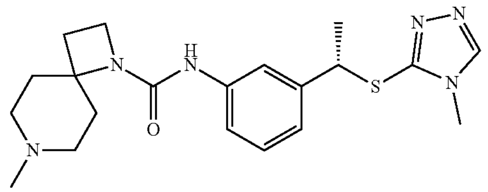 [SMILES: C[C@H](Sc1nncn1C)c1cccc(NC(=O)N2CCC23CCN(C)CC3)c1] |
| 127 | 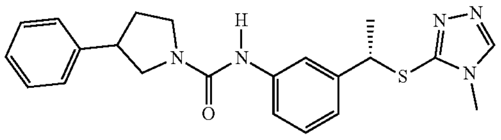 [SMILES: C[C@H](Sc1nncn1C)c1cccc(NC(=O)N2CCC(c3ccccc3)C2)c1] | 128 | 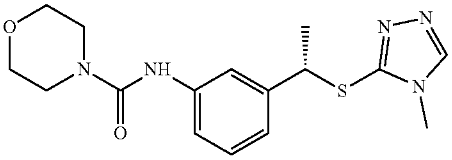 [SMILES: C[C@H](Sc1nncn1C)c1cccc(NC(=O)N2CCOCC2)c1] |
| 129 | 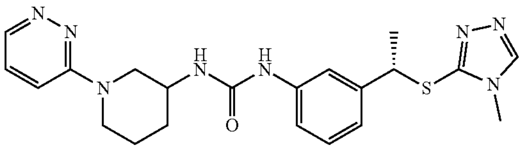 [SMILES: C[C@H](Sc1nncn1C)c1cccc(NC(=O)NC2CCCN(c3cccnn3)C2)c1] | 130 | 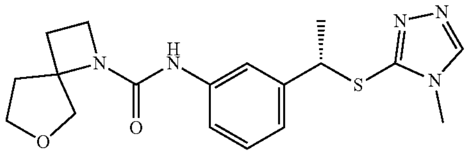 [SMILES: C[C@H](Sc1nncn1C)c1cccc(NC(=O)N2CCC23CCOC3)c1] |
| 131 | 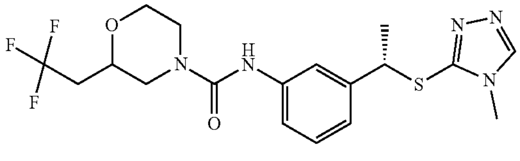 [SMILES: C[C@H](Sc1nncn1C)c1cccc(NC(=O)N2CCOC(CC(F)(F)F)C2)c1] | 132 | 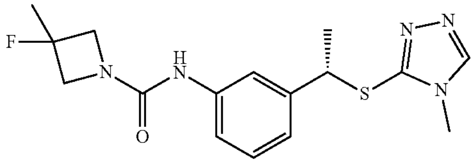 [SMILES: C[C@H](Sc1nncn1C)c1cccc(NC(=O)N2CC(C)(F)C2)c1] |
| 133 | 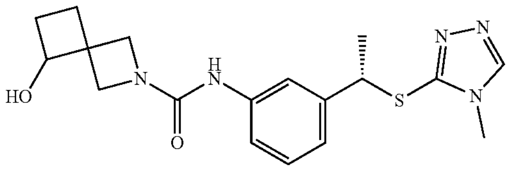 [SMILES: C[C@H](Sc1nncn1C)c1cccc(NC(=O)N2CC3(CCC3O)C2)c1] | 134 | 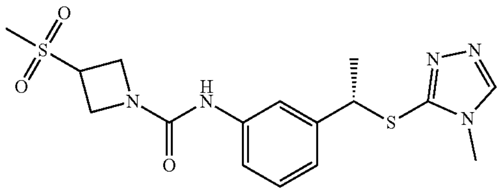 [SMILES: C[C@H](Sc1nncn1C)c1cccc(NC(=O)N2CC(S(C)(=O)=O)C2)c1] |

-continued
| Cmpd No. | Structure | Cmpd No. | Structure |
|---|---|---|---|
| 135 | 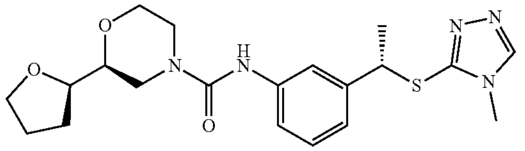 [SMILES: C[C@H](Sc1nncn1C)c1cccc(NC(=O)N2CCO[C@H]([C@H]3CCCO3)C2)c1] | 136 | 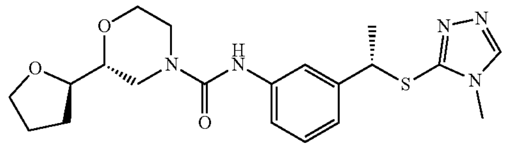 [SMILES: C[C@H](Sc1nncn1C)c1cccc(NC(=O)N2CCO[C@@H]([C@H]3CCCO3)C2)c1] |
| 137 | 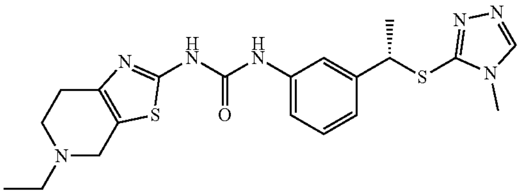 [SMILES: CCN1CCc2nc(NC(=O)Nc3cccc([C@H](C)Sc4nncn4C)c3)sc2C1] | 138 | 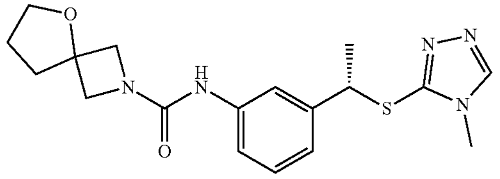 [SMILES: C[C@H](Sc1nncn1C)c1cccc(NC(=O)N2CC3(CCCO3)C2)c1] |
| 139 | 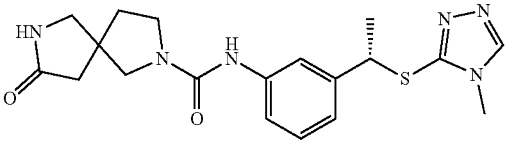 [SMILES: C[C@H](Sc1nncn1C)c1cccc(NC(=O)N2CCC3(CNC(=O)C3)C2)c1] | 140 | 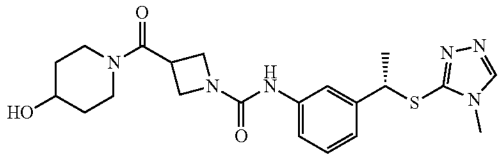 [SMILES: C[C@H](Sc1nncn1C)c1cccc(NC(=O)N2CC(C(=O)N3CCC(O)CC3)C2)c1] |
| 141 | 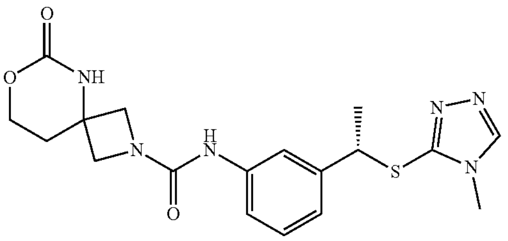 [SMILES: C[C@H](Sc1nncn1C)c1cccc(NC(=O)N2CC3(CCOC(=O)N3)C2)c1] | 142 | 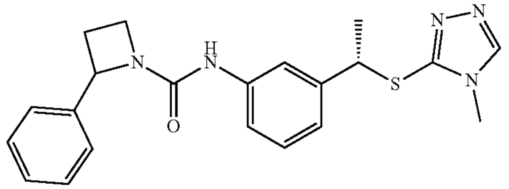 [SMILES: C[C@H](Sc1nncn1C)c1cccc(NC(=O)N2CCC2c2ccccc2)c1] |
| 143 | 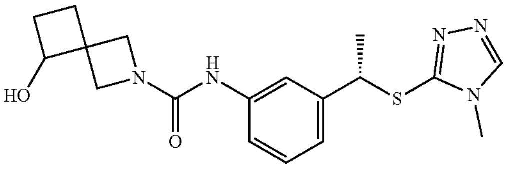 [SMILES: C[C@H](Sc1nncn1C)c1cccc(NC(=O)N2CC3(CCC3O)C2)c1] | 144 | 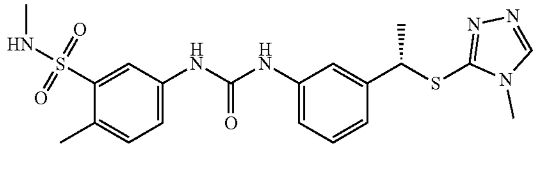 [SMILES: CNS(=O)(=O)c1cc(NC(=O)Nc2cccc([C@H](C)Sc3nncn3C)c2)ccc1C] |
| 145 | 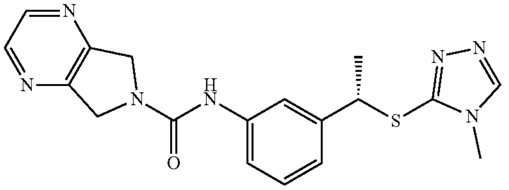 [SMILES: C[C@H](Sc1nncn1C)c1cccc(NC(=O)N2Cc3nccnc3C2)c1] | 146 | 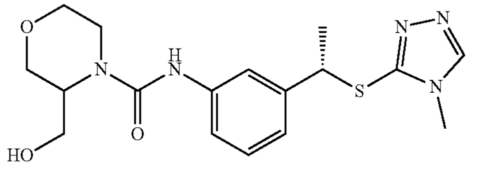 [SMILES: C[C@H](Sc1nncn1C)c1cccc(NC(=O)N2CCOCC2CO)c1] |
| 147 | 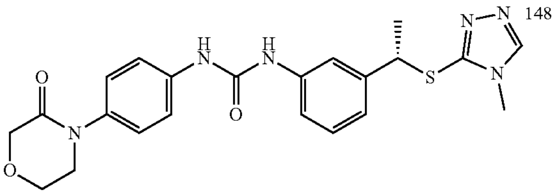 | 148 | 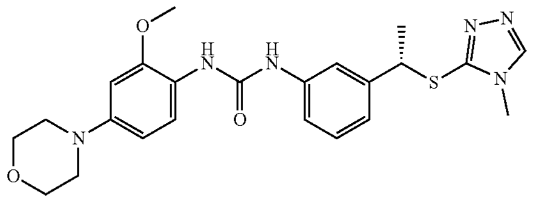 [SMILES: COc1cc(N2CCOCC2)ccc1NC(=O)Nc1cccc([C@H](C)Sc2nncn2C)c1] |

-continued
| Cmpd No. | Structure | Cmpd No. | Structure |
|---|---|---|---|
| 149 | 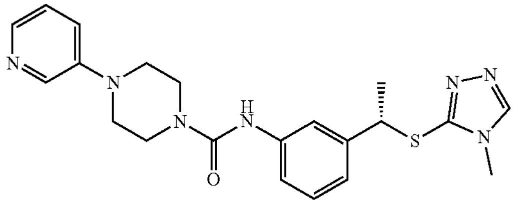 [SMILES: C[C@H](Sc1nncn1C)c1cccc(NC(=O)N2CCN(c3cccnc3)CC2)c1] | 150 | 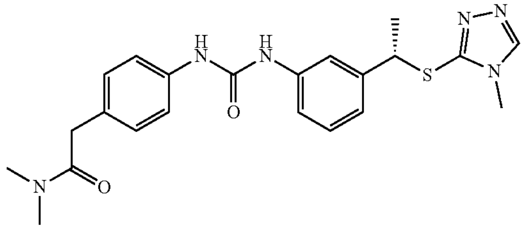 [SMILES: C[C@H](Sc1nncn1C)c1cccc(NC(=O)Nc2ccc(CC(=O)N(C)C)cc2)c1] |
| 151 | 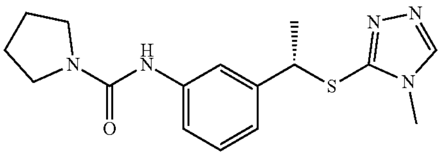 [SMILES: C[C@H](Sc1nncn1C)c1cccc(NC(=O)N2CCCC2)c1] | 152 | 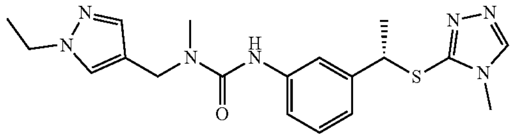 [SMILES: CCn1cc(CN(C)C(=O)Nc2cccc([C@H](C)Sc3nncn3C)c2)cn1] |
| 153 | 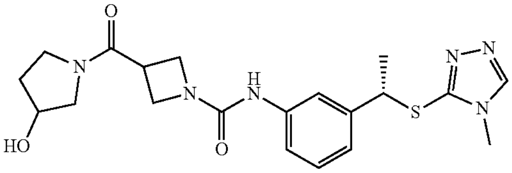 [SMILES: C[C@H](Sc1nncn1C)c1cccc(NC(=O)N2CC(C(=O)N3CCC(O)C3)C2)c1] | 154 | 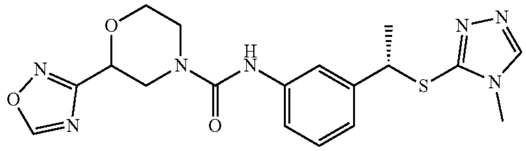 [SMILES: C[C@H](Sc1nncn1C)c1cccc(NC(=O)N2CCOC(c3ncon3)C2)c1] |
| 155 | 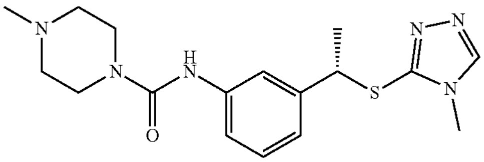 [SMILES: C[C@H](Sc1nncn1C)c1cccc(NC(=O)N2CCN(C)CC2)c1] | 156 | 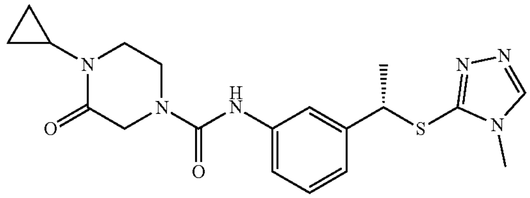 [SMILES: C[C@H](Sc1nncn1C)c1cccc(NC(=O)N2CCN(C3CC3)C(=O)C2)c1] |
| 157 | 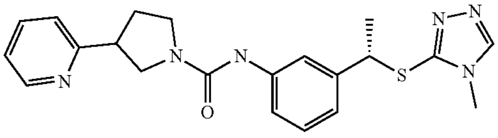 | 158 | 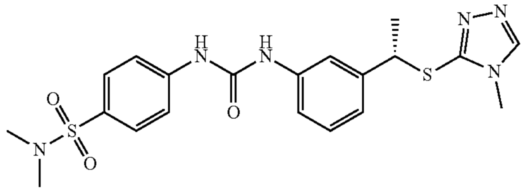 [SMILES: C[C@H](Sc1nncn1C)c1cccc(NC(=O)Nc2ccc(S(=O)(=O)N(C)C)cc2)c1] |
| 159 | 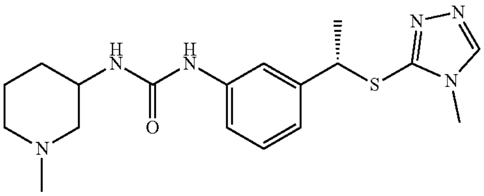 [SMILES: C[C@H](Sc1nncn1C)c1cccc(NC(=O)NC2CCCN(C)C2)c1] | 160 | 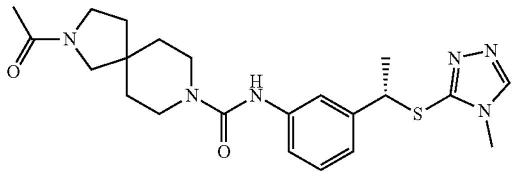 [SMILES: CC(=O)N1CCC2(CCN(C(=O)Nc3cccc([C@H](C)Sc4nncn4C)c3)CC2)C1] |
| 161 | 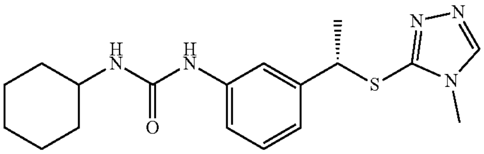 [SMILES: C[C@H](Sc1nncn1C)c1cccc(NC(=O)NC2CCCCC2)c1] | 162 | 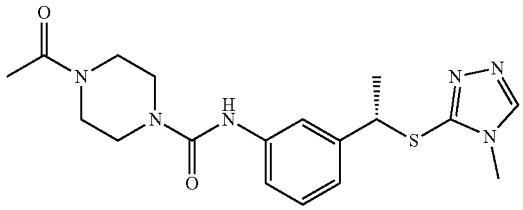 [SMILES: CC(=O)N1CCN(C(=O)Nc2cccc([C@H](C)Sc3nncn3C)c2)CC1] |

-continued
| Cmpd No. | Structure | Cmpd No. | Structure |
|---|---|---|---|
| 163 | 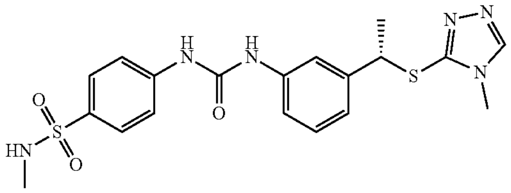 [SMILES: CNS(=O)(=O)c1ccc(NC(=O)Nc2cccc([C@H](C)Sc3nncn3C)c2)cc1] | 164 | 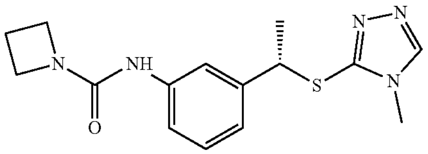 [SMILES: C[C@H](Sc1nncn1C)c1cccc(NC(=O)N2CCC2)c1] |
| 165 | 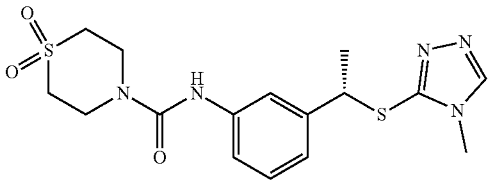 [SMILES: C[C@H](Sc1nncn1C)c1cccc(NC(=O)N2CCS(=O)(=O)CC2)c1] | 166 | 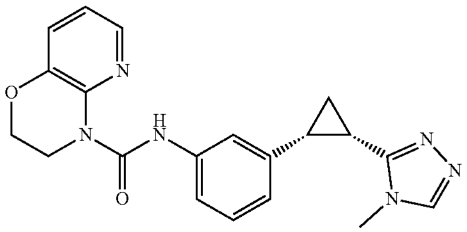 [SMILES: Cn1cnnc1[C@H]1C[C@H]1c1cccc(NC(=O)N2CCOc3cccnc32)c1] |
or a tautomer of the compound, or a pharmaceutically acceptable salt of the compound or the tautomer.
25. A pharmaceutical composition comprising the compound of claim 1, or a tautomer of the compound, or a pharmaceutically acceptable salt of the compound or the tautomer, and a pharmaceutically acceptable excipient.
* * * * *

SEQUENCE LISTING

<160> NUMBER OF SEQ ID NOS: 1

<210> SEQ ID NO 1
<211> LENGTH: 392
<212> TYPE: PRT
<213> ORGANISM: Homo sapiens
<220> FEATURE:
<221> NAME/KEY: MISC_FEATURE
<223> OTHER INFORMATION: Cbl-b amino acid residues 36-427

<400> SEQUENCE: 1

Pro Lys Gln Ala Ala Ala Asp Arg Arg Thr Val Glu Lys Thr Trp Lys
1               5                   10                  15

Leu Met Asp Lys Val Val Arg Leu Cys Gln Asn Pro Lys Leu Gln Leu
            20                  25                  30

Lys Asn Ser Pro Pro Tyr Ile Leu Asp Ile Leu Pro Asp Thr Tyr Gln
        35                  40                  45

His Leu Arg Leu Ile Leu Ser Lys Tyr Asp Asp Asn Gln Lys Leu Ala
    50                  55                  60

Gln Leu Ser Glu Asn Glu Tyr Phe Lys Ile Tyr Ile Asp Ser Leu Met
65                  70                  75                  80

Lys Lys Ser Lys Arg Ala Ile Arg Leu Phe Lys Glu Gly Lys Glu Arg
                85                  90                  95

Met Tyr Glu Glu Gln Ser Gln Asp Arg Arg Asn Leu Thr Lys Leu Ser
            100                 105                 110

Leu Ile Phe Ser His Met Leu Ala Glu Ile Lys Ala Ile Phe Pro Asn
        115                 120                 125

Gly Gln Phe Gln Gly Asp Asn Phe Arg Ile Thr Lys Ala Asp Ala Ala
    130                 135                 140

Glu Phe Trp Arg Lys Phe Phe Gly Asp Lys Thr Ile Val Pro Trp Lys
145                 150                 155                 160

Val Phe Arg Gln Cys Leu His Glu Val His Gln Ile Ser Ser Gly Leu
                165                 170                 175

Glu Ala Met Ala Leu Lys Ser Thr Ile Asp Leu Thr Cys Asn Asp Tyr
            180                 185                 190

Ile Ser Val Phe Glu Phe Asp Ile Phe Thr Arg Leu Phe Gln Pro Trp
        195                 200                 205

Gly Ser Ile Leu Arg Asn Trp Asn Phe Leu Ala Val Thr His Pro Gly
    210                 215                 220

Tyr Met Ala Phe Leu Thr Tyr Asp Glu Val Lys Ala Arg Leu Gln Lys
225                 230                 235                 240

-continued

```
Tyr Ser Thr Lys Pro Gly Ser Tyr Ile Phe Arg Leu Ser Cys Thr Arg
                245                 250                 255

Leu Gly Gln Trp Ala Ile Gly Tyr Val Thr Gly Asp Gly Asn Ile Leu
            260                 265                 270

Gln Thr Ile Pro His Asn Lys Pro Leu Phe Gln Ala Leu Ile Asp Gly
        275                 280                 285

Ser Arg Glu Gly Phe Tyr Leu Tyr Pro Asp Gly Arg Ser Tyr Asn Pro
    290                 295                 300

Asp Leu Thr Gly Leu Cys Glu Pro Thr Pro His Asp His Ile Lys Val
305                 310                 315                 320

Thr Gln Glu Gln Tyr Glu Leu Tyr Cys Glu Met Gly Ser Thr Phe Gln
                325                 330                 335

Leu Cys Lys Ile Cys Ala Glu Asn Asp Lys Asp Val Lys Ile Glu Pro
            340                 345                 350

Cys Gly His Leu Met Cys Thr Ser Cys Leu Thr Ala Trp Gln Glu Ser
        355                 360                 365

Asp Gly Gln Gly Cys Pro Phe Cys Arg Cys Glu Ile Lys Gly Thr Glu
    370                 375                 380

Pro Ile Ile Val Asp Pro Phe Asp
385                 390
```